(12) United States Patent
Rodgers et al.

(10) Patent No.: US 9,309,246 B2
(45) Date of Patent: Apr. 12, 2016

(54) TRICYCLIC HETEROCYCLES AS BET PROTEIN INHIBITORS

(71) Applicant: Incyte Corporation, Wilmington, DE (US)

(72) Inventors: James D. Rodgers, Landenberg, PA (US); Stacey Shepard, Wilmington, DE (US); Haisheng Wang, Hockessin, DE (US); Lixin Shao, Newark (DE)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/575,284

(22) Filed: Dec. 18, 2014

(65) Prior Publication Data
US 2015/0175604 A1    Jun. 25, 2015

Related U.S. Application Data

(60) Provisional application No. 61/918,198, filed on Dec. 19, 2013.

(51) Int. Cl.
*C07D 471/14* (2006.01)

(52) U.S. Cl.
CPC .................................... *C07D 471/14* (2013.01)

(58) Field of Classification Search
CPC ............................ C07D 249/16; C07D 471/16
See application file for complete search history.

(56) References Cited

U.S. PATENT DOCUMENTS

| 5,589,476 | A | 12/1996 | Jegham et al. |
|---|---|---|---|
| 2007/0191447 | A1 | 8/2007 | Kodo et al. |
| 2013/0261109 | A1 | 10/2013 | Miyoshi et al. |
| 2013/0281396 | A1 | 10/2013 | McLure et al. |
| 2013/0281397 | A1 | 10/2013 | McLure et al. |
| 2013/0281398 | A1 | 10/2013 | McLure et al. |
| 2013/0281399 | A1 | 10/2013 | McLure et al. |
| 2014/0135316 | A1 | 5/2014 | Albrecht et al. |
| 2014/0275030 | A1 | 9/2014 | Combs et al. |
| 2015/0011540 | A1 | 1/2015 | Combs et al. |
| 2015/0148342 | A1 | 5/2015 | Yue et al. |
| 2015/0148372 | A1 | 5/2015 | Yue et al. |
| 2015/0148375 | A1 | 5/2015 | Yue et al. |

FOREIGN PATENT DOCUMENTS

| CA | 2171579 | 9/1996 |
|---|---|---|
| EP | 0 732 334 | 9/1996 |
| EP | 1462103 | 9/2004 |
| EP | 2 239 264 | 10/2010 |
| FR | 2747678 | 10/1997 |
| JP | 2013/010719 | 1/2013 |
| WO | WO 02/00196 | 1/2002 |
| WO | WO 2004/024736 | 3/2004 |
| WO | WO 2007/018998 | 2/2007 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.

Bamborough et al., "Fragment-Based Discovery of Bromodomain Inhibitors Part 2: Optimization of Phenylisoxazole Sulfonamides," J Med Chem., 2012, 55:587-596.

Bartholomeeusen et al., "BET bromodomain inhibition activates transcription via a transient release of P-TEFb from 7SK snRNP," JBC, 2012, 16 pages.

(Continued)

*Primary Examiner* — Rita Desai
(74) *Attorney, Agent, or Firm* — Fish & Richardson P.C.

(57) ABSTRACT

The present invention relates to tricyclic heterocycles which are inhibitors of BET proteins such as BRD2, BRD3, BRD4, and BRD-t and are useful in the treatment of diseases such as cancer.

32 Claims, No Drawings

(56) References Cited

FOREIGN PATENT DOCUMENTS

| | | |
|---|---|---|
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | 2015013635 | 1/2015 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |

OTHER PUBLICATIONS

Belkina and Denis, "BET domain co-regulators in obesity inflammation and cancer," Nat Rev Cancer, Jul. 2012, 12:465-477.

Chiang, "Brd4 engagement from chromatin targeting to transcriptional regulation: selective contact with acetylated histone H3 and H4," Biology Reports, Dec. 2009, 1:98, 7 pages.

Chung et al., "Discovery and Characterization of Small Molecule Inhibitors of the BET Family Bromodomains," J Med Chem., 2011, 54:3827-3838.

Chung et al., "Fragment-Based Discovery of Bromodomain Inhibitors Part 1. Inhibitor Binding Modes and Implications for Lead Discovery," J Med Chem., 2011, 11 pages.

Chung et al., "Fragment-based discovery of bromodomain inhibitors part 1: inhibitor binding modes and implications for lead discovery," Supporting Information, 2011, 6 pages.

Dawson et al., "Inhibition of BET recruitment to chromatin as an effective treatment for MLL-fusion leukaemia," Nature, 2011, 5 pages.

Dawson, "Supplementary Information. Inhibition of BET recruitment to chromatin as an effective treatment for MLL-fusion leukaemia," Nature, 2011, 50 pages.

Delmore et al., "BET bromodomain inhibition as a therapeutic strategy to target c-Myc," Cell, 2011, 146(6):904-917, Supplemental Information: S1-S11.

Draker et al., "A Combination of H2A.Z and H4 Acetylation Recruits Brd2 to Chromatin during Transcriptional Activation," PLoS Genet., Nov. 2012, 8(11):e1003047, 17 pages.

Dorwald, F. Zaragoza. Side Reactions in Organic Synthesis: A Guide to Successful Synthesis Design, Weinheim: WILEY-VCH Verlag GmbH & Co. KGaA, 2005, Preface.

Filippakopoulos and Knapp, "Targeting bromodomains: epigenetic readers of lysine acetylation," Nature Rev Drug Disc., May 2014, 13:337-356.

Filippakopoulos et al., "Benzodiazepines and benzotriazepines as protein interaction inhibitors targeting bromodomains of the Bet family," Bioorg Med Chem., 2011, 9 pages.

Filippakopoulos et al., "Histone Recognition and Large-Scale Structural Analysis of the Human Bromodomain Family," Cell, Mar. 2012, 149:214-231.

Filippakopoulos et al., "Supplemental Information: Selective inhibition of BET bromodomains," Nature, 2010, 468:1067-1073.

Floyd et al., "Supplemental Information: The bromodomain protein Brd4 insulates chromatin from DNA damage signalling," Nature, 2013, 14 pages.

Floyd et al., "The bromodomain protein Brd4 insulates chromatin from DNA damage signalling," Nature, 2013, 498:246-250.

French et al., "BRD—NUT oncoproteins: a family of closely related nuclear proteins that block epithelial differentiation and maintain the growth of carcinoma cells," Oncogene, 2008, 27:2237-2242.

French, "Demystified molecular pathology of NUT midline carcinomas," J Clin Pathol., 2010, 63:492-496.

French, "NUT midline carcinoma," Cancer Genet Cytogenetics, 2010, 203:16-20.

Frizzo et al., "Structural and thermodynamic properties of new pyrazolo[3,4-d] pyridazinones," Thermochimica Acta., Oct. 2013, 574:63-72.

Hewings et al., "3,5-Dimethylisoxazoles Act As Acetyl-lysine-mimetic Bromodomain Ligands," J Med Chem., 2011, 54:6761-6770.

Hewings et al., "Progress in the Development and Applciation of Small Molecule Inhibitors of Bromodomain-Acetyl-lysine Interactions," J Med Chem., Nov. 2012, 104 pages (Author Manuscript).

Houzelstein et al., "Growth and Early Postimplantation Defects in Mice Deficient for the Bromodomain-Containing Protein Brd4," Mole Cell Biol., Jun. 2002, 22(11):3794-3802.

International Search Report and Written Opinion in International Application No. PCT/US2014/067598, mailed Feb. 13, 2015, 9 pages.

International Search Report and Written Opinion in International Application No. PCT/US2014/067629, mailed Feb. 16, 2015, 11 pages.

International Search Report and Written Opinion in International Application No. PCT/US2014/067691, mailed Feb. 2, 2015, 10 pages.

International Search Report and Written Opinion in International Application No. PCT/US2014/071102, mailed Feb. 13, 2015, 9 pages.

International Preliminary Report on Patentability in International Application No. PCT/US2014/027872, dated Sep. 24, 2015, 8 pages.

International Search Report and Written Opinion in International Application No. PCT/US2015/027047, dated Jul. 10, 2015, 14 pages.

(56) References Cited

OTHER PUBLICATIONS

Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "What do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zuber et al., "An integrated approach to dissecting oncogene addiction implicates a Myb-coordinated self-renewal program as essential for leukemia maintenance," Genes Dev., 2011, 25:1628-1640.
Zuber et al., "Supplemental Information: RNAi screen identifies Brd4 as a therapeutic target in acute myeloid leukaemia," Nature, 2011, 33 pages.
International Search Report and Written Opinion in International Application No. PCT/US2014/027872, mailed Jun. 30, 2014, 12 pages.
International Search Report and Written Opinion in International Application No. PCT/US2014/045543, mailed Sep. 10, 2014, 11 pages.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Delmore et al., "BET bromodomain inhibition as a therapeutic strategy to target c-Myc," Cell, 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Filippakopoulos et al., "Selective inhibition of BET bromodomains," Nature, 2010, 468:1067-1073.
French et al., "BRD4-NUT fusion oncogene: a novel mechanism in aggressive carcinoma," Cancer Res., 2003, 63(2):304-307.
French et al., "Midline carcinoma of children and young adults with NUT rearrangement," J Clin. Oneal., 2004, 22(20):4135-4139.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Hewings et al., "Progress in the Development and Applciation of Small Molecule Inhibitors of Bromodomain-Acetyl-lysine Interactions," J Med Chem., Nov. 2012, 55(22):9393-9413.

(56) References Cited

OTHER PUBLICATIONS

Huang et al., "Brd4 coactivates transcriptional activation of NF-κB via specific binding to acetylated RelA," Mol. Cell Biol., 2009, 29(5):1375-1387.
Jang et al., "The bromodomain protein Brd4 is a positive regulatory component of P-TEFb and stimulates RNA polymerase II-dependent transcription," Mol. Cell, 2005, 19(4):523-534.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, 2008, 30(1):51-60.
Mochizuki et al., "The bromodomain protein Brd4 stimulates G1 gene transcription and promotes progression to S phase," J Biol. Chem. 2008, 283(14):9040-9048.
Peturssion et al., "Protecting Groups in Carbohydrate Chemistry," J Chem. Educ., 1997, 74(11):1297-1303.
Ravin, "Preformulation," Remington's Pharmaceutical Sciences, 17th Ed., (Mack Publishing Company, Easton, 1985), pp. 1409-1423.
Wang et al., "Brd2 disruption in mice causes severe obesity without Type 2 diabetes," Biochem. J., 2010, 425(1):71-83.
You et al., "Interaction of the bovine papillomavirus E2 protein with Brd4 tethers the viral DNA to host mitotic chromosomes," Cell, 2004, 117(3):349-60.
Zhu et al., "Reactivation of latent HIV-1 by inhibition of BRD4," Cell Reports, 2012, 2(4):807-816.
Zuber et al., "RNAi screen identifies Brd4 as a therapeutic target in acute myeloid leukaemia," Nature, 2011, 478(7370):524-528.

TRICYCLIC HETEROCYCLES AS BET PROTEIN INHIBITORS

FIELD OF THE INVENTION

The present invention relates to tricyclic heterocycles which are inhibitors of BET proteins such as BRD2, BRD3, BRD4, and BRD-t and are useful in the treatment of diseases such as cancer.

BACKGROUND OF THE INVENTION

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitiously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146:904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY OF THE INVENTION

The present invention provides, inter alia, a compound of Formula I:

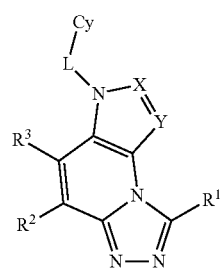

or a pharmaceutically acceptable salt thereof; wherein the variables are as defined below.

The present invention also provides a pharmaceutical composition comprising a compound of Formula I, or a pharmaceutically acceptable salt thereof, and at least one pharmaceutically acceptable carrier.

The present invention also provides a method of inhibiting a BET protein comprising contacting a compound of Formula I, or a pharmaceutically acceptable salt thereof, with the BET protein.

The present invention also provides a method of treating cancer and other diseases comprising administering to a patient a therapeutically effective amount of a compound of Formula I, or a pharmaceutically acceptable salt thereof.

The present invention also provides a compound of Formula I, or a pharmaceutically acceptable salt thereof, for use in therapy.

The present invention also provides use of a compound of Formula I, or a pharmaceutically acceptable salt thereof, in the preparation of a medicament for use in therapy.

DETAILED DESCRIPTION

The present invention provides, inter alia, a compound of Formula I:

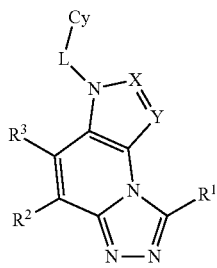

I or a pharmaceutically acceptable salt thereof; wherein
X is N or CR$^4$;
Y is N or CR$^5$;
L is C$_{1-6}$ alkylene, —(C$_{1-4}$ alkylene)$_n$-C(=O)—(C$_{1-4}$ alkylene)$_m$-, —(C$_{1-4}$ alkylene)$_n$-C(=O)NR$^6$—(C$_{1-4}$ alkylene)$_m$-, —(C$_{1-4}$ alkylene)$_n$-NR$^6$—(C$_{1-4}$ alkylene)$_m$-, —(C$_{1-4}$ alkylene)$_n$-NR$^6$—C(=O)NR$^7$—(C$_{1-4}$ alkylene)$_m$-, —(C$_{1-4}$ alkylene)$_n$-C(=O)O—(C$_{1-4}$ alkylene)$_m$-, —(C$_{1-4}$ alkylene)$_n$-S(=O)—(C$_{1-4}$ alkylene)$_m$-, —(C$_{1-4}$ alkylene)$_n$-S(=O)$_2$—(C$_{1-4}$ alkylene)$_m$-, —(C$_{1-4}$ alkylene)$_n$-O—(C$_{1-4}$ alkylene)$_m$-, or —(C$_{1-4}$ alkylene)$_n$-S—(C$_{1-4}$ alkylene)$_m$— wherein each alkylene moiety of any of the aforementioned L groups is optionally substituted by 1, 2, or 3 substituents independently selected from F, Cl, OH, C$_{1-4}$ alkoxy, CF$_3$, and CN;
wherein when the L group includes a —O—, —S—, —NR$^6$—, or —NR$^7$— moiety, then the —O—, —S—, —NR$^6$—, or —NR$^7$— moiety of L is not bonded directly to N of the tricyclic core structure, but is connected to N via a C$_{1-4}$ alkylene moiety of L;
Cy is C$_{6-10}$ aryl, C$_{3-10}$ cycloalkyl, 5-10 membered heteroaryl, 4-10 membered heterocycloalkyl, each of which is optionally substituted by 1, 2, or 3 R$^{Cy}$;
R$^1$ is H, C$_{1-6}$ alkyl, cyclopropyl, cyclobutyl, C$_{2-6}$ alkenyl, C$_{2-6}$ alkynyl, C$_{1-6}$ haloalkyl, or C$_{1-6}$ hydroxyalkyl;
R$^2$ and R$^3$ are each independently selected from H, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, and C$_{2-6}$ alkynyl are each optionally substituted with 1, 2, 3, 4, or 5 substituents independently selected from halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;
R$^4$ is H, halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, (4-10 membered heterocycloalkyl)-C$_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$ S(O)R$^{b1}$, NR$^{c1}$ S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl are each optionally substituted with 1, 2, 3, 4, or 5 substituents independently selected from R$^A$;
R$^5$ is H, halo, C$_{1-4}$ alkyl, C$_{2-4}$ alkenyl, C$_{1-4}$ haloalkyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, or S(O)$_2$NR$^{c2}$R$^{d2}$;
R$^6$ and R$^7$ are each independently selected from H and C$_{1-4}$ alkyl;
each R$^{Cy}$ is independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, (4-10 membered heterocycloalkyl)-C$_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{c3}$)R$^{b3}$, C(=NR$^{c3}$)NR$^{c3}$R$^{d3}$, NR$^{c3}$C(=NR$^{c3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{c3}$)NR$^{c3}$R$^{d3}$, NR$^{c3}$C(=NR$^{c3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c4}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;
each R$^A$ is independently selected from Cy$^1$, halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{c4}$)R$^{b4}$, C(=NR$^{c4}$)NR$^{c4}$R$^{d4}$, NR$^{c4}$C(=NR$^{c4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, and C$_{2-6}$ alkynyl are each optionally substituted with 1, 2, 3, 4, or 5 substituents independently selected from Cy$^1$, halo, C$_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a1}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, INK $S(O)_2NR^{c6}R^{d6}$, and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$$NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2$ $NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR', SR', $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^e$, $R^{e1}$, $R^{e3}$, $R^{e4}$, and $R^{e5}$ is independently selected from H, $C_{1-4}$ alkyl, CN, $OR^{a6}$, $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e6}$ is independently selected from H, $C_{1-4}$ alkyl, and CN;

n is 0 or 1; and m is 0 or 1.

In some embodiments, X is N.

In some embodiments, X is $CR^4$.

In some embodiments, Y is N.

In some embodiments, Y is $CR^5$.

In some embodiments, L is $C_{1-6}$ alkylene or $—(C_{1-4}$ alkylene)$_n$-S(=O)$_2$—(C_{1-4}$ alkylene)$_m$-, wherein each alkylene moiety of any of the aforementioned L groups is optionally substituted by 1, 2, or 3 substituents independently selected from F, Cl, OH, $C_{1-4}$ alkoxy, $CF_3$, and CN.

In some embodiments, L is $CH_2$, $S(=O)_2$, —CH($CH_2OH$)—, or —CH(($CH_2$)$_3CH_3$)—.

In some embodiments, L is $CH_2$ or $S(=O)_2$.

In some embodiments, L is $S(=O)_2$.

In some embodiments, L is —$CH_2CH_2$—.

In some embodiments, L is $CH_2$.

In some embodiments, Cy is $C_{6-10}$ aryl, $C_{3-10}$ cycloalkyl, or 5-10 membered heteroaryl, each of which is optionally substituted by 1, 2, or 3 $R^{Cy}$.

In some embodiments, Cy is $C_{3-6}$ cycloalkyl optionally substituted by 1, 2, or 3 $R^{Cy}$.

In some embodiments, Cy is 5-10 membered heteroaryl optionally substituted by 1, 2, or 3 $R^{Cy}$.

In some embodiments, Cy is 5-6 membered heteroaryl optionally substituted by 1, 2, or 3 $R^{Cy}$.

In some embodiments, Cy is phenyl, cyclopentyl, quinolinyl, or pyridyl, each of which is optionally substituted by 1, 2, or 3 $R^{Cy}$.

In some embodiments, Cy is phenyl or pyridyl, each of which is optionally substituted by 1, 2, or 3 $R^{Cy}$.

In some embodiments, Cy is phenyl optionally substituted by 1, 2, or 3 $R^{Cy}$.

In some embodiments, Cy is pyridyl optionally substituted by 1, 2, or 3 $R^{Cy}$.

In some embodiments, each $R^{Cy}$ is independently selected from halo, $C_{1-6}$ alkyl, $C_{1-4}$ haloalkyl, (4-10 membered heterocycloalkyl)-$C_{1-4}$ alkyl, CN, $OR^{a3}$, $C(O)NR^{c3}R^{d3}$, $NR^{c3}C(O)R^{b3}$, and $NR^{c3}C(O)NR^{c3}R^{d3}$ wherein said $C_{1-6}$ alkyl and (4-10 membered heterocycloalkyl)-$C_{1-4}$ alkyl are each optionally substituted with 1, 2, or 3 substituents independently selected from halo, $C_{1-6}$ alkyl, $OR^{a3}$, and $NR^{c3}R^{d3}$.

In some embodiments, each $R^{Cy}$ is independently selected from halo, $C_{1-6}$ alkyl, (4-10 membered heterocycloalkyl)-$C_{1-4}$ alkyl, CN, $OR^{a3}$, $C(O)NR^{c3}R^{d3}$, $NR^{c3}C(O)R^{b3}$, and $NR^{c3}C(O)NR^{c3}R^{d3}$ wherein said $C_{1-6}$ alkyl and (4-10 membered heterocycloalkyl)-$C_{1-4}$ alkyl are each optionally substituted with 1, 2, or 3 substituents independently selected from $C_{1-6}$ alkyl, $OR^{a3}$, and $NR^{c3}R^{d3}$.

In some embodiments, each $R^{Cy}$ is independently selected from $C_{1-6}$ alkyl substituted by $NR^{c3}R^{d3}$.

In some embodiments, each $R^{a3}$, $R^{b3}$, $R^{c3}$, and $R^{d3}$ is independently selected from methyl, ethyl, propyl, and butyl.

In some embodiments, each $R^{Cy}$ is independently selected from fluoro, chloro, methyl, cyano, hydroxy, methoxy, aminocarbonyl, methylcarbonylamino, methylaminocarbonyl, ethylaminocarbonyl, azetidinylmethyl, pyrrolidinylmethyl, piperidinylmethyl, piperazinylmethyl, morpholinomethyl, ureido, and ethylureido, wherein said methyl, azetidinylmethyl, pyrrolidinylmethyl, piperidinylmethyl, piperazinylmethyl, and morpholinomethyl are each optionally substituted with 1, 2, or 3 substituents independently selected from fluoro, methyl, hydroxy, methoxy, methylamino, ethylamino, dimethylamino, hydroxycyclobutylamino, hydroxyethyl(methyl)amino, and hydroxyethylamino.

In some embodiments, each $R^{Cy}$ is independently selected from fluoro and chloro.

In some embodiments, $R^1$ is H or $C_{1-6}$ alkyl.

In some embodiments, $R^1$ is $C_{1-6}$ alkyl.

In some embodiments, $R^1$ is methyl.

In some embodiments, $R^1$ is H.

In some embodiments, $R^2$ and $R^3$ are both H.

In some embodiments, $R^2$ is H.

In some embodiments, $R^3$ is H.

In some embodiments, $R^2$ is H, $OR^a$, $NR^cR^d$, $NR^cC(O)R^b$, $NR^cC(O)OR^a$, $NR^cC(O)NR^cR^d$, or $NR^cS(O)_2R^b$.

In some embodiments, $R^2$ is H, —OH, —NHC(=O)OCH$_3$, —NHC(=O)CH$_3$—, NHC(=O)CH$_2$CH$_3$, —NHC(=O)CH$_2$CH$_2$CH$_3$, —NHC(=O)CH(CH$_3$)$_2$, —NHS(=O)$_2$CH$_3$, —OCH$_3$, —NHCH$_3$, —NHCH$_2$CH$_3$, —NHCH(CH$_3$)$_2$, —NHCH$_2$CH$_2$CH$_3$, —NH-(phenyl), —NH-(imidazolyl), —NH-(pyridyl), —NHCH$_2$CH$_2$NH$_2$, —NHCH$_2$CH$_2$CH$_2$NH$_2$, —NHC(=O)NH$_2$, —NHC(=O)NH(CH$_3$), —NHC(=O)N(CH$_3$)$_2$, —NHC(=O)NHCH(CH$_3$)$_2$, —NHC(=O)NHCH$_2$CH$_\beta$, —NHC(=O)O-(t-butyl), —NH-(hydroxycyclobutyl), —NHCH$_2$CH$_2$N(CH$_3$)$_2$, —NHCH$_2$CH$_2$CH$_2$N(CH$_3$)$_2$, —NH-(t-butyloxycarbonylazetidinyl), —NH-(t-butyloxycarbonylazetidinylmethyl), —NH-(t-butyloxycarbonylpiperidinylmethyl), —NH-(cyclobutylmethyl), —NH-(cyclohexyl), —NH-(cyclopropylmethyl), —NH-(8-azabicyclo[3,2,1]octan-3-yl), —NH-(dimethylpiperidinyl), —NH-(methylpiperidinyl), —NH-(piperidinyl), —NH-(methylpiperidinyl), —NH-(dimethylaminocyclohexyl), —NH-(methylaminocyclohexyl), —NH-(aminocyclohexyl), —NH-(acetylpiperidinyl), —NH-(cyanocyclohexyl), —NH-(t-butyloxycarbonylpiperidinyl), —NH-(2-propylpiperidinyl), —NH-(ethylpiperidinyl), —NH-(methylsulfonylpiperidinyl), —NHCH$_2$CH$_2$OH, —NHCH$_2$CH$_2$OCH$_3$, —NH-(morpholinoethyl), —NH-(benzimidazolyl), —NH-(benzoxazolyl), —NH-(methylpyrazolyl), —NH-(pyrimidinyl), —NH-(pyrazolyl), —NH-(pyrrolidinyl), —NH-(methylpyrrolidinyl), —NH-(t-butyloxycarbonylpyrrolidinyl), —NH-(tetrahydrofuranyl), or —NH-(tetrahydropyranyl).

In some embodiments, $R^a$, $R^b$, $R^c$ and $R^d$ are independently selected from H, —CH$_3$, —CH$_2$CH$_3$, —CH$_2$CH$_2$CH$_3$, —CH(CH$_3$)$_2$, —CH$_2$CH$_2$CH$_2$CH$_3$, i-butyl, s-butyl, t-butyl, —CH$_2$CH$_2$NH$_2$, —CH$_2$CH$_2$CH$_2$NH$_2$, —CH$_2$CH$_2$N(CH$_3$)$_2$, —CH$_2$CH$_2$CH$_2$N(CH$_3$)$_2$, —CH$_2$CH$_2$OH, —CH$_2$CH$_2$OCH$_3$, phenyl, pyridyl, imidazolyl, azetidinyl, azetidinylmethyl-, piperidinyl, piperidinylmethyl-, methylpiperidinyl-, acetylpiperidinyl-, 2-propylpiperidinyl-, ethylpiperidinyl-, methylsulfonylpiperidinyl-, pyrrolidinyl-, methylpyrrolidinyl-, benzimidazolyl-, benzoxazolyl-, pyrazolyl-, pyrimidinyl-, tetrahydrofuranyl-, methylpyrazolyl-, tetrahydropyranyl-, cyclobutyl-, hydroxycyclobutyl-, cyclopropylmethyl-, cyclobutylmethyl-, cyclohexyl-, dimethylaminocyclohexyl-, methylaminocyclohexyl-, aminocyclohexyl-, cyanocyclohexyl-, and morpholinoethyl-.

In some embodiments, $R^a$, $R^b$, $R^c$ and $R^d$ are independently selected from H and C$_{1-6}$ alkyl.

In some embodiments, $R^4$ is H, CN, C$_{1-6}$ alkyl, C$_{1-4}$ haloalkyl, 5-10 membered heteroaryl, (5-10 membered heteroaryl)-C$_{1-4}$ alkyl, 4-10 membered heterocycloalkyl, C(O)NR$^{c1}$R$^{d1}$, C(O)OR$^{a1}$, or NR$^{c1}$R$^{d1}$; wherein said C$_{1-6}$ alkyl, 5-10 membered heteroaryl, 4-10 membered heterocycloalkyl and (5-10 membered heteroaryl)-C$_{1-4}$ alkyl are each optionally substituted with 1, 2, 3, 4, or 5 substituents independently selected from $R^A$.

In some embodiments, $R^4$ is H, C$_{1-6}$ alkyl, 5-10 membered heteroaryl, (5-10 membered heteroaryl)-C$_{1-4}$ alkyl, C(O)NR$^{c1}$R$^{d1}$ C(O)OR$^{a1}$, or NR$^{c1}$R$^{d1}$; wherein said C$_{1-6}$ alkyl, 5-10 membered heteroaryl, and (5-10 membered heteroaryl)-C$_{1-4}$ alkyl are each optionally substituted with 1, 2, 3, 4, or 5 substituents independently selected from $R^A$.

In some embodiments, $R^4$ is H, C$_{1-4}$ alkyl, 5 to 6-membered heteroaryl, (5-membered heteroaryl)-C$_{1-4}$ alkyl, C(O)NR$^{c1}$R$^{d1}$, C(O)OR$^{a1}$, or NR$^{c1}$R$^{d1}$; wherein said C$_{1-6}$ alkyl, 5-10 membered heteroaryl, and (5-10 membered heteroaryl)-C$_{1-4}$ alkyl are each optionally substituted with 1, 2, 3, 4, or 5 substituents independently selected from $R^A$.

In some embodiments, $R^4$ is C$_{1-4}$ alkyl optionally substituted with 1, 2, or 3 substituents independently selected from $R^A$.

In some embodiments, $R^4$ is 5 to 6-membered heteroaryl optionally substituted with 1, 2, or 3 substituents independently selected from $R^A$.

In some embodiments, $R^4$ is 5-membered heteroaryl optionally substituted with 1 or 2 substituents independently selected from $R^A$.

In some embodiments, $R^4$ is (5-membered heteroaryl)-C$_{1-4}$ alkyl optionally substituted with for 2 substituents independently selected from $R^A$.

In some embodiments, $R^4$ is C(O)NR$^{c1}$R$^{d1}$.

In some embodiments, $R^4$ is 4 to 6-membered heterocycloalkyl optionally substituted with 1 or 2 substituents independently selected from $R^A$.

In some embodiments, $R^4$ is H, C$_{1-4}$ alkyl, pyrazolyl, imidazolyl, thienyl, thiazolyl, pyridyl, imidazolylmethyl, C(O)NR$^{c1}$R$^{d1}$, C(O)OR$^{a1}$, or NR$^{c1}$R$^{d1}$; wherein said C$_{1-4}$ alkyl, pyrazolyl, imidazolyl, thienyl, thiazolyl, pyridyl, and imidazolylmethyl, are each optionally substituted with 1, 2, or 3 substituents independently selected from $R^A$.

In some embodiments, $R^4$ is H, CN, methyl, ethyl, pyrazolyl, imidazolyl, thienyl, thiazolyl, pyridyl, imidazolylmethyl, oxadiazolyl, oxazolyl, dihydrooxazolyl, pyrrolidinyl, —C(=O)NH-(methyl), —C(=O)NH-(ethyl), —C(=O)—NH-(t-butyl), —C(=O)—NH-(s-butyl), —C(=O)NH-(pyridylmethyl), —C(=O)NH-(isopropyl), —C(=O)NH-(hydroxypropyl), —C(=O)NH-(azetidinylmethyl), —C(=O)NH-(morpholinoethyl), —C(=O)-(methylazetidinyl), —C(=O)NH-(hydroxyethyl), —C(=O)-(morpholino), —C(=O)NH-(dimethylaminoethyl), —C(=O)NH-(cyclopropylmethyl), —C(=O)NH-(cyclobutyl), —C(=O)NH-(cyanocyclobutyl), —C(=O)NH$_2$, —C(=O)N(CH$_3$)$_2$, —C(=O)NH-(2,2,2-trifluoro-1-methylethyl), or —C(=O)-(cyanoazetidinyl), wherein said methyl, ethyl, pyrazolyl, imidazolyl, thienyl, thiazolyl, pyridyl, imidazolylmethyl, oxadiazolyl, oxazolyl, dihydrooxazolyl, and pyrrolidinyl are each optionally substituted with 1, 2, or 3 substituents independently selected from $R^A$.

In some embodiments, $R^4$ is pyrazolyl optionally substituted with $R^A$.

In some embodiments, $R^4$ is imidazolyl optionally substituted with $R^A$.

In some embodiments, $R^4$ is thienyl optionally substituted with $R^A$.

In some embodiments, $R^4$ is thiazolyl optionally substituted with $R^A$.

In some embodiments, $R^4$ is pyridyl optionally substituted with $R^A$.

In some embodiments, $R^4$ is imidazolylmethyl optionally substituted with $R^A$.

In some embodiments, $R^4$ is oxadiazolyl optionally substituted with $R^A$.

In some embodiments, $R^4$ is oxazolyl optionally substituted with $R^A$.

In some embodiments, $R^4$ is pyrrolidinyl optionally substituted with $R^A$.

In some embodiments, $R^4$ is dihydrooxazolyl optionally substituted with $R^A$.

In some embodiments, each $R^A$ is independently selected from Cy$^1$, C(O)R$^{b4}$, and C$_{1-6}$ alkyl, wherein said C$_{1-6}$ alkyl is optionally substituted with 1, 2, or 3 substituents independently selected from Cy$^1$, CN, OR$^{a4}$, C(O)NR$^{c4}$R$^{d4}$, and NR$^{c4}$R$^{d4}$.

In some embodiments, each $R^A$ is independently selected from Cy$^1$ and C$_{1-6}$ alkyl, wherein said C$_{1-6}$ alkyl is optionally substituted with 1, 2, or 3 substituents independently selected from Cy$^1$, CN, C(O)NR$^{c4}$R$^{d4}$, and NR$^{c4}$R$^{d4}$.

In some embodiments, each $R^A$ is C$_{1-4}$ alkyl optionally substituted with 1, 2, or 3 substituents independently selected from Cy$^1$, halo, C$_{1-3}$ alkyl, C$_{2-3}$ alkenyl, C$_{2-3}$ alkynyl, C$_{1-3}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{c4}$)NR$^{c4}$R$^{d4}$, NR$^{c4}$C(=NR$^{c4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, each $R^A$ is ethyl optionally substituted with 1, 2, or 3 substituents independently selected from Cy', halo, $C_{1-3}$ alkyl, $C_{2-3}$ alkenyl, $C_{2-3}$ alkynyl, $C_{1-3}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, each $R^A$ is Cy$^1$.

In some embodiments, each $R^A$ is Cy$^1$ wherein Cy$^1$ is selected from 4-6 membered heterocycloalkyl optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{n5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$.

In some embodiments, each $R^A$ is azetidinyl optionally substituted by 1 or 2 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$.

In some embodiments, $R^{c1}$ and $R^{d1}$ are independently selected from H, $C_{1-6}$ alkyl, $C_{3-6}$ cycloalkyl, and 4-6 membered heterocycloalkyl, $C_{3-6}$ cycloalkyl-$C_{1-6}$ alkyl, and (4-6 membered heterocycloalkyl)-$C_{1-6}$ alkyl, wherein said $C_{1-6}$ alkyl, $C_{3-6}$ cycloalkyl, 4-6 membered heterocycloalkyl, $C_{3-6}$ cycloalkyl-$C_{1-6}$ alkyl, and (4-6 membered heterocycloalkyl)-$C_{1-6}$ alkyl is optionally substituted with 1, 2, or 3 substituents independently selected from $C_{1-4}$ alkyl, $C_{1-4}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$.

In some embodiments, $R^{c1}$ and $R^{d1}$ together with the N atom to which they are attached form a 4-, 5-, or 6-membered heterocycloalkyl group optionally substituted with 1 or 2 substituents independently selected from $C_{1-4}$ alkyl, $C_{1-4}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$.

In some embodiments, $R^5$ is H.

In some embodiments, the compounds of the invention have Formula IIa:

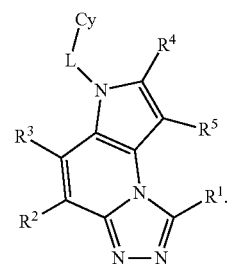

IIa

In some embodiments, the compounds of the invention have Formula IIb:

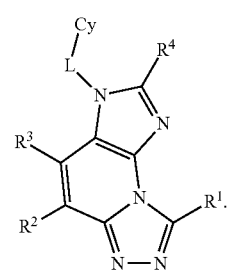

IIb

In some embodiments, the compounds of the invention have Formula IIc:

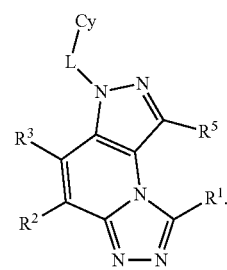

IIc

In some embodiments, the compounds of the invention have Formula III:

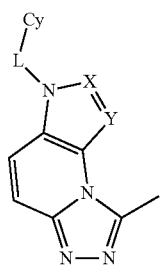

III

In some embodiments, the compounds of the invention have Formula IVa, IVb, or IVc:

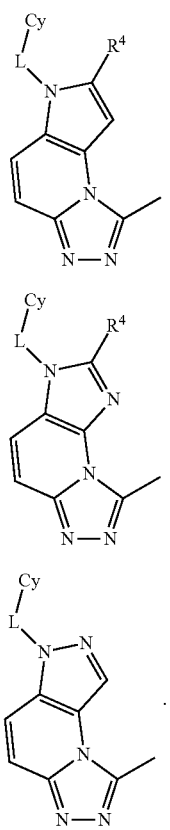

IVa

IVb

IVc

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-6}$, and the like.

The term "p-membered" where p is an integer typically describes the number of ring-forming atoms in a moiety where the number of ring-forming atoms is p. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

In regard to linking group L in Formula I, the groups listed as choices for L are not intended to have directionality. For example, when L is —($C_{1-4}$ alkylene)$_n$C(=O)NR$^6$—($C_{1-4}$ alkylene)$_m$-, it is meant to include both Cy-($C_{1-4}$ alkylene)$_n$-C(=O)NR$^6$—($C_{1-4}$ alkylene)$_m$-N and Cy-($C_{1-4}$ alkylene)$_m$-NR$^6$C(=O)—($C_{1-4}$ alkylene)$_n$-N.

Additionally, the phrase "wherein when the L group includes a —O—, —S—, —NR$^6$—, or —NR$^7$— moiety, then the —O—, —S—, —NR$^6$—, or —NR$^7$— moiety of L is not bonded directly to N of the tricyclic core structure, but is connected to N via a $C_{1-4}$ alkyene moiety of L" is meant to exclude unstable linkages such as —O—N, —S—N, or —N—N— linkages by requiring the presence of at least one carbon atom between the —O—, —S—, —NR$^6$—, or —NR$^7$— moiety of L and the N atom of the tricyclic core.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkylene," employed alone or in combination with other terms, refers to a divalent linking alkyl group that may be straight-chain or branched, having i to j carbons. In some embodiments, the alkyene group contains from 1 to 4 carbon atoms, or from 1 to 3 carbon atoms. Examples of alkylene moieties include, but are not limited to, methylene, ethylene (e.g., 1,1-ethylene or 1,2-ethylene), n-propylene, isopropylene, n-butylene, isobutylene, n-pentylene (e.g., 1,1-pentylene), etc.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated, straight-chained or branched, hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms. Example, alkylamino groups include, but are not limited to, methylamino, ethylamino, propylamino, and butylamino.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. Example, di-$C_{i-j}$-alkylamino groups include, but are not limited to, dimethylamino, diethylamino, and (methyl)(ethyl)amino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. Example, $C_{i-j}$ alkylthio groups include, but are not limited to, methyl-S—, and ethyl-S—.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is C$_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "C$_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems, including spirocyclic and bridged ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is C$_{3-7}$ cycloalkyl. In some embodiments, cycloalkyl is C$_{3-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, the cycloalkyl groups include cyclopropyl, cyclobutyl, cyclopentyl, cyclohexyl, cyclopentenyl, and cyclohexenyl.

As used herein, "C$_{i-j}$ haloalkoxy," employed alone or in combination with other terms, refers to a group of formula O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 or 1 to 3 carbon atoms.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "C$_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered. In some embodiments, the heteroaryl group is 5- to 6-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, and the like. In some embodiments, the heteroaryl group is pyridine, quinoline, thiophene, imidazole, pyrazole, or thiazole.

A 5-membered heteroaryl is a heteroaryl group having five ring-forming atoms comprising wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming atoms include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. In some embodiments, the 5-membered heteroaryl group is thiophene, imidazole, pyrazole, or thiazole.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl. In some embodiments, the 6-membered heteroaryl group is pyridine.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, CH$_2$, C(O), N, NH, O, S, S(O), and S(O)$_2$. Heterocycloalkyl groups can include mono- or polycyclic (e.g., having 2, 3 or 4 fused rings) ring systems, including spiro systems and bridged systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered. In some embodiments, heterocycloalkyl is 5- to 6-membered. Examples of heterocycloalkyl groups include 1,2,3,4-tetrahydroquinolinyl, dihydrobenzofuranyl, azetidinyl, azepanyl, pyrrolidinyl, piperidinyl, piperazinyl, morpholinyl, thiomorpholinyl, tetrahydropyranyl, tetrahydropyranyl, oxetanyl, dihydrooxazolyl, and 8-azabicyclo[3.2.1]octanyl.

As used herein, the term "$C_{i-j}$ hydroxyalkyl," employed alone or in combination with other terms, refers to an alkyl group substituted by a hydroxy group. In some embodiments, the hydroxyalkyl group has 1 to 6 or 1 to 4 carbon atoms.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone enol pairs, amide-imidic acid pairs, lactam lactim pairs, amide-imidic acid pairs, enamine imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: ACN (acetonitrile); AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DIAD (N, N'-diisopropyl azidodicarboxylate); DIPEA (N,N-diisopropylethylamine); DMF (N,N-dimethylformamide); DMSO (dimethylsulfoxide); DMAP (4-(dimethylamino)pyridine); dppf (1,1'-bis(diphenylphosphino)ferrocene); Et (ethyl); EtOAc (ethyl acetate); g (gram(s)); h (hour(s)); HATU (N,N,N',N'-tetramethyl-O-(7-azabenzotriazol-1-yl) uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl3 (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter (s)); μM (micromolar); wt % (weight percent), XPhos-Pd-G2 (chloro(2-dicyclohexylphosphino-2',4',6'-triisopropyl-1,1'-biphenyl)[2-(2'-amino-1,1'-biphenyl)]palladium(II)).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4th Ed., Wiley & Sons, Inc., New York (2006), which is incorporated herein by reference in its entirety.

The compounds of the invention can be prepared according to Scheme 1. Briefly, the cyclic amine 1-1 is alkylated, for example, in the presence of a base like K$_2$CO$_3$ to produce alkylated intermediate 1-2. The alkylated intermediate is then treated with di-tert-butyl hydrazine-1,2-dicarboxylate and base in the presence of Pd catalyst and dppf or XPhos-Pd-G2 as catalyst, with heating to form hydrazine intermediate 1-3. Ring closure is accomplished by reacting the hydrazine intermediate with acid R$^1$COOH (e.g., acetic acid) with heating to form the tricyclic product 1-4.

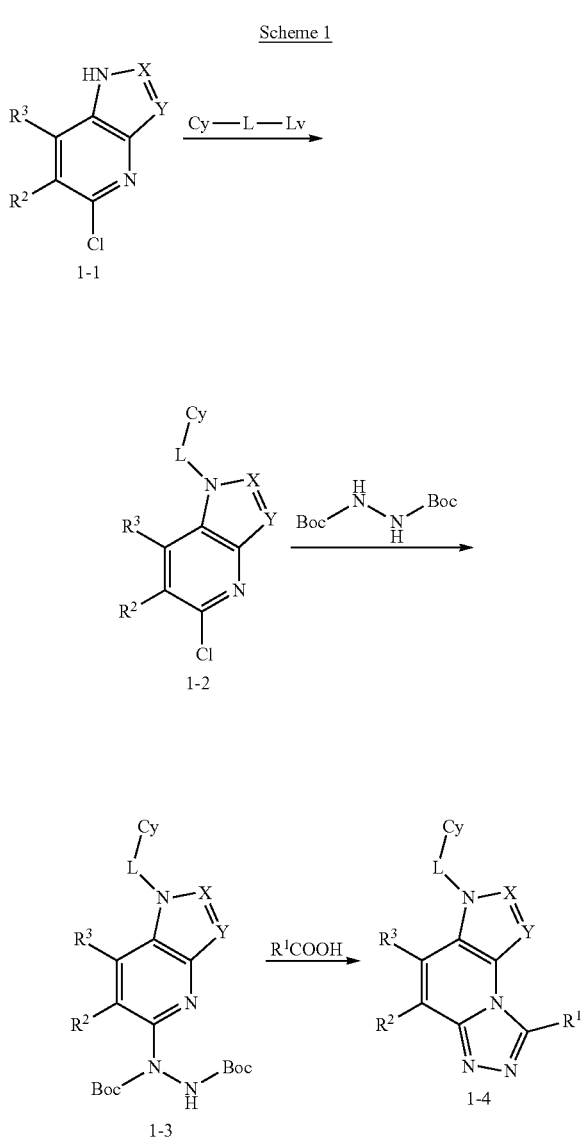

1H-Imidazo[4,5-b]pyridine intermediates 2-3 can be provided by the method of Scheme 2. Diaminopyridine 2-1 is subjected to reductive amination with an aldehyde to form intermediate 2-2, followed by cyclization to form an imidazole 2-3 (such as heating with triethylorthoacetate and p-toluenesulfonic acid in EtOH) that can further undergo triazole annulation as illustrated in Scheme 1. Use of alternative aldehydes and reagents for imidazole formation can provide alternative substitution on ring nitrogen and carbon atoms.

Scheme 2

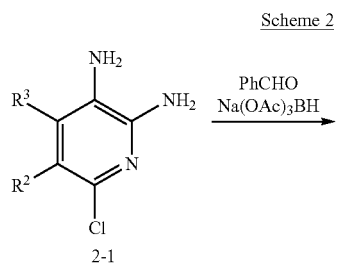
2-1

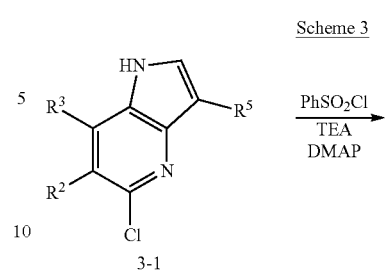

Scheme 3

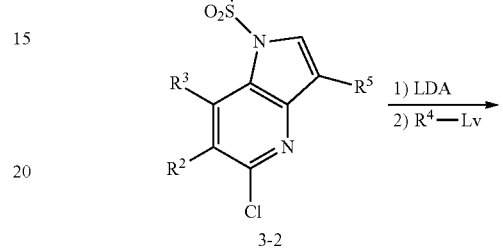
3-1

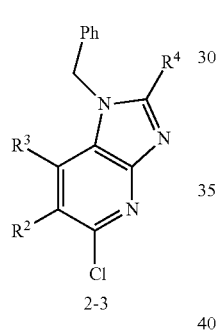
2-2

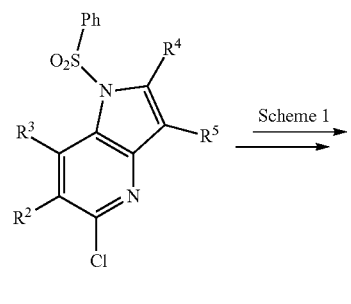
3-2

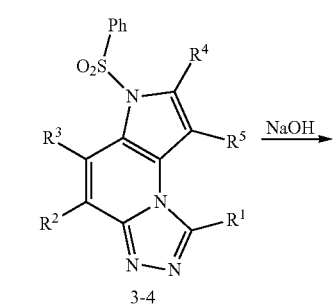
3-3

6H-Pyrrolo[2,3-e][1,2,4]triazolo[4,3-a]pyridines can be prepared by the general synthetic steps shown in Scheme 3. The nitrogen in starting material 3-1 is first protected with an appropriate protecting group forming, for example, the phenylsulfonyl derivative 3-2. Then a base such as LDA is used to deprotonate the adjacent carbon yielding an intermediate that can be reacted with a variety of electrophiles, $R^4$-Lv (where Lv is a leaving group such as halide, carbonate, sulfate, amine, and others) to provide intermediates 3-3. For example, methyl iodide, DMF, di-tertbutyldicarbonate, ethyl chloroformate, 1,3,2-dioxathiolane-2,2-dioxide, 1,2-dibromo-1,1,2,2-tetrachloroethane, and the like can be used to provide alkyl, carboxaldehyde, carboxylic ester, hydroxyethyl and bromide substituents, and others are possible. Triazole formation can be carried out according to the last two steps of Scheme 1, to provide 3-4.

Hydrolytic removal of the phenylsulfonyl group, followed by alkylation with Cy-1-Lv in the presence of a base such as NaH or $K_2CO_3$ and at temperatures from about 20 to about 50° C. affords 3-6. Substitutents placed on nitrogen or carbon via Scheme 3 can also undergo further functional group manipulations as designed by one skilled in the art. In some cases (due to functionality present or protecting groups employed), the order of the last three steps of Scheme 3 can be changed. For example, the deprotection of phenylsulfonyl can be performed first, followed by alkylation and then by triazole formation.

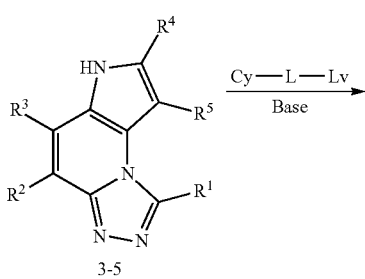
3-4

3-5

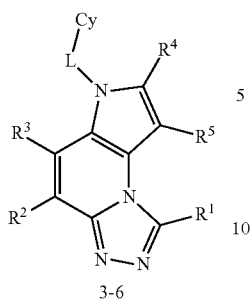

3-6

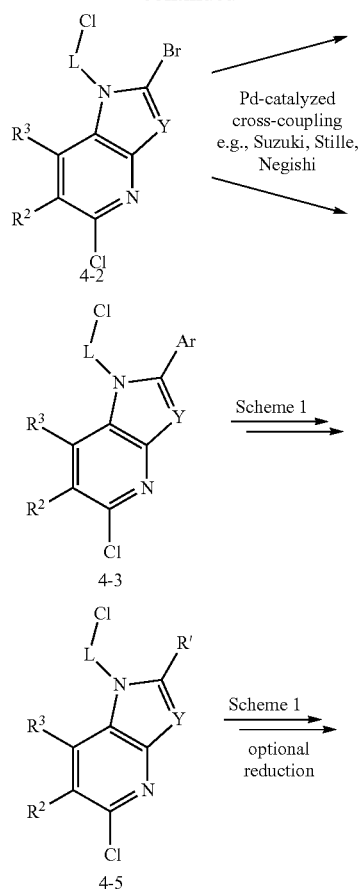

Via intermediate 4-1, Palladium-catalyzed cross-coupling reactions such as Suzuki, Stille, Negishi, and the like, can be utilized to substitute the core with aromatic rings (Ar). The cross coupling step can be performed after removal of the phenylsulfonyl protecting group of 4-1 with base, followed by alkylation with Cy-1-Lv to provide cross-coupling substrates of type 4-2. Palladium-catalyzed cross-coupling can be carried out using, for example, $Pd(PPh_3)_4$ as catalyst and under conditions of heating. Triazole formation can subsequently be carried out as described in Scheme 1 to provide compounds 4-4.

Alternatively, Palladium-catalyzed cross-coupling reactions such as Suzuki, Stille, or Negishi can be utilized to substitute the core with non-aromatic rings (n-Ar). In certain cases, the cross-coupling reaction may substitute the core with non-aromatic rings to form compounds of the invention 4-6 in a single step from the brominated intermediate 4-2. In other cases, the bromide intermediate 4-2 can be coupled with appropriate partners (for example, boronic acids, boronate esters, organotrifluoroborates or organostannane reagents) having an unsaturated, non-aromatic ring system R' to yield compound 4-5. After the triazole formation is carried out according to Scheme 1, the R' of 4-5 can optionally be reduced to form a saturated ring system to provide compounds of the invention 4-6.

Substitutents placed on nitrogen or carbon via Scheme 4 can also be further functionalized as desired and appropriate by conventional methods.

Scheme 4

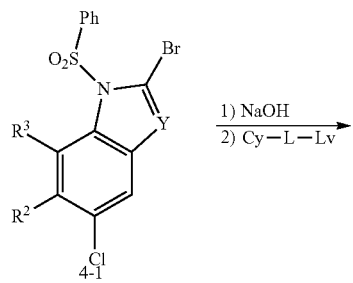

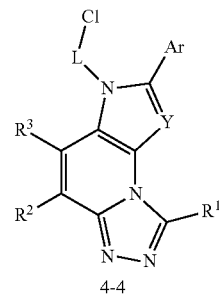

4-4

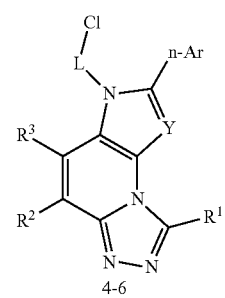

4-6

Buchwald coupling reactions can be utilized to substitute the core with amines as shown in Scheme 5. The bromide intermediate 5-1 can be coupled with amines in the presence of base, a palladium catalyst and ligand, with heating, to form intermediates 5-2. Subsequent triazole formation can be carried out according to Scheme 1 to afford compounds such as 5-3.

Substitutents placed on carbon via Scheme 5 can also be further functionalized as desired and appropriate by conventional methods.

Scheme 5

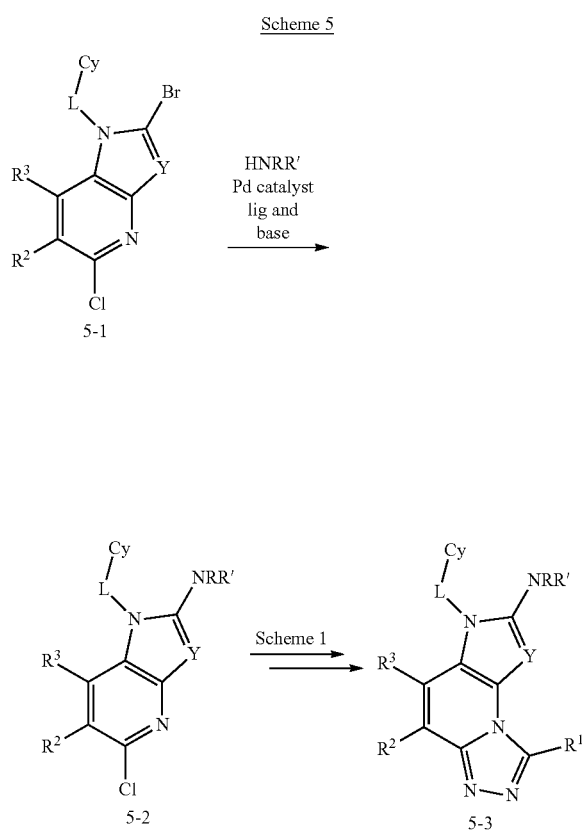

Intermediates 6-1 (where R is, e.g., alkyl) can be converted to amides 6-3 by the general sequence shown in Scheme 6. Treatment with a base such as NaOH hydrolyzes the ester and removes the phenylsulfonyl protecting group. Alkylation with Cy-1-Lv in the presence of base (e.g., NaH, $K_2CO_3$, $Cs_2CO_3$, etc) results in alkylation of both nitrogen and carboxylate, and the resulting ester is again hydrolyzed by treatment with NaOH. The free carboxylic acid can be converted to carboxamides by reaction with amines in the presence of HATU or other coupling agents and in the presence of Hunig's base or other bases.

Scheme 6

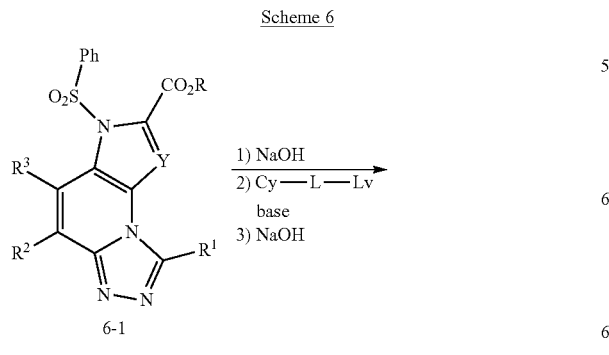

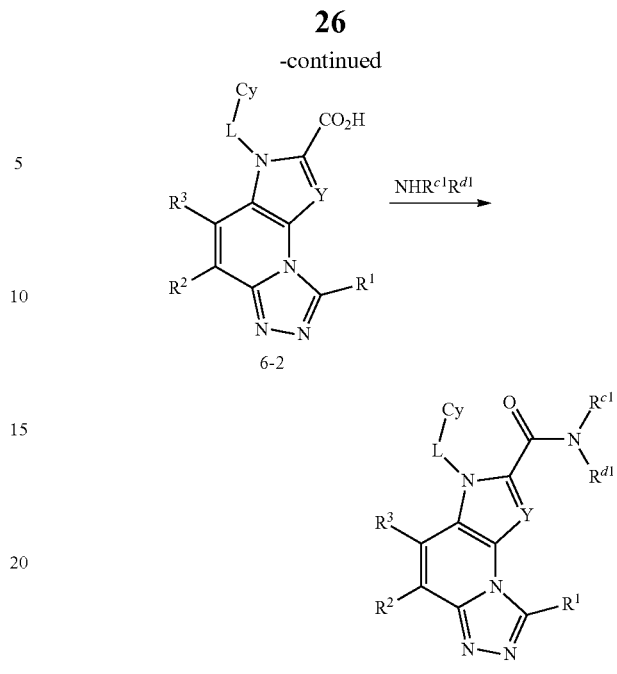

Amides 7-5 can be prepared by an alternative route shown in Scheme 7. Treatment with a base such as NaOH hydrolyzes the ester and removes the phenylsulfonyl protecting group of starting material 7-1. Alkylation with Cy-1-Lv (Lv is a leaving group) in the presence of base (NaH, $K_2CO_3$, $Cs_2CO_3$, etc) results in alkylation of both nitrogen and carboxylate, to give intermediate 7-2. Triazole formation using the method described in Scheme 1 affords 7-3. Hydrolysis to 7-4 followed by reaction with amines using HATU or other coupling agents in the presence of Hunig's base or other bases results in the formation of desired amides 7-5.

Scheme 7

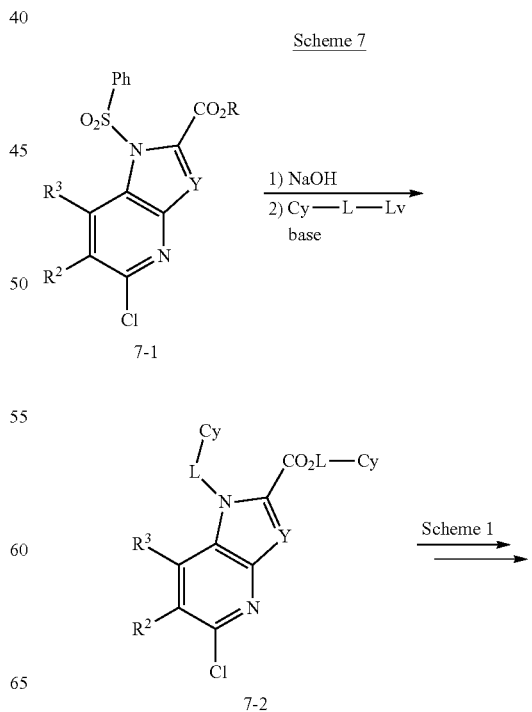

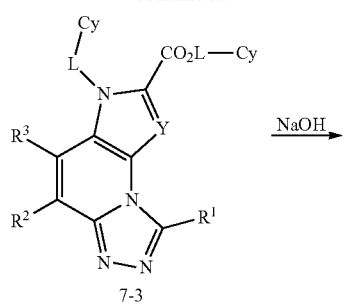

7-3

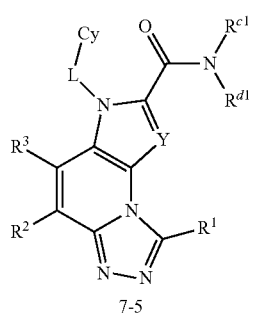

7-4

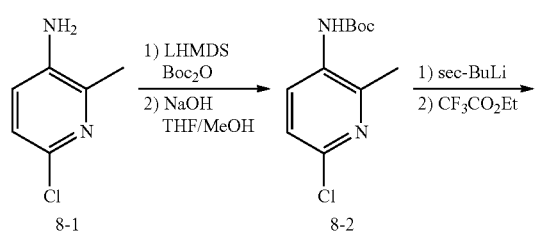

7-5

An alternative method of preparing intermediates is shown in Scheme 8. 6-Chloro-2-methylpyridin-3-amine (8-1) can be mono-Boc protected by treating with base and di-tert-butyl-dicarbonate, followed by base, to afford 8-2. The methyl group of 8-2 may be deprotonated using a strong base such as sec-butyllithium and reacted with an appropriate ester, such as ethyl trifluoroacetate, to afford a ketone intermediate as shown in 8-3. Deprotection of the aniline followed by cyclization on treatment with acid furnishes substituted pyrrolo[3,2-b]pyridine 8-4. Intermediates such as 8-4 are useful for synthesizing tricyclic compounds of the invention such as 8-5.

Scheme 8

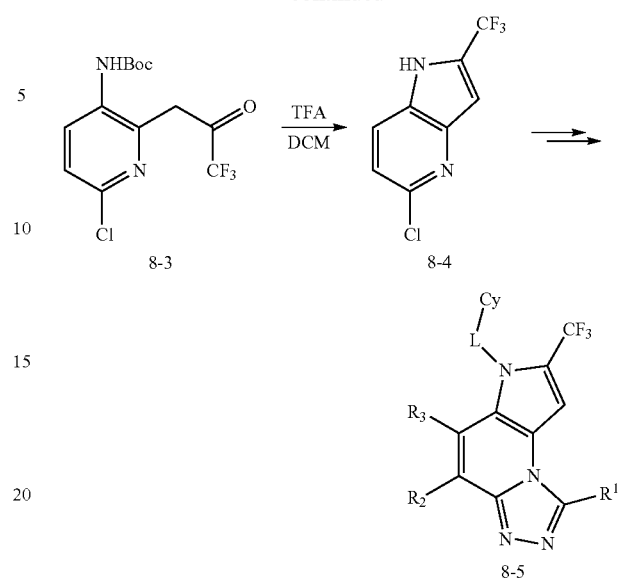

As shown in Scheme 9, tricyclic intermediates such as 9-1 can be treated with halogenating reagents such as N-chlorosuccinimide or N-bromosuccinimide to afford halogenated intermediates 9-2 (X=halogen) that can be used for cross couplings. Removal of the protecting group provides 9-3, and the desired substituent can be introduced by alkylation to afford 9-4. Intermediates 9-4 are useful for Buchwald-Hartwig amination, Suzuki, Stille or Negishi cross couplings, to name a few. These transformations furnish products such as amines, amides, ureas, carbamates, arylated and heteroarylated products, for example (9-5, 9-6, 9-7, R'=alkyl, cyclic, etc.). Heating in the presence of an alkoxide can afford products such as 9-8. Additionally, suitable products may be further functionalized if desired.

Scheme 9

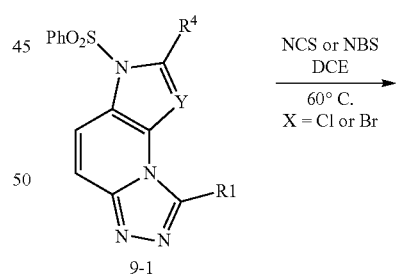

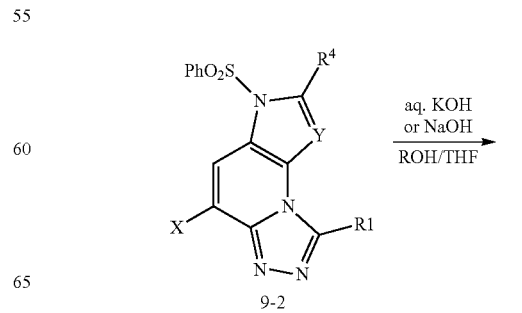

Scheme 10

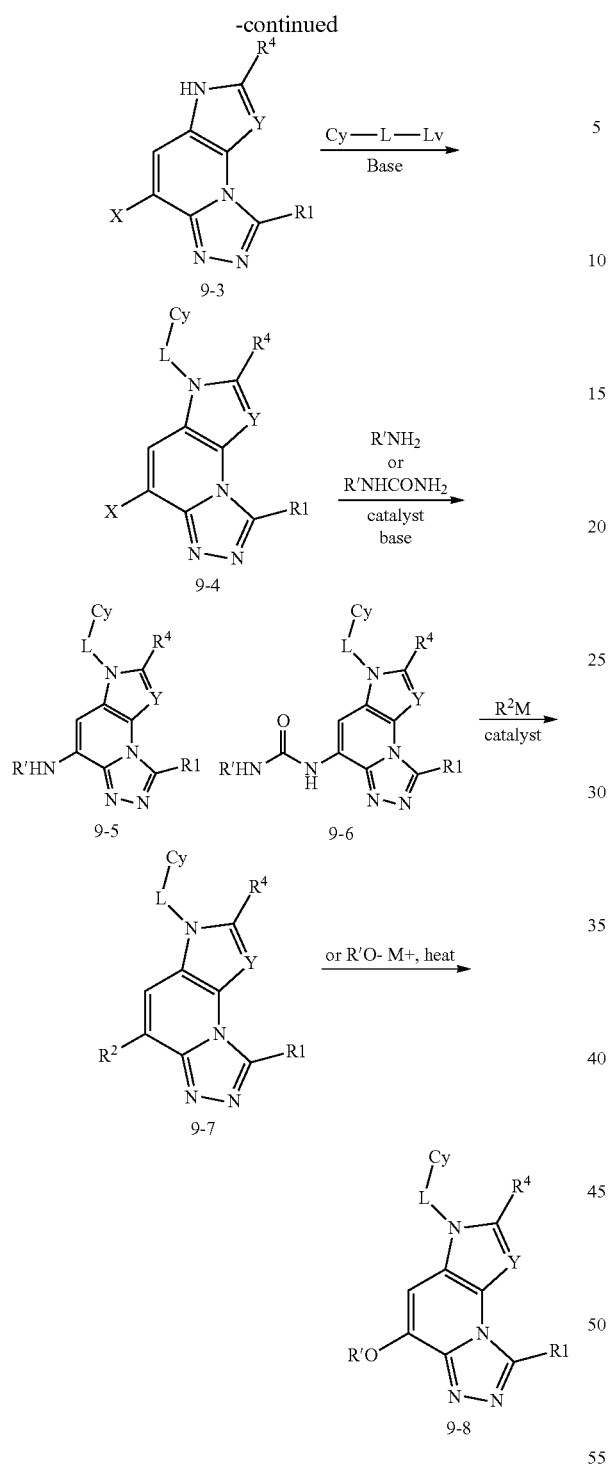

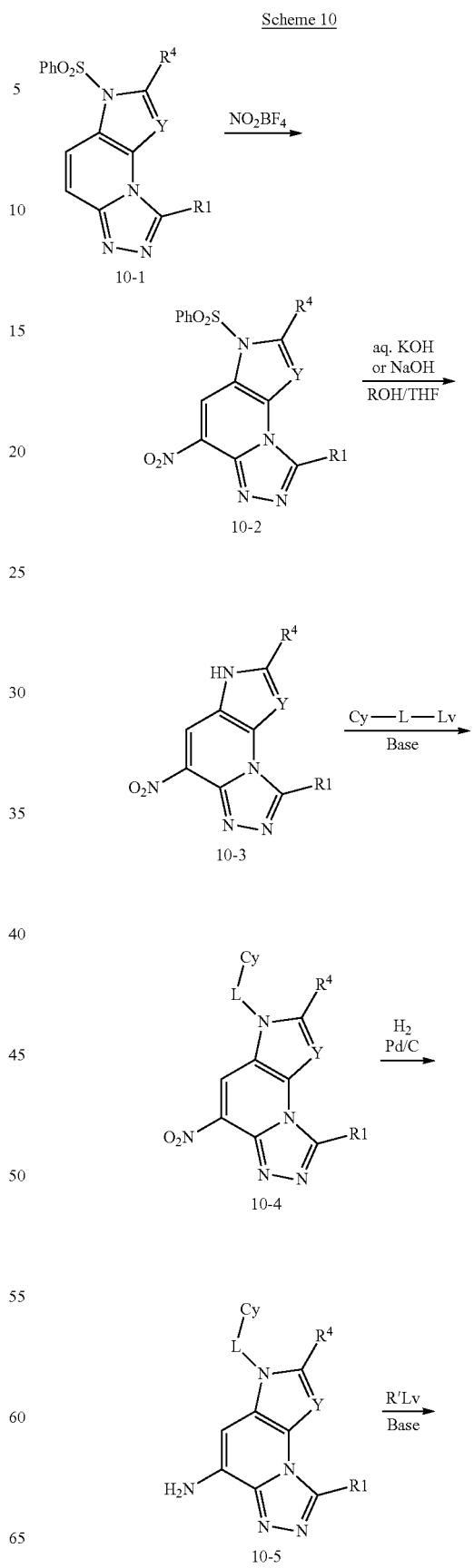

As shown in Scheme 10, tricyclic intermediates such as 10-1 can be treated with nitrating reagents such as nitronium tetrafluoroborate to afford nitrated intermediates 10-2 that can be used for reduction and functionalization. Removal of the protecting group provides 10-3. The desired substituent can be introduced by alkylation to provide intermediates 10-4. Intermediates 10-4 can be reduced, for example using hydrogenation over palladium on carbon to afford aniline 10-5. Products such as 10-5 may be treated with acylating and sulfonylating reagents (Lv=leaving group, R'=alkyl, cyclic, etc.), for example, to furnish products 10-6.

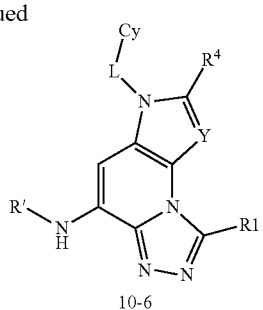

10-6

Methods of Use

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of the invention can inhibit one or more of BET proteins BRD2, BRD3, BRD4, and BRD-t. In some embodiments, the BET protein is BRD2. In some embodiments, the BET protein is BRD3. In some embodiments, the BET protein is BRD4. In some embodiments, the BET protein is BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

In some embodiments, the present invention is directed to a method of inhibiting BRD2 comprising contacting a compound of the invention with BRD2. In some embodiments, the present invention is directed to a method of inhibiting BRD3 comprising contacting a compound of the invention with BRD3. In some embodiments, the present invention is directed to a method of inhibiting BRD4 comprising contacting a compound of the invention with BRD4. In some embodiments, the present invention is directed to a method of inhibiting BRD-t comprising contacting a compound of the invention with BRD-t.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

The compounds of the invention can also be used to treat heart disease such as heart failure.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e. arresting further development of the pathology and/or symptomatology) or ameliorating the disease; for example, ameliorating a disease, condition or disorder in an individual who is experiencing or displaying the pathology or symptomatology of the disease, condition or disorder (i.e. reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib or other JAK inhibitors, including JAK1 selective inhibitors. Additionally, the compounds of the invention can be used in combination with inhibitors of PI3Kd, PI3Kg, FGFR1, FGFR2, FGFR3, FGFR4, PIM1, PIM2, and PIM3.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, LantibioTRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-

HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro BET protein labeling and competition assays, compounds that incorporate $^3H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge C18 5 μm, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

6-benzyl-1-methyl-6H-pyrrolo[2,3-e][1,2,4]triazolo[4,3-a]pyridine

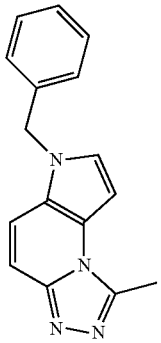 [SMILES: Cc1nnc2ccc3c(ccn3Cc3ccccc3)n12]

Step 1. 1-benzyl-5-chloro-1H-pyrrolo[3,2-b]pyridine

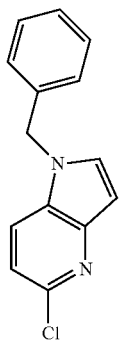 [SMILES: Clc1ccc2c(ccn2Cc2ccccc2)n1]

To a mixture of 5-chloro-1H-pyrrolo[3,2-b]pyridine (0.50 g, 3.3 mmol, Adesis) and K$_2$CO$_3$ (1.4 g, 9.8 mmol) in DMF (12 mL) at 0° C. was added benzyl bromide (0.43 mL, 3.6 mmol, Aldrich) dropwise. The mixture was allowed to warm to ambient temperature and stir overnight. The reaction mixture was partitioned between EtOAc and water. The organic layer was washed with water (3×), brine, dried over sodium sulfate, filtered and concentrated. Flash chromatography, eluting with a gradient from 0-20% EtOAc in hexanes afforded product as a clear oil (0.77 g, 97%).

$^1$H NMR (300 MHz, CDCl$_3$) δ 7.48 (d, J=8.6 Hz, 1H), 7.38 (d, J=3.2 Hz, 1H), 7.37-7.27 (m, 3H), 7.13-7.05 (m, 2H), 7.07 (d, J=8.6 Hz, 1H), 6.68 (d, J=3.2 Hz, 1H), 5.32 (s, 2H); LCMS (M+H)$^+$: 243.0, 244.9.

Step 2. di-tert-butyl 1-(1-benzyl-1H-pyrrolo[3,2-b]pyridin-5-yl)hydrazine-1,2-dicarboxylate

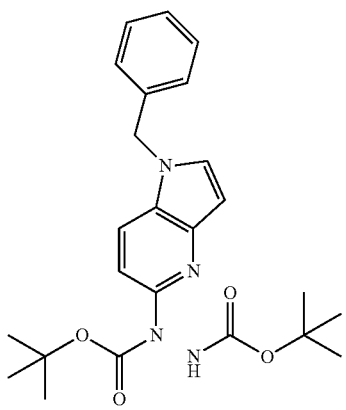

A sealable vial was charged with 1-benzyl-5-chloro-1H-pyrrolo[3,2-b]pyridine (0.25 g, 1.0 mmol, from Step 1), di-tert-butyl hydrazine-1,2-dicarboxylate (0.239 g, 1.03 mmol, Aldrich), tris(dibenzylideneacetone)dipalladium(0) (0.075 g, 0.082 mmol, Aldrich), 1,1'-bis(diphenylphosphino)ferrocene (0.0685 g, 0.124 mmol, Aldrich), cesium carbonate (0.336 g, 1.03 mmol), and toluene (2 mL). The mixture was degassed by a stream of nitrogen through the solution and the vial was then sealed and heated to 100° C. for 2 days. The crude reaction mixture was diluted with DCM, filtered and concentrated. Flash chromatography, eluting with a gradient from 0-50% EtOAc in hexanes afforded product (0.13 g, 29%).

$^1$H NMR (300 MHz, CDCl$_3$) δ 7.55 (d, J=8.7 Hz, 1H), 7.47-7.02 (m, 7H), 6.67 (d, J=3.1 Hz, 1H), 5.31 (s, 2H), 1.49 (s, 9H), 1.46 (s, 9H); LCMS (M+H)$^+$: 439.1.

Step 3. 6-benzyl-1-methyl-6H-pyrrolo[2,3-e][1,2,4]triazolo[4,3-a]pyridine di-tert-Butyl 1-(1-benzyl-1H-pyrrolo[3,2-b]pyridin-5-yl)hydrazine-1,2-dicarboxylate (31 mg, 0.071 mmol, from Step 2) in acetic acid (4.0 mL) was heated in the microwave to 180° C. for 5 minutes. The solvent was removed in vacuo and the mixture was reconstituted in MeOH and purified using preparative HPLC-MS (Waters XBridge C18, eluting with a gradient of MeCN/H$_2$O containing 0.15% NH$_4$OH) and the eluent was frozen and lyophilized to afford a white powder (12 mg, 65%).

¹H NMR (300 MHz, CDCl₃) δ 7.41-7.22 (m, 5H), 7.17-7.04 (m, 3H), 6.79 (d, J=3.1 Hz, 1H), 5.37 (s, 2H), 2.99 (s, 3H); LCMS (M+H)⁺: 263.1.

Example 2

6-benzyl-1,7-dimethyl-6H-pyrrolo[2,3-e][1,2,4]triazolo[4,3-a]pyridine

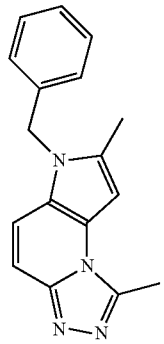

Step 1. 5-chloro-1-(phenylsulfonyl)-1H-pyrrolo[3,2-b]pyridine

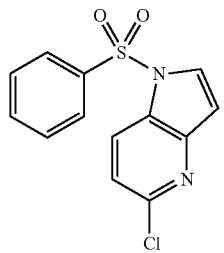 [SMILES: O=S(=O)(c1ccccc1)n1ccc2nc(Cl)ccc21]

To a suspension of 5-chloro-1H-pyrrolo[3,2-b]pyridine (5.0 g, 33 mmol, Adesis) in DCM (42 mL) was added benzenesulfonyl chloride (5.4 mL, 43 mmol, Aldrich), triethylamine (7.3 mL, 52 mmol) and 4-dimethylaminopyridine (0.40 g, 3.3 mmol). After stirring at room temperature for 1 hour, the mixture was diluted with EtOAc, washed with water (2×), brine, dried over sodium sulfate, filtered and concentrated. The product was purified by flash chromatography, eluting with a gradient from 0-20% EtOAc in hexanes to afford product as a white solid (8.7 g, 90%).

¹H NMR (300 MHz, CDCl₃) δ 8.23 (d, J=8.7 Hz, 1H), 7.86 (d, J=7.5 Hz, 2H), 7.81 (d, J=3.7 Hz, 1H), 7.61 (t, J=7.4 Hz, 1H), 7.49 (dd, J=7.7, 7.7 Hz, 2H), 7.26 (d, J=8.6 Hz, 1H), 6.81 (d, J=3.7 Hz, 1H); LCMS (M+H)⁺: 292.9, 294.9.

Step 2. 5-chloro-2-methyl-1-(phenylsulfonyl)-1H-pyrrolo[3,2-b]pyridine

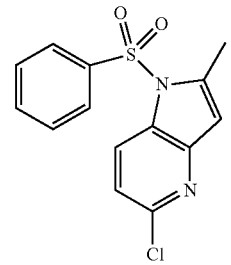 [SMILES: Cc1cc2nc(Cl)ccc2n1S(=O)(=O)c1ccccc1]

1.6 M n-butyllithium in hexanes (24 mL, 39 mmol) was added to a solution of N,N-diisopropylamine (5.8 mL, 42 mmol) in THF (80 mL) at −78° C. Following complete addition, the mixture was allowed to stir at 0° C. for 30 minutes and was then re-cooled to −78° C. A solution of 5-chloro-1-(phenylsulfonyl)-1H-pyrrolo[3,2-b]pyridine (7.6 g, 26 mmol, from Step 1) in THF (38 mL) was added dropwise. After stirring at −78° C. for 1 hour, methyl iodide (3.2 mL, 52 mmol) was added. The mixture was allowed to slowly reach room temperature, at which time it was quenched by the addition of saturated NH₄Cl. The product was extracted with EtOAc, and the extracts were washed with water (2×), brine, dried over sodium sulfate, filtered and concentrated to afford product as a yellow oil which was used without further purification (8.0 g, 100%).

¹H NMR (400 MHz, CDCl₃) δ 8.37 (d, J=8.7 Hz, 1H), 7.75 (d, J=7.5 Hz, 2H), 7.61 (t, J=7.5 Hz, 1H), 7.48 (dd, J=7.8, 7.8 Hz, 2H), 7.21 (d, J=8.7 Hz, 1H), 6.49 (s, 1H), 2.63 (s, 3H); LCMS (M+H)⁺: 306.9, 308.9.

Step 3. di-tert-butyl 1-[2-methyl-1-(phenylsulfonyl)-1H-pyrrolo[3,2-b]pyridin-5-yl]hydrazine-1,2-dicarboxylate

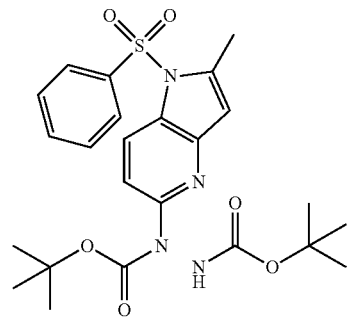

A flask was charged with 5-chloro-2-methyl-1-(phenylsulfonyl)-1H-pyrrolo[3,2-b]pyridine (9.0 g, 29 mmol, prepared as described in Step 2), di-tert-butyl hydrazine-1,2-dicarboxylate (6.8 g, 29 mmol, Aldrich), dicyclohexyl(2',4',6'-triisopropylbiphenyl-2-yl)phosphine-(2'-aminobiphenyl-2-yl)(chloro)palladium (1:1) (2.3 g, 2.9 mmol, Aldrich), cesium carbonate (9.56 g, 29.3 mmol), and toluene (94 mL). The mixture was degassed by a stream of nitrogen through the solution. The mixture was then heated to 100° C. overnight. After cooling to room temperature, the reaction mixture was diluted with DCM, filtered and concentrated. Flash chromatography, eluting with a gradient from 0-30% EtOAc in hexanes afforded product as a white solid (9.5 g, 64%).

$^1$H NMR (400 MHz, cdcl$_3$) δ 8.39 (dd, J=8.9, 0.6 Hz, 1H), 7.76 (dd, J=8.5, 1.2 Hz, 2H), 7.62-7.55 (m, 2H), 7.50-7.42 (m, 2H), 7.03 (br s, 1H), 6.47-6.46 (m, 1H), 2.62 (d, J=1.1 Hz, 3H), 1.51 (s, 9H), 1.46 (s, 9H); LCMS (M+H)$^+$: 503.2.

Step 4. 1,7-dimethyl-6-(phenylsulfonyl)-6H-pyrrolo[2,3-e][1,2,4]triazolo[4,3-a]pyridine Example 2a

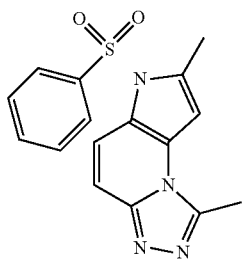

di-tert-Butyl 1-[2-methyl-1-(phenylsulfonyl)-1H-pyrrolo[3,2-b]pyridin-5-yl]hydrazine-1,2-dicarboxylate (9.4 g, 19 mmol, from Step 3) in AcOH (150 mL) was heated in the range of 115-120° C. for 20 hours. Upon cooling to room temperature, the solvent was removed in vacuo. After this cyclization, purification via HPLC-MS (Waters XBridge C18, eluting with a gradient of MeCN/H$_2$O containing 0.15% NH$_4$OH) afforded 1,7-dimethyl-6-(phenylsulfonyl)-6H-pyrrolo[2,3-e][1,2,4]triazolo[4,3-a]pyridine.

$^1$H NMR (400 MHz, CDCl$_3$) δ 8.20 (d, J=10.0 Hz, 1H), 7.81 (dd, J=8.4, 1.1 Hz, 2H), 7.63 (tt, J=6.9, 1.1 Hz, 1H), 7.52 (d, J=10.0 Hz, 1H), 7.54-7.48 (m, 2H), 6.71 (s, 1H), 2.93 (s, 3H), 2.68 (s, 3H); LCMS (M+H)$^+$: 327.1.

Step 5. 1,7-dimethyl-6H-pyrrolo[2,3-e][1,2,4]triazolo[4,3-a]pyridine

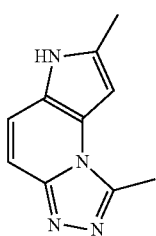

The crude residue obtained on evaporation of AcOH in Step 4 was re-dissolved in 1:1 THF:MeOH (304 mL) and 2.8 M sodium hydroxide in water (170 mL, 490 mmol) was added. The reaction was stirred for 20 minutes. The mixture was diluted with brine, extracted with three portions of DCM, and also one portion of CHCl$_3$ containing 10% iPrOH (250 mL). The combined organic extracts were dried over sodium sulfate, filtered and concentrated. Flash chromatography, eluting with a gradient from 0-10% MeOH in DCM afforded product as a yellow solid (2.8 g, 79%).

$^1$H NMR (300 MHz, d$_6$-DMSO) δ 11.72 (br s, 1H), 7.43 (d, J=9.5 Hz, 1H), 7.17 (d, J=9.5 Hz, 1H), 6.64 (m, 1H), 2.84 (s, 3H), 2.42 (s, 3H); LCMS (M+H)$^+$: 187.1.

Step 6. 6-benzyl-1,7-dimethyl-6H-pyrrolo[2,3-e][1,2,4]triazolo[4,3-a]pyridine

A solution of 1,7-dimethyl-6H-pyrrolo[2,3-e][1,2,4]triazolo[4,3-a]pyridine (10. mg, 0.054 mmol, from Step 5) in DMF (1.5 mL) was treated with K$_2$CO$_3$ (22 mg, 0.16 mmol) and a solution of benzyl bromide (6.4 μL, 0.054 mmol, Aldrich) in DMF (0.10 mL). After stirring for 2 hours, the mixture was diluted with MeCN, filtered and purified via preparative HPLC-MS (Waters XBridge C18, eluting with a gradient of MeCN/H$_2$O containing 0.15% NH$_4$OH) to afford product (12 mg, 81%).

$^1$H NMR (300 MHz, CDCl$_3$) δ 7.30-7.08 (m, 5H), 6.92-6.83 (m, 2H), 6.55 (s, 1H), 5.28 (s, 2H), 2.92 (s, 3H), 2.35 (s, 3H); LCMS (M+H)$^+$: 277.2.

Example 3

1-methyl-6-(phenylsulfonyl)-6H-pyrrolo[2,3-e][1,2,4]triazolo[4,3-a]pyridine

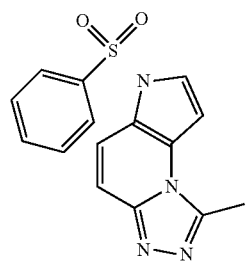

This compound was isolated from the mixture obtained in Example 2, Steps 1-4, during a preparation wherein the methylation in Step 2 was incomplete. The product was isolated by preparative HPLC-MS (Waters XBridge C18, eluting with a gradient of 18.2% to 40.4% MeCN/H$_2$O containing 0.15% NH$_4$OH, over 12 minutes at a flow rate of 60 mL/min).

$^1$H NMR (300 MHz, CDCl$_3$) δ 7.97 (d, J=10.0 Hz, 1H), 7.95-7.88 (m, 2H), 7.68 (d, J=3.7 Hz, 1H), 7.67-7.60 (m, 1H), 7.57 (d, J=10.0 Hz, 1H), 7.52 (dd, J=7.7, 7.7 Hz, 2H), 6.99 (d, J=3.7 Hz, 1H), 2.95 (s, 3H); LCMS (M+H)$^+$: 313.0.

Example 4

1-methyl-6-(1-phenylethyl)-6H-pyrrolo[2,3-e][1,2,4]triazolo[4,3-a]pyridine (racemic mixture)

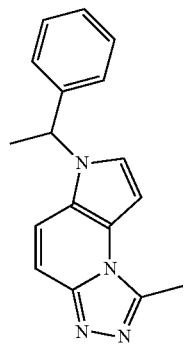 [SMILES: Cc1nnc2ccc3c(ccn3C(C)c3ccccc3)n12]

To a mixture of 1-methyl-6H-pyrrolo[2,3-e][1,2,4]triazolo[4,3-a]pyridine (10 mg, 0.058 mmol, isolated from Example 2, Step 5 during a preparation wherein the methylation of Step 2 of that Example was incomplete) and K$_2$CO$_3$ (0.024 g, 0.17 mmol) in DMF (0.22 mL) was added 1-(bromoethyl)benzene (12 µL, 0.087 mmol, Acros). The mixture was heated to 45° C. for 3 hours. The mixture was diluted with MeCN and filtered, then the product was isolated by preparative HPLC-MS (Waters XBridge C18, eluting with a gradient of MeCN/H$_2$O containing 0.15% NH$_4$OH) (3.3 mg, 20%).

$^1$H NMR (300 MHz, CDCl$_3$) δ 7.45-7.16 (m, 6H), 7.16-7.00 (m, 2H), 6.82 (d, J=3.2 Hz, 1H), 5.68 (q, J=7.0 Hz, 1H), 2.99 (s, 3H), 1.97 (d, J=7.0 Hz, 3H); LCMS (M+H)$^+$: 277.1.

Examples 5a and 5b (S)-1,7-dimethyl-6-(1-phenylethyl)-6H-pyrrolo[2,3-e][1,2,4]triazolo[4,3-a]pyridine (5a) and (R)-1,7-dimethyl-6-(1-phenylethyl)-6H-pyrrolo[2,3-e][1,2,4]triazolo[4,3-a]pyridine (5b) (single enantiomers isolated)

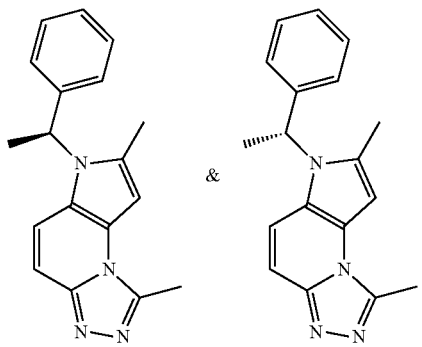 [SMILES: Cc1cc2c(ccc3nnc(C)n32)n1[C@@H](C)c1ccccc1 ; Cc1cc2c(ccc3nnc(C)n32)n1[C@H](C)c1ccccc1]

K$_2$CO$_3$ (56 mg, 0.40 mmol) and (1-bromoethyl)-benzene (27 µL, 0.20 mmol) were added to a solution of 1,7-dimethyl-6H-pyrrolo[2,3-e][1,2,4]triazolo[4,3-a]pyridine (25 mg, 0.13 mmol, from Example 2, Step 5) in DMF (3.8 mL). The reaction was stirred overnight. Additional (1-bromoethyl)-benzene (18 µL, 0.13 mmol, Acros) was added and the reaction mixture was heated at 50° C. for one hour. Upon cooling to room temperature, the reaction mixture was diluted with ACN and filtered, then was purified via preparative HPLC-MS (Waters XBridge C18, eluting with a gradient of MeCN/H$_2$O containing 0.15% NH$_4$OH) to afford the racemic product (12.6 mg, 32%). The enantiomers were separated by chiral chromatography (Phenomenex Lux Cellulose C-1, 5 µm, 21.2×250 mm, 45% EtOH/hexane at 18 mL/min, loading 6 mg/900 µL). Enantiomer 1 retention time: 7.7 min, obtained 4.3 mg, 11% yield. Enantiomer 2 retention time: 16.5 min, obtained 5.1 mg, 13% yield.

Enantiomer 1: $^1$H NMR (400 MHz, CDCl$_3$) δ 7.45-7.27 (m, 3H), 7.21-7.06 (m, 3H), 6.99 (d, J=9.8 Hz, 1H), 6.59 (s, 1H), 5.77 (q, J=7.1 Hz, 1H), 2.97 (s, 3H), 2.47 (s, 3H), 1.98 (d, J=7.2 Hz, 3H); LCMS (M+H)$^+$: 291.0.

Enantiomer 2: $^1$H NMR (400 MHz, CDCl$_3$) δ 7.45-7.27 (m, 3H), 7.21-7.06 (m, 3H), 6.99 (d, J=9.8 Hz, 1H), 6.59 (s, 1H), 5.77 (q, J=7.0 Hz, 1H), 2.97 (s, 3H), 2.47 (s, 3H), 1.98 (d, J=7.2 Hz, 3H); LCMS (M+H)$^+$: 291.0.

Example 6

1,7-dimethyl-6-(2-phenylethyl)-6H-pyrrolo[2,3-e][1,2,4]-triazolo[4,3-a]pyridine

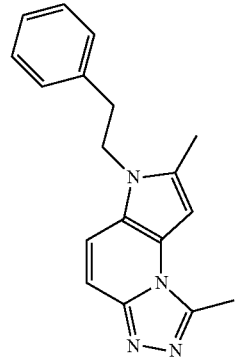 [SMILES: Cc1cc2c(ccc3nnc(C)n32)n1CCc1ccccc1]

Sodium hydride (6.4 mg, 0.16 mmol, 60% in mineral oil) was added to a solution of 1,7-dimethyl-6H-pyrrolo[2,3-e][1,2,4]triazolo[4,3-a]pyridine (15 mg, 0.080 mmol, Example 2, Step 5) in DMF (2.2 mL). After stirring for 10 minutes, 1-bromo-2-phenylethane (22 µL, 0.16 mmol, Aldrich) was added dropwise. After stirring for 1 hour, additional sodium hydride (3.2 mg, 0.080 mmol, 60% in mineral oil) and 1-bromo-2-phenylethane (11 µL, 0.080 mmol) were added. The crude reaction mixture was diluted with water and MeOH, filtered and purified by preparative HPLC-MS (Waters XBridge C18, eluting with a gradient of MeCN/H$_2$O containing 0.15% NH$_4$OH) to afford product as a light yellow powder (4.8 mg, 20%).

$^1$H NMR (400 MHz, CDCl$_3$) δ 7.32-7.16 (m, 5H), 7.00-6.89 (m, 2H), 6.46 (s, 1H), 4.32 (t, J=6.8 Hz, 2H), 3.04 (t, J=6.8 Hz, 2H), 2.96 (s, 3H), 2.14 (s, 3H); LCMS (M+H)$^+$: 291.2.

Example 7

1,7-dimethyl-6-(pyridin-2-ylmethyl)-6H-pyrrolo[2,3-e][1,2,4]-triazolo[4,3-a]pyridine

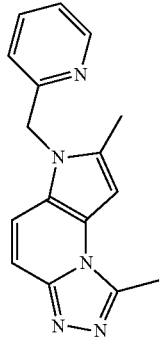 [SMILES: Cc1cc2c(ccc3nnc(C)n32)n1Cc1ccccn1]

K$_2$CO$_3$ (44 mg, 0.32 mmol) and 2-(bromomethyl)pyridine hydrobromide (0.027 g, 0.11 mmol, Aldrich) were added to a solution of 1,7-dimethyl-6H-pyrrolo[2,3-e][1,2,4]triazolo[4,3-a]pyridine (20. mg, 0.11 mmol) in DMF (3.0 mL, 39 mmol). After stirring at room temperature for 2 hours, the reaction was heated to 50° C. for 35 minutes. The reaction mixture was diluted with MeCN, filtered and purified by preparative HPLC-MS (Waters XBridge C18, eluting with a gradient of MeCN/H$_2$O containing 0.15% NH$_4$OH) to afford product (8.9 mg, 30%).

$^1$H NMR (300 MHz, CDCl$_3$) δ 8.54 (d, J=4.8 Hz, 1H), 7.52 (td, J=7.7, 1.7 Hz, 1H), 7.26 (d, J=9.7 Hz, 1H), 7.20 (d, J=9.7 Hz, 1H), 7.15 (dd, J=7.2, 4.6 Hz, 1H), 6.58 (s, 1H), 6.52 (d, J=7.9 Hz, 1H), 5.39 (s, 2H), 2.92 (s, 3H), 2.39 (s, 3H); LCMS (M+H)$^+$: 278.0.

Example 8

6-(2-chlorobenzyl)-1,7-dimethyl-6H-pyrrolo[2,3-e][1,2,4]triazolo[4,3-a]pyridine

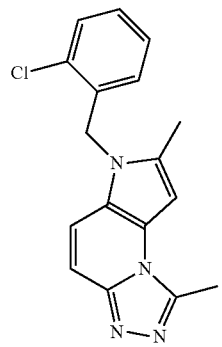 [SMILES: Cc1cc2c(ccc3nnc(C)n32)n1Cc1ccccc1Cl]

K$_2$CO$_3$ (44 mg, 0.32 mmol) and 1-(bromomethyl)-2-chloro-benzene (0.022 g, 0.11 mmol, Aldrich) were added to a solution of 1,7-dimethyl-6H-pyrrolo[2,3-e][1,2,4]triazolo[4,3-a]pyridine (20. mg, 0.11 mmol, from Example 2, Step 5) in DMF (3.0 mL). The reaction was heated to 50° C. for 35 minutes. The reaction mixture was diluted with MeCN, filtered and purified by preparative HPLC-MS (Waters XBridge C18, eluting with a gradient of MeCN/H$_2$O containing 0.15% NH$_4$OH) (2.6 mg, 8%).

$^1$H NMR (300 MHz, CD$_3$OD) δ 7.56 (d, J=9.7 Hz, 1H), 7.49 (dd, J=7.9, 1.0 Hz, 1H), 7.27 (td, J=7.9, 1.4 Hz, 1H), 7.22 (d, J=9.7 Hz, 1H), 7.14 (td, J=7.7, 0.7 Hz, 1H), 6.90 (s, 1H), 6.27 (dd, J=7.7, 0.7 Hz, 1H), 5.58 (s, 2H), 2.99 (s, 3H), 2.41 (s, 3H); LCMS (M+H)$^+$: 311.0, 313.0.

Example 9

6-(3-chlorobenzyl)-1,7-dimethyl-6H-pyrrolo[2,3-e][1,2,4]triazolo[4,3-a]pyridine

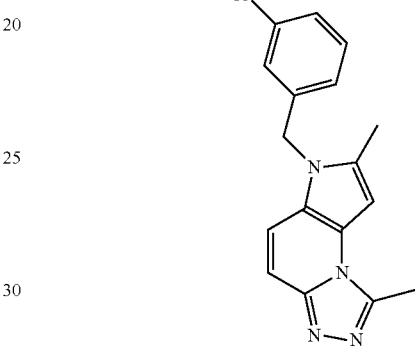

The title compound was prepared according to the procedures of Example 8, using 1-(bromomethyl)-3-chloro-benzene (0.022 g, 0.11 mmol, Aldrich) (1.8 mg, 5%).

$^1$H NMR (300 MHz, CD$_3$OD) δ 7.62 (d, J=9.7 Hz, 1H), 7.33-7.25 (m, 2H), 7.22 (d, J=9.7 Hz, 1H), 7.03-6.96 (m, 1H), 6.92-6.86 (m, 1H), 6.86-6.83 (m, 1H), 5.51 (s, 2H), 2.97 (s, 3H), 2.44 (s, 3H); LCMS (M+H)$^+$: 311.0, 313.0.

Example 10

6-(4-chlorobenzyl)-1,7-dimethyl-6H-pyrrolo[2,3-e][1,2,4]triazolo[4,3-a]pyridine

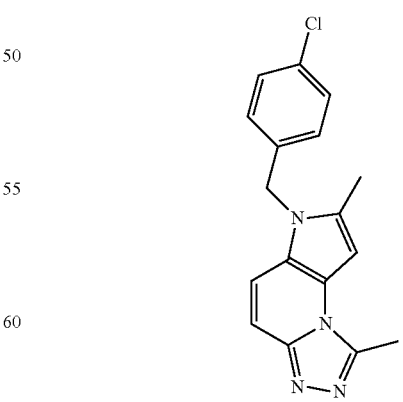

The title compound was prepared according to the procedures of Example 8, using 1-(bromomethyl)-4-chlorobenzene (0.022 g, 0.11 mmol, Aldrich) (1.9 mg, 6%).

¹H NMR (300 MHz, CD₃OD) δ 7.63 (dd, 1H), 7.30 (d, J=8.6 Hz, 2H), 7.22 (d, J=9.7 Hz, 1H), 6.97 (d, J=8.7 Hz, 2H), 6.84 (t, J=0.8 Hz, 1H), 5.49 (s, 2H), 2.97 (s, 3H), 2.44 (d, J=0.7 Hz, 3H), LCMS (M+H)⁺: 311.0, 312.9.

Example 11

1,7-dimethyl-6-(pyridin-3-ylmethyl)-6H-pyrrolo[2,3-e][1,2,4]triazolo[4,3-a]pyridine

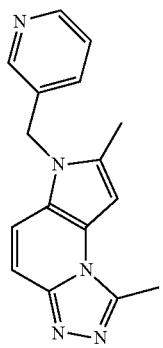 [SMILES: Cc1cc2c(ccc3nnc(C)n32)n1Cc1cccnc1]

Sodium hydride (13 mg, 0.32 mmol, 60% in mineral oil) was added to a solution of 1,7-dimethyl-6H-pyrrolo[2,3-e][1,2,4]triazolo[4,3-a]pyridine (20 mg, 0.1 mmol, from Example 2, Step 5) in DMF (3.0 mL). After stirring for 10 minutes, a solution of 3-(bromomethyl)pyridine hydrobromide (0.027 g, 0.11 mmol, Aldrich) in DMF (0.3 mL) was added. The mixture was stirred for 45 minutes and then quenched by the addition of water, diluted to 5 mL with MeCN, filtered and purified by preparative HPLC-MS (Waters XBridge C18, eluting with a gradient of MeCN/H₂O containing 0.15% NH₄OH) (8 mg, 30%).
¹H NMR (300 MHz, CD₃OD) δ 8.44 (dd, J=4.2, 2.2 Hz, 1H), 8.29 (s, 1H), 7.64 (d, J=9.7 Hz, 1H), 7.43-7.32 (m, 2H), 7.22 (d, J=9.7 Hz, 1H), 6.84 (s, 1H), 5.58 (s, 2H), 2.95 (s, 3H), 2.45 (s, 3H); LCMS (M+H)⁺: 278.1.

Example 12

1,7-dimethyl-6-(pyridin-4-ylmethyl)-6H-pyrrolo[2,3-e][1,2,4]triazolo[4,3-a]pyridine

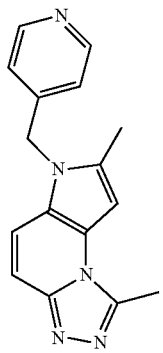 [SMILES: Cc1cc2c(ccc3nnc(C)n32)n1Cc1ccncc1]

Sodium hydride (13 mg, 0.32 mmol, 60% in mineral oil) was added to a solution of 1,7-dimethyl-6H-pyrrolo[2,3-e][1,2,4]triazolo[4,3-a]pyridine (20 mg, 0.1 mmol, from Example 2, Step 5) in DMF (3.0 mL). After stirring for 10 minutes, a solution of 4-(bromomethyl)pyridine hydrobromide (0.027 g, 0.11 mmol, Aldrich) in DMF (0.8 mL) was added. The mixture was stirred for 45 minutes and then quenched by the addition of water, diluted to 5 mL with MeCN, filtered and purified by preparative HPLC-MS (Waters XBridge C18, eluting with a gradient of MeCN/H₂O containing 0.15% NH₄OH) (1.0 mg, 3%).
¹H NMR (300 MHz, CD₃OD) δ 8.46 (d, J=6.1 Hz, 2H), 7.62 (d, J=9.8 Hz, 1H), 7.24 (d, J=9.7 Hz, 1H), 7.01 (d, J=5.9 Hz, 2H), 6.91 (s, 1H), 5.62 (s, 2H), 3.00 (s, 3H), 2.44 (s, 3H); LCMS (M+H)⁺: 278.2.

Example 13

6-(cyclopentylmethyl)-1,7-dimethyl-6H-pyrrolo[2,3-e][1,2,4]triazolo[4,3-a]pyridine

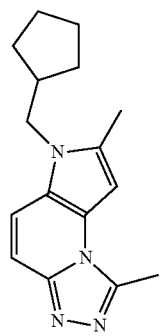 [SMILES: Cc1cc2c(ccc3nnc(C)n32)n1CC1CCCC1]

Sodium hydride (13 mg, 0.32 mmol, 60% in mineral oil) was added to a solution of 1,7-dimethyl-6H-pyrrolo[2,3-e][1,2,4]triazolo[4,3-a]pyridine (20 mg, 0.1 mmol, from Example 2, Step 5) in DMF (3.0 mL). After stirring for 15 minutes, (iodomethyl)cyclopentane (0.022 g, 0.11 mmol, Acros) was added. After stirring for 45 minutes at room temperature, excess NaH (13 mg, 0.32 mmol, 60% in mineral oil) and (iodomethyl)cyclopentane (0.022 g, 0.11 mmol) were added and the reaction was continued for 20 minutes and then was quenched by the addition of water and diluted to 5 mL volume with MeCN. The resulting solution was filtered and purified by preparative HPLC-MS (Waters XBridge C18, eluting with a gradient of MeCN/H₂O containing 0.15% NH₄OH) (4 mg, 10%).
¹H NMR (300 MHz, CD₃OD) δ 7.74 (d, J=9.7 Hz, 1H), 7.22 (d, J=9.7 Hz, 1H), 6.74 (s, 1H), 4.18 (d, J=7.7 Hz, 2H), 2.95 (s, 3H), 2.52 (s, 3H), 2.45-2.32 (m, 1H), 1.82-1.50 (m, 6H), 1.41-1.26 (m, 2H); LCMS (M+H)+: 269.1.

Example 14

6-(2-fluorobenzyl)-1,7-dimethyl-6H-pyrrolo[2,3-e][1,2,4]-triazolo[4,3-a]pyridine

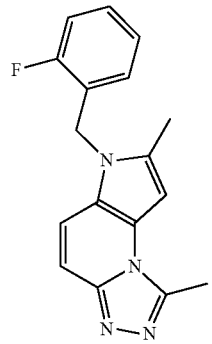 [SMILES: Cc1cc2c(ccc3nnc(C)n32)n1Cc1ccccc1F]

To a solution of 1,7-dimethyl-6H-pyrrolo[2,3-e][1,2,4]triazolo[4,3-a]pyridine (10.0 mg, 0.0537 mmol, from Example 2, Step 5) in DMF (1.5 mL) was added sodium hydride (0.0065 g, 0.16 mmol, 60% in mineral oil). After stirring for 10 minutes, 1-(bromomethyl)-2-fluorobenzene (0.010 g, 0.054 mmol, Aldrich) was added. After stirring for 45 minutes, the reaction was quenched with water, diluted with MeCN and filtered, then was purified by preparative HPLC-MS (Waters XBridge C18, eluting with a gradient of MeCN/H$_2$O containing 0.15% NH$_4$OH) (7 mg, 40%).

$^1$H NMR (300 MHz, CD$_3$OD) δ 7.66 (d, J=10.1 Hz, 1H), 7.36-7.27 (m, 1H), 7.23 (d, J=9.7 Hz, 1H), 7.16 (ddd, J=10.4, 8.3, 1.1 Hz, 1H), 7.05 (td, J=7.6, 1.1 Hz, 1H), 6.90-6.77 (m, 1H), 6.66-6.59 (m, 1H), 5.57 (s, 2H), 2.98 (s, 3H), 2.46 (s, 3H); LCMS (M+H)+: 295.0.

Example 15

6-(3-fluorobenzyl)-1,7-dimethyl-6H-pyrrolo[2,3-e][1,2,4]triazolo[4,3-a]pyridine

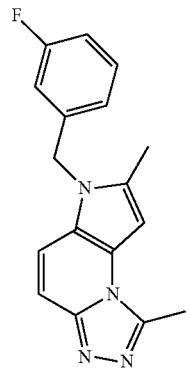 [SMILES: Cc1cc2c(ccc3nnc(C)n32)n1Cc1cccc(F)c1]

The title compound was prepared as described in Example 14, using α-bromo-3-fluorotoluene (0.010 g, 0.054 mmol, Aldrich) (7 mg, 40%).

$^1$H NMR (300 MHz, CD$_3$OD) δ 7.63 (dd, J=9.7, 0.7 Hz, 1H), 7.32 (td, J=8.0, 5.9 Hz, 1H), 7.23 (d, J=9.7 Hz, 1H), 7.04-6.94 (m, 1H), 6.89-6.83 (m, 1H), 6.79 (ddd, J=7.7, 1.6, 0.8 Hz, 1H), 6.75-6.67 (m, 1H), 5.53 (s, 2H), 2.98 (s, 3H), 2.45 (d, J=0.6 Hz, 3H); LCMS (M+H)+: 295.0.

Example 16

6-(4-fluorobenzyl)-1,7-dimethyl-6H-pyrrolo[2,3-e][1,2,4]triazolo[4,3-a]pyridine

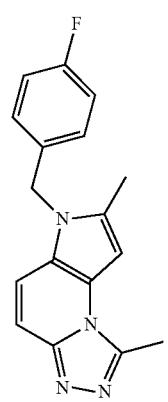

The title compound was prepared as described in Example 14, using α-bromo-4-fluorotoluene (0.010 g, 0.054 mmol, Aldrich) (7 mg, 40%).

$^1$H NMR (300 MHz, CD$_3$OD) δ 7.63 (d, J=9.7 Hz, 1H), 7.21 (d, J=9.7 Hz, 1H), 7.03 (m, 4H), 6.83 (s, 1H), 5.48 (s, 2H), 2.96 (s, 3H), 2.44 (s, 3H); LCMS (M+H)+: 295.0.

Example 17

1,7-dimethyl-6-(2-methylbenzyl)-6H-pyrrolo[2,3-e][1,2,4]triazolo[4,3-a]pyridine

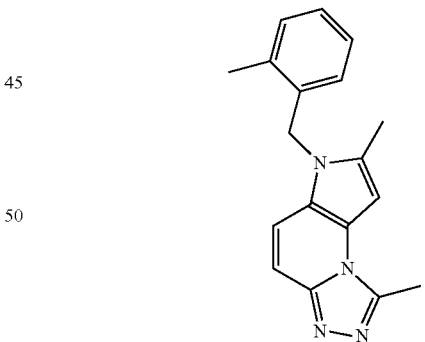

To a solution of 1,7-dimethyl-6H-pyrrolo[2,3-e][1,2,4]triazolo[4,3-a]pyridine (15.0 mg, 0.0806 mmol, from Example 2, Step 5) in DMF (2.2 mL) was added sodium hydride (0.0098 g, 0.24 mmol, 60% in mineral oil). After stirring for 10 minutes, 1-(bromomethyl)-2-methylbenzene (0.015 g, 0.080 mmol, Aldrich) was added. After stirring for 45 minutes, the reaction was quenched by the addition of water and diluted to 5 mL volume with MeCN. The solution was filtered and purified by preparative HPLC-MS (Waters XBridge C18, eluting with a gradient of MeCN/H$_2$O containing 0.15% NH$_4$OH) (9 mg, 40%).

¹H NMR (300 MHz, CD₃OD) δ 7.51 (d, J=9.7 Hz, 1H), 7.29-7.08 (m, 3H), 6.97 (dd, J=7.5, 7.5 Hz, 1H), 6.86 (s, 1H), 6.09 (d, J=7.6 Hz, 1H), 5.46 (s, 2H), 2.99 (s, 3H), 2.44 (s, 3H), 2.38 (s, 3H); LCMS (M+H)⁺: 291.0.

Example 18

1,7-dimethyl-6-(3-methylbenzyl)-6H-pyrrolo[2,3-e][1,2,4]triazolo[4,3-a]pyridine

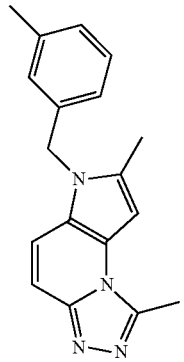

The title compound was prepared as described in Example 17, using 1-(bromomethyl)-3-methylbenzene (0.015 g, 0.080 mmol, Aldrich) (8 mg, 30%).

¹H NMR (300 MHz, CD₃OD) δ 7.60 (d, J=9.7 Hz, 1H), 7.19 (d, J=9.7 Hz, 1H), 7.16 (t, J=7.6 Hz, 1H), 7.06 (d, J=7.6 Hz, 1H), 6.82 (s, 1H), 6.80 (s, 1H), 6.76 (d, J=7.6 Hz, 1H), 5.44 (s, 2H), 2.96 (s, 3H), 2.43 (s, 3H), 2.24 (s, 3H); LCMS (M+H)⁺: 291.0.

Example 19

1,7-dimethyl-6-(4-methylbenzyl)-6H-pyrrolo[2,3-e][1,2,4]triazolo[4,3-a]pyridine

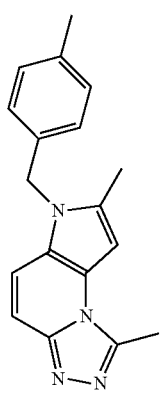 [SMILES: Cc1ccc(Cn2c(C)cc3c2ccc2nnc(C)n23)cc1]

The title compound was prepared as described in Example 17, using 1-(bromomethyl)-4-methylbenzene (0.015 g, 0.080 mmol, Aldrich) (8 mg, 30%).

¹H NMR (300 MHz, CD₃OD) δ 7.60 (dd, J=9.7, 0.6 Hz, 1H), 7.18 (d, J=9.7 Hz, 1H), 7.10 (d, J=7.9 Hz, 2H), 6.88 (d, J=8.1 Hz, 2H), 6.79 (s, 1H), 5.42 (s, 2H), 2.95 (s, 3H), 2.43 (s, 3H), 2.27 (s, 3H); LCMS (M+H)⁺: 291.0.

Example 20

3-[(1,7-dimethyl-6H-pyrrolo[2,3-e][1,2,4]triazolo[4,3-a]pyridine-6-yl)methyl]benzonitrile

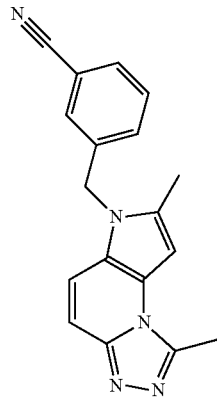 [SMILES: Cc1cc2c(ccc3nnc(C)n32)n1Cc1cccc(C#N)c1]

The title compound was prepared as described in Example 17, using m-cyanobenzyl bromide (0.016 g, 0.080 mmol, Aldrich) (4 mg, 20%).

¹H NMR (300 MHz, CD₃OD) δ 7.67-7.62 (m, 1H), 7.63 (dd, J=9.8, 0.6 Hz, 1H), 7.50 (t, J=7.8 Hz, 1H), 7.38 (s, 1H), 7.24 (d, J=9.6 Hz, 1H), 7.27-7.21 (m, 1H), 6.93-6.86 (m, 1H), 5.60 (s, 2H), 2.99 (s, 3H), 2.46 (d, J=0.5 Hz, 3H); LCMS (M+H)⁺: 302.0.

Example 21

1,7-dimethyl-6-(quinolin-2-ylmethyl)-6H-pyrrolo[2,3-e][1,2,4]triazolo[4,3-a]pyridine

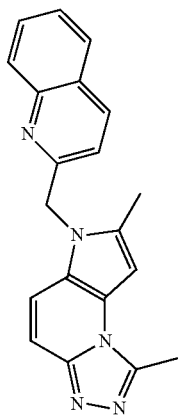 [SMILES: Cc1cc2c(ccc3nnc(C)n32)n1Cc1ccc2ccccc2n1]

The title compound was prepared as described in Example 17, using 2-(chloromethyl)quinoline hydrochloride (0.017 g, 0.080 mmol, TCI) (4 mg, 20%).

¹H NMR (300 MHz, CD₃OD) δ 8.25 (d, J=8.5 Hz, 1H), 8.03-7.97 (m, 1H), 7.89 (dd, J=8.1, 1.1 Hz, 1H), 7.77 (ddd, J=8.4, 6.9, 1.4 Hz, 1H), 7.73 (d, J=9.8 Hz, 1H), 7.59 (ddd, J=8.2, 7.0, 1.2 Hz, 1H), 7.23 (d, J=9.7 Hz, 1H), 6.97 (d, J=8.5 Hz, 1H), 6.90 (s, 1H), 5.78 (s, 2H), 3.00 (s, 3H), 2.52 (s, 3H); LCMS (M+H)+: 328.0.

Example 22

6-(3-methoxybenzyl)-1,7-dimethyl-6H-pyrrolo[2,3-e][1,2,4]triazolo[4,3-a]pyridine

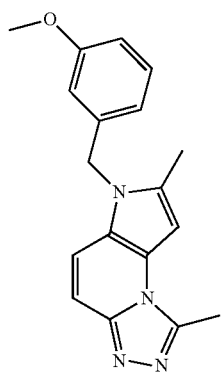

To a solution of 1,7-dimethyl-6H-pyrrolo[2,3-e][1,2,4]triazolo[4,3-a]pyridine (50.0 mg, 0.268 mmol, from Example 2, Step 5) in DMF (4 mL) was added sodium hydride (0.032 g, 0.81 mmol, 60% in mineral oil). After stirring for 10 minutes, 1-(bromomethyl)-3-methoxybenzene (0.038 mL, 0.27 mmol, Aldrich) was added and the reaction was stirred for 45 minutes and was quenched by the addition of water and diluted with MeCN, filtered and purified by preparative HPLC-MS (Waters XBridge C18, eluting with a gradient of MeCN/H2O containing 0.15% NH4OH) (0.04 g, 50%).

1H NMR (400 MHz, d6-DMSO) δ 7.63 (d, J=9.7 Hz, 1H), 7.23 (d, J=9.7 Hz, 1H), 7.21 (t, J=7.9 Hz, 1H), 6.85-6.78 (m, 1H), 6.81 (s, 1H), 6.58 (s, 1H), 6.48 (d, J=7.6 Hz, 1H), 5.48 (s, 2H), 3.68 (s, 3H), 2.87 (s, 3H), 2.38 (s, 3H); LCMS (M+H)+: 307.1.

Example 23

3-[(1,7-dimethyl-6H-pyrrolo[2,3-e][1,2,4]triazolo[4,3-a]pyridin-6-yl)methyl]phenol

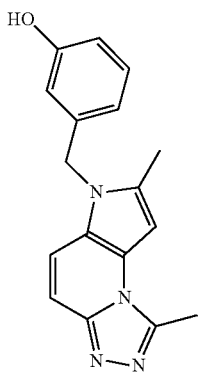 [SMILES: Cc1cc2c(ccc3nnc(C)n32)n1Cc1cccc(O)c1]

To 6-(3-methoxybenzyl)-1,7-dimethyl-6H-pyrrolo[2,3-e][1,2,4]triazolo[4,3-a]pyridine (0.030 g, 0.098 mmol, from Example 22) in DCM (4 mL) at −78° C. was added 1.0 M BBr3 in DCM (0.57 mL, 0.57 mmol, Aldrich) and the mixture was allowed to warm to ambient temperature. The reaction was quenched by the addition of water, and saturated NaHCO3 solution was added. DCM was removed by rotary evaporation and the aqueous mixture was diluted with MeOH, filtered and purified by preparative HPLC-MS (Waters XBridge C18, eluting with a gradient of MeCN/H2O containing 0.15% NH4OH) (0.02 g, 70%).

1H NMR (400 MHz, d6-DMSO) δ 9.37 (br s, 1H), 7.63 (d, J=9.7 Hz, 1H), 7.23 (d, J=9.7 Hz, 1H), 7.09 (t, J=7.9 Hz, 1H), 6.81 (s, 1H), 6.61 (dd, J=8.0, 2.2 Hz, 1H), 6.45 (d, J=7.5 Hz, 1H), 6.39-6.24 (m, 1H), 5.43 (s, 2H), 2.87 (s, 3H), 2.37 (s, 3H); LCMS (M+H)+: 293.1.

Example 24

1,7-dimethyl-6-(1-phenylpentyl)-6H-pyrrolo[2,3-e][1,2,4]triazolo[4,3-a]pyridine (racemic mixture)

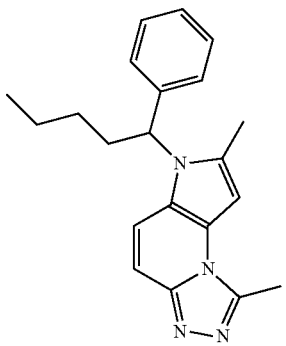 [SMILES: CCCCC(c1ccccc1)n1c(C)cc2c1ccc1nnc(C)n12]

Step 1. (1-bromopentyl)benzene (racemic mixture prepared)

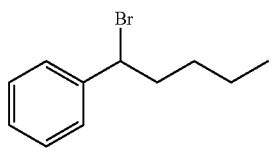

PBr3 (0.171 mL, 1.82 mmol, Aldrich) was added to a solution of 1-phenylpentan-1-ol (0.500 g, 3.04 mmol, Alfa Aesar) in Et2O (3.2 mL) at 0° C. The reaction was allowed to reach ambient temperature and then was quenched with ice water and diluted with hexanes. The layers were separated and the organic layer was washed with water and then with brine, dried over sodium sulfate, filtered and concentrated. Flash chromatography, eluting with hexanes afforded product (0.15 g, 22%).

1H NMR (300 MHz, CDCl3) δ 7.44-7.26 (m, 5H), 4.95 (t, J=7.5 Hz, 1H), 2.48-1.87 (m, 2H), 1.52-1.12 (m, 4H), 0.89 (t, J=7.0 Hz, 3H).

Step 2. 1,7-dimethyl-6-(1-phenylpentyl)-6H-pyrrolo[2,3-e][1,2,4]triazolo[4,3-a]pyridine (racemic mixture prepared)

Sodium hydride (0.011 g, 0.27 mmol, 60% in mineral oil) was added to a solution of 1,7-dimethyl-6H-pyrrolo[2,3-e][1, 2,4]triazolo[4,3-a]pyridine (50.0 mg, 0.268 mmol, from Example 2, Step 5) in DMF (6 mL). After stirring for 10 minutes, (1-bromopentyl)benzene (0.061 g, 0.27 mmol, from Step 1) was added. After stirring for 45 minutes, the reaction was quenched by the addition of water and the mixture was diluted with MeCN, filtered and purified via preparative HPLC-MS (Waters XBridge C18, eluting with a gradient of MeCN/H$_2$O containing 0.15% NH$_4$OH) (0.01 g, 10%).

$^1$H NMR (400 MHz, d$_6$-DMSO) δ 7.39 (d, J=9.0 Hz, 1H), 7.34 (dd, J=7.4, 7.4 Hz, 2H), 7.26 (t, J=7.1 Hz, 1H), 7.19 (d, J=7.6 Hz, 2H), 7.11 (d, J=9.8 Hz, 1H), 6.80 (s, 2H), 5.78 (dd, J=10.7, 4.5 Hz, 1H), 2.86 (s, 3H), 2.54-2.27 (m, 2H), 2.42 (s, 3H), 1.41-1.20 (m, 4H), 0.92-0.80 (m, 2H), 0.79 (t, J=7.0 Hz, 3H); LCMS (M+H)$^+$: 333.2.

Example 25

N-{3-[(1,7-dimethyl-6H-pyrrolo[2,3-e][1,2,4]triazolo[4,3-a]pyridin-6-yl)methyl]phenyl}acetamide trifluoroacetate salt

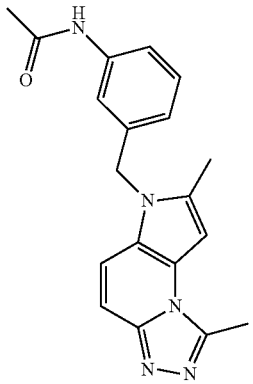 [SMILES: CC(=O)Nc1cccc(Cn2c(C)cc3c2ccc2nnc(C)n23)c1]

Step 1. 1,7-dimethyl-6-(3-nitrobenzyl)-6H-pyrrolo[2,3-e][1,2,4]triazolo[4,3-a]pyridine

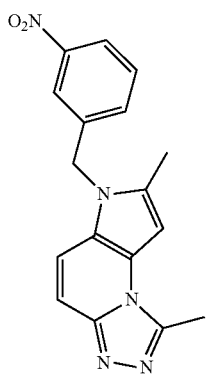

Sodium hydride (0.011 g, 0.27 mmol, 60% in mineral oil) was added to a solution of 1,7-dimethyl-6H-pyrrolo[2,3-e][1,2,4]triazolo[4,3-a]pyridine (50.0 mg, 0.268 mmol, from Example 2, Step 5) in DMF (6 mL). After stirring for 10 minutes, 1-(chloromethyl)-3-nitro-benzene, (0.058 g, 0.34 mmol, Aldrich) was added. After stirring for 45 minutes, the reaction was quenched by the addition of water and the mixture was diluted with MeCN, filtered and purified via preparative HPLC-MS to afford product as a yellow solid (Waters XBridge C18, eluting with a gradient of MeCN/H$_2$O containing 0.15% NH$_4$OH) (0.065 g, 75%).

$^1$H NMR (300 MHz, CDCl$_3$) δ 8.15 (d, J=8.1 Hz, 1H), 7.90 (s, 1H), 7.50 (t, J=7.9 Hz, 1H), 7.34 (d, J=9.7 Hz, 1H), 7.22-7.11 (m, 2H), 6.68 (s, 1H), 5.45 (s, 2H), 3.00 (s, 3H), 2.43 (s, 3H); LCMS (M+H)$^+$: 322.1.

Step 2. N-{3-[(1,7-dimethyl-6-pyrrolo[2,3-e][1,2,4]triazolo[4,3-a]pyridin-6-yl)methyl]phenyl}acetamide trifluoroacetate salt A mixture of 1,7-dimethyl-6-(3-nitrobenzyl)-6H-pyrrolo[2,3-e][1,2,4]triazolo[4,3-a]pyridine (0.030 g, 0.093 mmol, from Step 1), iron (0.026 g, 0.47 mmol) and NH$_4$Cl (0.010 g, 0.19 mmol) in EtOH (2 mL) and H$_2$O (0.4 mL) was heated to 90° C. for 30 minutes. Upon cooling to room temperature, the reaction mixture was diluted with EtOAc and filtered through celite. The filtrate was dried over sodium sulfate, decanted and concentrated. The crude product was dissolved in DCM (2 mL) and Ac$_2$O (0.0088 mL, 0.093 mmol, Sigma-Aldrich) and DMAP (0.004 g, 0.03 mmol) were added. The reaction was stirred overnight. 1.0 M NaOH (2 mL) and MeOH (2 mL) were added. After stirring for 15 minutes, the reaction mixture was diluted with water, and extracted with three portions of DCM and three portions of EtOAc. All extracts were combined, dried over sodium sulfate, filtered and concentrated. The product was purified by preparative HPLC-MS (Waters XBridge C18, eluting with a gradient of MeCN/H$_2$O containing 0.15% NH$_4$OH followed by a further purification: Waters SunFire C18, eluting with a gradient of MeCN/H$_2$O containing 0.1% TFA) (0.01 g, 24%).

$^1$H NMR (300 MHz, CD$_3$OD) δ 8.29 (d, J=9.5 Hz, 1H), 7.45 (d, J=9.5 Hz, 1H), 7.38 (s, 1H), 7.31-7.23 (m, 2H), 7.13 (s, 1H), 6.89-6.80 (m, 1H), 5.64 (s, 2H), 3.10 (s, 3H), 2.58 (s, 3H), 2.03 (s, 3H); $^{19}$F NMR (282 MHz, CD$_3$OD) δ −77.69 (s); LCMS (M+H)$^+$: 334.1.

Example 26

{3-[(1,7-dimethyl-6H-pyrrolo[2,3-e][1,2,4]triazolo[4,3-a]pyridin-6-yl)methyl]phenyl}methanol trifluoroacetate salt

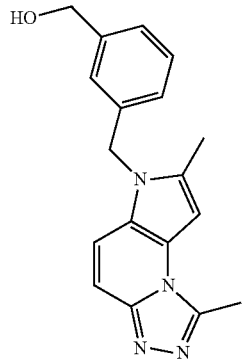

Step 1. methyl 3-[(1,7-dimethyl-6H-pyrrolo[2,3-e][1,2,4]triazolo[4,3-a]pyridin-6-yl)methyl]benzoate

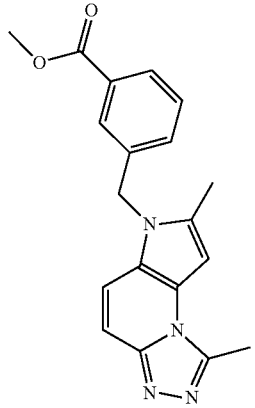

Sodium hydride (0.043 g, 1.1 mmol, 60% in mineral oil) was added to a solution of 1,7-dimethyl-6H-pyrrolo[2,3-e][1,2,4]triazolo[4,3-a]pyridine (200.0 mg, 1.074 mmol, from Example 2, Step 5) in DMF (20 mL). After 10 minutes, methyl 3-(bromomethyl)benzoate (0.25 g, 1.1 mmol, Alfa Aesar) was added. After 45 minutes, the reaction mixture was poured into pH 7 buffer and the product was extracted with three portions of EtOAc. The combined organic extracts were washed with water, then brine, dried over sodium sulfate, filtered and concentrated and used without further purification.
LCMS (M+H)+: 335.1.

Step 2. {3-[(1,7-dimethyl-6H-pyrrolo[2,3-e][1,2,4]triazolo[4,3-a]pyridin-6-yl)methyl]phenyl}methanol trifluoroacetate salt To a solution of methyl 3-[(1,7-dimethyl-6H-pyrrolo[2,3-e][1,2,4]triazolo[4,3-a]pyridin-6-yl)methyl]benzoate (0.090 g, 0.27 mmol, from Step 1) in THF (3 mL) and EtOH (2 mL) at 0° C. was added LiBH4 (0.038 g, 1.6 mmol, 90% purity reagent, Aldrich) and the mixture was allowed to warm to room temperature. After 2 hours, additional LiBH4 (0.078 g, 3.2 mmol) was added and THF (2 mL) was used to rinse material down from the walls of the flask. The reaction was stirred overnight. MeOH (2 mL) and additional LiBH4 (0.069 g, 2.9 mmol) were then added. After an additional few hours, the reaction was quenched by the addition of brine, and the product was extracted using EtOAc. The extracts were dried over sodium sulfate, filtered and concentrated and the crude product was used in the next step. A portion was purified by preparative HPLC-MS (Waters SunFire C18, eluting with a gradient of MeCN/H2O containing 0.1% TFA).
1H NMR (300 MHz, CD3OD) δ 8.28 (d, J=9.3 Hz, 1H), 7.45 (d, J=9.5 Hz, 1H), 7.37-7.22 (m, 2H), 7.13 (s, 1H), 7.03 (s, 1H), 6.95 (d, J=7.1 Hz, 1H), 5.66 (s, 2H), 4.52 (s, 2H), 3.10 (s, 3H), 2.58 (s, 3H); 19F NMR (282 MHz, CD3OD) δ −77.47 (s); LCMS (M+H)+: 307.1.

Example 27

1-(3-((1,7-dimethyl-6H-pyrrolo[2,3-e][1,2,4]triazolo[4,3-a]pyridin-6-yl)methyl)benzyl)azetidin-3-ol bis-trifluoroacetate salt

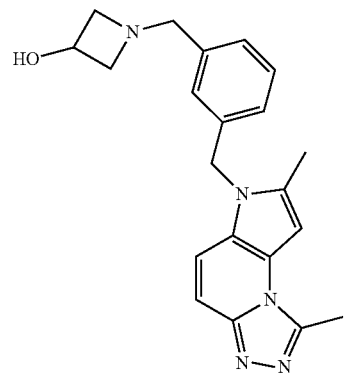 [SMILES: Cc1cc2c(ccc3nnc(C)n32)n1Cc1cccc(CN2CC(O)C2)c1]

Diisopropylethylamine (0.14 mL, 0.81 mmol) and methanesulfonic anhydride (0.094 g, 0.54 mmol, Aldrich) were added to a solution of the crude product of Example 26, Step 2 in DCM (5 mL) at 0° C. After 30 minutes, solvent was removed in vacuo and the residue was dissolved in THF (2 mL) and MeOH (2 mL). Half of this solution was treated with excess 3-hydroxyazetidine HCl (130 mg, 1.19 mmol, Oakwood) and diisopropylethylamine (0.3 mL, 1.72 mmol) and was stirred overnight. The product was purified by preparative HPLC-MS (Waters SunFire C18, eluting with a gradient of MeCN/H2O containing 0.1% TFA) (7.5 mg, 10%).
1H NMR (300 MHz, CD3OD) δ 8.17 (d, J=9.6 Hz, 1H), 7.49-7.33 (m, 3H), 7.16 (s, 1H), 7.14-7.07 (m, 2H), 5.69 (s, 2H), 4.70-4.42 (m, 1H), 4.33 (s, 2H), 4.30-4.16 (m, 2H), 3.97-3.75 (m, 2H), 3.09 (s, 3H), 2.55 (s, 3H); 19F NMR (282 MHz, CD3OD) δ −77.38 (s); LCMS (M+H)+: 362.1.

Example 28

6-[3-(azetidin-1-ylmethyl)benzyl]-1,7-dimethyl-6H-pyrrolo[2,3-e][1,2,4]triazolo[4,3-a]pyridine

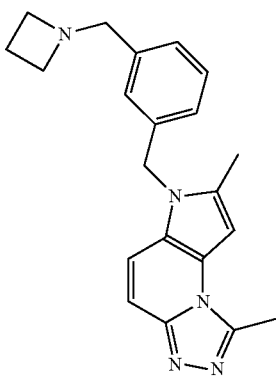 [SMILES: Cc1cc2c(ccc3nnc(C)n32)n1Cc1cccc(CN2CCC2)c1]

Half of the solution of intermediate mesylate from Example 27 was treated with excess azetidine (0.1 mL, 1.5 mmol, Aldrich) and diisopropylethylamine (0.15 mL, 0.86 mmol) and the reaction was stirred overnight. The product was purified by preparative HPLC-MS (Waters SunFire C18, eluting with a gradient of MeCN/H$_2$O containing 0.1% TFA then followed by further purification: Waters XBridge C18, eluting with a gradient of MeCN/H$_2$O containing 0.15% NH$_4$OH) (3 mg, 10%).

$^1$H NMR (300 MHz, d$_6$-DMSO) δ 7.64 (dd, J=9.7, 0.5 Hz, 1H), 7.29-7.16 (m, 2H), 7.10 (d, J=7.8 Hz, 1H), 6.94 (s, 1H), 6.84-6.75 (m, 2H), 5.49 (s, 2H), 3.41 (s, 2H), 3.01 (t, J=6.9 Hz, 4H), 2.86 (s, 3H), 2.37 (s, 3H), 1.89 (p, J=7.0 Hz, 2H); LCMS (M+H)$^+$: 346.0.

Example 29

2-(1,7-dimethyl-6H-pyrrolo[2,3-e][1,2,4]triazolo[4,3-a]pyridin-6-yl)-2-phenylethanol (racemic mixture prepared)

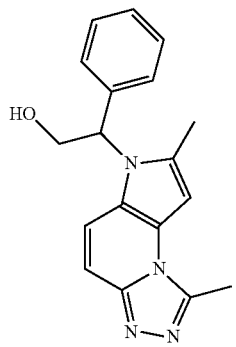 [SMILES: Cc1cc2c(ccc3nnc(C)n32)n1C(CO)c1ccccc1]

Step 1. ethyl (1,7-dimethyl-6H-pyrrolo[2,3-e][1,2,4]triazolo[4,3-a]pyridin-6-yl)(phenyl)acetate (racemic mixture prepared)

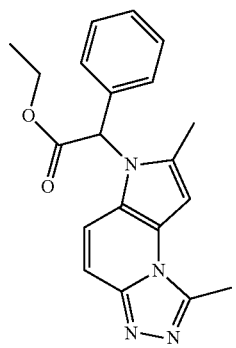 [SMILES: CCOC(=O)C(c1ccccc1)n1c(C)cc2c1ccc1nnc(C)n12]

Sodium hydride (110 mg, 2.7 mmol, 60% in mineral oil) was added to a solution of 1,7-dimethyl-6H-pyrrolo[2,3-e][1,2,4]triazolo[4,3-a]pyridine (0.500 g, 2.68 mmol, from Example 2, Step 5) in DMF (50 mL). After 15 minutes, a solution of ethyl-alpha-bromophenyl acetate (0.70 mL, 4.0 mmol, Aldrich) in DMF (10 mL) was added dropwise. The mixture was stirred for 15 minutes at room temperature and then was poured into pH 7 buffer and diluted with EtOAc and water. The layers were separated and the aqueous was extracted again with EtOAc. The combined organic extracts were washed with water, then brine, dried over sodium sulfate, filtered and concentrated. The product was purified by flash chromatography, eluting with a gradient from 5-10% MeOH in DCM (187 mg, 20%).

LCMS (M+H)$^+$: 349.2.

Step 2. 2-(1,7-dimethyl-6H-pyrrolo[2,3-e][1,2,4]triazolo[4,3-a]pyridin-6-yl)-2-phenylethanol (racemic mixture prepared)

Ethyl (1,7-dimethyl-6H-pyrrolo[2,3-e][1,2,4]triazolo[4,3-a]pyridin-6-yl)(phenyl)acetate (0.008 g, 0.02 mmol, from Step 1) was dissolved in MeOH (0.5 mL) and THF (0.5 mL) and LiBH$_4$ (0.0025 g, 0.10 mmol, 90% purity, Aldrich) was added. The reaction was stirred for 4 hours and additional LiBH$_4$ (0.006 g, 0.25 mmol) was added and the reaction continued for a further 3 hours. The reaction was quenched by the addition of water and diluted with MeCN, filtered and purified by preparative HPLC-MS (Waters XBridge C18, eluting with a gradient of MeCN/H$_2$O containing 0.15% NH$_4$OH) (5 mg, 70%).

$^1$H NMR (400 MHz, CD$_3$OD) δ 7.41-7.27 (m, 4H), 7.26-7.19 (m, 2H), 7.04 (d, J=9.8 Hz, 1H), 6.84 (s, 1H), 5.85 (dd, J=8.6, 5.3 Hz, 1H), 4.58 (dd, J=11.6, 5.2 Hz, 1H), 4.43 (dd, J=11.6, 8.7 Hz, 1H), 2.97 (s, 3H), 2.55 (s, 3H); LCMS (M+H)$^+$: 307.1.

Example 30

3-((1,7-dimethyl-6H-pyrrolo[2,3-e][1,2,4]triazolo[4,3-a]pyridin-6-yl)methyl)benzamide trifluoroacetate salt

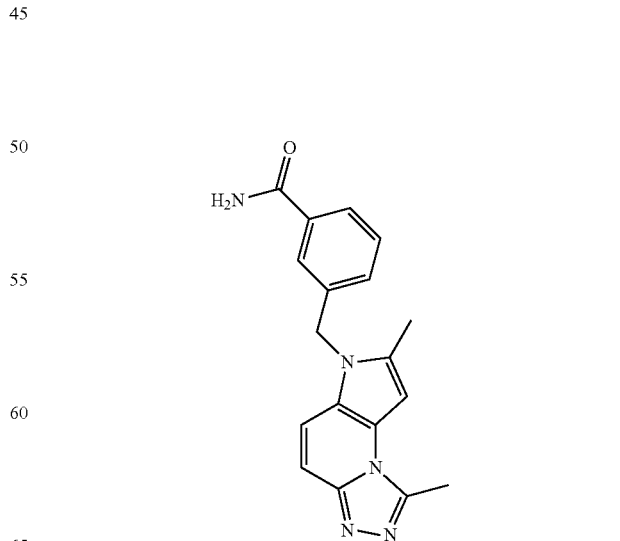

Step 1. 3-[(1,7-dimethyl-6H-pyrrolo[2,3-e][1,2,4]triazolo[4,3-a]pyridin-6-yl)methyl]benzoic acid ammonium salt

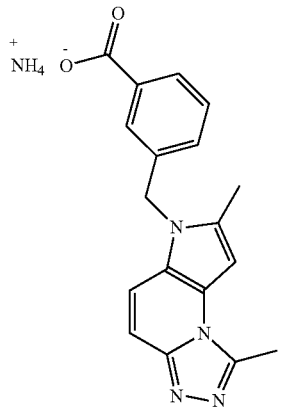

To a solution of methyl 3-[(1,7-dimethyl-6H-pyrrolo[2,3-e][1,2,4]triazolo[4,3-a]pyridin-6-yl)methyl]benzoate (0.090 g, 0.27 mmol, prepared as in Example 26, Step 1) in 1,4-dioxane (2 mL), $H_2O$ (1 mL) and MeOH (1 mL) was added LiOH, monohydrate (0.056 g, 1.3 mmol) and the reaction was stirred overnight. Further LiOH—$H_2O$ (0.050 g, 1.1 mmol) was added and the reaction was continued for 8 hours. The reaction mixture was diluted with additional water, filtered and purified via preparative HPLC-MS (Waters XBridge C18, eluting with a gradient of MeCN/$H_2O$ containing 0.15% $NH_4OH$) (74 mg, 86%).

LCMS (M+H)$^+$: 321.1.

Step 2. 3-((1,7-dimethyl-6H-pyrrolo[2,3-e][1,2,4]triazolo[4,3-a]pyridin-6-yl)methyl)benzamide, trifluoroacetate salt To a solution of 3-[(1,7-dimethyl-6H-pyrrolo[2,3-e][1,2,4]triazolo[4,3-a]pyridin-6-yl)methyl]benzoic acid (0.074 g, 0.23 mmol, as ammonium salt, from Step 1) in DCM (5 mL) containing DMF (0.004 mL, 0.05 mmol) was added oxalyl chloride (0.020 mL, 0.23 mmol, Aldrich). Additional portions of oxalyl chloride (0.020 mL, 0.24 mmol) were added (twice) and the reaction was stirred for 30 minutes. The mixture was heated to reflux and a single additional portion of oxalyl chloride (0.020 mL, 0.23 mmol) was added while the solution was hot. One-third of this solution was added to ammonium hydroxide solution (2 mL, 14.8 N). MeCN (1 mL) was added and the biphasic mixture was stirred vigorously overnight. DCM was removed in vacuo and the remaining aqueous mixture was diluted with additional MeCN, filtered and purified by preparative HPLC-MS (Waters SunFire C18, eluting with a gradient of MeCN/$H_2O$ containing 0.1% TFA) (8 mg, 24%).

$^1$H NMR (500 MHz, $d_6$-DMSO) δ 8.21 (d, J=9.4 Hz, 1H), 7.94 (br s, 1H), 7.76 (d, J=8.0 Hz, 1H), 7.58 (s, 1H), 7.48 (d, J=9.4 Hz, 1H), 7.39 (t, J=7.7 Hz, 1H), 7.35 (br s, 1H), 7.14 (d, J=7.9 Hz, 1H), 7.10 (s, 1H), 5.69 (s, 2H), 2.98 (s, 3H), 2.49 (s, 3H); $^{19}$F NMR (282 MHz, $d_6$-DMSO) δ −74.35 (s); LCMS (M+H)$^+$: 320.0.

Example 31

3-[(1,7-dimethyl-6H-pyrrolo[2,3-e][1,2,4]triazolo[4,3-a]pyridin-6-yl)methyl]-N-hydroxybenzamide trifluoroacetate salt

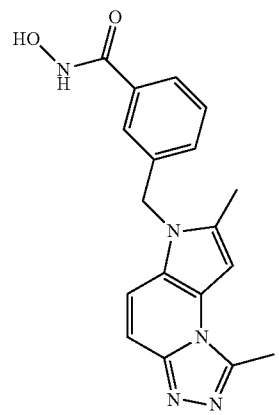 [SMILES: Cc1cc2c(ccc3nnc(C)n32)n1Cc1cccc(C(=O)NO)c1]

One-third portion of the crude acid chloride (0.077 mmol) from Example 30, Step 2 was added to a solution of hydroxylamine HCl (0.048 g, 0.69 mmol, Aldrich) and diisopropylethylamine (0.12 mL, 0.69 mmol) in DCM (1 mL). MeCN (1 mL) was added and the reaction was stirred overnight. DCM was removed in vacuo and the reaction mixture was diluted with MeOH, filtered and purified by preparative HPLC-MS (Waters SunFire C18, eluting with a gradient of MeCN/$H_2O$ containing 0.1% TFA) (10 mg, 29%).

$^1$H NMR (300 MHz, $d_6$-DMSO) δ 11.21 (s, 1H), 9.04 (br s, 1H), 8.22 (d, J=9.7 Hz, 1H), 7.61 (d, J=7.8 Hz, 1H), 7.49 (d, J=9.6 Hz, 1H), 7.45 (s, 1H), 7.39 (t, J=7.7 Hz, 1H), 7.14 (d, J=8.2 Hz, 1H), 7.10 (s, 1H), 5.70 (s, 2H), 2.98 (s, 3H), 2.49 (s, 3H); $^{19}$F NMR (282 MHz, $d_6$-DMSO) δ −74.27 (s); LCMS (M+H)$^+$: 336.0.

Example 32

3-[(1,7-dimethyl-6H-pyrrolo[2,3-e][1,2,4]triazolo[4,3-a]pyridin-6-yl)methyl]-N-methylbenzamide trifluoroacetate salt

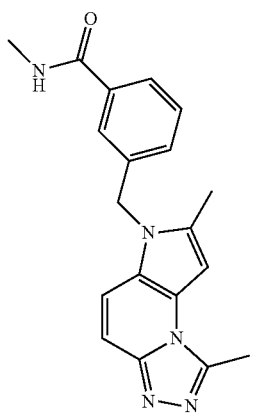

To a solution of 3-[(1,7-dimethyl-6H-pyrrolo[2,3-e][1,2,4]triazolo[4,3-a]pyridin-6-yl)methyl]benzoic acid (0.025 g, 0.078 mmol, prepared as in Example 30, Step 1 and isolated by preparative HPLC-MS [Waters SunFire C18, eluting with a gradient of MeCN/H₂O containing 0.1% TFA]) in DMF (1.0 mL) was added diisopropylethylamine (0.054 mL, 0.31 mmol) and N,N,N',N'-tetramethyl-O-(7-azabenzotriazol-1-yl)uronium hexafluorophosphate (0.055 g, 0.14 mmol, Aldrich). After stirring for 10 minutes, 2.0 M methylamine in THF (0.50 mL, 1.0 mmol, Aldrich) was added and the reaction was stirred for 2 hours. The reaction mixture was diluted with MeOH and purified by preparative HPLC-MS (Waters SunFire C18, eluting with a gradient of MeCN/H₂O containing 0.1% TFA) (10 mg, 40%).

¹H NMR (300 MHz, d₆-DMSO) δ 8.44 (q, J=4.3 Hz, 1H), 8.31 (d, J=9.6 Hz, 1H), 7.71 (d, J=7.9 Hz, 1H), 7.60-7.46 (m, 2H), 7.40 (t, J=7.7 Hz, 1H), 7.20-7.09 (m, 2H), 5.72 (s, 2H), 3.00 (s, 3H), 2.72 (d, J=4.5 Hz, 3H), 2.50 (s, 3H); ¹⁹F NMR (282 MHz, d₆-DMSO) δ −74.49 (s); LCMS (M+H)⁺: 334.0.

Example 33

3-[(1,7-dimethyl-6H-pyrrolo[2,3-e][1,2,4]triazolo[4,3-a]pyridin-6-yl)methyl]N-ethylbenzamide trifluoroacetate salt

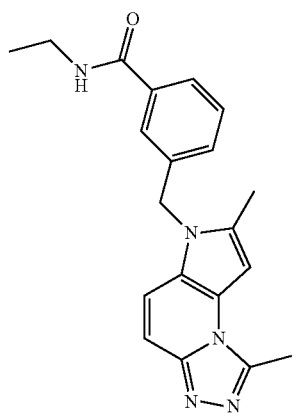 [SMILES: CCNC(=O)c1cccc(Cn2c(C)cc3c2ccc2nnc(C)n23)c1]

The title compound was prepared as described for Example 32, using ethylamine (0.050 mL, 0.89 mmol, Aldrich) (10 mg, 40%).

¹H NMR (300 MHz, d₆-DMSO) δ 8.49 (t, J=5.4 Hz, 1H), 8.31 (d, J=9.6 Hz, 1H), 7.72 (d, J=7.9 Hz, 1H), 7.57 (s, 1H), 7.53 (d, J=9.5 Hz, 1H), 7.40 (t, J=7.7 Hz, 1H), 7.15 (s, 1H), 7.10 (d, J=7.6 Hz, 1H), 5.72 (s, 2H), 3.36-3.07 (m, 2H), 3.00 (s, 3H), 2.50 (s, 3H), 1.07 (t, J=7.2 Hz, 3H); ¹⁹F NMR (282 MHz, d₆-DMSO) δ −74.49 (s); LCMS (M+H)⁺: 348.0.

Example 34

6-(4-methoxybenzyl)-1,7-dimethyl-6H-pyrrolo[2,3-e][1,2,4]triazolo[4,3-a]pyridine

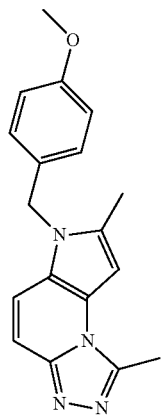 [SMILES: COc1ccc(Cn2c(C)cc3c2ccc2nnc(C)n23)cc1]

Sodium hydride (0.032 g, 0.81 mmol, 60% in mineral oil) was added to a solution of 1,7-dimethyl-6H-pyrrolo[2,3-e][1,2,4]triazolo[4,3-a]pyridine (50.0 mg, 0.268 mmol, Example 2, Step 5) in DMF (4 mL). After 10 minutes, p-methoxybenzyl chloride (0.036 mL, 0.27 mmol, Aldrich) was added. The reaction was stirred for 45 minutes, then was quenched with water, diluted with MeCN, filtered and purified by preparative HPLC-MS (Waters XBridge C18, eluting with a gradient of MeCN/H₂O containing 0.15% NH₄OH) to afford product as a white solid (49 mg, 60%).

¹H NMR (300 MHz, CDCl₃) δ 7.31 (d, J=9.6 Hz, 1H), 7.24 (d, J=9.6 Hz, 1H), 6.89 (d, J=8.7 Hz, 2H), 6.83 (d, J=8.8 Hz, 2H), 6.61-6.59 (m, 1H), 5.28 (s, 2H), 3.77 (s, 3H), 2.98 (s, 3H), 2.42 (s, 3H); LCMS (M+H)⁺: 307.2.

Example 35

4-[(1,7-dimethyl-6H-pyrrolo[2,3-e][1,2,4]-triazolo[4,3-a]pyridin-6-yl)methyl]phenol

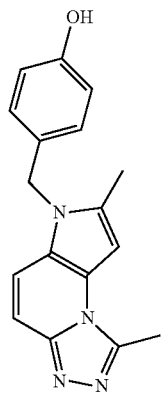

1.0 M Boron tribromide in DCM (0.54 mL, 0.54 mmol, Aldrich) was added to a solution of 6-(4-methoxybenzyl)-1, 7-dimethyl-6H-pyrrolo[2,3-e][1,2,4]triazolo[4,3-a]pyridine (42 mg, 0.137 mmol, from Example 34) in DCM (4 mL) at −78° C., and the reaction was allowed to slowly reach room temperature. The reaction was quenched by the addition of water, followed by saturated NaHCO$_3$ solution. DCM was removed in vacuo and the mixture was diluted with MeOH, filtered and purified by preparative HPLC-MS (Waters XBridge C18, eluting with a gradient of MeCN/H$_2$O containing 0.15% NH$_4$OH) (27 mg, 67%). $^1$H NMR (400 MHz, CDCl$_3$) δ 7.21 (d, J=9.7 Hz, 1H), 7.14 (d, J=9.7 Hz, 1H), 6.81 (d, J=8.6 Hz, 2H), 6.72 (d, J=8.6 Hz, 2H), 6.56 (s, 1H), 5.23 (s, 2H), 2.95 (s, 3H), 2.45 (s, 3H); LCMS (M+H)$^+$: 293.1.

Example 36

2-({3-[(1,7-dimethyl-6H-pyrrolo[2,3-e][1,2,4]-triazolo[4,3-a]pyridin-6-yl)methyl]benzyl}amino)ethanol

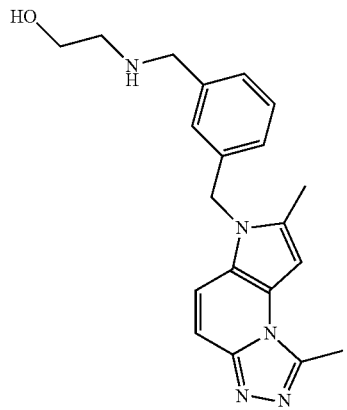 [SMILES: Cc1cc2c(ccc3nnc(C)n32)n1Cc1cccc(CNCCO)c1]

Step 1. {3-[(1,7-dimethyl-6H-pyrrolo[2,3-e][1,2,4]triazolo[4,3-a]pyridin-6-yl)methyl]phenyl}methanol

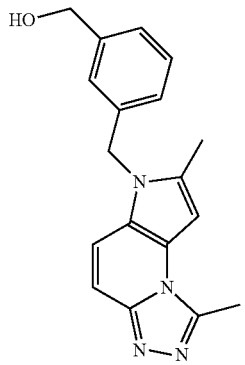 [SMILES: Cc1cc2c(ccc3nnc(C)n32)n1Cc1cccc(CO)c1]

To a suspension of methyl 3-[(1,7-dimethyl-6H-pyrrolo[2,3-e][1,2,4]triazolo[4,3-a]pyridin-6-yl)methyl]benzoate (0.96 g, 2.7 mmol, prepared as in Example 26, Step 1) in THF (90 mL) at 0° C. was added dropwise a solution of 1.0 M LiAlH$_4$ in THF (4.0 mL, 4.0 mmol, Aldrich). After 20 minutes, additional 1.0 M LiAlH$_4$ in THF (1.3 mL, 1.3 mmol) was added. After 20 additional minutes, the reaction was quenched by the dropwise addition of water. The reaction was cooled to 0° C. and excess Rochelle's salt was added and stirred until the solution was clear. Sodium sulfate was then added, the mixture was filtered through celite and the solvent was removed in vacuo. Flash chromatography, eluting with a gradient from 0-10% MeOH in DCM afforded product as a light yellow solid (0.61 g, 74%).

$^1$H NMR (400 MHz, CDCl$_3$) δ 7.35-7.24 (m, 3H), 7.21 (d, J=9.7 Hz, 1H), 7.01 (s, 1H), 6.85-6.80 (m, 1H), 6.62 (s, 1H), 5.35 (s, 2H), 4.66 (s, 2H), 2.98 (s, 3H), 2.43 (s, 3H), 1.98 (br s, 1H). LCMS (M+H)$^+$: 307.0.

Step 2. 2-({3-[(1,7-dimethyl-6H-pyrrolo[2,3-e][1,2,4]triazolo[4,3-a]pyridin-6-yl)methyl]benzyl}amino)ethanol Diisopropylethylamine (26 µL, 0.15 mmol) and methanesulphonic anhydride (13 mg, 0.073 mmol, Aldrich) were added to a solution of {3-[(1,7-dimethyl-6H-pyrrolo[2,3-e][1,2,4]triazolo[4,3-a]pyridin-6-yl)methyl]phenyl}methanol (15 mg, 0.049 mmol, from Step 1) in DCM (1.0 mL). The mixture was stirred until mesylate formation was determined complete as judged by LCMS, and the mixture was then concentrated. The residue was re-dissolved in a mixture of THF (0.50 mL) and MeOH (0.50 mL) and ethanolamine (12 µL, 0.20 mmol, Aldrich) was added and the reaction was stirred for 1.5 hours. The crude reaction mixture was purified using preparative HPLC-MS (Waters XBridge C18, eluting with a gradient of MeCN/H$_2$O containing 0.15% NH$_4$OH) (8.5 mg, 50%).

$^1$H NMR (300 MHz, d$_6$-DMSO) δ 7.64 (dd, J=9.7, 0.6 Hz, 1H), 7.27-7.15 (m, 3H), 7.05 (s, 1H), 6.81 (s, 1H), 6.76 (dt, J=6.7, 1.9 Hz, 1H), 5.49 (s, 2H), 4.44 (t, J=5.2 Hz, 1H), 3.62 (s, 2H), 3.39 (q, J=5.6 Hz, 2H), 2.87 (s, 3H), 2.49-2.44 (m, 2H), 2.38 (s, 3H); LCMS (M+H)$^+$: 350.2.

Example 37

2-[{3-[(1,7-dimethyl-6H-pyrrolo[2,3-e][1,2,4]triazolo[4,3-a]pyridin-6-yl)methyl]benzyl}(methyl)amino]ethanol

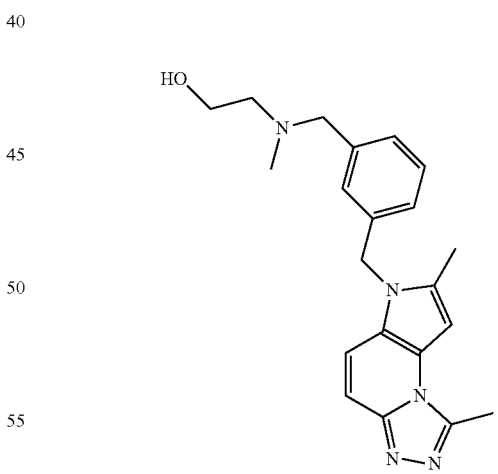

The title compound was prepared according to the methods of Example 36 using 2-(methylamino)ethanol (16 µL, 0.20 mmol, Aldrich) (10 mg, 56%).

$^1$H NMR (300 MHz, d$_6$-DMSO) δ 7.65 (d, J=9.7 Hz, 1H), 7.28-7.13 (m, 3H), 7.06 (s, 1H), 6.80 (s, 1H), 6.77 (d, J=7.3 Hz, 1H), 5.50 (s, 2H), 4.35 (t, J=5.4 Hz, 1H), 3.48-3.40 (m, 2H), 3.42 (s, 2H), 2.87 (s, 3H), 2.40-2.32 (m, 2H), 2.38 (s, 3H), 2.09 (s, 3H).

LCMS (M+H)$^+$: 364.2.

Example 38

1,7-dimethyl-6-[3-(morpholin-4-ylmethyl)benzyl]-6H-pyrrolo[2,3-e][1,2,4]triazolo[4,3-a]pyridine

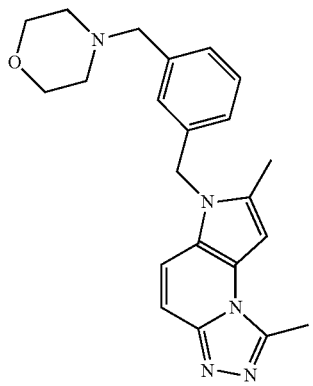 [SMILES: Cc1cc2c(ccc3nnc(C)n32)n1Cc1cccc(CN2CCOCC2)c1]

The title compound was prepared according to the methods of Example 36 using morpholine (17 μL, 0.20 mmol, Aldrich) (8.8 mg, 48%).

$^1$H NMR (300 MHz, d$_6$-DMSO) δ 7.63 (d, J=9.7 Hz, 1H), 7.28-7.19 (m, 2H), 7.15 (d, J=7.5 Hz, 1H), 6.99 (s, 1H), 6.86-6.77 (m, 2H), 5.51 (s, 2H), 3.53-3.42 (m, 4H), 3.38 (s, 2H), 2.87 (s, 3H), 2.38 (s, 3H), 2.33-2.20 (m, 4H); LCMS (M+H)$^+$: 376.2.

Example 39

(1r,3r)-3-((3-((1,7-dimethyl-6H-pyrrolo[2,3-e][1,2,4]triazolo[4,3-a]pyridin-6-yl)methyl)benzyl)amino)cyclobutanol

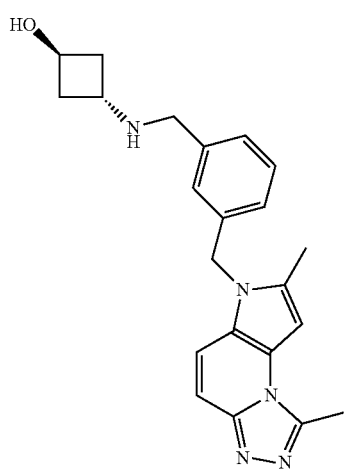 [SMILES: Cc1cc2c(ccc3nnc(C)n32)n1Cc1cccc(CN[C@H]2C[C@H](O)C2)c1]

Prepared by the method of Example 36 using trans-3-aminocyclobutanol hydrochloride (24 mg, 0.20 mmol, Advanced ChemBlocks, Inc.) and diisopropylethylamine (43 μL, 0.24 mmol) and stirring the displacement reaction overnight (5.9 mg, 32%).

$^1$H NMR (300 MHz, d$_6$-DMSO) δ 7.64 (d, J=9.7 Hz, 1H), 7.26-7.14 (m, 3H), 7.06 (s, 1H), 6.81 (s, 1H), 6.76-6.70 (m, 1H), 5.49 (s, 2H), 4.80 (d, J=4.4 Hz, 1H), 4.27-4.13 (m, 1H), 3.50 (s, 2H), 2.87 (s, 3H), 2.39 (s, 3H), 1.98-1.76 (m, 4H). LCMS (M+H)$^+$: 376.2.

Example 40

1-{3-[(1,7-dimethyl-6H-pyrrolo[2,3-e][1,2,4]triazolo[4,3-a]pyridin-6-yl)methyl]phenyl}-N,N-dimethylmethanamine

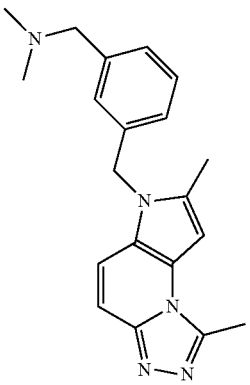

The title compound was prepared according to the methods of Example 36 using 2.0 M dimethylamine in THF (98 μL, 0.20 mmol, Aldrich) (7.9 mg, 48%).

$^1$H NMR (300 MHz, d$_6$-DMSO) δ 7.65 (d, J=9.7 Hz, 1H), 7.28-7.18 (m, 2H), 7.14 (d, J=7.6 Hz, 1H), 7.03 (s, 1H), 6.84-6.75 (m, 2H), 5.51 (s, 2H), 3.30 (s, 2H), 2.87 (s, 3H), 2.37 (s, 3H), 2.06 (s, 6H); LCMS (M+H)$^+$: 334.0.

Example 41

1-{3-[(1,7-dimethyl-6H-pyrrolo[2,3-e][1,2,4]triazolo[4,3-a]pyridin-6-yl)methyl]phenyl}-N-methylmethanamine

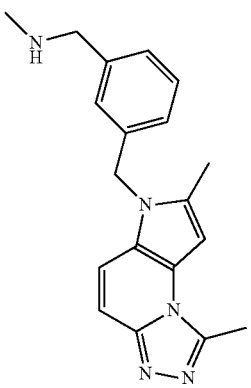

The title compound was prepared according to the methods of Example 36 using 2.0 M methylamine in THF (98 μL, 0.20 mmol, Aldrich) and stirring the displacement reaction overnight (4.5 mg, 29%).

$^1$H NMR (300 MHz, d$_6$-DMSO) δ 7.64 (d, J=9.7 Hz, 1H), 7.27-7.13 (m, 3H), 7.04 (s, 1H), 6.81 (s, 1H), 6.80-6.71 (m,

1H), 5.49 (s, 2H), 3.54 (s, 2H), 2.87 (s, 3H), 2.38 (s, 3H), 2.18 (s, 3H); LCMS (M+H)+: 320.0.

Example 42

N-{3-[(1,7-dimethyl-6H-pyrrolo[2,3-e][1,2,4]triazolo[4,3-a]pyridin-6-yl)methyl]benzyl}ethanamine

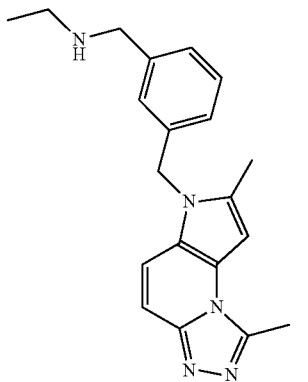 [SMILES: CCNCc1cccc(Cn2c(C)cc3c2ccc2nnc(C)n23)c1]

The title compound was prepared according to the methods of Example 36 using ethylamine (27.6 μL, 0.490 mmol, Aldrich) (9.0 mg, 55%).

1H NMR (300 MHz, d6-DMSO) δ 7.63 (d, J=9.7 Hz, 1H), 7.26-7.14 (m, 3H), 7.03 (s, 1H), 6.81 (s, 1H), 6.79-6.73 (m, 1H), 5.49 (s, 2H), 3.59 (s, 2H), 2.87 (s, 3H), 2.43 (q, J=7.1 Hz, 2H), 2.38 (s, 3H), 0.93 (t, J=7.1 Hz, 3H); LCMS (M+H)+: 334.2.

Example 43

N-{3-[(1,7-dimethyl-6H-pyrrolo[2,3-e][1,2,4]triazolo[4,3-a]pyridin-6-yl)methyl]phenyl}-N'-ethylurea trifluoroacetate salt

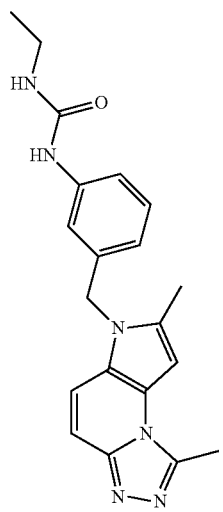 [SMILES: CCNC(=O)Nc1cccc(Cn2c(C)cc3c2ccc2nnc(C)n23)c1]

Step 1. 3-[(1,7-dimethyl-6H-pyrrolo[2,3-e][1,2,4]triazolo[4,3-a]pyridin-6-yl)methyl]aniline

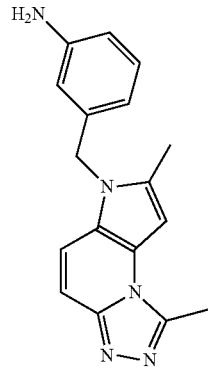

1,7-Dimethyl-6-(3-nitrobenzyl)-6H-pyrrolo[2,3-e][1,2,4]triazolo[4,3-a]pyridine (0.16 g, 0.50 mmol, from Example 25, Step 1) in methanol (100 mL) was hydrogenated for 6.5 hours under 1 atmosphere of hydrogen provided by a balloon, over 10% palladium on activated carbon (100 mg, 0.10 mmol, Degussa type, Aldrich). The reaction mixture was filtered through celite and concentrated to afford product as light yellow solid, which was used without further purification (0.14 g, 96%).

LCMS (M+H)+: 292.0.

Step 2. N-{3-[(1,7-dimethyl-6H-pyrrolo[2,3-e][1,2,4]triazolo[4,3-a]pyridin-6-yl)methyl]phenyl}-N'-ethylurea trifluoroacetate salt 3-[(1,7-Dimethyl-6H-pyrrolo[2,3-e][1,2,4]triazolo[4,3-a]pyridin-6-yl)methyl]aniline (10 mg, 0.034 mmol, from Step 1) was dissolved in a mixture of THF (1.0 mL) and DCM (0.40 mL) and triethylamine (14 μL, 0.10 mmol) and ethane, isocyanato- (12 μL, 0.17 mmol, Aldrich) were added. The product was purified by preparative HPLC-MS (Waters SunFire C18, eluting with a gradient of MeCN/H2O containing 0.1% TFA) (8.3 mg, 51%).

1H NMR (300 MHz, d6-DMSO) δ 8.47 (s, 1H), 8.24 (d, J=9.6 Hz, 1H), 7.50 (d, J=9.5 Hz, 1H), 7.26-7.10 (m, 3H), 7.09 (s, 1H), 6.52 (d, J=7.6 Hz, 1H), 6.11 (t, J=5.4 Hz, 1H), 5.58 (s, 2H), 3.05 (dq, J=7.1, 5.3 Hz, 2H), 2.98 (s, 3H), 2.50 (s, 3H), 0.99 (t, J=7.2 Hz, 3H); LCMS: (M+H)+: 363.2.

Example 44

N-{3-[(1,7-dimethyl-6H-pyrrolo[2,3-e][1,2,4]-triazolo[4,3-a]pyridin-6-yl)methyl]phenyl}urea

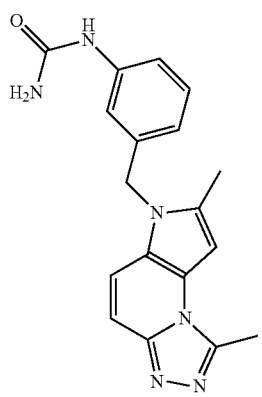 [SMILES: Cc1cc2c(ccc3nnc(C)n32)n1Cc1cccc(NC(N)=O)c1]

To a solution of 3-[(1,7-dimethyl-6H-pyrrolo[2,3-e][1,2,4]triazolo[4,3-a]pyridin-6-yl)methyl]aniline (16 mg, 0.055 mmol, from Example 43, Step 1) in THF (1.6 mL) and DCM (0.64 mL) were added triethylamine (23 µL, 0.16 mmol) and triphosgene (16 mg, 0.055 mmol, Aldrich). The mixture was stirred for 15 minutes, then NH₄OH solution (43 µL, 14.8 N) was added. After stirring for 30 minutes, the product was precipitated as a yellow solid, re-dissolved in MeOH and filtered, then purified via preparative HPLC-MS (Waters XBridge C18, eluting with a gradient of MeCN/H₂O containing 0.15% NH₄OH) (5.5 mg, 30%).

¹H NMR (300 MHz, d₆-DMSO) δ 8.46 (s, 1H), 7.64 (d, J=9.7 Hz, 1H), 7.33 (d, J=8.2 Hz, 1H), 7.23 (d, J=9.7 Hz, 1H), 7.13 (t, J=7.9 Hz, 1H), 6.95 (t, J=1.7 Hz, 1H), 6.81 (s, 1H), 6.53 (d, J=7.6 Hz, 0H), 5.76 (s, 2H), 5.45 (s, 2H), 2.87 (s, 3H), 2.38 (s, 3H); LCMS (M+H)+: 335.2.

Example 45

1,7-dimethyl-6-[3-(pyrrolidin-1-ylmethyl)benzyl]-6H-pyrrolo[2,3-e][1,2,4]triazolo[4,3-a]pyridine

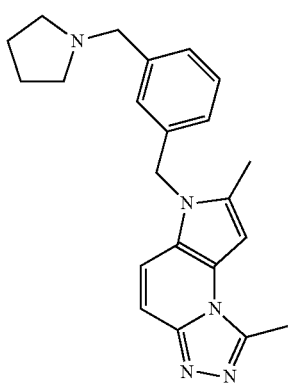 [SMILES: Cc1cc2c(ccc3nnc(C)n32)n1Cc1cccc(CN2CCCC2)c1]

To {3-[(1,7-dimethyl-6H-pyrrolo[2,3-e][1,2,4]triazolo[4,3-a]pyridin-6-yl)methyl]phenyl}methanol (15 mg, 0.049 mmol, from Example 36, Step 1) in DCM (1.0 mL) was added diisopropylethylamine (26 µL, 0.15 mmol) followed by methanesulphonic anhydride (17 mg, 0.098 mmol). After mesylate formation was determined to be complete as judged by LCMS, solvent was removed in vacuo and the residue was re-dissolved in a mixture of THF (0.50 mL) and methanol (0.50 mL). Pyrrolidine (0.016 mL, 0.20 mmol, Aldrich) was added and the reaction was stirred for 2.5 hours. The product was purified using preparative HPLC-MS (Waters XBridge C18, eluting with a gradient of MeCN/H₂O containing 0.15% NH₄OH) (11.4 mg, 65%).

¹H NMR (300 MHz, d₆-DMSO) δ 7.64 (d, J=9.7 Hz, 1H), 7.22 (d, J=9.7 Hz, 1H), 7.22 (t, J=7.5 Hz, 1H), 7.15 (d, J=7.6 Hz, 1H), 7.01 (s, 1H), 6.80 (s, 1H), 6.78 (d, J=7.6 Hz, 1H), 5.51 (s, 2H), 3.47 (s, 2H), 2.87 (s, 3H), 2.37 (s, 3H), 2.35-2.23 (m, 4H), 1.60 (p, J=3.0 Hz, 4H); LCMS (M+H)+: 360.2.

Example 46

1,7-dimethyl-6-[3-(piperidin-1-ylmethyl)benzyl]-6H-pyrrolo[2,3-e][1,2,4]triazolo[4,3-a]pyridine

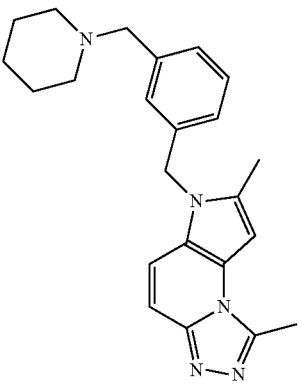 [SMILES: Cc1cc2c(ccc3nnc(C)n32)n1Cc1cccc(CN2CCCCC2)c1]

The title compound was prepared according to the procedures of Example 45, using piperidine (0.019 mL, 0.20 mmol, Aldrich) (11.1 mg, 61%).

¹H NMR (300 MHz, d₆-DMSO) δ 7.63 (d, J=9.7 Hz, 1H), 7.22 (t, J=7.5 Hz, 1H), 7.22 (d, J=9.7 Hz, 1H), 7.13 (d, J=7.7 Hz, 1H), 6.97 (s, 1H), 6.84-6.78 (m, 1H), 6.81 (s, 1H), 5.51 (s,

2H), 3.33 (s, 2H), 2.87 (s, 3H), 2.38 (s, 3H), 2.24-2.15 (m, 4H), 1.43-1.26 (m, 6H); LCMS (M+H)+: 374.2.

Example 47

1,7-dimethyl-6-{3-[(4-methylpiperazin-1-yl)methyl] benzyl}-6H-pyrrolo[2,3-e][1,2,4]triazolo[4,3-a]pyridine

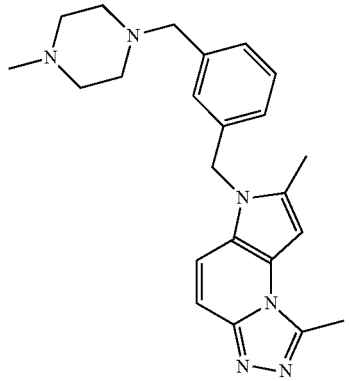

The title compound was prepared according to the procedures of Example 45, using 1-methyl-piperazine (0.022 mL, 0.20 mmol, Aldrich) (10.7 mg, 56%).

$^1$H NMR (300 MHz, d$_6$-DMSO) δ 7.62 (d, J=9.7 Hz, 1H), 7.23 (t, J=7.6 Hz, 1H), 7.21 (d, J=9.8 Hz, 1H), 7.12 (d, J=7.6 Hz, 1H), 6.92 (s, 1H), 6.84 (d, J=7.7 Hz, 1H), 6.81 (s, 1H), 5.51 (s, 2H), 3.35 (s, 2H), 2.87 (s, 3H), 2.37 (s, 3H), 2.31-2.07 (m, 8H), 2.05 (s, 3H); LCMS (M+H)+: 389.2.

Example 48

1,7-dimethyl-6-[3-(piperazin-1-ylmethyl)benzyl]-6H-pyrrolo[2,3-e][1,2,4]triazolo[4,3-a]pyridine

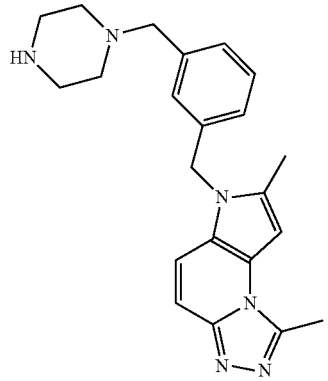 [SMILES: Cc1cc2c(ccc3nnc(C)n32)n1Cc1cccc(CN2CCNCC2)c1]

The title compound was prepared according to the procedures of Example 45, using tert-butyl piperazine-1-carboxylate (36 mg, 0.20 mmol, Beta Pharma). Following the displacement step, solvent was removed in vacuo and replaced with DCM (0.50 mL) and 4.0 M hydrogen chloride in dioxane (0.25 mL, 1.0 mmol). After stirring for 20 minutes, solvent was again removed in vacuo and the residue was re-dissolved in MeOH/H$_2$O and purified using preparative HPLC-MS (Waters XBridge C18, eluting with a gradient of MeCN/H$_2$O containing 0.15% NH$_4$OH) (12.8 mg, 70%).

$^1$H NMR (300 MHz, d$_6$-DMSO) δ 7.63 (d, J=9.7 Hz, 1H), 7.28-7.18 (m, 2H), 7.14 (d, J=7.6 Hz, 1H), 6.99 (s, 1H), 6.85-6.76 (m, 2H), 5.51 (s, 2H), 3.34 (s, 2H), 2.87 (s, 3H), 2.57 (dd, J=4.6, 4.6 Hz, 4H), 2.38 (s, 3H), 2.28-2.10 (m, 4H); LCMS (M+H)+: 375.2

Example 49

{4-[(1,7-dimethyl-6H-pyrrolo[2,3-e][1,2,4]triazolo[4,3-a]pyridin-6-yl)methyl]phenyl}methanol

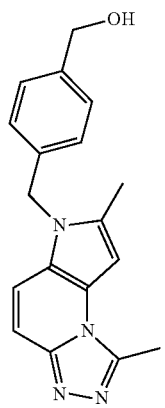

Step 1. methyl 4-[(1,7-dimethyl-6H-pyrrolo[2,3-e][1,2,4]triazolo[4,3-a]pyridin-6-yl)methyl]benzoate

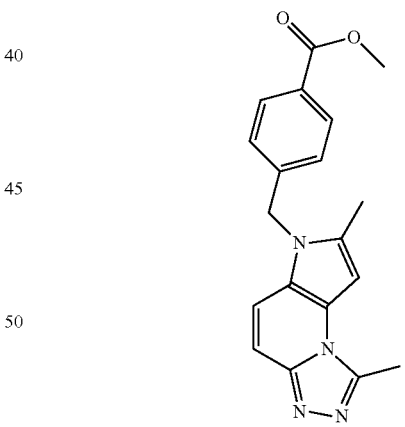

To a solution of 1,7-dimethyl-6H-pyrrolo[2,3-e][1,2,4] triazolo[4,3-a]pyridine (0.15 g, 0.80 mmol, prepared as in Example 2, Step 5) in DMF (20 mL) was added sodium hydride (42 mg, 1.0 mmol, 60% in mineral oil). This was stirred for 10 minutes, followed by the addition of methyl 4-bromomethylbenzoate (0.18 g, 0.80 mmol, Aldrich). After 45 minutes, the reaction mixture was poured into saturated NH$_4$Cl solution and extracted with six portions of EtOAc. The combined extracts were washed twice with water, once with brine, dried over sodium sulfate, filtered and concentrated afford product as a light yellow solid, which was used without further purification in the next Step.

Step 2. {4-[(1,7-dimethyl-6H-pyrrolo[2,3-e][1,2,4]triazolo[4,3-a]pyridin-6-yl)methyl]phenyl}methanol 1.0 M LiAlH$_4$ in THF (1.6 mL, 1.6 mmol, Aldrich) was added dropwise to a solution of the crude product of Step 1 in THF (27 mL) at 0° C. After 30 minutes, the reaction was quenched at 0° C. by the dropwise addition of a small amount of water, followed by excess amount of Rochelle's salt. After 10 minutes, sodium sulfate was added and enough DCM to afford a transparent yellow solution. The mixture was then filtered through celite and the solvent was removed in vacuo. Flash chromatography, eluting with a gradient from 0-10% MeOH in DCM afforded product as a light yellow solid (0.11 g, 44% for two steps).

$^1$H NMR (300 MHz, d$_6$-DMSO) δ 7.64 (d, J=9.7 Hz, 1H), 7.24 (d, J=8.0 Hz, 2H), 7.22 (d, J=9.7 Hz, 1H), 6.95 (d, J=8.2 Hz, 2H), 6.81 (s, 1H), 5.49 (s, 2H), 5.13 (t, J=5.7 Hz, 1H), 4.42 (d, J=5.6 Hz, 2H), 2.87 (s, 3H), 2.39 (s, 3H); LCMS (M+H)$^+$: 307.2.

Example 50

6-[4-(azetidin-1-ylmethyl)benzyl]-1,7-dimethyl-6H-pyrrolo[2,3-e][1,2,4]triazolo[4,3-a]pyridine

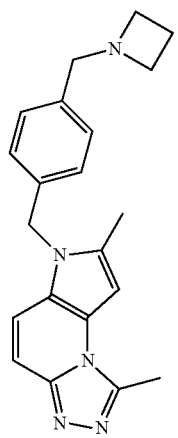 [SMILES: Cc1cc2c(ccc3nnc(C)n32)n1Cc1ccc(CN2CCC2)cc1]

The title compound was prepared according to the procedures of Example 45, using the alcohol of Example 49 as starting material and using azetidine (0.013 mL, 0.20 mmol, Aldrich) in the displacement, which was performed overnight (8.0 mg, 47%).

$^1$H NMR (400 MHz, d$_6$-DMSO) δ 7.64 (d, J=9.7 Hz, 1H), 7.22 (d, J=9.7 Hz, 1H), 7.17 (d, J=8.1 Hz, 2H), 6.92 (d, J=8.1 Hz, 2H), 6.80 (s, 1H), 5.48 (s, 2H), 3.42 (s, 2H), 3.03 (t, J=6.9 Hz, 4H), 2.86 (s, 3H), 2.37 (s, 3H), 1.91 (p, J=6.9 Hz, 2H); LCMS (M+H)$^+$: 346.2.

Example 51

1,7-dimethyl-6-[4-(pyrrolidin-1-ylmethyl)benzyl]-6H-pyrrolo[2,3-e][1,2,4]triazolo[4,3-a]pyridine

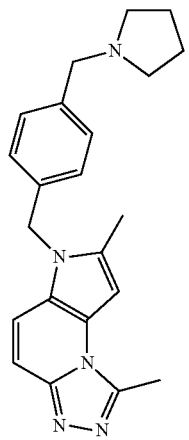 [SMILES: Cc1cc2c(ccc3nnc(C)n32)n1Cc1ccc(CN2CCCC2)cc1]

The title compound was prepared according to the procedures of Example 45, using the alcohol of Example 49 as starting material and using pyrrolidine (0.016 mL, 0.20 mmol, Aldrich) in the displacement, which was performed overnight (11.2 mg, 64%).

$^1$H NMR (300 MHz, d$_6$-DMSO) δ 7.65 (d, J=9.7 Hz, 1H), 7.22 (d, J=9.8 Hz, 1H), 7.22 (d, J=7.7 Hz, 2H), 6.93 (d, J=8.1 Hz, 2H), 6.80 (s, 1H), 5.49 (s, 2H), 3.48 (s, 2H), 2.87 (s, 3H), 2.38 (s, 3H), 2.37-2.31 (m, 4H), 1.63 (p, J=3.1 Hz, 4H); LCMS (M+H)$^+$: 360.2.

Example 52

1-{4-[(1,7-dimethyl-6H-pyrrolo[2,3-e][1,2,4]triazolo[4,3-a]pyridin-6-yl)methyl]benzyl}azetidin-3-ol

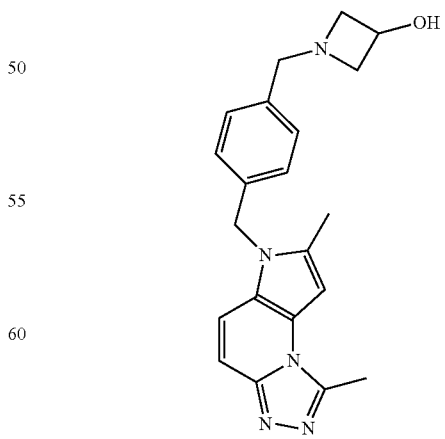

The title compound was prepared according to the procedures of Example 45, using the alcohol of Example 49 as starting material and using azetidin-3-ol hydrochloride (21 mg, 0.20 mmol, Oakwood) and diisopropylethylamine (34 μL, 0.20 mmol) in the displacement, which was performed overnight (10.3 mg, 58%).

¹H NMR (300 MHz, d₆-DMSO) δ 7.64 (d, J=9.7 Hz, 1H), 7.22 (d, J=9.7 Hz, 1H), 7.17 (d, J=8.0 Hz, 2H), 6.92 (d, J=8.0 Hz, 2H), 6.80 (s, 1H), 5.48 (s, 2H), 5.25 (d, J=6.5 Hz, 1H), 4.11 (p, J=6.3 Hz, 1H), 3.46 (s, 2H), 3.40 (td, J=6.0, 1.9 Hz, 2H), 2.87 (s, 3H), 2.68 (td, J=6.2, 1.9 Hz, 2H), 2.38 (s, 3H); LCMS (M+H)⁺: 362.0

Example 53

1-{4-[(1,7-dimethyl-6H-pyrrolo[2,3-e][1,2,4]triazolo[4,3-a]pyridin-6-yl)methyl]phenyl}-N,N-dimethylmethanamine

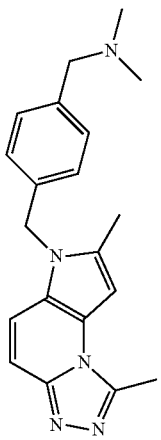 [SMILES: Cc1cc2c(ccc3nnc(C)n32)n1Cc1ccc(CN(C)C)cc1]

The title compound was prepared according to the procedures of Example 45, using the alcohol of Example 49 as starting material and using 2.0 M dimethylamine in THF (0.15 mL, 0.30 mmol, Aldrich) in the displacement (8.0 mg, 49%).

¹H NMR (400 MHz, d₆-DMSO) δ 7.65 (d, J=9.7 Hz, 1H), 7.22 (d, J=9.5 Hz, 1H), 7.20 (d, J=8.0 Hz, 2H), 6.94 (d, J=8.0 Hz, 2H), 6.80 (s, 1H), 5.49 (s, 2H), 3.29 (s, 2H), 2.87 (s, 3H), 2.38 (s, 3H), 2.07 (s, 6H); LCMS (M+H)+: 334.2.

Example 54

6-{3-[(3-methoxyazetidin-1-yl)methyl]benzyl}-1,7-dimethyl-6H-pyrrolo[2,3-e][1,2,4]triazolo[4,3-a]pyridine

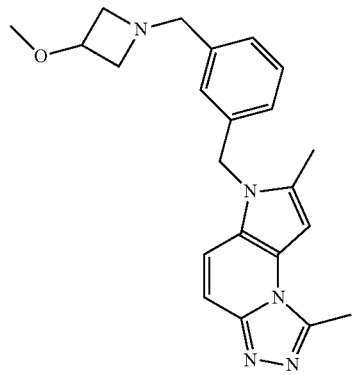

To {3-[(1,7-dimethyl-6H-pyrrolo[2,3-e][1,2,4]triazolo[4,3-a]pyridin-6-yl)methyl]phenyl}methanol (25 mg, 0.082 mmol, from Example 36, Step 1) in DCM (1.7 mL) was added N,N-diisopropylethylamine (43 μL, 0.24 mmol) followed by methanesulphonic anhydride (28 mg, 0.16 mmol). When mesylate formation was deemed complete as judged by LCMS, solvent was removed in vacuo. The residue was re-dissolved in a mixture of THF (0.83 mL) and methanol (0.83 mL) and 3-methoxyazetidine hydrochloride (60. mg, 0.49 mmol) and N,N-diisopropylethylamine (85 μL, 0.49 mmol) were added. When the displacement step was complete, the product was purified by preparative HPLC-MS (Waters XBridge C18, eluting with a gradient of MeCN/H₂O containing 0.15% NH₄OH) (11.1 mg, 36%).

¹H NMR (400 MHz, DMSO) δ 7.64 (d, J=9.7 Hz, 1H), 7.22 (d, J=9.7 Hz, 1H), 7.23-7.18 (m, 1H), 7.11 (d, J=7.6 Hz, 1H), 6.94 (s, 1H), 6.86-6.71 (m, 2H), 5.50 (s, 2H), 3.88 (p, J=5.7 Hz, 1H), 3.47 (s, 2H), 3.08 (s, 3H), 2.87 (s, 3H), 3.35 (td, J=6.1, 1.8 Hz, 2H), 2.73 (td, J=5.8, 1.7 Hz, 2H), 2.37 (s, 3H); LCMS (M+H)⁺: 376.2.

Example 55

3-benzyl-2,8-dimethyl-3H-imidazo[4,5-e][1,2,4]triazolo[4,3-a]pyridine

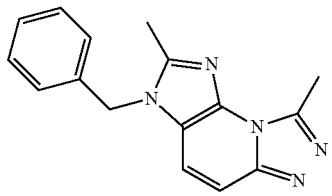 [SMILES: CC(=N)n1c(=N)ccc2c1nc(C)n2Cc1ccccc1]

Step 1. N3-benzyl-6-chloropyridine-2,3-diamine

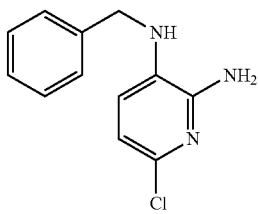 [SMILES: Nc1nc(Cl)ccc1NCc1ccccc1]

A mixture of 6-chloro-2,3-diaminopyridine (2.00 g, 13.9 mmol, Combi-Blocks) and benzaldehyde (1.48 g, 13.9 mmol, Aldrich) in 1,2-dichloroethane (50 mL) was treated with acetic acid (0.2 mL, 3 mmol) and the mixture was allowed to stir for 30 minutes. Na(OAc)$_3$BH (8.8 g, 42 mmol) was added and the reaction was stirred overnight. The reaction was quenched with water, then poured into saturated NaHCO$_3$ solution. The product was extracted with three portions of DCM, and the combined extracts were washed with saturated NaHCO$_3$ solution and brine, dried over sodium sulfate, filtered and concentrated. Flash chromatography, eluting with a gradient from 0-75% EtOAc in hexanes was used to afford purified product.

LCMS (M+H)$^+$: 234.1, 236.1.

Step 2. 1-benzyl-5-chloro-2-methyl-1H-imidazo[4,5-b]pyridine

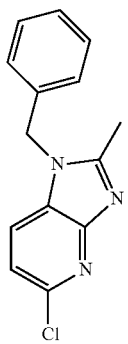

A mixture of N3-benzyl-6-chloropyridine-2,3-diamine (2.56 g, 11.0 mmol, from Step 1), triethyl orthoacetate (15.7 mL, 85.6 mmol, Aldrich) and p-toluenesulfonic acid (0.59 g, 3.4 mmol, Aldrich) in EtOH (55 mL) was heated to reflux for 1.5 hours. The reaction was cooled to room temperature and solvent was evaporated. The residue was partitioned between EtOAc and water. The organic layer was washed with saturated NaHCO$_3$ solution, and brine, dried over sodium sulfate, filtered and concentrated. The product began to crystallize and was triturated with hexanes over the weekend. The white solid was isolated by filtration (2.0 g, 71%).

$^1$H NMR (400 MHz, CDCl$_3$) δ 7.42 (d, J=8.3 Hz, 1H), 7.37-7.29 (m, 3H), 7.13 (d, J=8.3 Hz, 1H), 7.05-7.00 (m, 2H), 5.32 (s, 2H), 2.64 (s, 3H); LCMS (M+H)$^+$: 258.0, 260.1.

Step 3. di-tert-butyl 1-(1-benzyl-2-methyl-1H-imidazo[4,5-b]pyridin-5-yl)hydrazine-1,2-dicarboxylate

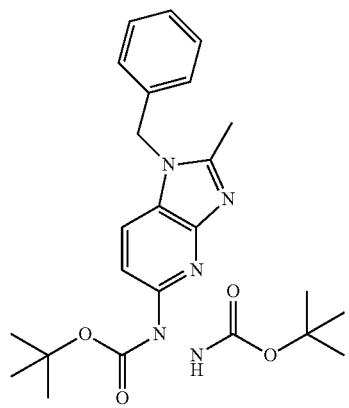

A reaction vessel was charged with 1-benzyl-5-chloro-2-methyl-1H-imidazo[4,5-b]pyridine (1.00 g, 3.88 mmol, from Step 2), di-tert-butyl hydrazine-1,2-dicarboxylate (1.0 g, 4.3 mmol, Aldrich), cesium carbonate (1.26 g, 3.88 mmol), dicyclohexyl(2',4',6'-triisopropylbiphenyl-2-yl)phosphine-(2'-aminobiphenyl-2-yl)(chloro)palladium (1:1) (0.305 g, 0.39 mmol, Aldrich) and toluene (20 mL). The mixture was degassed by bubbling a stream of nitrogen through the solution for 10-15 minutes. The vessel was then sealed and heated to 110° C. for 9 hours. Upon cooling to room temperature, the mixture was applied to silica gel for flash chromatography, and a first pass purification was performed by eluting with a gradient from 0-100% EtOAc in hexanes, followed by elution with a gradient from 0-10% MeOH/DCM. A second purification of the material thus isolated was performed eluting with 100% EtOAc. (0.97 g, 55%).

$^1$H NMR (300 MHz, CD$_3$OD) δ 7.80 (d, J=8.6 Hz, 1H), 7.49 (d, J=8.6 Hz, 1H), 7.43-7.24 (m, 3H), 7.18-7.08 (m, 2H), 5.49 (s, 2H), 2.61 (s, 3H), 1.50 (s, 9H), 1.49 (s, 9H); LCMS (M+H)$^+$: 454.2.

Step 4. 3-benzyl-2,8-dimethyl-3H-imidazo[4,5-e][1,2,4]triazolo[4,3-a]pyridine di-tert-Butyl 1-(1-benzyl-2-methyl-1H-imidazo[4,5-b]pyridin-5-yl)hydrazine-1,2-dicarboxylate (0.075 g, 0.16 mmol, from Step 3) was dissolved in acetic acid (3 mL) and was heated in the microwave to 180° C. for 5 minutes. Solvent was removed in vacuo, the crude product was reconstituted in MeCN and purified via preparative HPLC-MS (Waters XBridge C18, eluting with a gradient of MeCN/H$_2$O containing 0.15% NH$_4$OH) to afford product (27 mg, 59%).

¹H NMR (300 MHz, CD₃OD) δ 7.67 (d, J=9.7 Hz, 1H), 7.43-7.26 (m, 4H), 7.21-7.12 (m, 2H), 5.57 (s, 2H), 3.11 (s, 3H), 2.62 (s, 3H); LCMS (M+H)⁺: 278.0.

Example 56

(6-benzyl-1-methyl-6H-pyrrolo[2,3-e][1,2,4]triazolo[4,3-a]pyridin-7-yl)methanol

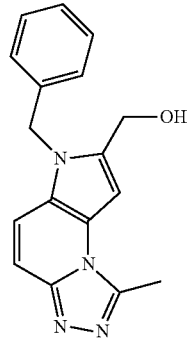 [SMILES: Cc1nnc2ccc3c(cc(CO)n3Cc3ccccc3)n12]

Step 1. 5-chloro-1-(phenylsulfonyl)-1H-pyrrolo[3,2-b]pyridine-2-carbaldehyde

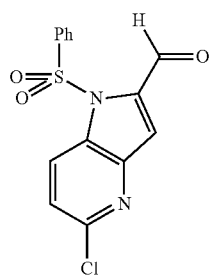 [SMILES: O=Cc1cc2nc(Cl)ccc2n1S(=O)(=O)c1ccccc1]

1.6 M n-Butyllithium in hexanes (1.6 mL, 2.6 mmol) was added dropwise to a solution of N,N-diisopropylamine (0.38 mL, 2.7 mmol) in THF (5.5 mL) at −78° C. Upon complete addition, the reaction temperature was raised to 0° C. for 30 minutes. After re-cooling to −78° C., 5-chloro-1-(phenylsulfonyl)-1H-pyrrolo[3,2-b]pyridine (0.50 g, 1.7 mmol, prepared as in Example 2, Step 1) in THF (2.5 mL) was added dropwise. After stirring for 1 hour at −78° C., N,N-dimethylformamide (0.26 mL, 3.4 mmol) was added. After 25 minutes, the reaction was quenched by the addition of saturated NH₄Cl solution into the −78° C. mixture. After warming to room temperature, the mixture was diluted with water and extracted with EtOAc. The combined extracts were washed twice with water, once with brine, dried over sodium sulfate, filtered and concentrated. Flash chromatography, eluting with a gradient from 0-20% EtOAc in hexanes afforded product as a white solid (0.43 g, 78%).

¹H NMR (300 MHz, CDCl₃) δ 10.53 (s, 1H), 8.52 (d, J=8.9 Hz, 1H), 7.80 (d, J=7.5 Hz, 2H), 7.63 (t, J=7.5 Hz, 1H), 7.55-7.45 (m, 2H), 7.45 (d, J=9.0 Hz, 1H). LCMS (M+H)⁺: 321.0.

Step 2. 5-chloro-1H-pyrrolo[3,2-b]pyridine-2-carbaldehyde

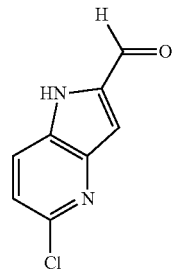 [SMILES: O=Cc1cc2nc(Cl)ccc2[nH]1]

A solution of 5-chloro-1-(phenylsulfonyl)-1H-pyrrolo[3,2-b]pyridine-2-carbaldehyde (0.42 g, 1.3 mmol, prepared in Step 1) in THF (10 mL) was added to a mixture of 2.8 M NaOH (12 mL, 34 mmol) and MeOH (10 mL) at 0° C. After 40 minutes, the reaction was allowed to come to room temperature and stir for 30 minutes. Saturated NH₄Cl was added and was extracted twice with DCM. The extracts were washed with water and then with brine, dried over sodium sulfate, filtered and concentrated. Flash chromatography, eluting with a gradient from 0-30% EtOAc in hexanes afforded product as a white solid (0.19 g, 80%).

¹H NMR (300 MHz, CDCl₃) δ 9.96 (s, 1H), 9.14 (s, 1H), 7.77 (dd, J=8.7, 0.9 Hz, 1H), 7.38 (dd, J=2.1, 0.9 Hz, 1H), 7.33 (d, J=8.7 Hz, 1H). LCMS (M+H)⁺: 180.9.

Step 3. (1-benzyl-5-chloro-1H-pyrrolo[3,2-b]pyridin-2-yl)methanol

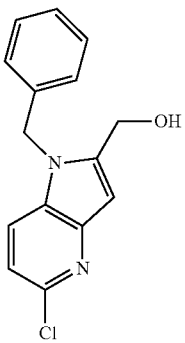 [SMILES: OCc1cc2nc(Cl)ccc2n1Cc1ccccc1]

K₂CO₃ (0.39 g, 2.8 mmol) and benzyl bromide (0.12 mL, 1.0 mmol) were added to a solution of 5-chloro-1H-pyrrolo[3,2-b]pyridine-2-carbaldehyde (0.17 g, 0.94 mmol, from Step 1) in DMF (3.6 mL). After 15 minutes, the reaction mixture was partitioned between EtOAc and water, and the organic layer was washed with two portions of water, one portion of brine, then dried over sodium sulfate, filtered and concentrated to afford 0.26 g of crude 1-benzyl-5-chloro-1H-pyrrolo[3,2-b]pyridine-2-carbaldehyde as a yellow solid. Sodium tetrahydroborate (53 mg, 1.4 mmol) was added to a solution of the crude aldehyde in THF (5.0 mL) and EtOH (5.0 mL). After 15 minutes, the reaction mixture was quenched with saturated NH$_4$Cl, and was extracted with EtOAc. The extracts were washed with water followed by brine, dried over sodium sulfate, filtered and concentrated. Flash chromatography, eluting with a gradient from 0-40% EtOAc in hexanes afforded purified product as a white solid (0.21 g, 82%). $^1$H NMR (300 MHz, CDCl$_3$) δ 7.45 (d, J=8.6 Hz, 1H), 7.33-7.25 (m, 3H), 7.06 (d, J=8.6 Hz, 1H), 7.03-6.88 (m, 2H), 6.66 (s, 1H), 5.47 (s, 2H), 4.78 (s, 2H).

LCMS (M+H)$^+$: 273.1.

Step 4. 1-benzyl-2-({[tert-butyl(dimethyl)silyl]oxy}methyl)-5-chloro-1H-pyrrolo[3,2-b]pyridine tert-Butyldimethylsilyl chloride (0.12 g, 0.81 mmol) and 1H-imidazole (60. mg, 0.88 mmol) were added to a solution of (1-benzyl-5-chloro-1H-pyrrolo[3,2-b]pyridin-2-yl)methanol (0.20 g, 0.73 mmol, from Step 2) in DCM (10 mL). After stirring for 4 hours, additional tert-butyldimethylsilyl chloride (33 mg, 0.22 mmol) and 1H-imidazole (15 mg, 0.22 mmol) were added and the reaction was continued for one hour. The mixture was filtered and the filtrate was concentrated. The product was purified by flash chromatography, eluting with a gradient from 0-10% EtOAc in hexanes to afford a white solid (0.26 g, 92%).

$^1$H NMR (300 MHz, CDCl$_3$) δ 7.40 (d, J=8.6 Hz, 1H), 7.33-7.20 (m, 3H), 7.03 (d, J=8.6 Hz, 1H), 6.99-6.92 (m, 2H), 6.59 (s, 1H), 5.44 (s, 2H), 4.78 (s, 2H), 0.85 (s, 9H), 0.03 (s, 6H). LCMS (M+H)$^+$: 387.0.

Step 5. di-tert-butyl 1-[1-benzyl-2-({[tert-butyl(dimethyl)silyl]oxy}methyl)-1H-pyrrolo[3,2-b]pyridin-5-yl]hydrazine-1,2-dicarboxylate

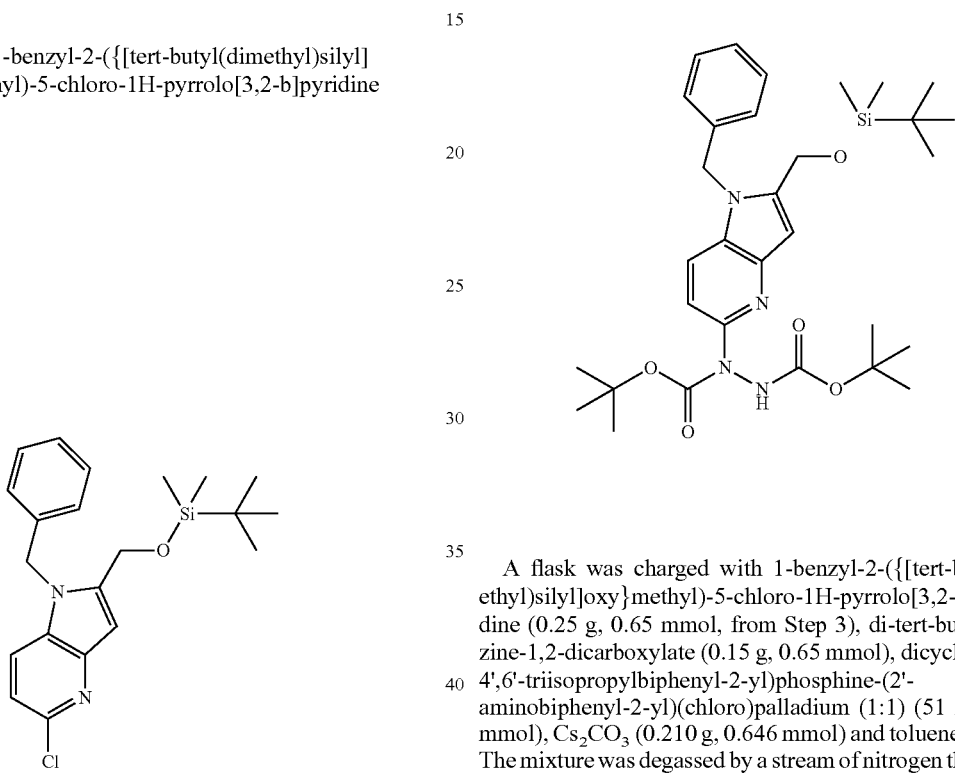

A flask was charged with 1-benzyl-2-({[tert-butyl(dimethyl)silyl]oxy}methyl)-5-chloro-1H-pyrrolo[3,2-b]pyridine (0.25 g, 0.65 mmol, from Step 3), di-tert-butyl hydrazine-1,2-dicarboxylate (0.15 g, 0.65 mmol), dicyclohexyl(2',4',6'-triisopropylbiphenyl-2-yl)phosphine-(2'-aminobiphenyl-2-yl)(chloro)palladium (1:1) (51 mg, 0.065 mmol), Cs$_2$CO$_3$ (0.210 g, 0.646 mmol) and toluene (2.1 mL). The mixture was degassed by a stream of nitrogen through the solution. The mixture was then sealed and heated to 105° C. for 70 minutes. The reaction was diluted with DCM, filtered and concentrated. Purification via flash chromatography, eluting with a gradient from 0-10% EtOAc in hexanes afforded product as a white solid (0.20 g, 53%).

$^1$H NMR (300 MHz, CDCl$_3$) δ 7.47 (d, J=8.6 Hz, 1H), 7.35-7.18 (m, 4H), 6.99 (d, J=7.9 Hz, 2H), 6.57 (s, 1H), 5.44 (s, 2H), 4.77 (s, 2H), 1.49 (s, 9H), 1.46 (s, 9H), 0.85 (s, 9H), 0.02 (s, 6H). LCMS (M+H)$^+$: 583.3.

Step 6. (6-benzyl-1-methyl-6H-pyrrolo[2,3-e][1,2,4]triazolo[4,3-a]pyridin-7-yl)methanol di-tert-Butyl 1-[1-benzyl-2-({[tert-butyl(dimethyl)silyl]oxy}methyl)-1H-pyrrolo[3,2-b]pyridin-5-yl]hydrazine-1,2-dicarboxylate (0.20 g, 0.34 mmol, from Step 4) in AcOH (2.7 mL) was heated in the microwave to a temperature of 180° C. for 5 minutes. Acetic acid was removed in vacuo and the residue was then stirred with NaOH (69 mg, 1.7 mmol) in THF (2.0 mL) and water (2 mL) for 20 minutes. The product was purified by preparative HPLC-MS (C18 eluting with a gradient of MeCN and H$_2$O containing 0.15% NH$_4$OH). Yield: (38 mg, 38%).

¹H NMR (300 MHz, CDCl₃) δ 7.40-7.18 (m, 5H), 7.03-6.94 (m, 2H), 6.72 (s, 1H), 5.54 (s, 2H), 4.76 (d, J=5.2 Hz, 2H), 2.95 (s, 3H). LCMS (M+H)⁺: 293.1.

Example 57

6-benzyl-7-(1H-imidazol-1-ylmethyl)-1-methyl-6H-pyrrolo[2,3-e][1,2,4]triazolo[4,3-a]pyridine

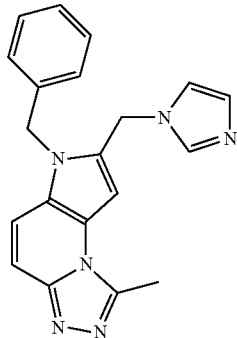 [SMILES: Cc1nnc2ccc3c(cc(Cn4ccnc4)n3Cc3ccccc3)n12]

(6-Benzyl-1-methyl-6H-pyrrolo[2,3-e][1,2,4]triazolo[4,3-a]pyridin-7-yl)methanol (13 mg, 0.044 mmol, from Example 56) and N,N-carbonyldiimidazole (14 mg, 0.089 mmol, Aldrich) in MeCN (2.0 mL) were stirred for 75 minutes, followed by the addition of N,N-carbonyldiimidazole (7.2 mg, 0.044 mmol) and 1H-imidazole (26 mg, 0.38 mmol). The reaction was then stirred overnight and purified via preparative HPLC-MS (C18 eluting with a gradient of MeCN and H₂O containing 0.15% NH₄OH) to afford product (2.5 mg, 16%).

¹H NMR (300 MHz, CD₃OD) δ 7.64 (s, 1H), 7.60 (d, J=9.8 Hz, 1H), 7.32 (d, J=9.8 Hz, 1H), 7.27-7.19 (m, 3H), 7.15 (s, 1H), 7.09 (s, 1H), 6.89 (s, 1H), 6.87-6.80 (m, 2H), 5.56 (s, 2H), 5.47 (s, 2H), 3.00 (s, 3H). LCMS (M+H)⁺: 343.1.

Example 58

6-benzyl-1-methyl-6H-pyrrolo[2,3-e][1,2,4]triazolo[4,3-a]pyridine-7-carboxamide

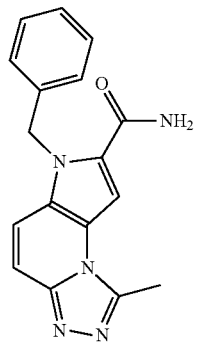 [SMILES: Cc1nnc2ccc3c(cc(C(N)=O)n3Cc3ccccc3)n12]

Step 1. tert-butyl 5-chloro-1-(phenylsulfonyl)-1H-pyrrolo[3,2-b]pyridine-2-carboxylate

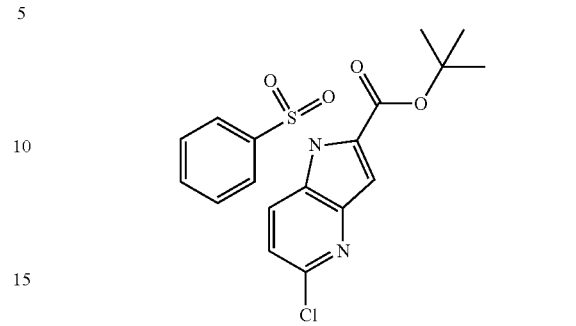

1.6 M n-Butyllithium in hexanes (1.9 mL, 3.1 mmol) was added dropwise to a solution of N,N-diisopropylamine (0.46 mL, 3.3 mmol) in tetrahydrofuran (6.6 mL, 82 mmol) at −78° C. After complete addition, the reaction temperature was raised to 0° C. for 30 minutes, followed by re-cooling to −78° C. A solution of 5-chloro-1-(phenylsulfonyl)-1H-pyrrolo[3,2-b]pyridine (0.600 g, 2.05 mmol, prepared as in Example 2, Step 1) in THF (3.0 mL) was then added dropwise, and the reaction was stirred at −78° C. for 1 hour. Di-tert-butyldicarbonate (0.89 g, 4.1 mmol, Aldrich) dissolved in THF (3.0 mL) was then added and the mixture was poured cold (from −78° C. bath) into a reparatory funnel containing water. Ethyl acetate was added, and the mixture was extracted and layers separated. The aqueous phase was extracted with an additional three portions of EtOAc. The combined organics were washed with water, followed by brine, were dried over sodium sulfate, decanted, and the solvent removed in vacuo. Flash chromatography, eluting with a gradient from 0-50% EtOAc in hexanes afforded purified product (0.58 g, 72%).

¹H NMR (300 MHz, CDCl₃) δ 8.32 (d, 1H), 8.08-7.97 (m, 2H), 7.68-7.58 (m, 1H), 7.57-7.47 (m, 2H), 7.32 (d, J=8.8 Hz, 1H), 7.05 (s, 1H), 1.61 (s, 9H). LCMS (M+H)⁺: 393.1395.1

Step 2. di-tert-butyl 1-[2-(tert-butoxycarbonyl)-1-(phenylsulfonyl)-1H-pyrrolo[3,2-b]pyridin-5-yl]hydrazine-1,2-dicarboxylate

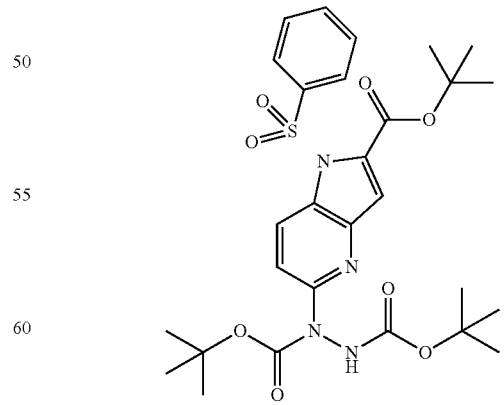

tert-Butyl 5-chloro-1-(phenylsulfonyl)-1H-pyrrolo[3,2-b]pyridine-2-carboxylate (0.500 g, 1.27 mmol, from Step 1), di-tert-butyl hydrazine-1,2-dicarboxylate (0.32 g, 1.4 mmol)

and Cs₂CO₃ (0.41 g, 1.3 mmol) were combined in toluene (6 mL) and dicyclohexyl(2',4',6'-triisopropylbiphenyl-2-yl)phosphine-(2'-aminobiphenyl-2-yl)(chloro)palladium (1:1) (0.10 g, 0.13 mmol) was added. The mixture was degassed by a stream of nitrogen through the solution for 10 minutes and was heated to 110° C. for 4 hours. The reaction mixture was cooled to room temperature, partitioned between EtOAc and water, the aqueous phase was extracted a total of three times. The combined extracts were dried over sodium sulfate, filtered and concentrated. Flash chromatography, eluting with a gradient from 0-30% EtOAc in hexanes afforded purified product (0.43 g, 57%).

¹H NMR (300 MHz, CDCl₃) δ 8.33 (d, J=9.1 Hz, 1H), 8.29 (s, 1H), 8.00 (d, J=8.0 Hz, 2H), 7.77 (d, J=8.9 Hz, 1H), 7.57 (t, J=7.4 Hz, 1H), 7.47 (t, J=7.7 Hz, 2H), 7.14 (s, 1H), 1.57 (s, 9H), 1.43 (s, 9H), 1.39 (s, 9H). LCMS (M+H)⁺: 589.0.

Step 3. 1-methyl-6-(phenylsulfonyl)-6H-pyrrolo[2,3-e][1,2,4]triazolo[4,3-a]pyridine-7-carboxylic acid

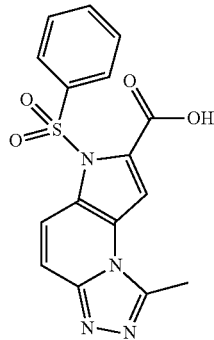 [SMILES: Cc1nnc2ccc3c(cc(C(=O)O)n3S(=O)(=O)c3ccccc3)n12]

A solution of di-tert-butyl 1-[2-(tert-butoxycarbonyl)-1-(phenylsulfonyl)-1H-pyrrolo[3,2-b]pyridin-5-yl]hydrazine-1,2-dicarboxylate (0.430 g, 0.730 mmol, from Step 2) in AcOH (7 mL) was heated in the microwave to a temperature of 180° C. for 3 minutes. The solid product was isolated by filtration and air dried, and used without further purification. Yield: (0.106 g, 41%). LCMS (M+H)+: 357.1.

Step 4. 6-benzyl-1-methyl-6H-pyrrolo[2,3-e][1,2,4]triazolo[4,3-a]pyridine-7-carboxylic acid

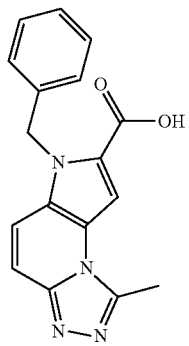 [SMILES: Cc1nnc2ccc3c(cc(C(=O)O)n3Cc3ccccc3)n12]

To a suspension of 1-methyl-6-(phenylsulfonyl)-6H-pyrrolo[2,3-e][1,2,4]triazolo[4,3-a]pyridine-7-carboxylic acid (0.106 g, 0.297 mmol, from Step 3) in THF (2 mL) and methanol (2 mL) was added 1.0 M NaOH (2 mL, 2 mmol) and the reaction was stirred for 1 hour. The reaction was diluted with methanol and was purified by preparative HPLC-MS (C18 eluting with a gradient of MeCN and H₂O containing 0.15% NH₄OH). The eluent was evaporated and the resulting solid was dissolved in DMF (3 mL). K₂CO₃ (0.16 g, 1.2 mmol) followed by benzyl bromide (0.053 mL, 0.45 mmol) were added and the reaction was stirred overnight. The reaction was diluted with water and extracted with three portions of ethyl acetate. The combined extracts were washed with water, then brine, dried over sodium sulfate, filtered and concentrated. The residue was stirred with 1.0 N NaOH (2 mL) in THF (2 mL) and MeOH (2 mL) for 1 hour. Purified via preparative HPLC-MS (C18 eluting with a gradient of MeCN and H₂O containing 0.15% NH₄OH) afforded product (34 mg, 37%). ¹H NMR (300 MHz, CD₃OD) δ 7.62 (dd, J=9.8, 0.7 Hz, 1H), 7.44 (d, J=0.6 Hz, 1H), 7.29 (d, J=9.8 Hz, 1H), 7.26-7.08 (m, 5H), 6.15 (s, 2H), 2.99 (s, 3H). LCMS (M+H)⁺: 307.1.

Step 5. 6-benzyl-1-methyl-6H-pyrrolo[2,3-e][1,2,4]triazolo[4,3-a]pyridine-7-carboxamide To a solution of 6-benzyl-1-methyl-6H-pyrrolo[2,3-e][1,2,4]triazolo[4,3-a]pyridine-7-carboxylic acid (0.0096 g, 0.031 mmol, from Step 4) in DMF (0.5 mL) was added N,N-diisopropylethylamine (0.022 mL, 0.12 mmol) followed by N,N,N',N'-tetramethyl-O-(7-azabenzotriazol-1-yl)uronium hexafluorophosphate (0.021 g, 0.056 mmol). The reaction was stirred for 2 minutes before 28% NH₄OH was added (0.1 mL). The mixture was diluted with MeOH and purified via preparative HPLC-MS (C18 eluting with a gradient of MeCN and H₂O containing 0.15% NH₄OH). Yield: (5 mg, 50%).

¹H NMR (300 MHz, CD₃OD) δ 7.72 (d, J=10.9 Hz, 1H), 7.70 (s, 1H), 7.42 (dd, J=9.8, 1.3 Hz, 1H), 7.34-7.16 (m, 3H), 7.11 (d, J=7.6 Hz, 2H), 6.04 (s, 2H), 3.00 (s, 3H). LCMS (M+H)⁺: 306.0.

Example 59

6-benzyl-N-ethyl-1-methyl-6H-pyrrolo[2,3-e][1,2,4]triazolo[4,3-a]pyridine-7-carboxamide

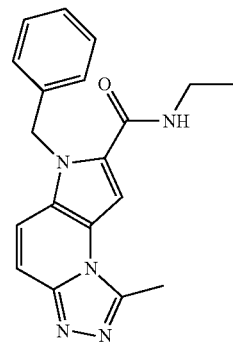 [SMILES: CCNC(=O)c1cc2c(ccc3nnc(C)n32)n1Cc1ccccc1]

To a solution of 6-benzyl-1-methyl-6H-pyrrolo[2,3-e][1,2,4]triazolo[4,3-a]pyridine-7-carboxylic acid (0.0067 g, 0.022 mmol, Example 58, Step 4) in DMF (0.3 mL) was added N,N-diisopropylethylamine (0.015 mL, 0.087 mmol, Aldrich) followed by N,N,N',N'-tetramethyl-O-(7-azabenzotriazol-1-yl)uronium hexafluorophosphate (0.015 g, 0.039 mmol, Aldrich). After 2 minutes, ethylamine (0.0123 mL, 0.219 mmol, Aldrich) was introduced. When the reaction was determined complete by LCMS, the mixture was diluted with MeOH and purified via preparative HPLC-MS (C18 eluting with a gradient of MeCN and H₂O containing 0.15% NH₄OH). Yield: (5 mg, 70%).

¹H NMR (300 MHz, CD₃OD) δ 7.73 (d, J=9.9 Hz, 1H), 7.58 (s, 1H), 7.41 (dd, J=9.9, 0.9 Hz, 1H), 7.32-7.17 (m, 3H), 7.10 (d, J=8.1 Hz, 2H), 6.00 (s, 2H), 3.39 (q, J=7.3 Hz, 2H), 3.01 (s, 3H), 1.21 (t, J=7.2 Hz, 3H). LCMS (M+H)⁺: 334.0.

Example 60

1-[(6-benzyl-1-methyl-6H-pyrrolo[2,3-e][1,2,4]triazolo[4,3-a]pyridin-7-yl)carbonyl]azetidine-3-carbonitrile

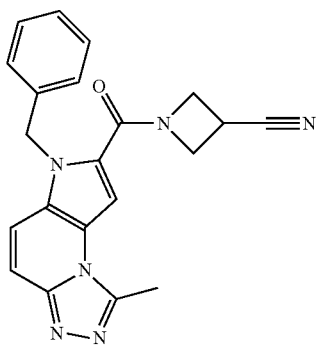 [SMILES: Cc1nnc2ccc3c(cc(C(=O)N4CC(C#N)C4)n3Cc3ccccc3)n12]

To a solution of 6-benzyl-1-methyl-6H-pyrrolo[2,3-e][1,2,4]triazolo[4,3-a]pyridine-7-carboxylic acid (0.010 g, 0.034 mmol, Example 58, Step 4) in DMF (0.5 mL) was added N,N-diisopropylethylamine (0.035 mL, 0.20 mmol) followed by N,N,N',N'-tetramethyl-O-(7-azabenzotriazol-1-yl)uronium hexafluorophosphate (0.023 g, 0.060 mmol). After stirring for 2 minutes, azetidine-3-carbonitrile hydrochloride (0.012 g, 0.10 mmol, PharmaBlock) was added. When the reaction was determined complete by LCMS, the mixture was diluted with MeOH and purified via preparative HPLC-MS (C18 eluting with a gradient of MeCN and H₂O containing 0.15% NH₄OH). Yield: (6 mg, 50%).

¹H NMR (300 MHz, CD₃OD) δ 7.76 (d, J=9.8 Hz, 1H), 7.46 (dd, J=9.9, 1.1 Hz, 1H), 7.33 (s, 1H), 7.31-7.18 (m, 3H), 7.11 (d, J=7.8 Hz, 2H), 5.86 (s, 2H), 4.56 (br m, 4H), 3.74 (ddd, J=15.6, 8.7, 6.6 Hz, 1H), 3.00 (s, 3H). LCMS (M+H)⁺: 371.0.

Example 61

2-(6-benzyl-1-methyl-6H-pyrrolo[2,3-e][1,2,4]triazolo[4,3-a]pyridin-7-yl)ethanol

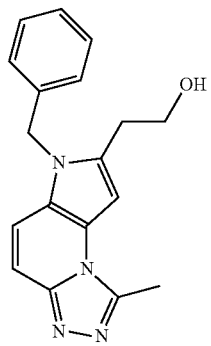 [SMILES: Cc1nnc2ccc3c(cc(CCO)n3Cc3ccccc3)n12]

Step 1. 2-(2-{[tert-butyl(dimethyl)silyl]oxy}ethyl)-5-chloro-1-(phenylsulfonyl)-1H-pyrrolo[3,2-b]pyridine

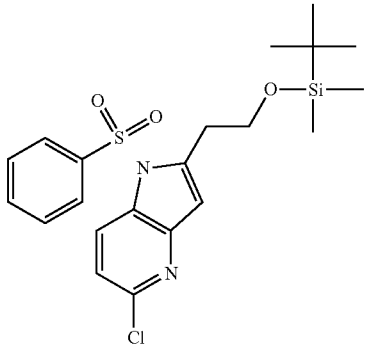

1.6 M n-Butyllithium in hexanes (12 mL, 19 mmol) was added dropwise to a solution of N,N-diisopropylamine (2.9 mL, 20. mmol) in THF (41 mL) at −78° C. After complete addition, the reaction temperature was raised to 0° C. for 30 minutes, followed by re-cooling to −78° C. A solution of 5-chloro-1-(phenylsulfonyl)-1H-pyrrolo[3,2-b]pyridine (3.74 g, 12.8 mmol, prepared as in Example 2, Step 1) in THF (19 mL) was added dropwise. After stirring for 1 h at −78° C., 1,3,2-dioxathiolane 2,2-dioxide (3.2 g, 26 mmol, Aldrich) in THF (9.4 mL) was added. The cold bath was then removed and the mixture was allowed to warm to room temperature over 1 hour. The reaction was cooled to 0° C. and 12.0 M hydrogen chloride in water (6.4 mL, 77 mmol), then was allowed to warm to room temperature and stir overnight. The mixture was then neutralized with NaHCO₃ and was extracted with two portions of EtOAc. The combined extracts were dried over sodium sulfate, filtered and concentrated to afford the crude alcohol, which was dissolved in DCM (100. mL), and tert-butyldimethylsilyl chloride (2.9 g, 19 mmol, Aldrich) and 1H-imidazole (1.4 g, 20. mmol, Aldrich) were added. After 15 minutes, the mixture was washed with water, brine, dried over sodium sulfate, filtered and concentrated. Flash chromatography, eluting with a gradient from 0-10% EtOAc in hexanes afforded product as a light yellow oil (5.02 g, 87%).

$^1$H NMR (300 MHz, CDCl$_3$) δ 8.37 (dd, J=8.7, 0.7 Hz, 1H), 7.75-7.65 (m, 2H), 7.63-7.53 (m, 1H), 7.49-7.41 (m, 2H), 7.20 (d, J=8.7 Hz, 1H), 6.68-6.56 (m, 1H), 3.97 (t, J=6.2 Hz, 2H), 3.21 (t, J=6.2 Hz, 2H), 0.84 (s, 9H), −0.00 (s, 6H). LCMS (M+H)$^+$: 450.9.

Step 2. di-tert-butyl 1-[2-(2-{[tert-butyl(dimethyl)silyl]oxy}ethyl)-1-(phenylsulfonyl)-1H-pyrrolo[3,2-b]pyridin-5-yl]hydrazine-1,2-dicarboxylate

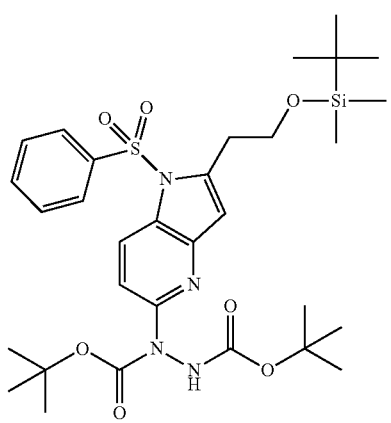 [SMILES: CC(C)(C)OC(=O)NN(C(=O)OC(C)(C)C)c1ccc2c(cc(CCO[Si](C)(C)C(C)(C)C)n2S(=O)(=O)c2ccccc2)n1]

A flask was charged with 2-(2-{[tert-butyl(dimethyl)silyl]oxy}ethyl)-5-chloro-1-(phenylsulfonyl)-1H-pyrrolo[3,2-b]pyridine (5.0 g, 11 mmol, from Step 1), di-tert-butyl hydrazine-1,2-dicarboxylate (2.8 g, 12 mmol, Aldrich), dicyclohexyl(2',4',6'-triisopropylbiphenyl-2-yl)phosphine-(2'-aminobiphenyl-2-yl)(chloro)palladium (1:1) (0.77 g, 0.98 mmol, Aldrich), Cs$_2$CO$_3$ (3.61 g, 11.1 mmol, Aldrich) and toluene (35 mL). The mixture was degassed by a stream of nitrogen through the solution. The mixture was then heated to 108° C. for 3 h then overnight at 100° C. The mixture was cooled to room temperature and diluted with DCM, then was filtered and the filtrate was concentrated. Flash chromatography, eluting with a gradient from 0-20% EtOAc in hexanes afforded product as a light yellow solid (4.9 g, 68%).

$^1$H NMR (300 MHz, CDCl$_3$) δ 8.39 (d, J=9.0 Hz, 1H), 7.77-7.65 (m, 2H), 7.65-7.50 (m, 2H), 7.50-7.38 (m, 2H), 7.01 (s, 1H), 6.59 (s, 1H), 3.97 (t, J=6.4 Hz, 2H), 3.22 (t, J=6.4 Hz, 2H), 1.51 (s, 9H), 1.47 (s, 9H), 0.86 (s, 9H), 0.02 (s, 6H). LCMS (M+H)$^+$: 647.2.

Step 3. 7-(2-{[tert-butyl(dimethyl)silyl]oxy}ethyl)-1-methyl-6H-pyrrolo[2,3-e][1,2,4]triazolo[4,3-a]pyridine

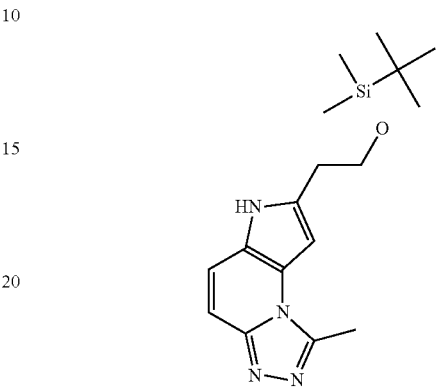

di-tert-Butyl 1-[2-(2-{[tert-butyl(dimethyl)silyl]oxy}ethyl)-1-(phenylsulfonyl)-1H-pyrrolo[3,2-b]pyridin-5-yl]hydrazine-1,2-dicarboxylate (4.9 g, 7.6 mmol, from Step 2) in AcOH (60 mL) was divided into portions and each was heated in the microwave to a temperature of 180° C. for 4 minutes. The portions were combined and AcOH was removed in vacuo and the residue was dissolved in tetrahydrofuran (61 mL) and methanol (61 mL) and cooled to 0° C. 2.8 M NaOH (70 mL, 200 mmol) was added. After stirring for 15 minutes, sat'd NH$_4$Cl was added and the product was extracted with DCM. The combined extracts were dried over sodium sulfate, filtered and concentrated. Flash chromatography, eluting with a gradient from 0-10% MeOH in DCM afforded product as an off-white solid (1.2 g, 48%).

$^1$H NMR (300 MHz, CDCl$_3$) δ 9.42 (br s, 1H), 7.35 (d, J=9.7 Hz, 1H), 7.30 (d, J=9.6 Hz, 1H), 6.56 (s, 1H), 3.97 (t, J=5.5 Hz, 2H), 3.01 (t, J=5.5 Hz, 2H), 2.97 (s, 3H), 0.96 (s, 9H), 0.11 (s, 6H). LCMS (M+H)$^+$: 331.0.

Step 4. 2-(6-benzyl-1-methyl-6H-pyrrolo[2,3-e][1,2,4]triazolo[4,3-a]pyridin-7-yl)ethanol Sodium hydride (0.10 g, 2.5 mmol, 60% in mineral oil) was added to a solution of 7-(2-{[tert-butyl(dimethyl)silyl]oxy}ethyl)-1-methyl-6H-pyrrolo[2,3-e][1,2,4]triazolo[4,3-a]pyridine (0.64 g, 1.9 mmol, from Step 3) in DMF (40 mL) at 0° C. After 10 minutes, benzyl bromide (0.28 mL, 2.3 mmol) was added and the reaction was stirred for 15 minutes. The reaction was quenched by the addition of sat'd NH$_4$Cl and the product was extracted with EtOAc. The combined extracts were washed with two portions of water, one portion of brine, dried over sodium sulfate, filtered and concentrated to afford the crude benzylated product as a yellow solid. The silyl protecting group was removed by stirring with 12.0 M HCl (1.0 mL, 12 mmol) in EtOH (40 mL) for 80 minutes. The reaction was neutralized with sat'd NaHCO$_3$ solution and the aqueous layer was saturated by the addition of solid NaCl, then the product was extracted with DCM. The extract was dried over sodium sulfate, filtered and concentrated. The product was purified by flash chromatography, eluting with a gradient from 0-10% MeOH in DCM to afford product as a white solid (0.46 g, 78%).

¹H NMR (300 MHz, CDCl₃) δ 7.32-7.22 (m, 3H), 7.01 (s, 2H), 6.93-6.86 (m, 2H), 6.51 (s, 1H), 5.45 (s, 2H), 4.45 (br s, 1H), 4.03 (t, J=5.5 Hz, 2H), 2.95 (t, J=5.7 Hz, 2H), 2.88 (s, 3H). LCMS (M+H)⁺: 307.0.

Example 62

6-benzyl-1-methyl-7-(1H-pyrazol-5-yl)-6H-pyrrolo[2,3-e][1,2,4]-triazolo[4,3-a]pyridine

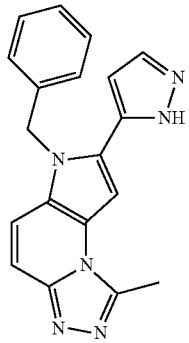 [SMILES: Cc1nnc2ccc3c(cc(-c4ccn[nH]4)n3Cc3ccccc3)n12]

Step 1. 2-bromo-5-chloro-1-(phenylsulfonyl)-1H-pyrrolo[3,2-b]pyridine trifluoroacetate salt

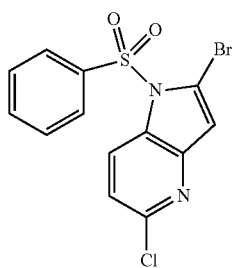 [SMILES: O=S(=O)(c1ccccc1)n1c(Br)cc2nc(Cl)ccc21]

1.6 M n-Butyllithium in hexanes (1.6 mL, 2.6 mmol) was added to N,N-diisopropylamine (0.38 mL, 2.7 mmol) in THF (5.5 mL) at −78° C. Upon complete addition, the reaction temperature was raised to 0° C. for 30 minutes, then was re-cooled to −78° C. A solution of 5-chloro-1-(phenylsulfonyl)-1H-pyrrolo[3,2-b]pyridine (0.500 g, 1.71 mmol, prepared as in Example 2, Step 1) in THF (1 mL) was added dropwise and the reaction was allowed to stir for 1 hour at −78° C. at which time 1,2-dibromo-1,1,2,2-tetrachloroethane (0.89 g, 2.7 mmol, Aldrich) as a solution in THF (1 mL) was added. The reaction was allowed to stir with warming to room temperature overnight. The reaction was quenched with water and the product was extracted with ethyl acetate four times. The combined organics were washed with water, followed by brine, dried over sodium sulfate, decanted, and the solvent removed in vacuo. Flash chromatography, eluting with a gradient from 0-30% EtOAc in hexanes afford the crude product. The product so obtained was purified in several injections of 45 mg/5 mL of THF via preparative HPLC-MS (C18 eluting with a gradient of MeCN and H₂O containing 0.1% TFA). Eluent was evaporated to afford product as the TFA salt (268 mg, 32%).

¹H NMR (300 MHz, CDCl₃) δ 8.48 (d, J=8.8 Hz, 1H), 7.95-7.79 (m, 2H), 7.70-7.58 (m, 1H), 7.57-7.43 (m, 2H), 7.27 (d, J=8.8 Hz, 1H), 6.87 (s, 1H). LCMS (M+H)⁺: 370.9372.9.

Step 2. 1-benzyl-2-bromo-5-chloro-1H-pyrrolo[3,2-b]pyridine

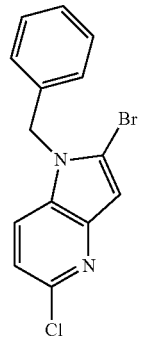 [SMILES: Clc1ccc2c(cc(Br)n2Cc2ccccc2)n1]

1.0 M NaOH in water (5 mL, 5 mmol) was added to a solution of 2-bromo-5-chloro-1-(phenylsulfonyl)-1H-pyrrolo[3,2-b]pyridine trifluoroacetate (0.268 g, 0.552 mmol, from Step 1) in THF (5 mL) and methanol (5 mL) and the reaction was stirred for 1 hour. Water was added and THF and MeOH were removed in vacuo. The product was extracted with EtOAc. The extracts were dried over sodium sulfate, filtered and concentrated. A solution of this residue in DMF (3 mL) was treated with K₂CO₃ (0.23 g, 1.6 mmol) and benzyl bromide (0.0656 mL, 0.552 mmol, Aldrich). After stirring overnight, the reaction was partitioned between water and ethyl acetate and extracted a total of three times. The combined extracts were dried over sodium sulfate, filtered and concentrated. The product was purified by flash chromatography, eluting with a gradient from 0-30% EtOAc in hexanes to afford product as a white crystalline solid. Yield: (177 mg, 99%).

¹H NMR (300 MHz, CDCl₃) δ 7.41 (d, J=8.6 Hz, 1H), 7.34-7.21 (m, 3H), 7.08-6.97 (m, 3H), 6.80 (s, 1H). LCMS (M+H)⁺: 322.8 (most abundant).

Step 3. 1-benzyl-5-chloro-2-[1-(tetrahydro-2H-pyran-2-yl)-1H-pyrazol-5-yl]-1H-pyrrolo[3,2-b]pyridine

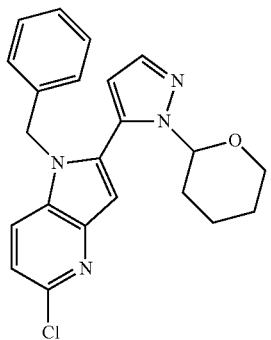 [SMILES: Clc1ccc2c(cc(-c3ccnn3C3CCCCO3)n2Cc2ccccc2)n1]

A mixture of 1-benzyl-2-bromo-5-chloro-1H-pyrrolo[3,2-b]pyridine (0.088 g, 0.27 mmol, from Step 2), 1-(tetrahydro-2H-pyran-2-yl)-5-(4,4,5,5-tetramethyl-1,3,2-dioxaborolan-2-yl)-1H-pyrazole (0.084 g, 0.30 mmol, Aldrich) and Na₂CO₃ (0.14 g, 1.4 mmol) in 1,2-dimethoxyethane (3 mL) and water (0.5 mL) was degassed by a stream of nitrogen through the solution for 10 minutes. Tetrakis(triphenylphosphine)palladium(0) (0.032 g, 0.027 mmol, Strem) was added, the vial was capped and heated to reflux for 15 minutes. After cooling to room temperature, the mixture was partitioned between 10% sodium thiosulfate solution and EtOAc. The aqueous layer was extracted three times with ethyl acetate. The combined extracts were dried over sodium sulfate, filtered and concentrated. Flash chromatography, eluting with 25% EtOAc in hexanes afforded product. Yield: (75 mg, 68%).

¹H NMR (300 MHz, CDCl₃) δ 7.63 (d, J=1.7 Hz, 1H), 7.51 (d, J=8.6 Hz, 1H), 7.29-7.20 (m, 3H), 7.14 (d, J=8.6 Hz, 1H), 6.95 (s, 1H), 6.91-6.80 (m, 2H), 6.31 (d, J=1.8 Hz, 1H), 5.35 (d, J=16.8 Hz, 1H), 5.28 (d, J=16.8 Hz, 1H), 5.18 (dd, J=10.5, 2.2 Hz, 1H), 4.09-3.98 (m, 1H), 3.52 (td, J=11.7, 2.2 Hz, 1H), 2.57-2.39 (m, 1H), 2.20-1.89 (m, 1H), 1.81-1.57 (m, 2H), 1.56-1.41 (m, 2H). LCMS (M+H)⁺: 393.1395.1.

Step 4. di-tert-butyl 1-{1-benzyl-2-[1-(tetrahydro-2H-pyran-2-yl)-1H-pyrazol-5-yl]-1H-pyrrolo[3,2-b]pyridin-5-yl}hydrazine-1,2-dicarboxylate

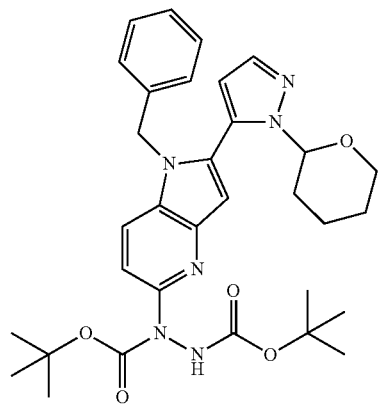 [SMILES: CC(C)(C)OC(=O)NN(C(=O)OC(C)(C)C)c1ccc2c(cc(-c3ccnn3C3CCCCO3)n2Cc2ccccc2)n1]

1-Benzyl-5-chloro-2-[1-(tetrahydro-2H-pyran-2-yl)-1H-pyrazol-5-yl]-1H-pyrrolo[3,2-b]pyridine (0.075 g, 0.19 mmol, from Step 3), di-tert-butyl hydrazine-1,2-dicarboxylate (0.049 g, 0.21 mmol, Aldrich) and Cs₂CO₃ (0.062 g, 0.19 mmol, Aldrich) were combined in toluene (1.7 mL) and dicyclohexyl(2',4',6'-triisopropylbiphenyl-2-yl)phosphine-(2'-aminobiphenyl-2-yl)(chloro)palladium (1:1) (0.015 g, 0.019 mmol, Aldrich) was added. The mixture was degassed by a stream of nitrogen through the solution for 10 minutes. The vial was sealed and heated to 110° C. for 3 hours. Additional reagents and catalyst (same of each as the initial quantities) were added, the mixture was degassed again and the reaction mixture was then heated in the microwave to 140° C. for 10 minutes. After cooling to room temperature, the reaction mixture was partitioned between EtOAc and water, the aqueous layer was extracted three times, and the combined extracts were dried over sodium sulfate, filtered and concentrated. The product was purified via preparative HPLC-MS (C18 eluting with a gradient of MeCN and H₂O containing 0.15% NH₄OH). Yield: (45 mg, 40%).

¹H NMR (300 MHz, CDCl₃) δ 7.62 (d, J=1.5 Hz, 1H), 7.58 (d, J=8.7 Hz, 1H), 7.55-7.46 (br, 1H), 7.27-7.12 (m, 4H), 6.91 (s, 1H), 6.90-6.84 (m, 2H), 6.29 (d, J=1.8 Hz, 1H), 5.33 (d, J=16.8 Hz, 1H), 5.26 (d, J=16.9 Hz, 1H), 5.22-5.14 (m, 1H), 4.09-3.97 (m, 1H), 3.59-3.47 (m, 1H), 2.46 (qd, J=13.2, 12.7, 3.9 Hz, 1H), 2.07-1.23 (m, 5H), 1.51 (s, 9H), 1.48 (s, 9H). LCMS (M+H)⁺: 589.3.

Step 5. 6-benzyl-1-methyl-7-(1H-pyrazol-5-yl)-6H-pyrrolo[2,3-e][1,2,4]triazolo[4,3-a]pyridine A mixture of di-tert-butyl 1-{1-benzyl-2-[1-(tetrahydro-2H-pyran-2-yl)-1H-pyrazol-5-yl]-1H-pyrrolo[3,2-b]pyridin-5-yl}hydrazine-1,2-dicarboxylate (0.045 g, 0.076 mmol, from Step 4) in AcOH (3 mL) was heated in the microwave to 180° C. for 5 minutes. The AcOH was removed in vacuo and the residue was re-dissolved in MeOH and purified via preparative HPLC-MS (C18 eluting with a gradient of MeCN and H₂O containing 0.15% NH₄OH). Yield: (6 mg, 20%).

¹H NMR (300 MHz, CDCl₃) δ 7.65 (d, J=2.2 Hz, 1H), 7.36 (d, J=9.7 Hz, 1H), 7.30-7.20 (m, 4H), 7.08 (s, 1H), 7.05 (d, J=6.4 Hz, 2H), 6.58 (d, J=2.3 Hz, 1H), 5.87 (s, 2H), 3.04 (s, 3H). LCMS (M+H)⁺: 329.1.

Example 63

6-benzyl-1-methyl-7-(1H-pyrazol-4-yl)-6H-pyrrolo[2,3-e][1,2,4]triazolo[4,3-a]pyridine

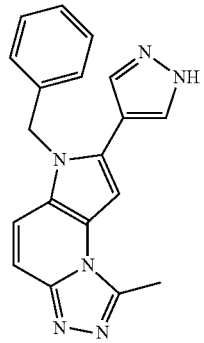 [SMILES: Cc1nnc2ccc3c(cc(-c4cn[nH]c4)n3Cc3ccccc3)n12]

Step 1. 1-benzyl-5-chloro-2-[1-(tetrahydro-2H-pyran-2-yl)-1H-pyrazol-4-yl]-1H-pyrrolo[3,2-b]pyridine

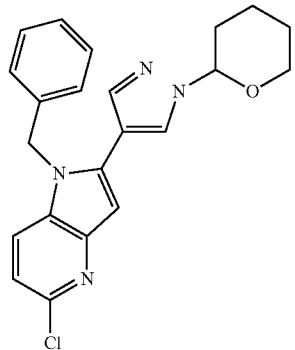 [SMILES: N=C/C(=C\NC1CCCCO1)c1cc2nc(Cl)ccc2n1Cc1ccccc1]

A mixture of 1-benzyl-2-bromo-5-chloro-1H-pyrrolo[3,2-b]pyridine (0.120 g, 0.373 mmol, from Example 62, Step 2), 1-(tetrahydro-2H-pyran-2-yl)-4-(4,4,5,5-tetramethyl-1,3,2-dioxaborolan-2-yl)-1H-pyrazole (0.11 g, 0.41 mmol, Aldrich) and Na$_2$CO$_3$ (0.20 g, 1.9 mmol) in 1,2-dimethoxyethane (4 mL) and water (0.7 mL) was degassed by a stream of nitrogen through the solution for 10 minutes. Tetrakis(triphenylphosphine)palladium(0) (0.043 g, 0.037 mmol) was added, and the reaction was heated to reflux for 1.5 hours. Upon cooling to room temperature, the mixture was partitioned between water and EtOAc, and the aqueous layer was extracted a total of three times. The combined extracts were dried over sodium sulfate, filtered and concentrated. Flash chromatography, eluting with a gradient from 0-50% EtOAc in hexanes afforded product. Yield: (0.106 g, 72%).

$^1$H NMR (400 MHz, CDCl$_3$) δ 7.70 (d, J=0.7 Hz, 1H), 7.58 (d, J=0.7 Hz, 1H), 7.40 (dd, J=8.5, 0.8 Hz, 1H), 7.34-7.26 (m, 3H), 7.03 (d, J=8.5 Hz, 1H), 6.99-6.94 (m, 2H), 6.73 (d, J=0.8 Hz, 1H), 5.40 (s, 2H), 5.38 (dd, J=6.6, 5.5 Hz, 1H), 4.09-4.02 (m, 1H), 3.74-3.65 (m, 1H), 2.13-1.95 (m, 3H), 1.77-1.58 (m, 3H). LCMS (M+H)$^+$: 393.1.

Step 2. di-tert-butyl 1-{1-benzyl-2-[1-(tetrahydro-2H-pyran-2-yl)-1H-pyrazol-4-yl]-1H-pyrrolo[3,2-b]pyridin-5-yl}hydrazine-1,2-dicarboxylate

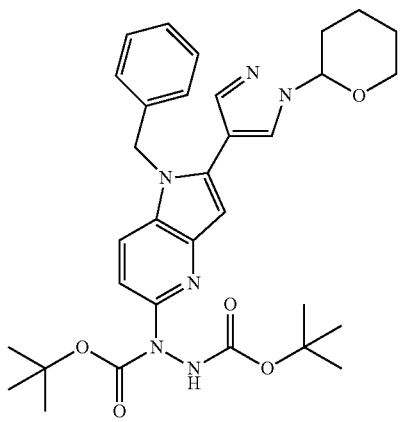 [SMILES: CC(C)(C)OC(=O)NN(C(=O)OC(C)(C)C)c1ccc2c(cc(/C(C=N)=C/NC3CCCCO3)n2Cc2ccccc2)n1]

1-Benzyl-5-chloro-2-[1-(tetrahydro-2H-pyran-2-yl)-1H-pyrazol-4-yl]-1H-pyrrolo[3,2-b]pyridine (0.106 g, 0.270 mmol, from Step 1), di-tert-butyl hydrazine-1,2-dicarboxylate (0.069 g, 0.30 mmol) and Cs$_2$CO$_3$ (0.088 g, 0.27 mmol) were combined in toluene (2.4 mL) and dicyclohexyl(2',4',6'-triisopropylbiphenyl-2-yl)phosphine-(2'-aminobiphenyl-2-yl)(chloro)palladium (1:1) (0.021 g, 0.027 mmol) was added. The mixture was degassed by a stream of nitrogen through the solution for 10 minutes. The reaction was heated to 110° C. for 1.5 hours, at which time additional reagents and catalyst were added (same of each as the initial quantities) and the mixture was degassed again and was heated in the microwave to 140° C. for 10 minutes. The reaction mixture was partitioned between EtOAc and water, extracted three times and the combined extracts were dried over sodium sulfate, filtered, and concentrated. The resulting product was purified via preparative HPLC-MS (C18 eluting with a gradient of MeCN and H$_2$O containing 0.15% NH$_4$OH). Yield (71 mg, 44%).

$^1$H NMR (400 MHz, CDCl$_3$) δ 7.65 (s, 1H), 7.58 (d, J=0.6 Hz, 1H), 7.46 (d, J=8.6 Hz, 1H), 7.34-7.23 (m, 4H), 7.03-6.96 (m, 2H), 6.72 (s, 1H), 5.39 (s, 2H), 5.39-5.34 (m, 1H), 4.11- 4.00 (m, 1H), 3.77-3.61 (m, 1H), 2.16-1.98 (m, 3H), 1.77-1.57 (m, 3H), 1.49 (s, 9H), 1.46 (s, 9H). LCMS (M+H)$^+$: 589.1.

Step 3. 6-benzyl-1-methyl-7-(1H-pyrazol-4-yl)-6H-pyrrolo[2,3-e][1,2,4]triazolo[4,3-a]pyridine di-tert-Butyl 1-{1-benzyl-2-[1-(tetrahydro-2H-pyran-2-yl)-1H-pyrazol-4-yl]-1H-pyrrolo[3,2-b]pyridin-5-yl}hydrazine-1,2-dicarboxylate (68 mg, 0.12 mmol, from Step 2) in AcOH (4 mL) was heated in the microwave to 180° C. for 9 minutes. The acetic acid was removed in vacuo, and the residue was reconstituted in MeOH and purified via preparative HPLC-MS (C18 eluting with a gradient of MeCN and H$_2$O containing 0.15% NH$_4$OH). Yield: (17 mg, 45%).

$^1$H NMR (400 MHz, CD$_3$OD) δ 7.85 (br s, 1H), 7.73 (br s, 1H), 7.63 (d, J=9.7 Hz, 1H), 7.36-7.21 (m, 4H), 7.17 (s, 1H), 6.99 (d, J=6.9 Hz, 2H), 5.63 (s, 2H), 3.03 (s, 3H). LCMS (M+H)$^+$: 329.0.

Example 64

[4-(6-benzyl-1-methyl-6H-pyrrolo[2,3-e][1,2,4]triazolo[4,3-a]pyridin-7-yl)-1H-pyrazol-1-yl]acetonitrile

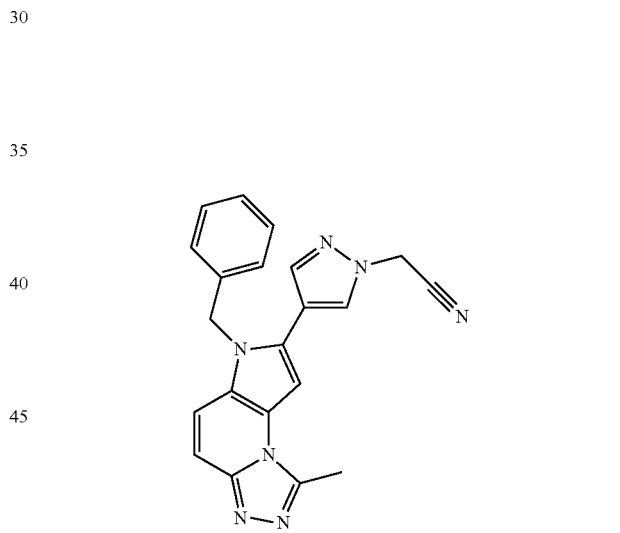

A solution of 6-benzyl-1-methyl-7-(1H-pyrazol-4-yl)-6H-pyrrolo[2,3-e][1,2,4]triazolo[4,3-a]pyridine (14 mg, 0.043 mmol, from Example 63) in DMF (0.56 mL, 7.2 mmol) was treated with NaH (5.1 mg, 0.21 mmol). After 10 minutes, the mixture was treated with chloroacetonitrile (8.1 μL, 0.13 mmol, Fluka). After 10 minutes, the reaction was quenched by the addition of water. The product was purified via preparative HPLC-MS (C18 eluting with a gradient of MeCN and H$_2$O containing 0.15% NH$_4$OH). Yield: (7.0 mg, 45%).

$^1$H NMR (400 MHz, CDCl$_3$) δ 7.64 (d, J=0.6 Hz, 1H), 7.55 (s, 1H), 7.38 (d, J=9.7 Hz, 1H), 7.36-7.30 (m, 3H), 7.23 (dd,

J=9.8, 0.6 Hz, 1H), 7.00-6.93 (m, 2H), 6.88 (d, J=0.6 Hz, 1H), 5.44 (s, 2H), 5.10 (s, 2H), 3.03 (s, 3H). LCMS (M+H)$^+$: 368.0.

Example 65

[3-(6-benzyl-1-methyl-6H-pyrrolo[2,3-e][1,2,4]triazolo[4,3-a]pyridin-7-yl)-1H-pyrazol-1-yl]acetonitrile

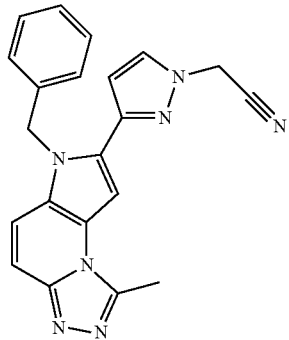 [SMILES: Cc1nnc2ccc3c(cc(-c4ccn(CC#N)n4)n3Cc3ccccc3)n12]

By the method of Example 62, Step 5, followed by the method of Example 64, [3-(6-benzyl-1-methyl-6H-pyrrolo[2,3-e][1,2,4]triazolo[4,3-a]pyridin-7-yl)-1H-pyrazol-1-yl]acetonitrile was prepared from di-tert-butyl 1-{1-benzyl-2-[1-(tetrahydro-2H-pyran-2-yl)-1H-pyrazol-5-yl]-1H-pyrrolo[3,2-b]pyridin-5-yl}hydrazine-1,2-dicarboxylate (20 mg, 0.034 mmol, from Example 62, Step 4). The major isomer was isolated. Yield: (2.5 mg, 20% over the two steps).

$^1$H NMR (500 MHz, CDCl$_3$) δ 7.60 (d, J=2.4 Hz, 1H), 7.39 (d, J=9.7 Hz, 1H), 7.31-7.22 (m, 4H), 7.06 (s, 1H), 7.04 (d, J=7.3 Hz, 2H), 6.61 (d, J=2.4 Hz, 1H), 5.88 (s, 2H), 5.10 (s, 2H), 3.03 (s, 3H). LCMS (M+H)$^+$: 368.0.

Example 66

6-benzyl-1-methyl-7-(1,3-thiazol-4-yl)-6H-pyrrolo[2,3-e][1,2,4]triazolo[4,3-a]pyridine

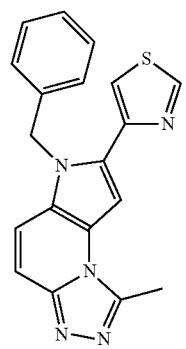 [SMILES: Cc1nnc2ccc3c(cc(-c4cscn4)n3Cc3ccccc3)n12]

Step 1. 1-benzyl-5-chloro-2-(1,3-thiazol-4-yl)-1H-pyrrolo[3,2-b]pyridine

A mixture of 1-benzyl-2-bromo-5-chloro-1H-pyrrolo[3,2-b]pyridine (0.10 g, 0.31 mmol, from Example 62, Step 2) and 4-(tributylstannyl)-1,3-thiazole (0.12 g, 0.31 mmol, Synthonix) in toluene (6.0 mL) was degassed by a stream of nitrogen through the solution. Tetrakis(triphenylphosphine)palladium(0) (36 mg, 0.031 mmol) was added and the mixture was heated to 110° C. for 2 hours, then at 100° C. overnight. Solvent was removed in vacuo and the residue was dissolved in MeCN and filtered, then purified via preparative HPLC-MS (C18 eluting with a gradient of MeCN and H$_2$O containing 0.15% NH$_4$OH). Yield: (35 mg, 34%).

$^1$H NMR (400 MHz, d$_6$-DMSO) δ 9.30 (d, J=1.9 Hz, 1H), 8.29 (d, J=1.9 Hz, 1H), 7.99 (dd, J=8.6, 0.8 Hz, 1H), 7.27-7.13 (m, 4H), 7.10 (d, J=0.7 Hz, 1H), 6.98-6.91 (m, 2H), 5.97 (s, 2H). LCMS (M+H)$^+$: 326.1328.1.

Step 2. 6-benzyl-1-methyl-7-(1,3-thiazol-4-yl)-6H-pyrrolo[2,3-e][1,2,4]triazolo[4,3-a]pyridine 1-Benzyl-5-chloro-2-(1,3-thiazol-4-yl)-1H-pyrrolo[3,2-b]pyridine (32 mg, 0.098 mmol, from Step 1), di-tert-butyl hydrazine-1,2-dicarboxylate (27 mg, 0.12 mmol) and Cs$_2$CO$_3$ (32 mg, 0.098 mmol) were combined in toluene (3.0 mL) and dicyclohexyl(2',4',6'-triisopropylbiphenyl-2-yl)phosphine-(2'-aminobiphenyl-2-yl)(chloro)palladium (1:1) (7.7 mg, 0.0098 mmol) was added. The mixture was degassed by a stream of nitrogen through the solution for 10 minutes. The reaction was heated to 108° C. overnight. Additional di-tert-butyl hydrazine-1,2-dicarboxylate (23 mg, 0.098 mmol) and dicyclohexyl(2',4',6'-triisopropylbiphenyl-2-yl)phosphine-(2'-aminobiphenyl-2-yl)(chloro)palladium (1:1) (7.7 mg, 0.0098 mmol) were added. The reaction was heated to 110° C. over a second night. The mixture was partitioned between EtOAc and water, extracted three times, and the combined extracts were dried over sodium sulfate, filtered and concentrated. The intermediate di-tert-butyl 1-[1-benzyl-2-(1,3-thiazol-4-yl)-1H-pyrrolo[3,2-b]pyridin-5-yl]hydrazine-1,2-dicarboxylate was purified via preparative HPLC-MS (C18 eluting with a gradient of MeCN and H$_2$O containing 0.15% NH$_4$OH) and the eluent was evaporated. The product was dissolved in AcOH (0.60 mL) and was heated in the microwave to a temperature of 156° C. for 5 minutes. The AcOH was removed in vacuo and the sample was reconstituted and purified via preparative HPLC-MS (C18 eluting with a gradient of MeCN and H$_2$O containing 0.15% NH$_4$OH). Yield: (1.0 mg, 2.9%).

$^1$H NMR (400 MHz, CD$_3$OD) δ 9.11 (d, J=2.0 Hz, 1H), 7.93 (d, J=2.0 Hz, 1H), 7.70 (d, J=9.6 Hz, 1H), 7.42 (d, J=0.5

Hz, 1H), 7.32 (d, J=9.8 Hz, 1H), 7.26-7.15 (m, 3H), 7.03-6.97 (m, 2H), 6.00 (s, 2H), 3.04 (s, 3H). LCMS (M+H)⁺: 346.1.

Example 67

6-benzyl-1-methyl-7-(1,3-thiazol-2-yl)-6H-pyrrolo[2,3-e][1,2,4]triazolo[4,3-a]pyridine

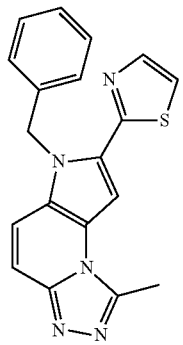 [SMILES: Cc1nnc2ccc3c(cc(-c4nccs4)n3Cc3ccccc3)n12]

Step 1. 1-benzyl-5-chloro-2-(1,3-thiazol-2-yl)-1H-pyrrolo[3,2-b]pyridine

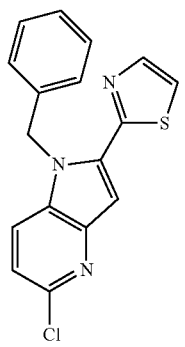

A mixture of 1-benzyl-2-bromo-5-chloro-1H-pyrrolo[3,2-b]pyridine (0.10 g, 0.31 mmol, from Example 62, Step 2) and 2-(tributylstannyl)-1,3-thiazole (0.12 g, 0.31 mmol, Aldrich) in toluene (6.0 mL) was degassed by a stream of nitrogen through the solution. Tetrakis(triphenylphosphine)palladium (0) (36 mg, 0.031 mmol) was added and the mixture was heated to 110° C. for 4 hours. Toluene was removed in vacuo and the residue was dissolved in MeCN, filtered, and purified via preparative HPLC-MS (C18 eluting with a gradient of MeCN and H₂O containing 0.15% NH₄OH). Yield: (33 mg, 32%).
¹H NMR (400 MHz, d₆-DMSO) δ 8.05 (dd, J=8.7, 0.8 Hz, 1H), 8.02 (d, J=3.3 Hz, 1H), 7.93 (d, J=3.3 Hz, 1H), 7.30 (d, J=0.7 Hz, 1H), 7.28 (d, J=8.7 Hz, 1H), 7.26-7.15 (m, 3H), 7.03-6.96 (m, 2H), 6.10 (s, 2H). LCMS (M+H)⁺: 326.1328.1.

Step 2. 6-benzyl-1-methyl-7-(1,3-thiazol-2-yl)-6H-pyrrolo[2,3-e][1,2,4]triazolo[4,3-a]pyridine 1-Benzyl-5-chloro-2-(1,3-thiazol-2-yl)-1H-pyrrolo[3,2-b]pyridine (30 mg, 0.092 mmol, from Step 1), di-tert-butyl hydrazine-1,2-dicarboxylate (26 mg, 0.11 mmol) and Cs₂CO₃ (30 mg, 0.092 mmol) were combined in toluene (2.8 mL) and dicyclohexyl(2',4',6'-triisopropylbiphenyl-2-yl)phosphine-(2'-aminobiphenyl-2-yl)(chloro)palladium (1:1) (7.2 mg, 0.0092 mmol) was added. The mixture was degassed by a stream of nitrogen through the solution for 10 minutes. The reaction was heated to 110° C. overnight. The intermediate di-tert-butyl 1-[1-benzyl-2-(1,3-thiazol-2-yl)-1H-pyrrolo[3,2-b]pyridin-5-yl]hydrazine-1,2-dicarboxylate was purified via preparative HPLC-MS (C18 eluting with a gradient of MeCN and H₂O containing 0.15% NH₄OH) and was isolated in the amount of 20 mg after evaporation of eluent. The resulting residue was dissolved in acetic acid (1.9 mL) and heated in the microwave to a temperature of 165° C. for 5 minutes. AcOH was removed in vacuo and the residue was reconstituted and purified via preparative HPLC-MS (C18 eluting with a gradient of MeCN and H₂O containing 0.15% NH₄OH). Yield: (4.6 mg, 14%).
¹H NMR (400 MHz, d₆-DMSO) δ 7.95 (d, J=3.3 Hz, 1H), 7.85 (d, J=3.3 Hz, 1H), 7.70 (dd, J=9.8, 0.6 Hz, 1H), 7.56 (d, J=0.5 Hz, 1H), 7.46 (d, J=9.8 Hz, 1H), 7.30-7.16 (m, 3H), 7.08-6.98 (m, 2H), 6.18 (s, 2H), 2.97 (s, 3H). LCMS (M+H)⁺: 346.1.

Example 68

6-benzyl-1-methyl-7-pyridin-2-yl-6H-pyrrolo[2,3-e][1,2,4]triazolo[4,3-a]pyridine

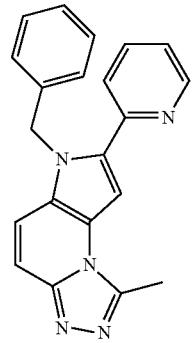 [SMILES: Cc1nnc2ccc3c(cc(-c4ccccn4)n3Cc3ccccc3)n12]

Step 1. 1-benzyl-5-chloro-2-pyridin-2-yl-1H-pyrrolo[3,2-b]pyridine

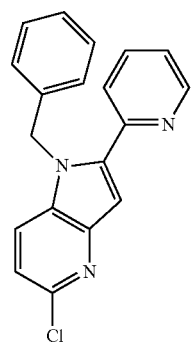 [SMILES: Clc1ccc2c(cc(-c3ccccn3)n2Cc2ccccc2)n1]

A mixture of 1-benzyl-2-bromo-5-chloro-1H-pyrrolo[3,2-b]pyridine (0.10 g, 0.31 mmol, from Example 62, Step 2) and 2-(tributylstannyl)pyridine (0.11 g, 0.31 mmol, Aldrich) in toluene (6.0 mL) was degassed by a stream of nitrogen through the solution for 10 minutes. Tetrakis(triphenylphosphine)palladium(0) (36 mg, 0.031 mmol) was added and the mixture was stirred at 110° C. for 6 hours. Solvent was removed in vacuo and the residue was dissolved in MeCN, filtered and concentrated. Flash chromatography, eluting with a gradient from 0-20% EtOAc in hexanes afforded desired product (40 mg, 40%).

$^1$H NMR (400 MHz, CDCl$_3$) δ 8.66-8.63 (m, 1H), 7.79-7.73 (m, 2H), 7.52 (dd, J=8.6, 0.8 Hz, 1H), 7.28-7.15 (m, 4H), 7.08 (d, J=8.6 Hz, 1H), 7.02 (d, J=0.8 Hz, 1H), 6.99-6.93 (m, 2H), 5.97 (s, 2H). LCMS (M+H)$^+$: 319.9.

Step 2. 6-benzyl-1-methyl-7-pyridin-2yl-6H-pyrrolo[2,3-e][1,2,4]triazolo[4,3-a]pyridine 1-Benzyl-5-chloro-2-pyridin-2-yl-1H-pyrrolo[3,2-b]pyridine (38 mg, 0.12 mmol, from Step 1), di-tert-butyl hydrazine-1,2-dicarboxylate (41 mg, 0.18 mmol) and Cs$_2$CO$_3$ (58 mg, 0.18 mmol) were combined in toluene (4.1 mL) and dicyclohexyl(2',4',6'-triisopropylbiphenyl-2-yl)phosphine-(2'-aminobiphenyl-2-yl)(chloro)palladium (1:1) (9.3 mg, 0.012 mmol) was added. The mixture was degassed by a stream of nitrogen through the solution for 10 minutes. The reaction was heated to 110° C. overnight. The mixture was diluted with DCM, filtered and concentrated. Flash chromatography, eluting with a gradient from 0-40% EtOAc in hexanes afforded 20 mg of intermediate di-tert-butyl 1-(1-benzyl-2-pyridin-2-yl-1H-pyrrolo[3,2-b]pyridin-5-yl)hydrazine-1,2-dicarboxylate, which was then dissolved in AcOH (2.4 mL) and heated in the microwave to a temperature of 180° C. for 6 minutes. The resulting product was purified via preparative HPLC-MS (C18 eluting with a gradient of MeCN and H$_2$O containing 0.15% NH$_4$OH). Yield: (4.0 mg, 10%).

$^1$H NMR (400 MHz, d$_6$-DMSO) δ 8.62 (ddd, J=4.8, 1.8, 0.9 Hz, 1H), 8.03 (dt, J=8.1, 1.0 Hz, 1H), 7.90 (td, J=7.8, 1.8 Hz, 1H), 7.70 (dd, J=9.8, 0.6 Hz, 1H), 7.60 (d, J=0.6 Hz, 1H), 7.39 (d, J=9.8 Hz, 1H), 7.34 (ddd, J=7.5, 4.8, 1.1 Hz, 1H), 7.24-7.10 (m, 3H), 7.00-6.94 (m, 2H), 6.23 (s, 2H), 2.96 (s, 3H). LCMS (M+H)$^+$: 340.0.

Example 69

6-benzyl-1-methyl-7-(1,3-thiazol-5-yl)-6H-pyrrolo[2,3-e][1,2,4]triazolo[4,3-a]pyridine

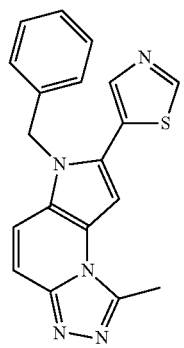 [SMILES: Cc1nnc2ccc3c(cc(-c4cncs4)n3Cc3ccccc3)n12]

Step 1. 1-benzyl-5-chloro-2-(1,3-thiazol-5-yl)-1H-pyrrolo[3,2-b]pyridine

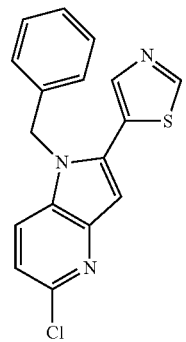

A mixture of 1-benzyl-2-bromo-5-chloro-1H-pyrrolo[3,2-b]pyridine (0.15 g, 0.47 mmol, from Example 62, Step 2) and 5-(tributylstannyl)-1,3-thiazole (0.17 g, 0.47 mmol, Synthonix) in toluene (9.0 mL) was degassed using a stream of nitrogen through the solution. Tetrakis(triphenylphosphine)palladium(0) (54 mg, 0.047 mmol) was added and the mixture was heated to 110° C. for 5 hours. Solvent was removed in vacuo and the residue was dissolved in MeCN, filtered, and purified by flash chromatography, eluting with a gradient from 0-40% EtOAc in hexanes. Yield: (67 mg, 44%). LCMS (M+H)$^+$: 325.9.

Step 2. 6-benzyl-1-methyl-7-(1,3-thiazol-5-yl)-6H-pyrrolo[2,3-e][1,2,4]triazolo[4,3-a]pyridine 1-Benzyl-5-chloro-2-(1,3-thiazol-5-yl)-1H-pyrrolo[3,2-b]pyridine (67 mg, 0.20 mmol, from Step 1), di-tert-butyl hydrazine-1,2-dicarboxylate (72 mg, 0.31 mmol) and Cs$_2$CO$_3$ (100 mg, 0.31 mmol) were combined in toluene (7.2 mL) and dicyclohexyl(2',4',6'-triisopropylbiphenyl-2-yl)phosphine-(2'-aminobiphenyl-2-yl)(chloro)palladium (1:1) (16 mg, 0.020 mmol) was added. The mixture was degassed by a stream of nitrogen through the solution for 10 minutes. The reaction was stirred at 110° C. overnight, then was cooled, diluted with DCM, filtered and concentrated. Flash chromatography, eluting with a gradient from 0-50% EtOAc in hexanes afforded intermediate di-tert-butyl 1-[1-benzyl-2-(1,3-thiazol-5-yl)-1H-pyrrolo[3,2-b]pyridin-5-yl]hydrazine-1,2-dicarboxylate. This intermediate was heated in the microwave as a solution in AcOH (3.0 mL) to 180° C. for 6 minutes. AcOH was removed in vacuo, the residue was reconstituted, and the product was concentrated and purified via preparative HPLC-MS (C18 eluting with a gradient of MeCN and H$_2$O containing 0.15% NH$_4$OH). Yield: (12.5 mg, 18%).

$^1$H NMR (400 MHz, d$_6$-DMSO) δ 9.17 (d, J=0.6 Hz, 1H), 8.10 (d, J=0.6 Hz, 1H), 7.73 (dd, J=9.8, 0.5 Hz, 1H), 7.41 (d,

J=9.8 Hz, 1H), 7.37 (s, 1H), 7.31-7.17 (m, 3H), 6.90 (d, J=7.0 Hz, 2H), 5.71 (s, 2H), 2.93 (s, 3H). LCMS (M+H)⁺: 346.1.

Example 70

6-benzyl-1-methyl-7-(1-methyl-1H-imidazol-4-yl)-6H-pyrrolo[2,3-e][1,2,4]triazolo[4,3-a]pyridine

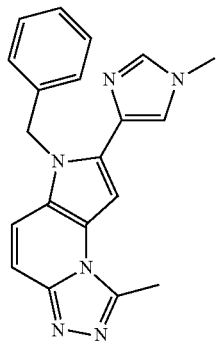 [SMILES: Cc1nnc2ccc3c(cc(-c4cn(C)cn4)n3Cc3ccccc3)n12]

Step 1. 1-benzyl-5-chloro-2-(1-methyl-1H-imidazol-4-yl)-1H-pyrrolo[3,2-b]pyridine

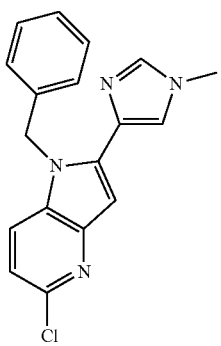 [SMILES: Cn1cnc(-c2cc3nc(Cl)ccc3n2Cc2ccccc2)c1]

A mixture of 1-benzyl-2-bromo-5-chloro-1H-pyrrolo[3,2-b]pyridine (0.10 g, 0.31 mmol, from Example 62, Step 2) and 1-methyl-4-(tributylstannyl)-1H-imidazole (0.12 g, 0.31 mmol, Aldrich) in toluene (6.0 mL) was degassed. Tetrakis(triphenylphosphine)palladium(0) (36 mg, 0.031 mmol) was added and the mixture was heated to 110° C. for 7 hours. Toluene was removed in vacuo and the mixture was dissolved in MeCN and filtered. Flash chromatography, eluting with a gradient from 0-70% EtOAc in hexanes afforded purified product (24 mg, 24%).
¹H NMR (400 MHz, CDCl₃) δ 7.49 (d, J=1.0 Hz, 1H), 7.39 (dd, J=8.5, 0.8 Hz, 1H), 7.26-7.16 (m, 4H), 7.03-6.97 (m, 2H), 6.98 (d, J=8.5 Hz, 1H), 6.79 (d, J=0.7 Hz, 1H), 5.88 (s, 2H), 3.73 (s, 3H). LCMS (M+H)⁺: 323.1.

Step 2. 6-benzyl-1-methyl-7-(1-methyl-1H-imidazol-4-yl)-6H-pyrrolo[2,3-e][1,2,4]triazolo[4,3-a]pyridine 1-Benzyl-5-chloro-2-(1-methyl-1H-imidazol-4-yl)-1H-pyrrolo[3,2-b]pyridine (22 mg, 0.068 mmol, from Step 1), di-tert-butyl hydrazine-1,2-dicarboxylate (24 mg, 0.10 mmol) and Cs₂CO₃ (33 mg, 0.10 mmol) were combined in toluene (2.4 mL) and dicyclohexyl(2',4',6'-triisopropylbiphenyl-2-yl)phosphine-(2'-aminobiphenyl-2-yl)(chloro)palladium (1:1) (5.4 mg, 0.0068 mmol) was added. The mixture was degassed by a stream of nitrogen through the solution for 10 minutes. The reaction was stirred at 120° C. overnight. The mixture was diluted with DCM, filtered and concentrated. Purification via preparative HPLC-MS (C18 eluting with a gradient of MeCN and H₂O containing 0.15% NH₄OH) afforded 5.6 mg of intermediate di-tert-butyl 1-[1-benzyl-2-(1-methyl-1H-imidazol-4-yl)-1H-pyrrolo[3,2-b]pyridin-5-yl]hydrazine-1,2-dicarboxylate which was dissolved in acetic acid (1.1 mL) and heated in the microwave to 180° C. for 6 minutes. AcOH was removed in vacuo and the sample was reconstituted and purified via preparative HPLC-MS (C18 eluting with a gradient of MeCN and H₂O containing 0.15% NH₄OH). Yield: (3.0 mg 13%).
¹H NMR (400 MHz, CD₃OD) δ 7.75 (s, 1H), 7.62 (d, J=9.7 Hz, 1H), 7.33 (s, 1H), 7.28-7.16 (m, 5H), 7.01-6.95 (m, 2H), 5.82 (s, 2H), 3.75 (s, 3H), 3.02 (s, 3H). LCMS (M+H)⁺: 343.0.

Example 71

6-benzyl-1-methyl-7-(1-methyl-1H-imidazol-5-yl)-6H-pyrrolo[2,3-e][1,2,4]triazolo[4,3-a]pyridine

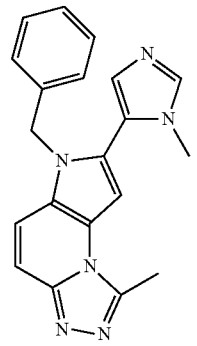 [SMILES: Cc1nnc2ccc3c(cc(-c4cncn4C)n3Cc3ccccc3)n12]

Step 1. 1-benzyl-5-chloro-2-(1-methyl-1H-imidazol-5-yl)-1H-pyrrolo[3,2-b]pyridine

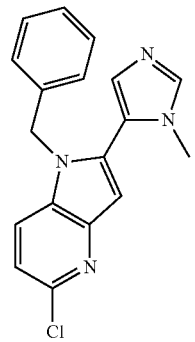 [SMILES: Cn1cncc1-c1cc2nc(Cl)ccc2n1Cc1ccccc1]

A mixture of 1-benzyl-2-bromo-5-chloro-1H-pyrrolo[3,2-b]pyridine (0.10 g, 0.31 mmol, from Example 62, Step 2) and 1-methyl-5-(tributylstannyl)-1H-imidazole (0.12 g, 0.31 mmol, Aldrich) in toluene (6.0 mL) was degassed by a stream of nitrogen through the solution. Tetrakis(triphenylphosphine)palladium(0) (36 mg, 0.031 mmol) was added and the mixture was stirred at 110° C. for 7 hours. Toluene was removed in vacuo, and the residue was dissolved in MeCN and filtered. Flash chromatography, eluting with a gradient from 0-70% EtOAc in hexanes afforded product as a white solid (35 mg, 35%).

$^1$H NMR (400 MHz, CDCl$_3$) δ 7.58 (s, 1H), 7.53 (dd, J=8.6, 0.8 Hz, 1H), 7.28-7.21 (m, 3H), 7.14 (d, J=8.6 Hz, 1H), 7.10 (d, J=1.0 Hz, 1H), 6.90-6.81 (m, 2H), 6.78 (d, J=0.8 Hz, 1H), 5.33 (s, 2H), 3.48-3.35 (m, 3H). LCMS (M+H)$^+$: 322.9.

Step 2. 6-benzyl-1-methyl-7-(1-methyl-1H-imidazol-5-yl)-6H-pyrrolo[2,3-d][1,2,4]triazolo[4,3-a]pyridine 1-Benzyl-5-chloro-2-(1-methyl-1H-imidazol-5-yl)-1H-pyrrolo[3,2-b]pyridine (33 mg, 0.10 mmol, from Step 1), di-tert-butyl hydrazine-1,2-dicarboxylate (36 mg, 0.15 mmol) and Cs$_2$CO$_3$ (50 mg, 0.15 mmol) were combined in toluene (3.6 mL) and dicyclohexyl(2',4',6'-triisopropylbiphenyl-2-yl)phosphine-(2'-aminobiphenyl-2-yl)(chloro)palladium (1:1) (8.0 mg, 0.010 mmol) was added. The mixture was degassed by a stream of nitrogen through the solution for 10 minutes. The reaction was stirred at 120° C. overnight. The mixture was diluted with DCM, filtered and concentrated. Purification via preparative HPLC-MS (C18 eluting with a gradient of MeCN and H$_2$O containing 0.15% NH$_4$OH) afforded intermediate di-tert-butyl 1-[1-benzyl-2-(1-methyl-1H-imidazol-5-yl)-1H-pyrrolo[3,2-b]pyridin-5-yl]hydrazine-1,2-dicarboxylate as 10 mg of light yellow oil. The oil was dissolved in AcOH (1.6 mL) and heated in the microwave to a temperature of 180° C. for 7 minutes. The AcOH was removed in vacuo and the product was purified via preparative HPLC-MS (C18 eluting with a gradient of MeCN and H$_2$O containing 0.15% NH$_4$OH). Yield: (4.5 mg, 13%).

$^1$H NMR (400 MHz, CD$_3$OD) δ 7.80-7.76 (m, 2H), 7.40 (d, J=9.8 Hz, 1H), 7.25 (ddd, J=8.3, 5.2, 1.1 Hz, 4H), 7.08 (s, 1H), 6.88 (dd, J=7.6, 1.9 Hz, 1H), 5.47 (s, 2H), 3.42 (s, 3H), 3.01 (s, 3H). LCMS (M+H)$^+$: 343.0.

Example 72

6-benzyl-1-methyl-7-(3-thienyl)-6H-pyrrolo[2,3-e][1,2,4]triazolo[4,3-a]pyridine

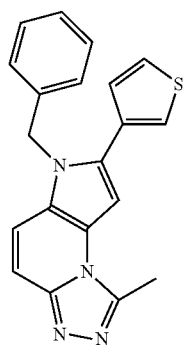 [SMILES: Cc1nnc2ccc3c(cc(-c4ccsc4)n3Cc3ccccc3)n12]

Step 1. 1-benzyl-5-chloro-2-(3-thienyl)-1H-pyrrolo[3,2-b]pyridine

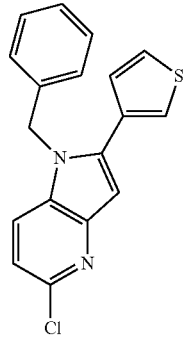 [SMILES: Clc1ccc2c(cc(-c3ccsc3)n2Cc2ccccc2)n1]

A mixture of 1-benzyl-2-bromo-5-chloro-1H-pyrrolo[3,2-b]pyridine (0.10 g, 0.31 mmol, from Example 62, Step 2) and 3-thienylboronic acid (0.044 g, 0.34 mmol, Aldrich) and Na$_2$CO$_3$ (0.16 g, 1.6 mmol) in 1,2-dimethoxyethane (3 mL) and water (0.6 mL) was degassed by a stream of nitrogen through the solution for 10 minutes. Tetrakis(triphenylphosphine)palladium(0) (0.036 g, 0.031 mmol) was added and the reaction was stirred at reflux for 15 minutes. Upon cooling to room temperature, the reaction was diluted with water. The product was extracted with EtOAc, and the combined extracts were washed with brine, dried over sodium sulfate, filtered, and concentrated. Flash chromatography, eluting with a gradient from 0-20% EtOAc in hexanes afforded product as a light yellow solid (47 mg, 47%). $^1$H NMR (400 MHz, CDCl$_3$) δ 7.43-7.37 (m, 2H), 7.36-7.27 (m, 4H), 7.20 (dd, J=5.0, 1.3 Hz, 1H), 7.05 (d, J=8.5 Hz, 1H), 7.02-6.96 (m, 2H), 6.80 (d, J=0.8 Hz, 1H), 5.43 (s, 2H). LCMS (M+H)$^+$: 324.9.

Step 2. 6-benzyl-1-methyl-7-(3-thienyl)-6H-pyrrolo[2,3-e][1,2,4]triazolo[4,3-a]pyridine 1-Benzyl-5-chloro-2-(3-thienyl)-1H-pyrrolo[3,2-b]pyridine (44 mg, 0.14 mmol, from Step 1), di-tert-butyl hydrazine-1,2-dicarboxylate (47 mg, 0.20 mmol) and Cs$_2$CO$_3$ (66 mg, 0.20 mmol) were combined in toluene (4.7 mL) and dicyclohexyl(2',4',6'-triisopropylbiphenyl-2-yl)phosphine-(2'-aminobiphenyl-2-yl)(chloro)palladium (1:1) (11 mg, 0.014 mmol) was added. The mixture was degassed by a stream of nitrogen through the solution for 10 minutes. The reaction was stirred at 120° C. overnight. The mixture was then diluted with DCM, filtered, and concentrated. Purification via preparative HPLC-MS (C18 eluting with a gradient of MeCN and H$_2$O containing 0.15% NH$_4$OH) afforded intermediate di-tert-butyl 1-[1-benzyl-2-(3-thienyl)-1H-pyrrolo[3,2-b]pyridin-5-yl]hydrazine-1,2-dicarboxylate (30.4 mg). This intermediate was dissolved in AcOH (2.2 mL) and heated in the microwave at a temperature of 180° C. for 7 minutes. AcOH was removed in vacuo and the product was purified via preparative HPLC-MS (C18 eluting with a gradient of MeCN and H$_2$O containing 0.15% NH$_4$OH). Yield: (12.4 mg, 26%).

¹H NMR (300 MHz, CDCl₃) δ 7.48-7.14 (m, 8H), 7.01 (d, J=7.0 Hz, 2H), 6.93 (s, 1H), 5.50 (s, 2H), 3.04 (s, 3H). LCMS (M+H)⁺: 345.2.

Example 73

6-benzyl-1-methyl-7-(2-thienyl)-6H-pyrrolo[2,3-e][1,2,4]triazolo[4,3-a]pyridine

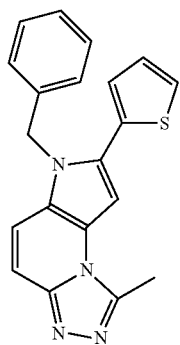 [SMILES: Cc1nnc2ccc3c(cc(-c4cccs4)n3Cc3ccccc3)n12]

Step 1. 1-benzyl-5-chloro-2-(2-thienyl)-1H-pyrrolo[3,2-a]pyridine

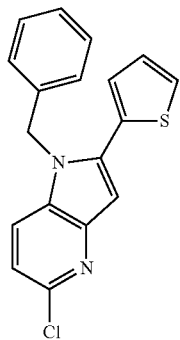 [SMILES: Clc1ccc2c(cc(-c3cccs3)n2Cc2ccccc2)n1]

A mixture of 1-benzyl-2-bromo-5-chloro-1H-pyrrolo[3,2-b]pyridine (0.10 g, 0.31 mmol, from Example 62, Step 2) and tributyl(2-thienyl)stannane (0.12 g, 0.31 mmol, Aldrich) in toluene (6.0 mL) was degassed. Tetrakis(triphenylphosphine)palladium(0) (36 mg, 0.031 mmol) was added and the mixture was heated to 110° C. for 3 hours. Solvent was removed in vacuo. Flash chromatography, eluting with a gradient from 0-20% EtOAc in hexanes afforded product as a light yellow solid (88 mg, 87%).
¹H NMR (400 MHz, CDCl₃) δ 7.44-7.38 (m, 2H), 7.34-7.26 (m, 3H), 7.12-7.03 (m, 3H), 7.02-6.96 (m, 2H), 6.86 (d, J=0.8 Hz, 1H), 5.49 (s, 2H). LCMS (M+H)⁺: 324.9.

Step 2. 6-benzyl-1-methyl-7-(2-thienyl)-6H-pyrrolo[2,3-e][1,2,4]triazolo[4,3-a]pyridine 1-Benzyl-5-chloro-2-(2-thienyl)-1H-pyrrolo[3,2-b]pyridine (84 mg, 0.26 mmol, from Step 1), di-tert-butyl hydrazine-1,2-dicarboxylate (90 mg, 0.39 mmol) and Cs₂CO₃ (130 mg, 0.39 mmol) were combined in toluene (5.0 mL) and dicyclohexyl(2',4',6'-triisopropylbiphenyl-2-yl)phosphine-(2'-aminobiphenyl-2-yl)(chloro)palladium (1:1) (20 mg, 0.026 mmol) was added. The mixture was degassed by a stream of nitrogen through the solution for 10 minutes. The reaction was stirred at 120° C. overnight. The mixture was diluted with DCM, filtered and concentrated, then reconstituted and purified via preparative HPLC-MS (C18 eluting with a gradient of MeCN and H₂O containing 0.15% NH₄OH) to afford 30.8 mg of di-tert-butyl 1-[1-benzyl-2-(2-thienyl)-1H-pyrrolo[3,2-b]pyridin-5-yl]hydrazine-1,2-dicarboxylate. This intermediate was dissolved in AcOH (2.2 mL) and was heated in the microwave to a temperature of 180° C. for 7 minutes. AcOH was removed in vacuo and the product was purified via preparative HPLC-MS (C18 eluting with a gradient of MeCN and H₂O containing 0.15% NH₄OH). Yield: (11.3 mg, 13%).
¹H NMR (300 MHz, CDCl₃) δ 7.45-7.27 (m, 5H), 7.21 (d, J=9.8 Hz, 1H), 7.12-7.04 (m, 2H), 7.03-6.99 (m, 2H), 6.98 (s, 1H), 5.55 (s, 2H), 3.04 (s, 3H). LCMS (M+H)⁺: 345.2.

Example 74

6-benzyl-7-(1H-imidazol-4-yl)-1-methyl-6H-pyrrolo[2,3-e][1,2,4]-triazolo[4,3-a]pyridine

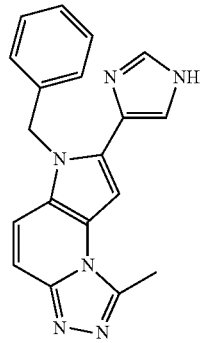 [SMILES: Cc1nnc2ccc3c(cc(-c4c[nH]cn4)n3Cc3ccccc3)n12]

Step 1. 1-benzyl-5-chloro-2-(1-trityl-1H-imidazol-4-yl)-1H-pyrrolo[3,2-b]pyridine

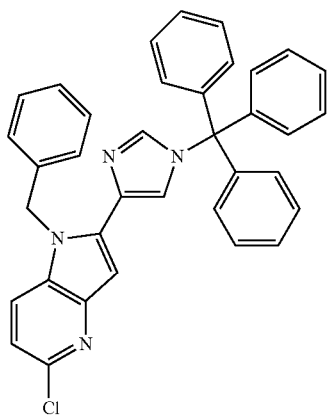 [SMILES: Clc1ccc2c(cc(-c3cn(C(c4ccccc4)(c4ccccc4)c4ccccc4)cn3)n2Cc2ccccc2)n1]

A mixture of 1-benzyl-2-bromo-5-chloro-1H-pyrrolo[3,2-b]pyridine (0.15 g, 0.47 mmol, from Example 62, Step 2) and 4-(tributylstannyl)-1-trityl-1H-imidazole (0.28 g, 0.47 mmol, Synthonix) in toluene (9.0 mL) was degassed. Tetrakis(triphenylphosphine)palladium(0) (54 mg, 0.047 mmol) was added and the reaction was stirred at 110° C. for 17 h. Solvent was removed in vacuo and the product was purified by flash chromatography, eluting with a gradient from 0-35% EtOAc in hexanes to afford product as a white solid (0.17 g, 66%).

¹H NMR (400 MHz, CDCl₃) δ 7.51 (d, J=1.4 Hz, 1H), 7.43 (dd, J=8.5, 0.8 Hz, 1H), 7.38-7.28 (m, 9H), 7.22-7.17 (m, 3H), 7.14-7.06 (m, 6H), 7.04 (d, J=1.4 Hz, 1H), 6.99 (d, J=8.5 Hz, 1H), 6.95-6.86 (m, 2H), 6.77 (d, J=0.7 Hz, 1H), 5.74 (s, 2H). LCMS (M+H)⁺: 551.2.

Step 2. 6-benzyl-7-(1H-imidazol-4-yl)-1-methyl-6H-pyrrolo[2,3-e][1,2,4]triazolo[4,3-a]pyridine 1-Benzyl-5-chloro-2-(1-trityl-1H-imidazol-4-yl)-1H-pyrrolo[3,2-b]pyridine (160 mg, 0.29 mmol, from Step 1), di-tert-butyl hydrazine-1,2-dicarboxylate (0.10 g, 0.44 mmol) and Cs₂CO₃ (0.14 g, 0.44 mmol) were combined in toluene (10 mL) and dicyclohexyl(2',4',6'-triisopropylbiphenyl-2-yl)phosphine-(2'-aminobiphenyl-2-yl)(chloro)palladium (1:1) (23 mg, 0.029 mmol) was added. The mixture was degassed with a stream of nitrogen through the solution and was then heated in the microwave to 140° C. for 30 minutes. Excess reagents were added, the mixture was again degassed, then heated in the microwave to 140° C. for 66 additional minutes. The reaction was cooled and diluted with DCM, filtered, and concentrated. Flash chromatography, eluting with a gradient from 0-50% EtOAc in hexanes afforded di-tert-butyl 1-[1-benzyl-2-(1-trityl-1H-imidazol-4-yl)-1H-pyrrolo[3,2-b]pyridin-5-yl]hydrazine-1,2-dicarboxylate as a light yellow oil (67 mg). This intermediate was dissolved in AcOH (3.0 mL) and heated in the microwave to 180° C. for 15 minutes. Acetic acid was removed in vacuo. The product was purified via preparative HPLC-MS (C18 eluting with a gradient of MeCN and H₂O containing 0.15% NH₄OH). Yield: (16 mg, 17%).

¹H NMR (300 MHz, CD₃OD) δ 7.84 (s, 1H), 7.66 (d, J=9.7 Hz, 1H), 7.42-7.10 (m, 6H), 6.99 (d, J=7.5 Hz, 2H), 5.81 (s, 2H), 3.03 (s, 3H). LCMS (M+H)⁺: 329.0.

Example 75

6-benzyl-1-methyl-7-[1-(2-morpholin-4-ylethyl)-1H-imidazol-4-yl]-6H-pyrrolo[2,3-e][1,2,4]triazolo[4,3-a]pyridine

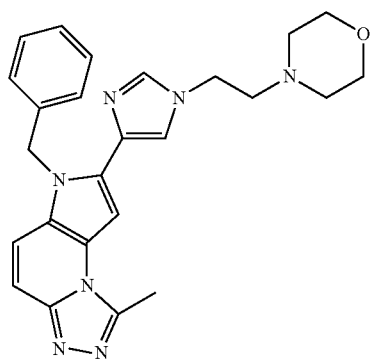 [SMILES: Cc1nnc2ccc3c(cc(-c4cn(CCN5CCOCC5)cn4)n3Cc3ccccc3)n12]

A mixture of 6-benzyl-7-(1H-imidazol-4-yl)-1-methyl-6H-pyrrolo[2,3-e][1,2,4]triazolo[4,3-a]pyridine (4.2 mg, 0.013 mmol, from Example 74), 4-(2-chloroethyl)morpholine hydrochloride (7.1 mg, 0.038 mmol, Aldrich) and Cs₂CO₃ (21 mg, 0.064 mmol) in DMF (0.21 mL) was stirred at 70° C. for one hour, followed by heating in the microwave to 140° C. for 30 minutes. The product was purified via preparative HPLC-MS (C18 eluting with a gradient of MeCN and H₂O containing 0.15% NH₄OH). Yield: (1.6 mg, 28%).

¹H NMR (300 MHz, CD₃OD) δ 7.84 (s, 1H), 7.64 (d, J=9.8 Hz, 1H), 7.44 (s, 1H), 7.32-7.17 (m, 5H), 7.05-6.93 (m, 2H), 5.82 (s, 2H), 4.16 (t, J=6.0 Hz, 2H), 3.66-3.48 (m, 4H), 3.03 (s, 3H), 2.68 (t, J=6.0 Hz, 2H), 2.50-2.35 (m, 4H). LCMS (M+H)⁺: 442.0.

Example 76

6-benzyl-1-methyl-7-(1-methyl-1H-pyrazol-3-yl)-6H-pyrrolo[2,3-e][1,2,4]triazolo[4,3-a]pyridine

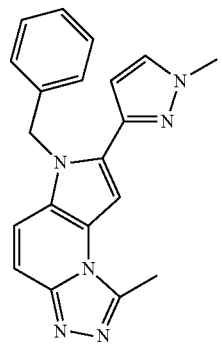 [SMILES: Cc1nnc2ccc3c(cc(-c4ccn(C)n4)n3Cc3ccccc3)n12]

Sodium hydride (4.0 mg, 0.099 mmol, 60% in mineral oil) was added to a solution of 6-benzyl-1-methyl-7-(1H-pyrazol-5-yl)-6H-pyrrolo[2,3-e][1,2,4]triazolo[4,3-a]pyridine (6.5 mg, 0.020 mmol, from Example 62) in DMF (0.20 mL). After 10 minutes, methyl iodide (3.7 μL, 0.059 mmol, Aldrich) was added. After 15 minutes reaction time, the reaction was quenched with water. The product was purified via preparative HPLC-MS (C18 eluting with a gradient of MeCN and H₂O containing 0.15% NH₄OH) and the major isomer was isolated. Yield: (2.7 mg, 40%).

¹H NMR (500 MHz, d₆-DMSO) δ 7.79 (d, J=2.3 Hz, 1H), 7.60 (d, J=9.8 Hz, 1H), 7.58-7.48 (m, 1H), 7.30 (s, 1H), 7.28 (d, J=9.7 Hz, 1H), 7.26-7.22 (m, 2H), 7.20-7.15 (m, 1H), 7.04

(d, J=7.3 Hz, 2H), 6.76 (d, J=2.3 Hz, 1H), 6.04 (s, 2H), 3.88 (s, 3H), 2.93 (s, 3H). LCMS (M+H)+: 343.0.

Example 77

6-benzyl-1-methyl-7-[1-(2-morpholin-4-ylethyl)-1H-pyrazol-3-yl]-6H-pyrrolo[2,3-e][1,2,4]triazolo[4,3-a]pyridine

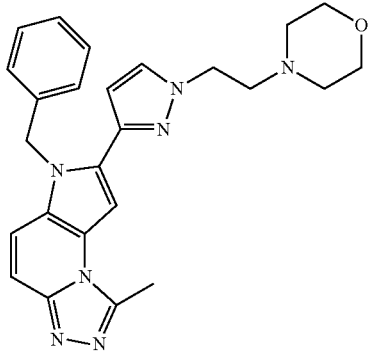 [SMILES: Cc1nnc2ccc3c(cc(-c4ccn(CCN5CCOCC5)n4)n3Cc3ccccc3)n12]

A mixture of 6-benzyl-1-methyl-7-(1H-pyrazol-5-yl)-6H-pyrrolo[2,3-e][1,2,4]triazolo[4,3-a]pyridine (4.2 mg, 0.013 mmol, from Example 62), 4-(2-chloroethyl)morpholine hydrochloride (7.1 mg, 0.038 mmol, Aldrich) and Cs$_2$CO$_3$ (21 mg, 0.064 mmol) in DMF (0.21 mL) was heated at 70° C. overnight. The product was purified via preparative HPLC-MS (C18 eluting with a gradient of MeCN and H$_2$O containing 0.15% NH$_4$OH) and the major isomer was isolated. Yield: (2.4 mg, 42%).

$^1$H NMR (300 MHz, CD$_3$OD) δ 7.72 (d, J=2.4 Hz, 1H), 7.63 (dd, J=9.7, 0.6 Hz, 1H), 7.33-7.13 (m, 5H), 7.07-6.97 (m, 2H), 6.68 (d, J=2.3 Hz, 1H), 6.03 (s, 2H), 4.30 (t, J=6.3 Hz, 2H), 3.70-3.45 (m, 4H), 3.02 (s, 3H), 2.78 (t, J=6.3 Hz, 2H), 2.51-2.27 (m, 4H). LCMS (M+H)+: 442.0.

Example 78

3-[3-(6-benzyl-1-methyl-6H-pyrrolo[2,3-e][1,2,4]triazolo[4,3-a]pyridin-7-yl)-1H-pyrazol-1-yl]propanenitrile

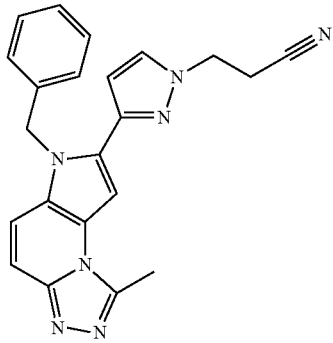 [SMILES: Cc1nnc2ccc3c(cc(-c4ccn(CCC#N)n4)n3Cc3ccccc3)n12]

2-Propenenitrile (3.0 μL, 0.046 mmol, Aldrich) and 1,8-diazabicyclo[5.4.0]undec-7-ene (2.3 μL, 0.015 mmol) were added to a solution of 6-benzyl-1-methyl-7-(1H-pyrazol-5-yl)-6H-pyrrolo[2,3-e][1,2,4]triazolo[4,3-a]pyridine (5.0 mg, 0.015 mmol, from Example 62) in acetonitrile (0.20 mL). After 3 minutes at room temperature, the reaction was found to be complete and was purified via preparative HPLC-MS (C18 eluting with a gradient of MeCN and H$_2$O containing 0.15% NH$_4$OH). Yield: (3.9 mg, 67%).

$^1$H NMR (300 MHz, CD$_3$OD) δ 7.78 (d, J=2.4 Hz, 1H), 7.65 (d, J=9.8 Hz, 1H), 7.33-7.15 (m, 5H), 7.10-7.01 (m, 2H), 6.74 (d, J=2.4 Hz, 1H), 6.03 (s, 2H), 4.45 (t, J=6.3 Hz, 2H), 3.02 (s, 3H), 2.98 (t, J=6.3 Hz, 2H). LCMS (M+H)+: 382.0.

Example 79

6-benzyl-7-(1-ethyl-1H-pyrazol-3-yl)-1-methyl-6H-pyrrolo[2,3-e][1,2,4]triazolo[4,3-a]pyridine

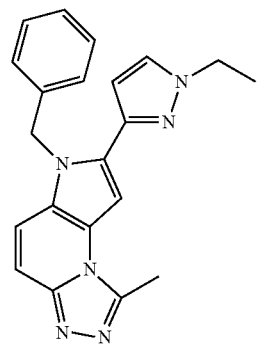 [SMILES: CCn1ccc(-c2cc3c(ccc4nnc(C)n43)n2Cc2ccccc2)n1]

Sodium hydride (3.3 mg, 0.082 mmol, 60% in mineral oil) was added to a solution of 6-benzyl-1-methyl-7-(1H-pyrazol-5-yl)-6H-pyrrolo[2,3-e][1,2,4]triazolo[4,3-a]pyridine (5.4 mg, 0.016 mmol, from Example 62) in DMF (0.20 mL). After 10 minutes, iodoethane (3.9 μL, 0.049 mmol, Aldrich) was introduced. After 15 minutes reaction time, the reaction was quenched with water. The product was purified via preparative HPLC-MS (C18 eluting with a gradient of MeCN and H$_2$O containing 0.15% NH$_4$OH). Yield: (3.1 mg, 53%).

$^1$H NMR (400 MHz, CD$_3$OD) δ 7.68 (d, J=2.3 Hz, 1H), 7.63 (dd, J=9.7, 0.6 Hz, 1H), 7.32-7.09 (m, 5H), 7.09-6.96 (m,

2H), 6.63 (d, J=2.3 Hz, 1H), 5.98 (s, 2H), 4.21 (q, J=7.3 Hz, 2H), 3.01 (s, 3H), 1.45 (t, J=7.3 Hz, 3H). LCMS (M+H)+: 357.2.

Example 80

6-benzyl-7-(1-ethyl-1H-imidazol-4-yl)-1-methyl-6H-pyrrolo[2,3-e][1,2,4]triazolo[4,3-a]pyridine

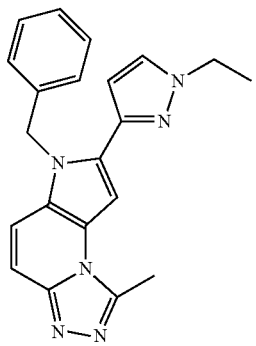 [SMILES: CCn1ccc(-c2cc3c(ccc4nnc(C)n43)n2Cc2ccccc2)n1]

Sodium hydride (3.1 mg, 0.078 mmol, 60% in mineral oil) was added to a solution of 6-benzyl-7-(1H-imidazol-4-yl)-1-methyl-6H-pyrrolo[2,3-e][1,2,4]triazolo[4,3-a]pyridine (5.1 mg, 0.016 mmol, from Example 74) in DMF (0.20 mL). After 10 minutes, iodoethane (3.7 µL, 0.046 mmol, Aldrich) was introduced and the reaction was allowed to proceed for 15 minutes, at which time it was quenched with water. Purification via preparative HPLC-MS (C18 eluting with a gradient of MeCN and H$_2$O containing 0.15% NH$_4$OH) afforded product (3.4 mg, 61%).

$^1$H NMR (300 MHz, CD$_3$OD) δ 7.81 (s, 1H), 7.64 (d, J=9.7 Hz, 1H), 7.40 (s, 1H), 7.30-7.13 (m, 5H), 7.02-6.93 (m, 2H), 5.82 (s, 2H), 4.08 (q, J=7.3 Hz, 2H), 3.01 (s, 3H), 1.44 (t, J=7.3 Hz, 3H). LCMS (M+H)+: 357.2.

Example 81

3-[4-(6-benzyl-1-methyl-6H-pyrrolo[2,3-e][1,2,4]triazolo[4,3-a]pyridin-7-yl)-1H-imidazol-1-yl]propanenitrile

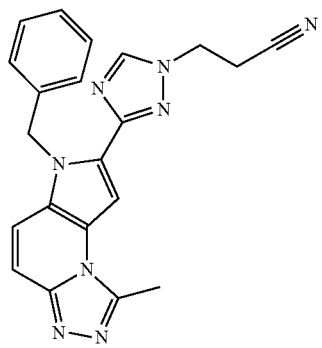 [SMILES: Cc1nnc2ccc3c(cc(-c4ncn(CCC#N)n4)n3Cc3ccccc3)n12]

A mixture of 6-benzyl-7-(1H-imidazol-4-yl)-1-methyl-6H-pyrrolo[2,3-e][1,2,4]triazolo[4,3-a]pyridine (4.3 mg, 0.013 mmol, from Example 74) and 2-propenenitrile (2.6 µL, 0.039 mmol, Aldrich) in MeCN (0.17 mL) was treated with 1,8-diazabicyclo[5.4.0]undec-7-ene (2.0 µL, 0.013 mmol, Aldrich). The reaction was allowed to proceed for 15 minutes, then was purified via preparative HPLC-MS (C18 eluting with a gradient of MeCN and H$_2$O containing 0.15% NH$_4$OH). Yield: (3.3 mg, 66%).

$^1$H NMR (400 MHz, CD$_3$OD) δ 7.91 (d, J=1.0 Hz, 1H), 7.65 (dd, J=9.7, 0.6 Hz, 1H), 7.50 (d, J=1.1 Hz, 1H), 7.30-7.15 (m, 5H), 7.04-6.97 (m, 2H), 4.37 (t, J=6.4 Hz, 2H), 3.01 (s, 3H), 3.01 (t, J=6.4 Hz, 2H). LCMS (M+H)+: 382.0.

Example 82

6-benzyl-N,1-dimethyl-6H-pyrrolo[2,3-e][1,2,4]triazolo[4,3-a]pyridine-7-carboxamide

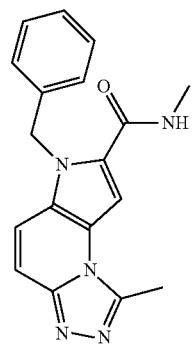 [SMILES: CNC(=O)c1cc2c(ccc3nnc(C)n32)n1Cc1ccccc1]

Step 1. ethyl 5-chloro-1-(phenylsulfonyl)-1H-pyrrolo[3,2-b]pyridine-2-carboxylate

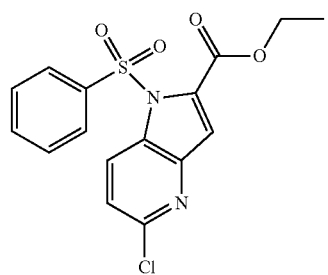 [SMILES: CCOC(=O)c1cc2nc(Cl)ccc2n1S(=O)(=O)c1ccccc1]

1.6 M n-Butyllithium in hexanes (9.6 mL, 15 mmol) was added dropwise to a solution of N,N-diisopropylamine (2.3 mL, 16 mmol) in THF (43 mL) at −78° C. Following complete addition, the temperature of the reaction was raised to 0° C. for 30 minutes and then was re-cooled to −78° C. 5-Chloro-1-(phenylsulfonyl)-1H-pyrrolo[3,2-b]pyridine (3.00 g, 10.2 mmol, from Example 2, Step 1) in THF (8 mL) was added dropwise and the reaction was stirred for 1 hour, at which time ethyl chloroformate (1.4 mL, 14 mmol, Alfa Aesar) was added. The reaction was allowed to stir at −78° C. for 2 hours and was then allowed to warm to room temperature. The mixture was poured into dilute HCl and extracted with three portions of ethyl acetate. The combined extracts were dried over sodium sulfate, decanted, and the solvent was removed in vacuo. Flash chromatography eluting with a gradient from 0-50% EtOAc in hexanes afforded product as an off white solid (1.8 g, 48%).

¹H NMR (400 MHz, CDCl₃) δ 8.41 (dd, J=8.9, 0.8 Hz, 1H), 8.07-8.01 (m, 2H), 7.67-7.62 (m, 1H), 7.58-7.51 (m, 2H), 7.37 (d, J=8.9 Hz, 1H), 7.21 (d, J=0.7 Hz, 1H), 4.42 (q, J=7.1 Hz, 2H), 1.40 (t, J=7.1 Hz, 3H). LCMS (M+H)⁺: 364.8.

Step 2. di-tert-butyl 1-[2-(ethoxycarbonyl)-1-(phenylsulfonyl)-1H-pyrrolo[3,2-b]pyridin-5-yl]hydrazine-1,2-dicarboxylate

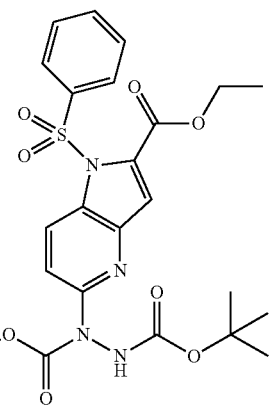

Ethyl 5-chloro-1-(phenylsulfonyl)-1H-pyrrolo[3,2-b]pyridine-2-carboxylate (1.80 g, 4.93 mmol, from Step 1), di-tert-butyl hydrazine-1,2-dicarboxylate (1.3 g, 5.4 mmol, Aldrich) and Cs₂CO₃ (1.6 g, 4.9 mmol, Aldrich) were combined in toluene (20 mL, 200 mmol) and dicyclohexyl(2',4',6'-triisopropylbiphenyl-2-yl)phosphine-(2'-aminobiphenyl-2-yl)(chloro)palladium (1:1) (0.39 g, 0.49 mmol, Aldrich) was added. The mixture was degassed by a stream of nitrogen through the solution for 10 minutes. The reaction was stirred at 110° C. for 3.5 hours. The reaction was cooled to room temperature, water was added and the product was extracted with five portions of EtOAc. The combined extracts were dried over sodium sulfate, filtered and concentrated. Flash chromatography, eluting with a gradient from 0-50% EtOAc in hexanes afforded product as a yellow foam (2.11 g, 76%).

¹H NMR (400 MHz, CDCl₃) δ 8.42 (dd, J=9.2, 0.8 Hz, 1H), 8.06-7.97 (m, 2H), 7.80 (br d, J=8.9 Hz, 1H), 7.66-7.56 (m, 1H), 7.54-7.48 (m, 2H), 7.33 (br s, 1H), 7.23 (d, J=0.6 Hz, 1H), 4.40 (q, J=7.1 Hz, 2H), 1.50 (s, 9H), 1.46 (d, J=3.3 Hz, 9H), 1.38 (t, J=7.1 Hz, 3H). LCMS (M+H)⁺: 560.9.

Step 3. 1-methyl-6H-pyrrolo[2,3-e][1,2,4]triazolo[4,3-a]pyridine-7-carboxylic acid

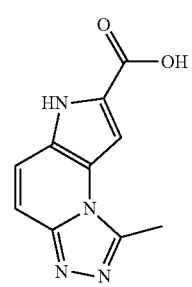 [SMILES: Cc1nnc2ccc3[nH]c(C(=O)O)cc3n12]

A solution of di-tert-butyl 1-[2-(ethoxycarbonyl)-1-(phenylsulfonyl)-1H-pyrrolo[3,2-b]pyridin-5-yl]hydrazine-1,2-dicarboxylate (2.11 g, 3.76 mmol, from Step 2) in AcOH (32 mL) was split into four portions and each was heated in the microwave to a temperature of 180° C. for 3 minutes. The reaction contents were pooled and the AcOH was removed in vacuo. The residue was azeotroped with toluene twice. The residue was reconstituted in EtOH (10 mL) and was treated with 1.0 M NaOH (10 mL, 10 mmol) overnight. Purification via preparative HPLC-MS (C18 eluting with a gradient of MeCN and H₂O containing 0.15% NH₄OH) afforded product (0.42 g, 50%).

¹H NMR (300 MHz, d₆-DMSO) δ 7.44 (dd, J=9.6, 0.5 Hz, 1H), 7.22 (d, J=9.5 Hz, 1H), 6.88 (d, J=0.5 Hz, 1H), 2.86 (s, 3H). LCMS (M+H)⁺: 216.9.

Step 4. 6-benzyl-1-methyl-6H-pyrrolo[2,3-e][1,2,4]triazolo[4,3-a]pyridine-7-carboxylic acid trifluoroacetate salt

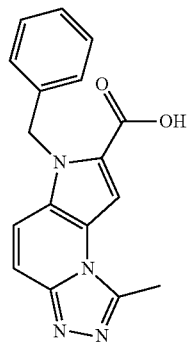 [SMILES: Cc1nnc2ccc3c(cc(C(=O)O)n3Cc3ccccc3)n12]

The mixture from Step 3 containing 1-methyl-6H-pyrrolo[2,3-e][1,2,4]triazolo[4,3-a]pyridine-7-carboxylic acid (0.298 g, 1.38 mmol) was mixed in DMF (6 mL) and acetonitrile (6 mL) and was treated with Cs₂CO₃ (1.8 g, 5.5 mmol) and was stirred for 10 minutes before the addition of benzyl bromide (0.30 mL, 2.5 mmol, Aldrich). The reaction was stirred overnight. Water was added and the product was extracted with three portions of EtOAc. The combined extracts were dried over sodium sulfate, filtered and concentrated. Flash chromatography, eluting with a gradient from 0-10% MeOH in DCM, was used to purify the desired alkylated ester (265 mg). This was stirred with 1.0 M NaOH (10 mL, 10 mmol) and methanol (10 mL) overnight. Some TFA was used to aid in dissolving insolubles and the product was purified via preparative HPLC-MS (C18 eluting with a gradient of MeCN and H₂O containing 0.1% TFA). Yield: (44 mg, 7%). LCMS (M+H)⁺: 307.0.

Step 5. 6-benzyl-N,1-dimethyl-6H-pyrrolo[2,3-e][1,2,4]triazolo[4,3-a]pyridine-7-carboxamide To a solution of 6-benzyl-1-methyl-6H-pyrrolo[2,3-e][1,2,4]triazolo[4,3-a]pyridine-7-carboxylic acid trifluoroacetate (0.044 g, 0.10 mmol, from Step 4) in DMF (1 mL) was added N,N-diisopropylethylamine (0.17 mL, 0.98 mmol) followed by N,N,N',N'-tetramethyl-O-(7-azabenzotriazol-1-yl)uronium hexafluorophosphate (0.14 g, 0.37 mmol). After stirring this combination for 2 minutes, 2.0 M methylamine in THF (0.42 mL, 0.84 mmol) was added. After a reaction time of 15 minutes, the reaction was diluted with MeOH, and the product was purified via preparative HPLC-MS (C18 eluting with a gradient of MeCN and H₂O containing 0.15% NH₄OH) (0.03 g, 90%).

¹H NMR (400 MHz, CD₃OD) δ 7.71 (d, J=9.9 Hz, 1H), 7.56 (s, 1H), 7.40 (d, J=9.9 Hz, 1H), 7.31-7.16 (m, 3H), 7.09 (m, 2H), 6.01 (s, 2H), 2.99 (s, 3H), 2.91 (s, 3H). LCMS (M+H)⁺: 319.9.

Example 83

6-benzyl-1-methyl-N-propyl-6H-pyrrolo[2,3-e][1,2,4]triazolo[4,3-a]pyridine-7-carboxamide

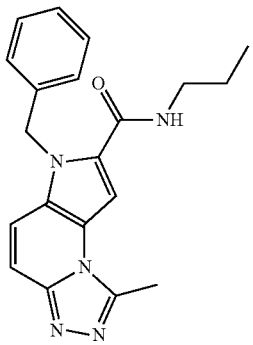 [SMILES: CCCNC(=O)c1cc2c(ccc3nnc(C)n32)n1Cc1ccccc1]

Step 1. ethyl 5-chloro-1-(phenylsulfonyl)-1H-pyrrolo[3,2-b]pyridine-2-carboxylate

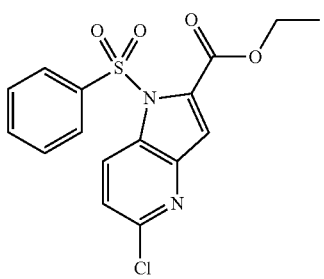 [SMILES: CCOC(=O)c1cc2nc(Cl)ccc2n1S(=O)(=O)c1ccccc1]

1.6 M n-Butyllithium in hexanes (9.6 mL, 15 mmol) was added to a solution of N,N-diisopropylamine (2.3 mL, 16 mmol) in THF (43 mL) at −78° C. Upon complete addition, the reaction was warmed to 0° C. for 30 minutes and then was re-cooled to −78° C. A solution of 5-chloro-1-(phenylsulfonyl)-1H-pyrrolo[3,2-b]pyridine (3.00 g, 10.2 mmol, from Example 2, Step 1) in THF (8 mL) was added dropwise. After stirring for one hour at −78° C., ethyl chloroformate (1.4 mL, 14 mmol, Alfa Aesar) was added and the reaction was stirred at −78° C. for 2 hours, after which time it was allowed to warm to room temperature. The reaction was poured into dilute HCl and the product was extracted with three portions of ethyl acetate. The combined extracts were dried over sodium sulfate, decanted, and the solvent removed in vacuo. Flash chromatography, eluting with a gradient from 0-30% EtOAc in hexanes afforded product as a yellow solid (2.15 g, 57%).

¹H NMR (300 MHz, CDCl₃) δ 8.41 (dd, J=8.9, 0.8 Hz, 1H), 8.08-8.00 (m, 2H), 7.70-7.61 (m, 1H), 7.59-7.49 (m, 2H), 7.37 (d, J=8.8 Hz, 1H), 7.21 (d, J=0.8 Hz, 1H), 4.42 (q, J=7.1 Hz, 2H), 1.40 (t, J=7.1 Hz, 2H). LCMS (M+H)⁺: 365.0.

Step 2. di-tert-butyl 1-[2-(ethoxycarbonyl)-1-(phenylsulfonyl)-1H-pyrrolo[3,2-b]pyridin-5-yl]hydrazine-1,2-dicarboxylate

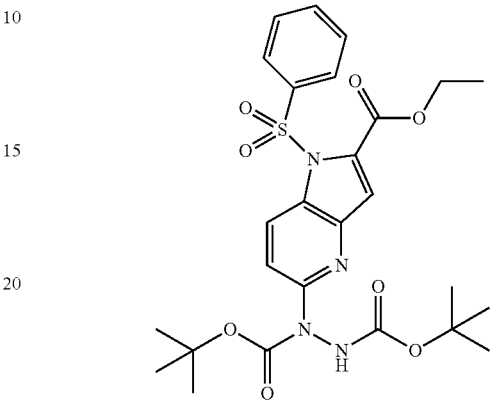

Ethyl 5-chloro-1-(phenylsulfonyl)-1H-pyrrolo[3,2-b]pyridine-2-carboxylate (2.15 g, 5.89 mmol, from Step 1), di-tert-butyl hydrazine-1,2-dicarboxylate (1.5 g, 6.5 mmol, Aldrich) and Cs₂CO₃ (1.9 g, 5.9 mmol, Aldrich) were combined in toluene (30 mL) and dicyclohexyl(2',4',6'-triisopropylbiphenyl-2-yl)phosphine-(2'-aminobiphenyl-2-yl)(chloro)palladium (1:1) (0.46 g, 0.59 mmol, Aldrich) was added. The mixture was degassed by a stream of nitrogen through the solution for 10 minutes. The reaction was stirred at 110° C. for 3 hours. Upon cooling to room temperature, water was added and the product was extracted with three portions of EtOAc. The combined extracts were dried over sodium sulfate, filtered, and concentrated. Flash chromatography, eluting with a gradient from 0-40% EtOAc in hexanes afforded product as a yellow foam (2.54 g, 77%).

¹H NMR (300 MHz, CDCl₃) δ 8.43 (d, J=9.1 Hz, 1H), 8.03 (d, J=8.0 Hz, 2H), 7.80 (d, J=9.2 Hz, 1H), 7.62 (t, J=7.2 Hz, 1H), 7.52 (t, J=7.7 Hz, 2H), 7.22 (s, 1H), 7.11 (br s, 1H), 4.41 (q, J=7.0 Hz, 2H), 1.52 (s, 9H), 1.47 (s, 9H), 1.39 (t, J=7.1 Hz, 3H). LCMS (M+H)⁺: 561.2.

Step 3. ethyl 1-methyl-6-(phenylsulfonyl)-6H-pyrrolo[2,3-e][1,2,4]triazolo[4,3-a]pyridine-7-carboxylate

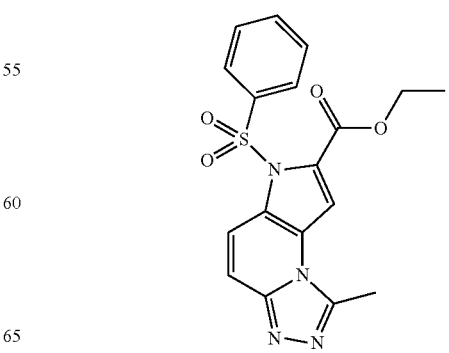

A solution of di-tert-butyl 1-[2-(ethoxycarbonyl)-1-(phenylsulfonyl)-1H-pyrrolo[3,2-b]pyridin-5-yl]hydrazine-1,2-dicarboxylate (2.5 g, 4.4 mmol, from Step 2) in AcOH (40 mL) was split into 5 batches and each was heated in the microwave to a temperature of 180° C. for 3 minutes. The reaction contents were pooled and AcOH was removed in vacuo. The residue was dissolved in EtOAc and washed with sat'd NaHCO$_3$ solution, followed by brine. The organic layer was dried over sodium sulfate, filtered and concentrated. Flash chromatography, eluting with a gradient from 0-100% EtOAc in hexanes, followed by 10% MeOH in DCM as mobile phase afforded solid product (1.27 g, 74%).

$^1$H NMR (400 MHz, CDCl$_3$) δ 8.17 (dd, J=10.1, 0.7 Hz, 1H), 8.15-8.09 (m, 2H), 7.71 (d, J=10.1 Hz, 1H), 7.71-7.66 (m, 1H), 7.61-7.55 (m, 2H), 7.41 (d, J=0.7 Hz, 1H), 4.42 (q, J=7.1 Hz, 2H), 2.97 (s, 3H), 1.41 (t, J=7.1 Hz, 3H). LCMS (M+H)$^+$: 384.9.

Step 4. methyl 6-benzyl-1-methyl-6H-pyrrolo[2,3-e][1,2,4]triazolo[4,3-a]pyridine-7-carboxylate

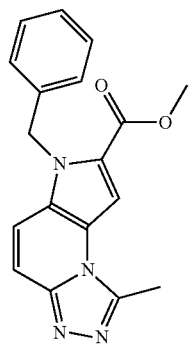 [SMILES: COC(=O)c1cc2c(ccc3nnc(C)n32)n1Cc1ccccc1]

To a suspension of ethyl 1-methyl-6-(phenylsulfonyl)-6H-pyrrolo[2,3-e][1,2,4]triazolo[4,3-a]pyridine-7-carboxylate (1.27 g, 3.30 mmol, Step 3) in THF (10 mL) was added 1.0 M NaOH (10 mL, 10 mmol). The reaction was stirred for 3 hours. Additional 1.0 M NaOH (50 mL, 20 mmol), NaOH solid (5.0 g, 120 mmol) and THF (30 mL) were added and stirring was continued overnight. Some solids were removed by filtration and were rinsed with water. The filtrate was acidified to pH ~4 by the addition of conc. HCl. The solid that was then suspended in the aqueous layer was filtered off to obtain product containing 1-methyl-6H-pyrrolo[2,3-e][1,2,4]triazolo[4,3-a]pyridine-7-carboxylic acid as a yellow solid. LCMS (M+H)$^+$: 217.1.

Potassium carbonate (0.73 g, 5.3 mmol) and benzyl bromide (0.260 mL, 2.19 mmol, Aldrich) were added to the carboxylic acid intermediate in DMF (10 mL). The reaction was stirred for 1 hour. Sodium hydride (0.053 g, 1.3 mmol, 60% in mineral oil) was added and the reaction was continued for 30 minutes before pouring into water and filtering to prepare for HPLC purification. Samples prepared with the addition of some MeOH stood overnight and the methyl ester was then observed in significant amount. Purification via preparative HPLC-MS (C18 eluting with a gradient of MeCN and H$_2$O containing 0.15% NH$_4$OH) afforded methyl ester as product (80 mg, 7%).

$^1$H NMR (400 MHz, CDCl$_3$) δ 7.53 (d, J=9.9 Hz, 1H), 7.50 (d, J=0.7 Hz, 1H), 7.35-7.23 (m, 4H), 7.06-7.01 (m, 2H), 5.93 (s, 2H), 3.91 (s, 3H), 3.00 (s, 3H). LCMS (M+H)$^+$: 320.9.

Step 5. 6-benzyl-1-methyl-6H-pyrrolo[2,3-e][1,2,4]triazolo[4,3-a]pyridine-7-carboxylic acid trifluoroacetate salt

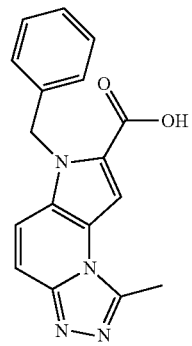 [SMILES: Cc1nnc2ccc3c(cc(C(=O)O)n3Cc3ccccc3)n12]

Methyl 6-benzyl-1-methyl-6H-pyrrolo[2,3-e][1,2,4]triazolo[4,3-a]pyridine-7-carboxylate (0.080 g, 0.25 mmol, from Step 4) was stirred with 1.0 M NaOH (4.0 mL, 4.0 mmol) in methanol (4.0 mL) overnight. Purification via preparative HPLC-MS (C18 eluting with a gradient of MeCN and H$_2$O containing 0.1% TFA) afforded product as TFA salt (71 mg, 70%). LCMS (M+H)$^+$: 307.1.

Step 6. 6-benzyl-1-methyl-N-propyl-6H-pyrrolo[2,3-e][1,2,4]triazolo[4,3-a]pyridine-7-carboxamide To a solution of 6-benzyl-1-methyl-6H-pyrrolo[2,3-e][1,2,4]triazolo[4,3-a]pyridine-7-carboxylic acid trifluoroacetate salt (0.013 g, 0.031 mmol, from Step 5) in DMF (0.5 mL) was added N,N-diisopropylethylamine (0.023 mL, 0.13 mmol) followed by N,N,N',N'-tetramethyl-O-(7-azabenzotriazol-1-yl)uronium hexafluorophosphate (0.022 g, 0.059 mmol). After stirring for 2 minutes, 1-propanamine (0.011 mL, 0.13 mmol, Aldrich) was added. The reaction was stirred for 15 minutes, then was diluted with MeOH and purified via preparative HPLC-MS (C18 eluting with a gradient of MeCN and H$_2$O containing 0.15% NH$_4$OH). Yield: (3.5 mg, 32%).

$^1$H NMR (400 MHz, d$_6$-DMSO) δ 8.61 (t, J=5.5 Hz, 1H), 7.72 (d, J=9.8 Hz, 1H), 7.69 (s, 1H), 7.45 (d, J=9.8 Hz, 1H), 7.30-7.23 (m, 2H), 7.23-7.16 (m, 1H), 7.13-7.02 (m, 2H), 6.02 (s, 2H), 3.21 (q, J=6.7 Hz, 2H), 2.91 (s, 3H), 1.52 (h, J=7.4 Hz, 2H), 0.87 (t, J=7.4 Hz, 3H). LCMS (M+H)⁺: 348.2.

Example 84

6-benzyl-N-isopropyl-1-methyl-6H-pyrrolo[2,3-e][1,2,4]triazolo[4,3-a]pyridine-7-carboxamide

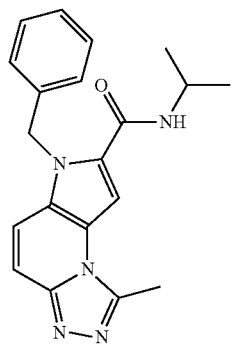 [SMILES: Cc1nnc2ccc3c(cc(C(=O)NC(C)C)n3Cc3ccccc3)n12]

Prepared as in Example 83, using 2-propanamine (0.011, 0.13 mmol, Aldrich) in Step 6. Yield: (3.5 mg, 32%).

¹H NMR (400 MHz, CD₃OD) δ 7.75 (dd, J=9.9, 0.7 Hz, 1H), 7.60 (d, J=0.7 Hz, 1H), 7.41 (d, J=9.9 Hz, 1H), 7.32-7.16 (m, 3H), 7.14-7.06 (m, 2H), 5.98 (s, 2H), 4.16 (p, J=6.6 Hz, 1H), 3.01 (s, 3H), 1.24 (d, J=6.6 Hz, 6H). LCMS (M+H)⁺: 348.1.

Example 85

6-benzyl-N-cyclobutyl-1-methyl-6H-pyrrolo[2,3-e][1,2,4]triazolo[4,3-a]pyridine-7-carboxamide

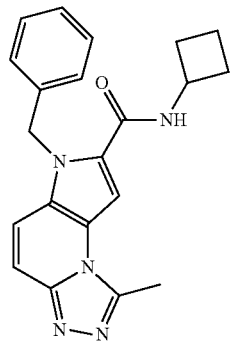 [SMILES: Cc1nnc2ccc3c(cc(C(=O)NC4CCC4)n3Cc3ccccc3)n12]

Prepared as in Example 83, using cyclobutanamine (0.011, 0.13 mmol, Aldrich) in Step 6. Yield: (3.5 mg, 31%).

¹H NMR (400 MHz, CD₃OD) δ 7.73 (dd, J=9.9, 0.5 Hz, 1H), 7.65 (d, J=0.5 Hz, 1H), 7.41 (d, J=9.9 Hz, 1H), 7.30-7.18 (m, 3H), 7.12-7.04 (m, 2H), 5.98 (s, 2H), 4.46 (p, J=8.4 Hz, 1H), 3.02 (s, 3H), 2.49-2.25 (m, 2H), 2.23-1.99 (m, 2H), 1.90-1.70 (m, 2H). LCMS (M+H)⁺: 360.1.

Example 86

6-benzyl-1-methyl-N-[(1R)-2,2,2-trifluoro-1-methylethyl]-6H-pyrrolo[2,3-e][1,2,4]triazolo[4,3-a]pyridine-7-carboxamide

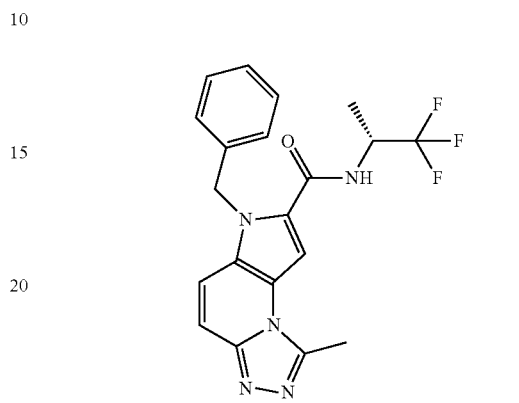

Prepared as in Example 83, using (2R)-1,1,1-trifluoropropan-2-amine hydrochloride (0.020 g, 0.13 mmol, SynQuest Labs) and additional N,N-diisopropylethylamine (0.046 mL, 0.26 mmol) in Step 6. Yield: (3 mg, 20%).

¹H NMR (400 MHz, CD₃OD) δ 7.77 (dd, J=9.9, 0.7 Hz, 1H), 7.73 (d, J=0.6 Hz, 1H), 7.45 (d, J=9.9 Hz, 1H), 7.30-7.17 (m, 3H), 7.14-7.07 (m, 2H), 6.01 (s, 2H), 4.88-4.78 (m, 1H), 3.02 (s, 3H), 1.42 (d, J=7.1 Hz, 3H). LCMS (M+H)⁺: 402.0.

Example 87

3-[3-(6-benzyl-1-methyl-6H-pyrrolo[2,3-e][1,2,4]triazolo[4,3-a]pyridin-7-yl)-1H-pyrazol-1-yl]butanenitrile trifluoroacetate salt (racemate)

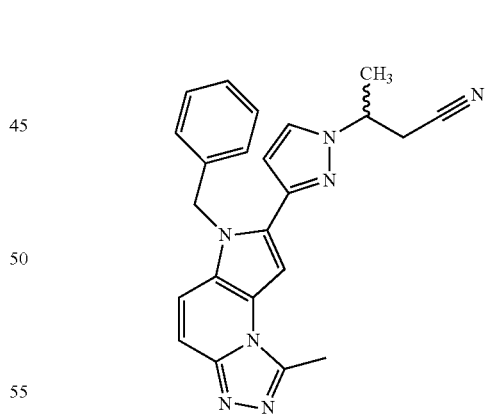

To a solution of 6-benzyl-1-methyl-7-(1H-pyrazol-5-yl)-6H-pyrrolo[2,3-e][1,2,4]triazolo[4,3-a]pyridine trifluoroacetate salt (0.013 g, 0.030 mmol, prepared as in Example 62 but purified via preparative HPLC-MS (C18 eluting with a gradient containing MeCN and H₂O containing 0.1% TFA to provide the TFA salt) in acetonitrile (0.5 mL) was added 2-butenenitrile (0.016 mL, 0.2 mmol, Aldrich) and 1,8-diazabicyclo[5.4.0]undec-7-ene (0.024 mL, 0.160 mmol, Aldrich) and the reaction was stirred overnight. The product was purified via preparative HPLC-MS (C18 eluting with a gradient of MeCN and H₂O containing 0.15% NH₄OH) followed by subjecting to a second preparative HPLC-MS purification (C18 eluting with a gradient of MeCN and H₂O containing 0.1% TFA). Yield: (6 mg, 40%).

¹H NMR (300 MHz, CD₃OD) δ 8.30 (d, J=9.3 Hz, 1H), 7.87 (d, J=2.4 Hz, 1H), 7.60 (s, 1H), 7.50 (d, J=9.5 Hz, 1H), 7.31-7.17 (m, 3H), 7.15-7.04 (m, 2H), 6.91 (d, J=2.4 Hz, 1H), 6.20 (s, 2H), 4.85-4.70 (m, 1H), 3.15 (s, 3H), 2.97 (d, J=6.4 Hz, 2H), 1.58 (d, J=6.7 Hz, 3H). LCMS (M+H)⁺: 396.0.

Example 88

3-[3-(6-benzyl-1-methyl-6H-pyrrolo[2,3-e][1,2,4]triazolo[4,3-a]pyridin-7-yl)-1H-pyrazol-1-yl]-2-methylpropanenitrile trifluoroacetate salt (racemate)

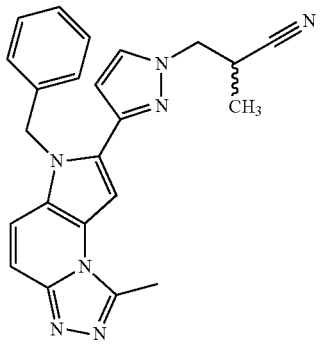 [SMILES: Cc1nnc2ccc3c(cc(-c4ccn(CC(C)C#N)n4)n3Cc3ccccc3)n12]

Prepared as in Example 87, using 2-propenenitrile, 2-methyl- (0.04 mL, 0.5 mmol, Aldrich) and 1,8-diazabicyclo[5.4.0]undec-7-ene (0.06 mL, 0.4 mmol, Aldrich), which were added incrementally over the 24 hours that the reaction was conducted. Yield: (3 mg, 20%).

¹H NMR (300 MHz, CD₃OD) δ 8.21 (d, J=9.6 Hz, 1H), 7.84 (d, J=2.4 Hz, 1H), 7.57 (s, 1H), 7.47 (d, J=9.6 Hz, 1H), 7.32-7.15 (m, 3H), 7.13-7.02 (m, 2H), 6.91 (d, J=2.4 Hz, 1H), 6.20 (s, 2H), 4.41 (d, J=6.7 Hz, 2H), 3.36-3.27 (m, 1H), 3.14 (s, 3H), 1.23 (d, J=7.1 Hz, 3H). LCMS (M+H)⁺: 396.0.

Example 89

2-[3-(6-benzyl-1-methyl-6H-pyrrolo[2,3-e][1,2,4]triazolo[4,3-a]pyridin-7-yl)-1H-pyrazol-1-yl]-N,N-dimethylethanamine

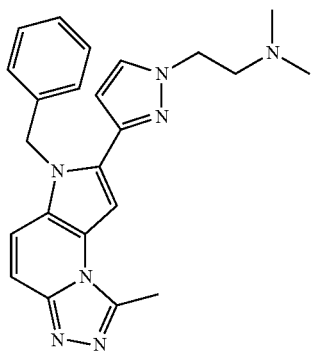 [SMILES: Cc1nnc2ccc3c(cc(-c4ccn(CCN(C)C)n4)n3Cc3ccccc3)n12]

Sodium hydride (0.0041 g, 0.10 mmol, 60% in mineral oil) was added to a solution of 6-benzyl-1-methyl-7-(1H-pyrazol-5-yl)-6H-pyrrolo[2,3-e][1,2,4]triazolo[4,3-a]pyridine trifluoroacetate salt (0.013 g, 0.029 mmol, prepared as in Example 62 but purified via preparative HPLC-MS (C18 eluting with a gradient containing MeCN and H₂O containing 0.1% TFA to provide the TFA salt) and β-Dimethylaminoethyl chloride hydrochloride (0.0063 g, 0.044 mmol, Aldrich) in DMF (0.5 mL). The reaction was stirred at room temperature for 2 hours. Additional NaH (0.004 g, 0.1 mmol, 60% in mineral oil) was added and the reaction was continued for 2 additional hours. The reaction was quenched by the addition of water, and was diluted with MeCN, filtered, and purified via preparative HPLC-MS (C18 eluting with a gradient of MeCN and H₂O containing 0.15% NH₄OH). Yield: (6 mg, 50%).

¹H NMR (300 MHz, CD₃OD) δ 7.71 (d, J=2.4 Hz, 1H), 7.65 (d, J=9.8 Hz, 1H), 7.34-7.15 (m, 5H), 7.09-6.98 (m, 2H), 6.68 (d, J=2.4 Hz, 1H), 6.03 (s, 2H), 4.29 (t, J=6.6 Hz, 2H), 3.03 (s, 3H), 2.78 (t, J=6.6 Hz, 2H), 2.20 (s, 6H). LCMS (M+H)⁺: 400.1.

Example 90

{3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile

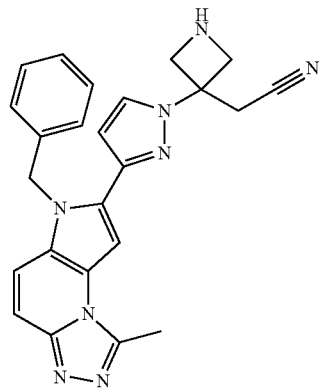 [SMILES: Cc1nnc2ccc3c(cc(-c4ccn(C5(CC#N)CNC5)n4)n3Cc3ccccc3)n12]

tert-Butyl 3-(cyanomethylene)azetidine-1-carboxylate (59 mg, 0.30 mmol, prepared as described in WO 2009114512) and 1,8-diazabicyclo[5.4.0]undec-7-ene (23 μL, 0.15 mmol) were added to a solution of 6-benzyl-1-methyl-7-(1H-pyrazol-5-yl)-6H-pyrrolo[2,3-e][1,2,4]triazolo[4,3-a]pyridine (50 mg, 0.15 mmol, from Example 62) in acetonitrile (2.0 mL). After stirring for 20 minutes, 4.0 M HCl in dioxane (0.50 mL, 2.0 mmol) was added. After a further reaction time of 22 minutes, the solvent was removed in vacuo and the residue was dissolved in MeOH. Aqueous ammonia was added to adjust pH=10. Purification via preparative HPLC-MS (C18 eluting with a gradient of MeCN and H₂O containing 0.15% NH₄OH) afforded product as a white solid (28 mg, 44%).

¹H NMR (400 MHz, CD₃OD) δ 7.98 (d, J=2.5 Hz, 1H), 7.70 (d, J=9.8 Hz, 1H), 7.38 (s, 1H), 7.30 (d, J=9.7 Hz, 1H), 7.28-7.15 (m, 3H), 7.09-7.01 (m, 2H), 6.88 (d, J=2.5 Hz, 1H), 6.05 (s, 2H), 4.09 (d, J=10.1 Hz, 2H), 3.78 (d, J=10.2 Hz, 2H), 3.34 (s, 2H), 3.05 (s, 3H). LCMS (M+H)⁺: 423.2.

Example 91

{1-acetyl-3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile

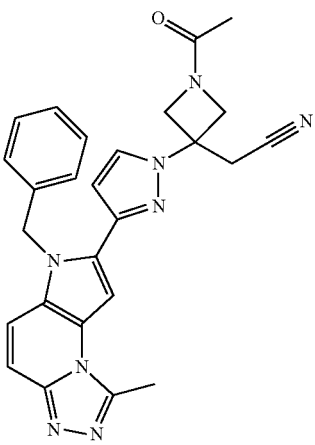 [SMILES: CC(=O)N1CC(CC#N)(n2ccc(-c3cc4c(ccc5nnc(C)n54)n3Cc3ccccc3)n2)C1]

To {3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile (8.0 mg, 0.019 mmol, from Example 90) was added acetyl chloride (1.6 μL, 0.022 mmol, Aldrich) in DCM (0.50 mL), followed by triethylamine (5.3 μL, 0.038 mmol). The reaction was complete in 5 minutes. Purification via preparative HPLC-MS (C18 eluting with a gradient of MeCN and H₂O containing 0.15% NH₄OH) afforded desired product (8.2 mg, 93%).

$^1$H NMR (400 MHz, d$_6$-DMSO) δ 8.20 (d, J=2.5 Hz, 1H), 7.74 (d, J=9.9 Hz, 1H), 7.44 (s, 1H), 7.36 (d, J=9.7 Hz, 1H), 7.28-7.14 (m, 3H), 7.08-7.01 (m, 2H), 6.99 (d, J=2.5 Hz, 1H), 6.05 (d, J=16.6 Hz, 1H), 6.01 (d, J=16.6 Hz, 1H), 4.54 (d, J=9.4 Hz, 1H), 4.40 (d, J=9.3 Hz, 1H), 4.24 (d, J=10.4 Hz, 1H), 4.12 (d, J=10.4 Hz, 1H), 3.55 (s, 2H), 2.95 (s, 3H), 1.78 (s, 3H). LCMS (M+H)$^+$: 465.2.

Example 92

[3-[3-(6-benzyl-1-methyl-6H-pyrrolo[2,3-e][1,2,4]triazolo[4,3-a]pyridin-7-yl)-1H-pyrazol-1-yl]-1-(methylsulfonyl)azetidin-3-yl]acetonitrile

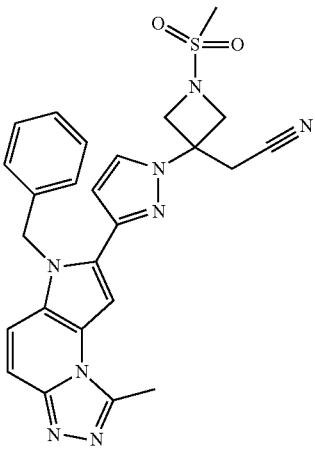 [SMILES: Cc1nnc2ccc3c(cc(-c4ccn(C5(CC#N)CN(S(C)(=O)=O)C5)n4)n3Cc3ccccc3)n12]

To {3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile (6.0 mg, 0.014 mmol, from Example 90) was added methanesulfonyl chloride (1.3 μL, 0.017 mmol, Aldrich) in DCM (0.50 mL), followed by triethylamine (4.0 μL, 0.028 mmol). The reaction was complete in 4 minutes. Purification via preparative HPLC-MS (C18 eluting with a gradient of MeCN and H₂O containing 0.15% NH₄OH) afforded product (5.9 mg, 83%).

$^1$H NMR (400 MHz, d$_6$-DMSO) δ 8.24 (d, J=2.5 Hz, 1H), 7.73 (d, J=9.8 Hz, 1H), 7.45 (s, 1H), 7.35 (d, J=9.7 Hz, 1H), 7.27-7.12 (m, 3H), 7.09-7.02 (m, 2H), 7.00 (d, J=2.5 Hz, 1H), 6.04 (s, 2H), 4.39 (d, J=9.4 Hz, 2H), 4.20 (d, J=9.4 Hz, 2H), 3.55 (s, 2H), 3.02 (s, 3H), 2.95 (s, 3H). LCMS (M+H)$^+$: 501.2.

Example 93

{3-[3-(6-benzyl-1-methyl-6H-pyrrolo[2,3-e][1,2,4]triazolo[4,3-a]pyridin-7-yl)-1H-pyrazol-1-yl]-1-methylazetidin-3-yl}acetonitrile

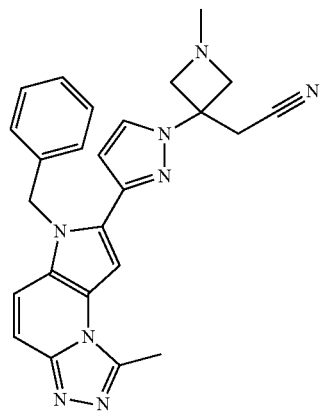 [SMILES: Cc1nnc2ccc3c(cc(-c4ccn(C5(CC#N)CN(C)C5)n4)n3Cc3ccccc3)n12]

To a mixture of {3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile (11 mg, 0.026 mmol, from Example 90) in DCM (0.50 mL) was added formaldehyde (10 mg, 0.13 mmol, 37 wt % in water, Aldrich), followed by sodium triacetoxyborohydride (16 mg, 0.078 mmol). The reaction was complete in 18 minutes. Purification via preparative HPLC-MS (C18 eluting with a gradient of MeCN and H₂O containing 0.15% NH₄OH) afforded product. Yield: (8.2 mg, 72%).

$^1$H NMR (400 MHz, d$_6$-DMSO) δ 8.13 (d, J=2.5 Hz, 1H), 7.73 (d, J=9.7 Hz, 1H), 7.41 (s, 1H), 7.34 (d, J=9.7 Hz, 1H), 7.27-7.14 (m, 3H), 7.08-7.01 (m, 2H), 6.93 (d, J=2.5 Hz, 1H), 6.03 (s, 2H), 3.50 (d, J=7.8 Hz, 2H), 3.47 (d, J=7.8 Hz, 2H), 3.41 (s, 2H), 2.94 (s, 3H), 2.27 (s, 3H). LCMS (M+H)$^+$: 437.2.

Example 94

6-benzyl-N,N,1-trimethyl-6H-pyrrolo[2,3-e][1,2,4]-triazolo[4,3-a]pyridine-7-carboxamide

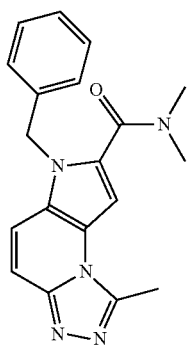 [SMILES: Cc1nnc2ccc3c(cc(C(=O)N(C)C)n3Cc3ccccc3)n12]

To a solution of 6-benzyl-1-methyl-6H-pyrrolo[2,3-e][1,2,4]triazolo[4,3-a]pyridine-7-carboxylic acid trifluoroacetate (0.015 g, 0.036 mmol, from Example 83, Step 5) in DMF (0.3 mL) was added N,N-diisopropylethylamine (0.058 mL, 0.33 mmol) followed by N,N,N',N'-tetramethyl-O-(7-azabenzotriazol-1-yl)uronium hexafluorophosphate (0.048 g, 0.12 mmol). After stirring for 2 minutes, 2.0 M dimethylamine in THF (0.14 mL, 0.28 mmol, Aldrich) was added. After 15 minutes reaction time, the reaction was diluted with MeOH and purified via preparative HPLC-MS (C18 eluting with a gradient of MeCN and H$_2$O containing 0.15% NH$_4$OH). Yield: (1.2 mg, 10%).

$^1$H NMR (300 MHz, CD$_3$OD) δ 7.84 (d, J=9.9 Hz, 1H), 7.44 (d, J=9.8 Hz, 1H), 7.36-7.24 (m, 3H), 7.22 (s, 1H), 7.17-7.07 (m, 2H), 5.62 (s, 2H), 2.98 (s, 3H), 3.09-2.87 (broad, 6H). LCMS (M+H)$^+$: 334.1.

Example 95

3-[3-(6-benzyl-1-methyl-6H-pyrrolo[2,3-e][1,2,4]triazolo[4,3-a]pyridin-7-yl)-1H-pyrazol-1-yl]-N,N-dimethylpropanamide

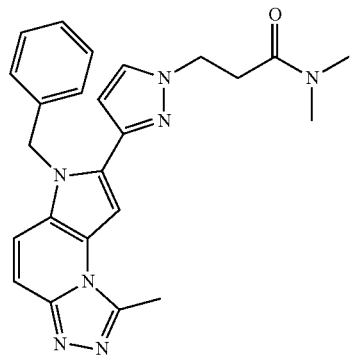 [SMILES: Cc1nnc2ccc3c(cc(-c4ccn(CCC(=O)N(C)C)n4)n3Cc3ccccc3)n12]

Step 1. 3-[3-(6-benzyl-1-methyl-6H-pyrrolo[2,3-e][1,2,4]triazolo[4,3-a]pyridin-7-yl)-1H-pyrazol-1-yl]propanoic acid

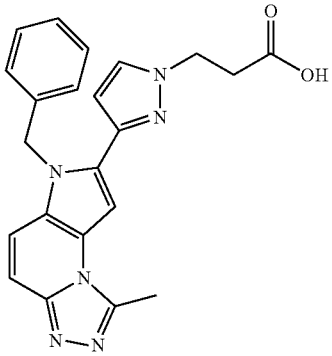 [SMILES: Cc1nnc2ccc3c(cc(-c4ccn(CCC(=O)O)n4)n3Cc3ccccc3)n12]

Methyl acrylate (41 μL, 0.46 mmol, Aldrich) and 1,8-diazabicyclo[5.4.0]undec-7-ene (23 μL, 0.15 mmol, Aldrich) were added to 6-benzyl-1-methyl-7-(1H-pyrazol-5-yl)-6H-pyrrolo[2,3-e][1,2,4]triazolo[4,3-a]pyridine (50 mg, 0.15 mmol, from Example 62) in acetonitrile (2.0 mL, 38 mmol) and the reaction was stirred for 15 minutes. Purification via preparative HPLC-MS (C18 eluting with a gradient of MeCN and H$_2$O containing 0.15% NH$_4$OH) afforded ester intermediate (36 mg, 57%). LCMS (M+H)$^+$: 415.1.

1.0 M NaOH (1.0 mL, 1.0 mmol) was added to the ester in THF (1.0 mL) and the reaction was continued for 20 minutes before being acidified to pH ~3-4 by the addition of 1.0 N HCl to cause the precipitation of the product as a white solid. Most of the THF was removed in vacuo and the product was isolated by filtration and air dried. Yield: (31 mg, 51%).

$^1$H NMR (400 MHz, d$_6$-DMSO) δ 7.84-7.79 (m, 1H), 7.68 (d, J=9.8 Hz, 1H), 7.31 (d, J=9.7 Hz, 2H), 7.31 (s, 1H), 7.26-7.14 (m, 3H), 7.07-7.01 (m, 2H), 6.75 (d, J=2.3 Hz, 1H), 6.03 (s, 2H), 4.34 (t, J=6.7 Hz, 2H), 2.93 (s, 3H), 2.77 (t, J=6.7 Hz, 2H). LCMS (M+H)$^+$: 401.0.

Step 2. 3-[3-(6-benzyl-1-methyl-6H-pyrrolo[2,3-e][1,2,4]triazolo[4,3-a]pyridin-7-yl)-1H-pyrazol-1-yl]-N,N-dimethylpropanamide To a solution of 3-[3-(6-benzyl-1-methyl-6H-pyrrolo[2,3-e][1,2,4]triazolo[4,3-a]pyridin-7-yl)-1H-pyrazol-1-yl]propanoic acid (7.0 mg, 0.017 mmol, from Step 1) in DMF (0.3 mL) was added N,N-diisopropylethylamine (12 μL, 0.070 mmol, Aldrich) followed by N,N,N',N'-tetramethyl-O-(7-azabenzotriazol-1-yl)uronium hexafluorophosphate (12 mg, 0.031 mmol, Aldrich). After stirring for 2 minutes, 2.0 M dimethylamine in THF (0.070 mL, 0.14 mmol, Aldrich) was added. After 15 minutes, the reaction was diluted with MeOH and purified via preparative HPLC-MS (C18 eluting with a gradient of MeCN and H$_2$O containing 0.15% NH$_4$OH). Yield: (4.3 mg, 58%).

$^1$H NMR (400 MHz, d$_6$-DMSO) δ 7.81 (d, J=2.3 Hz, 1H), 7.65 (d, J=9.8 Hz, 1H), 7.32 (s, 1H), 7.30 (d, J=9.7 Hz, 1H), 7.27-7.14 (m, 3H), 7.07-7.00 (m, 2H), 6.75 (d, J=2.3 Hz, 1H), 6.05 (s, 2H), 4.34 (t, J=6.8 Hz, 2H), 2.93 (s, 3H), 2.82 (t, J=6.9 Hz, 2H), 2.80 (s, 3H), 2.75 (s, 3H). LCMS (M+H)$^+$: 428.0.

Example 96

3-[3-(6-benzyl-1-methyl-6H-pyrrolo[2,3-e][1,2,4]triazolo[4,3-a]pyridin-7-yl)-1H-pyrazol-1-yl]-N-ethylpropanamide

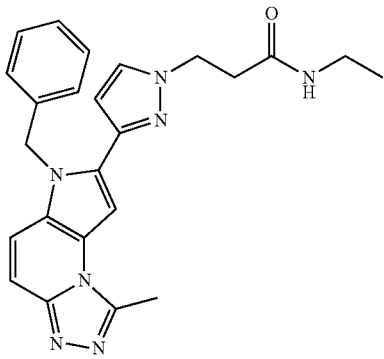 [SMILES: CCNC(=O)CCn1ccc(-c2cc3c(ccc4nnc(C)n43)n2Cc2ccccc2)n1]

To a solution of 3-[3-(6-benzyl-1-methyl-6H-pyrrolo[2,3-e][1,2,4]triazolo[4,3-a]pyridin-7-yl)-1H-pyrazol-1-yl]propanoic acid (8.0 mg, 0.020 mmol, prepared as in Example 95, Step 1) in DMF (0.40 mL) was added N,N-diisopropylethylamine (14 μL, 0.080 mmol, Aldrich) followed by N,N,N',N'-tetramethyl-O-(7-azabenzotriazol-1-yl)uronium hexafluorophosphate (14 mg, 0.036 mmol, Aldrich). After stirring for 2 minutes, ethylamine (11 μL, 0.20 mmol, neat, Aldrich) was introduced, and the reaction was stirred for 15 minutes. The reaction was diluted with MeOH, and purified via preparative HPLC-MS (C18 eluting with a gradient of MeCN and H$_2$O containing 0.15% NH$_4$OH). Yield: (3.3 mg, 39%).

$^1$H NMR (400 MHz, d$_6$-DMSO) δ 7.88 (t, J=5.3 Hz, 1H), 7.77 (d, J=2.3 Hz, 1H), 7.66 (d, J=9.8 Hz, 1H), 7.30 (d, J=9.7 Hz, 1H), 7.30 (s, 1H), 7.26-7.15 (m, 3H), 7.07-7.01 (m, 2H), 6.73 (d, J=2.3 Hz, 1H), 6.04 (s, 2H), 4.35 (t, J=6.9 Hz, 2H), 3.00 (qd, J=7.2, 5.6 Hz, 2H), 2.93 (s, 3H), 2.62 (t, J=6.9 Hz, 2H), 0.94 (t, J=7.2 Hz, 3H). LCMS (M+H)$^+$: 428.0.

Example 97

3-[3-(6-benzyl-1-methyl-6H-pyrrolo[2,3-e][1,2,4]triazolo[4,3-a]pyridin-7-yl)-1H-pyrazol-1-yl]-N-methylpropanamide

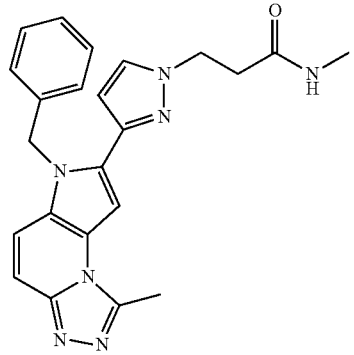 [SMILES: CNC(=O)CCn1ccc(-c2cc3c(ccc4nnc(C)n43)n2Cc2ccccc2)n1]

Prepared by the method of Example 96, using 2.0 M methylamine in THF (80. μL, 0.16 mmol, Aldrich). Yield: (3.7 mg, 45%).

$^1$H NMR (400 MHz, d$_6$-DMSO) δ 7.84 (q, J=4.4 Hz, 1H), 7.77 (d, J=2.3 Hz, 1H), 7.66 (d, J=9.8 Hz, 1H), 7.30 (d, J=9.7 Hz, 1H), 7.30 (s, 1H), 7.26-7.14 (m, 3H), 7.07-7.01 (m, 2H), 6.73 (d, J=2.3 Hz, 1H), 6.04 (s, 2H), 4.35 (t, J=6.9 Hz, 2H), 2.93 (s, 3H), 2.63 (t, J=6.9 Hz, 2H), 2.50 (s, 3H). LCMS (M+H)$^+$: 414.0.

Example 98

3-[3-(6-benzyl-1-methyl-6H-pyrrolo[2,3-e][1,2,4]triazolo[4,3-a]pyridin-7-yl)-1H-pyrazol-1-yl]propanamide

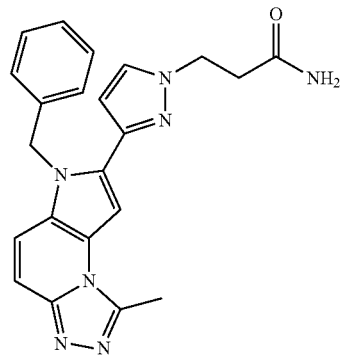 [SMILES: Cc1nnc2ccc3c(cc(-c4ccn(CCC(N)=O)n4)n3Cc3ccccc3)n12]

Prepared by the method of Example 96, using ammonia gas (Aldrich), which was bubbled through the mixture for 20 seconds. Yield: (3.4 mg, 43%).

$^1$H NMR (400 MHz, d$_6$-DMSO) δ 7.77 (d, J=2.3 Hz, 1H), 7.67 (d, J=9.8 Hz, 1H), 7.38 (s, 1H), 7.30 (d, J=9.7 Hz, 1H), 7.30 (s, 1H), 7.27-7.14 (m, 3H), 7.07-7.01 (m, 2H), 6.92 (s, 1H), 6.73 (d, J=2.3 Hz, 1H), 6.03 (s, 2H), 4.33 (t, J=6.9 Hz, 2H), 2.93 (s, 3H), 2.63 (t, J=6.9 Hz, 2H). LCMS (M+H)$^+$: 400.2.

Example 99

6-(3-chlorobenzyl)-N,1-dimethyl-6H-pyrrolo[2,3-e][1,2,4]triazolo[4,3-a]pyridine-7-carboxamide

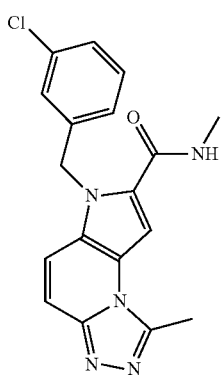 [SMILES: CNC(=O)c1cc2c(ccc3nnc(C)n32)n1Cc1cccc(Cl)c1]

Step 1. 5-chloro-1H-pyrrolo[3,2-b]pyridine-2-carboxylic acid

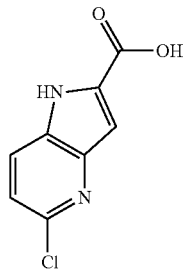 [SMILES: O=C(O)c1cc2nc(Cl)ccc2[nH]1]

To a suspension of ethyl 5-chloro-1-(phenylsulfonyl)-1H-pyrrolo[3,2-b]pyridine-2-carboxylate (2.50 g, 6.85 mmol, prepared as in Example 82, Step 1) in THF (20 mL) was added 1.0 M NaOH (20 mL, 20 mmol) and the reaction was stirred overnight. Concentrated HCl was added to acidify (to pH ~2). The product was extracted with ethyl acetate. The combined extracts were dried over sodium sulfate, filtered and concentrated to afford a white solid. The yield was close to theoretical and the product was used without further purification.

$^1$H NMR (400 MHz, CD$_3$OD) δ 7.89 (dd, J=8.7, 0.9 Hz, 1H), 7.30 (d, J=8.7 Hz, 1H), 7.14 (d, J=0.9 Hz, 1H). LCMS (M+H)$^+$: 196.8.

Step 2. 3-chlorobenzyl 5-chloro-1-(3-chlorobenzyl)-1H-pyrrolo[3,2-b]pyridine-2-carboxylate

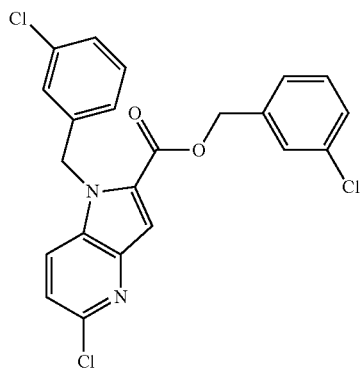 [SMILES: O=C(OCc1cccc(Cl)c1)c1cc2nc(Cl)ccc2n1Cc1cccc(Cl)c1]

5-Chloro-1H-pyrrolo[3,2-b]pyridine-2-carboxylic acid (0.200 g, 1.02 mmol, from Step 1) in DMF (4 mL) was treated with Cs$_2$CO$_3$ (1.3 g, 4.1 mmol). After 10 minutes, benzene, 1-(bromomethyl)-3-chloro- (0.27 mL, 2.0 mmol, Aldrich) was added. The reaction was stirred over 4 nights. The reaction mixture was partitioned between water and ethyl acetate and after separation of the layers, the aqueous layer was extracted with EtOAc three times. The combined extracts were dried over sodium sulfate, filtered, and concentrated. The product was purified by flash chromatography, eluting with a gradient from 0-50% EtOAc in hexanes. Yield: (0.210 g, 46%).

$^1$H NMR (300 MHz, CDCl$_3$) δ 7.60 (dd, J=8.8, 0.8 Hz, 1H), 7.49 (d, J=0.8 Hz, 1H), 7.44-7.13 (m, 7H), 7.01-6.94 (m, 1H), 6.88-6.80 (m, 1H), 5.79 (s, 2H), 5.31 (s, 2H).
LCMS (M+H)+: 444.9446.9.

Step 3. di-tert-butyl 1-(1-(3-chlorobenzyl)-2-{[(3-chlorobenzyl)oxy]carbonyl}-1H-pyrrolo[3,2-b]pyridin-5-yl)hydrazine-1,2-dicarboxylate

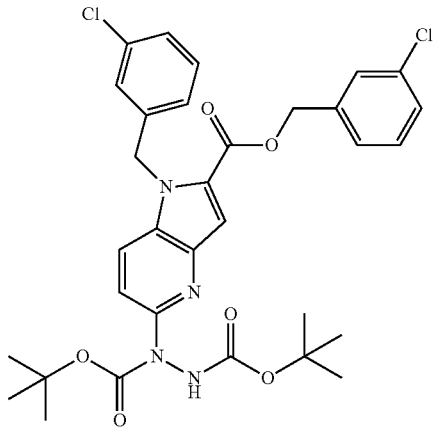 [SMILES: CC(C)(C)OC(=O)NN(C(=O)OC(C)(C)C)c1ccc2c(cc(C(=O)OCc3cccc(Cl)c3)n2Cc2cccc(Cl)c2)n1]

3-Chlorobenzyl 5-chloro-1-(3-chlorobenzyl)-1H-pyrrolo[3,2-b]pyridine-2-carboxylate (0.210 g, 0.471 mmol, from Step 2), di-tert-butyl hydrazine-1,2-dicarboxylate (0.12 g, 0.52 mmol, Aldrich) and Cs$_2$CO$_3$ (0.15 g, 0.47 mmol, Aldrich) were combined in toluene (4.2 mL) and dicyclohexyl (2',4',6'-triisopropylbiphenyl-2-yl)phosphine-(2'-aminobiphenyl-2-yl)(chloro)palladium (1:1) (0.037 g, 0.047 mmol, Aldrich) was added. The mixture was degassed by a stream of nitrogen through the solution for 10 minutes. The reaction mixture was heated to 140° C. for 30 minutes. Upon cooling to room temperature, the reaction mixture was partitioned between EtOAc and water. The aqueous layer was extracted three times and the combined organic extracts were dried over sodium sulfate, filtered, and concentrated. Flash chromatography (eluting with a slow gradient from 0-20% EtOAc in hexanes, hold, then increase rapidly up to 80% EtOAc in hexanes) afforded purified product (146 mg, 48%). LCMS (M+H)$^+$: 641.0643.0.

Step 4. 6-(3-chlorobenzyl)-1-methyl-6H-pyrrolo[2,3-e][1,2,4]triazolo[4,3-a]pyridine-7-carboxylic acid

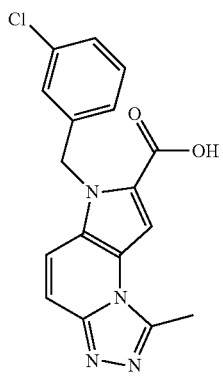

A solution of di-tert-butyl 1-(1-(3-chlorobenzyl)-2-{[(3-chlorobenzyl)oxy]carbonyl}-1H-pyrrolo[3,2-b]pyridin-5- yl)hydrazine-1,2-dicarboxylate (0.146 g, 0.228 mmol, from Step 3) in AcOH (4 mL) was heated in the microwave to a temperature of 180° C. for 5 minutes. LCMS (M+H)+: 465.0467.0.

AcOH was removed in vacuo. The residue was dissolved in methanol (1 mL) and 1.0 M sodium hydroxide in water (5 mL, 5 mmol) was added. Tetrahydrofuran (2 mL) was then added to aid in solubility. The reaction was stirred for 15 minutes, then was filtered and purified via preparative HPLC-MS (C18 eluting with a gradient of MeCN and H$_2$O containing 0.15% NH$_4$OH). Yield: (34 mg, 44%). LCMS (M+H)+: 341.0.

Step 5. 6-(3-chlorobenzyl)-N,1-dimethyl-6H-pyrrolo[2,3-e][1,2,4]triazolo[4,3-a]pyridine-7-carboxamide To a solution of 6-(3-chlorobenzyl)-1-methyl-6H-pyrrolo[2,3-e][1,2,4]triazolo[4,3-a]pyridine-7-carboxylic acid (0.034 g, 0.10 mmol, from Step 4) in DMF (2 mL) was added N,N-diisopropylethylamine (0.16 mL, 0.93 mmol, Aldrich) followed by N,N,N',N'-tetramethyl-O-(7-azabenzotriazol-1-yl)uronium hexafluorophosphate (0.12 g, 0.32 mmol, Aldrich) and then by 2.0 M methylamine in THF (0.40 mL, 0.80 mmol, Aldrich). After stirring for 15 minutes, the reaction mixture was diluted with MeCN and purified via preparative HPLC-MS (C18 eluting with a gradient of MeCN and H$_2$O containing 0.15% NH$_4$OH). Yield: (25 mg, 71%).

$^1$H NMR (400 MHz, d$_6$-DMSO) δ 8.63 (q, J=4.3 Hz, 1H), 7.72 (d, J=9.6 Hz, 1H), 7.71 (s, 1H), 7.47 (d, J=9.9 Hz, 1H), 7.34-7.25 (m, 2H), 7.16 (s, 1H), 7.04-6.93 (m, 1H), 6.02 (s, 2H), 2.91 (s, 3H), 2.79 (d, J=4.6 Hz, 3H). LCMS (M+H)+: 354.1.

Example 100

6-benzyl-N-(trans-3-cyanocyclobutyl)-1-methyl-6H-pyrrolo[2,3-e][1,2,4]triazolo[4,3-a]pyridine-7-carboxamide

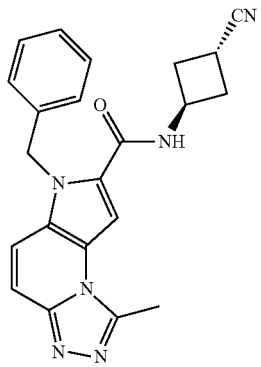 [SMILES: Cc1nnc2ccc3c(cc(C(=O)N[C@H]4C[C@H](C#N)C4)n3Cc3ccccc3)n12]

Step 1. benzyl 1-benzyl-5-chloro-1H-pyrrolo[3,2-b]pyridine-2-carboxylate

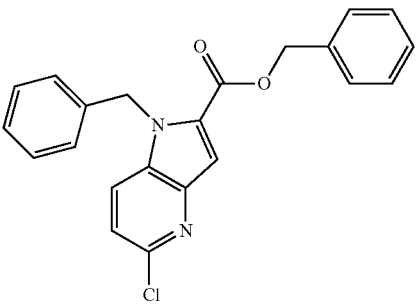 [SMILES: O=C(OCc1ccccc1)c1cc2nc(Cl)ccc2n1Cc1ccccc1]

5-Chloro-1H-pyrrolo[3,2-b]pyridine-2-carboxylic acid (0.68 g, 3.4 mmol, from Example 99, Step 1) in DMF (20 mL) was treated with Cs$_2$CO$_3$ (4.5 g, 14 mmol, Aldrich) and after 10 minutes, benzyl bromide (0.82 mL, 6.9 mmol, Aldrich) was added. The reaction was stirred overnight. Water was added and the product was extracted with three portions of EtOAc. The combined organic extracts were washed with water and brine, dried over sodium sulfate, filtered, and concentrated. Flash chromatography, eluting with a gradient from 0-40% EtOAc in hexanes afforded product as a white crystalline solid (1.13 g, 87%).

$^1$H NMR (400 MHz, CDCl$_3$) δ 7.61 (dd, J=8.8, 0.8 Hz, 1H), 7.48 (d, J=0.8 Hz, 1H), 7.43-7.23 (m, 8H), 7.20 (d, J=8.8 Hz, 1H), 7.02-6.94 (m, 2H), 5.84 (s, 2H), 5.35 (s, 2H). LCMS (M+H)+: 377.0.

Step 2. di-tert-butyl 1-{1-benzyl-2-[(benzyloxy)carbonyl]-1H-pyrrolo[3,2-b]pyridin-5-yl}hydrazine-1,2-dicarboxylate

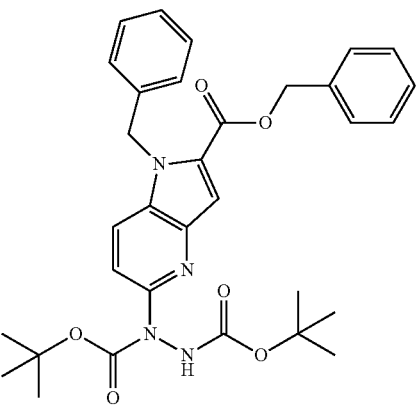 [SMILES: CC(C)(C)OC(=O)NN(C(=O)OC(C)(C)C)c1ccc2c(cc(C(=O)OCc3ccccc3)n2Cc2ccccc2)n1]

Benzyl 1-benzyl-5-chloro-1H-pyrrolo[3,2-b]pyridine-2-carboxylate (1.13 g, 3.00 mmol, from Step 1) and di-tert-butyl hydrazine-1,2-dicarboxylate (0.77 g, 3.3 mmol, Aldrich), dicyclohexyl(2',4',6'-triisopropylbiphenyl-2-yl)phosphine-(2'-aminobiphenyl-2-yl)(chloro)palladium (1:1) (0.24 g, 0.30 mmol, Aldrich) and Cs$_2$CO$_3$ (0.98 g, 3.0 mmol, Aldrich) were combined in toluene (27 mL) and the mixture was degassed by bubbling a stream of nitrogen through the solution for 10 minutes. The reaction was stirred at 110° C. for 5 hours. The reaction mixture was partitioned between water and ethyl acetate, the aqueous was extracted three times, the combined organic extracts were dried over sodium sulfate, filtered and concentrated. Flash chromatography, eluting with a gradient from 0-40% EtOAc in hexanes was used to purify the product. Yield: (1.12 g, 65%).

$^1$H NMR (400 MHz, CDCl$_3$) δ 7.66 (d, J=8.8 Hz, 1H), 7.68-7.59 (m, 1H), 7.49 (s, 1H), 7.42-7.32 (m, 5H), 7.31-7.19 (m, 4H), 7.05-6.98 (m, 2H), 5.82 (s, 2H), 5.33 (s, 2H). LCMS (M+H)$^+$: 573.0.

Step 3. 6-benzyl-1-methyl-6H-pyrrolo[2,3-e][1,2,4]triazolo[4,3-a]pyridine-7-carboxylic acid

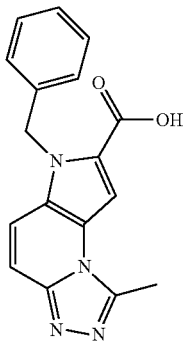 [SMILES: Cc1nnc2ccc3c(cc(C(=O)O)n3Cc3ccccc3)n12]

A solution of di-tert-butyl 1-{1-benzyl-2-[(benzyloxy)carbonyl]-1H-pyrrolo[3,2-b]pyridin-5-yl}hydrazine-1,2-dicarboxylate (1.125 g, 1.964 mmol, from Step 2) in AcOH (30 mL) was split into portions and each was heated in the microwave to 180° C. for 10 minutes. The reactions were pooled and the AcOH was removed in vacuo. LCMS (M+H)$^+$: 397.1.

The residue was dissolved in methanol (9 mL) and THF (20 mL) and 1.0 M NaOH (30 mL, 30 mmol) was added. When the hydrolysis reaction was complete the volatile solvents were evaporated and the solution was filtered and purified via preparative HPLC-MS (C18 eluting with a gradient of MeCN/H$_2$O containing 0.15% NH$_4$OH) in injections of 40 mg/5 mL. Yield: (0.55 g, 91%).

$^1$H NMR (400 MHz, d$_6$-DMSO) δ 7.50 (d, J=9.8 Hz, 1H), 7.20 (d, J=9.7 Hz, 1H), 7.27-7.10 (m, 5H), 7.07 (s, 1H), 6.23 (s, 2H), 2.87 (s, 3H). LCMS (M+H)$^+$: 306.9.

Step 4. trans-3-aminocyclobutanecarbonitrile trifluoroacetate salt

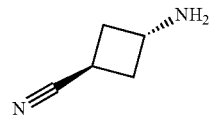

tert-Butyl (cis-3-hydroxycyclobutyl)carbamate (1.00 g, 5.34 mmol, Synthonix) was treated with triethylamine (1.5 mL, 11 mmol) and methanesulfonyl chloride (0.50 mL, 6.4 mmol, Aldrich) in DCM (10 mL) at 0° C. for 2 hours. Water was added and the product was extracted with EtOAc three times. The combined extracts were dried over sodium sulfate, filtered, and concentrated to afford cis-3-[(tert-butoxycarbonyl)amino]cyclobutyl methanesulfonate. Yield: (1.4 g, 99%).

cis-3-[(tert-Butoxycarbonyl)amino]cyclobutyl methanesulfonate (0.200 g, 0.754 mmol) in DMF (3 mL) was treated with NaCN (55 mg, 1.13 mmol, Aldrich) and the reaction was heated in the microwave to 140° C. for 10 minutes, followed by stirring overnight at 125° C. with an additional 55 mg (1.13 mmol) of NaCN having been added. The reaction mixture was partitioned between saturated NaHCO$_3$ solution and EtOAc. The aqueous layer was extracted three additional times with EtOAc. The combined extracts were dried over sodium sulfate, decanted, and the solvent was removed in vacuo. Flash chromatography, eluting with a gradient from 0-50% EtOAc in hexanes, afforded tert-butyl (trans-3-cyanocyclobutyl)carbamate. Yield: (61 mg, 41%).

$^1$H NMR (400 MHz, CDCl$_3$) δ 4.77 (br s, 1H), 4.54-4.27 (m, 1H), 3.03 (ttd, J=9.4, 3.9, 1.3 Hz, 1H), 2.79-2.57 (m, 2H), 2.49-2.26 (m, 2H), 1.43 (s, 9H).

tert-Butyl (trans-3-cyanocyclobutyl)carbamate (0.061 g, 0.31 mmol) was stirred with TFA (2 mL) in DCM (4 mL) for 1 hour. The solvents were removed in vacuo and the residue was reconstituted in DCM and subjected to rotary evaporation an additional 2 times to rid of excess TFA in the product, which was used without further purification in Step 5.

Step 5. 6-benzyl-N-(trans-3-cyanocyclobutyl)-1-methyl-6H-pyrrolo[2,3-e][1,2,4]triazolo[4,3-a]pyridine-7-carboxamide To a solution of 6-benzyl-1-methyl-6H-pyrrolo[2,3-e][1,2,4]triazolo[4,3-a]pyridine-7-carboxylic acid (0.045 g, 0.15 mmol, from Step 3) in DMF (1 mL) was added N,N-diisopropylethylamine (0.15 mL, 0.86 mmol, Aldrich) followed by N,N,N',N'-tetramethyl-O-(7-azabenzotriazol-1-yl)uronium hexafluorophosphate (0.125 g, 0.329 mmol, Aldrich). After about 30 seconds, trans-3-aminocyclobutanecarbonitrile trifluoroacetate (0.060 g, 0.28 mmol, from Step 4) in DMF (2 mL) was added and the reaction was stirred overnight. The reaction was diluted with MeCN and filtered, then purified via preparative HPLC-MS (C18 eluting with a gradient of MeCN/H$_2$O containing 0.15% NH$_4$OH). Yield: (35 mg, 62%).

$^1$H NMR (400 MHz, CD$_3$OD) δ 7.73 (dd, J=9.9, 0.5 Hz, 1H), 7.65 (d, J=0.5 Hz, 1H), 7.43 (d, J=9.9 Hz, 1H), 7.30-7.18 (m, 3H), 7.13-7.04 (m, 2H), 5.98 (s, 2H), 4.75 (pd, J=8.0, 1.2

Hz, 1H), 3.30-3.22 (m, 1H), 3.01 (s, 3H), 2.78-2.64 (m, 2H), 2.63-2.47 (m, 2H). LCMS (M+H)+: 384.9.

Example 101

6-benzyl-N-(cis-3-cyanocyclobutyl)-1-methyl-6H-pyrrolo[2,3-e][1,2,4]triazolo[4,3-a]pyridine-7-carboxamide

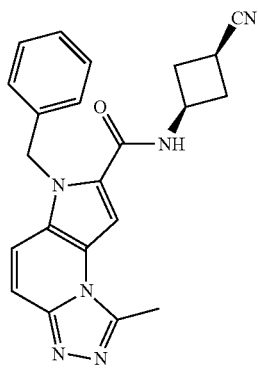 [SMILES: Cc1nnc2ccc3c(cc(C(=O)N[C@H]4C[C@@H](C#N)C4)n3Cc3ccccc3)n12]

Prepared by the method of Example 100, using cis-3-aminocyclobutanecarbonitrile trifluoroacetate (0.040 g, 0.19 mmol, prepared as described in Example 100, Step 4, using tert-butyl (trans-3-hydroxycyclobutyl)carbamate obtained from Synthonix). Yield: (40 mg, 71%).

$^1$H NMR (400 MHz, CD$_3$OD) δ 7.72 (d, J=9.9 Hz, 1H), 7.67 (s, 1H), 7.42 (d, J=9.9 Hz, 1H), 7.29-7.16 (m, 3H), 7.11-7.01 (m, 2H), 5.98 (s, 2H), 4.56-4.45 (m, 1H), 3.11-2.99 (m, 1H), 3.02 (s, 3H), 2.86-2.75 (m, 2H), 2.50-2.38 (m, 2H). LCMS (M+H)+: 385.0.

Example 102

6-(3-fluorobenzyl)-N,1-dimethyl-6H-pyrrolo[2,3-e][1,2,4]triazolo[4,3-a]pyridine-7-carboxamide

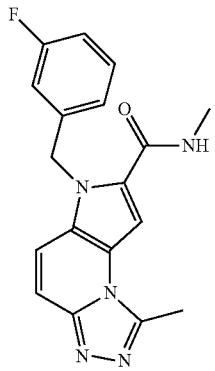 [SMILES: CNC(=O)c1cc2c(ccc3nnc(C)n32)n1Cc1cccc(F)c1]

Step 1. 3-fluorobenzyl 5-chloro-1-(3-fluorobenzyl)-1H-pyrrolo[3,2-b]pyridine-2-carboxylate

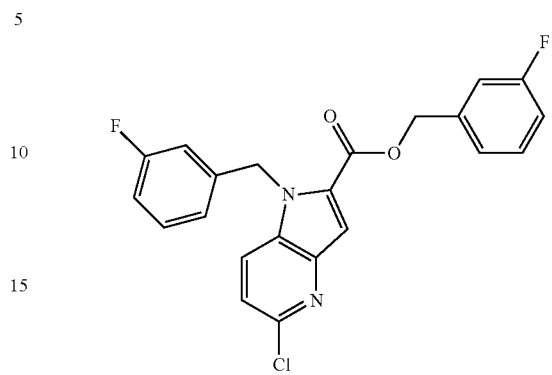

5-Chloro-1H-pyrrolo[3,2-b]pyridine-2-carboxylic acid (0.20 g, 1.0 mmol, from Example 99, Step 1) in DMF (4 mL) was treated with Cs$_2$CO$_3$ (1.3 g, 4.1 mmol, Aldrich) and after 10 minutes, α-bromo-3-fluorotoluene (0.25 mL, 2.0 mmol, Aldrich) was added. After stirring overnight, water was added and the product was extracted with three portions of EtOAc. The combined organic extracts were washed with water and brine, dried over sodium sulfate, filtered and concentrated. Flash chromatography, eluting with a gradient from 0-40% EtOAc in hexanes afforded product as a white crystalline solid (0.40 g, 95%).

$^1$H NMR (400 MHz, CDCl$_3$) δ 7.61 (dd, J=8.8, 0.7 Hz, 1H), 7.50 (d, J=0.7 Hz, 1H), 7.34 (td, J=7.9, 5.9 Hz, 1H), 7.24 (d, J=8.8 Hz, 1H), 7.27-7.20 (m, 1H), 7.16 (d, J=7.8 Hz, 1H), 7.09 (dt, J=9.6, 1.8 Hz, 1H), 7.04 (td, J=8.3, 2.6 Hz, 1H), 6.94 (td, J=8.5, 2.3 Hz, 1H), 6.76 (d, J=7.6 Hz, 1H), 6.69-6.63 (m, 1H), 5.82 (s, 2H), 5.33 (s, 2H). LCMS (M+H)+: 412.9.

Step 2. di-tert-butyl 1-(1-(3-fluorobenzyl)-2-{[(3-fluorobenzyl)oxy]carbonyl}-1H-pyrrolo[3,2-b]pyridin-5-yl)hydrazine-1,2-dicarboxylate

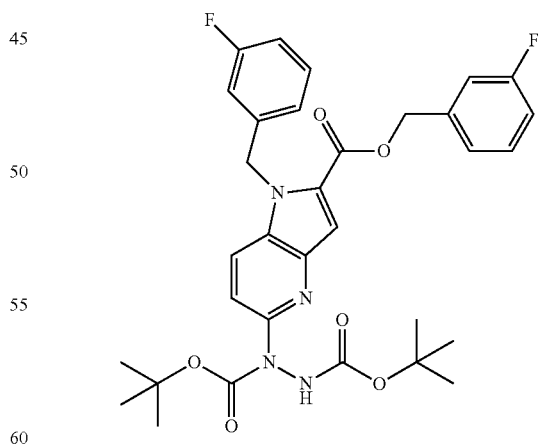

3-Fluorobenzyl 5-chloro-1-(3-fluorobenzyl)-1H-pyrrolo[3,2-b]pyridine-2-carboxylate (0.40 g, 0.97 mmol, from Step 1), di-tert-butyl hydrazine-1,2-dicarboxylate (0.25 g, 1.1 mmol, Aldrich), dicyclohexyl(2',4',6'-triisopropylbiphenyl-2-yl)phosphine-(2'-aminobiphenyl-2-yl)(chloro)palladium (1:1) (0.076 g, 0.097 mmol, Aldrich), and Cs$_2$CO$_3$ (0.32 g, 0.97 mmol, Aldrich) were combined in toluene (8.6 mL) and the mixture was degassed by a stream of nitrogen through the solution for 10 minutes. The reaction was stirred at 110° C. for 6 hours. The reaction mixture was partitioned between water and ethyl acetate, the aqueous was extracted three times, and the combined extracts were dried over sodium sulfate, filtered and concentrated. Flash chromatography, eluting with a gradient from 0-40% EtOAc in hexanes, was used to purify the product. Yield: (0.33 g, 56%).

$^1$H NMR (400 MHz, CDCl$_3$) δ 8.64 (br s, 1H), 7.76-7.53 (m, 3H), 7.32 (td, J=7.9, 5.8 Hz, 1H), 7.21 (td, J=8.0, 5.9 Hz, 1H), 7.14 (d, J=7.7 Hz, 1H), 7.07 (dt, J=9.5, 1.9 Hz, 1H), 7.02 (td, J=8.7, 2.2 Hz, 1H), 6.91 (td, J=8.4, 2.1 Hz, 1H), 6.79 (d, J=7.7 Hz, 1H), 6.68 (dt, J=9.6, 1.9 Hz, 1H), 5.80 (s, 2H), 5.30 (s, 2H), 1.41 (s, 9H), 1.37 (s, 9H). LCMS (M+H)$^+$: 609.0.

Step 3. 6-(3-fluorobenzyl)-1-methyl-6H-pyrrolo[2,3-e][1,2,4]triazolo[4,3-a]pyridine-7-carboxylic acid

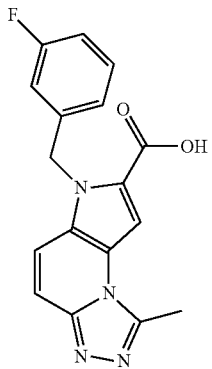

A solution of di-tert-butyl 1-(1-(3-fluorobenzyl)-2-{[(3-fluorobenzyl)oxy]carbonyl}-1H-pyrrolo[3,2-b]pyridin-5-yl)hydrazine-1,2-dicarboxylate (0.33 g, 0.54 mmol, from Step 2) in AcOH (10 mL) was heated in portions, in the microwave, to 180° C. for 10 minutes each. The reactions were pooled and AcOH was removed in vacuo. The residue was dissolved in methanol (2 mL) and 1.0 M NaOH in water (10 mL, 10 mmol) was added. When the hydrolysis reaction was complete, it was filtered, diluted with MeCN and H$_2$O and then purified via preparative HPLC-MS (C18 eluting with a gradient of MeCN/H$_2$O containing 0.15% NH$_4$OH). Yield: (0.17 g, 97%). LCMS (M+H)$^+$: 325.3.

Step 4. 6-(3-fluorobenzyl)-N,1-dimethyl-6H-pyrrolo[2,3-e][1,2,4]triazolo[4,3-a]pyridine-7-carboxamide To a solution of 6-(3-fluorobenzyl)-1-methyl-6H-pyrrolo[2,3-e][1,2,4]triazolo[4,3-a]pyridine-7-carboxylic acid (0.050 g, 0.15 mmol, from Step 3) in DMF (3 mL) was added N,N-diisopropylethylamine (0.25 mL, 1.4 mmol, Aldrich) followed by N,N,N',N'-tetramethyl-O-(7-azabenzotriazol-1-yl)uronium hexafluorophosphate (0.18 g, 0.49 mmol, Aldrich). After the reaction was stirred for 30 seconds, 2.0 M Methylamine in THF (0.62 mL, 1.2 mmol, Aldrich) was added. After 1 hour, the reaction was diluted with MeCN and purified via preparative HPLC-MS (C18 eluting with a gradient of MeCN/H$_2$O containing 0.15% NH$_4$OH). Yield: (35 mg, 67%).

$^1$H NMR (300 MHz, CD$_3$OD) δ 7.74 (d, J=9.9 Hz, 1H), 7.62 (s, 1H), 7.45 (d, J=9.8 Hz, 1H), 7.40-7.24 (m, 1H), 7.06-6.91 (m, 2H), 6.91-6.82 (m, 1H), 6.04 (s, 2H), 3.02 (s, 3H), 2.92 (s, 3H). LCMS (M+H)$^+$: 337.9.

Example 103

3-{3-[6-(3-chlorobenzyl)-1-methyl-6H-pyrrolo[2,3-e][1,2,4]triazolo[4,3-a]pyridin-7-yl]-1H-pyrazol-1-yl}-N,N-dimethylpropanamide

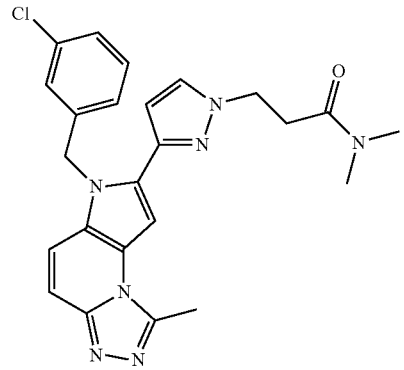 [SMILES: Cc1nnc2ccc3c(cc(-c4ccn(CCC(=O)N(C)C)n4)n3Cc3cccc(Cl)c3)n12]

Step 1. 2-bromo-5-chloro-1H-pyrrolo[3,2-b]pyridine

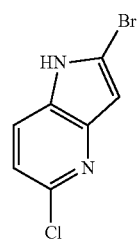 [SMILES: Clc1ccc2[nH]c(Br)cc2n1]

2-Bromo-5-chloro-1-(phenylsulfonyl)-1H-pyrrolo[3,2-b]pyridine (20.7 g, 44.6 mmol, prepared as in Example 62, Step 1, but isolated as the free base) in THF (300 mL) was stirred with 1N NaOH (300 mL, 300 mmol) overnight. The reaction mixture was extracted with EtOAc three times. The combined extracts were dried over sodium sulfate, filtered, and concentrated to afford 2-bromo-5-chloro-1H-pyrrolo[3,2-b]pyridine in theoretical yield. LCMS (M+H)+: 233.0 (most abundant).

Step 2. 2-bromo-5-chloro-1-(3-chlorobenzyl)-1H-pyrrolo[3,2-b]pyridine

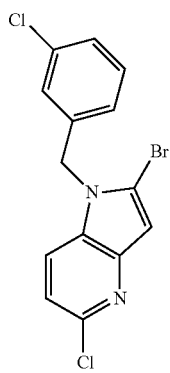

K₂CO₃ (0.97 g, 7.0 mmol) and 1-(bromomethyl)-3-chlorobenzene (0.74 mL, 5.6 mmol, Aldrich) were added to a solution of 2-bromo-5-chloro-1H-pyrrolo[3,2-b]pyridine (1.5 g, 4.7 mmol, from Step 1) in DMF (20 mL). After a reaction time of 75 minutes, the reaction was diluted with ethyl acetate and washed with water three times, followed by one wash with brine. The organic layer was dried over sodium sulfate, filtered, and concentrated. Flash chromatography, loading in DCM, eluting with a gradient from 0-10% EtOAc in hexanes, afforded product as a white solid. Yield (1.3 g, 70%).

¹H NMR (300 MHz, CDCl₃) δ 7.41 (d, J=8.6 Hz, 1H), 7.30-7.19 (m, 2H), 7.07 (d, J=8.7 Hz, 1H), 7.07-7.04 (m, 1H), 6.91-6.84 (m, 1H), 6.82 (s, 1H), 5.38 (s, 2H). LCMS (M+H)+: 357.0 (most abundant).

Step 3. 5-chloro-1-(3-chlorobenzyl)-2-[1-(tetrahydro-2H-pyran-2-yl)-1H-pyrazol-5-yl]-1H-pyrrolo[3,2-b]pyridine

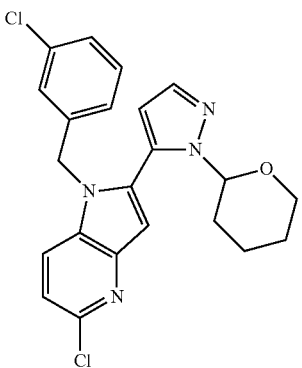 [SMILES: Clc1cccc(Cn2c(-c3ccnn3C3CCCCO3)cc3nc(Cl)ccc32)c1]

A mixture of 2-bromo-5-chloro-1-(3-chlorobenzyl)-1H-pyrrolo[3,2-b]pyridine (1.3 g, 3.3 mmol, from Step 2), 1-(tetrahydro-2H-pyran-2-yl)-5-(4,4,5,5-tetramethyl-1,3,2-dioxaborolan-2-yl)-1H-pyrazole (1.1 g, 3.9 mmol, Aldrich), and Na₂CO₃ (1.7 g, 16 mmol) in 1,2-dimethoxyethane (40 mL) and water (6 mL) was degassed by a stream of nitrogen through the solution for 10 minutes. Tetrakis(triphenylphosphine)palladium(0) (0.38 g, 0.33 mmol, Strem) was added, and the reaction was heated to reflux for 35 minutes. Upon cooling to room temperature, the reaction was diluted with water and extracted with EtOAc three times. The combined extracts were dried over sodium sulfate, filtered, and concentrated. Flash chromatography, eluting with a gradient from 0-30% EtOAc in hexanes afforded product as a light yellow oil (0.87 g, 56%).

¹H NMR (400 MHz, CDCl₃) δ 7.64 (d, J=1.8 Hz, 1H), 7.49 (dd, J=8.6, 0.8 Hz, 1H), 7.25-7.14 (m, 2H), 7.17 (d, J=8.6 Hz, 1H), 6.97 (d, J=0.8 Hz, 1H), 6.86-6.81 (m, 1H), 6.74 (dt, J=7.1, 1.5 Hz, 1H), 6.31 (d, J=1.8 Hz, 1H), 5.32 (d, J=17.0 Hz, 1H), 5.26 (d, J=17.0 Hz, 1H), 5.21 (dd, J=10.5, 2.3 Hz, 1H), 4.08-4.01 (m, 1H), 3.53 (td, J=11.8, 2.2 Hz, 1H), 2.59-2.41 (m, 1H), 2.10-1.43 (m, 5H). LCMS (M+H)+: 426.9, 428.1.

Step 4. di-tert-butyl 1-{1-(3-chlorobenzyl)-2-[1-(tetrahydro-2H-pyran-2-yl)-1H-pyrazol-5-yl]-1H-pyrrolo[3,2-b]pyridin-5-yl}hydrazine-1,2-dicarboxylate

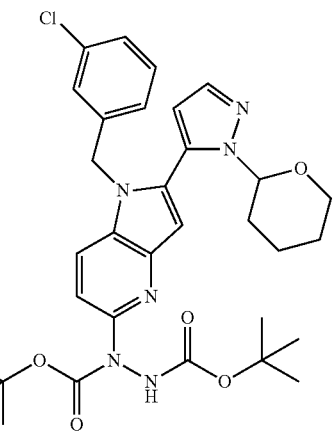

5-Chloro-1-(3-chlorobenzyl)-2-[1-(tetrahydro-2H-pyran-2-yl)-1H-pyrazol-5-yl]-1H-pyrrolo[3,2-b]pyridine (0.87 g, 1.8 mmol, from Step 3), di-tert-butyl hydrazine-1,2-dicarboxylate (0.64 g, 2.7 mmol, Aldrich) and Cs₂CO₃ (0.90 g, 2.7 mmol, Aldrich) were combined in toluene (16 mL) and dicyclohexyl(2',4',6'-triisopropylbiphenyl-2-yl)phosphine-(2'-aminobiphenyl-2-yl)(chloro)palladium (1:1) (0.14 g, 0.18 mmol, Aldrich) was added. The mixture was degassed by a stream of nitrogen through the solution for 10 minutes. The reaction was heated in a sealed vial to 130° C. for 55 minutes, then at 135° C. for 40 minutes. Additional di-tert-butyl hydrazine-1,2-dicarboxylate (0.32 g, 1.4 mmol), Cs₂CO₃ (0.45 g, 1.4 mmol) and dicyclohexyl(2',4',6'-triisopropylbiphenyl-2-yl)phosphine-(2'-aminobiphenyl-2-yl)(chloro)palladium (1:1) (0.10 g, 0.13 mmol) were added. The mixture was again degassed, then sealed and heated to 140° C. for 40 minutes. After cooling to room temperature, the mixture was diluted with DCM, filtered and concentrated. Flash chromatography, eluting with a gradient from 0-50% EtOAc in hexanes afforded product as a white solid (0.51 g, 40%). LCMS (M+H)⁺: 623.3.

Step 5. 6-(3-chlorobenzyl)-1-methyl-7-(1H-pyrazol-5-yl)-6H-pyrrolo[2,3-e][1,2,4]triazolo[4,3-a]pyridine

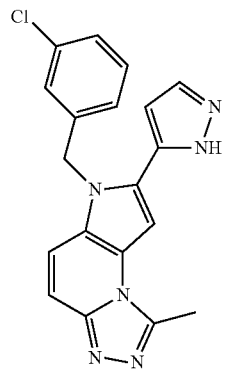 [SMILES: Cc1nnc2ccc3c(cc(-c4ccn[nH]4)n3Cc3cccc(Cl)c3)n12]

A solution of di-tert-butyl 1-{1-(3-chlorobenzyl)-2-[1-(tetrahydro-2H-pyran-2-yl)-1H-pyrazol-5-yl]-1H-pyrrolo[3,2-b]pyridin-5-yl}hydrazine-1,2-dicarboxylate (0.50 g, 0.72 mmol, from Step 4) in AcOH (20 mL) and was heated in the microwave to a temperature of 180° C. for 8 minutes. The AcOH was removed in vacuo and the product was purified via preparative HPLC-MS (C18 eluting with a gradient of MeCN/H₂O containing 0.15% NH₄OH). Yield (78 mg, 30%).

¹H NMR (400 MHz, d₆-DMSO) δ 13.13 (br s, 1H), 7.87 (s, 1H), 7.63 (d, J=9.7 Hz, 1H), 7.39 (s, 1H), 7.32 (d, J=9.7 Hz, 1H), 7.30-7.22 (m, 2H), 7.12 (s, 1H), 6.94 (d, J=5.6 Hz, 1H), 6.86 (s, 1H), 6.09 (s, 2H), 2.95 (s, 3H). LCMS (M+H)⁺: 362.7.

Step 6. 3-{3-[6-(3-chlorobenzyl)-1-methyl-6H-pyrrolo[2,3-e][1,2,4]triazolo[4,3-a]pyridin-7-yl]-1H-pyrazol-1-yl}propanoic acid

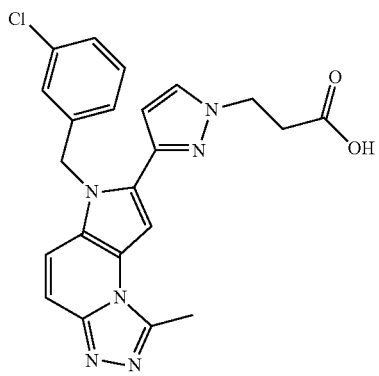 [SMILES: Cc1nnc2ccc3c(cc(-c4ccn(CCC(=O)O)n4)n3Cc3cccc(Cl)c3)n12]

Methyl acrylate (19 µL, 0.21 mmol, Aldrich) and 1,8-diazabicyclo[5.4.0]undec-7-ene (10. µL, 0.069 mmol, Aldrich) were added to a mixture of 6-(3-chlorobenzyl)-1-methyl-7-(1H-pyrazol-5-yl)-6H-pyrrolo[2,3-e][1,2,4]triazolo[4,3-a]pyridine (25 mg, 0.069 mmol, from Step 5) in acetonitrile (0.90 mL). After a reaction time of 70 minutes, the product was purified via preparative HPLC-MS (C18 eluting with a gradient of MeCN/H₂O containing 0.15% NH₄OH) to afford 31 mg of adduct. This was stirred with 1.0 M NaOH in water (0.45 mL, 0.45 mmol) in THF (0.45 mL) for 25 minutes, then pH was adjusted to the range of 3-4 by the addition of 1N HCl and the product precipitated as white solid which was isolated by filtration, rinsed with water, and air dried (21 mg, 70%).

¹H NMR (400 MHz, d₆-DMSO) δ 12.41 (s, 1H), 7.83 (d, J=2.3 Hz, 1H), 7.71 (d, J=10.0 Hz, 1H), 7.35 (s, 1H), 7.34 (d, J=9.7 Hz, 1H), 7.27-7.23 (m, 2H), 7.15 (br m, 1H), 7.01-6.90 (m, 1H), 6.78 (d, J=2.3 Hz, 1H), 6.04 (s, 2H), 4.34 (t, J=6.7 Hz, 2H), 2.94 (s, 3H), 2.78 (t, J=6.7 Hz, 2H). LCMS (M+H)⁺: 434.6.

Step 7. 3-{3-[6-(3-chlorobenzyl)-1-methyl-6H-pyrrolo[2,3-e][1,2,4]triazolo[4,3-a]pyridin-7-yl]-1H-pyrazol-1-yl}-N,N-dimethylpropanamide To a solution of 3-{3-[6-(3-chlorobenzyl)-1-methyl-6H-pyrrolo[2,3-e][1,2,4]triazolo[4,3-a]pyridin-7-yl]-1H-pyrazol-1-yl}propanoic acid (8.0 mg, 0.018 mmol, from Step 6) in DMF (0.25 mL) was added N,N-diisopropylethylamine (13 µL, 0.074 mmol, Aldrich) followed by N,N,N',N'-tetramethyl-O-(7-azabenzotriazol-1-yl)uronium hexafluorophosphate (12 mg, 0.033 mmol, Aldrich). After 2 minutes, 2.0 M dimethylamine in THF (0.074 mL, 0.15 mmol, Aldrich) was added. After 15 minutes, the reaction was diluted with MeOH and purified via preparative HPLC-MS (C18 eluting with a gradient of MeCN/H₂O containing 0.15% NH₄OH). Yield: (5.5 mg, 65%).

¹H NMR (400 MHz, d₆-DMSO) δ 7.82 (d, J=2.3 Hz, 1H), 7.69 (d, J=9.8 Hz, 1H), 7.35 (s, 1H), 7.33 (d, J=9.7 Hz, 1H), 7.30-7.24 (m, 2H), 7.15 (s, 1H), 6.99-6.93 (m, 1H), 6.78 (d, J=2.3 Hz, 1H), 6.05 (s, 2H), 4.33 (t, J=6.8 Hz, 2H), 2.94 (s, 3H), 2.81 (t, J=6.7 Hz, 2H), 2.80 (s, 3H), 2.75 (s, 3H). LCMS (M+H)⁺: 462.1.

Example 104

7-[1-(3-azetidin-1-yl-3-oxopropyl)-1H-pyrazol-3-yl]-6-(3-chlorobenzyl)-1-methyl-6H-pyrrolo[2,3-e][1,2,4]triazolo[4,3-a]pyridine

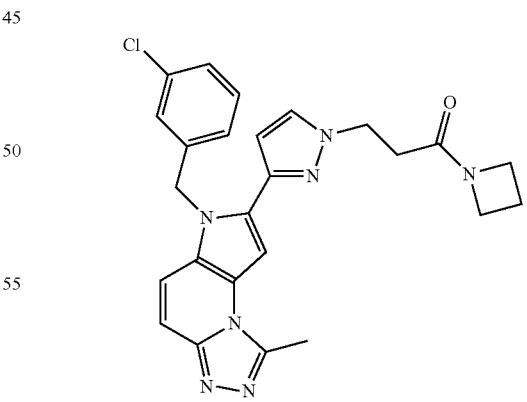

Prepared in the manner of Example 103, using azetidine (4.0 µL, 0.060 mmol, Aldrich). Yield: (4.0 mg, 56%).

¹H NMR (400 MHz, d₆-DMSO) δ 7.80 (d, J=2.3 Hz, 1H), 7.68 (d, J=9.5 Hz, 1H), 7.36 (s, 1H), 7.33 (d, J=9.7 Hz, 1H), 7.31-7.25 (m, 2H), 7.18-7.13 (m, 1H), 7.02-6.91 (m, 1H), 6.80 (d, J=2.3 Hz, 1H), 6.07 (s, 2H), 4.32 (t, J=6.7 Hz, 2H), 3.83 (t, J=7.6 Hz, 2H), 3.74 (t, J=7.7 Hz, 2H), 2.94 (s, 3H), 2.52 (t, J=6.7 Hz, 2H), 2.04 (p, J=7.7 Hz, 2H). LCMS: (M+H)⁺: 474.1.

Example 105

6-(3-chlorobenzyl)-1-methyl-7-{1-[3-(4-methylpiperazin-1-yl)-3-oxopropyl]-1H-pyrazol-3-yl}-6H-pyrrolo[2,3-e][1,2,4]triazolo[4,3-a]pyridine

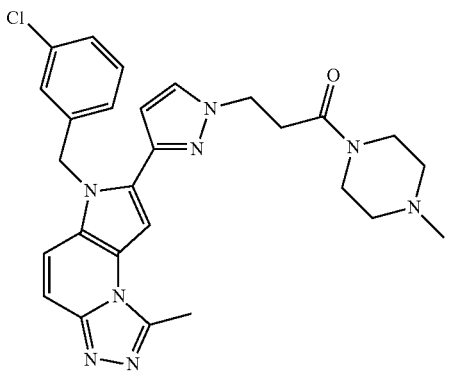 [SMILES: Cc1nnc2ccc3c(cc(-c4ccn(CCC(=O)N5CCN(C)CC5)n4)n3Cc3cccc(Cl)c3)n12]

Prepared in the manner of Example 103, using piperazine, 1-methyl- (6.6 μL, 0.060 mmol, Aldrich). Yield: (4.0 mg, 52%).

¹H NMR (400 MHz, d₆-DMSO) δ 7.82 (d, J=2.3 Hz, 1H), 7.70 (d, J=9.7 Hz, 1H), 7.35 (s, 1H), 7.33 (d, J=9.7 Hz, 1H), 7.30-7.24 (m, 2H), 7.18-7.13 (m, 1H), 7.01-6.93 (m, 1H), 6.78 (d, J=2.3 Hz, 1H), 6.05 (s, 2H), 4.34 (t, J=6.8 Hz, 2H), 3.41-3.35 (m, 2H), 3.30-3.20 (m, 2H), 2.94 (s, 3H), 2.83 (t, J=6.9 Hz, 2H), 2.15 (q, J=4.9 Hz, 4H), 2.11 (s, 3H). LCMS (M+H)⁺: 517.3.

Example 106

(1-acetyl-3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile

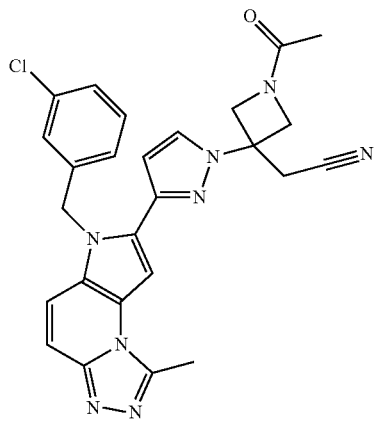 [SMILES: CC(=O)N1CC(CC#N)(n2ccc(-c3cc4c(ccc5nnc(C)n54)n3Cc3cccc(Cl)c3)n2)C1]

Step 1. (3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile

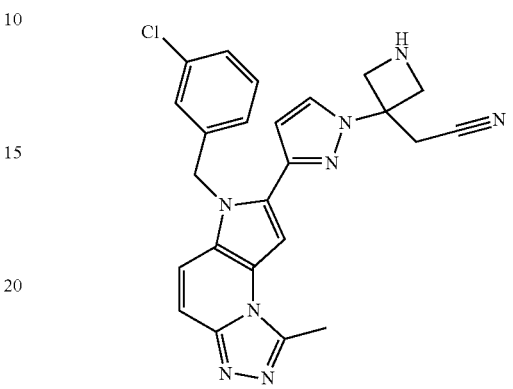

6-(3-Chlorobenzyl)-1-methyl-7-(1H-pyrazol-5-yl)-6H-pyrrolo[2,3-e][1,2,4]triazolo[4,3-a]pyridine (25 mg, 0.069 mmol, from Example 103, Step 5) in acetonitrile (0.90 mL), was treated with tert-butyl 3-(cyanomethylene)azetidine-1-carboxylate (27 mg, 0.14 mmol, prepared as described in WO 2009114512) and 1,8-diazabicyclo[5.4.0]undec-7-ene (10. μL, 0.069 mmol, Aldrich). After 70 minutes, 4.0 M hydrogen chloride in dioxane (0.23 mL, 0.90 mmol) was added into the reaction. After 30 minutes, the reaction was diluted with methanol, and adjusted to pH~10 by the addition of a small amount of aqueous ammonia. Purification via preparative HPLC-MS (C18 eluting with a gradient of MeCN/H₂O containing 0.15% NH₄OH) afforded product (23 mg, 73%).

¹H NMR (400 MHz, d₆-DMSO) δ 8.12 (d, J=2.5 Hz, 1H), 7.77 (d, J=9.8 Hz, 1H), 7.44 (s, 1H), 7.37 (d, J=9.7 Hz, 1H), 7.29-7.21 (m, 2H), 7.19-7.12 (m, 1H), 6.96 (d, J=2.5 Hz, 1H), 6.97-6.92 (m, 1H), 6.03 (s, 2H), 3.86 (d, J=9.0 Hz, 2H), 3.58 (d, J=9.3 Hz, 2H), 3.45 (s, 2H), 2.95 (s, 3H). LCMS (M+H)⁺: 456.6.

Step 2. (1-acetyl-3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile Acetyl chloride (1.1 μL, 0.016 mmol, Aldrich) in DCM (0.35 mL) was added to (3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile (6.0 mg, 0.013 mmol, from Step 1). Triethylamine (3.7 μL, 0.026 mmol) was then added and the reaction was stirred for 10 minutes. Purification via preparative HPLC-MS (C18 eluting with a gradient of MeCN/H₂O containing 0.15% NH₄OH) afforded product (4.0 mg, 61%).

¹H NMR (400 MHz, d₆-DMSO) δ 8.21 (d, J=2.5 Hz, 1H), 7.76 (d, J=9.8 Hz, 1H), 7.47 (s, 1H), 7.38 (d, J=9.8 Hz, 1H), 7.29-7.23 (m, 2H), 7.17-7.11 (m, 1H), 7.01 (d, J=2.5 Hz, 1H), 6.97-6.90 (m, 1H), 6.03 (s, 2H), 4.52 (d, J=9.4 Hz, 1H), 4.40

(d, J=9.4 Hz, 1H), 4.24 (d, J=10.4 Hz, 1H), 4.11 (d, J=10.4 Hz, 1H), 3.55 (s, 2H), 2.95 (s, 3H), 1.78 (s, 3H). LCMS (M+H)+: 499.1.

Example 107

[3-{3-[6-(3-chlorobenzyl)-1-methyl-6H-pyrrolo[2,3-e][1,2,4]triazolo[4,3-a]pyridin-7-yl]-1H-pyrazol-1-yl}-1-(methylsulfonyl)azetidin-3-yl]acetonitrile

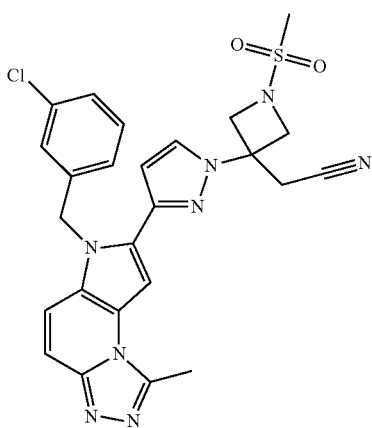 [SMILES: Cc1nnc2ccc3c(cc(-c4ccn(C5(CC#N)CN(S(C)(=O)=O)C5)n4)n3Cc3cccc(Cl)c3)n12]

To (3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile (6.0 mg, 0.013 mmol, from Example 106, Step 1) was added methanesulfonyl chloride (1.2 μL, 0.016 mmol, Aldrich) in DCM (0.46 mL), followed by triethylamine (3.7 μL, 0.026 mmol). After 10 minutes, the product was purified via preparative HPLC-MS (C18 eluting with a gradient of MeCN/H2O containing 0.15% NH4OH). Yield: (4.6 mg, 65%).

1H NMR (400 MHz, d6-DMSO) δ 8.25 (d, J=2.6 Hz, 1H), 7.75 (d, J=9.8 Hz, 1H), 7.48 (s, 1H), 7.38 (d, J=9.8 Hz, 1H), 7.30-7.21 (m, 2H), 7.19-7.10 (m, 1H), 7.03 (d, J=2.5 Hz, 1H), 6.99-6.92 (m, 1H), 6.05 (s, 2H), 4.38 (d, J=9.4 Hz, 2H), 4.20 (d, J=9.4 Hz, 2H), 3.54 (s, 2H), 3.03 (s, 3H), 2.95 (s, 3H). LCMS (M+H)+: 535.1.

Example 108

7-[1-(1-acetylazetidin-3-yl)-1H-pyrazol-3-yl]-6-(3-chlorobenzyl)-1-methyl-6H-pyrrolo[2,3-e][1,2,4]triazolo[4,3-a]pyridine

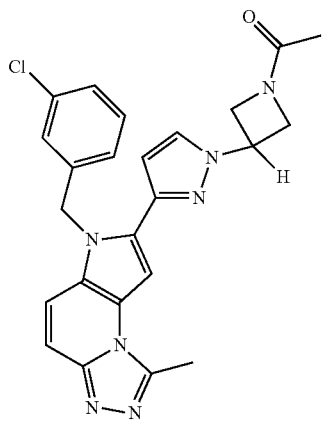 [SMILES: CC(=O)N1CC(n2ccc(-c3cc4c(ccc5nnc(C)n54)n3Cc3cccc(Cl)c3)n2)C1]

Step 1. 7-(1-azetidin-3-yl-1H-pyrazol-3-yl)-6-(3-chlorobenzyl)-1-methyl-6H-pyrrolo[2,3-e][1,2,4]triazolo[4,3-a]pyridine

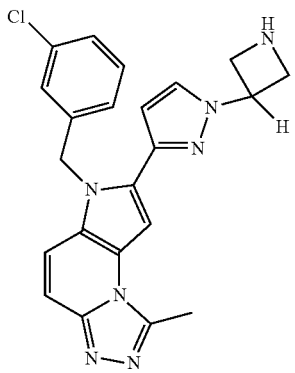 [SMILES: Cc1nnc2ccc3c(cc(-c4ccn(C5CNC5)n4)n3Cc3cccc(Cl)c3)n12]

6-(3-Chlorobenzyl)-1-methyl-7-(1H-pyrazol-5-yl)-6H-pyrrolo[2,3-e][1,2,4]triazolo[4,3-a]pyridine (25 mg, 0.069 mmol, from Example 103, Step 5) in DMF (1.5 mL) was treated with Cs2CO3 (34 mg, 0.10 mmol, Aldrich) and tert-butyl 3-[(methylsulfonyl)oxy]azetidine-1-carboxylate (26 mg, 0.10 mmol, prepared as in WO 2012004703). The mixture was heated at 70° C. for 14 hours. After cooling to room temperature, the mixture was diluted with water and extracted with three portions of EtOAc. The combined extracts were washed twice with brine, then were dried over sodium sulfate, filtered, and concentrated. The residue, dissolved in acetonitrile (1.0 mL) was treated with 4.0 M HCl in dioxane (0.40 mL, 1.6 mmol). After 20 minutes, the solvent and excess HCl were removed in vacuo. The residue was re-dissolved in methanol and pH was made basic by the addition of a few drops of NH4OH solution. Purification via preparative HPLC-MS (C18 eluting with a gradient of MeCN/H$_2$O containing 0.15% NH$_4$OH) afforded clean product (13.2 mg, 46%).

$^1$H NMR (300 MHz, d$_6$-DMSO) δ 7.93 (d, J=2.3 Hz, 1H), 7.75 (d, J=9.8 Hz, 1H), 7.39 (s, 1H), 7.36 (d, J=9.7 Hz, 1H), 7.32-7.22 (m, 2H), 7.21-7.15 (m, 1H), 7.02-6.93 (m, 1H), 6.84 (d, J=2.4 Hz, 1H), 6.09 (s, 2H), 5.20 (p, J=7.5 Hz, 1H), 3.87 (t, J=7.7 Hz, 2H), 3.69 (t, J=8.0 Hz, 2H), 2.95 (s, 3H). LCMS (M+H)$^+$: 418.2.

Step 2. 7-[1-(1-acetylazetidin-3-yl)-1H-pyrazol-3-yl]-6-(3-chlorobenzyl)-1-methyl-6H-pyrrolo[2,3-e][1,2,4]triazolo[4,3-a]pyridine

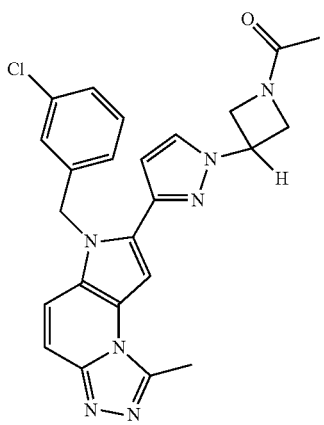 [SMILES: CC(=O)N1CC(n2ccc(-c3cc4c(ccc5nnc(C)n54)n3Cc3cccc(Cl)c3)n2)C1]

1H), 4.32-4.19 (m, 2H), 4.04 (dd, J=9.9, 5.3 Hz, 1H), 2.95 (s, 3H), 1.76 (s, 3H). LCMS (M+H)$^+$: 460.2.

Example 109

6-(3-chlorobenzyl)-1-methyl-7-{1-[1-(methylsulfonyl)azetidin-3-yl]-1H-pyrazol-3-yl}-6H-pyrrolo[2,3-e][1,2,4]triazolo[4,3-a]pyridine

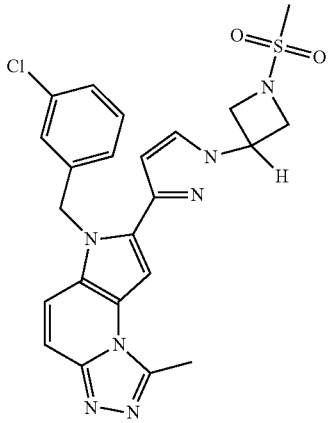 [SMILES: Cc1nnc2ccc3c(cc(C(=N)/C=C\NC4CN(S(C)(=O)=O)C4)n3Cc3cccc(Cl)c3)n12]

To 7-(1-azetidin-3-yl-1H-pyrazol-3-yl)-6-(3-chlorobenzyl)-1-methyl-6H-pyrrolo[2,3-e][1,2,4]triazolo[4,3-a]pyridine (6.0 mg, 0.014 mmol, from Step 1) was added acetyl chloride (1.2 μL, 0.017 mmol, Aldrich) in DCM (0.38 mL). Triethylamine (4.0 μL, 0.029 mmol) was then added and the reaction was complete in 2 minutes. Purification via preparative HPLC-MS (C18 eluting with a gradient of MeCN/H$_2$O containing 0.15% NH$_4$OH) afforded clean product (4.6 mg, 70%).

$^1$H NMR (400 MHz, d$_6$-DMSO) δ 7.98 (d, J=2.4 Hz, 1H), 7.74 (d, J=9.8 Hz, 1H), 7.43 (s, 1H), 7.37 (d, J=9.7 Hz, 1H), 7.30-7.22 (m, 2H), 7.11-7.05 (m, 1H), 7.03-6.94 (m, 1H), 6.89 (d, J=2.4 Hz, 1H), 6.09 (d, J=16.5 Hz, 1H), 6.02 (d, J=16.7 Hz, 1H), 5.26 (tt, J=8.0, 5.3 Hz, 1H), 4.52 (t, J=8.3 Hz,

To 7-(1-azetidin-3-yl-1H-pyrazol-3-yl)-6-(3-chlorobenzyl)-1-methyl-6H-pyrrolo[2,3-e][1,2,4]triazolo[4,3-a]pyridine (6.0 mg, 0.014 mmol, from Example 108, Step 1) was added methanesulfonyl chloride (1.3 μL, 0.017 mmol, Aldrich) in DCM (0.50 mL). This was followed by triethylamine (4.0 μL, 0.029 mmol) and the reaction was stirred for 2 minutes. Purification via preparative HPLC-MS (C18 eluting with a gradient of MeCN/H$_2$O containing 0.15% NH$_4$OH) afforded clean product (4.7 mg, 66%).

$^1$H NMR (400 MHz, d$_6$-DMSO) δ 7.98 (d, J=2.4 Hz, 1H), 7.69 (d, J=9.9 Hz, 1H), 7.45 (s, 1H), 7.36 (d, J=9.7 Hz, 1H), 7.32-7.24 (m, 2H), 7.16-7.11 (m, 1H), 7.06-6.98 (m, 1H), 6.92 (d, J=2.4 Hz, 1H), 6.10 (s, 2H), 5.33 (p, J=7.1 Hz, 1H), 4.28-4.20 (m, 4H), 2.95 (s, 3H), 2.93 (s, 3H). LCMS (M+H)+: 496.2.

Example 110

{3-[3-(6-benzyl-1-methyl-6H-pyrrolo[2,3-e][1,2,4]triazolo[4,3-a]pyridin-7-yl)-1H-pyrazol-1-yl]-1-ethylazetidin-3-yl}acetonitrile

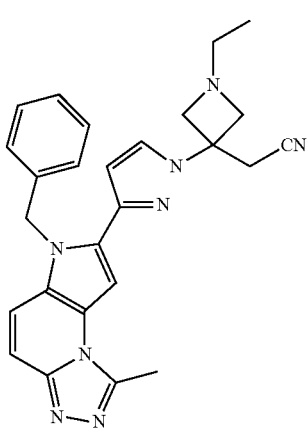 [SMILES: CCN1CC(CC#N)(N/C=C\C(=N)c2cc3c(ccc4nnc(C)n43)n2Cc2ccccc2)C1]

Prepared by the method of Example 93, using {3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile (8.5 mg, 0.020 mmol, from Example 90) in DCM (0.4 mL), and acetaldehyde (5.6 µL, 0.10 mmol, Aldrich), followed by sodium triacetoxyborohydride (13 mg, 0.060 mmol). Yield: (6.7 mg, 74%).

$^1$H NMR (400 MHz, d$_6$-DMSO) δ 8.12 (d, J=2.5 Hz, 1H), 7.73 (d, J=9.7 Hz, 1H), 7.41 (s, 1H), 7.34 (d, J=9.7 Hz, 1H), 7.27-7.13 (m, 3H), 7.10-7.00 (m, 2H), 6.93 (d, J=2.5 Hz, 1H), 6.03 (s, 2H), 3.46 (d, J=8.0 Hz, 2H), 3.44 (d, J=8.0 Hz, 2H), 3.41 (s, 2H), 2.94 (s, 3H), 2.44 (q, J=7.1 Hz, 2H), 0.86 (t, J=7.1 Hz, 3H). LCMS (M+H)+: 451.0.

Example 111

{3-[3-(6-benzyl-1-methyl-6H-pyrrolo[2,3-e][1,2,4]triazolo[4,3-a]pyridin-7-yl)-1H-pyrazol-1-yl]-1-isopropylazetidin-3-yl}acetonitrile

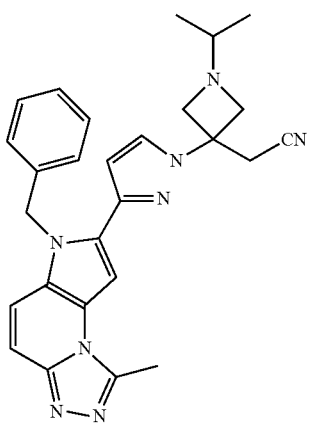 [SMILES: Cc1nnc2ccc3c(cc(C(=N)/C=C\NC4(CC#N)CN(C(C)C)C4)n3Cc3ccccc3)n12]

Prepared by the method of Example 110, using acetone (7.4 µL, 0.10 mmol, EMD). Yield: (5.0 mg, 53%).

$^1$H NMR (400 MHz, d$_6$-DMSO) δ 8.12 (d, J=2.5 Hz, 1H), 7.73 (d, J=9.8 Hz, 1H), 7.41 (s, 1H), 7.34 (d, J=9.7 Hz, 1H), 7.28-7.12 (m, 3H), 7.10-6.97 (m, 2H), 6.93 (d, J=2.5 Hz, 1H), 6.03 (s, 2H), 3.47 (d, J=8.2 Hz, 2H), 3.42 (d, J=8.2 Hz, 2H), 3.39 (s, 2H), 2.94 (s, 3H), 2.35 (hept, J=6.1 Hz, 1H), 0.84 (d, J=6.2 Hz, 6H). LCMS (M+H)+: 465.0.

Example 112

6-benzyl-1-methyl-6H-pyrazolo[3,4-e][1,2,4]triazolo[4,3-a]pyridine

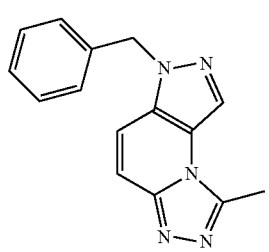 [SMILES: Cc1nnc2ccc3c(cnn3Cc3ccccc3)n12]

Step 1. 1-benzyl-5-chloro-1H-pyrazolo[4,3-b]pyridine and 2-benzyl-5-chloro-2H-pyrazolo[4,3-b]pyridine

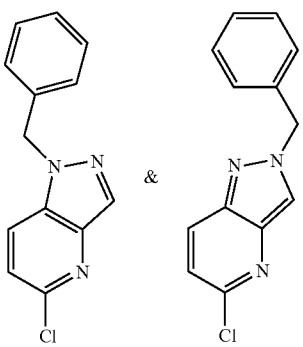 [SMILES: Clc1ccc2c(cnn2Cc2ccccc2)n1 ; Clc1ccc2nn(Cc3ccccc3)cc2n1]

To a suspension of sodium hydride (94 mg, 2.3 mmol, 60% in mineral oil) in DMF (4.0 mL) was added dropwise a solution of 5-chloro-1H-pyrazolo[4,3-b]pyridine (0.30 g, 2.0 mmol, J&W Pharmlab) in DMF (1.0 mL). The mixture was stirred for 10 minutes, then benzyl bromide (0.244 mL, 2.05 mmol, Aldrich) was added. After 70 minutes, the mixture was quenched by the addition of water and the product was extracted with EtOAc. The combined extracts were washed with water, followed by brine, dried over sodium sulfate, filtered, and concentrated. Flash chromatography, eluting with a gradient from 0-20% EtOAc in hexanes afforded two isomeric products: Peak 1 (first to elute, 1-benzyl-5-chloro-1H-pyrazolo[4,3-b]pyridine): 0.21 g, 44% yield. Peak 2 (second to elute, 2-benzyl-5-chloro-2H-pyrazolo[4,3-b]pyridine): 0.10 g, 21% yield.

Peak 1 (first to elute, 1-benzyl-5-chloro-1H-pyrazolo[4,3-b]pyridine): $^1$H NMR (500 MHz, CDCl$_3$) δ 8.19 (d, J=0.8 Hz, 1H), 7.56 (dd, J=8.8, 0.7 Hz, 1H), 7.38-7.27 (m, 3H), 7.22 (d, J=8.8 Hz, 1H), 7.18 (dd, J=7.7, 1.5 Hz, 2H), 5.59 (s, 2H); LCMS (M+H)$^+$: 244.1, 246.1.

Peak 2 (second to elute, 2-benzyl-5-chloro-2H-pyrazolo[4,3-b]pyridine): $^1$H NMR (500 MHz, CDCl$_3$) δ 8.07 (d, J=0.8 Hz, 1H), 8.00 (dd, J=9.0, 0.8 Hz, 1H), 7.41-7.33 (m, 3H), 7.29 (dd, J=7.6, 1.7 Hz, 2H), 7.19 (d, J=9.0 Hz, 1H), 5.60 (s, 2H); LCMS (M+H)$^+$: 244.1, 246.1.

Step 2. di-tert-butyl 1-(1-benzyl-1H-pyrazolo[4,3-b]pyridin-5-yl)hydrazine-1,2-dicarboxylate

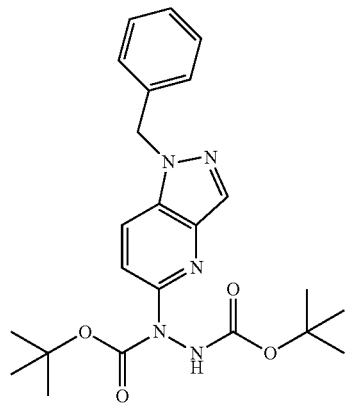 [SMILES: CC(C)(C)OC(=O)NN(C(=O)OC(C)(C)C)c1ccc2c(cnn2Cc2ccccc2)n1]

A reaction vial was charged with 1-benzyl-5-chloro-1H-pyrazolo[4,3-b]pyridine (0.210 g, 0.862 mmol) (Peak 1 from Step 1), di-tert-butyl hydrazine-1,2-dicarboxylate (0.22 g, 0.96 mmol, Aldrich), cesium carbonate (0.281 g, 0.862 mmol, Aldrich) and toluene (2 mL, 20 mmol). Dicyclohexyl(2',4',6'-triisopropylbiphenyl-2-yl)phosphine-(2'-aminobiphenyl-2-yl)(chloro)palladium (1:1) (0.068 g, 0.086 mmol, Aldrich) was added and the mixture was degassed by a stream of nitrogen through the solution for 15 minutes. The reaction vial was sealed and heated to 110° C. for 2 hours, then was stirred at room temperature for 3 days. The reaction mixture was partitioned between ethyl acetate and water and the aqueous was extracted with two further portions of EtOAc. The combined extracts were dried over sodium sulfate, filtered and concentrated. Flash chromatography, eluting with a gradient from 0-50% EtOAc in hexanes afforded product (0.19 g, 50%).

$^1$H NMR (300 MHz, CD$_3$OD) δ 8.12 (s, 1H), 7.97 (d, J=9.1 Hz, 1H), 7.63 (d, J=9.1 Hz, 1H), 7.34-7.14 (m, 5H), 5.63 (s, 2H), 1.50 (s, 9H), 1.49 (s, 9H); LCMS (M+H)$^+$: 440.0.

Step 3. 6-benzyl-1-methyl-6H-pyrazolo[3,4-e][1,2,4]triazolo[4,3-a]pyridine di-tert-Butyl 1-(1-benzyl-1H-pyrazolo[4,3-b]pyridin-5-yl)hydrazine-1,2-dicarboxylate (0.030 g, 0.068 mmol, from Step 2) in AcOH (3 mL) was heated in the microwave to 180° C. for 5 minutes. The AcOH was removed in vacuo, the residue was reconstituted in MeOH, and purified via preparative HPLC-MS (Waters XBridge C18, eluting with a gradient of MeCN/H$_2$O containing 0.15% NH$_4$OH) to afford product (8 mg, 40%).

¹H NMR (300 MHz, CDCl₃) δ 8.12 (d, J=0.8 Hz, 1H), 7.55 (d, J=9.9 Hz, 1H), 7.39-7.17 (m, 6H), 5.63 (s, 2H), 2.98 (s, 3H); LCMS (M+H)⁺: 264.1.

Example 113

6-(3-Chlorobenzyl)-N-ethyl-1-methyl-6H-pyrrolo[2,3-e][1,2,4]triazolo[4,3-a]pyridine-7-carboxamide trifluoroacetate salt

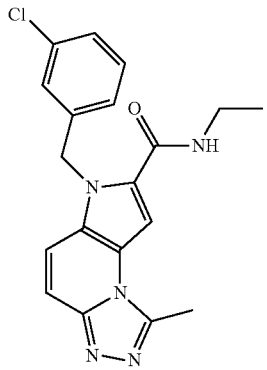 [SMILES: CCNC(=O)c1cc2c(ccc3nnc(C)n32)n1Cc1cccc(Cl)c1]

To a suspension of 6-(3-chlorobenzyl)-1-methyl-6H-pyrrolo[2,3-e][1,2,4]triazolo[4,3-a]pyridine-7-carboxylic acid (0.023 g, 0.067 mmol, prepared as in Example 99, Step 4) in DMF (1.5 mL) was added N,N-diisopropylethylamine (0.035 mL, 0.20 mmol) followed by HATU (0.0385 g, 0.101 mmol) and ethylamine (2.0 M in THF, 0.17 mL, 0.34 mmol, Aldrich). After stirring overnight, the reaction was diluted with MeCN and purified by preparative HPLC-MS (Waters SunFire C18, eluting with a gradient of MeCN/H₂O containing 0.1% TFA). Yield: (0.01 g, 30%).

¹H NMR (400 MHz, CD₃OD) δ 8.27 (d, J=9.8 Hz, 1H), 7.77 (d, J=0.5 Hz, 1H), 7.65 (d, J=9.7 Hz, 1H), 7.30-7.21 (m, 2H), 7.15-7.11 (m, 1H), 7.08 (dt, J=6.8, 1.9 Hz, 1H), 6.06 (s, 2H), 3.42 (q, J=7.3 Hz, 2H), 3.10 (s, 3H), 1.23 (t, J=7.3 Hz, 3H); LCMS (M+H)⁺: 368.2.

Example 114

6-(3-Chlorobenzyl)-N-(cyclopropylmethyl)-1-methyl-6H-pyrrolo[2,3-e][1,2,4]triazolo[4,3-a]pyridine-7-carboxamide trifluoroacetate salt

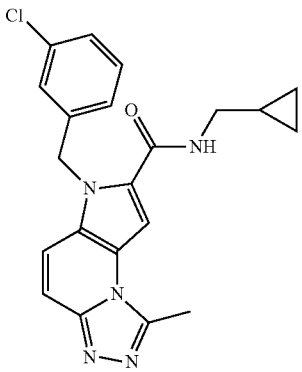 [SMILES: Cc1nnc2ccc3c(cc(C(=O)NCC4CC4)n3Cc3cccc(Cl)c3)n12]

The title compound was prepared according to the methods of Example 113 using 1-cyclopropylmethanamine hydrochloride (0.014 g, 0.13 mmol, Aldrich). Yield: (0.01 g, 30%).

¹H NMR (400 MHz, CD₃OD) δ 8.33 (d, J=9.7 Hz, 1H), 7.81 (d, J=0.5 Hz, 1H), 7.67 (d, J=9.7 Hz, 1H), 7.30-7.21 (m, 2H), 7.16-7.11 (m, 1H), 7.09 (dt, J=6.7, 1.9 Hz, 1H), 6.07 (s, 2H), 3.25 (d, J=7.0 Hz, 2H), 3.12 (s, 3H), 1.14-1.03 (m, 1H), 0.71-0.38 (m, 2H), 0.38-0.07 (m, 2H); LCMS (M+H)⁺: 394.2.

Example 115

6-(3-Chlorobenzyl)-N-[2-(dimethylamino)ethyl]-1-methyl-6H-pyrrolo[2,3-e][1,2,4]triazolo[4,3-a]pyridine-7-carboxamide bis(trifluoroacetate) salt

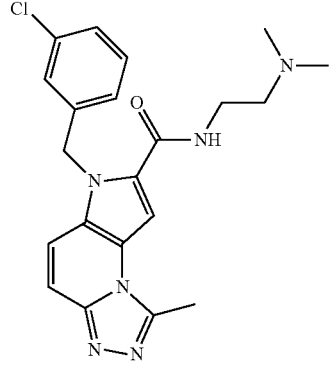 [SMILES: Cc1nnc2ccc3c(cc(C(=O)NCCN(C)C)n3Cc3cccc(Cl)c3)n12]

The title compound was prepared according to the methods of Example 113 using N,N-dimethyl-1,2-ethanediamine (0.022 mL, 0.20 mmol, Aldrich). Yield: (0.01 g, 20%).

¹H NMR (400 MHz, CD₃OD) δ 8.12 (d, J=9.7 Hz, 1H), 7.80 (d, J=0.5 Hz, 1H), 7.63 (d, J=9.8 Hz, 1H), 7.32-7.23 (m, 2H), 7.15-7.10 (m, 1H), 7.09-7.04 (m, 1H), 6.08 (s, 2H), 3.78 (t, J=6.0 Hz, 2H), 3.38 (t, J=6.0 Hz, 2H), 3.09 (s, 3H), 2.98 (s, 6H); LCMS (M+H)⁺: 411.3.

Example 116

6-(3-Chlorobenzyl)-1-methyl-7-(morpholin-4-ylcarbonyl)-6H-pyrrolo[2,3-e][1,2,4]triazolo[4,3-a]pyridine trifluoroacetate salt

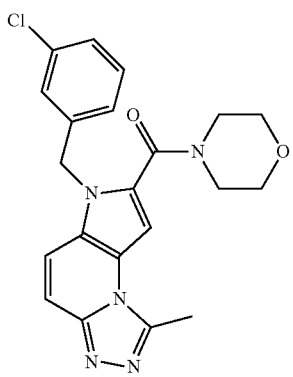 [SMILES: Cc1nnc2ccc3c(cc(C(=O)N4CCOCC4)n3Cc3cccc(Cl)c3)n12]

The title compound was prepared according to the methods of Example 113 using morpholine (0.018 mL, 0.20 mmol, Aldrich). Yield: (0.01 g, 30%).

¹H NMR (400 MHz, CD₃OD) δ 8.44 (d, J=9.7 Hz, 1H), 7.69 (d, J=9.7 Hz, 1H), 7.43 (d, J=0.6 Hz, 1H), 7.36-7.29 (m, 2H), 7.20-7.16 (m, 1H), 7.14-7.07 (m, 1H), 5.73 (s, 2H), 3.80-3.20 (br m, 8H), 3.09 (s, 3H); LCMS (M+H)⁺: 410.2.

Example 117

6-(3-Chlorobenzyl)-N-(2-hydroxyethyl)-1-methyl-6H-pyrrolo[2,3-e][1,2,4]triazolo[4,3-a]pyridine-7-carboxamide trifluoroacetate salt

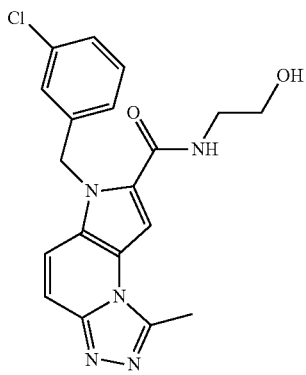 [SMILES: Cc1nnc2ccc3c(cc(C(=O)NCCO)n3Cc3cccc(Cl)c3)n12]

The title compound was prepared according to the methods of Example 113 using ethanolamine (0.012 mL, 0.20 mmol, Aldrich). Yield: (0.01 g, 30%).

¹H NMR (400 MHz, CD₃OD) δ 8.27 (d, J=9.8 Hz, 1H), 7.85 (d, J=0.6 Hz, 1H), 7.65 (d, J=9.7 Hz, 1H), 7.31-7.21 (m, 2H), 7.17-7.13 (m, 1H), 7.09 (dt, J=6.9, 1.9 Hz, 1H), 6.07 (s, 2H), 3.72 (t, J=5.7 Hz, 2H), 3.52 (t, J=5.7 Hz, 2H), 3.11 (s, 3H); LCMS (M+H)⁺: 384.0.

Example 118

6-(3-Chlorobenzyl)-1-methyl-N-(1-methylazetidin-3-yl)-6H-pyrrolo[2,3-e][1,2,4]triazolo[4,3-a]pyridine-7-carboxamide bis(trifluoroacetate) salt

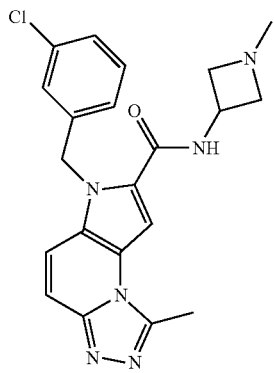 [SMILES: Cc1nnc2ccc3c(cc(C(=O)NC4CN(C)C4)n3Cc3cccc(Cl)c3)n12]

The title compound was prepared according to the methods of Example 113 using 1-methylazetidin-3-amine (0.017 g, 0.20 mmol, Synthonix). Yield: (0.01 g, 20%).

¹H NMR (400 MHz, CD₃OD) δ 8.21 (d, J=9.8 Hz, 1H), 7.89 (d, J=5.3 Hz, 1H), 7.67 (d, J=9.8 Hz, 1H), 7.31-7.21 (m, 2H), 7.16-7.10 (m, 1H), 7.10-7.02 (m, 1H), 6.10 (s, 1H, rotamers), 6.06 (s, 1H, rotamers), 4.88-4.53 (m, 3H), 4.34 (t, J=9.8 Hz, 1H), 4.26 (t, J=9.7 Hz, 1H), 3.11 (s, 3H), 3.04 (s, 1.5H, rotamers), 2.98 (s, 1.5H, rotamers); LCMS (M+H)⁺: 409.1.

Example 119

6-(3-Chlorobenzyl)-1-methyl-N-(2-morpholin-4-ylethyl)-6H-pyrrolo[2,3-e][1,2,4]triazolo[4,3-a]pyridine-7-carboxamide trifluoroacetate salt

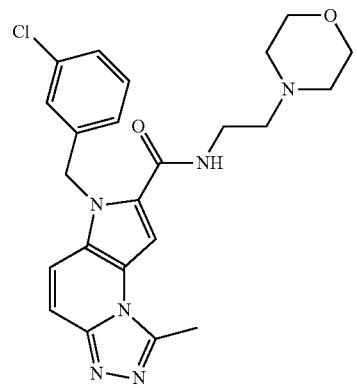 [SMILES: Cc1nnc2ccc3c(cc(C(=O)NCCN4CCOCC4)n3Cc3cccc(Cl)c3)n12]

The title compound was prepared according to the methods of Example 113, using 6-(3-chlorobenzyl)-1-methyl-6H-pyrrolo[2,3-e][1,2,4]triazolo[4,3-a]pyridine-7-carboxylic acid (0.050 g, 0.15 mmol), N,N-diisopropylethylamine (0.077 mL, 0.44 mmol), HATU (0.084 g, 0.22 mmol) and N-(2-aminoethyl)morpholine (0.057 g, 0.44 mmol, Aldrich) in N,N-dimethylformamide (3.3 mL). The reaction time was 1 hour. Yield: (8 mg, 10%).

¹H NMR (300 MHz, d₆-DMSO) δ 9.93 (br s, 1H), 9.05 (t, J=5.8 Hz, 1H), 7.93 (d, J=9.9 Hz, 1H), 7.81 (s, 1H), 7.62 (d, J=9.8 Hz, 1H), 7.38-7.28 (m, 2H), 7.20 (s, 1H), 7.10-7.01 (m, 1H), 6.04 (s, 2H), 3.98 (br m, 2H), 3.77-3.42 (m, 6H), 3.32 (t, J=6.1 Hz, 2H), 3.18 (br m, 2H), 2.96 (s, 3H); LCMS (M+H)⁺: 453.1.

Example 120

N-(tert-Butyl)-6-(3-chlorobenzyl)-1-methyl-6H-pyrrolo[2,3-e][1,2,4]triazolo[4,3-a]pyridine-7-carboxamide trifluoroacetate salt

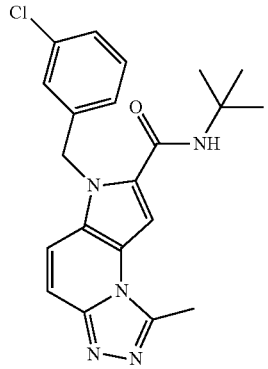 [SMILES: Cc1nnc2ccc3c(cc(C(=O)NC(C)(C)C)n3Cc3cccc(Cl)c3)n12]

The title compound was prepared according to the methods of Example 113, using 6-(3-chlorobenzyl)-1-methyl-6H-pyrrolo[2,3-e][1,2,4]triazolo[4,3-a]pyridine-7-carboxylic acid (0.050 g, 0.15 mmol), N,N-diisopropylethylamine (0.077 mL, 0.44 mmol), HATU (0.084 g, 0.22 mmol) and tert-butylamine (0.032 g, 0.44 mmol, Aldrich) in N,N-dimethylformamide (3.3 mL). The reaction time was 1 hour. Yield: (8 mg, 10%).

$^1$H NMR (300 MHz, $d_6$-DMSO) δ 8.05 (d, J=9.7 Hz, 1H), 8.05 (s, 1H), 7.69 (s, 1H), 7.59 (d, J=9.8 Hz, 1H), 7.35-7.26 (m, 2H), 7.20 (s, 1H), 7.10-7.00 (m, 1H), 5.98 (s, 2H), 2.96 (s, 3H), 1.38 (s, 9H); LCMS (M+H)$^+$: 396.1.

Example 121

6-[3-(Azetidin-1-ylmethyl)benzyl]-N-ethyl-1-methyl-6H-pyrrolo[2,3-e][1,2,4]triazolo[4,3-a]pyridine-7-carboxamide bis(trifluoroacetate) salt

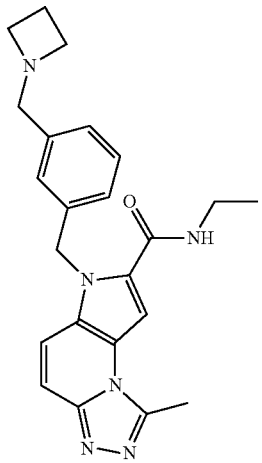 [SMILES: CCNC(=O)c1cc2c(ccc3nnc(C)n32)n1Cc1cccc(CN2CCC2)c1]

Step 1. [3-({[tert-Butyl(diphenyl)silyl]oxy}methyl)phenyl]methanol

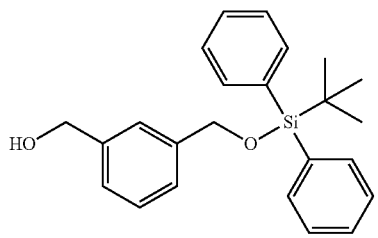 [SMILES: CC(C)(C)[Si](OCc1cccc(CO)c1)(c1ccccc1)c1ccccc1]

To a solution of 1,3-phenylenedimethanol (10.00 g, 72.38 mmol, Aldrich) in DCM (200 mL) was added 1H-imidazole (5.17 g, 76.0 mmol, Aldrich), followed by the addition of tert-butylchlorodiphenylsilane (19.8 mL, 76.0 mmol, Aldrich) and 4-dimethylaminopyridine (0.88 g, 7.2 mmol, Aldrich). After stirring overnight, the reaction was partitioned between DCM and water, the organic layer was dried over sodium sulfate, filtered and concentrated. The product was purified by flash chromatography (gradient elution, 0 to 20% EtOAc/hexanes). Yield: (7.9 g, 29%).

$^1$H NMR (300 MHz, CDCl$_3$) δ 7.73-7.63 (m, 4H), 7.48-7.21 (m, 10H), 4.77 (s, 2H), 4.68 (d, J=5.8 Hz, 2H), 1.09 (s, 9H); LCMS (M+0H+H)$^+$: 394.2.

Step 2. tert-butyl{[3-(chloromethyl)benzyl]oxy}diphenylsilane

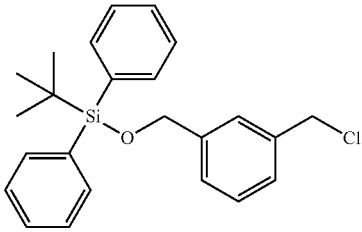 [SMILES: CC(C)(C)[Si](OCc1cccc(CCl)c1)(c1ccccc1)c1ccccc1]

To a solution of [3-({[tert-butyl(diphenyl)silyl]oxy}methyl)phenyl]methanol (7.9 g, 21 mmol, from Step 1) in methylene chloride (100 mL) at 0° C. was added triethylamine (5.85 mL, 42.0 mmol), followed by the addition of methanesulfonyl chloride (1.62 mL, 21.0 mmol, Aldrich). The reaction was stirred at 0° C. for 30 minutes, after which time the reaction was allowed to warm to room temperature for 1 hour. Water was added and the layers were separated. The aqueous layer was extracted with another portion of DCM. The combined organic extracts were washed sequentially with water and brine, dried over sodium sulfate, filtered and concentrated. The product was isolated by flash chromatography (gradient elution, 0 to 25% EtOAc/hexanes). The product was used further in Step 3. Yield: (3.9 g, 47%).

$^1$H NMR (300 MHz, CDCl$_3$) δ 7.73-7.64 (m, 4H), 7.48-7.23 (m, 10H), 4.77 (s, 2H), 4.59 (s, 2H), 1.10 (s, 9H).

Step 3. 3-({[tert-Butyl(diphenyl)silyl]oxy}methyl)benzyl 1-[3-({[tert-butyl(diphenyl)silyl]oxy}methyl)benzyl]-5-chloro-1H-pyrrolo[3,2-b]pyridine-2-carboxylate

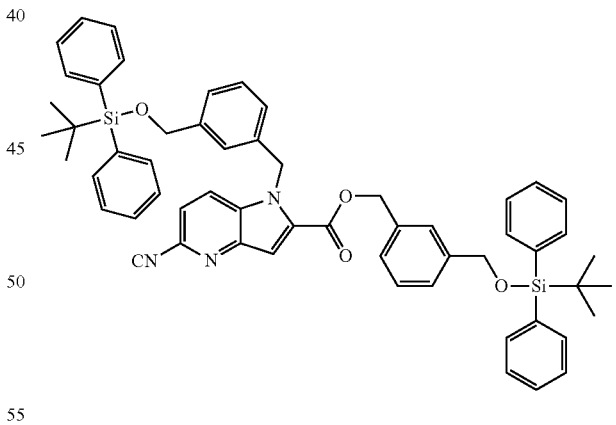

5-Chloro-1H-pyrrolo[3,2-b]pyridine-2-carboxylic acid (0.803 g, 4.08 mmol, from Example 99, Step 1) in DMF (20 mL) was treated with Cs$_2$CO$_3$ (4.0 g, 12 mmol), followed by the addition of tert-butyl{[3-(chloromethyl)benzyl]oxy}diphenylsilane (3.9 g, 9.9 mmol, from Step 2). After stirring overnight, the crude reaction mixture was partitioned between water and ethyl acetate and the aqueous layer was extracted with an additional two portions of ethyl acetate. The combined organic extracts were washed sequentially with water and brine, dried over sodium sulfate, filtered and concentrated. The product was purified by flash chromatography, eluting with a slow gradient from 0-20% EtOAc/hexanes. Yield: (2.18 g, 58%).

$^1$H NMR (400 MHz, CDCl$_3$) δ 7.70-7.64 (m, 4H), 7.62-7.55 (m, 5H), 7.46 (d, J=0.7 Hz, 1H), 7.44-7.10 (m, 19H), 6.97 (s, 1H), 6.94 (d, J=7.5 Hz, 1H), 5.82 (s, 2H), 5.32 (s, 2H), 4.76 (s, 2H), 4.64 (s, 2H), 1.08 (s, 9H), 0.98 (s, 9H); LCMS (M+H)$^+$: 913.1.

Step 4. Di-tert-butyl 1-[1-[3-({[tert-butyl(diphenyl)silyl]oxy}methyl)benzyl]-2-({[3-({[tert-butyl(diphenyl)silyl]oxy}methyl)benzyl]oxy}carbonyl)-1H-pyrrolo[3,2-b]pyridin-5-yl]hydrazine-1,2-dicarboxylate

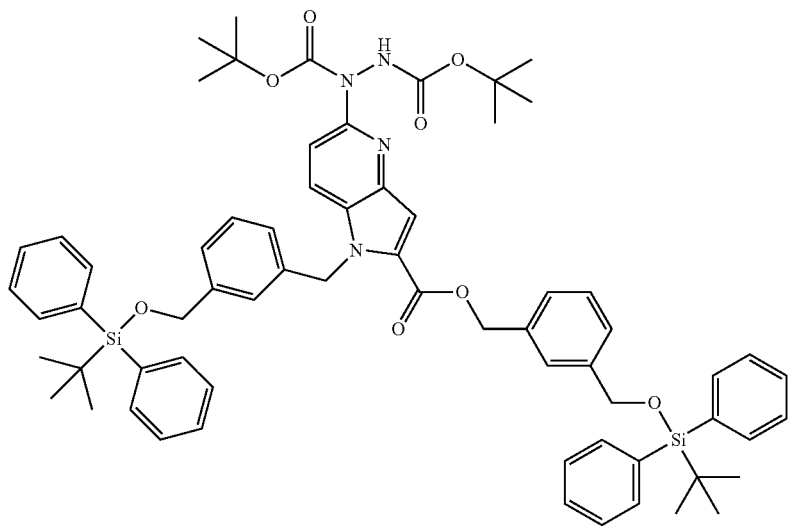 [SMILES: CC(C)(C)OC(=O)NN(C(=O)OC(C)(C)C)c1ccc2c(cc(C(=O)OCc3cccc(CO[Si](c4ccccc4)(c4ccccc4)C(C)(C)C)c3)n2Cc2cccc(CO[Si](c3ccccc3)(c3ccccc3)C(C)(C)C)c2)n1]

3-({[tert-Butyl(diphenyl)silyl]oxy}methyl)benzyl 1-[3-({[tert-butyl(diphenyl)silyl]oxy}methyl)benzyl]-5-chloro-1H-pyrrolo[3,2-b]pyridine-2-carboxylate (2.18 g, 2.38 mmol, from Step 3) and di-tert-butyl hydrazine-1,2-dicarboxylate (0.71 g, 3.1 mmol, Aldrich), dicyclohexyl(2',4',6'-triisopropylbiphenyl-2-yl)phosphine-(2'-aminobiphenyl-2-yl)(chloro)palladium (1:1) (0.22 g, 0.28 mmol, Aldrich) and Cs$_2$CO$_3$ (0.91 g, 2.8 mmol) were combined in toluene (27 mL) and the mixture was degassed by a stream of nitrogen bubbled through the solution for 10 minutes. The reaction vessel was sealed and heated at 110° C. for 3 hours. The reaction mixture was partitioned between water and ethyl acetate, the aqueous layer was extracted three times and the combined organic extracts were dried over sodium sulfate, filtered and concentrated. The product was purified by flash chromatography, eluting with a gradient from 0-25% EtOAc/hexanes. Yield: (1.31 g, 50%).

LCMS (M+H)$^+$: 1109.3.

Step 5. 3-({[tert-Butyl(diphenyl)silyl]oxy}methyl)benzyl 6-[3-({[tert-butyl(diphenyl)silyl]oxy}methyl)benzyl]-1-methyl-6H-pyrrolo[2,3-e][1,2,4]triazolo[4,3-a]pyridine-7-carboxylate

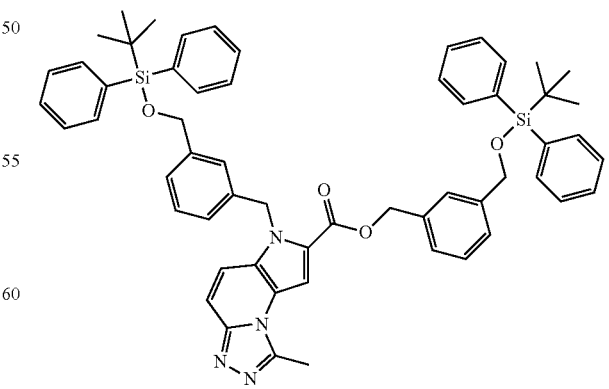

Di-tert-butyl 1-[1-[3-({[tert-butyl(diphenyl)silyl]oxy}methyl)benzyl]-2-({[3-({[tert-butyl(diphenyl)silyl]

oxy}methyl)benzyl]oxy}carbonyl)-1H-pyrrolo[3,2-b]pyridin-5-yl]hydrazine-1,2-dicarboxylate (1.30 g, 1.18 mmol, from Step 4) in acetic acid (17 mL) was divided into three equal portions and each was heated in the microwave to 180° C. for 5 minutes. The batches were recombined and acetic acid was removed in vacuo. The crude residue was partitioned between an additional NaHCO₃ solution and EtOAc. The aqueous layer was extracted further with two portions of EtOAc. The combined organic extracts were dried over sodium sulfate, filtered and concentrated. The product was used without further purification. Yield: (900. mg, 87%).

¹H NMR (400 MHz, CDCl₃) δ 7.73-7.66 (m, 4H), 7.63-7.56 (m, 4H), 7.52 (d, J=9.9 Hz, 1H), 7.49 (s, 1H), 7.44-7.20 (m, 18H), 7.18-7.13 (m, 1H), 7.03-6.96 (m, 2H), 5.94 (s, 2H), 5.34 (s, 2H), 4.80 (s, 2H), 4.67 (s, 2H), 2.90 (s, 3H), 1.10 (s, 9H), 0.95 (s, 9H); LCMS (M+H)⁺: 933.2.

Step 6. 3-(Azetidin-1-ylmethyl)benzyl 6-[3-(azetidin-1-ylmethyl)benzyl]-1-methyl-6H-pyrrolo[2,3-e][1,2,4]triazolo[4,3-a]pyridine-7-carboxylate tris(trifluoroacetate) salt

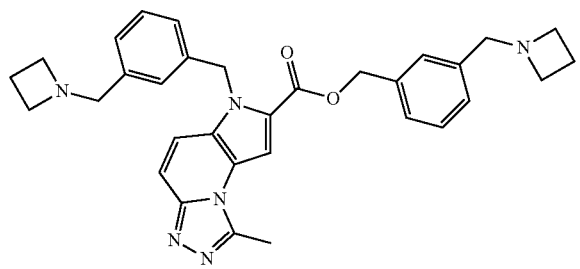 [SMILES: Cc1nnc2ccc3c(cc(C(=O)OCc4cccc(CN5CCC5)c4)n3Cc3cccc(CN4CCC4)c3)n12]

3-({[tert-Butyl(diphenyl)silyl]oxy}methyl)benzyl 6-[3-({[tert-butyl(diphenyl)silyl]oxy}methyl)benzyl]-1-methyl-6H-pyrrolo[2,3-e][1,2,4]triazolo[4,3-a]pyridine-7-carboxylate (0.890 g, 0.954 mmol, from Step 5) was dissolved in 1,4-dioxane (20 mL) and 4.0 M solution of HCl in dioxane (20 mL, 80 mmol) was added. The reaction was stirred for 1 h at 110° C. Three additional portions of 4.0 M HCl in dioxane (10 mL, 40 mmol) were added periodically over the course of 6.5 hours at 110° C. After the third addition, the reaction mixture was heated at 110° C. in a sealed vessel for 48 hours. When the reaction was complete, the dioxane was evaporated and the residue was neutralized by the addition of saturated NaHCO₃ solution. The product was extracted with three portions of EtOAc. The combined organic extracts were dried over sodium sulfate, filtered and concentrated. Flash chromatography, eluting with a gradient from 0-10% MeOH/DCM was used to isolate 3-(chloromethyl)benzyl 6-[3-(hydroxymethyl)benzyl]-1-methyl-6H-pyrrolo[2,3-e][1,2,4]triazolo[4,3-a]pyridine-7-carboxylate, which was used in the displacement reaction that follows.

To 3-(chloromethyl)benzyl 6-[3-(hydroxymethyl)benzyl]-1-methyl-6H-pyrrolo[2,3-e][1,2,4]triazolo[4,3-a]pyridine-7-carboxylate (0.26 g, 0.53 mmol) in N,N-dimethylformamide (5 mL) was added K₂CO₃ (0.29 g, 2.1 mmol) and N,N-diisopropylethylamine (0.28 mL, 1.6 mmol). Azetidine (0.14 mL, 2.1 mmol, Aldrich) was added and the reaction was stirred at 60° C. for 5 hours. The reaction mixture was cooled and partitioned between water and ethyl acetate. The aqueous layer was extracted with three portions of EtOAc. The extracts were dried over sodium sulfate, filtered and concentrated. The product was purified by preparative HPLC-MS (Waters SunFire C18, eluting with a gradient of MeCN/H₂O containing 0.1% TFA). Yield: (0.15 g, 29%).

¹H NMR (400 MHz, CD₃OD) δ 8.30 (d, J=9.8 Hz, 1H), 7.87 (s, 1H), 7.76 (d, J=9.8 Hz, 1H), 7.60-7.32 (m, 6H), 7.22 (s, 1H), 7.17-7.10 (m, 1H), 6.13 (s, 2H), 5.42 (s, 2H), 4.38 (s, 2H), 4.28 (s, 2H), 4.24-3.93 (m, 8H), 3.12 (s, 3H), 2.62-2.30 (m, 4H); LCMS (M+H)⁺: 535.3.

Step 7. 6-[3-(Azetidin-1-ylmethyl)benzyl]-1-methyl-6H-pyrrolo[2,3-e][1,2,4]triazolo[4,3-a]pyridine-7-carboxylic acid

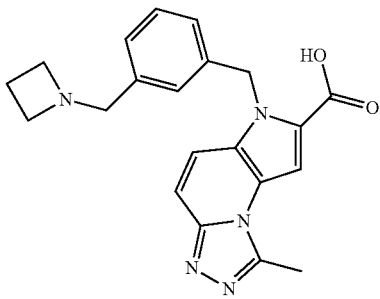 [SMILES: Cc1nnc2ccc3c(cc(C(=O)O)n3Cc3cccc(CN4CCC4)c3)n12]

3-(Azetidin-1-ylmethyl)benzyl 6-[3-(azetidin-1-ylmethyl)benzyl]-1-methyl-6H-pyrrolo[2,3-e][1,2,4]triazolo[4,3-a]pyridine-7-carboxylate tris(trifluoroacetate) (0.15 g, 0.17 mmol, from Step 6) was dissolved in tetrahydrofuran (5 mL) and 1.0 M NaOH (5 mL, 5 mmol) was added. The reaction was stirred for 1 hour. The product was purified by preparative HPLC-MS (Waters XBridge C18, eluting with a gradient of MeCN/H₂O containing 0.15% NH₄OH) Yield: (0.033 g, 51%).

LCMS (M+H)⁺: 535.3.

Step 8. 6-[3-(Azetidin-1-ylmethyl)benzyl]-N-ethyl-1-methyl-6H-pyrrolo[2,3-e][1,2,4]triazolo[4,3-a]pyridine-7-carboxamide bis(trifluoroacetate) salt To a solution of 6-[3-(azetidin-1-ylmethyl)benzyl]-1-methyl-6H-pyrrolo[2,3-e][1,2,4]triazolo[4,3-a]pyridine-7-carboxylic acid (0.017 g, 0.045 mmol, from Step 7) in N-methylpyrrolidinone (1 mL) was added N,N-diisopropylethylamine (0.032 mL, 0.18 mmol) and ethylamine (0.010 g, 0.018 mmol, Aldrich), followed by the addition of HATU (0.022 g, 0.059 mmol). When the reaction was complete as determined by LCMS, the reaction was diluted with MeCN, and TFA was added to aid in solubility. The product was purified via preparative HPLC-MS (Waters SunFire C18, 5 μm 30×100 mm, (H₂O, 0.1% TFA) MeOH, flow rate: 60 mL/min). Yield: (10 mg, 35%).

¹H NMR (400 MHz, CD₃OD) δ 8.16 (d, J=9.6 Hz, 1H), 7.79 (s, 1H), 7.62 (d, J=9.7 Hz, 1H), 7.42-7.31 (m, 2H), 7.29-7.26 (m, 1H), 7.19-7.14 (m, 1H), 6.08 (s, 2H), 4.29 (s,

2H), 4.18-3.94 (m, 4H), 3.40 (q, J=7.3 Hz, 2H), 3.10 (s, 3H), 2.60-2.46 (m, 1H), 2.46-2.31 (m, 1H), 1.22 (t, J=7.3 Hz, 3H); LCMS (M+H)+: 403.2.

Example 122

6-[3-(Azetidin-1-ylmethyl)benzyl]-N,1-dimethyl-6H-pyrrolo[2,3-e][1,2,4]triazolo[4,3-a]pyridine-7-carboxamide bis(trifluoroacetate) salt

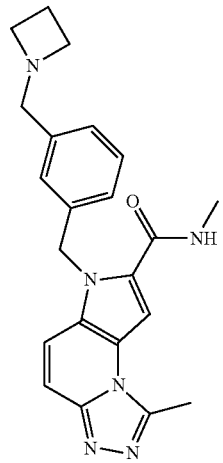 [SMILES: CNC(=O)c1cc2c(ccc3nnc(C)n32)n1Cc1cccc(CN2CCC2)c1]

The title compound was prepared according to the methods of Example 121, Step 8, using methylamine hydrochloride (0.0053 g, 0.078 mmol, Alfa Aesar). Yield: (10 mg, 35%).
1H NMR (400 MHz, CD3OD) δ 8.11 (d, J=9.8 Hz, 1H), 7.75 (s, 1H), 7.60 (d, J=9.8 Hz, 1H), 7.43-7.31 (m, 2H), 7.30-7.26 (m, 1H), 7.20-7.13 (m, 1H), 6.09 (s, 2H), 4.29 (s, 2H), 4.21-3.97 (m, 4H), 3.09 (s, 3H), 2.92 (s, 3H), 2.60-2.47 (m, 1H), 2.47-2.34 (m, 1H); LCMS (M+H)+: 389.1.

Example 123

6-Benzyl-N-(3-hydroxypropyl)-1-methyl-6H-pyrrolo[2,3-e][1,2,4]triazolo[4,3-a]pyridine-7-carboxamide trifluoroacetate salt

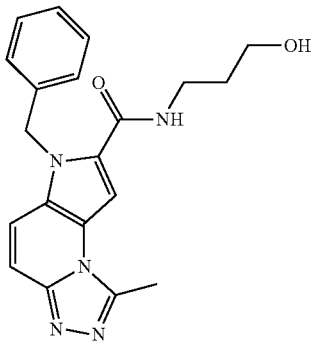 [SMILES: Cc1nnc2ccc3c(cc(C(=O)NCCCO)n3Cc3ccccc3)n12]

To a suspension of 6-benzyl-1-methyl-6H-pyrrolo[2,3-e][1,2,4]triazolo[4,3-a]pyridine-7-carboxylic acid (0.01 g, 0.04 mmol, from Example 100, Step 3) in N,N-dimethylformamide (1.0 mL) was added N,N-diisopropylethylamine (0.024 mL, 0.13 mmol), followed by the addition of HATU (0.0257 g, 0.0675 mmol) and 3-amino-1-propanol (0.010 g, 0.13 mmol, Aldrich). When the reaction was complete, the reaction mixture was diluted with MeCN and the product was purified by preparative HPLC-MS (Waters SunFire C18, eluting with a gradient of MeCN/H2O containing 0.1% TFA). Yield: (8 mg, 40%).
1H NMR (500 MHz, d6-DMSO) δ 8.75 (t, J=5.6 Hz, 1H), 8.20 (d, J=9.6 Hz, 1H), 7.84 (s, 1H), 7.66 (d, J=9.8 Hz, 1H), 7.31-7.25 (m, 2H), 7.25-7.20 (m, 1H), 7.14-7.09 (m, 2H), 6.10 (s, 2H), 3.47 (t, J=6.3 Hz, 2H), 3.35 (q, J=6.7 Hz, 2H), 3.01 (s, 3H), 1.70 (p, J=6.5 Hz, 2H); LCMS (M+H)+: 364.2.

Example 124

N-(Azetidin-3-ylmethyl)-6-benzyl-1-methyl-6H-pyrrolo[2,3-e][1,2,4]triazolo[4,3-a]pyridine-7-carboxamide bis(trifluoroacetate) salt

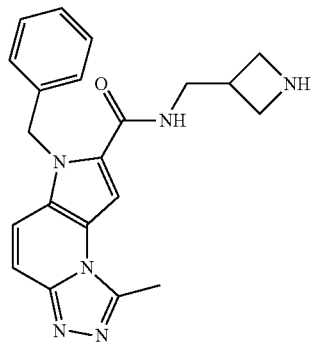 [SMILES: Cc1nnc2ccc3c(cc(C(=O)NCC4CNC4)n3Cc3ccccc3)n12]

The title compound was prepared according to the methods of Example 123, using tert-butyl 3-(aminomethyl)azetidine-1-carboxylate (0.025 g, 0.13 mmol, Astatech) in the coupling step. After completing an aqueous workup, the Boc protecting group was removed from the product by stirring with 1:1 TFA:DCM for 1 hour. Solvents were evaporated in vacuo. The final purification was performed according to the methods of Example 123. Yield: (6 mg, 20%).
1H NMR (500 MHz, d6-DMSO) δ 8.92 (t, J=5.8 Hz, 1H), 8.65 (br d, 2H), 7.98 (d, J=9.8 Hz, 1H), 7.77 (s, 1H), 7.60 (d, J=9.8 Hz, 1H), 7.31-7.26 (m, 2H), 7.26-7.20 (m, 1H), 7.14-

7.03 (m, 2H), 6.05 (s, 2H), 4.02-3.89 (m, 2H), 3.83-3.72 (m, 2H), 3.51 (t, J=6.3 Hz, 2H), 3.07-2.98 (m, 1H), 2.97 (s, 3H); LCMS (M+H)+: 375.2.

Example 125

6-Benzyl-N-isobutyl-1-methyl-6H-pyrrolo[2,3-e][1,2,4]triazolo[4,3-a]pyridine-7-carboxamide trifluoroacetate

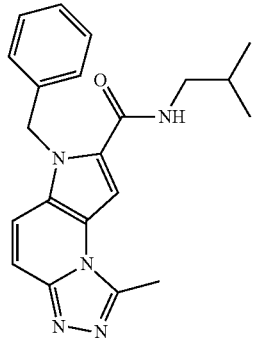 [SMILES: Cc1nnc2ccc3c(cc(C(=O)NCC(C)C)n3Cc3ccccc3)n12]

The title compound was prepared according to the methods of Example 123, using 2-methyl-1-propanamine (9.9 mg, 0.13 mmol, Aldrich). Yield: (4 mg, 20%).

1H NMR (500 MHz, d6-DMSO) δ 8.73 (t, J=5.9 Hz, 1H), 8.14 (d, J=9.8 Hz, 1H), 7.82 (s, 1H), 7.63 (d, J=9.8 Hz, 1H), 7.30-7.24 (m, 2H), 7.24-7.18 (m, 1H), 7.14-7.03 (m, 2H), 6.08 (s, 2H), 3.11 (t, J=6.5 Hz, 2H), 3.00 (s, 3H), 1.90-1.75 (m, 1H), 0.89 (d, J=6.7 Hz, 6H); LCMS (M+H)+: 362.2.

Example 126

6-Benzyl-1-methyl-N-(pyridin-4-ylmethyl)-6H-pyrrolo[2,3-e][1,2,4]triazolo[4,3-a]pyridine-7-carboxamide bis(trifluoroacetate) salt

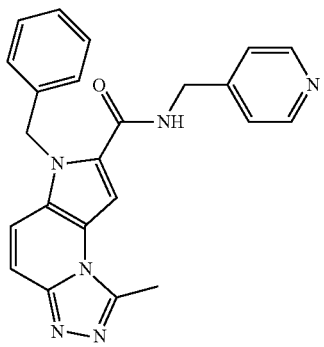 [SMILES: Cc1nnc2ccc3c(cc(C(=O)NCc4ccncc4)n3Cc3ccccc3)n12]

The title compound was prepared according to the methods of Example 123, using 4-(aminomethyl)pyridine (0.014 g, 0.13 mmol, Aldrich). Yield: (9 mg, 30%).

1H NMR (500 MHz, d6-DMSO) δ 9.48 (t, J=5.9 Hz, 1H), 8.71 (d, J=6.3 Hz, 2H), 8.05 (d, J=9.8 Hz, 1H), 7.93 (s, 1H), 7.68-7.59 (m, 3H), 7.32-7.20 (m, 3H), 7.10-7.02 (m, 2H), 6.05 (s, 2H), 4.67 (d, J=5.9 Hz, 2H), 2.99 (s, 3H); LCMS (M+H)+: 397.2.

Example 127

6-(3-Chlorobenzyl)-N-(3-hydroxypropyl)-1-methyl-6H-pyrrolo[2,3-e][1,2,4]triazolo[4,3-a]pyridine-7-carboxamide trifluoroacetate salt

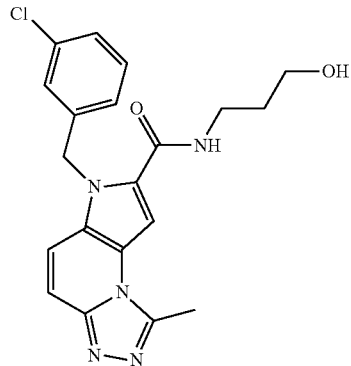 [SMILES: Cc1nnc2ccc3c(cc(C(=O)NCCCO)n3Cc3cccc(Cl)c3)n12]

To a suspension of 6-(3-chlorobenzyl)-1-methyl-6H-pyrrolo[2,3-e][1,2,4]triazolo[4,3-a]pyridine-7-carboxylic acid (0.004 g, 0.01 mmol, from Example 99, Step 4) in DMF (0.5 mL) was added N,N-diisopropylethylamine (0.014 mL, 0.078 mmol), followed by the addition of HATU (0.010 g, 0.026 mmol). After 1 minute, 3-amino-1-propanol (5.9 mg, 0.078 mmol, Aldrich) was added to the reaction mixture. The reaction mixture was diluted with MeCN and purified by preparative HPLC-MS (Waters SunFire C18, eluting with a gradient of MeCN/H2O containing 0.1% TFA). Yield: (4.8 mg, 70%).

1H NMR (500 MHz, d6-DMSO) δ 8.75 (t, J=5.7 Hz, 1H), 8.12 (d, J=9.8 Hz, 1H), 7.84 (s, 1H), 7.65 (d, J=9.8 Hz, 1H), 7.35-7.27 (m, 2H), 7.19 (s, 1H), 7.09-7.01 (m, 1H), 6.07 (s, 2H), 3.47 (t, J=6.3 Hz, 2H), 3.34 (app q, J=6.6 Hz, 2H), 2.99 (s, 3H), 1.70 (app p, J=6.5 Hz, 2H); LCMS (M+H)+: 398.1.

Example 128

N-(Azetidin-3-ylmethyl)-6-(3-chlorobenzyl)-1-methyl-6H-pyrrolo[2,3-e][1,2,4]triazolo[4,3-a]pyridine-7-carboxamide bis(trifluoroacetate) salt

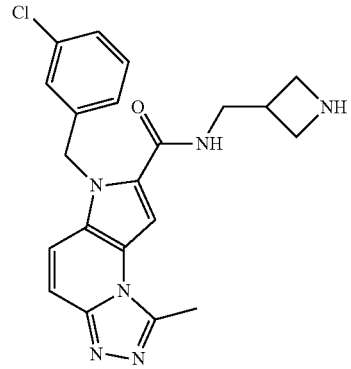 [SMILES: Cc1nnc2ccc3c(cc(C(=O)NCC4CNC4)n3Cc3cccc(Cl)c3)n12]

The title compound was prepared as in Example 127, using tert-butyl 3-(aminomethyl)azetidine-1-carboxylate (14 mg, 0.078 mmol, Astatech). After the coupling step was complete, the crude reaction mixture was diluted with water and the product was extracted with EtOAc. The combined organic layers were dried over sodium sulfate, filtered, and the solvent removed in vacuo. The crude residue was dissolved in 1:1 mixture of TFA:DCM and the resultant reaction mixture was stirred for 1 hour until the Boc group was removed. The title product was purified according to the methods of Example 127. Yield: (5.4 mg, 60%).

$^1$H NMR (500 MHz, $d_6$-DMSO) δ 8.93 (t, J=5.8 Hz, 1H), 8.63 (br s, 2H), 7.95 (d, J=9.9 Hz, 1H), 7.79 (s, 1H), 7.60 (d, J=9.8 Hz, 1H), 7.37-7.26 (m, 2H), 7.19 (s, 1H), 7.09-6.97 (m, 1H), 6.03 (s, 2H), 4.03-3.92 (m, 2H), 3.83-3.73 (m, 2H), 3.52 (t, J=6.3 Hz, 2H), 3.07-2.98 (m, 1H), 2.96 (s, 3H); LCMS (M+H)$^+$: 409.2.

Example 129

6-(3-Chlorobenzyl)-N-isobutyl-1-methyl-6H-pyrrolo[2,3-e][1,2,4]triazolo[4,3-a]pyridine-7-carboxamide trifluoroacetate salt

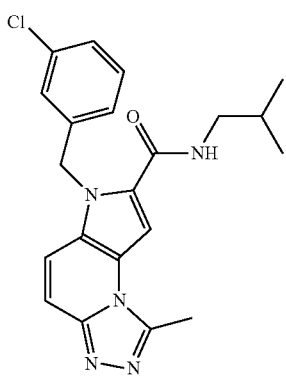 [SMILES: Cc1nnc2ccc3c(cc(C(=O)NCC(C)C)n3Cc3cccc(Cl)c3)n12]

The title compound was prepared according to the methods of Example 127, using 2-methyl-1-propanamine (5.7 mg, 0.078 mmol, Aldrich). Yield: (4.3 mg, 60%).

$^1$H NMR (500 MHz, $d_6$-DMSO) δ 8.76 (t, J=5.9 Hz, 1H), 8.19 (d, J=9.8 Hz, 1H), 7.85 (s, 1H), 7.67 (d, J=9.8 Hz, 1H), 7.35-7.27 (m, 2H), 7.17 (s, 1H), 7.09-7.02 (m, 1H), 6.07 (s, 2H), 3.11 (t, J=6.4 Hz, 2H), 3.01 (s, 3H), 1.84 (dp, J=13.3, 6.7 Hz, 1H), 0.89 (d, J=6.7 Hz, 6H); LCMS (M+H)$^+$: 396.1.

Example 130

6-(3-Chlorobenzyl)-1-methyl-N-(pyridin-4-ylmethyl)-6H-pyrrolo[2,3-e][1,2,4]triazolo[4,3-a]pyridine-7-carboxamide bis(trifluoroacetate) salt

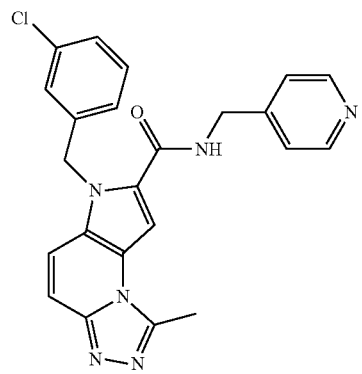 [SMILES: Cc1nnc2ccc3c(cc(C(=O)NCc4ccncc4)n3Cc3cccc(Cl)c3)n12]

The title compound was prepared according to the methods of Example 127, using 4-(aminomethyl)pyridine (8.5 mg, 0.078 mmol, Aldrich). Yield: (4.2 mg, 50%).

$^1$H NMR (500 MHz, $d_6$-DMSO) δ 9.49 (t, J=5.9 Hz, 1H), 8.70 (d, J=6.3 Hz, 2H), 8.03 (d, J=9.8 Hz, 1H), 7.95 (s, 1H), 7.67-7.60 (m, 3H), 7.34-7.28 (m, 2H), 7.14 (s, 1H), 7.03-6.98 (m, 1H), 6.04 (s, 2H), 4.66 (d, J=5.9 Hz, 2H), 2.99 (s, 3H); LCMS (M+H)$^+$: 431.1.

Example 131

6-[3-(Azetidin-1-ylmethyl)-5-chlorobenzyl]-N,1-dimethyl-6H-pyrrolo[2,3-e][1,2,4]triazolo[4,3-a]pyridine-7-carboxamide bis(trifluoroacetate) salt

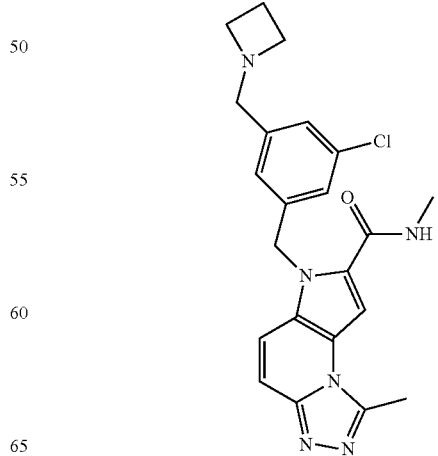

Step 1. Methyl 3-chloro-5-(hydroxymethyl)benzoate

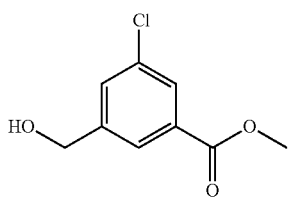

To a solution of dimethyl 5-chloroisophthalate (10.0 g, 43.7 mmol, Astatech) in methanol (50 mL) and methylene chloride (50 mL) at 0° C. was added sodium borohydride (5.5 g, 140 mmol, Aldrich). The reaction was allowed to gradually reach room temperature and stir for 1 hour. Additional portions of sodium borohydride (0.50 g, 13 mmol) were added at 2 hours and 3 hours. The reaction mixture was cooled to 0° C. and the reaction was quenched with water. The layers were separated and the aqueous layer was extracted with three portions of DCM. The combined organic extracts were dried over sodium sulfate, filtered and concentrated. The product was purified by flash chromatography, eluting with a gradient from 0-25% EtOAc in hexanes. Yield: (4.51 g, 51%).

$^1$H NMR (400 MHz, CDCl$_3$) δ 7.92-7.90 (m, 1H), 7.90-7.88 (m, 1H), 7.57-7.55 (m, 1H), 4.73 (s, 2H), 3.92 (s, 3H); LCMS (M+H)$^+$: 201.1203.1.

Step 2. [3-({[tert-Butyl(diphenyl)silyl]oxy}methyl)-5-chlorophenyl]methanol

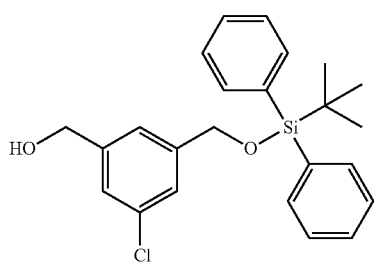 [SMILES: CC(C)(C)[Si](OCc1cc(Cl)cc(CO)c1)(c1ccccc1)c1ccccc1]

To a solution of methyl 3-chloro-5-(hydroxymethyl)benzoate (4.51 g, 22.5 mmol, from Step 1) in methylene chloride (60 mL) was added 1H-imidazole (1.61 g, 23.6 mmol), followed by the addition of tert-butylchlorodiphenylsilane (6.14 mL, 23.6 mmol) and 4-dimethylaminopyridine (0.27 g, 2.2 mmol). The reaction mixture was stirred for 3 hours, transferred to a reparatory funnel and washed with water. The aqueous layer was extracted with three portions of EtOAc and the extracts were combined with the original DCM layer. The combined organic extracts were washed with water, followed by brine, dried over sodium sulfate, filtered and concentrated. The intermediate ester was used without further purification in the following reduction reaction.

The intermediate ester was dissolved in toluene (60 mL) and DCM (20 mL) and the reaction mixture was cooled to −40° C. 1.0 M solution of diisobutylaluminum hydride in toluene (45 mL, 45 mmol, Aldrich) was added dropwise. After complete addition, cooling bath was removed and the reaction was allowed to warm to room temperature. The reaction was cooled again to −40° C. and additional 1.0 M diisobutylaluminum hydride in DCM (45 mL, 45 mmol) was added. Upon completion of the second addition, the cooling bath was removed and the reaction was allowed to warm to room temperature. The reaction was quenched by the addition of a solution of Rochelle's salt and the resulting mixture was stirred overnight. The layers were separated, and the aqueous layer was extracted with two further portions of DCM. The combined organic extracts were dried over sodium sulfate, filtered and concentrated. The product was purified by flash chromatography, eluting with a gradient from 0-50% EtOAc in hexanes. Yield: (7.86 g, 85%).

$^1$H NMR (400 MHz, CDCl$_3$) δ 7.70-7.64 (m, 4H), 7.47-7.35 (m, 6H), 7.28-7.26 (m, 1H), 7.26-7.23 (m, 1H), 7.15-7.12 (m, 1H), 4.72 (s, 2H), 4.65 (d, J=5.9 Hz, 2H), 1.09 (s, 9H); LCMS (M+Na)$^+$: 433.3.

Step 3. 3-({[tert-butyl(diphenyl)silyl]oxy}methyl)-5-chlorobenzyl methanesulfonate

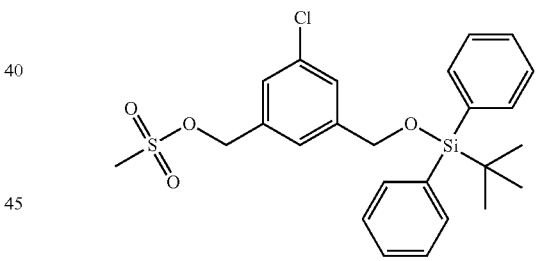

Triethylamine (7.8 mL, 56 mmol) and methanesulfonyl chloride (2.9 mL, 37 mmol) were added to a solution of [3-({[tert-butyl(diphenyl)silyl]oxy}methyl)-5-chlorophenyl]methanol (7.65 g, 18.6 mmol, from Step 2) in DCM (50 mL) at 0° C. The cooling bath was removed and after reaction mixture warmed to room temperature, the reaction mixture was diluted with DCM and washed with water. The aqueous layer was extracted with two further portions of DCM. The combined organic extracts were washed with brine, dried over sodium sulfate, filtered and concentrated. The product was purified by flash chromatography, eluting with a gradient from 0-40% EtOAc/hexanes. Yield: (6.8 g, 75%).

¹H NMR (400 MHz, CDCl₃) δ 7.69-7.64 (m, 4H), 7.47-7.36 (m, 6H), 7.36-7.34 (m, 1H), 7.29-7.27 (m, 1H), 7.22-7.20 (m, 1H), 5.17 (s, 2H), 4.73 (s, 2H), 2.96 (s, 3H), 1.10 (s, 9H).

Step 4. 3-({[tert-butyl(diphenyl)silyl]oxy}methyl)-5-chlorobenzyl 1-[3-({[tert-butyl(diphenyl)silyl]oxy}methyl)-5-chlorobenzyl]-5-chloro-1H-pyrrolo[3,2-b]pyridine-2-carboxylate

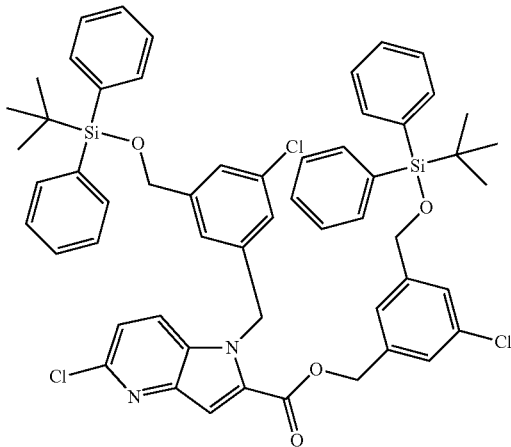 [SMILES: CC(C)(C)[Si](OCc1cc(Cl)cc(COC(=O)c2cc3nc(Cl)ccc3n2Cc2cc(Cl)cc(CO[Si](c3ccccc3)(c3ccccc3)C(C)(C)C)c2)c1)(c1ccccc1)c1ccccc1]

5-Chloro-1H-pyrrolo[3,2-b]pyridine-2-carboxylic acid (0.645 g, 3.28 mmol, from Example 99, Step 1) and Cs₂CO₃ (3.2 g, 9.8 mmol) were added to a solution of 3-({[tert-butyl(diphenyl)silyl]oxy}methyl)-5-chlorobenzyl methanesulfonate (3.88 g, 7.93 mmol, from Step 3) in DMF (13 mL). Concurrently, a separate batch of 5-chloro-1H-pyrrolo[3,2-b]pyridine-2-carboxylic acid (0.558 g, 2.81 mmol) was treated with the same reagents under the same conditions. After stirring each reaction overnight, the reactions were combined, diluted with water and extracted with three portions of EtOAc. The combined organic extracts were washed sequentially with water and brine, dried over sodium sulfate, filtered and concentrated. The product was purified by flash chromatography, eluting with a gradient from 0-50% EtOAc in hexanes. Yield: (3.11 g, 52%).

¹H NMR (400 MHz, CDCl₃) δ 7.69-7.62 (m, 4H), 7.60-7.53 (m, 5H), 7.50-7.18 (m, 16H), 7.18-7.15 (m, 1H), 7.15-7.10 (m, 1H), 6.96-6.92 (m, 1H), 6.81-6.79 (m, 1H), 5.77 (s, 2H), 5.27 (s, 2H), 4.71 (s, 2H), 4.59 (s, 2H), 1.08 (s, 9H), 0.98 (s, 9H); LCMS (M+H)⁺: 983.3.

Step 5. Di-tert-butyl 1-[1-[3-({[tert-butyl(diphenyl)silyl]oxy}methyl)-5-chlorobenzyl]-2-({[3-({[tert-butyl(diphenyl)silyl]oxy}methyl)-5-chlorobenzyl]oxy}carbonyl)-1H-pyrrolo[3,2-b]pyridin-5-yl]hydrazine-1,2-dicarboxylate A degassed mixture of 3-({[tert-butyl(diphenyl)silyl]oxy}methyl)-5-chlorobenzyl 1-[3-({[tert-butyl(diphenyl)silyl]oxy}methyl)-5-chlorobenzyl]-5-chloro-1H-pyrrolo[3,2-b]pyridine-2-carboxylate (3.11 g, 3.16 mmol, from Step 4), di-tert-butyl hydrazine-1,2-dicarboxylate (0.81 g, 3.5 mmol, Aldrich), dicyclohexyl(2',4',6'-triisopropylbiphenyl-2-yl)phosphine-(2'-aminobiphenyl-2-yl)(chloro)palladium (1:1) (0.29 g, 0.37 mmol, Aldrich) and Cs₂CO₃ (1.1 g, 3.5 mmol) in toluene (36 mL) was sealed and heated at 110° C. for 4 hours. The reaction mixture was partitioned between water and ethyl acetate and the aqueous was extracted three times. The combined organic extracts were dried over sodium sulfate, filtered and concentrated. The product was purified by flash chromatography, eluting with a gradient from 0-25% EtOAc in hexanes. Yield: (1.19 g, 32%).

LCMS (M+H)⁺: 1179.2.

Step 6. 3-({[tert-butyl(diphenyl)silyl]oxy}methyl)-5-chlorobenzyl 6-[3-({[tert-butyl(diphenyl)silyl]oxy}methyl)-5-chlorobenzyl]-1-methyl-6H-pyrrolo[2,3-e][1,2,4]triazolo[4,3-a]pyridine-7-carboxylate A solution of di-tert-butyl 1-[1-[3-({[tert-butyl(diphenyl)silyl]oxy}methyl)-5-chlorobenzyl]-2-({[3-({[tert-butyl(diphenyl)silyl]oxy}methyl)-5-chlorobenzyl]oxy}carbonyl)-1H-pyrrolo[3,2-b]pyridin-5-yl]hydrazine-1,2-dicarboxylate (1.19 g, 1.01 mmol, from Step 5) in acetic acid (40 mL) was partitioned equally into four microwavable vials. Each was heated to 180° C. in the microwave for 5 minutes. The batches were combined and the acetic acid was removed in vacuo. An additional NaHCO₃ solution was added and the product was extracted with EtOAc. The combined organic extracts were dried over sodium sulfate, filtered and concentrated. The product was used without further purification. Yield: (0.75 g, 74%).

¹H NMR (400 MHz, CDCl₃) δ 7.70-7.24 (m, 25H), 7.23-7.20 (m, 1H), 7.15-7.12 (m, 1H), 6.98-6.94 (m, 1H), 6.83-6.79 (m, 1H), 5.87 (s, 2H), 5.28 (s, 2H), 4.73 (s, 2H), 4.61 (s, 2H), 2.93 (s, 3H), 1.08 (s, 9H), 0.94 (s, 9H); LCMS (M+H)⁺: 1001.11003.1.

Step 7. 3-Chloro-5-formylbenzyl 6-(3-chloro-5-formylbenzyl)-1-methyl-6H-pyrrolo[2,3-e][1,2,4]triazolo[4,3-a]pyridine-7-carboxylate

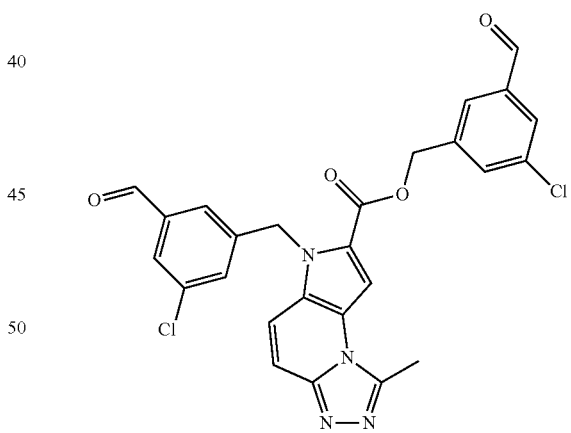

Acetic acid (0.041 mL, 0.72 mmol) and 1.0 M solution of TBAF in THF (0.79 mL, 0.79 mmol, Aldrich) were added to a solution of 3-({[tert-butyl(diphenyl)silyl]oxy}methyl)-5-chlorobenzyl 6-[3-({[tert-butyl(diphenyl)silyl]oxy}methyl)-5-chlorobenzyl]-1-methyl-6H-pyrrolo[2,3-e][1,2,4]triazolo[4,3-c]pyridine-7-carboxylate (0.36 g, 0.36 mmol, from Step 1) in THF (20 mL). After stirring for 3 hours, the reaction was poured into pH7 buffer and extracted with three portions of EtOAc. The combined organic extracts were dried over Na₂SO₄, filtered and concentrated.

Manganese (IV) oxide (0.2 g, 2 mmol, Aldrich) was added to a DCM (20 mL) solution of the bis-alcohol intermediate.

After stirring overnight, additional manganese (IV) oxide was added (total of 1.3 g, 15 mmol, in three portions over 4.5 hours) to drive the reaction to completion. The reaction mixture was diluted with further DCM, and Celite was added into the reaction, which was then swirled and allowed to settle. The mixture was filtered through a well-packed pad of Celite and rinsed with several portions of DCM. The filtrate was dried over sodium sulfate, and filtered, and the solvent was removed in vacuo. The product was purified by flash chromatography, eluting with a gradient from 0-10% MeOH in DCM. Yield: (70 mg, 37%).

$^1$H NMR (400 MHz, CDCl$_3$) δ 9.98 (s, 1H), 9.88 (s, 1H), 7.85-7.83 (m, 1H), 7.82-7.79 (m, 1H), 7.76-7.73 (m, 1H), 7.66-7.64 (m, 1H), 7.62 (d, J=9.9 Hz, 1H), 7.58 (d, J=0.5 Hz, 1H), 7.42-7.39 (m, 1H), 7.30 (dd, J=9.9, 0.5 Hz, 1H), 7.25-7.22 (m, 1H), 5.94 (s, 2H), 5.38 (s, 2H), 3.03 (s, 3H); LCMS (M+H)$^+$: 521.0523.0.

Step 8. 3-(Azetidin-1-ylmethyl)-5-chlorobenzyl 6-[3-(azetidin-1-ylmethyl)-5-chlorobenzyl]-1-methyl-6H-pyrrolo[2,3-e][1,2,4]triazolo[4,3-a]pyridine-7-carboxylate tris(trifluoroacetate) salt

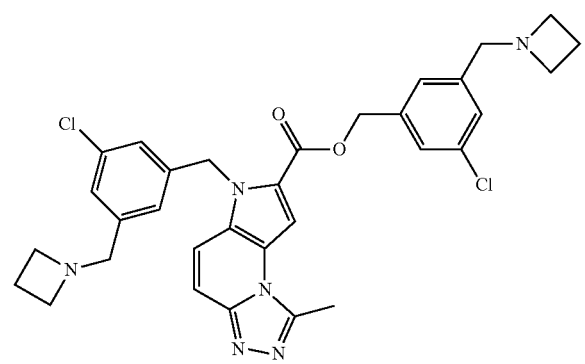 [SMILES: Cc1nnc2ccc3c(cc(C(=O)OCc4cc(Cl)cc(CN5CCC5)c4)n3Cc3cc(Cl)cc(CN4CCC4)c3)n12]

Sodium triacetoxyborohydride (0.2 g, 1 mmol, Aldrich) was added to a mixture of 3-chloro-5-formylbenzyl 6-(3-chloro-5-formylbenzyl)-1-methyl-6H-pyrrolo[2,3-e][1,2,4]triazolo[4,3-a]pyridine-7-carboxylate (0.070 g, 0.13 mmol, from Step 7) and azetidine (0.08 mL, 1 mmol, Aldrich) in DCM (4 mL). After 2 hours, additional azetidine (0.020 mL, 0.30 mmol) and sodium triacetoxyborohydride (0.050 g, 0.24 mmol) were added and the reaction was continued for 30 minutes. Solvent was removed in vacuo, the crude residue was dissolved in MeCN and water, filtered and purified by preparative HPLC-MS (Waters SunFire C18, eluting with a gradient of MeCN/H$_2$O containing 0.1% TFA). Yield: (80 mg, 63%).

$^1$H NMR (400 MHz, CD$_3$OD) δ 8.30 (d, J=9.8 Hz, 1H), 7.92 (s, 1H), 7.78 (d, J=9.8 Hz, 1H), 7.58-7.54 (m, 1H), 7.54-7.49 (m, 2H), 7.45-7.38 (m, 1H), 7.17-7.11 (m, 2H), 6.09 (s, 2H), 5.41 (s, 2H), 4.39 (s, 2H), 4.28 (s, 2H), 4.24-3.97 (m, 8H), 3.13 (s, 3H), 2.64-2.33 (m, 4H); LCMS (M+H)$^+$: 603.3.

Step 9. 6-[3-(Azetidin-1-ylmethyl)-5-chlorobenzyl]-1-methyl-6H-pyrrolo[2,3-e][1,2,4]triazolo[4,3-a]pyridine-7-carboxylic acid

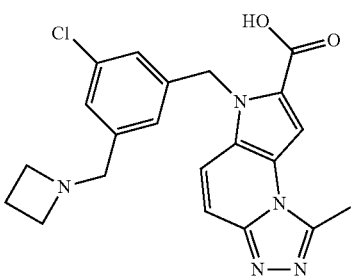 [SMILES: Cc1nnc2ccc3c(cc(C(=O)O)n3Cc3cc(Cl)cc(CN4CCC4)c3)n12]

3-(Azetidin-1-ylmethyl)-5-chlorobenzyl 6-[3-(azetidin-1-ylmethyl)-5-chlorobenzyl]-1-methyl-6H-pyrrolo[2,3-e][1,2,4]triazolo[4,3-a]pyridine-7-carboxylate trifluoroacetate salt (0.080 g, 0.085 mmol, from Step 8) in THF (2 mL) was treated with 1.0 M solution of NaOH in water (2 mL, 2 mmol). After 1 hour, MeCN and MeOH were added to make the reaction monophasic, and the product was purified by preparative HPLC-MS (Waters XBridge C18, eluting with a gradient of MeCN/H$_2$O containing 0.15% NH$_4$OH). Yield: (35 mg, 100%).

LCMS (M+H)$^+$: 410.2.

Step 10. 6-[3-(Azetidin-1-ylmethyl)-5-chlorobenzyl]-N,1-dimethyl-6H-pyrrolo[2,3-e][1,2,4]triazolo[4,3-a]pyridine-7-carboxamide bis(trifluoroacetate) salt To a solution of 6-[3-(azetidin-1-ylmethyl)-5-chlorobenzyl]-1-methyl-6H-pyrrolo[2,3-e][1,2,4]triazolo[4,3-a]pyridine-7-carboxylic acid (0.035 g, 0.085 mmol, from Step 9) in NMP (2 mL) was added N,N-diisopropylethylamine (0.059 mL, 0.34 mmol), methylamine hydrochloride (9.9 mg, 0.15 mmol, Alfa Aesar) and HATU (0.042 g, 0.11 mmol). After 30 minutes, the reaction was complete, and the reaction mixture was diluted with MeCN and a small amount of TFA. The product was purified by preparative HPLC-MS (Waters SunFire C18, Sum 30×100 mm, H$_2$O (0.1% TFA) MeOH @ 60 mL/min). Yield: (0.01 g, 30%).

$^1$H NMR (400 MHz, CD$_3$OD) δ 8.04 (d, J=9.6 Hz, 1H), 7.76 (s, 1H), 7.59 (d, J=9.7 Hz, 1H), 7.43-7.39 (m, 1H), 7.22-7.19 (m, 1H), 7.19-7.16 (m, 1H), 6.06 (s, 2H), 4.29 (s,

2H), 4.19-4.00 (m, 4H), 3.08 (s, 3H), 2.92 (s, 3H), 2.61-2.32 (m, 2H); LCMS (M+H)+: 423.2.

Example 132

6-[3-Chloro-5-(pyrrolidin-1-ylmethyl)benzyl]-N,1-dimethyl-6H-pyrrolo[2,3-e][1,2,4]triazolo[4,3-a]pyridine-7-carboxamide 2.5 x (trifluoroacetate) salt

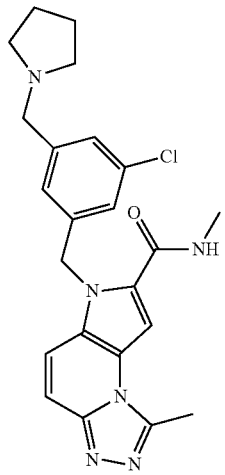 [SMILES: CNC(=O)c1cc2c(ccc3nnc(C)n32)n1Cc1cc(Cl)cc(CN2CCCC2)c1]

Step 1. 6-[3-Chloro-5-(pyrrolidin-1-ylmethyl)benzyl]-1-methyl-6H-pyrrolo[2,3-e][1,2,4]triazolo[4,3-a]pyridine-7-carboxylic acid

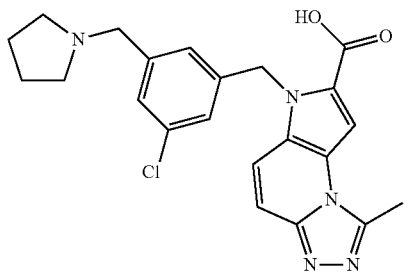 [SMILES: Cc1nnc2ccc3c(cc(C(=O)O)n3Cc3cc(Cl)cc(CN4CCCC4)c3)n12]

3-Chloro-5-formylbenzyl 6-(3-chloro-5-formylbenzyl)-1-methyl-6H-pyrrolo[2,3-e][1,2,4]triazolo[4,3-a]pyridine-7-carboxylate (0.035 g, 0.067 mmol, from Example 131, Step 7) was suspended in DCM (4 mL) and pyrrolidine (0.03 g, 0.4 mmol, Aldrich) and sodium triacetoxyborohydride (0.2 g, 0.8 mmol, Aldrich) were added. After stirring overnight, the reaction mixture was made basic by the addition of 1N solution of NaOH, and the product was extracted with EtOAc. The organic extract was dried over sodium sulfate, filtered and concentrated. The crude product was stirred with 1.0 M solution of NaOH (2 mL, 2 mmol) and THF (2 mL) for 1.5 hours. The product was purified by preparative HPLC-MS (Waters XBridge C18, eluting with a gradient of MeCN/H₂O containing 0.15% NH₄OH). Yield: (5 mg, 18%). LCMS (M+H)+: 424.2.

Step 2. 6-[3-Chloro-5-(pyrrolidin-1-ylmethyl)benzyl]-N,1-dimethyl-6H-pyrrolo[2,3-e][1,2,4]triazolo[4,3-a]pyridine-7-carboxamide 2.5 x (trifluoroacetate) salt N,N-Diisopropylethylamine (0.025 mL, 0.14 mmol), methylamine hydrochloride (0.0071 g, 0.10 mmol, Alfa Aesar) and HATU (0.011 g, 0.028 mmol) were added to a solution of 6-[3-chloro-5-(pyrrolidin-1-ylmethyl)benzyl]-1-methyl-6H-pyrrolo[2,3-e][1,2,4]triazolo[4,3-a]pyridine-7-carboxylic acid (0.006 g, 0.01 mmol, from Step 1) in NMP (2 mL). The reaction mixture was stirred for 30 min and was diluted with MeCN. The product was purified by preparative HPLC-MS (Waters SunFire C18, eluting with a gradient of MeCN/H₂O containing 0.1% TFA). Yield: (7 mg, 100%).

¹H NMR (300 MHz, CD₃OD) δ 8.09 (d, J=9.8 Hz, 1H), 7.77 (s, 1H), 7.61 (d, J=9.8 Hz, 1H), 7.49-7.44 (m, 1H), 7.26-7.22 (m, 1H), 7.22-7.16 (m, 1H), 6.07 (s, 2H), 4.31 (s, 2H), 3.52-3.35 (m, 2H), 3.18-3.02 (m, 2H), 3.08 (s, 3H), 2.91 (s, 3H), 2.25-1.88 (m, 4H); LCMS (M+H)+: 437.1.

Example 133

6-[3-Chloro-5-(pyrrolidin-1-ylmethyl)benzyl]-N-ethyl-1-methyl-6H-pyrrolo[2,3-e][1,2,4]triazolo[4,3-a]pyridine-7-carboxamide bis(trifluoroacetate) salt

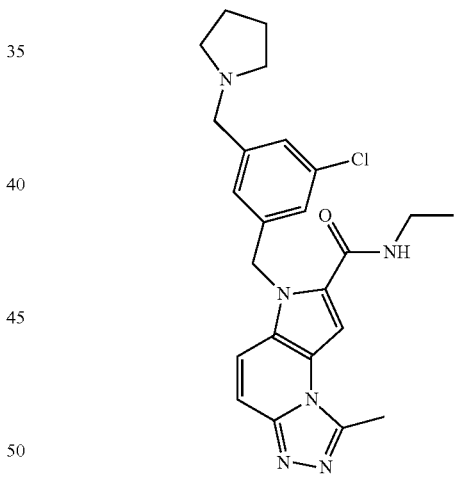

The title compound was prepared according to the methods of Example 132, Step 2, using 6-[3-chloro-5-(pyrrolidin-1-ylmethyl)benzyl]-1-methyl-6H-pyrrolo[2,3-e][1,2,4]triazolo[4,3-a]pyridine-7-carboxylic acid (0.015 g, 0.035 mmol, from Example 132, Step 1), N,N-diisopropylethylamine (0.031 mL, 0.18 mmol), ethylamine hydrochloride (0.014 g, 0.18 mmol, Aldrich), HATU (0.014 g, 0.037 mmol), and NMP (3 mL). Yield: (6 mg, 25%).

¹H NMR (400 MHz, CD₃OD) δ 8.07 (d, J=9.8 Hz, 1H), 7.79 (s, 1H), 7.60 (d, J=9.8 Hz, 1H), 7.49-7.46 (m, 1H), 7.29-7.26 (m, 1H), 7.19-7.14 (m, 1H), 6.06 (s, 2H), 4.32 (s, 2H), 3.51-3.42 (br m, 2H), 3.40 (q, J=7.2 Hz, 2H), 3.18-3.09 (br m, 2H), 3.09 (s, 3H), 2.22-2.07 (br m, 2H), 2.05-1.89 (br m, 2H), 1.23 (t, J=7.3 Hz, 3H); LCMS (M+H)+: 451.3.

Example 134

6-{3-Chloro-5-[(3,3-difluoropyrrolidin-1-yl)methyl]benzyl}-N,1-dimethyl-6H-pyrrolo[2,3-e][1,2,4]triazolo[4,3-a]pyridine-7-carboxamide 2.4 x (trifluoroacetate) salt

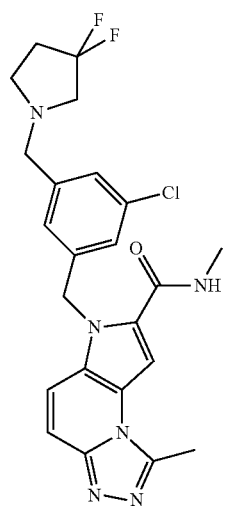 [SMILES: CNC(=O)c1cc2c(ccc3nnc(C)n32)n1Cc1cc(Cl)cc(CN2CCC(F)(F)C2)c1]

The title compound was prepared according to the methods of Example 132, Steps 1 and 2, using 3,3-difluoropyrrolidine hydrochloride (55 mg, 0.38 mmol, Synthonix) and N,N-diisopropylethylamine (0.067 mL, 0.38 mmol) in Step 1. Yield: (10 mg, 20% over the two steps).

$^1$H NMR (300 MHz, CD$_3$OD) δ 8.16 (d, J=9.8 Hz, 1H), 7.78 (s, 1H), 7.63 (d, J=9.8 Hz, 1H), 7.46-7.40 (m, 1H), 7.24-7.20 (m, 1H), 7.18-7.13 (m, 1H), 6.07 (s, 2H), 4.19 (s, 2H), 3.54 (t, J=12.0 Hz, 2H), 3.39 (t, J=7.5 Hz, 2H), 3.10 (s, 3H), 2.92 (s, 3H), 2.53 (tt, J=14.3, 7.4 Hz, 2H); $^{19}$F NMR (282 MHz, CD$_3$OD) δ −77.61 (s, 7.2 F), −94.75-97.06 (m, 2F); LCMS (M+H)$^+$: 473.1.

Example 135

6-{3-Chloro-5-[(3,3-dimethylazetidin-1-yl)methyl]benzyl}-N,1-dimethyl-6H-pyrrolo[2,3-e][1,2,4]triazolo[4,3-a]pyridine-7-carboxamide bis(trifluoroacetate) salt

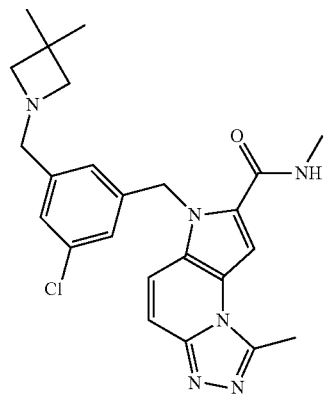 [SMILES: CNC(=O)c1cc2c(ccc3nnc(C)n32)n1Cc1cc(Cl)cc(CN2CC(C)(C)C2)c1]

The title compound was prepared according to the methods of Example 132, Steps 1 and 2, using 3,3-dimethylazetidine hydrochloride (0.066 g, 0.55 mmol, Synthonix) and N,N-diisopropylethylamine (0.095 mL, 0.55 mmol) in Step 1. Yield: (15 mg, 23% over the two steps).

$^1$H NMR (400 MHz, CD$_3$OD) δ 8.03 (d, J=9.7 Hz, 1H), 7.75 (s, 1H), 7.59 (d, J=9.8 Hz, 1H), 7.45-7.41 (m, 1H), 7.27-7.23 (m, 1H), 7.17-7.12 (m, 1H), 6.06 (s, 2H), 4.31 (s, 2H), 3.96-3.76 (m, 4H), 3.08 (s, 3H), 2.92 (s, 3H), 1.36 (s, 3H), 1.31 (s, 3H); LCMS (M+H)$^+$: 451.2.

Example 136

N,1-dimethyl-6-[3-(trifluoromethyl)benzyl]-6H-pyrrolo[2,3-e][1,2,4]triazolo[4,3-a]pyridine-7-carboxamide trifluoroacetate salt

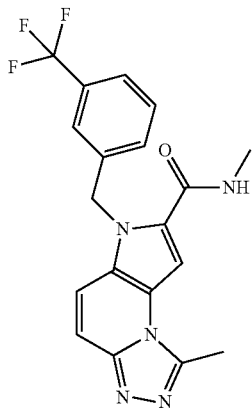 [SMILES: CNC(=O)c1cc2c(ccc3nnc(C)n32)n1Cc1cccc(C(F)(F)F)c1]

Step 1. 3-(Trifluoromethyl)benzyl 5-chloro-1-[3-(trifluoromethyl)benzyl]-1H-pyrrolo[3,2-b]pyridine-2-carboxylate

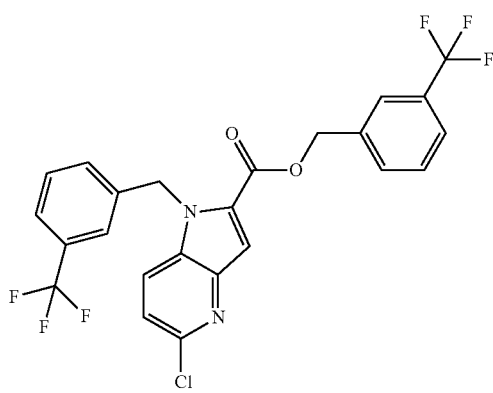 [SMILES: O=C(OCc1cccc(C(F)(F)F)c1)c1cc2nc(Cl)ccc2n1Cc1cccc(C(F)(F)F)c1]

5-Chloro-1H-pyrrolo[3,2-b]pyridine-2-carboxylic acid (0.250 g, 1.27 mmol, from Example 99, Step 1) in DMF (6 mL) was treated with $Cs_2CO_3$ (1.6 g, 5.1 mmol) and 1-(bromomethyl)-3-(trifluoromethyl)benzene (0.39 mL, 2.5 mmol, Aldrich). After stirring overnight, additional 1-(bromomethyl)-3-(trifluoromethyl)benzene (0.21 mL, 1.4 mmol) was added and stirring continued for an additional 24 hours. Water was added and the product was extracted with three portions of EtOAc. The extract was washed sequentially with water and brine, dried over sodium sulfate, filtered and concentrated. The product was used without further purification in Step 2.

LCMS (M+H)⁺: 513.0515.0.

Step 2. Di-tert-butyl 1-[1-[3-(trifluoromethyl)benzyl]-2-({[3-(trifluoromethyl)benzyl]oxy}carbonyl)-1H-pyrrolo[3,2-b]pyridin-5-yl]hydrazine-1,2-dicarboxylate

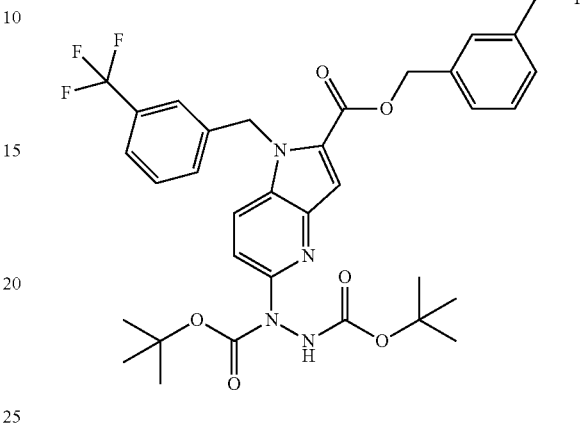

A degassed mixture of 3-(trifluoromethyl)benzyl 5-chloro-1-[3-(trifluoromethyl)benzyl]-1H-pyrrolo[3,2-b]pyridine-2-carboxylate (3.2 g, 6.2 mmol, prepared as in Step 1), di-tert-butyl hydrazine-1,2-dicarboxylate (1.6 g, 6.9 mmol, Aldrich), dicyclohexyl(2',4',6'-triisopropylbiphenyl-2-yl)phosphine-(2'-aminobiphenyl-2-yl)(chloro)palladium (1:1) (0.58 g, 0.74 mmol, Aldrich) and $Cs_2CO_3$ (2.2 g, 6.9 mmol) in toluene (71 mL) was heated at 110° C. for 2 hours. Upon cooling, water was added, and the layers were separated. The aqueous layer was further extracted with three portions of EtOAc. The combined organic extracts were dried over sodium sulfate, filtered and concentrated. Flash chromatography, eluting with a gradient from 0-50% EtOAc in hexanes was used to purify the product. Yield: (0.28 g, 6% over the two steps). LCMS (M+H)⁺: 709.1.

Step 3. 1-Methyl-6-[3-(trifluoromethyl)benzyl]-6H-pyrrolo[2,3-e][1,2,4]triazolo[4,3-a]pyridine-7-carboxylic acid

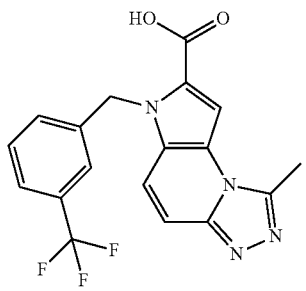 [SMILES: Cc1nnc2ccc3c(cc(C(=O)O)n3Cc3cccc(C(F)(F)F)c3)n12]

Di-tert-butyl 1-[1-[3-(trifluoromethyl)benzyl]-2-({[3-(trifluoromethyl)benzyl]oxy}carbonyl)-1H-pyrrolo[3,2-b]pyridin-5-yl]hydrazine-1,2-dicarboxylate (0.28 g, 0.40 mmol, from Step 2) in acetic acid (10 mL) was heated to 180° C. in the microwave for 5 minutes. The acetic acid was then removed in vacuo. The residue was dissolved in THF (10 mL)

and 1.0 M NaOH (10 mL, 10 mmol) was added. After stirring for 20 minutes, MeOH was added to make the mixture monophasic and the product was purified by preparative HPLC-MS (Waters XBridge C18, eluting with a gradient of MeCN/H₂O containing 0.15% NH₄OH). Yield: 45 mg, 30%.

LCMS (M+H)⁺: 375.3.

Step 4. N,1-Dimethyl-6-[3-(trifluoromethyl)benzyl]-6H-pyrrolo[2,3-e][1,2,4]triazolo[4,3-a]pyridine-7-carboxamide trifluoroacetate salt To a solution of 1-methyl-6-[3-(trifluoromethyl)benzyl]-6H-pyrrolo[2,3-e][1,2,4]triazolo[4,3-a]pyridine-7-carboxylic acid (0.022 g, 0.059 mmol, from Step 3) in NMP (2 mL) was added N,N-diisopropylethylamine (0.051 mL, 0.29 mmol), methylamine hydrochloride (0.020 g, 0.29 mmol, Alfa Aesar) followed by HATU (0.027 g, 0.070 mmol). The product was purified by preparative HPLC-MS (Waters SunFire C18, eluting with a gradient of MeOH/H₂O containing 0.1% TFA). Yield: 7 mg, 20%.

¹H NMR (400 MHz, CD₃OD) δ 7.99 (d, J=9.8 Hz, 1H), 7.69 (s, 1H), 7.56 (d, J=7.8 Hz, 1H), 7.54 (d, J=9.9 Hz, 1H), 7.52-7.45 (m, 2H), 7.36 (d, J=7.5 Hz, 1H), 6.12 (s, 2H), 3.05 (s, 3H), 2.92 (s, 3H); LCMS (M+H)⁺: 388.1.

Example 137

N-Ethyl-1-methyl-6-[3-(trifluoromethyl)benzyl]-6H-pyrrolo[2,3-e][1,2,4]triazolo[4,3-a]pyridine-7-carboxamide trifluoroacetate salt

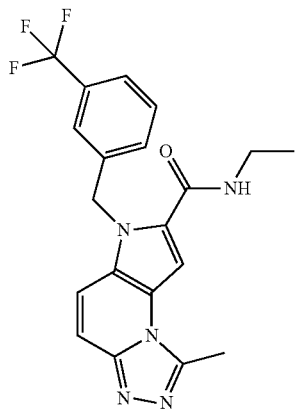 [SMILES: CCNC(=O)c1cc2c(ccc3nnc(C)n32)n1Cc1cccc(C(F)(F)F)c1]

The title compound was prepared according to the methods of Example 136, using ethylamine hydrochloride (0.024 g, 0.29 mmol, Aldrich). Yield: (0.01 g, 30%).

¹H NMR (400 MHz, CD₃OD) δ 8.23 (d, J=9.7 Hz, 1H), 7.77 (d, J=0.6 Hz, 1H), 7.63 (d, J=9.8 Hz, 1H), 7.57 (d, J=7.9 Hz, 1H), 7.53-7.45 (m, 2H), 7.39 (d, J=7.7 Hz, 1H), 6.15 (s, 2H), 3.41 (q, J=7.3 Hz, 2H), 3.10 (s, 3H), 1.22 (t, J=7.3 Hz, 3H); LCMS (M+H)⁺: 402.2.

Example 138

6-Benzyl-1-methyl-7-(trifluoromethyl)-6H-pyrrolo[2,3-e][1,2,4]triazolo[4,3-a]pyridine trifluoroacetate salt

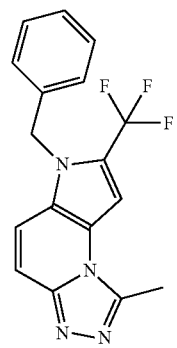 [SMILES: Cc1nnc2ccc3c(cc(C(F)(F)F)n3Cc3ccccc3)n12]

Step 1. tert-butyl (6-chloro-2-methylpyridin-3-yl)carbamate

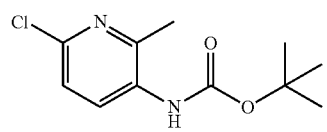 [SMILES: Cc1nc(Cl)ccc1NC(=O)OC(C)(C)C]

To 6-chloro-2-methylpyridin-3-amine (9.50 g, 66.6 mmol, Matrix) and di-tert-butyldicarbonate (14 g, 67 mmol, Aldrich) in THF (280 mL) at −20° C. was added dropwise 1.0 M LHMDS (lithium bis(trimethylsilyl)amide) in THF (67 mL, 67 mmol, Aldrich). After 45 minutes, additional di-tert-butyldicarbonate (14 g, 67 mmol) and 1.0 M LHMDS in THF (67 mL, 67 mmol) were introduced. After 45 minutes, additional 1.0 M LHMDS in THF (20.0 mL, 20.0 mmol) was added and the reaction was complete after 1 hour. Water was added, the layers were separated, and the aqueous layer was further extracted with three portions of ethyl acetate. The combined organic extracts were dried over sodium sulfate, filtered and concentrated. The crude product was treated with 1.0 M NaOH in water (200 mL, 200 mmol) in 2:1 THF/MeOH (300 mL). Additional solid NaOH (11 g, 270 mmol) was added and the reaction was stirred overnight. Volatile solvents were removed in vacuo. The product was extracted from the remaining aqueous mixture using EtOAc. The combined organic extracts were washed sequentially with water and brine, dried over sodium sulfate, filtered and concentrated. The product was purified via flash chromatography, eluting with a gradient from 0-50% EtOAc in hexanes. Yield: (15.4 g, 95%).

$^1$H NMR (400 MHz, CDCl$_3$) δ 8.16 (br s, 1H), 7.14 (d, J=8.6 Hz, 1H), 6.32 (s, 1H), 2.46 (s, 3H), 1.51 (s, 6H); LCMS (M+H)$^+$: 243.1245.1.

Step 2. 5-Chloro-1-(phenylsulfonyl)-2-(trifluoromethyl)-1H-pyrrolo[3,2-b]pyridine

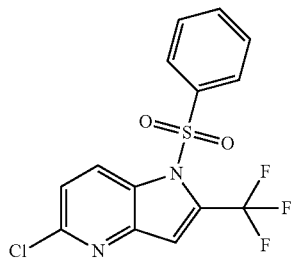 [SMILES: O=S(=O)(c1ccccc1)n1c(C(F)(F)F)cc2nc(Cl)ccc21]

To a solution of tert-butyl (6-chloro-2-methylpyridin-3-yl) carbamate (7.00 g, 28.8 mmol, from Step 1) in THF (100 mL) at −78° C. was added 1.3 M sec-butyllithium in cyclohexane (46.6 mL, 60.6 mmol, Pfaltz and Bauer). After 15 minutes, ethyl trifluoroacetate (4.12 mL, 34.6 mmol, Aldrich) in THF (60 mL) was introduced. After 30 min, the reaction was poured into 1N HCl and the aqueous layer was extracted with three portions of Et$_2$O. The combined organic extracts were dried over sodium sulfate, filtered and concentrated.

The crude trifluoromethyl ketone was stirred overnight in a mixture of TFA (35 mL) and DCM (175 mL). Solvent was removed in vacuo. The residue was partitioned between EtOAc and NaHCO$_3$ solution. The aqueous layer was extracted further with two portions of EtOAc, and the combined organic extracts were washed with brine, dried over sodium sulfate, filtered and concentrated.

The crude pyrrolopyridine was treated with triethylamine (6.0 mL, 43 mmol), benzenesulfonyl chloride (4.0 mL, 32 mmol, Aldrich) and 4-dimethylaminopyridine (0.4 g, 3 mmol, Aldrich) in DCM (100 mL). After stirring overnight, the reaction mixture was partitioned between water and EtOAc. The organic layer was washed with brine, then dried over sodium sulfate, filtered and concentrated. The product was purified by flash chromatography, eluting with a gradient from 0-25% EtOAc in hexanes. Yield: (8.07 g, 77%).

$^1$H NMR (400 MHz, CDCl$_3$) δ 8.53 (dd, J=8.9, 0.7 Hz, 1H), 7.89-7.84 (m, 2H), 7.67-7.60 (m, 1H), 7.53-7.46 (m, 2H), 7.43 (d, J=8.9 Hz, 1H), 7.29 (s, 1H); LCMS (M+H)$^+$: 361.0363.0.

Step 3. Di-tert-butyl 1-[1-(phenylsulfonyl)-2-(trifluoromethyl)-1H-pyrrolo[3,2-b]pyridin-5-yl]hydrazine-1,2-dicarboxylate

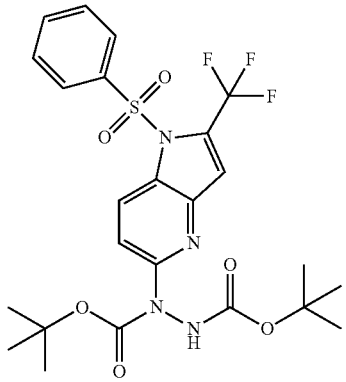 [SMILES: CC(C)(C)OC(=O)NN(C(=O)OC(C)(C)C)c1ccc2c(cc(C(F)(F)F)n2S(=O)(=O)c2ccccc2)n1]

A degassed mixture of 5-chloro-1-(phenylsulfonyl)-2-(trifluoromethyl)-1H-pyrrolo[3,2-b]pyridine (0.500 g, 1.39 mmol, from Step 2), di-tert-butyl hydrazine-1,2-dicarboxylate (0.35 g, 1.5 mmol, Aldrich), dicyclohexyl(2',4',6'-triisopropylbiphenyl-2-yl)phosphine-(2'-aminobiphenyl-2-yl)(chloro)palladium (1:1) (0.13 g, 0.16 mmol, Aldrich) and Cs$_2$CO$_3$ (0.50 g, 1.5 mmol) in toluene (11.5 mL) was heated at 110° C. for 2 hours. After cooling to room temperature, water was added, and the aqueous layer was extracted with three portions of EtOAc. The combined organic extracts were dried over sodium sulfate, filtered and concentrated. The product was purified by flash chromatography, eluting with a gradient from 0-50% EtOAc in hexanes. (Yield: 0.66 g, 86%).

LCMS (M+H)$^+$: 557.2.

Step 4. 1-Methyl-7-(trifluoromethyl)-6H-pyrrolo[2,3-e][1,2,4]triazolo[4,3-a]pyridine

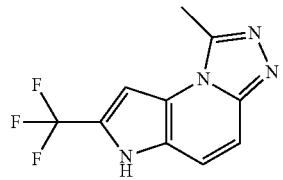 [SMILES: Cc1nnc2ccc3[nH]c(C(F)(F)F)cc3n12]

A solution of di-tert-butyl 1-[1-(phenylsulfonyl)-2-(trifluoromethyl)-1H-pyrrolo[3,2-b]pyridin-5-yl]hydrazine-1,2-dicarboxylate (0.66 g, 1.2 mmol, from Step 3) in acetic acid (20 mL) was heated at 180° C. for 5 minutes in the microwave. The acetic acid was removed in vacuo. The residue was dissolved in EtOAc and washed with an additional NaHCO$_3$ solution. The organic layer was dried over sodium sulfate, filtered and concentrated. The product was purified by flash chromatography, eluting with a gradient from 0-10% MeOH in DCM. Yield: (0.14 g, 49%).

LCMS (M+H)$^+$: 241.0.

Step 5. 6-Benzyl-1-methyl-7-(trifluoromethyl)-6H-pyrrolo[2,3-e][1,2,4]triazolo[4,3-a]pyridine bis(trifluoroacetate) salt A solution of 1-methyl-7-(trifluoromethyl)-6H-pyrrolo[2,3-e][1,2,4]triazolo[4,3-a]pyridine (0.020 g, 0.083 mmol, from Step 4) in DMF (0.5 mL) was treated with Cs$_2$CO$_3$ (0.054 g, 0.17 mmol) and benzyl bromide (0.010 mL, 0.084 mmol, Aldrich). After stirring overnight, the reaction was diluted with water and MeOH. The product was purified by preparative HPLC-MS (Waters SunFire C18, eluting with a gradient of MeCN/H$_2$O containing 0.1% TFA). Yield: (6 mg, 12%).

$^1$H NMR (400 MHz, CD$_3$OD) δ 8.12 (d, J=9.8 Hz, 1H), 7.77 (s, 1H), 7.70 (d, J=9.8 Hz, 1H), 7.35-7.25 (m, 3H), 7.08-7.02 (m, 2H), 5.79 (s, 2H), 3.11 (s, 3H); LCMS (M+H)$^+$: 331.0.

Example 139

1-(3-Chloro-5-{[1-methyl-7-(1,3,4-oxadiazol-2-yl)-6H-pyrrolo[2,3-e][1,2,4]triazolo[4,3-a]pyridin-6-yl]methyl}benzyl)azetidin-3-ol

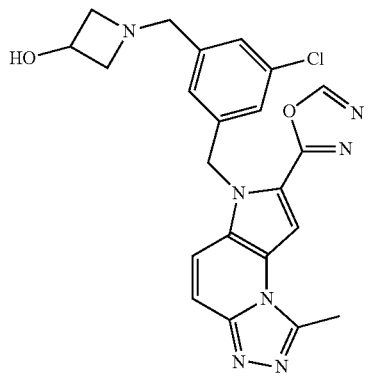 [SMILES: Cc1nnc2ccc3c(cc(C(=N)OC=N)n3Cc3cc(Cl)cc(CN4CC(O)C4)c3)n12]

Step 1. 5-Chloro-2-(1,3,4-oxadiazol-2-yl)-1H-pyrrolo[3,2-b]pyridine

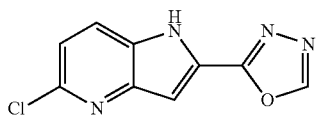 [SMILES: Clc1ccc2[nH]c(-c3nnco3)cc2n1]

To 5-chloro-1H-pyrrolo[3,2-b]pyridine-2-carboxylic acid (2.00 g, 10.2 mmol, from Example 99, Step 1) in THF (40 mL) at 0° C. was added 4-methylmorpholine (1.3 mL, 12 mmol, Aldrich) and isobutyl chloro formate (1.38 mL, 10.7 mmol, Aldrich). After 20 minutes, hydrazine hydrate (3.0 mL, 61 mmol, Aldrich) was added. Cooling was discontinued and the reaction was stirred overnight. The reaction mixture was diluted with EtOAc and washed sequentially with an additional NaHCO$_3$ and brine. The aqueous layer was extracted with EtOAc. Insoluble material at the interface of the layers was collected by filtration. The combined organic extracts were dried over sodium sulfate, filtered and concentrated. The product from the extracts and the solid from the filtration were combined and dissolved in trimethylorthoformate (35 mL, Aldrich). p-Toluenesulfonic acid (150 mg, 0.87 mmol, Aldrich) was added and the mixture was heated to 90° C. for 2 hours. Trimethylorthoformate was removed from the filtrate in vacuo to yield a crude product which was used in step 2 without purification.

LCMS (M+H)$^+$: 221.0223.0.

Step 2. 1-[3-({[tert-Butyl(diphenyl)silyl]oxy}methyl)-5-chlorobenzyl]-5-chloro-2-(1,3,4-oxadiazol-2-yl)-1H-pyrrolo[3,2-b]pyridine

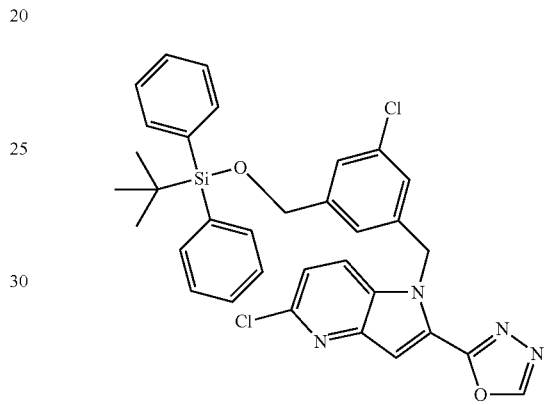

Triethylamine (0.71 mL, 5.1 mmol) and methanesulfonyl chloride (0.29 mL, 3.7 mmol, Aldrich) were added to a solution of [3-({[tert-butyl(diphenyl)silyl]oxy}methyl)-5-chlorophenyl]methanol (1.40 g, 3.40 mmol, from Example 131, Step 2) in DCM (10 mL) at 0° C. After 1 hour, the reaction mixture was diluted with DCM, washed sequentially with water and brine, dried over sodium sulfate, filtered and concentrated to afford the crude mesylate.

5-Chloro-2-(1,3,4-oxadiazol-2-yl)-1H-pyrrolo[3,2-b]pyridine (0.750 g, 3.40 mmol, from Step 1) in N,N-dimethylformamide (10 mL) was treated with Cs$_2$CO$_3$ (3.3 g, 10. mmol) followed by a solution of the crude mesylate generated above as a solution in DMF (5 mL). After 1.5 hours, the mixture was diluted with water and the aqueous layer was extracted three times with EtOAc. The combined organic extracts were dried over sodium sulfate, filtered and concentrated. The product was purified by flash chromatography, eluting with a gradient from 0-50% EtOAc in hexanes. Yield: (1.0 g, 48%).

$^1$H NMR (400 MHz, CDCl$_3$) δ 8.49 (s, 1H), 7.59 (dd, J=8.7, 0.8 Hz, 1H), 7.57-7.52 (m, 4H), 7.45-7.38 (m, 3H), 7.37-7.30 (m, 4H), 7.21 (d, J=8.7 Hz, 1H), 7.16-7.11 (m, 1H), 7.01-6.97 (m, 1H), 6.85-6.81 (m, 1H), 6.03 (s, 2H), 4.59 (s, 2H), 0.97 (s, 9H); LCMS (M+H)+: 613.0615.0.

Step 3. Di-tert-butyl 1-[1-[3-({[tert-butyl(diphenyl)silyl]oxy}methyl)-5-chlorobenzyl]-2-(1,3,4-oxadiazol-2-yl)-1H-pyrrolo[3,2-b]pyridin-5-yl]hydrazine-1,2-dicarboxylate

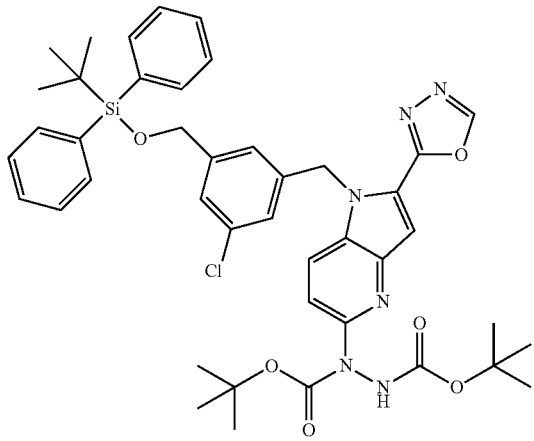 [SMILES: CC(C)(C)OC(=O)NN(C(=O)OC(C)(C)C)c1ccc2c(cc(-c3nnco3)n2Cc2cc(Cl)cc(CO[Si](c3ccccc3)(c3ccccc3)C(C)(C)C)c2)n1]

A degassed mixture of 1-[3-({[tert-butyl(diphenyl)silyl]oxy}methyl)-5-chlorobenzyl]-5-chloro-2-(1,3,4-oxadiazol-2-yl)-1H-pyrrolo[3,2-b]pyridine (0.500 g, 0.815 mmol, from Step 2), di-tert-butyl hydrazine-1,2-dicarboxylate (0.21 g, 0.90 mmol, Aldrich), dicyclohexyl(2',4',6'-triisopropylbiphenyl-2-yl)phosphine-(2'-aminobiphenyl-2-yl)(chloro)palladium (1:1) (0.076 g, 0.096 mmol, Aldrich) and $Cs_2CO_3$ (0.29 g, 0.90 mmol) in toluene (7 mL) was heated at 110° C. for 4 h. Additional di-tert-butyl hydrazine-1,2-dicarboxylate (0.1 g, 0.43 mmol), $Cs_2CO_3$ (0.15 g, 0.46 mmol), and dicyclohexyl(2',4',6'-triisopropylbiphenyl-2-yl)phosphine-(2'-aminobiphenyl-2-yl)(chloro)palladium (1:1) (0.050 g, 0.063 mmol) were added and heating was continued for 5 h. Upon cooling, the reaction mixture was diluted with water and extracted with three portions of EtOAc. The combined organic extracts were dried over sodium sulfate, filtered and concentrated. Flash chromatography, eluting with a gradient from 0-50% EtOAc in hexanes was used to purify product. Yield: (0.26 g, 39%).

$^1$H NMR (400 MHz, $CDCl_3$) δ 8.46 (s, 1H), 7.66-7.29 (m, 13H), 7.20-7.15 (m, 1H), 6.97-6.93 (m, 1H), 6.91-6.84 (m, 1H), 6.00 (s, 2H), 4.61 (s, 2H), 1.49 (s, 9H), 1.47 (s, 9H), 1.00 (s, 9H); LCMS (M+H)+: 809.2.

Step 4. (3-Chloro-5-{[1-methyl-7-(1,3,4-oxadiazol-2-yl)-6H-pyrrolo[2,3-e][1,2,4]triazolo[4,3-a]pyridin-6-yl]methyl}phenyl)methanol

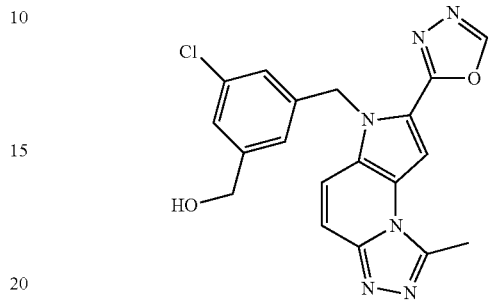

A solution of di-tert-butyl 1-[1-[3-({[tert-butyl(diphenyl)silyl]oxy}methyl)-5-chlorobenzyl]-2-(1,3,4-oxadiazol-2-yl)-1H-pyrrolo[3,2-b]pyridin-5-yl]hydrazine-1,2-dicarboxylate (0.26 g, 0.32 mmol, from Step 3) in acetic acid (15 mL) was heated at 180° C. for 5 minutes in the microwave. Acetic acid was removed in vacuo. The residue was partitioned between an additional $NaHCO_3$ and EtOAc. The aqueous layer was further extracted with two portions of EtOAc. The combined organic layers were dried over sodium sulfate, decanted and concentrated. The product was dissolved in THF (5 mL) and was treated with 1.0 M TBAF in THF (0.64 mL, 0.64 mmol, Aldrich). When the reaction was complete as determined by LCMS, the reaction mixture was poured into pH 7 buffer and extracted with three portions of EtOAc. The combined organics were dried over sodium sulfate, filtered and concentrated. Flash chromatography, eluting with a gradient from 0-10% MeOH in DCM was used to purify the product. Yield: (0.045 g, 35%).

LCMS (M+H)+: 395.1397.1.

Step 5. 1-(3-Chloro-5-{[1-methyl-7-(1,3,4-oxadiazol-2-yl)-6H-pyrrolo[2,3-e][1,2,4]triazolo[4,3-a]pyridin-6-yl]methyl}benzyl)azetidin-3-ol Triethylamine (49 µL, 0.35 mmol) and methanesulfonyl chloride (22 µL, 0.28 mmol, Aldrich) were added to a mixture of (3-chloro-5-{[1-methyl-7-(1,3,4-oxadiazol-2-yl)-6H-pyrrolo[2,3-e][1,2,4]triazolo[4,3-c]pyridin-6-yl]methyl}phenyl)methanol (0.033 g, 0.084 mmol, from Step 4) in DCM (4.9 mL). After 30 minutes, additional triethylamine (49 µL, 0.35 mmol) and methanesulfonyl chloride (22 µL, 0.28 mmol) were added. After 30 additional minutes, the mixture was briefly heated to reflux and then cooled. The solvent was removed in vacuo. The crude mesylate was reconstituted in THF (1.9 mL) and Methanol (1.9 mL). Half of this solution was added to azetidin-3-ol hydrochloride (37 mg, 0.33 mmol, Aldrich) and triethylamine (46 µL, 0.33 mmol) in THF (0.2 mL). [The other half of the mesylate solution was used in Example 140]. After 20 minutes, additional azetidin-3-ol hydrochloride (125 mg, 1.12 mmol, Aldrich) and triethylamine (156 µL, 1.12 mmol) were added and the mixture was stirred overnight. Sequential preparative HPLC-MS runs were used to purify the product (Waters SunFire C18, eluting with a gradient of $MeCN/H_2O$ containing 0.1% TFA, followed by Waters XBridge C18, eluting with a gradient of MeCN/H₂O containing 0.15% NH₄OH). Yield: (5 mg, 10%).

¹H NMR (500 MHz, DMSO) δ 9.43 (s, 1H), 7.78 (d, J=9.9 Hz, 1H), 7.74 (s, 1H), 7.59 (d, J=9.8 Hz, 1H), 7.18-7.16 (m, 1H), 7.00-6.98 (m, 1H), 6.97-6.94 (m, 1H), 6.11 (s, 2H), 5.23 (d, J=6.4 Hz, 1H), 4.11 (h, J=6.1 Hz, 1H), 3.45 (s, 2H), 3.40-3.35 (m, 2H), 2.98 (s, 3H), 2.68-2.63 (m, 2H); LCMS (M+H)⁺: 450.2.

Example 140

6-[3-(Azetidin-1-ylmethyl)-5-chlorobenzyl]-1-methyl-7-(1,3,4-oxadiazol-2-yl)-6H-pyrrolo[2,3-e][1,2,4]triazolo[4,3-a]pyridine

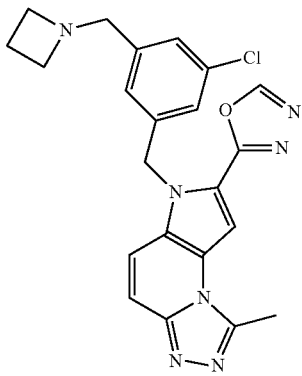 [SMILES: Cc1nnc2ccc3c(cc(C(=N)OC=N)n3Cc3cc(Cl)cc(CN4CCC4)c3)n12]

The remaining mesylate solution prepared in Example 139, Step 5 was treated with the solution of azetidine (0.023 mL, 0.33 mmol, Aldrich) in THF (0.2 mL). After 20 minutes, additional azetidine (0.078 mL, 1.1 mmol, Aldrich) was added and the reaction was stirred overnight. The product was isolated by preparative HPLC-MS (Waters XBridge C18, eluting with a gradient of MeCN/H₂O containing 0.15% NH₄OH). Yield: (5 mg, 10%).

¹H NMR (400 MHz, CD₃OD) δ 9.07 (s, 1H), 7.81-7.77 (m, 2H), 7.54 (d, J=10.0 Hz, 1H), 7.21-7.18 (m, 1H), 7.09-7.06 (m, 1H), 6.93-6.90 (m, 1H), 6.16 (s, 2H), 3.48 (s, 2H), 3.17 (t, J=7.2 Hz, 4H), 3.06 (s, 3H), 2.04 (p, J=7.1 Hz, 2H); LCMS (M+H)⁺: 434.2.

Example 141

6-(3-Chlorobenzyl)-1-methyl-7-(1,3,4-oxadiazol-2-yl)-6H-pyrrolo[2,3-e][1,2,4]triazolo[4,3-a]pyridine trifluoroacetate salt

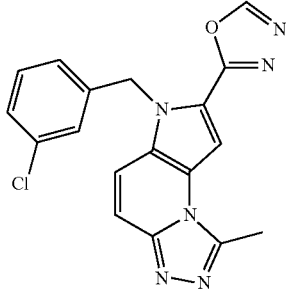 [SMILES: Cc1nnc2ccc3c(cc(C(=N)OC=N)n3Cc3cccc(Cl)c3)n12]

Step 1. 5-Chloro-1-(3-chlorobenzyl)-2-(1,3,4-oxadiazol-2-yl)-1H-pyrrolo[3,2-b]pyridine

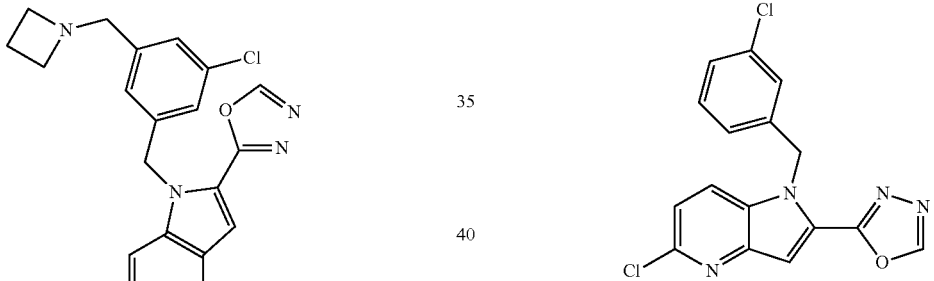

5-Chloro-2-(1,3,4-oxadiazol-2-yl)-1H-pyrrolo[3,2-b]pyridine (0.060 g, 0.27 mmol, from Example 139, Step 1) in DMF (5 mL) was treated with Cs₂CO₃ (0.222 g, 0.681 mmol) and 1-(bromomethyl)-3-chloro-benzene (0.046 mL, 0.35 mmol). After 1 hour, additional 1-(bromomethyl)-3-chlorobenzene (0.040 mL, 0.30 mmol, Aldrich) was added and stirring continued for 1 hour. Water was added, and the solution was extracted with three portions of EtOAc. The combined organic extracts were washed sequentially with water and brine, dried over sodium sulfate, filtered and concentrated. Flash chromatography, eluting with a gradient from 0-40% EtOAc in hexanes afforded purified product. Yield: (67 mg, 71%).

LCMS (M+H)⁺: 345.0346.9.

Step 2. 6-(3-chlorobenzyl)-1-methyl-7-(1,3,4-oxadiazol-2-yl)-6H-pyrrolo[2,3-e][1,2,4]triazolo[4,3-a]pyridine trifluoroacetate salt A degassed mixture of 5-chloro-1-(3-chlorobenzyl)-2-(1,3,4-oxadiazol-2-yl)-1H-pyrrolo[3,2-b]pyridine (0.067 g, 0.19 mmol, from Step 1), di-tert-butyl hydrazine-1,2-dicarboxylate (0.050 g, 0.21 mmol, Aldrich), dicyclohexyl(2',4',6'-triisopropylbiphenyl-2-yl)phosphine-(2'-aminobiphenyl- 2-yl)(chloro)palladium (1:1) (0.018 g, 0.023 mmol, Aldrich) and Cs₂CO₃ (0.070 g, 0.21 mmol) in toluene (3 mL) was heated at 110° C. for 5.5 h. After cooling to room temperature, water was added, and the layers were separated. The aqueous layer was further extracted with three portions of EtOAc. The combined organic extracts were dried over sodium sulfate, filtered and concentrated. The intermediate di-tert-butyl 1-(1-(3-chlorobenzyl)-2-(1,3,4-oxadiazol-2-yl)-1H-pyrrolo[3,2-b]pyridin-5-yl)hydrazine-1,2-dicarboxylate was purified by flash chromatography, eluting with a gradient from 0-50% EtOAc. The intermediate product was dissolved in acetic acid (5 mL) and heated at 180° C. for 5 minutes in the microwave, and the title product was purified by preparative HPLC-MS (Waters SunFire C18, eluting with a gradient of MeCN/H₂O containing 0.1% TFA). Yield: (6 mg, 7%).

¹H NMR (500 MHz, DMSO) δ 9.44 (s, 1H), 7.91 (d, J=9.8 Hz, 1H), 7.79 (s, 1H), 7.64 (d, J=9.8 Hz, 1H), 7.36-7.28 (m, 2H), 7.23-7.18 (m, 1H), 7.02-6.94 (m, 1H), 6.15 (s, 2H), 3.00 (s, 3H); LCMS (M+H)⁺: 365.1.

Example 142

N-{6-[3-Chloro-5-(pyrrolidin-1-ylmethyl)benzyl]-1,7-dimethyl-6H-pyrrolo[2,3-e][1,2,4]triazolo[4,3-a]pyridin-4-yl}-N'-methylurea bis(trifluoroacetate) salt

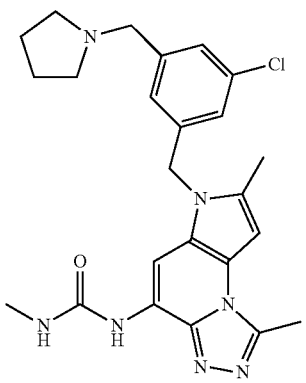

Step 1. 4-Bromo-1,7-dimethyl-6-(phenylsulfonyl)-6H-pyrrolo[2,3-e][1,2,4]triazolo[4,3-c]pyridine

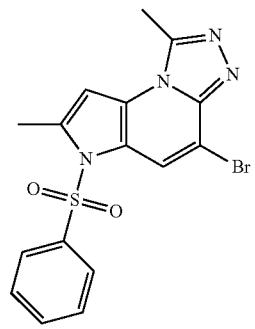 [SMILES: Cc1cc2c(cc(Br)c3nnc(C)n32)n1S(=O)(=O)c1ccccc1]

1,7-Dimethyl-6-(phenylsulfonyl)-6H-pyrrolo[2,3-e][1,2,4]triazolo[4,3-a]pyridine (4.00 g, 12.2 mmol, from Example 2, Step 4) in 1,2-dichloroethane (100 mL) was treated with N-bromosuccinimide (2.18 g, 12.2 mmol, Aldrich) at 60° C. for 1 hour. Additional N-bromosuccinimide (1.08 g, 6.07 mmol) was added and heating continued for 1 hour. The reaction mixture was cooled to room temperature and diluted with DCM, then washed sequentially with an additional NaHCO₃ and brine, dried over sodium sulfate, filtered and concentrated. Flash chromatography, eluting with a gradient from 0-10% MeOH in DCM, afforded purified product. Yield: (1.57 g, 31%).

LCMS (M+H)⁺: 405.0407.0.

Step 2. 4-Bromo-1,7-dimethyl-6H-pyrrolo[2,3-e][1,2,4]triazolo[4,3-a]pyridine

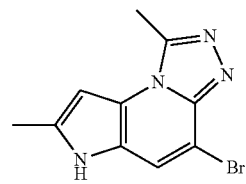

1.0 M NaOH in water (15 mL, 15 mmol) was added to 4-bromo-1,7-dimethyl-6-(phenylsulfonyl)-6H-pyrrolo[2,3-e][1,2,4]triazolo[4,3-a]pyridine (1.57 g, 3.87 mmol, from Step 1) in THF (15 mL) and EtOH (15 mL). The reaction was continued for 1 hour, and a precipitate formed. The solid product was isolated by filtration. The solid was then suspended in Et₂O, filtered and air dried. Yield: (0.86 g, 84%).

¹H NMR (400 MHz, d₆-DMSO): δ 11.83 (s, 1H), 7.78 (d, J=0.7 Hz, 1H), 6.69 (s, 1H), 2.86 (s, 3H), 2.42 (s, 3H); LCMS (M+H)⁺: 265.0267.0.

Step 3. 4-Bromo-6-[3-({[tert-butyl(diphenyl)silyl]oxy}methyl)-5-chlorobenzyl]-1,7-dimethyl-6H-pyrrolo[2,3-e][1,2,4]triazolo[4,3-a]pyridine

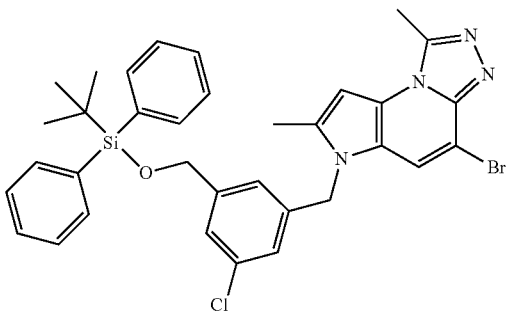 [SMILES: Cc1cc2c(cc(Br)c3nnc(C)n32)n1Cc1cc(Cl)cc(CO[Si](c2ccccc2)(c2ccccc2)C(C)(C)C)c1]

Triethylamine (0.68 mL, 4.9 mmol) and methanesulfonyl chloride (0.301 mL, 3.89 mmol, Aldrich) were added to [3-({[tert-butyl(diphenyl)silyl]oxy}methyl)-5-chlorophenyl]methanol (1.47 g, 3.57 mmol, from Example 131, Step 2) in DCM (10 mL) at 0° C. After 1 hour, the reaction mixture was diluted with DCM, and was washed sequentially with water and brine, dried over sodium sulfate, filtered and concentrated to afford a crude intermediate. The crude intermediate was dissolved in DMF (5 mL) and added to a mixture of 4-bromo-1,7-dimethyl-6H-pyrrolo[2,3-e][1,2,4]triazolo[4,3-a]pyridine (0.86 g, 3.2 mmol, from Step 2) and Cs₂CO₃ (3.2 g, 9.7 mmol) in DMF (10 mL). After 2 hours, the reaction mixture was diluted with water and extracted with three portions of EtOAc. The combined organic extracts were dried over sodium sulfate, filtered and concentrated. The product was purified by flash chromatography, eluting first with a gradient of 0-100% EtOAc in hexanes, and then eluting with a gradient from 5-10% MeOH in DCM.

LCMS (M+H)+: 659.2.

Step 4. {3-[(4-Bromo-1,7-dimethyl-6H-pyrrolo[2,3-e][1,2,4]triazolo[4,3-a]pyridin-6-yl)methyl]-5-chlorophenyl}methanol

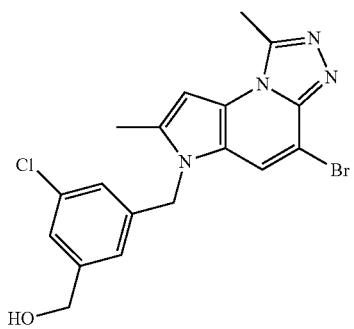 [SMILES: Cc1cc2c(cc(Br)c3nnc(C)n32)n1Cc1cc(Cl)cc(CO)c1]

4-Bromo-6-[3-({[tert-butyl(diphenyl)silyl]oxy}methyl)-5-chlorobenzyl]-1,7-dimethyl-6H-pyrrolo[2,3-e][1,2,4]triazolo[4,3-a]pyridine (2.1 g, 3.2 mmol, from Step 3) in THF (30 mL) was treated with 1.0 M TBAF in THF (6.4 mL, 6.4 mmol, Aldrich) for 1 hour. The reaction mixture was diluted with water and extracted with three portions of EtOAc. The combined organic extracts were washed with brine, dried over sodium sulfate, filtered and concentrated. The product was purified by flash chromatography, eluting with a gradient from 0-10% MeOH. Yield: (0.722 g, 54% over the two steps).

LCMS (M+H)+: 419.0421.0.

Step 5. 4-Bromo-6-[3-chloro-5-(pyrrolidin-1-ylmethyl)benzyl]-1,7-dimethyl-6H-pyrrolo[2,3-e][1,2,4]triazolo[4,3-a]pyridine

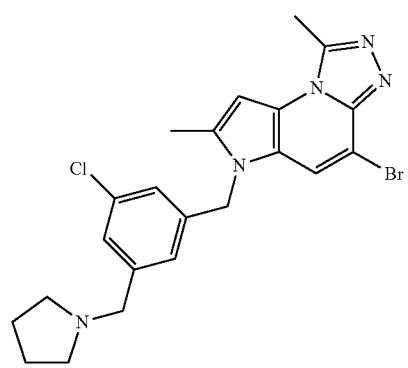 [SMILES: Cc1cc2c(cc(Br)c3nnc(C)n32)n1Cc1cc(Cl)cc(CN2CCCC2)c1]

A solution of {3-[(4-bromo-1,7-dimethyl-6H-pyrrolo[2,3-e][1,2,4]triazolo[4,3-a]pyridin-6-yl)methyl]-5-chlorophenyl}methanol (0.360 g, 0.858 mmol, from Step 4) in DCM (50. mL) was treated with triethylamine (510 μL, 3.6 mmol) and methanesulfonyl chloride (220 μL, 2.9 mmol, Aldrich). After 30 minutes, the solvent was removed in vacuo, and the residue was dissolved in a mixture of THF (20. mL) and methanol (20. mL). The solution was added to a mixture of pyrrolidine (0.42 mL, 5 mmol, aldrich) and triethylamine (0.61 mL, 4.3 mmol) in THF (10 mL). The reaction was stirred for 1 hour, and then the solvent was removed in vacuo. The residue was partitioned between water and DCM. The organic layer was dried over sodium sulfate, filtered and concentrated. Flash chromatography, eluting with a gradient from 0-10% MeOH in DCM, was used to purify product. Yield: (0.30 g, 74%).

$^1$H NMR (400 MHz, CD$_3$OD) δ 7.84 (s, 1H), 7.28-7.24 (m, 1H), 6.94-6.90 (m, 1H), 6.84-6.81 (m, 1H), 6.76 (s, 1H), 5.43 (s, 2H), 3.55 (s, 2H), 2.92 (s, 3H), 2.51-2.41 (m, 4H), 2.39 (s, 3H), 1.79-1.68 (m, 4H); LCMS (M+H)+: 472.1474.1.

Step 6. N-{6-[3-chloro-5-(pyrrolidin-1-ylmethyl)benzyl]-1,7-dimethyl-6H-pyrrolo[2,3-e][1,2,4]triazolo[4,3-a]pyridin-4-yl}-N'-methylurea bis(trifluoroacetate) salt A degassed suspension of 4-bromo-6-[3-chloro-5-(pyrrolidin-1-ylmethyl)benzyl]-1,7-dimethyl-6H-pyrrolo[2,3-e][1,2,4]triazolo[4,3-a]pyridine (110.0 mg, 0.2326 mmol, from Step 5), tBuBrettPhos Pd G3 (tert-BuBrettPhos-Pd-G3, [(2-Di-tert-butylphosphino-3,6-dimethoxy-2',4',6'-triisopropyl-1,1'-biphenyl)-2-(2'-amino-1,1'-biphenyl)]palladium(II) methanesulfonate) (24 mg, 0.028 mmol, Aldrich), N-methylurea (25 mg, 0.33 mmol, Aldrich), Water (0.082 mL, 4.6 mmol), and Cs$_2$CO$_3$ (116.7 mg, 0.3583 mmol) in N-Methylpyrrolidinone (1 mL) was heated at 80° C. for 1 hour, then at 90° C. for 1 hour. The reaction mixture was diluted with water and MeCN and was purified by preparative HPLC-MS (Waters SunFire C18, eluting with a gradient of MeCN/H$_2$O containing 0.1% TFA). The purest fractions were collected, eluent removed in vacuo and the product repurified by HPLC-MS (Waters SunFire C18, eluting with a gradient of MeOH/H$_2$O containing 0.1% TFA). Yield: (5 mg, 3%).

$^1$H NMR (400 MHz, CD$_3$OD) δ 8.15 (s, 1H), 7.52-7.50 (m, 1H), 7.15-7.12 (m, 2H), 7.07-7.03 (m, 1H), 5.62 (s, 2H), 4.31 (s, 2H), 3.54-3.38 (br m, 2H), 3.16-3.03 (br m, 2H), 3.09 (s, 3H), 2.80 (s, 3H), 2.54 (s, 3H), 2.21-2.06 (br m, 2H), 2.06-1.89 (br m, 2H); LCMS (M+H)+: 466.2.

Example 143

6-benzyl-1-methyl-7-(1,3-oxazol-2-yl)-6H-pyrrolo[2,3-e][1,2,4]-triazolo[4,3-a]pyridine trifluoroacetate salt

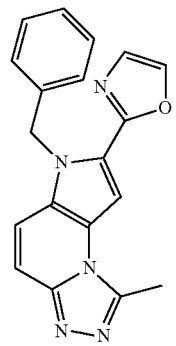 [SMILES: Cc1nnc2ccc3c(cc(-c4ncco4)n3Cc3ccccc3)n12]

Step 1. 5-chloro-2-(1,3-oxazol-2-yl)-1-(phenylsulfonyl)-1H-pyrrolo[3,2-b]pyridine

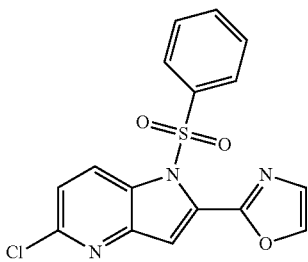 [SMILES: O=S(=O)(c1ccccc1)n1c(-c2ncco2)cc2nc(Cl)ccc21]

A degassed mixture of 2-bromo-5-chloro-1-(phenylsulfonyl)-1H-pyrrolo[3,2-b]pyridine (4.3 g, 12 mmol, prepared by the procedure of Example 62, Step 1 but purified by flash chromatography to afford the free base), 2-(tributylstannyl)-1,3-oxazole (5.0 g, 14 mmol, Aldrich), and Tetrakis(triphenylphosphine)palladium(0) (1.3 g, 1.2 mmol, Strem) in toluene (69 mL) was heated to 110° C. for 14 hours. Solvent was removed in vacuo, and the residue was purified by flash chromatography, eluting with a gradient from 0-100% EtOAc in hexanes. Yield: (2.09 g, 50%).
LCMS (M+H)+: 360.0/362.0.

Step 2. 5-chloro-2-(1,3-oxazol-2-yl)-1H-pyrrolo[3,2-b]pyridine

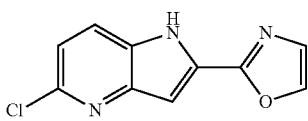 [SMILES: Clc1ccc2[nH]c(-c3ncco3)cc2n1]

A solution of 5-chloro-2-(1,3-oxazol-2-yl)-1-(phenylsulfonyl)-1H-pyrrolo[3,2-b]pyridine (2.09 g, 5.81 mmol, from Step 2) in THF (30 mL) and EtOH (10 mL) was treated with 1.0 M NaOH in water (30 mL, 30 mmol). After stirring for 1 hour, the reaction mixture was diluted with water, and the volatile components were removed in vacuo. The aqueous mixture was extracted with three portions of EtOAc. The combined organic extracts were washed with brine, dried over sodium sulfate, filtered and concentrated. The product was triturated in EtOAc/DCM/MeOH, and the yellow solid was isolated by filtration and air dried. Yield: (0.78 g, 61%).

1H NMR (300 MHz, CD3OD) δ 8.05 (s, 1H), 7.88 (d, J=8.6 Hz, 1H), 7.37 (s, 1H), 7.27 (d, J=8.6 Hz, 1H), 7.13 (s, 1H); LCMS (M+H)+: 220.0/222.0.

Step 3. 1-benzyl-5-chloro-2-(1,3-oxazol-2-yl)-1H-pyrrolo[3,2-b]pyridine

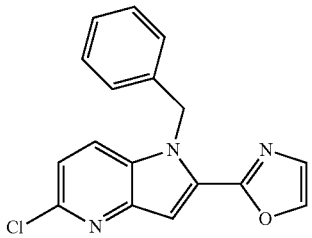 [SMILES: Clc1ccc2c(cc(-c3ncco3)n2Cc2ccccc2)n1]

To a well stirred mixture of 5-chloro-2-(1,3-oxazol-2-yl)-1H-pyrrolo[3,2-b]pyridine (0.39 g, 1.8 mmol, from Step 2) in DMF (8 mL) was added Cs2CO3 (1.7 g, 5.3 mmol) and benzyl bromide (0.21 mL, 1.8 mmol, Aldrich). After stirring overnight, the reaction mixture was partitioned between water and ethyl acetate. The aqueous layer was extracted with an additional two portions of EtOAc. The combined organic extracts were dried over sodium sulfate, filtered and concentrated. The resulting light yellow crystalline solid was used directly in Step 4. LCMS (M+H)+: 310.1/312.1.

Step 4. di-tert-butyl 1-[1-benzyl-2-(1,3-oxazol-2-yl)-1H-pyrrolo[3,2-b]pyridin-5-yl]hydrazine-1,2-dicarboxylate

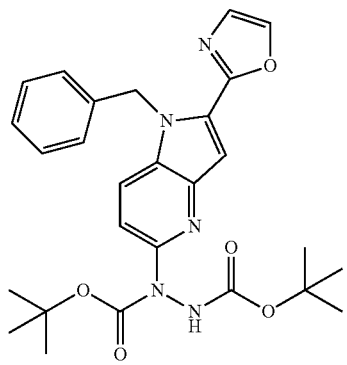 [SMILES: CC(C)(C)OC(=O)NN(C(=O)OC(C)(C)C)c1ccc2c(cc(-c3ncco3)n2Cc2ccccc2)n1]

A degassed mixture of 1-benzyl-5-chloro-2-(1,3-oxazol-2-yl)-1H-pyrrolo[3,2-b]pyridine (0.55 g, 1.8 mmol, from Step 3), di-tert-butyl hydrazine-1,2-dicarboxylate (0.50 g, 2.2 mmol, Aldrich), Cs2CO3 (0.70 g, 2.2 mmol) and dicyclohexyl (2',4',6'-triisopropylbiphenyl-2-yl)phosphine-(2'-aminobiphenyl-2-yl)(chloro)palladium (1:1) (0.18 g, 0.24 mmol, Aldrich) in toluene (16.8 mL) was heated to 110° C. for 4 hours. Upon cooling, the reaction was partitioned between water and EtOAc. The aqueous layer was extracted with an additional two portions of EtOAc. The combined organic extracts were dried over sodium sulfate, filtered and concentrated. Flash chromatography, eluting with 25% then 40% EtOAc in hexanes afforded purified product. Yield: (0.59 g, 65%).
LCMS (M+H)+: 506.2.

Step 5. 6-benzyl-1-methyl-7-(1,3-oxazol-2-yl)-6H-pyrrolo[2,3-e][1,2,4]triazolo[4,3-a]pyridine, trifluoroacetate salt A solution of di-tert-butyl 1-[1-benzyl-2-(1,3-oxazol-2-yl)-1H-pyrrolo[3,2-b]pyridin-5-yl]hydrazine-1,2-dicarboxylate (0.59 g, 1.2 mmol, from Step 4) in acetic acid (20 mL) was prepared. The solution was partitioned equally into three microwavable vials and each was heated in the microwave at 180° C. for 5 minutes. The acetic acid was removed in vacuo from the combined batches. The residue was dissolved in EtOAc and washed with saturated solution of $NaHCO_3$. The aqueous layer was extracted with two further portions of EtOAc. The combined organic extracts were dried over sodium sulfate, filtered and concentrated. The product was purified via preparative HPLC-MS (Waters SunFire C18, eluting with a gradient of $MeCN/H_2O$ containing 0.1% TFA). Yield: (0.15 g, 39%).

$^1$H NMR (400 MHz, $CD_3OD$) δ 8.31 (dd, J=0.6, 9.7 Hz, 1H), 8.10 (d, J=0.7 Hz, 1H), 7.86 (d, J=0.6 Hz, 1H), 7.64 (d, J=9.7 Hz, 1H), 7.41 (d, J=0.7 Hz, 1H), 7.30-7.18 (m, 3H), 7.15-7.06 (m, 2H), 6.32 (s, 2H), 3.16 (s, 3H); LCMS (M+H)$^+$: 330.1.

Example 144

6-benzyl-1,7-dimethyl-N-(1-methylpiperidin-3-yl)-6H-pyrrolo[2,3-e][1,2,4]triazolo[4,3-a]pyridin-4-amine (racemic)

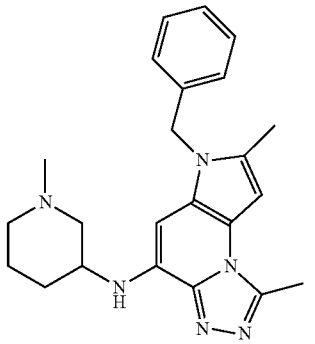 [SMILES: Cc1cc2c(cc(NC3CCCN(C)C3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (25.0 mg, 0.0804 mmol, Example 228, Step 7), 1-methylpiperidin-3-amine (37 mg, 0.32 mmol, racemic, ChemBridge), Sodium tert-butoxide (15 mg, 0.16 mmol, Aldrich), (9,9-dimethyl-9H-xanthene-4,5-diyl)bis(diphenylphosphine) (9.3 mg, 0.016 mmol, Aldrich) and tris(dibenzylideneacetone)dipalladium(0) (7.4 mg, 0.0080 mmol, Aldrich) in toluene (1.2 mL) was heated at 100° C. overnight. Additional 1-methylpiperidin-3-amine (37 mg, 0.32 mmol), sodium tert-butoxide (15 mg, 0.16 mmol), (9,9-dimethyl-9H-xanthene-4,5-diyl)bis(diphenylphosphine) (46 mg, 0.080 mmol) and tris(dibenzylideneacetone)dipalladium(0) (44 mg, 0.040 mmol), were added, the mixture was again degassed and heating at 100° C. was continued for 3 hours. The reaction mixture was partitioned between water and EtOAc. The aqueous layer was extracted with two further portions of EtOAc. The combined organic extracts were dried over sodium sulfate, filtered and concentrated. The product was purified via preparative HPLC-MS (Waters SunFire C18, eluting with a gradient of $MeOH/H_2O$ containing 0.1% TFA), followed by repurification using HPLC-MS (Waters SunFire C18, eluting with a gradient of $MeCN/H_2O$ containing 0.1% TFA), again followed by a final purification using HPLC-MS (Waters XBridge C18, eluting with a gradient of $MeCN/H_2O$ containing 0.15% $NH_4OH$) to afford product as the free base. Yield: (3 mg, 10%).

$^1$H NMR (500 MHz, $CD_3OD$) δ 7.32-7.26 (m, 2H), 7.26-7.20 (m, 1H), 7.00 (d, J=7.4 Hz, 2H), 6.66 (s, 1H), 6.55 (s, 1H), 5.47-5.37 (m, 2H), 3.62-3.51 (m, 1H), 3.08-2.98 (m, 1H), 2.93 (s, 3H), 2.84-2.73 (m, 1H), 2.38 (s, 3H), 2.29 (s, 3H), 2.23-2.07 (m, 1H), 2.06-1.91 (m, 2H), 1.87-1.76 (m, 1H), 1.75-1.60 (m, 1H), 1.42-1.24 (m, 1H); LCMS (M+H)$^+$: 389.2.

Example 145

6-benzyl-1,7-dimethyl-N-(1-methylpyrrolidin-3-yl)-6H-pyrrolo[2,3-e][1,2,4]triazolo[4,3-a]pyridin-4-amine bis(trifluoroacetate) salt (racemic)

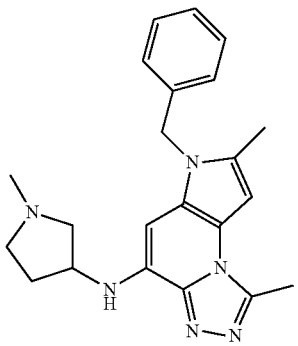 [SMILES: Cc1cc2c(cc(NC3CCN(C)C3)c3nnc(C)n32)n1Cc1ccccc1]

Prepared by the procedure of Example 144, using 1-methylpyrrolidin-3-amine (0.032 g, 0.32 mmol, racemic, ChemBridge), and purified via preparative HPLC-MS (Waters SunFire C18, eluting with a gradient of $MeCN/H_2O$ containing 0.1% TFA). Yield: 2 mg, 4%.

¹H NMR (500 MHz, CD₃OD) δ 7.32-7.27 (m, 2H), 7.27-7.22 (m, 1H), 7.00 (d, J=7.2 Hz, 2H), 6.71 (s, 1H), 6.62 (s, 1H), 5.46 (s, 2H), 4.39 (br m, 1H), 4.07-1.21 (m, 15H); LCMS (M+H)⁺: 375.2.

Example 146

6-benzyl-1,7-dimethyl-N-(tetrahydro-2H-pyran-4-yl)-6H-pyrrolo[2,3-e][1,2,4]triazolo[4,3-a]pyridin-4-amine

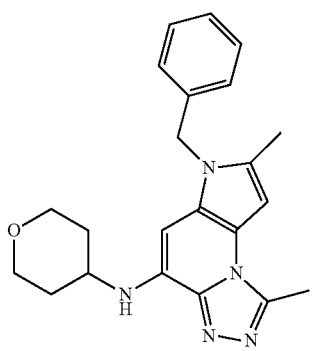 [SMILES: Cc1cc2c(cc(NC3CCOCC3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (25.0 mg, 0.0804 mmol, Example 228, Step 7), tetrahydro-2H-pyran-4-amine (32 mg, 0.32 mmol, CombiBlocks), sodium tert-butoxide (23 mg, 0.24 mmol, Aldrich), (9,9-dimethyl-9H-xanthene-4,5-diyl)bis(diphenylphosphine) (9.3 mg, 0.016 mmol, Aldrich) and tris(dibenzylideneacetone)dipalladium (0) (7.4 mg, 0.0080 mmol, Aldrich) in toluene (1.2 mL) was heated at 100° C. overnight. Toluene was removed in vacuo and the crude mixture was dissolved in MeOH/H₂O/MeCN and purified via preparative HPLC-MS (Waters XBridge C18, eluting with a gradient of MeCN/H₂O containing 0.15% NH₄OH). Yield: (3 mg, 10%).

¹H NMR (500 MHz, CD₃OD) δ 7.31-7.24 (m, 2H), 7.24-7.19 (m, 1H), 6.99 (d, J=7.3 Hz, 2H), 6.59 (s, 1H), 6.47 (s, 1H), 5.37 (s, 2H), 3.93 (dt, J=11.8, 3.6 Hz, 2H), 3.60 (tt, J=10.0, 4.0 Hz, 1H), 3.52 (td, J=11.5, 2.1 Hz, 2H), 2.90 (s, 3H), 2.37 (s, 3H), 2.01-1.90 (m, 2H), 1.51 (dtd, J=14.3, 10.7, 4.2 Hz, 2H); LCMS (M+H)⁺: 376.2.

Example 147

6-benzyl-1,7-dimethyl-N-[(3R)-tetrahydrofuran-3-yl]-6H-pyrrolo[2,3-e][1,2,4]triazolo[4,3-a]pyridin-4-amine

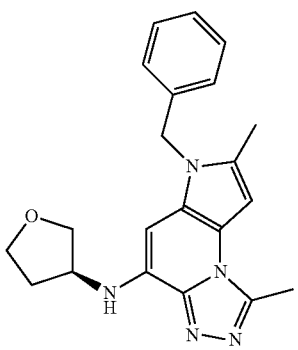 [SMILES: Cc1cc2c(cc(N[C@H]3CCOC3)c3nnc(C)n32)n1Cc1ccccc1]

The title compound was prepared according to the methods of Example 146, using (3R)-tetrahydrofuran-3-amine 4-methylbenzenesulfonate (40 mg, 0.15 mmol, Advanced Chem Blocks). Yield: (3 mg, 10%).

¹H NMR (500 MHz, CD₃OD) δ 7.31-7.26 (m, 2H), 7.26-7.20 (m, 1H), 7.02 (d, J=7.4 Hz, 2H), 6.65 (s, 1H), 6.46 (s, 1H), 5.41 (s, 2H), 4.16 (ddt, J=8.8, 6.8, 3.2 Hz, 1H), 4.00-3.88 (m, 2H), 3.82 (td, J=8.4, 5.3 Hz, 1H), 3.69 (dd, J=9.1, 3.2 Hz, 1H), 2.93 (s, 3H), 2.39 (s, 3H), 2.26 (dq, J=13.0, 7.4 Hz, 1H), 1.91 (dddd, J=12.6, 7.8, 5.0, 3.3 Hz, 1H); LCMS (M+H)⁺: 362.1.

Example 148

6-benzyl-1,7-dimethyl-N-[(3S)-tetrahydrofuran-3-yl]-6H-pyrrolo[2,3-e][1,2,4]triazolo[4,3-a]pyridin-4-amine The title compound was prepared according to the methods of Example 146, using (3S)-tetrahydrofuran-3-amine hydrochloride (20 mg, 0.16 mmol, Advanced Chem Blocks). Yield: 3 mg, 10%.

¹H NMR (500 MHz, CD₃OD) δ 7.31-7.26 (m, 2H), 7.26-7.21 (m, 1H), 7.01 (d, J=7.3 Hz, 2H), 6.64 (s, 1H), 6.45 (s, 1H), 5.41 (s, 2H), 4.16 (dp, J=8.9, 3.3 Hz, 1H), 3.98-3.89 (m,

2H), 3.82 (td, J=8.4, 5.3 Hz, 1H), 3.69 (dd, J=9.1, 3.2 Hz, 1H), 2.92 (s, 3H), 2.39 (s, 3H), 2.26 (dq, J=13.0, 7.5 Hz, 1H), 1.94-1.87 (m, 1H); LCMS (M+H)+: 362.1.

Example 149 tert-butyl (3R)-3-[(6-benzyl-1,7-dimethyl-6H-pyrrolo[2,3-e][1,2,4]triazolo[4,3-a]pyridin-4-yl)amino]pyrrolidine-1-carboxylate

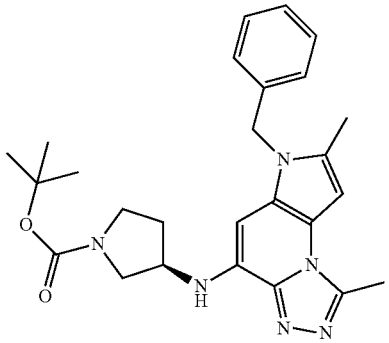 [SMILES: Cc1cc2c(cc(N[C@@H]3CCN(C(=O)OC(C)(C)C)C3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (200.0 mg, 0.6435 mmol, Example 228, Step 7), tert-butyl (3R)-3-aminopyrrolidine-1-carboxylate (0.40 mL, 2.3 mmol, Aldrich), sodium tert-butoxide (190 mg, 1.98 mmol, Aldrich), (9,9-dimethyl-9H-xanthene-4,5-diyl)bis(diphenylphosphine) (93 mg, 0.16 mmol, Aldrich) and tris(dibenzylideneacetone)dipalladium(0) (74 mg, 0.080 mmol, Aldrich) in toluene (12 mL) was heated at 100° C. for 3.5 hours, then at 125° C. for 2 hours. The reaction mixture was partitioned between water and ethyl acetate, and the aqueous layer was extracted further with two portions of EtOAc. The combined organic extracts were washed with brine, dried over sodium sulfate, decanted and concentrated. The product was purified by flash chromatography, eluting first with a gradient from 0-100% EtOAc in hexanes, then eluting with 5% MeOH in DCM. Yield: (190 mg, 64%). A portion of this material was then purified by preparative HPLC-MS (Waters XBridge C18, eluting with a gradient of MeCN/H2O containing 0.15% NH4OH) to provide a pure title compound.

$^{1}$H NMR (400 MHz, $d_6$-DMSO) δ 7.34-7.27 (m, 2H), 7.27-7.19 (m, 1H), 7.02 (d, J=7.4 Hz, 2H), 6.67 (d, J=4.3 Hz, 1H), 6.62 (s, 1H), 5.88-5.80 (m, 1H), 5.45 (s, 2H), 4.24-3.97 (m, 1H), 3.67-3.50 (m, 1H), 3.46-3.37 (m, 1H), 3.31-3.21 (m, 1H), 3.15 (td, J=10.8, 5.1 Hz, 1H), 2.83 (s, 3H), 2.31 (s, 1.5H, rotamers), 2.30 (s, 1.5H, rotamers), 2.20-2.06 (m, 1H), 2.04-1.84 (m, 1H), 1.39 (s, 4.5H, rotamers), 1.35 (s, 4.5H, rotamers); LCMS (M+H)+: 461.2.

Example 150 tert-butyl (3S)-3-[(6-benzyl-1,7-dimethyl-6H-pyrrolo[2,3-e][1,2,4]triazolo[4,3-a]pyridin-4-yl)amino]pyrrolidine-1-carboxylate

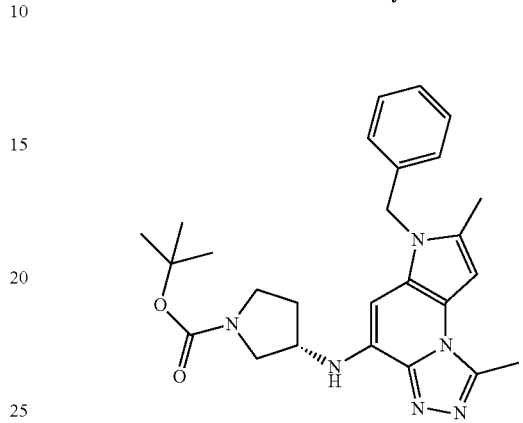

The title compound was prepared according to the methods of Example 149, using tert-butyl (3S)-3-aminopyrrolidine-1-carboxylate (0.40 mL, 2.3 mmol, Aldrich). The product was purified by flash chromatography, eluting with a gradient from 0-10% MeOH in DCM. Yield: (190 mg, 64%). A portion of this material was then purified by preparative HPLC-MS (Waters XBridge C18, eluting with a gradient of MeCN/H2O containing 0.15% NH4OH) to afford the pure title compound.

$^{1}$H NMR (400 MHz, $d_6$-DMSO) δ 7.34-7.27 (m, 2H), 7.27-7.20 (m, 1H), 7.02 (d, J=7.5 Hz, 2H), 6.67 (d, J=4.4 Hz, 1H), 6.62 (s, 1H), 5.88-5.80 (m, 1H), 5.44 (s, 2H), 4.23-4.03 (m, 1H), 3.66-3.51 (m, 1H), 3.48-3.37 (m, 1H), 3.32-3.20 (m, 1H), 3.20-3.08 (m, 1H), 2.83 (s, 3H), 2.31 (s, 1.5H, rotamers), 2.30 (s, 1.5H, rotamers), 2.20-2.05 (m, 1H), 2.05-1.88 (m, 1H), 1.39 (s, 4.5H, rotamers), 1.35 (s, 4.5H, rotamers); LCMS (M+H)+: 461.2.

Example 151

6-benzyl-1,7-dimethyl-N-[(3R)-pyrrolidin-3-yl]-6H-pyrrolo[2,3-e][1,2,4]triazolo[4,3-a]pyridin-4-amine bis(trifluoroacetate) salt

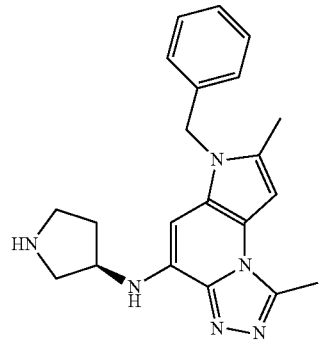 [SMILES: Cc1cc2c(cc(N[C@@H]3CCNC3)c3nnc(C)n32)n1Cc1ccccc1]

tert-butyl (3R)-3-[(6-benzyl-1,7-dimethyl-6H-pyrrolo[2,3-e][1,2,4]triazolo[4,3-a]pyridin-4-yl)amino]pyrrolidine-1-carboxylate (0.175 g, 0.380 mmol, from Example 149) in 1,4-dioxane (10 mL) was treated with 4.0 M solution of HCl in dioxane (4 mL, 20 mmol), and the reaction was stirred for 1 hour. Solvent and excess reagents were removed in vacuo. The product was purified by preparative HPLC-MS (Waters XBridge C18, eluting with a gradient of MeCN/H$_2$O containing 0.15% NH$_4$OH) and was then repurified by preparative HPLC-MS (Waters SunFire C18, eluting with a gradient of MeCN/H$_2$O containing 0.1% TFA) to yield the title product.

LCMS (M+H)$^+$: 361.2.

Example 152

6-benzyl-1,7-dimethyl-N-[(3S)-pyrrolidin-3-yl]-6H-pyrrolo[2,3-e][1,2,4]triazolo[4,3-a]pyridin-4-amine bis(trifluoroacetate) salt

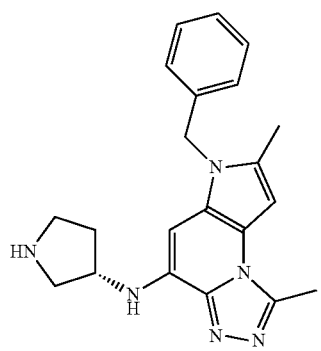 [SMILES: Cc1cc2c(cc(N[C@H]3CCNC3)c3nnc(C)n32)n1Cc1ccccc1]

The title compound was prepared according to the methods of Example 151, using tert-butyl (3S)-3-[(6-benzyl-1,7-dimethyl-6H-pyrrolo[2,3-e][1,2,4]triazolo[4,3-a]pyridin-4-yl)amino]pyrrolidine-1-carboxylate (Example 150).

LCMS (M+H)$^+$: 361.2.

Example 153

1,7-dimethyl-N-(1-methylpiperidin-4-yl)-6-(pyridin-2-ylmethyl)-6H-pyrrolo[2,3-e][1,2,4]triazolo[4,3-a]pyridin-4-amine

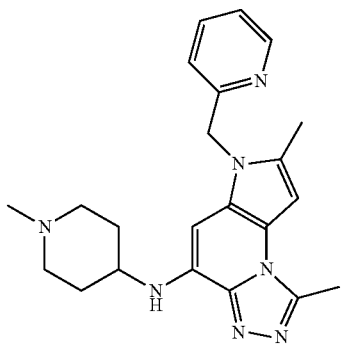

Step 1. 4-chloro-1,7-dimethyl-6-(pyridin-2-ylmethyl)-6H-pyrrolo[2,3-e][1,2,4]triazolo[4,3-a]pyridine

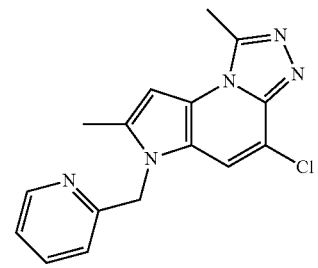 [SMILES: Cc1cc2c(cc(Cl)c3nnc(C)n32)n1Cc1ccccn1]

To 4-chloro-1,7-dimethyl-6H-pyrrolo[2,3-e][1,2,4]triazolo[4,3-a]pyridine (0.150 g, 0.680 mmol, from Example 228, Step 6) and Cs$_2$CO$_3$ (0.88 g, 2.7 mmol) in DMF (2.10 mL) was added 2-(chloromethyl)pyridine hydrochloride (0.139 g, 0.850 mmol, Aldrich). The reaction was stirred overnight, then diluted with water and extracted with three portions of 5% iPrOH in DCM. The combined organic extracts were dried over sodium sulfate, filtered and concentrated. The product was purified by flash chromatography, eluting with a gradient from 0-10% MeOH in DCM. Yield: (206 mg, 97%).

LCMS (M+H)$^+$: 312.1314.1.

Step 2. 1,7-dimethyl-N-(1-methylpiperidin-4-yl)-6-(pyridin-2-ylmethyl)-6H-pyrrolo[2,3-e][1,2,4]triazolo[4,3-a]pyridin-4-amine A degassed mixture of 4-chloro-1,7-dimethyl-6-(pyridin-2-ylmethyl)-6H-pyrrolo[2,3-e][1,2,4]triazolo[4,3-a]pyridine (50.0 mg, 0.160 mmol, from Step 1), 1-methylpiperidin-4-amine (0.072 mg, 0.48 mmol, Matrix), Sodium tert-butoxide (77 mg, 0.80 mmol, Aldrich), (9,9-dimethyl-9H-xanthene-4,5-diyl)bis(diphenylphosphine) (23 mg, 0.040 mmol, Aldrich) and tris(dibenzylideneacetone)dipalladium(0) (18 mg, 0.020 mmol, Aldrich) in toluene (3.1 mL) was heated at 125° C. for 2.5 hours. The product was purified via preparative HPLC-MS (Waters XBridge C18, eluting with a gradient of MeCN/H$_2$O containing 0.15% NH$_4$OH). Yield: (10 mg, 16%).

$^1$H NMR (500 MHz, d$_6$-DMSO) δ 8.52 (d, J=4.4 Hz, 1H), 7.71 (td, J=7.7, 1.7 Hz, 1H), 7.27 (dd, J=7.1, 5.0 Hz, 1H), 6.85 (d, J=7.9 Hz, 1H), 6.60 (s, 1H), 6.57 (s, 1H), 5.49 (s, 2H), 5.24 (d, J=8.6 Hz, 1H), 3.42-3.32 (m, 1H), 2.82 (s, 3H), 2.75-2.63

(m, 2H), 2.34 (s, 3H), 2.17 (s, 3H), 2.07-1.97 (m, 2H), 1.91-1.78 (m, 2H), 1.55-1.42 (m, 2H); LCMS (M+H)+: 390.3.

Example 154

1,7-dimethyl-N-(1-methylpiperidin-4-yl)-6-(pyridin-3-ylmethyl)-6H-pyrrolo[2,3-e][1,2,4]triazolo[4,3-a]pyridin-4-amine

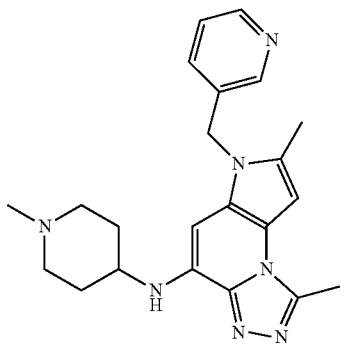

Prepared as in Example 153, using 3-(chloromethyl)pyridine hydrochloride (0.139 g, 0.850 mmol, Aldrich) in Step 1. Yield (Step 1): (136 mg, 64%). Yield (Step 2): (10 mg, 16%).

1H NMR (500 MHz, d6-DMSO) δ 8.45 (dd, J=2.8, 3.7 Hz, 1H), 8.38-8.35 (m, 1H), 7.33-7.31 (m, 2H), 6.61 (s, 1H), 6.58 (s, 1H), 5.48 (s, 2H), 5.28 (d, J=8.7 Hz, 1H), 3.44-3.34 (m, 1H), 2.82 (s, 3H), 2.74-2.64 (m, 2H), 2.33 (s, 3H), 2.17 (s, 3H), 2.02 (dd, J=1.9, 11.5 Hz, 2H), 1.91-1.82 (m, 2H), 1.56-1.43 (m, 2H); LCMS (M+H)+: 390.3.

Example 155

6-(3-chlorobenzyl)-1-methyl-7-(1H-pyrazol-5-yl)-6H-pyrrolo[2,3-e][1,2,4]triazolo[4,3-a]pyridine bis(trifluoroacetate) salt

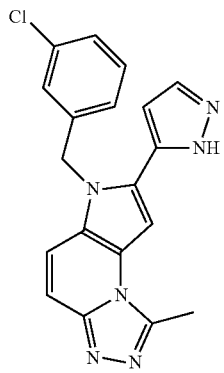 [SMILES: Cc1nnc2ccc3c(cc(-c4ccn[nH]4)n3Cc3cccc(Cl)c3)n12]

The title compound was prepared according to the methods of Example 103, Step 5, with the exception of the purification step. Title compound was purified via preparative HPLC-MS (Waters SunFire C18, eluting with a gradient of MeCN/H2O containing 0.1% TFA).

1H NMR (400 MHz, d6-DMSO) δ 13.31 (s, 1H), 8.19 (d, J=9.5 Hz, 1H), 7.95 (d, J=2.2 Hz, 1H), 7.65 (s, 1H), 7.55 (d, J=9.6 Hz, 1H), 7.34-7.24 (m, 2H), 7.17-7.10 (m, 1H), 7.04-6.94 (m, 2H), 6.21 (s, 2H), 3.06 (s, 3H); LCMS (M+H)+: 363.1.

Example 156

7-(1-azetidin-3-yl-1H-pyrazol-3-yl)-6-(3-chlorobenzyl)-1-methyl-6H-pyrrolo[2,3-e][1,2,4]triazolo[4,3-a]pyridine bis(trifluoroacetate) salt

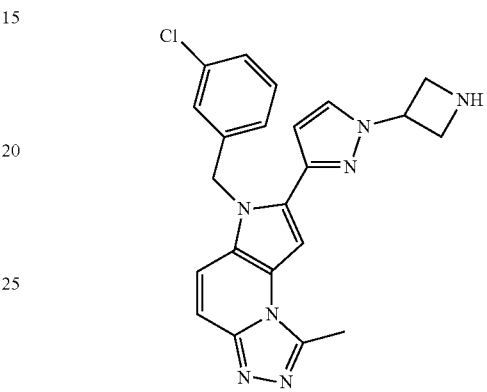

Tert-Butyl-3-hydroxyazetidine-1-carboxylate (0.20 g, 1.2 mmol, Aldrich) in THF (10 mL) at 0° C. was treated with triethylamine (0.32 mL, 2.3 mmol) and methanesulfonyl chloride (0.11 mL, 1.4 mmol, Aldrich). After 1.5 hours, water was added, and the aqueous mixture was extracted with EtOAc. The combined organic extracts were washed with brine, dried over Na2SO4, filtered and concentrated to afford crude tert-butyl 3-[(methylsulfonyl)oxy]azetidine-1-carboxylate, which was used in further step without purification.

To 6-(3-chlorobenzyl)-1-methyl-7-(1H-pyrazol-5-yl)-6H-pyrrolo[2,3-e][1,2,4]triazolo[4,3-a]pyridine (30. mg, 0.083 mmol, prepared according to the methods of Example 103, Step 5) in DMF (1.8 mL) was added Cs2CO3 (40. mg, 0.12 mmol), followed by tert-butyl 3-[(methylsulfonyl)oxy]azetidine-1-carboxylate (42 mg, 0.16 mmol, prepared above). The mixture was heated at 50° C. for 2 days. The reaction mixture was diluted with water and the product was extracted with three portions of EtOAc. The combined organic extracts were washed twice with brine, dried over sodium sulfate, filtered and concentrated. The residue was dissolved in MeCN (1.2 mL) and treated with 4.0 M HCl in dioxane (0.48 mL, 1.9 mmol) and stirred for 45 minutes. The reaction mixture was concentrated in vacuo. The title product was purified via preparative HPLC-MS (Waters SunFire C18, eluting with a gradient of MeCN/H2O containing 0.1% TFA). Yield: (23 mg, 43%).

Pure 7-(1-azetidin-3-yl-1H-pyrazol-3-yl)-6-(3-chlorobenzyl)-1-methyl-6H-pyrrolo[2,3-e][1,2,4]triazolo[4,3-a]pyridine was obtained by preparative HPLC-MS using the following conditions: Waters XBridge C18, eluting with a gradient of MeCN/H2O containing 0.15% NH4OH.

1H NMR (300 MHz, d6-DMSO) δ 7.94 (d, J=2.3 Hz, 1H), 7.76 (d, J=9.8 Hz, 1H), 7.40 (s, 1H), 7.37 (d, J=9.7 Hz, 1H), 7.34-7.22 (m, 2H), 7.22-7.15 (m, 1H), 7.03-6.95 (m, 1H), 6.85 (d, J=2.4 Hz, 1H), 6.10 (s, 2H), 5.21 (p, J=7.1 Hz, 1H), 3.88 (t, J=7.7 Hz, 2H), 3.70 (t, J=8.0 Hz, 2H), 2.96 (s, 3H); LCMS (M+H)$^+$: 418.2.

Example 157

(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile bis(trifluoroacetate) salt

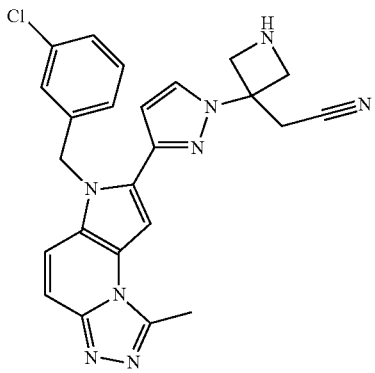 [SMILES: Cc1nnc2ccc3c(cc(-c4ccn(C5(CC#N)CNC5)n4)n3Cc3cccc(Cl)c3)n12]

6-(3-Chlorobenzyl)-1-methyl-7-(1H-pyrazol-5-yl)-6H-pyrrolo[2,3-e][1,2,4]triazolo[4,3-a]pyridine (25 mg, 0.069 mmol, prepared according to the methods of Example 103, Step 5) in acetonitrile (0.90 mL) was treated with tert-butyl 3-(cyanomethylene)azetidine-1-carboxylate (27 mg, 0.14 mmol, prepared as in WO2009/114512) and 1,8-diazabicyclo[5.4.0]undec-7-ene (10. µL, 0.069 mmol, Aldrich) for 70 minutes, after which time 4.0 M HCl in dioxane (0.23 mL, 0.90 mmol) was added to the reaction mixture. After 30 minutes, solvent was removed in vacuo and the residue was dissolved in MeOH and made basic by the addition of aq. NH$_4$OH. This solution was purified via preparative HPLC-MS (Waters XBridge C18, eluting with a gradient of MeCN/H$_2$O containing 0.15% NH$_4$OH). Yield: (23 mg, 73%).

$^1$H NMR (400 MHz, d$_6$-DMSO) δ 8.13 (d, J=2.5 Hz, 1H), 7.78 (d, J=9.8 Hz, 1H), 7.45 (s, 1H), 7.38 (d, J=9.7 Hz, 1H), 7.29-7.23 (m, 2H), 7.19-7.15 (m, 1H), 6.97 (d, J=2.5 Hz, 1H), 6.96-6.93 (m, 1H), 6.04 (s, 2H), 3.87 (d, J=9.1 Hz, 2H), 3.59 (d, J=9.3 Hz, 2H), 3.46 (s, 2H), 2.96 (s, 3H); LCMS (M+H)$^+$: 456.6.

A portion of this product (2.5 mg, 0.0055 mmol) was purified via preparative HPLC-MS (Waters SunFire C18, eluting with a gradient of MeCN/H$_2$O containing 0.1% TFA) to afford product as the bis(trifluoroacetate) salt. Yield: (3.0 mg, 80%).

LCMS (M+H)$^+$: 457.1.

Example 158

(3-{3-[6-(3-Chlorobenzyl)-1-methyl-6H-pyrrolo[2,3-e][1,2,4]triazolo[4,3-a]pyridin-7-yl]-1H-pyrazol-1-yl}-1-ethylazetidin-3-yl)acetonitrile bis(trifluoroacetate) salt

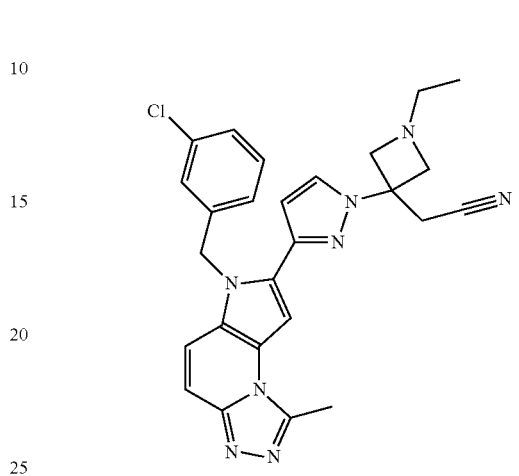

A solution of (3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile (5.5 mg, 0.012 mmol, from Example 157 as the free base) in MeOH (0.23 mL) was treated with acetaldehyde (3.4 µL, 0.060 mmol, Aldrich) and sodium triacetoxyborohydride (7.6 mg, 0.036 mmol, Aldrich). After 10 minutes, the product was purified via preparative HPLC-MS (Waters SunFire C18, eluting with a gradient of MeCN/H$_2$O containing 0.1% TFA). Yield: (5.5 mg, 64%).

$^1$H NMR (400 MHz, d$_6$-DMSO) δ 8.35 (br s, 1H), 8.12 (d, J=9.5 Hz, 1H), 7.68 (s, 1H), 7.58 (d, J=9.7 Hz, 1H), 7.35-7.26 (m, 2H), 7.22-7.15 (m, 2H), 7.03-6.95 (m, 1H), 6.15 (s, 2H), 4.56 (br m, 8H), 3.04 (s, 3H), 1.13-0.86 (m, 3H); LCMS (M+H)$^+$: 485.3.

Example 159

3-{3-[6-(3-Chlorobenzyl)-1-methyl-6H-pyrrolo[2,3-e][1,2,4]triazolo[4,3-a]pyridin-7-yl]-1H-pyrazol-1-yl}propanamide trifluoroacetate salt

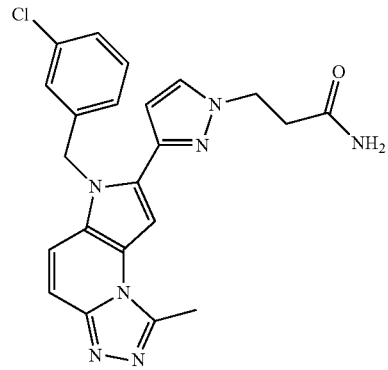 [SMILES: Cc1nnc2ccc3c(cc(-c4ccn(CCC(N)=O)n4)n3Cc3cccc(Cl)c3)n12]

Step 1. 3-{3-[6-(3-Chlorobenzyl)-1-methyl-6H-pyrrolo[2,3-e][1,2,4]triazolo[4,3-a]pyridin-7-yl]-1H-pyrazol-1-yl}propanoic acid

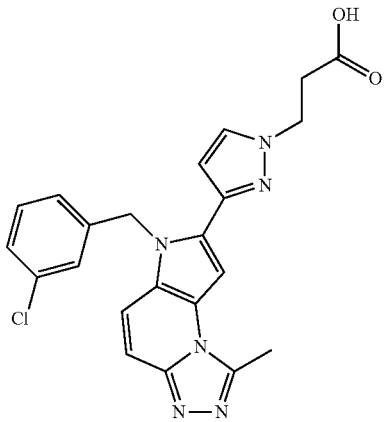 [SMILES: Cc1nnc2ccc3c(cc(-c4ccn(CCC(=O)O)n4)n3Cc3cccc(Cl)c3)n12]

6-(3-Chlorobenzyl)-1-methyl-7-(1H-pyrazol-5-yl)-6H-pyrrolo[2,3-e][1,2,4]triazolo[4,3-a]pyridine (25 mg, 0.069 mmol, from Example 103, Step 5) in acetonitrile (0.90 mL) was treated with methyl acrylate (19 μL, 0.21 mmol, Aldrich) and 1,8-diazabicyclo[5.4.0]undec-7-ene (10. μL, 0.069 mmol, Aldrich) and stirred for 70 minutes. Purification via preparative HPLC-MS (Waters XBridge C18, eluting with a gradient of MeCN/H$_2$O containing 0.15% NH$_4$OH) followed by evaporation of eluent afforded methyl 3-(3-(6-(3-chlorobenzyl)-1-methyl-6H-pyrrolo[2,3-e][1,2,4]triazolo[4,3-a]pyridin-7-yl)-1H-pyrazol-1-yl)propanoate. The ester intermediate was dissolved in THF (0.45 mL) and was treated with 1.0 M NaOH in water (0.45 mL, 0.45 mmol). After 25 minutes, the reaction was acidified to pH 3-4 by the addition of 1 N HCl. Water was added (3 mL), and the precipitated product was isolated by filtration and air dried. Yield: (21 mg, 70%).

$^1$H NMR (400 MHz, d$_6$-DMSO) δ 12.42 (s, 1H), 7.84 (d, J=2.3 Hz, 1H), 7.72 (d, J=10.0 Hz, 1H), 7.39-7.31 (m, 2H), 7.29-7.24 (m, 2H), 7.18-7.13 (m, 1H), 7.00-6.94 (m, 1H), 6.79 (d, J=2.3 Hz, 1H), 6.05 (s, 2H), 4.35 (t, J=6.7 Hz, 2H), 2.95 (s, 3H), 2.79 (t, J=6.7 Hz, 2H); LCMS (M+H)$^+$: 434.6.

Step 2. 3-{3-[6-(3-Chlorobenzyl)-1-methyl-6H-pyrrolo[2,3-e][1,2,4]triazolo[4,3-a]pyridin-7-yl]-1H-pyrazol-1-yl}propanamide trifluoroacetate salt A solution of 3-{3-[6-(3-chlorobenzyl)-1-methyl-6H-pyrrolo[2,3-e][1,2,4]triazolo[4,3-a]pyridin-7-yl]-1H-pyrazol-1-yl}propanoic acid (10. mg, 0.023 mmol, from Step 1) in DMF (0.46 mL) was treated with N,N-diisopropylethylamine (16 μL, 0.092 mmol) and HATU (16 mg, 0.041 mmol). After two minutes, ammonia (gas, Aldrich) was bubbled through the mixture for 30 seconds), and the reaction vessel was sealed and stirred for 15 minutes. The reaction mixture was diluted with MeOH, and the title product was purified via preparative HPLC-MS (Waters SunFire C18, eluting with a gradient of MeCN/H$_2$O containing 0.1% TFA). Yield: (10.2 mg, 81%).

$^1$H NMR (400 MHz, d$_6$-DMSO) δ 8.33 (d, J=9.6 Hz, 1H), 7.87 (d, J=2.3 Hz, 1H), 7.63 (s, 1H), 7.60 (d, J=9.6 Hz, 1H), 7.40 (br s, 1H), 7.34-7.25 (m, 2H), 7.18 (br s, 1H), 7.06-6.99 (m, 1H), 6.94 (br s, 1H), 6.93 (d, J=2.3 Hz, 1H), 6.19 (s, 2H), 4.37 (t, J=6.9 Hz, 2H), 3.06 (s, 3H), 2.65 (t, J=6.9 Hz, 2H); LCMS (M+H)$^+$: 434.2.

Example 160

6-(3-Chlorobenzyl)-7-[1-(1-ethylazetidin-3-yl)-1H-pyrazol-3-yl]-1-methyl-6H-pyrrolo[2,3-e][1,2,4]triazolo[4,3-a]pyridine bis(trifluoroacetate) salt

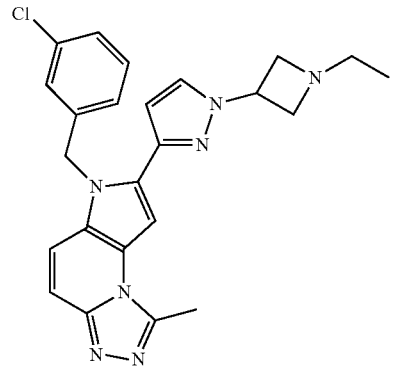 [SMILES: CCN1CC(n2ccc(-c3cc4c(ccc5nnc(C)n54)n3Cc3cccc(Cl)c3)n2)C1]

A solution of 7-(1-azetidin-3-yl-1H-pyrazol-3-yl)-6-(3-chlorobenzyl)-1-methyl-6H-pyrrolo[2,3-e][1,2,4]triazolo[4,3-c]pyridine bis(trifluoroacetate) salt (10.1 mg, 0.0156 mmol, prepared as in Example 156) in methanol (0.30 mL) was treated with triethylamine (8.7 μL, 0.062 mmol), acetaldehyde (4.4 μL, 0.078 mmol, Aldrich) and sodium triacetoxyborohydride (9.9 mg, 0.047 mmol, Aldrich). The reaction was complete in about 10 minutes, and the product was purified via preparative HPLC-MS (Waters SunFire C18, eluting with a gradient of MeCN/H$_2$O containing 0.1% TFA). Yield: (8.0 mg, 76%).

LCMS (M+H)$^+$: 446.1.

Example 161

3-{3-[6-(3-Chlorobenzyl)-1-methyl-6H-pyrrolo[2,3-e][1,2,4]triazolo[4,3-a]pyridin-7-yl]-1H-pyrazol-1-yl}-N,N-dimethylazetidine-1-sulfonamide bis(trifluoroacetate) salt

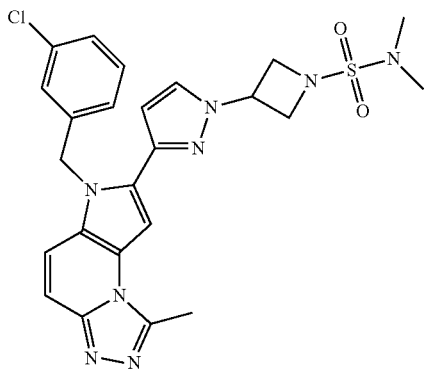 [SMILES: Cc1nnc2ccc3c(cc(-c4ccn(C5CN(S(=O)(=O)N(C)C)C5)n4)n3Cc3cccc(Cl)c3)n12]

A solution of 7-(1-azetidin-3-yl-1H-pyrazol-3-yl)-6-(3-chlorobenzyl)-1-methyl-6H-pyrrolo[2,3-e][1,2,4]triazolo[4, 3-a]pyridine bis(trifluoroacetate) salt (10.2 mg, 0.0158 mmol, prepared as in Example 156) in DCM (0.56 mL) was treated with triethylamine (11 μL, 0.079 mmol) and dimethylsulfamoyl chloride (2.5 μL, 0.024 mmol, Aldrich) and stirred for 35 minutes. Additional triethylamine (4.4 μL, 0.032 mmol) and dimethylsulfamoyl chloride (1.0 μL, 0.0093 mmol) were added. When the reaction was complete as determined by HPLC-MS, the product was purified via preparative HPLC-MS (Waters SunFire C18, eluting with a gradient of MeCN/H$_2$O containing 0.1% TFA). Yield: (6.3 mg, 90%).

$^1$H NMR (400 MHz, d$_6$-DMSO) δ 8.26 (d, J=9.7 Hz, 1H), 7.98 (d, J=2.4 Hz, 1H), 7.70 (s, 1H), 7.60 (d, J=9.6 Hz, 1H), 7.32-7.22 (m, 2H), 7.15-7.11 (m, 1H), 7.04 (d, J=2.4 Hz, 1H), 7.04-7.00 (m, 1H), 6.30 (s, 2H), 5.42-5.22 (m, 1H), 4.35-4.05 (m, 4H), 3.06 (s, 3H), 2.74 (s, 6H); LCMS (M+H)$^+$: 525.3.

Example 162

2-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)-N,N-dimethyl-2-oxoethanamine bis(trifluoroacetate) salt

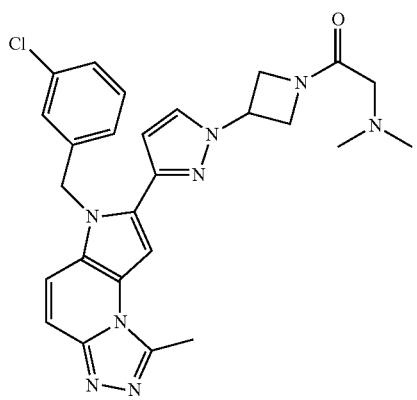 [SMILES: Cc1nnc2ccc3c(cc(-c4ccn(C5CN(C(=O)CN(C)C)C5)n4)n3Cc3cccc(Cl)c3)n12]

A solution of 7-(1-azetidin-3-yl-1H-pyrazol-3-yl)-6-(3-chlorobenzyl)-1-methyl-6H-pyrrolo[2,3-e][1,2,4]triazolo[4,3-a]pyridine (5.0 mg, 0.012 mmol, prepared as in Example 156, isolated as the free base) in DCM (0.50 mL) was treated with dimethylaminoacetyl chloride hydrochloride (2.8 mg, 0.018 mmol, Aldrich) and triethylamine (5.0 μL, 0.036 mmol). The reaction was complete within a few minutes and the product was purified via preparative HPLC-MS (Waters SunFire C18, eluting with a gradient of MeCN/H$_2$O containing 0.1% TFA). Yield: (6.7 mg, 76%).

$^1$H NMR (400 MHz, d$_6$-DMSO) δ 9.83 (s, 1H), 8.23 (d, J=9.8 Hz, 1H), 8.06 (d, J=2.4 Hz, 1H), 7.66 (s, 1H), 7.59 (d, J=9.7 Hz, 1H), 7.33-7.24 (m, 2H), 7.12-7.08 (m, 1H), 7.06-7.01 (m, 1H), 7.02 (d, J=2.4 Hz, 1H), 6.21 (d, J=16.5 Hz, 1H), 6.11 (d, J=16.5 Hz, 1H), 5.40 (ddd, J=13.5, 8.1, 5.4 Hz, 1H), 4.62 (t, J=8.8 Hz, 1H), 4.50-4.38 (m, 2H), 4.17 (dd, J=10.3, 5.3 Hz, 1H), 4.07 (d, J=16.2 Hz, 1H), 3.99 (d, J=15.6 Hz, 1H), 3.04 (s, 3H), 2.81 (s, 6H); LCMS (M+H)$^+$: 503.2.

Example 163

6-(3-Chlorobenzyl)-1-methyl-7-[1-(1-propionylazetidin-3-yl)-1H-pyrazol-3-yl]-6H-pyrrolo[2,3-e][1,2,4]triazolo[4,3-a]pyridine trifluoroacetate salt

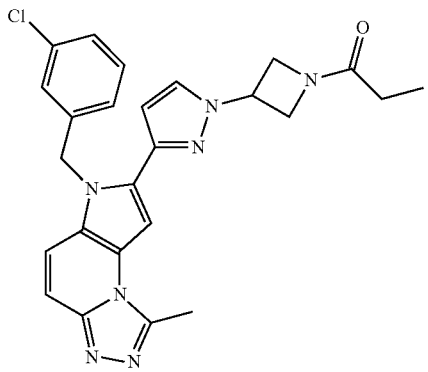 [SMILES: CCC(=O)N1CC(n2ccc(-c3cc4c(ccc5nnc(C)n54)n3Cc3cccc(Cl)c3)n2)C1]

The title compound was prepared according to the methods of Example 162, using propanoyl chloride (1.6 μL, 0.018 mmol, Aldrich). A drop of aqueous ammonia and MeOH (0.5 mL) were added to the reaction mixture before purification. Yield: (4.2 mg, 60%).

$^1$H NMR (400 MHz, d$_6$-DMSO) δ 8.27 (d, J=9.6 Hz, 1H), 8.05 (d, J=2.4 Hz, 1H), 7.69 (s, 1H), 7.59 (d, J=9.6 Hz, 1H), 7.32-7.25 (m, 2H), 7.13-7.08 (m, 1H), 7.07-7.00 (m, 1H), 7.03 (d, J=2.4 Hz, 1H), 6.21 (d, J=16.5 Hz, 1H), 6.13 (d, J=16.4 Hz, 1H), 5.31 (tt, J=8.1, 5.3 Hz, 1H), 4.54 (t, J=8.4 Hz, 1H), 4.32-4.23 (m, 2H), 4.06 (dd, J=10.1, 5.5 Hz, 1H), 3.06 (s, 3H), 2.05 (dq, J=11.1, 7.8 Hz, 2H), 0.96 (t, J=7.5 Hz, 3H); LCMS (M+H)$^+$: 474.2.

Example 164

6-(3-Chlorobenzyl)-7-{1-[1-(cyclopropylcarbonyl)azetidin-3-yl]-1H-pyrazol-3-yl}-1-methyl-6H-pyrrolo[2,3-e][1,2,4]triazolo[4,3-a]pyridine trifluoroacetate salt

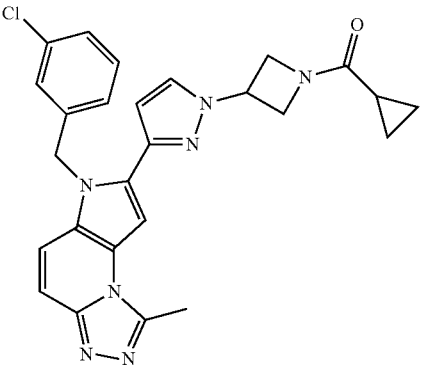 [SMILES: Cc1nnc2ccc3c(cc(-c4ccn(C5CN(C(=O)C6CC6)C5)n4)n3Cc3cccc(Cl)c3)n12]

The title compound was prepared according to the methods of Example 162, using cyclopropanecarbonyl chloride (1.6 μL, 0.018 mmol. Aldrich). Yield: (5.0 mg, 70%).

¹H NMR (400 MHz, d₆-DMSO) δ 8.33 (d, J=9.6 Hz, 1H), 8.06 (d, J=2.4 Hz, 1H), 7.71 (s, 1H), 7.62 (d, J=9.6 Hz, 1H), 7.31-7.26 (m, 2H), 7.09-7.05 (m, 2H), 7.04 (d, J=2.4 Hz, 1H), 6.22 (d, J=16.4 Hz, 1H), 6.15 (d, J=16.1 Hz, 1H), 5.36 (tt, J=7.8, 5.1 Hz, 1H), 4.70 (t, J=8.3 Hz, 1H), 4.43 (dd, J=8.8, 5.2 Hz, 1H), 4.31 (t, J=9.1 Hz, 1H), 4.10 (dd, J=9.9, 5.2 Hz, 1H), 3.07 (s, 3H), 1.59-1.51 (m, 1H), 0.79-0.67 (m, 4H); LCMS (M+H)⁺: 486.2.

Example 165

6-(3-Chlorobenzyl)-7-{1-[1-(cyclopropylsulfonyl)azetidin-3-yl]-1H-pyrazol-3-yl}-1-methyl-6H-pyrrolo[2,3-e][1,2,4]triazolo[4,3-a]pyridine trifluoroacetate salt

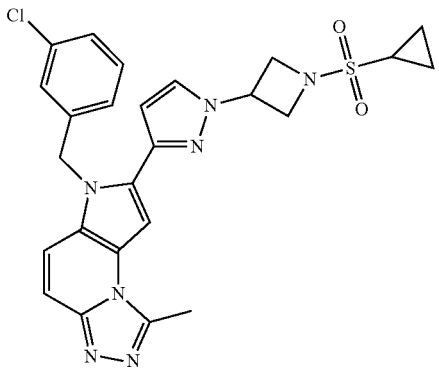 [SMILES: Cc1nnc2ccc3c(cc(-c4ccn(C5CN(S(=O)(=O)C6CC6)C5)n4)n3Cc3cccc(Cl)c3)n12]

The title compound was prepared according to the methods of Example 162, using cyclopropanesulfonyl chloride (1.8 µL, 0.018 mmol, Aldrich). Yield: (4.8 mg, 63%).
¹H NMR (400 MHz, d₆-DMSO) δ 8.19 (d, J=9.7 Hz, 1H), 8.02 (d, J=2.4 Hz, 1H), 7.68 (s, 1H), 7.58 (d, J=9.6 Hz, 1H), 7.35-7.25 (m, 2H), 7.17-7.12 (m, 1H), 7.08-7.03 (m, 2H), 6.24 (s, 2H), 5.44-5.34 (m, 1H), 4.33 (dd, J=8.5, 6.7 Hz, 2H), 4.26 (t, J=8.3 Hz, 2H), 3.05 (s, 3H), 2.66-2.58 (m, 1H), 0.97-0.89 (m, 4H); LCMS (M+H)⁺: 522.1.

Example 166

6-(3-Chlorobenzyl)-7-{1-[1-(ethylsulfonyl)azetidin-3-yl]-1H-pyrazol-3-yl}-1-methyl-6H-pyrrolo[2,3-e][1,2,4]triazolo[4,3-a]pyridine trifluoroacetate salt

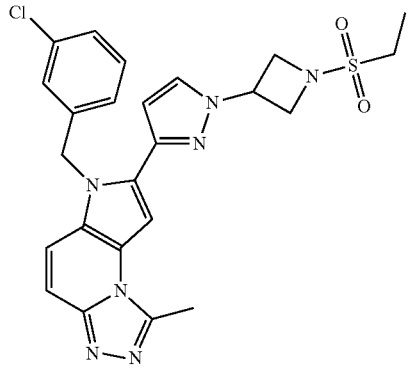 [SMILES: CCS(=O)(=O)N1CC(n2ccc(-c3cc4c(ccc5nnc(C)n54)n3Cc3cccc(Cl)c3)n2)C1]

The title compound was prepared according to the methods of Example 162, using ethanesulfonyl chloride (1.7 µL, 0.018 mmol, Aldrich). Yield: (5.3 mg, 71%).
¹H NMR (400 MHz, d₆-DMSO) δ 8.48 (d, J=9.6 Hz, 1H), 8.03 (d, J=2.4 Hz, 1H), 7.80 (s, 1H), 7.69 (d, J=9.6 Hz, 1H), 7.34-7.24 (m, 2H), 7.19-7.13 (m, 1H), 7.13-7.06 (m, 2H), 6.29 (s, 2H), 5.38 (p, J=7.0 Hz, 1H), 4.33-4.21 (m, 4H), 3.11 (q, J=7.3 Hz, 2H), 3.10 (s, 3H), 1.20 (t, J=7.3 Hz, 3H); LCMS (M+H)⁺: 510.2.

Example 167

Ethyl 3-{3-[6-(3-chlorobenzyl)-1-methyl-6H-pyrrolo[2,3-e][1,2,4]triazolo[4,3-a]pyridin-7-yl]-1H-pyrazol-1-yl}azetidine-1-carboxylate trifluoroacetate salt

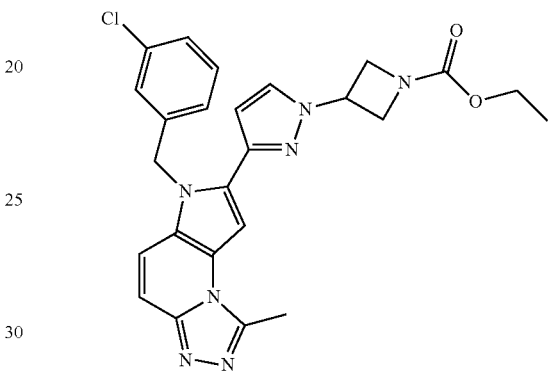

The title compound was prepared according to the methods of Example 162 using ethyl chloroformate (1.7 µL, 0.018 mmol, Alfa Aesar). Yield: (5.2 mg, 72%).
¹H NMR (400 MHz, d₆-DMSO) δ 8.30 (d, J=9.5 Hz, 1H), 8.03 (d, J=2.4 Hz, 1H), 7.69 (s, 1H), 7.61 (d, J=9.6 Hz, 1H), 7.32-7.25 (m, 2H), 7.13-7.09 (m, 1H), 7.05 (ddd, J=4.7, 3.4, 1.6 Hz, 1H), 7.02 (d, J=2.4 Hz, 1H), 6.18 (s, 2H), 5.30 (tt, J=8.0, 5.1 Hz, 1H), 4.41-4.28 (m, 2H), 4.14 (dd, J=8.6, 4.8 Hz, 2H), 4.02 (q, J=7.0 Hz, 2H), 3.06 (s, 3H), 1.17 (t, J=7.1 Hz, 3H); LCMS (M+H)⁺: 490.3.

Example 168

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-oxetan-3-ylpropanamide trifluoroacetate salt

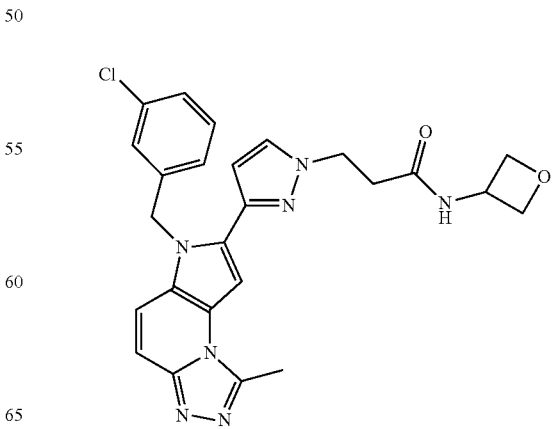

A solution of 3-{3-[6-(3-chlorobenzyl)-1-methyl-6H-pyrrolo[2,3-e][1,2,4]triazolo[4,3-c]pyridin-7-yl]-1H-pyrazol-1-yl}propanoic acid (5.0 mg, 0.011 mmol, prepared as in Example 159, Step 1) in DMF (0.23 mL) was treated with N,N-diisopropylethylamine (8.0 μL, 0.046 mmol) and HATU (7.9 mg, 0.021 mmol), followed by oxetan-3-amine (2.4 μL, 0.034 mmol, Synthonix). After 15 minutes, the reaction mixture was diluted with MeOH, and the product was isolated by preparative HPLC-MS (Waters SunFire C18, eluting with a gradient of MeCN/H$_2$O containing 0.1% TFA). Yield: (4.3 mg, 62%).

$^1$H NMR (400 MHz, d$_6$-DMSO, rotamers) δ 8.69 (d, J=6.5 Hz, 0.5H), 8.19 (d, J=9.7 Hz, 0.5H), 8.09 (d, J=9.7 Hz, 0.5H), 8.05-7.96 (m, 1H), 7.89 (d, J=2.4 Hz, 0.5H), 7.83 (d, J=2.3 Hz, 0.5H), 7.58-7.48 (m, 2H), 7.31-7.22 (m, 2H), 7.18-7.12 (m, 1H), 7.02-6.93 (m, 1H), 6.90 (d, J=2.3 Hz, 0.5H), 6.88 (d, J=2.3 Hz, 0.5H), 6.14 (s, 1H), 6.11 (s, 1H), 4.74-4.66 (m, 0.5H), 4.63 (t, J=6.7 Hz, 1H), 4.43 (t, J=6.7 Hz, 1H), 4.37 (t, J=6.7 Hz, 1H), 4.30 (t, J=6.3 Hz, 1H), 4.17-4.05 (m, 1H), 3.57 (dd, J=11.4, 4.7 Hz, 0.5H), 3.49 (dd, J=11.5, 5.8 Hz, 0.5H), 3.38-3.29 (m, 0.5H), 3.01 (s, 1.5H), 3.01 (s, 1.5H), 2.92 (t, J=6.7 Hz, 1H), 2.68 (t, J=6.8 Hz, 1H); LCMS (M+H)$^+$: 490.2.

Example 169

6-(3-Chlorobenzyl)-1-methyl-7-[1-(3-morpholin-4-yl-3-oxopropyl)-1H-pyrazol-3-yl]-6H-pyrrolo[2,3-e][1,2,4]triazolo[4,3-a]pyridine trifluoroacetate salt

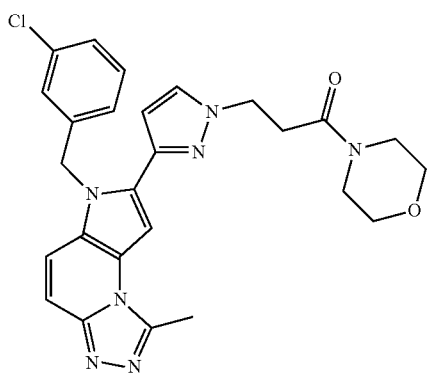 [SMILES: Cc1nnc2ccc3c(cc(-c4ccn(CCC(=O)N5CCOCC5)n4)n3Cc3cccc(Cl)c3)n12]

The title compound was prepared according to the methods of Example 168, using morpholine (3.0 μL, 0.034 mmol, Aldrich). Yield: (2.8 mg, 39%).

$^1$H NMR (400 MHz, d$_6$-DMSO) δ 8.27 (d, J=9.7 Hz, 1H), 7.90 (d, J=2.3 Hz, 1H), 7.63 (s, 1H), 7.58 (d, J=9.6 Hz, 1H), 7.33-7.26 (m, 2H), 7.20-7.15 (m, 1H), 7.04-6.97 (m, 1H), 6.94 (d, J=2.3 Hz, 1H), 6.18 (s, 2H), 4.40 (t, J=6.8 Hz, 2H), 3.50-3.41 (m, 4H), 3.38 (dd, J=5.6, 4.0 Hz, 2H), 3.30-3.23 (m, 2H), 3.05 (s, 3H), 2.87 (t, J=6.8 Hz, 2H); LCMS (M+H)$^+$: 504.3.

Example 170

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-(tetrahydro-2H-pyran-4-yl)propanamide trifluoroacetate salt

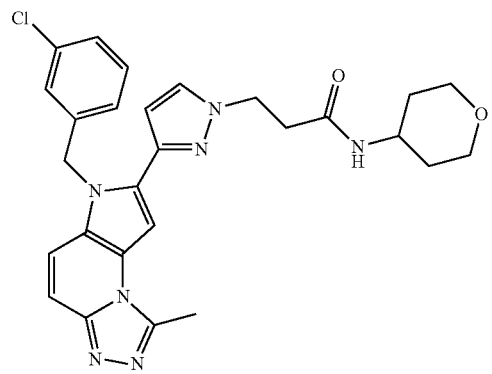 [SMILES: Cc1nnc2ccc3c(cc(-c4ccn(CCC(=O)NC5CCOCC5)n4)n3Cc3cccc(Cl)c3)n12]

The title compound was prepared according to the methods of Example 168, using tetrahydro-2H-pyran-4-amine (3.5 mg, 0.034 mmol, Combi-Blocks). Yield: (3.3 mg, 45%).

$^1$H NMR (400 MHz, d$_6$-DMSO) δ 8.19 (d, J=9.5 Hz, 1H), 7.91 (d, J=7.5 Hz, 1H), 7.84 (d, J=2.3 Hz, 1H), 7.59-7.52 (m, 2H), 7.33-7.25 (m, 2H), 7.22-7.16 (m, 1H), 7.04-6.96 (m, 1H), 6.90 (d, J=2.3 Hz, 1H), 6.16 (s, 2H), 4.39 (t, J=6.8 Hz, 2H), 3.76 (dt, J=11.7, 3.5 Hz, 2H), 3.69 (ddd, J=14.7, 7.2, 3.6 Hz, 1H), 3.29 (td, J=11.5, 2.1 Hz, 2H), 3.04 (s, 3H), 2.65 (t, J=6.8 Hz, 2H), 1.64-1.54 (m, 2H), 1.35-1.22 (m, 2H); LCMS (M+H)$^+$: 518.3.

Example 171

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-(1-methylazetidin-3-yl)propanamide bis(trifluoroacetate) salt

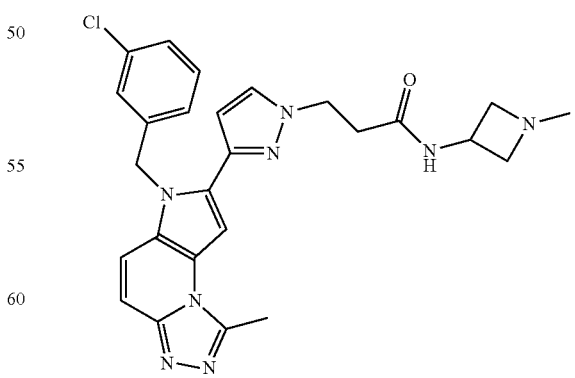

The title compound was prepared according to the methods of Example 168, using 1-methylazetidin-3-amine (3.0 mg, 0.034 mmol, Synthonix). Yield: (4.0 mg, 48%).

¹H NMR (400 MHz, d₆-DMSO) δ 9.75 (br s, 1H), 8.74-8.64 (m, 1H), 8.20 (d, J=9.5 Hz, 1H), 7.94-7.77 (m, 1H), 7.64-7.48 (m, 2H), 7.35-7.25 (m, 2H), 7.21-7.16 (m, 1H), 7.08-6.95 (m, 1H), 6.92 (d, J=2.3 Hz, 1H), 6.16 (s, 2H), 4.58-3.74 (m, 7H), 3.04 (s, 3H), 2.89-2.78 (m, 3H), 2.76-2.63 (m, 2H); LCMS (M+H)⁺: 503.3.

Example 172

6-(3-Chlorobenzyl)-7-(1H-imidazol-4-yl)-1-methyl-6H-pyrrolo[2,3-e][1,2,4]triazolo[4,3-a]pyridine bis(trifluoroacetate) salt

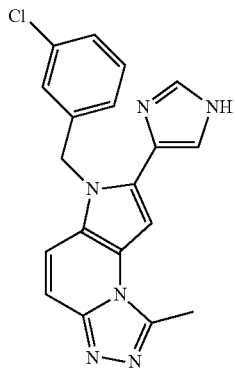 [SMILES: Cc1nnc2ccc3c(cc(-c4c[nH]cn4)n3Cc3cccc(Cl)c3)n12]

Step 1. 5-Chloro-1-(3-chlorobenzyl)-2-(1-trityl-1H-imidazol-4-yl)-1H-pyrrolo[3,2-b]pyridine

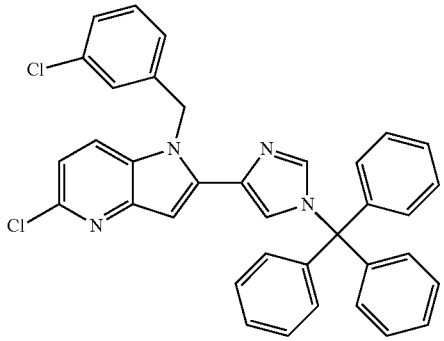 [SMILES: Clc1cccc(Cn2c(-c3cn(C(c4ccccc4)(c4ccccc4)c4ccccc4)cn3)cc3nc(Cl)ccc32)c1]

A mixture of 2-bromo-5-chloro-1-(3-chlorobenzyl)-1H-pyrrolo[3,2-b]pyridine (0.59 g, 1.7 mmol, prepared as in Example 103, Step 2) and 4-(tributylstannyl)-1-trityl-1H-imidazole (1.0 g, 1.7 mmol, Synthonix) in toluene (32 mL) was degassed. Tetrakis(triphenylphosphine)palladium(0) (0.19 g, 0.17 mmol, Strem) was added, and the mixture was heated at 110° C. for 17 hours. Solvent was removed in vacuo, and the product was purified by flash chromatography, eluting with a gradient from 0-35% EtOAc in hexanes. Yield: (0.61 g, 62%).
¹H NMR (400 MHz, CDCl₃) δ 7.51 (d, J=1.4 Hz, 1H), 7.41 (dd, J=8.5, 0.7 Hz, 1H), 7.38-7.30 (m, 9H), 7.18 (ddd, J=1.4, 1.9, 8.0 Hz, 1H), 7.15-7.08 (m, 7H), 7.06 (d, J=1.4 Hz, 1H), 7.01 (d, J=8.5 Hz, 1H), 6.97 (t, J=1.5 Hz, 1H), 6.79 (dt, J=7.5, 1.3 Hz, 1H), 6.75 (d, J=0.7 Hz, 1H), 5.76 (s, 2H); LCMS (M+H)⁺: 585.2.

Step 2. 6-(3-Chlorobenzyl)-7-(1H-imidazol-4-yl)-1-methyl-6H-pyrrolo[2,3-e][1,2,4]triazolo[4,3-a]pyridine bis(trifluoroacetate) salt A degassed mixture of 5-chloro-1-(3-chlorobenzyl)-2-(1-trityl-1H-imidazol-4-yl)-1H-pyrrolo[3,2-b]pyridine (0.61 g, 1.0 mmol, from Step 1), di-tert-butyl hydrazine-1,2-dicarboxylate (0.36 g, 1.6 mmol, Aldrich), Cs₂CO₃ (0.51 g, 1.6 mmol, Aldrich) and dicyclohexyl(2',4',6'-triisopropylbiphenyl-2-yl)phosphine-(2'-aminobiphenyl-2-yl)(chloro)palladium (1:1) (82 mg, 0.10 mmol, Aldrich) in toluene (21 mL) heated at 130° C. for 18 hours. The mixture was cooled to room temperature, diluted with DCM, and filtered. Solvent was removed in vacuo. The intermediate derivative of di-tert-butyl hydrazine-1,2-dicarboxylate was purified by flash chromatography, eluting with a gradient from 0-50% EtOAc in hexanes. The intermediate derivative of di-tert-butyl hydrazine-1,2-dicarboxylate was dissolved in acetic acid (20 mL) and evenly divided between two microwavable vials. Each vial was heated at 180° C. in the microwave for 8 minutes. The batches were combined, and acetic acid was removed in vacuo. The product was isolated by preparative HPLC-MS, sequential runs: first (Waters XBridge C18, eluting with a gradient of MeCN/H₂O containing 0.15% NH₄OH), followed by (Waters SunFire C18, eluting with a gradient of MeCN/H₂O containing 0.1% TFA).
¹H NMR (400 MHz, d₆-DMSO) δ 12.49 (br s, 1H), 7.82 (s, 1H), 7.71 (br s, 1H), 7.63 (d, J=9.7 Hz, 1H), 7.32-7.21 (m, 4H), 7.14 (s, 1H), 6.97 (d, J=5.1 Hz, 1H), 6.12 (s, 2H), 2.94 (s, 3H); LCMS (M+H)⁺: 363.2.

Example 173

3-{3-[6-(3-Chlorobenzyl)-1-methyl-6H-pyrrolo[2,3-e][1,2,4]triazolo[4,3-a]pyridin-7-yl]-1H-pyrazol-1-yl}propan-1-ol trifluoroacetate salt

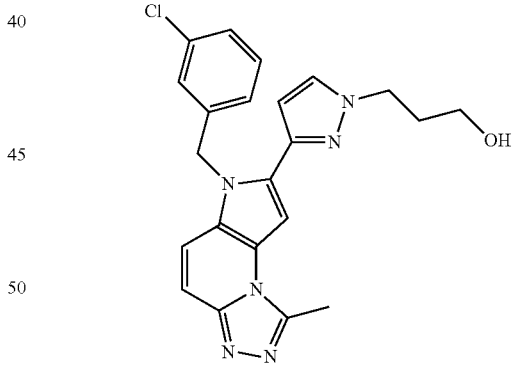

6-(3-Chlorobenzyl)-1-methyl-7-(1H-pyrazol-5-yl)-6H-pyrrolo[2,3-e][1,2,4]triazolo[4,3-a]pyridine (10. mg, 0.028 mmol, prepared as in Example 103, Step 5) in acetonitrile (0.36 mL) was treated with methyl acrylate (7.4 μL, 0.083 mmol, Aldrich) and 1,8-diazabicyclo[5.4.0]undec-7-ene (4.1 μL, 0.028 mmol, Aldrich). After 15 minutes, the solvent was removed in vacuo and replaced with THF (1.0 mL). 1.0 M LiAlH₄ in THF (55 μL, 0.055 mmol, Aldrich) was added to the reaction mixture. After 20 minutes, the reaction was quenched by the addition of a small amount of water, and the reaction mixture was diluted with acetonitrile and methanol. After stirring for 5 minutes, the mixture was filtered and the product was isolated via preparative HPLC-MS (Waters Sun- Fire C18, eluting with a gradient of MeCN/H$_2$O containing 0.1% TFA). Yield: (6.2 mg, 42%).

$^1$H NMR (300 MHz, d$_6$-DMSO) δ 8.21 (d, J=9.4 Hz, 1H), 7.90 (d, J=2.3 Hz, 1H), 7.58 (s, 1H), 7.55 (d, J=9.8 Hz, 1H), 7.33-7.23 (m, 2H), 7.18-7.11 (m, 1H), 7.04-6.95 (m, 1H), 6.92 (d, J=2.3 Hz, 1H), 6.16 (s, 2H), 4.22 (t, J=6.9 Hz, 2H), 3.33 (t, J=6.0 Hz, 2H), 3.04 (s, 3H), 1.91 (p, J=6.4 Hz, 2H); LCMS (M+H)$^+$: 421.1.

Example 174

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-methylpropanamide trifluoroacetate salt

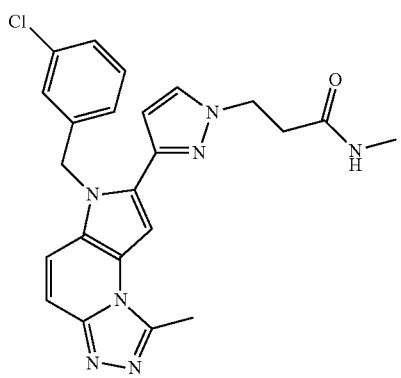 [SMILES: CNC(=O)CCn1ccc(-c2cc3c(ccc4nnc(C)n43)n2Cc2cccc(Cl)c2)n1]

A solution of 3-{3-[6-(3-chlorobenzyl)-1-methyl-6H-pyrrolo[2,3-e][1,2,4]triazolo[4,3-a]pyridin-7-yl]-1H-pyrazol-1-yl}propanoic acid (5.2 mg, 0.012 mmol, from Example 159, Step 1) in N,N-dimethylformamide (0.24 mL) was treated with N,N-diisopropylethylamine (8.3 μL, 0.048 mmol), HATU (8.2 mg, 0.022 mmol), and 2.0 M methylamine in THF (48 μL, 0.096 mmol, Aldrich). After 15 minutes, the reaction mixture was diluted with MeOH and the product was isolated by preparative HPLC-MS (Waters SunFire C18, eluting with a gradient of MeCN/H$_2$O containing 0.1% TFA). Yield: (3.5 mg, 52%).

$^1$H NMR (400 MHz, d$_6$-DMSO) δ 8.19 (d, J=9.6 Hz, 1H), 7.90-7.82 (m, 1H), 7.85 (d, J=2.3 Hz, 1H), 7.57 (s, 1H), 7.55 (d, J=9.6 Hz, 1H), 7.32-7.25 (m, 2H), 7.19-7.14 (m, 1H), 7.04-6.97 (m, 1H), 6.90 (d, J=2.3 Hz, 1H), 6.17 (s, 2H), 4.38 (t, J=6.8 Hz, 2H), 3.03 (s, 3H), 2.64 (t, J=6.9 Hz, 2H), 2.52 (s, 3H); LCMS (M+H)$^+$: 448.1.

Example 175

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-ethylpropanamide trifluoroacetate salt

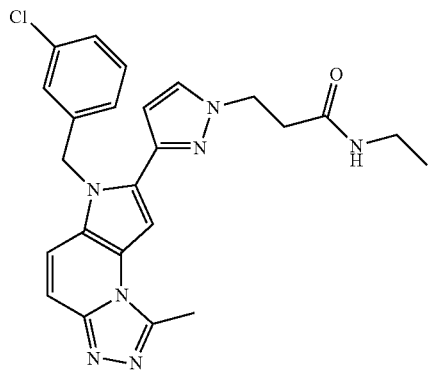 [SMILES: CCNC(=O)CCn1ccc(-c2cc3c(ccc4nnc(C)n43)n2Cc2cccc(Cl)c2)n1]

The title compound was prepared according to the methods of Example 174, using ethylamine (7 μL, 0.12 mmol, Aldrich). Yield: (3.0 mg, 44%).

$^1$H NMR (400 MHz, d$_6$-DMSO) δ 8.16 (d, J=9.5 Hz, 1H), 7.91 (t, J=5.4 Hz, 1H), 7.84 (d, J=2.3 Hz, 1H), 7.56 (s, 1H), 7.54 (d, J=9.6 Hz, 1H), 7.32-7.26 (m, 2H), 7.19-7.16 (m, 1H), 7.03-6.97 (m, 1H), 6.89 (d, J=2.3 Hz, 1H), 6.16 (s, 2H), 4.37 (t, J=6.9 Hz, 2H), 3.03 (s, 3H), 3.01 (dq, J=5.4, 7.2 Hz, 2H), 2.63 (t, J=6.9 Hz, 2H), 0.94 (t, J=7.2 Hz, 3H); LCMS (M+H)$^+$: 462.1.

Example 176

N-(tert-Butyl)-3-{3-[6-(3-chlorobenzyl)-1-methyl-6H-pyrrolo[2,3-e][1,2,4]triazolo[4,3-a]pyridin-7-yl]-1H-pyrazol-1-yl}propanamide trifluoroacetate salt

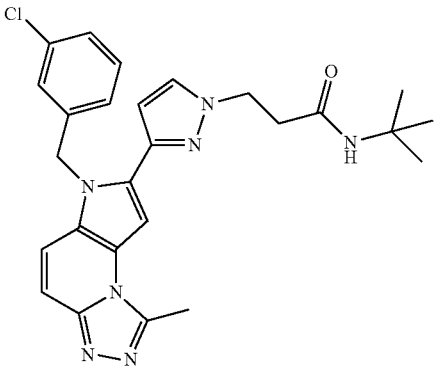 [SMILES: Cc1nnc2ccc3c(cc(-c4ccn(CCC(=O)NC(C)(C)C)n4)n3Cc3cccc(Cl)c3)n12]

The title compound was prepared according to the methods of Example 174, using tert-butylamine (10. μL, 0.096 mmol, Aldrich). Yield: (3.5 mg, 48%).

$^1$H NMR (400 MHz, d$_6$-DMSO) δ 8.27 (d, J=9.6 Hz, 1H), 7.84 (d, J=2.3 Hz, 1H), 7.61 (s, 1H), 7.58 (d, J=9.6 Hz, 1H), 7.51 (s, 1H), 7.32-7.25 (m, 2H), 7.21-7.17 (m, 1H), 7.04-6.98

(m, 1H), 6.92 (d, J=2.2 Hz, 1H), 6.19 (s, 2H), 4.35 (t, J=6.9 Hz, 2H), 3.05 (s, 3H), 2.61 (t, J=6.9 Hz, 2H), 1.19 (s, 9H); LCMS (M+H)+: 490.1.

Example 177

6-(3-Chlorobenzyl)-1-methyl-7-(1-oxetan-3-yl-1H-pyrazol-3-yl)-6H-pyrrolo[2,3-e][1,2,4]triazolo[4,3-a]pyridine trifluoroacetate salt

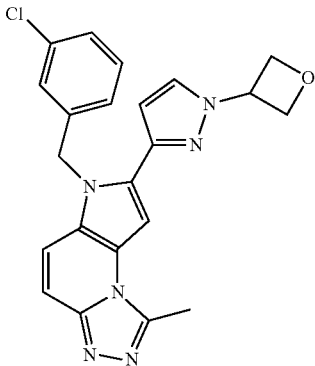 [SMILES: Cc1nnc2ccc3c(cc(-c4ccn(C5COC5)n4)n3Cc3cccc(Cl)c3)n12]

To a solution of 6-(3-chlorobenzyl)-1-methyl-7-(1H-pyrazol-5-yl)-6H-pyrrolo[2,3-e][1,2,4]triazolo[4,3-a]pyridine (7.1 mg, 0.020 mmol, prepared as in Example 103, Step 5) in DMF (0.10 mL) was added Cs₂CO₃ (13 mg, 0.039 mmol) and 3-iodooxetane (7.2 mg, 0.039 mmol, Synthonix). The mixture was heated in the microwave at 150° C. for 10 minutes. The product was isolated by preparative HPLC-MS (Waters SunFire C18, eluting with a gradient of MeCN/H₂O containing 0.1% TFA). Yield: (2.2 mg, 21%).
¹H NMR (400 MHz, CD₃OD) δ 8.31 (d, J=9.5 Hz, 1H), 7.82 (d, J=2.4 Hz, 1H), 7.64 (s, 1H), 7.54 (d, J=9.4 Hz, 1H), 7.28-7.19 (m, 2H), 7.11 (s, 1H), 7.07 (d, J=6.8 Hz, 1H), 6.95 (d, J=2.4 Hz, 1H), 6.27 (s, 2H), 5.60 (p, J=6.7 Hz, 1H), 5.02 (t, J=7.2 Hz, 2H), 4.98 (t, J=6.4 Hz, 2H), 3.16 (s, 3H); LCMS (M+H)+: 419.2.

Example 178

2-{3-[6-(3-Chlorobenzyl)-1-methyl-6H-pyrrolo[2,3-e][1,2,4]triazolo[4,3-a]pyridin-7-yl]-1H-pyrazol-1-yl}ethanol trifluoroacetate salt

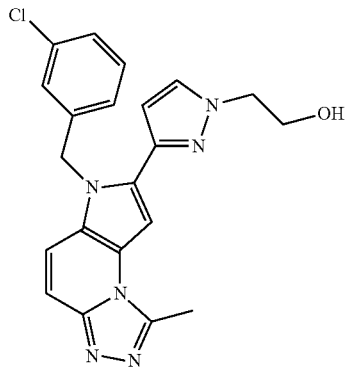 [SMILES: Cc1nnc2ccc3c(cc(-c4ccn(CCO)n4)n3Cc3cccc(Cl)c3)n12]

A solution of 6-(3-chlorobenzyl)-1-methyl-7-(1H-pyrazol-5-yl)-6H-pyrrolo[2,3-e][1,2,4]triazolo[4,3-a]pyridine (10. mg, 0.028 mmol, prepared as in Example 103, Step 5) in DMF (0.36 mL, 4.7 mmol) was treated with NaH (3.3 mg, 0.14 mmol, 60% in mineral oil). After 10 minutes, methyl bromoacetate (7.8 μL, 0.083 mmol, Aldrich) was added. After 20 minutes, the reaction was quenched by the addition of saturated ammonium hydroxide solution. The reaction mixture was diluted with water and extracted with three portions of EtOAc. The majority of the solvent was removed in vacuo, and DMF was removed azeotropically by repeated dissolution in and evaporation of MeCN. The crude intermediate ester was dissolved in THF (1.0 mL) and treated with LiAlH₄ (1.0 M in THF, 55 μL, 0.055 mmol, Aldrich). After 15 minutes, the mixture was quenched by the addition of water and was diluted with MeCN (3 mL) and MeOH (0.5 mL). After stirring for 5 minutes, the solution was filtered and product was isolated via preparative HPLC-MS (Waters SunFire C18, eluting with a gradient of MeCN/H₂O containing 0.1% TFA). Yield: (1.4 mg 9.8%).
¹H NMR (400 MHz, CD₃OD) δ 8.25 (d, J=9.5 Hz, 1H), 7.78 (d, J=2.4 Hz, 1H), 7.57 (s, 1H), 7.50 (d, J=9.6 Hz, 1H), 7.28-7.18 (m, 2H), 7.13-7.08 (m, 1H), 7.08-7.01 (m, 1H), 6.86 (d, J=2.4 Hz, 1H), 6.18 (s, 2H), 4.29 (t, J=5.3 Hz, 2H), 3.90 (t, J=5.4 Hz, 2H), 3.15 (s, 3H); LCMS (M+H)+: 407.1.

Example 179

2-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)ethanol bis(trifluoroacetate) salt

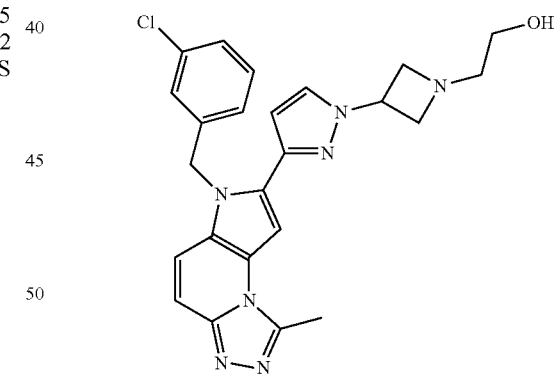

7-(1-Azetidin-3-yl-1H-pyrazol-3-yl)-6-(3-chlorobenzyl)-1-methyl-6H-pyrrolo[2,3-e][1,2,4]triazolo[4,3-a]pyridine (5.0 mg, 0.012 mmol, prepared as in Example 156, isolated as the free base) was treated with 2-bromoethanol (1.3 μL, 0.018 mmol, Aldrich) and K₂CO₃ (8.3 mg, 0.060 mmol) in DMF (0.20 mL) for 2 hours. The product was isolated via preparative HPLC-MS (Waters SunFire C18, eluting with a gradient of MeCN/H₂O containing 0.1% TFA). Yield: (2.4 mg 29%).
¹H NMR (400 MHz, CD₃OD) δ 8.23 (d, J=8.1 Hz, 1H), 7.88 (d, J=2.5 Hz, 1H), 7.71 (s, 1H), 7.56 (d, J=9.4 Hz, 1H), 7.37-7.23 (m, 2H), 7.19 (br s, 1H), 7.08 (br d, J=5.7 Hz, 1H), 7.02 (d, J=2.4 Hz, 1H), 6.24 (s, 2H), 5.55-5.40 (m, 1H), 4.80-4.60 (m, 2H), 4.42-4.29 (m, 2H), 3.66-3.54 (m, 2H), 3.17 (s, 3H), 3.11-2.99 (m, 2H); LCMS (M+H)+: 462.2.

Example 180

6-(3-Chlorobenzyl)-1-methyl-7-[1-(1-methylazetidin-3-yl)-1H-pyrazol-3-yl]-6H-pyrrolo[2,3-e][1,2,4]triazolo[4,3-a]pyridine bis(trifluoroacetate) salt

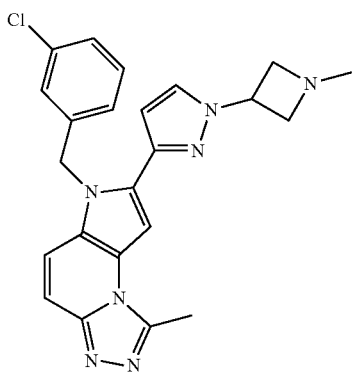 [SMILES: Cc1nnc2ccc3c(cc(-c4ccn(C5CN(C)C5)n4)n3Cc3cccc(Cl)c3)n12]

To a mixture of 7-(1-azetidin-3-yl-1H-pyrazol-3-yl)-6-(3-chlorobenzyl)-1-methyl-6H-pyrrolo[2,3-e][1,2,4]triazolo[4,3-c]pyridine trifluoroacetate salt (20. mg, 0.026 mmol, prepared as in Example 156) and formaldehyde solution (37 wt % in water, 11 mg, 0.13 mmol, Aldrich) in DCM (0.50 mL) was added Na(OAc)₃BH (17 mg, 0.079 mmol, Aldrich), and the reaction was stirred for 20 minutes. THF (0.50 mL) was added, and after additional stirring for 20 minutes, the reaction was quenched by the addition of water. The product was isolated via preparative HPLC-MS (Waters SunFire C18, eluting with a gradient of MeCN/H₂O containing 0.1% TFA). Yield: (12.9 mg, 74%).
LCMS (M+H)+: 432.1.

Example 181

3-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)propanenitrile bis(trifluoroacetate) salt

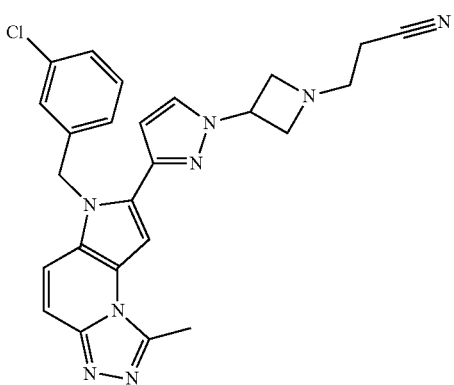 [SMILES: Cc1nnc2ccc3c(cc(-c4ccn(C5CN(CCC#N)C5)n4)n3Cc3cccc(Cl)c3)n12]

7-(1-Azetidin-3-yl-1H-pyrazol-3-yl)-6-(3-chlorobenzyl)-1-methyl-6H-pyrrolo[2,3-e][1,2,4]triazolo[4,3-a]pyridine trifluoroacetate salt (19 mg, 0.025 mmol, prepared as in Example 156) in MeCN (1.0 mL) was treated with K₂CO₃ (34 mg, 0.25 mmol) and 2-propenenitrile (3.3 µL, 0.050 mmol, Aldrich). The reaction was stirred at room temperature for 2 hours and then was heated at 40° C. for 2 hours. The reaction mixture was allowed to cool to room temperature and additional 2-propenenitrile (3.3 µL, 0.050 mmol, Aldrich) and 1,8-diazabicyclo[5.4.0]undec-7-ene (3.7 µL, 0.025 mmol, Aldrich) were added. After stirring at room temperature for 3 days, the reaction was diluted with MeOH (2 mL) and MeCN (2 mL) and was purified via preparative HPLC-MS (Waters SunFire C18, eluting with a gradient of MeCN/H₂O containing 0.1% TFA).
¹H NMR (400 MHz, d₆-DMSO) δ 8.24 (d, J=9.7 Hz, 1H), 8.04 (d, J=2.5 Hz, 1H), 7.70 (s, 1H), 7.61 (d, J=9.7 Hz, 1H), 7.36-7.26 (m, 2H), 7.17-7.10 (m, 1H), 7.06 (d, J=2.4 Hz, 1H), 7.01 (dt, J=6.6, 1.9 Hz, 1H), 6.24 (s, 2H), 5.41 (p, J=7.4 Hz, 1H), 4.61-4.50 (m, 2H), 4.43-4.15 (br m, 2H), 3.56-3.29 (br m, 2H), 3.06 (s, 3H), 2.92-2.83 (m, 2H); LCMS (M+H)+: 471.1.

Example 182

6-[3-(Azetidin-1-ylmethyl)benzyl]-1-methyl-7-(1H-pyrazol-3-yl)-6H-pyrrolo[2,3-e][1,2,4]triazolo[4,3-a]pyridine tris(trifluoroaceate) salt

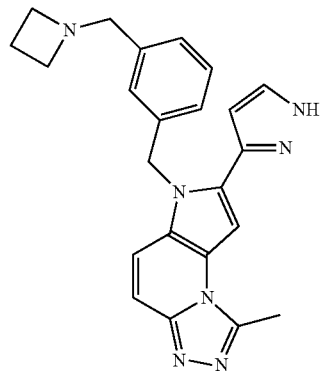 [SMILES: Cc1nnc2ccc3c(cc(C(=N)/C=C\N)n3Cc3cccc(CN4CCC4)c3)n12]

Step 1. 3[(2-Bromo-5-chloro-1H-pyrrolo[3,2-b]pyridin-1-yl)methyl]benzonitrile

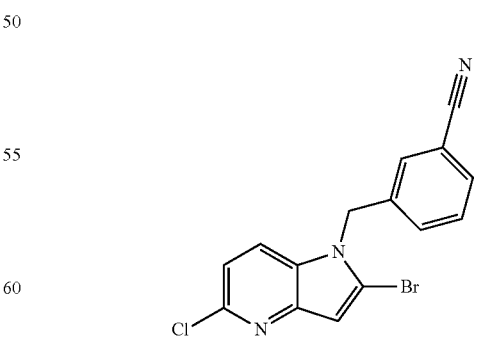

2-Bromo-5-chloro-1H-pyrrolo[3,2-b]pyridine (2.0 g, 8.6 mmol, prepared as in Example 103, Step 1) in DMF (20. mL) was treated with K₂CO₃ (1.8 g, 13 mmol) and m-cyanobenzyl bromide (1.9 g, 9.5 mmol, Aldrich) overnight. The reaction mixture was diluted with EtOAc and washed sequentially with water and brine. The combined organic extracts were dried over sodium sulfate, filtered and concentrated. The solid obtained was triturated with hexanes/diethyl ether and isolated by filtration. Yield: (2.3 g, 77%).

¹H NMR (300 MHz, CDCl₃) δ 7.59 (d, J=7.7 Hz, 1H), 7.49-7.32 (m, 3H), 7.21 (d, J=7.8 Hz, 1H), 7.10 (d, J=8.6 Hz, 1H), 6.85 (s, 1H), 5.44 (s, 2H); LCMS (M+H)⁺: 347.9, 345.9.

Step 2. 3-({5-Chloro-2-[1-(tetrahydro-2H-pyran-2-yl)-1H-pyrazol-5-yl]-1H-pyrrolo[3,2-b]pyridin-1-yl}methyl)benzonitrile

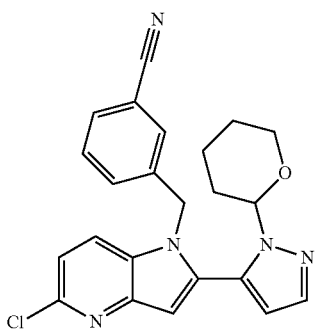 [SMILES: N#Cc1cccc(Cn2c(-c3ccnn3C3CCCCO3)cc3nc(Cl)ccc32)c1]

A mixture of 3-[(2-bromo-5-chloro-1H-pyrrolo[3,2-b]pyridin-1-yl)methyl]benzonitrile (2.24 g, 6.46 mmol, from Step 1), 1-(tetrahydro-2H-pyran-2-yl)-5-(4,4,5,5-tetramethyl-1,3,2-dioxaborolan-2-yl)-1H-pyrazole (2.88 g, 10.3 mmol, Aldrich) and Na₂CO₃ (3.4 g, 32 mmol) in 1,2-dimethoxyethane (70 mL) and H₂O (10 mL) was degassed. Tetrakis(triphenylphosphine)palladium(0) (0.75 g, 0.65 mmol, Strem) was added, and the reaction mixture was heated at reflux for 1 hour. Additional 1-(tetrahydro-2H-pyran-2-yl)-5-(4,4,5,5-tetramethyl-1,3,2-dioxaborolan-2-yl)-1H-pyrazole (2.0 g, 7.2 mmol, Aldrich) and Tetrakis(triphenylphosphine)palladium(0) (0.50 g, 0.43 mmol, Strem) were added, and the reaction mixture was heated for an additional 35 minutes. After cooling to room temperature, the reaction was diluted with water, and the aqueous layer was extracted with three portions of EtOAc. The combined organic extracts were dried over sodium sulfate, filtered and concentrated. The product was purified by flash chromatography, eluting with a gradient from 0-40% EtOAc in hexanes. Yield: (1.3 g, 48%).

¹H NMR (300 MHz, CDCl₃) δ 7.64 (d, J=1.8 Hz, 1H), 7.55 (d, J=7.7 Hz, 1H), 7.46 (d, J=8.6 Hz, 1H), 7.39 (t, J=7.8 Hz, 1H), 7.21-7.14 (m, 2H), 7.09 (d, J=7.9 Hz, 1H), 6.97 (s, 1H), 6.27 (d, J=1.8 Hz, 1H), 5.35 (d, J=17.1 Hz, 1H), 5.34 (d, J=17.1 Hz, 1H), 5.23 (dd, J=10.4, 2.3 Hz, 1H), 4.04 (ddt, J=11.5, 3.9, 1.8 Hz, 1H), 3.52 (td, J=11.6, 2.2 Hz, 1H), 2.50 (tdd, J=12.8, 10.8, 4.2 Hz, 1H), 2.13-1.42 (m, 5H); LCMS (M+H)⁺: 418.1.

Step 3. Di-tert-butyl 1-{1-(3-cyanobenzyl)-2-[1-(tetrahydro-2H-pyran-2-yl)-1H-pyrazol-5-yl]-1H-pyrrolo[3,2-b]pyridin-5-yl}hydrazine-1,2-dicarboxylate

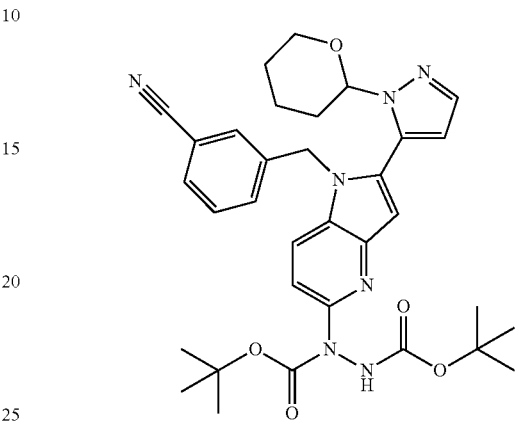

3-({5-Chloro-2-[1-(tetrahydro-2H-pyran-2-yl)-1H-pyrazol-5-yl]-1H-pyrrolo[3,2-b]pyridin-1-yl}methyl)benzonitrile (1.3 g, 3.1 mmol, from Step 2), di-tert-butyl hydrazine-1,2-dicarboxylate (1.4 g, 6.2 mmol, Aldrich) and Cs₂CO₃ (2.0 g, 6.2 mmol) were combined in toluene (20. mL) and dicyclohexyl(2',4',6'-triisopropylbiphenyl-2-yl)phosphine-(2'-aminobiphenyl-2-yl)(chloro)palladium (1:1) (0.24 g, 0.31 mmol, Aldrich) was added. The mixture was degassed and heated at 140° C. for 70 minutes. After cooling to room temperature, the mixture was diluted with DCM, filtered, and concentrated. Flash chromatography, eluting with a gradient from 0-60% EtOAc in hexanes, afforded purified product. Yield: (1.2 g, 63%).

¹H NMR (400 MHz, CDCl₃) δ 7.64 (d, J=1.7 Hz, 1H), 7.60-7.45 (m, 3H), 7.37 (t, J=7.8 Hz, 1H), 7.18 (s, 1H), 7.13-7.05 (m, 2H), 6.93 (s, 1H), 6.25 (d, J=1.8 Hz, 1H), 5.35 (d, J=17.5 Hz, 1H), 5.30 (d, J=16.9 Hz, 1H), 5.25 (dd, J=10.2, 1.9 Hz, 1H), 4.07-4.00 (m, 1H), 3.52 (td, J=11.7, 1.9 Hz, 1H), 2.58-2.40 (m, 1H), 2.08-1.42 (m, 5H), 1.52 (s, 9H), 1.48 (s, 9H). LCMS (M+H)⁺: 614.3.

Step 4. 3-{[1-Methyl-7-(1H-pyrazol-3-yl)-6H-pyrrolo[2,3-e][1,2,4]triazolo[4,3-a]pyridin-6-yl]methyl}benzonitrile

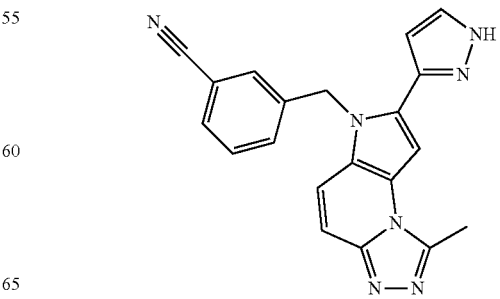

4.0 M HCl in dioxane (2.9 mL, 12 mmol) was added to a solution of di-tert-butyl 1-{1-(3-cyanobenzyl)-2-[1-(tetrahydro-2H-pyran-2-yl)-1H-pyrazol-5-yl]-1H-pyrrolo[3,2-b]pyridin-5-yl}hydrazine-1,2-dicarboxylate (1.2 g, 2.0 mmol, from Step 3) in DCM (50 mL) at 0° C. After 15 minutes, the reaction was quenched by the addition of aqueous ammonia and the pH was adjusted to 10. The mixture was diluted with water, and the aqueous solution was extracted with three portions of EtOAc. The combined organic extracts were washed with water followed by brine, dried over sodium sulfate, filtered and concentrated. The product was purified via flash chromatography, eluting with a gradient from 0-60% EtOAc in hexanes, to afford 0.83 g of deprotected pyrazole. LCMS (M+H)$^+$: 530.4.

The resulting solid was dissolved in acetic acid (35 mL) and heated in a sealed vessel at 130° C. for 40 minutes. Acetic acid was removed in vacuo to afford a yellow solid. The solid was suspended in a mixture of MeOH/MeCN containing aqueous ammonia (5 mL). After stirring for 10 minutes, the mixture was diluted with water, and the aqueous solution was extracted with 10% iPrOH in CHCl$_3$. The organic extract was dried over sodium sulfate, filtered and concentrated. The product was isolated by flash chromatography, eluting with a gradient from 0-10% MeOH in DCM. Yield: (0.36 g, 52%).

$^1$H NMR (400 MHz, d$_6$-DMSO) δ 13.13 (s, 1H), 7.89 (d, J=1.9 Hz, 1H), 7.70 (d, J=7.7 Hz, 1H), 7.66 (d, J=9.9 Hz, 1H), 7.58-7.54 (m, 1H), 7.47 (t, J=7.8 Hz, 1H), 7.42 (s, 1H), 7.33 (d, J=9.7 Hz, 1H), 7.28 (d, J=7.0 Hz, 1H), 6.89 (d, J=1.9 Hz, 1H), 6.14 (s, 2H), 2.96 (s, 3H); LCMS (M+H)$^+$: 354.2.

Step 5. 3-{[1-Methyl-7-(1H-pyrazol-3-yl)-6H-pyrrolo[2,3-e][1,2,4]triazolo[4,3-a]pyridin-6-yl]methyl}benzoic acid

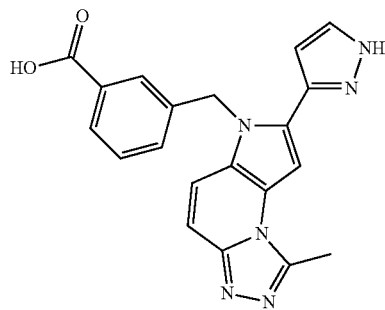 [SMILES: Cc1nnc2ccc3c(cc(-c4cc[nH]n4)n3Cc3cccc(C(=O)O)c3)n12]

A mixture of 3-{[1-methyl-7-(1H-pyrazol-3-yl)-6H-pyrrolo[2,3-e][1,2,4]triazolo[4,3-a]pyridin-6-yl]methyl}benzonitrile (0.29 g, 0.82 mmol, from Step 4) and KOH (0.46 g, 8.2 mmol) in EtOH (29 mL) was heated at 80° C. overnight in a sealed tube. Thereafter, the reaction was heated at 120-135° C. for 37 hours. Solvent was removed in vacuo. The reaction mixture was diluted with water, and the pH was adjusted to pH 4 by the addition of 1 N HCl. The brown solid that formed was isolated by filtration. The filtrate was saturated with solid NaCl, the pH was lowered to pH 3 by the addition of 1 N HCl and additional product was obtained by extraction with five portions of 10% iPrOH in CHCl$_3$. The extract was dried over sodium sulfate, filtered and concentrated. The solid obtained was combined with the solid that was isolated by filtration above. The 0.4 g of material containing crude product was used without further purification in Step 6.

LCMS (M+H)$^+$: 373.2.

Step 6. (3-((1-Methyl-7-(1H-pyrazol-3-yl)-6H-pyrrolo[2,3-e][1,2,4]triazolo[4,3-a]pyridin-6-yl)methyl)phenyl)methanol

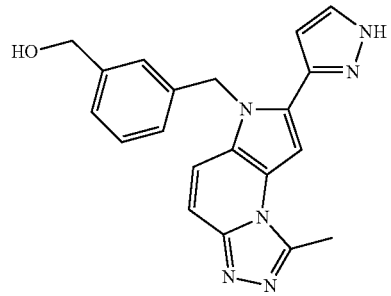 [SMILES: Cc1nnc2ccc3c(cc(-c4cc[nH]n4)n3Cc3cccc(CO)c3)n12]

A mixture of 3-{[1-methyl-7-(1H-pyrazol-3-yl)-6H-pyrrolo[2,3-e][1,2,4]triazolo[4,3-a]pyridin-6-yl]methyl}benzoic acid (0.40 g, from Step 5) in THF (40. mL) at 0° C. was treated with 1.0 M borane in THF (1.7 mL, 1.7 mmol, Aldrich) dropwise. The mixture was stirred for 1.5 hours, with warming to room temperature. Additional 1.0 M borane in THF (45 mL, 45 mmol) was added portionwise to the reaction mixture at room temperature over the course of 48 hours. The reaction mixture was cooled to 0° C. and cautiously quenched by the dropwise addition of water, followed by the addition of 1N HCl (55 mL). The mixture was then neutralized by the addition of solid NaHCO$_3$, and the product was extracted with 10% iPrOH in CHCl$_3$. Precipitate was dissolved in MeOH and combined with the organic extracts. The resulting solution was dried over sodium sulfate, filtered and concentrated. The product was purified by flash chromatography, eluting with a gradient from 0-10% MeOH in DCM. Yield: (0.12 g, 31%).

$^1$H NMR (400 MHz, d$_6$-DMSO) δ 13.11 (s, 1H), 7.88 (dd, J=1.5, 2.1 Hz, 1H), 7.57 (d, J=9.8 Hz, 1H), 7.36 (s, 1H), 7.29 (d, J=9.7 Hz, 1H), 7.19 (t, J=7.6 Hz, 1H), 7.16-7.11 (m, 1H), 7.09-7.04 (m, 1H), 6.85 (t, J=2.1 Hz, 1H), 6.84-6.81 (m, 1H), 6.10 (s, 2H), 5.12 (t, J=5.7 Hz, 1H), 4.37 (d, J=5.7 Hz, 2H), 2.96 (s, 3H); LCMS (M+H)$^+$: 359.3.

Step 7. 3-{[1-Methyl-7-(1H-pyrazol-3-yl)-6H-pyrrolo[2,3-e][1,2,4]triazolo[4,3-a]pyridin-6-yl]methyl}benzaldehyde

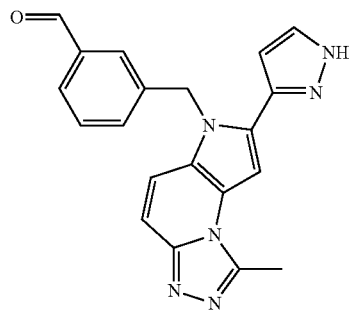 [SMILES: Cc1nnc2ccc3c(cc(-c4cc[nH]n4)n3Cc3cccc(C=O)c3)n12]

(3-((1-Methyl-7-(1H-pyrazol-3-yl)-6H-pyrrolo[2,3-e][1,2,4]triazolo[4,3-a]pyridin-6-yl)methyl)phenyl)methanol (0.12 g, 0.27 mmol, from Step 6) was treated with manganese (IV) oxide (0.23 g, 2.7 mmol, Aldrich) in CHCl₃ (24 mL). After stirring at room temperature for 80 minutes, the mixture was heated at 40° C. for 75 minutes and then at 50° C. for 2.5 hours. The mixture was filtered through Celite and rinsed with acetonitrile. Solvent was removed from the filtrate in vacuo to afford aldehyde, which was used in further step without purification. Yield: (75 mg, 63%).

$^1$H NMR (300 MHz, d$_6$-DMSO) δ 13.11 (s, 1H), 9.90 (s, 1H), 7.91-7.83 (m, 1H), 7.77 (d, J=7.4 Hz, 1H), 7.63 (d, J=9.8 Hz, 1H), 7.58 (s, 1H), 7.52 (t, J=7.6 Hz, 1H), 7.41 (s, 1H), 7.38-7.26 (m, 2H), 6.92-6.84 (m, 1H), 6.20 (s, 2H), 2.97 (s, 3H); LCMS (M+H)$^+$: 357.1.

Step 8. 6-[3-(Azetidin-1-ylmethyl)benzyl]-1-methyl-7-(1H-pyrazol-3-yl)-6H-pyrrolo[2,3-e][1,2,4]triazolo[4,3-a]pyridine tris(trifluoroacetate) salt A solution of 3-{[1-methyl-7-(1H-pyrazol-3-yl)-6H-pyrrolo[2,3-e][1,2,4]triazolo[4,3-a]pyridin-6-yl]methyl}benzaldehyde (30. mg, 0.067 mmol, from Step 7) in 1,2-dichloroethane (5.0 mL) was treated with azetidine (40 µL, 0.7 mmol, Aldrich) and acetic acid (57 µL, 1.0 mmol). The mixture was stirred for 15 minutes, followed by the addition of Na(OAc)₃BH (0.21 g, 1.0 mmol, Aldrich). After stirring overnight, the reaction was quenched with water, and the volatile components were removed in vacuo. The product was purified via preparative HPLC-MS (Waters XBridge C18, eluting with a gradient of MeCN/H₂O containing 0.15% NH₄OH). Yield: (15.4 mg, 58%).

The title compound was obtained via preparative HPLC-MS (Waters SunFire C18, eluting with a gradient of MeCN/H₂O containing 0.1% TFA).

$^1$H NMR (300 MHz, d$_6$-DMSO) δ 13.12 (s, 1H), 7.88 (s, 1H), 7.60 (d, J=9.7 Hz, 1H), 7.36 (s, 1H), 7.30 (d, J=9.8 Hz, 1H), 7.16 (t, J=7.5 Hz, 1H), 7.05 (d, J=7.8 Hz, 1H), 7.00 (s, 1H), 6.92-6.68 (m, 2H), 6.07 (s, 2H), 3.38 (s, 2H), 3.05-2.85 (m, 4H), 2.96 (s, 3H), 1.89 (p, J=6.8 Hz, 2H); LCMS (M+H)$^+$: 398.3.

Example 183

3-(3-{6-[3-(Azetidin-1-ylmethyl)benzyl]-1-methyl-6H-pyrrolo[2,3-e][1,2,4]triazolo[4,3-a]pyridin-7-yl}-1H-pyrazol-1-yl)propanenitrile bis(trifluoroacetate) salt

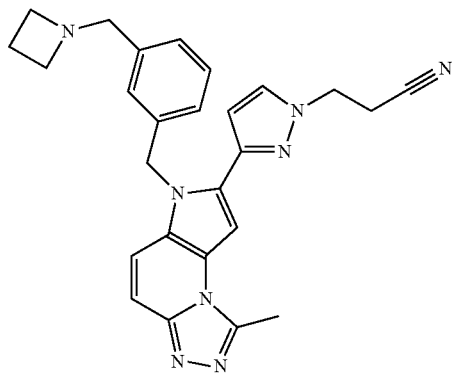 [SMILES: Cc1nnc2ccc3c(cc(-c4ccn(CCC#N)n4)n3Cc3cccc(CN4CCC4)c3)n12]

6-[3-(Azetidin-1-ylmethyl)benzyl]-1-methyl-7-(1H-pyrazol-3-yl)-6H-pyrrolo[2,3-e][1,2,4]triazolo[4,3-a]pyridine (7.0 mg, 0.018 mmol, from Example 182) in MeCN (0.23 mL) was treated with 2-propenenitrile (2.3 µL, 0.035 mmol, Aldrich) and 1,8-diazabicyclo[5.4.0]undec-7-ene (2.6 µL, 0.018 mmol, Aldrich) for 8 minutes. The product was purified via preparative HPLC-MS (Waters SunFire C18, eluting with a gradient of MeCN/H₂O containing 0.1% TFA). Yield: (9.8 mg, 82%).

$^1$H NMR (400 MHz, d$_6$-DMSO) δ 9.93 (s, 1H), 8.01-7.91 (m, 2H), 7.55 (s, 1H), 7.48 (d, J=9.7 Hz, 1H), 7.33 (t, J=7.6 Hz, 1H), 7.30-7.25 (m, 1H), 7.20-7.15 (m, 1H), 7.13-7.06 (m, 1H), 6.93 (d, J=2.3 Hz, 1H), 6.16 (s, 2H), 4.44 (t, J=6.3 Hz, 2H), 4.24 (d, J=6.0 Hz, 2H), 4.03-3.82 (m, 4H), 3.06 (t, J=6.3 Hz, 2H), 3.02 (s, 3H), 2.40-2.16 (m, 2H); LCMS (M+H)$^+$: 451.3.

Example 184

6-[3-(Azetidin-1-ylmethyl)benzyl]-1-methyl-7-(1-methyl-1H-pyrazol-3-yl)-6H-pyrrolo[2,3-e][1,2,4]triazolo[4,3-a]pyridine bis(trifluoroacetate) salt

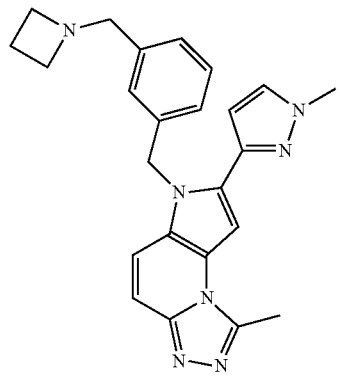 [SMILES: Cc1nnc2ccc3c(cc(-c4ccn(C)n4)n3Cc3cccc(CN4CCC4)c3)n12]

Step 1. 3-{[1-Methyl-7-(1-methyl-1H-pyrazol-3-yl)-6H-pyrrolo[2,3-e][1,2,4]triazolo[4,3-a]pyridin-6-yl]methyl}benzonitrile

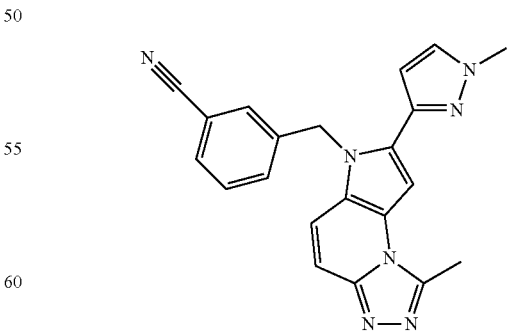

3-{[1-Methyl-7-(1H-pyrazol-3-yl)-6H-pyrrolo[2,3-e][1,2,4]triazolo[4,3-a]pyridin-6-yl]methyl}benzonitrile (50. mg, 0.14 mmol, from Example 182, Step 4) in DMF (3.0 mL) was treated with NaH (60% in mineral oil, 34 mg, 0.85 mmol).

After 10 minutes, MeI (26 μL, 0.42 mmol, Aldrich) was introduced. After 10 minutes, the reaction was quenched by the addition of water. The product was isolated via preparative HPLC-MS (Waters XBridge C18, eluting with a gradient of MeCN/H$_2$O containing 0.15% NH$_4$OH). Yield: (30 mg, 58%).

$^1$H NMR (400 MHz, CDCl$_3$) δ 7.54 (dt, J=7.8, 1.2 Hz, 1H), 7.43-7.34 (m, 4H), 7.30-7.26 (m, 1H), 7.20 (dd, J=9.7, 0.4 Hz, 1H), 7.05 (s, 1H), 6.52 (d, J=2.3 Hz, 1H), 5.95 (s, 2H), 3.92 (s, 3H), 3.05 (s, 3H); LCMS (M+H)$^+$: 368.3

Step 2. 6-[3-(Azetidin-1-ylmethyl)benzyl]-1-methyl-7-(1-methyl-1H-pyrazol-3-yl)-6H-pyrrolo[2,3-e][1,2,4]triazolo[4,3-a]pyridine bis(trifluoroacetate) salt 3-{[1-Methyl-7-(1-methyl-1H-pyrazol-3-yl)-6H-pyrrolo[2,3-e][1,2,4]triazolo[4,3-a]pyridin-6-yl]methyl}benzonitrile (24 mg, 0.065 mmol, from Step 1) was treated with KOH (37 mg, 0.65 mmol) in EtOH (2.3 mL) and the resultant reaction mixture was heated in a sealed vessel at 140° C. for 2 hours. The mixture was cooled to room temperature and acidified to pH 4 by the addition of 1 N HCl. Most of the solvent was removed in vacuo, and the crude carboxylic acid was isolated by filtration. LCMS (M+H)$^+$: 387.2.

Triethylamine (91 μL, 0.65 mmol) and isobutyl chloroformate (42 μL, 0.33 mmol, Aldrich) were added to the crude carboxylic acid in DCM (2.0 mL) and THF (3.0 mL) at 0° C. After 30 minutes, the reaction mixture was filtered through a short pad of Celite into a flask containing NaBH$_4$ (25 mg, 0.65 mmol, Aldrich) in H$_2$O (2.0 mL) at 0° C. The Celite was rinsed with THF (6 mL). The mixture was allowed to warm to room temperature and stirred for 30 minutes. The reaction was quenched by the addition of 1 N HCl and was neutralized by the addition of aqueous ammonia. The aqueous mixture was extracted with two portions of DCM, and the combined organic extracts were dried over sodium sulfate, filtered and concentrated.

The crude alcohol was dissolved in DCM (2.0 mL) and treated with N,N-diisopropylethylamine (57 μL, 0.33 mmol) and methanesulfonic anhydride (34 mg, 0.20 mmol, Aldrich). After 10 minutes, the mixture was concentrated, and the crude mesylate was dissolved in a mixture of THF (1.0 mL) and methanol (1.0 mL) and treated with azetidine (44 μL, 0.65 mmol, Aldrich). After a reaction time of 10 minutes, the product was isolated via preparative HPLC-MS (Waters SunFire C18, eluting with a gradient of MeCN/H$_2$O containing 0.1% TFA). Yield: (4.4 mg, 10%).

$^1$H NMR (400 MHz, d$_6$-DMSO) δ 10.01 (br s, 1H), 7.95 (d, J=9.8 Hz, 1H), 7.85 (d, J=2.3 Hz, 1H), 7.52 (s, 1H), 7.47 (d, J=9.7 Hz, 1H), 7.37-7.26 (m, 2H), 7.24-7.19 (m, 1H), 7.06-7.01 (m, 1H), 6.88 (d, J=2.3 Hz, 1H), 6.15 (s, 2H), 4.26 (d, J=6.0 Hz, 2H), 4.07-3.82 (m, 4H), 3.89 (s, 3H), 3.02 (s, 3H), 2.42-2.17 (m, 2H); LCMS (M+H)$^+$: 412.3.

Example 185

6-[3-(Azetidin-1-ylmethyl)-5-chlorobenzyl]-1-methyl-7-(1-methyl-1H-pyrazol-3-yl)-6H-pyrrolo[2,3-e][1,2,4]triazolo[4,3-a]pyridine tris(trifluoroacetate) salt

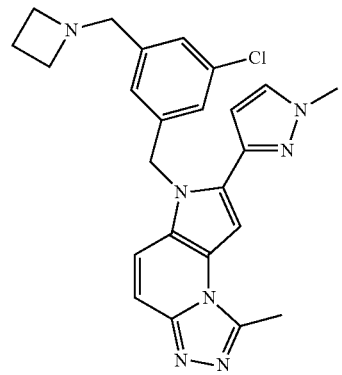 [SMILES: Cc1nnc2ccc3c(cc(-c4ccn(C)n4)n3Cc3cc(Cl)cc(CN4CCC4)c3)n12]

Step 1. 2-Bromo-1-[3-({[tert-butyl(diphenyl)silyl]oxy}methyl)-5-chlorobenzyl]-5-chloro-1H-pyrrolo[3,2-b]pyridine

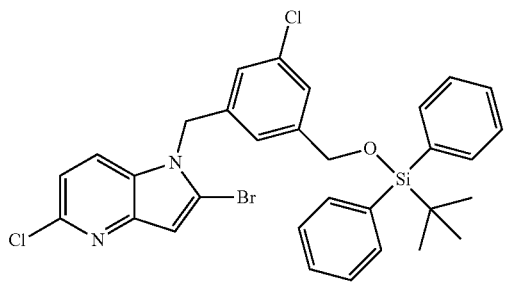 [SMILES: CC(C)(C)[Si](OCc1cc(Cl)cc(Cn2c(Br)cc3nc(Cl)ccc32)c1)(c1ccccc1)c1ccccc1]

To 2-bromo-5-chloro-1H-pyrrolo[3,2-b]pyridine (1.6 g, 6.7 mmol, prepared as in Example 103, Step 1) in DMF (50. mL) was added K$_2$CO$_3$ (1.4 g, 10. mmol) and 3-{[tert-butyl(diphenyl)silyl]oxy}-5-chlorobenzyl methanesulfonate (3.7 g, 7.8 mmol, prepared as in Example 131, Step 1-3), and the reaction mixture was stirred overnight. The mixture was diluted with EtOAc, washed sequentially with water and brine, then dried over sodium sulfate, filtered and concentrated. The product was purified by flash chromatography, eluting with a gradient from 0-10% EtOAc in hexanes. Yield: (3.6 g, 86%).

$^1$H NMR (400 MHz, CDCl$_3$) δ 7.60-7.55 (m, 4H), 7.45-7.32 (m, 7H), 7.19-7.15 (m, 1H), 7.05 (d, J=8.6 Hz, 1H), 7.00-6.98 (m, 1H), 6.86-6.83 (m, 1H), 6.81 (d, J=0.6 Hz, 1H), 5.36 (s, 2H), 4.62 (s, 2H), 1.01 (s, 9H); LCMS (M+H)$^+$: 625.2.

Step 2. 1-[3-({[tert-Butyl(diphenyl)silyl]oxy}methyl)-5-chlorobenzyl]-5-chloro-2-[1-(tetrahydro-2H-pyran-2-yl)-1H-pyrazol-5-yl]-1H-pyrrolo[3,2-b]pyridine

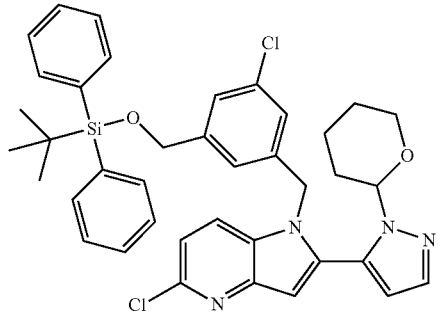 [SMILES: CC(C)(C)[Si](OCc1cc(Cl)cc(Cn2c(-c3ccnn3C3CCCCO3)cc3nc(Cl)ccc32)c1)(c1ccccc1)c1ccccc1]

Tetrakis(triphenylphosphine)palladium(0) (0.65 g, 0.56 mmol, Strem) was added to a degassed mixture of 2-bromo-1-[3-({[tert-butyl(diphenyl)silyl]oxy}methyl)-5-chlorobenzyl]-5-chloro-1H-pyrrolo[3,2-b]pyridine (3.5 g, 5.6 mmol, from Step 1), 1-(tetrahydro-2H-pyran-2-yl)-5-(4,4,5,5-tetramethyl-1,3,2-dioxaborolan-2-yl)-1H-pyrazole (2.5 g, 9.0 mmol, Aldrich) and Na$_2$CO$_3$ (3.0 g, 28 mmol) in 1,2-dimethoxyethane (60 mL) and Water (10 mL). The mixture was heated at reflux for 2 hours. Additional 1-(tetrahydro-2H-pyran-2-yl)-5-(4,4,5,5-tetramethyl-1,3,2-dioxaborolan-2-yl)-1H-pyrazole (0.50 g, 1.8 mmol) and tetrakis(triphenylphosphine)palladium(0) (0.32 g, 0.28 mmol) were added, and the reaction mixture was heated at reflux until LCMS indicated that the reaction was complete. After cooling to room temperature, the reaction was diluted with water, and the aqueous mixture was extracted with three portions of EtOAc. The combined organic extracts were washed with water, followed by brine, dried over Na$_2$SO$_4$, filtered and concentrated. Flash chromatography, eluting with a gradient from 0-20% EtOAc in hexanes afforded product as a light yellow oil. Yield: (2.73 g, 70%).

$^1$H NMR (400 MHz, CDCl$_3$) δ 7.62 (d, J=1.8 Hz, 1H), 7.58-7.52 (m, 4H), 7.47 (d, J=8.6 Hz, 1H), 7.41 (dq, J=6.5, 2.0 Hz, 2H), 7.38-7.31 (m, 4H), 7.18-7.15 (m, 1H), 7.13 (d, J=8.6 Hz, 1H), 6.96 (s, 1H), 6.76-6.71 (m, 2H), 6.28 (d, J=1.8 Hz, 1H), 5.27 (d, J=4.4 Hz, 2H), 5.21 (dd, J=10.4, 2.2 Hz, 1H), 4.60 (s, 2H), 4.08-3.98 (m, 1H), 3.52 (td, J=11.8, 2.1 Hz, 1H), 2.50 (tdd, J=13.1, 10.7, 4.3 Hz, 1H), 2.10-1.93 (m, 1H), 1.79-1.63 (m, 2H), 1.55-1.44 (m, 2H), 0.98 (s, 9H); LCMS (M+H)$^+$: 695.4.

Step 3. Di-tert-butyl 1-[1-[3-({[tert-butyl(diphenyl)silyl]oxy}methyl)-5-chlorobenzyl]-2-(1H-pyrazol-3-yl)-1H-pyrrolo[3,2-b]pyridin-5-yl]hydrazine-1,2-dicarboxylate

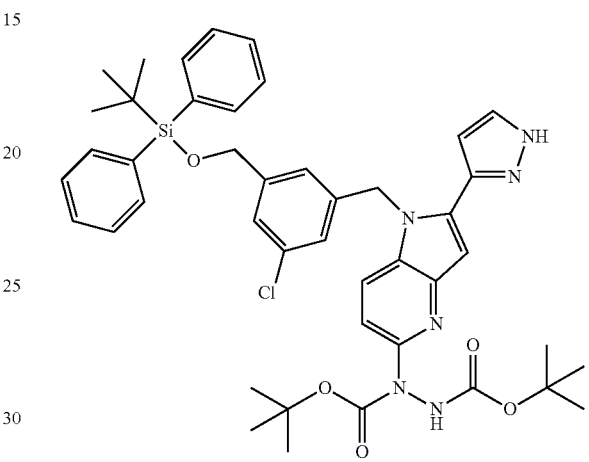

A mixture of 1-[3-({[tert-butyl(diphenyl)silyl]oxy}methyl)-5-chlorobenzyl]-5-chloro-2-[1-(tetrahydro-2H-pyran-2-yl)-1H-pyrazol-5-yl]-1H-pyrrolo[3,2-b]pyridine (2.7 g, 3.9 mmol, from Step 2), di-tert-butyl hydrazine-1,2-dicarboxylate (0.99 g, 4.3 mmol, Aldrich), Cs$_2$CO$_3$ (2.5 g, 7.8 mmol) and dicyclohexyl(2',4',6'-triisopropylbiphenyl-2-yl)phosphine-(2'-aminobiphenyl-2-yl)(chloro)palladium (1:1) (0.30 g, 0.39 mmol, Aldrich) in toluene (25 mL) was degassed and heated at 140° C. for 3 hours. Additional di-tert-butyl hydrazine-1,2-dicarboxylate (0.50 g, 2.2 mmol) and dicyclohexyl(2',4',6'-triisopropylbiphenyl-2-yl)phosphine-(2'-aminobiphenyl-2-yl)(chloro)palladium (1:1) (0.30 g, 0.38 mmol) were added and heating was continued for 1 hour. After addition of more di-tert-butyl hydrazine-1,2-dicarboxylate (0.20 g, 0.86 mmol) and heating for another 40 minutes, the mixture was cooled to room temperature and diluted with DCM, filtered and concentrated. The intermediate thus obtained was isolated by flash chromatography, eluting with a gradient from 0-25% EtOAc in hexanes (2.5 g). A solution of the intermediate in DCM (80 mL) at 0° C. was treated with 4.0 M HCl in dioxane (3.9 mL, 16 mmol). After stirring for 15 minutes, the reaction was quenched with aqueous ammonia. The reaction mixture was diluted with water, and the aqueous solution was extracted with three portions of EtOAc. The combined organic extracts were washed sequentially with water and brine, dried over sodium sulfate, filtered and concentrated. The title product was purified by flash chromatography, eluting with a gradient from 0-50% EtOAc in hexanes. Yield: (1.1 g, 35%).

LCMS (M+H)$^+$: M+H 807.4.

Step 4. 6-[3-({[tert-Butyl(diphenyl)silyl]oxy}methyl)-5-chlorobenzyl]-1-methyl-7-(1H-pyrazol-5-yl)-6H-pyrrolo[2,3-e][1,2,4]triazolo[4,3-a]pyridine

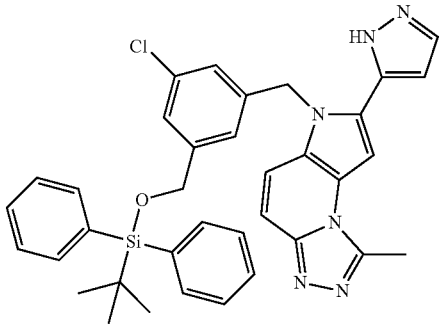 [SMILES: Cc1nnc2ccc3c(cc(-c4ccn[nH]4)n3Cc3cc(Cl)cc(CO[Si](c4ccccc4)(c4ccccc4)C(C)(C)C)c3)n12]

A solution of di-tert-butyl 1-[1-[3-({[tert-butyl(diphenyl)silyl]oxy}methyl)-5-chlorobenzyl]-2-(1H-pyrazol-3-yl)-1H-pyrrolo[3,2-b]pyridin-5-yl]hydrazine-1,2-dicarboxylate (1.1 g, 1.4 mmol, from Step 3) in acetic acid (28 mL) was heated at 130° C. for 1.5 hours. Acetic acid was removed in vacuo, and the residue was dissolved in DCM and washed with saturated NaHCO$_3$. The aqueous layer was extracted with DCM. The combined organic extracts were dried over sodium sulfate, filtered and concentrated. The product was purified by flash chromatography, eluting with a gradient from 0-10% MeOH in DCM. Yield: (0.66 g, 54%).

$^1$H NMR (300 MHz, CDCl$_3$) δ 7.63 (d, J=2.4 Hz, 1H), 7.60-7.51 (m, 4H), 7.45-7.18 (m, 8H), 7.18-7.10 (m, 1H), 7.05 (s, 1H), 7.02-6.98 (m, 1H), 6.92-6.84 (m, 1H), 6.58 (d, J=2.4 Hz, 1H), 5.87 (s, 2H), 4.60 (s, 2H), 3.01 (s, 3H), 0.94 (s, 9H); LCMS (M+H)$^+$: 631.3.

Step 5. 6-[3-({[tert-Butyl(diphenyl)silyl]oxy}methyl)-5-chlorobenzyl]-1-methyl-7-(1-methyl-1H-pyrazol-3-yl)-6H-pyrrolo[2,3-e][1,2,4]triazolo[4,3-a]pyridine

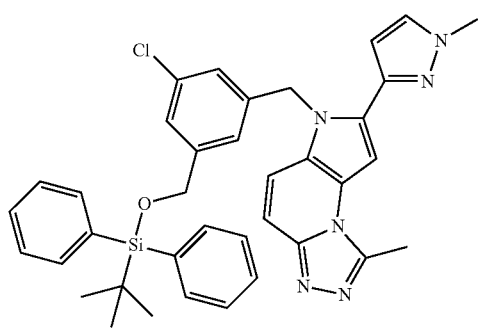 [SMILES: Cc1nnc2ccc3c(cc(-c4ccn(C)n4)n3Cc3cc(Cl)cc(CO[Si](c4ccccc4)(c4ccccc4)C(C)(C)C)c3)n12]

6-[3-({[tert-Butyl(diphenyl)silyl]oxy}methyl)-5-chlorobenzyl]-1-methyl-7-(1H-pyrazol-5-yl)-6H-pyrrolo[2,3-e][1,2,4]triazolo[4,3-a]pyridine (0.20 g, 0.22 mmol, from Step 4) in DMF (4.7 mL) was treated with NaH (60% in mineral oil, 27 mg, 0.66 mmol). After 10 minutes, MeI (41 μL, 0.66 mmol, Aldrich) was added to the reaction mixture. After 10 minutes, the reaction was quenched by the addition of water, and the product was purified via preparative HPLC-MS (Waters XBridge C18, eluting with a gradient of MeCN/H$_2$O containing 0.15% NH$_4$OH). Yield: (50 mg, 30%).

$^1$H NMR (400 MHz, CDCl$_3$) δ 7.58-7.53 (m, 4H), 7.42-7.28 (m, 8H), 7.21 (d, J=9.7 Hz, 1H), 7.17-7.13 (m, 1H), 7.01 (s, 1H), 7.01-6.96 (m, 1H), 6.87-6.83 (m, 1H), 6.45 (d, J=2.3 Hz, 1H), 5.85 (s, 2H), 4.60 (s, 2H), 3.93 (s, 3H), 3.01 (s, 3H), 0.94 (s, 9H); LCMS (M+H)$^+$: 645.0.

Step 6. 6-[3-(Azetidin-1-ylmethyl)-5-chlorobenzyl]-1-methyl-7-(1-methyl-1H-pyrazol-3-yl)-6H-pyrrolo[2,3-e][1,2,4]triazolo[4,3-a]pyridine tris(trifluoroacetate) salt A solution of 6-[3-({[tert-butyl(diphenyl)silyl]oxy}methyl)-5-chlorobenzyl]-1-methyl-7-(1-methyl-1H-pyrazol-3-yl)-6H-pyrrolo[2,3-e][1,2,4]triazolo[4,3-a]pyridine (47 mg, 0.073 mmol, from Step 5) in THF (4 mL) was treated with 1.0 M TBAF in THF (87 μL, 0.087 mmol, Aldrich) for 35 minutes. Upon complete conversion to the deprotected alcohol, DCM (5.0 mL), triethylamine (51 μL, 0.36 mmol) and methanesulfonyl chloride (22 μL, 0.29 mmol, Aldrich) were added. After 10 minutes, the solvent was removed in vacuo, and the residue was dissolved in a mixture of 1:1 THF:MeOH (4.0 mL). Azetidine (49 μL, 0.73 mmol, Aldrich) was added. After 35 minutes, the product was isolated from the reaction mixture via preparative HPLC-MS (Waters XBridge C18, eluting with a gradient of MeCN/H$_2$O containing 0.15% NH$_4$OH), followed by additional purification (Waters SunFire C18, eluting with a gradient of MeCN/H$_2$O containing 0.1% TFA) to afford the title product as the TFA salt. Yield: (28.6 mg, 50%).

$^1$H NMR (400 MHz, d$_6$-DMSO) δ 10.01 (s, 1H), 7.97 (d, J=9.4 Hz, 1H), 7.86 (d, J=2.3 Hz, 1H), 7.55 (s, 1H), 7.49 (d, J=9.7 Hz, 1H), 7.44-7.39 (m, 1H), 7.17-7.12 (m, 2H), 6.90 (d, J=2.3 Hz, 1H), 6.14 (s, 2H), 4.26 (d, J=5.6 Hz, 2H), 4.03-3.83 (m, 4H), 3.89 (s, 3H), 3.03 (s, 3H), 2.40-2.18 (m, 2H); LCMS (M+H)$^+$: 446.2.

Example 186

6-Benzyl-1-methyl-7-pyrrolidin-3-yl-6H-pyrrolo[2,3-e][1,2,4]triazolo[4,3-a]pyridine bis(trifluoroacetate) salt (racemic)

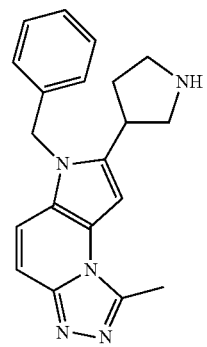 [SMILES: Cc1nnc2ccc3c(cc(C4CCNC4)n3Cc3ccccc3)n12]

Step 1. tert-Butyl 3-[5-chloro-1-(3-chlorobenzyl)-1H-pyrrolo[3,2-b]pyridin-2-yl]-2,5-dihydro-1H-pyrrole-1-carboxylate

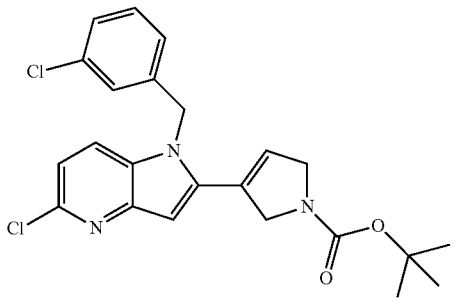 [SMILES: CC(C)(C)OC(=O)N1CC=C(c2cc3nc(Cl)ccc3n2Cc2cccc(Cl)c2)C1]

Tetrakis(triphenylphosphine)palladium(0) (0.13 g, 0.11 mmol, Strem) was added to a degassed mixture of 2-bromo-5-chloro-1-(3-chlorobenzyl)-1H-pyrrolo[3,2-b]pyridine (0.50 g, 1.1 mmol, prepared as in Example 103, Step 2), tert-butyl 3-(4,4,5,5-tetramethyl-1,3,2-dioxaborolan-2-yl)-2,5-dihydro-1H-pyrrole-1-carboxylate (0.414 g, 1.40 mmol, Combi-Blocks) and Na$_2$CO$_3$ (0.60 g, 5.6 mmol) in 1,2-dimethoxyethane (10 mL) and water (2 mL), and the sealed reaction mixture was heated at 106° C. for two hours. Additional tert-butyl 3-(4,4,5,5-tetramethyl-1,3,2-dioxaborolan-2-yl)-2,5-dihydro-1H-pyrrole-1-carboxylate (0.33 g, 1.1 mmol) and tetrakis(triphenylphosphine)palladium(0) (0.13 g, 0.11 mmol) were added, and heating was continued for additional two hours. Upon cooling to room temperature, the reaction mixture was diluted with water, and the aqueous layer was extracted with three portions of EtOAc. The combined organic extracts were dried over sodium sulfate, filtered and concentrated. The product was purified by flash chromatography, eluting with a gradient from 0-30% EtOAc in hexanes. Yield: (0.12 g, 24%).
LCMS (M+H)$^+$: 444.2.

Step 2. 6-Benzyl-1-methyl-7-pyrrolidin-3-yl-6H-pyrrolo[2,3-e][1,2,4]triazolo[4,3-a]pyridine bis(trifluoroacetate) salt (racemic)

A degassed mixture of tert-butyl 3-[5-chloro-1-(3-chlorobenzyl)-1H-pyrrolo[3,2-b]pyridin-2-yl]-2,5-dihydro-1H-pyrrole-1-carboxylate (0.12 g, 0.27 mmol, from Step 1), di-tert-butyl hydrazine-1,2-dicarboxylate (94 mg, 0.40 mmol, Aldrich), Cs$_2$CO$_3$ (0.18 g, 0.54 mmol) and dicyclohexyl(2',4',6'-triisopropylbiphenyl-2-yl)phosphine-(2'-aminobiphenyl-2-yl)(chloro)palladium (1:1) (21 mg, 0.027 mmol, Aldrich) in toluene (2.0 mL) was heated in a sealed vial at 140° C. for 70 minutes. Upon cooling to room temperature, the reaction mixture was diluted with DCM and filtered. The filtrate was concentrated, and the residue was purified by flash chromatography, eluting with a gradient from 0-40% EtOAc in hexanes. Yield: (29 mg). LCMS (M+H)$^+$: 640.3. The derivative of di-tert-butyl hydrazine-1,2-dicarboxylate this obtained was then hydrogenated (1 atm H2) over Pd (10% on carbon, 8.6 mg, 0.0081 mmol) in MeOH (4.0 mL) for 3 days. The reaction mixture was filtered, and the filtrate was concentrated in vacuo. The intermediate pyrrolidine as a solution in acetic acid (1.0 mL) was heated in the microwave at 180° C. for 5 minutes. The product was isolated via preparative HPLC-MS (Waters SunFire C18, eluting with a gradient of MeCN/H$_2$O containing 0.1% TFA). Yield: (2.4 mg, 2%).

$^1$H NMR (400 MHz, CD$_3$OD) δ 8.29 (d, J=9.5 Hz, 1H), 7.55 (d, J=9.6 Hz, 1H), 7.39-7.26 (m, 4H), 7.05-6.97 (m, 2H), 5.77 (s, 2H), 3.92 (p, J=8.8 Hz, 1H), 3.63-3.52 (m, 2H), 3.46-3.33 (m, 2H), 3.13 (s, 3H), 2.47-2.33 (m, 1H), 2.20 (dq, J=13.0, 8.9 Hz, 1H); LCMS (M+H)$^+$: 331.9.

Example 187

7-(1-Acetylpyrrolidin-3-yl)-6-benzyl-1-methyl-6H-pyrrolo[2,3-e][1,2,4]triazolo[4,3-a]pyridine trifluoroacetate salt (racemic)

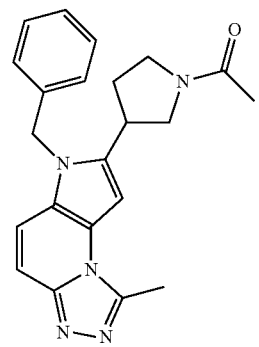 [SMILES: CC(=O)N1CCC(c2cc3c(ccc4nnc(C)n43)n2Cc2ccccc2)C1]

The title compound was obtained as a byproduct in Example 186, Step 2. The title product was isolated via preparative HPLC-MS (Waters SunFire C18, eluting with a gradient of MeCN/H$_2$O containing 0.1% TFA). Yield: (2.7 mg, 2%).

$^1$H NMR (400 MHz, d$_6$-DMSO) δ 8.26 (d, J=9.2 Hz, 1H), 7.56 (d, J=9.6 Hz, 0.5 H, rotamers), 7.55 (d, J=9.6 Hz, 0.5 H, rotamers), 7.37-7.23 (m, 3H), 7.30 (s, 1H), 7.04-6.94 (m, 2H), 5.79 (s, 2H), 3.83-3.20 (m, 5H), 3.02 (s, 3H), 2.23-1.98 (m, 2H), 1.96 (s, 1.5 H, rotamers), 1.90 (s, 1.5 H, rotamers); LCMS (M+H)$^+$: 373.8.

Example 188

6-(3-(Azetidin-1-ylmethyl)-5-chlorobenzyl)-7-(1-ethyl-1H-pyrazol-3-yl)-1-methyl-6H-pyrrolo[2,3-e][1,2,4]triazolo[4,3-a]pyridine tris(trifluoroacetate) salt

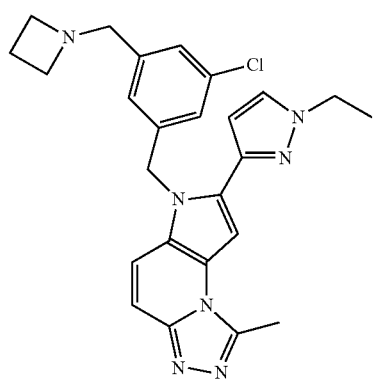 [SMILES: CCn1ccc(-c2cc3c(ccc4nnc(C)n43)n2Cc2cc(Cl)cc(CN3CCC3)c2)n1]

Step 1. 6-[3-({[tert-Butyl(diphenyl)silyl]oxy}methyl)-5-chlorobenzyl]-7-(1-ethyl-1H-pyrazol-3-yl)-1-methyl-6H-pyrrolo[2,3-e][1,2,4]triazolo[4,3-c]pyridine

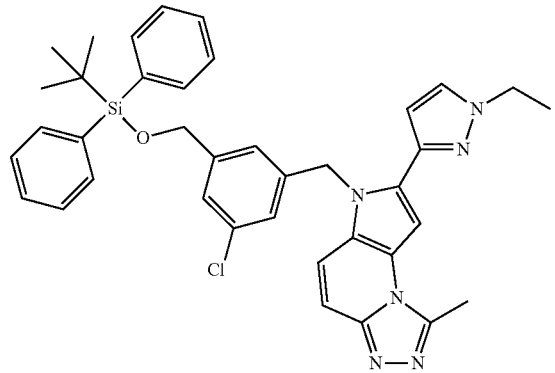 [SMILES: CCn1ccc(-c2cc3c(ccc4nnc(C)n43)n2Cc2cc(Cl)cc(CO[Si](c3ccccc3)(c3ccccc3)C(C)(C)C)c2)n1]

A solution of 6-[3-({[tert-butyl(diphenyl)silyl]oxy}methyl)-5-chlorobenzyl]-1-methyl-7-(1H-pyrazol-3-yl)-6H-pyrrolo[2,3-e][1,2,4]triazolo[4,3-a]pyridine (0.10 g, 0.11 mmol, from Example 185, Step 4) in DMF (2.3 mL) was treated with NaH (60% in mineral oil, 13 mg, 0.33 mmol). After 10 minutes, iodoethane (27 μL, 0.33 mmol, Sigma-Aldrich) was added. After 10 minutes, the reaction was quenched with water. The product was purified via preparative HPLC-MS (Waters XBridge C18, eluting with a gradient of MeCN/H$_2$O containing 0.15% NH$_4$OH).

Yield: (14 mg, 19%).

LCMS (M+H)$^+$: 659.3.

Step 2. 6-(3-(Azetidin-1-ylmethyl)-5-chlorobenzyl)-7-(1-ethyl-1H-pyrazol-3-yl)-1-methyl-6H-pyrrolo[2,3-e][1,2,4]triazolo[4,3-a]pyridine tris(trifluoroacetate) salt 6-[3-({[tert-Butyl(diphenyl)silyl]oxy}methyl)-5-chlorobenzyl]-7-(1-ethyl-1H-pyrazol-3-yl)-1-methyl-6H-pyrrolo[2,3-e][1,2,4]triazolo[4,3-c]pyridine (7.0 mg, 0.011 mmol, from Step 1) in THF (0.5 mL) was treated with 1.0 M TBAF in THF (12 μL, 0.012 mmol, Aldrich), and the reaction mixture was stirred for 35 minutes. The reaction mixture was then diluted with DCM (0.7 mL) and treated with triethylamine (7.4 μL, 0.053 mmol) and methanesulfonyl chloride (3.3 μL, 0.042 mmol, Aldrich). After 10 minutes, the solvents were removed in vacuo and the residue was dissolved in THF (0.3 mL) and MeOH (0.3 mL). Azetidine (3.6 μL, 0.053 mmol, Aldrich) was added, and the reaction was stirred for 35 minutes. Solvent was removed in vacuo, and the residue was dissolved in MeOH and the title product was isolated via preparative HPLC-MS (Waters SunFire C18, eluting with a gradient of MeCN/H$_2$O containing 0.1% TFA). Yield: (5.8 mg, 71%).

$^1$H NMR (400 MHz, d$_6$-DMSO) δ 10.10 (s, 1H), 8.09 (d, J=9.4 Hz, 1H), 7.91 (d, J=2.2 Hz, 1H), 7.58 (s, 1H), 7.54 (d, J=9.4 Hz, 1H), 7.44-7.39 (m, 1H), 7.21-7.17 (m, 1H), 7.16-7.13 (m, 1H), 6.91 (d, J=2.2 Hz, 1H), 6.15 (s, 2H), 4.25 (d, J=5.3 Hz, 2H), 4.17 (q, J=7.2 Hz, 2H), 4.05-3.82 (m, 4H), 3.04 (s, 3H), 2.41-2.14 (m, 2H), 1.35 (t, J=7.3 Hz, 3H); LCMS (M+H)$^+$: 460.2.

Example 189

6-(3-Chloro-5-(pyrrolidin-1-ylmethyl)benzyl)-7-(1-ethyl-1H-pyrazol-3-yl)-1-methyl-6H-pyrrolo[2,3-e][1,2,4]triazolo[4,3-a]pyridine tris(trifluoroacetate) salt

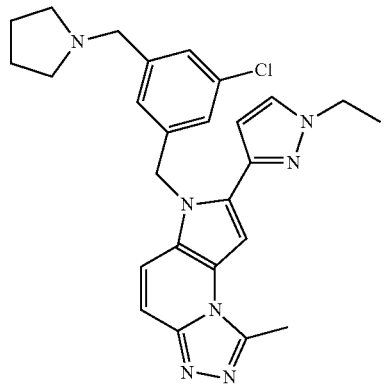 [SMILES: CCn1ccc(-c2cc3c(ccc4nnc(C)n43)n2Cc2cc(Cl)cc(CN3CCCC3)c2)n1]

The title compound was prepared according to the methods of Example 188, using pyrrolidine (4.4 μL, 0.053 mmol, Aldrich) in Step 2. Yield: (5.6 mg, 68%).

$^1$H NMR (400 MHz, d$_6$-DMSO) δ 9.89 (s, 1H), 8.13 (d, J=9.8 Hz, 1H), 7.91 (d, J=2.3 Hz, 1H), 7.60 (s, 1H), 7.55 (d, J=9.6 Hz, 1H), 7.52-7.47 (m, 1H), 7.21-7.18 (m, 1H), 7.18-7.16 (m, 1H), 6.92 (d, J=2.3 Hz, 1H), 6.16 (s, 2H), 4.26 (d, J=5.4 Hz, 2H), 4.17 (q, J=7.3 Hz, 2H), 3.34-3.17 (m, 2H), 3.05 (s, 3H), 3.01-2.89 (m, 2H), 2.03-1.89 (m, 2H), 1.88-1.72 (m, 2H), 1.35 (t, J=7.3 Hz, 3H); LCMS (M+H)$^+$: 474.2.

Example 190

6-[3-Chloro-5-(pyrrolidin-1-ylmethyl)benzyl]-1-methyl-7-(1-methyl-1H-pyrazol-3-yl)-6H-pyrrolo[2,3-e][1,2,4]triazolo[4,3-a]pyridine bis(trifluoroacetate) salt

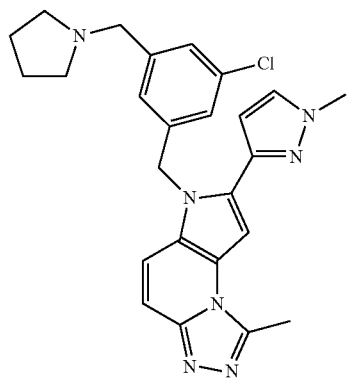 [SMILES: Cc1nnc2ccc3c(cc(-c4ccn(C)n4)n3Cc3cc(Cl)cc(CN4CCCC4)c3)n12]

The title compound was prepared according to the methods of Example 185, using pyrrolidine in Step 6. Yield: (4.8 mg, 45%).

¹H NMR (400 MHz, d₆-DMSO) δ 9.99 (s, 1H), 8.06 (d, J=9.5 Hz, 1H), 7.86 (d, J=2.3 Hz, 1H), 7.57 (s, 1H), 7.55-7.48 (m, 2H), 7.23-7.19 (m, 1H), 7.14-7.10 (m, 1H), 6.91 (d, J=2.3 Hz, 1H), 6.16 (s, 2H), 4.28 (d, J=4.0 Hz, 2H), 3.89 (s, 3H), 3.34-3.21 (m, 2H), 3.04 (s, 3H), 3.02-2.89 (m, 2H), 2.04-1.91 (m, 2H), 1.88-1.74 (m, 2H); LCMS (M+H)⁺: 460.2.

Example 191

1-(3-Chloro-5-{[1-methyl-7-(1-methyl-1H-pyrazol-3-yl)-6H-pyrrolo[2,3-e][1,2,4]triazolo[4,3-a]pyridin-6-yl]methyl}phenyl)-N,N-dimethylmethanamine bis(trifluoroacetate) salt

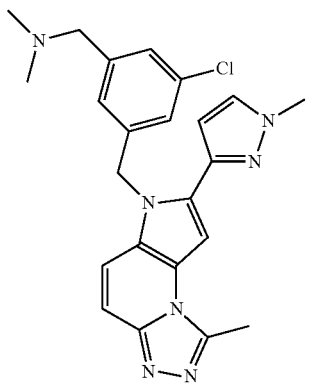

The title compound was prepared according to the methods of Example 185, using 2.0 M dimethylamine (Aldrich) in THF in Step 6. Yield: (3.2 mg, 31%).
¹H NMR (400 MHz, d₆-DMSO) δ 9.86 (s, 1H), 8.10 (d, J=9.7 Hz, 1H), 7.86 (d, J=2.3 Hz, 1H), 7.59 (s, 1H), 7.53 (d, J=9.6 Hz, 1H), 7.51-7.47 (m, 1H), 7.18-7.14 (m, 2H), 6.92 (d, J=2.3 Hz, 1H), 6.16 (s, 2H), 4.19 (s, 2H), 3.89 (s, 3H), 3.05 (s, 3H), 2.65 (s, 6H); LCMS (M+H)⁺: 434.2.

Example 192

6-[3-Chloro-5-(morpholin-4-ylmethyl)benzyl]-1-methyl-7-(1-methyl-1H-pyrazol-3-yl)-6H-pyrrolo[2,3-e][1,2,4]triazolo[4,3-a]pyridine bis(trifluoroacetate) salt

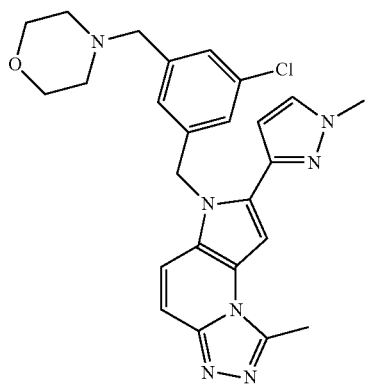 [SMILES: Cc1nnc2ccc3c(cc(-c4ccn(C)n4)n3Cc3cc(Cl)cc(CN4CCOCC4)c3)n12]

The title compound was prepared according to the methods of Example 185, using morpholine (Aldrich) in Step 6. Yield: (4.7 mg, 43%).

¹H NMR (400 MHz, d₆-DMSO) δ 8.09 (d, J=9.5 Hz, 1H), 7.87 (d, J=2.3 Hz, 1H), 7.60 (s, 1H), 7.54 (d, J=9.6 Hz, 1H), 7.51-7.46 (m, 1H), 7.19-7.14 (m, 1H), 7.14-7.11 (m, 1H), 3.18-2.92 (m, 4H), 6.92 (d, J=2.3 Hz, 1H), 6.17 (s, 2H), 4.23 (s, 2H), 3.89 (s, 3H), 3.99-3.50 (m, 4H), 3.05 (s, 3H); LCMS (M+H)⁺: 476.2.

Example 193

6-(3-Chlorobenzyl)-7-(4,5-dihydro-1,3-oxazol-2-yl)-1-methyl-6H-pyrrolo[2,3-e][1,2,4]triazolo[4,3-a]pyridine

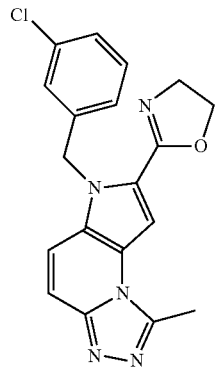 [SMILES: Cc1nnc2ccc3c(cc(C4=NCCO4)n3Cc3cccc(Cl)c3)n12]

To a solution of 6-(3-chlorobenzyl)-1-methyl-6H-pyrrolo[2,3-e][1,2,4]triazolo[4,3-a]pyridine-7-carboxylic acid (29 mg, 0.085 mmol, prepared as in Example 99, Step 4) in DMF (0.90 mL) was added N,N-diisopropylethylamine (30. μL, 0.17 mmol), followed by HATU (48 mg, 0.13 mmol). After stirring for 15 minutes, ethanolamine (10. μL, 0.17 mmol, Aldrich) was added to the reaction mixture. After stirring for 15 minutes, the intermediate amide was purified via preparative HPLC-MS (Waters XBridge C18, eluting with a gradient of MeCN/H₂O containing 0.15% NH₄OH) to afford a white solid (15 mg). The intermediate amide was treated with triethylamine (47 μL, 0.34 mmol) and methanesulfonic anhydride (37 mg, 0.21 mmol, Aldrich) in THF (2.0 mL) for 30 minutes at room temperature, and the reaction mixture was then heated at 50° C. for 1.5 hours. The title product was purified via preparative HPLC-MS (Waters XBridge C18, eluting with a gradient of MeCN/H₂O containing 0.15% NH₄OH). Yield: (9.2 mg, 30%).
¹H NMR (300 MHz, CDCl₃) δ 7.48 (d, J=8.7 Hz, 1H), 7.41-7.15 (m, 4H), 7.09-7.00 (m, 1H), 6.96-6.82 (m, 1H), 6.06 (s, 2H), 4.39 (t, J=8.6 Hz, 2H), 4.10 (t, J=8.4 Hz, 2H), 3.01 (s, 3H); LCMS (M+H)+: 366.0.

Example 194

6-(3-Chlorobenzyl)-1-methyl-7-(1,3-oxazol-2-yl)-6H-pyrrolo[2,3-e][1,2,4]triazolo[4,3-a]pyridine trifluoroacetate salt

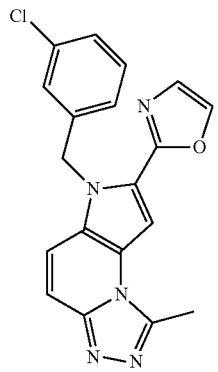 [SMILES: Cc1nnc2ccc3c(cc(-c4ncco4)n3Cc3cccc(Cl)c3)n12]

Step 1. 5-Chloro-2-(1,3-oxazol-2-yl)-1-(phenylsulfonyl)-1H-pyrrolo[3,2-b]pyridine

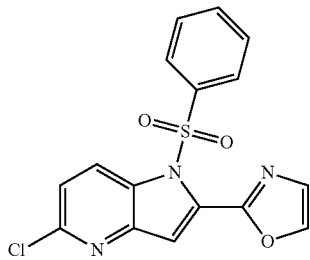 [SMILES: O=S(=O)(c1ccccc1)n1c(-c2ncco2)cc2nc(Cl)ccc21]

Tetrakis(triphenylphosphine)palladium(0) (0.31 g, 0.27 mmol) was added to a degassed mixture of 2-bromo-5-chloro-1-(phenylsulfonyl)-1H-pyrrolo[3,2-b]pyridine (1.0 g, 2.7 mmol, prepared as in Example 62, Step 1, isolated as the free base) and 2-(tributylstannyl)-1,3-oxazole (1.2 g, 3.4 mmol, Aldrich) in toluene (16 mL). The reaction was heated at 110° C. overnight. Upon cooling, solvent was removed in vacuo. The product was purified by flash chromatography, eluting with a gradient from 0-40% EtOAc in hexanes. Yield: (0.80 g, 83%).

$^1$H NMR (400 MHz, CDCl$_3$) δ 8.41 (dd, J=8.8, 0.7 Hz, 1H), 7.91 (d, J=0.7 Hz, 1H), 7.88-7.82 (m, 2H), 7.62-7.55 (m, 1H), 7.50-7.43 (m, 2H), 7.39 (d, J=0.7 Hz, 1H), 7.36 (d, J=8.8 Hz, 1H), 7.19 (d, J=0.7 Hz, 1H); LCMS (M+H)+: 360.1.

Step 2. 2-(1-Methyl-6H-pyrrolo[2,3-e][1,2,4]triazolo[4,3-a]pyridin-7yl)oxazole

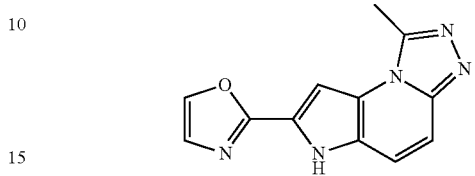

A degassed mixture of 5-chloro-2-(1,3-oxazol-2-yl)-1-(phenylsulfonyl)-1H-pyrrolo[3,2-b]pyridine (0.80 g, 2.2 mmol, from Step 1), di-tert-butyl hydrazine-1,2-dicarboxylate (1.0 g, 4.4 mmol, Aldrich), dicyclohexyl(2',4',6'-triisopropylbiphenyl-2-yl)phosphine-(2'-aminobiphenyl-2-yl)(chloro)palladium (1:1) (0.17 g, 0.22 mmol, Aldrich), and Cs$_2$CO$_3$ (1.1 g, 3.3 mmol, Aldrich) in toluene (10. mL) was heated at 140° C. for 2 hours. The mixture was cooled to room temperature, diluted with DCM, filtered and concentrated. Flash chromatography, eluting with a gradient from 0-50% EtOAc in hexanes afforded di-tert-butyl 1-[2-(1,3-oxazol-2-yl)-1-(phenylsulfonyl)-1H-pyrrolo[3,2-b]pyridin-5-yl]hydrazine-1,2-dicarboxylate (yield: 0.18 g, 14%; LCMS (M+H)+: 556.2) and also di-tert-butyl 1-[2-(1,3-oxazol-2-yl)-1H-pyrrolo[3,2-b]pyridin-5-yl]hydrazine-1,2-dicarboxylate (yield: 0.12 g, 13%; LCMS (M+H)+: 416.2). Each of these products was dissolved separately in acetic acid (5.0 mL) and heated in the microwave at 180° C. for 5 minutes. Both reaction mixtures were combined, and the acetic acid was removed in vacuo. The residue thus obtained was dissolved in THF (20 mL) and treated with 2.8 M NaOH in water (10 mL, 28 mmol) for 40 minutes, after which time the reaction mixture was treated with 1 N HCl to achieve pH~10, and then saturated with solid NaCl. The aqueous solution was extracted with 15% iPrOH in CHCl$_3$. The organic extract was dried over sodium sulfate, filtered and concentrated. The product was purified by flash chromatography, eluting with a gradient from 0-10% MeOH in DCM. Yield: (76 mg, 9%).

$^1$H NMR (300 MHz, d$_6$-DMSO) δ 12.94 (s, 1H), 8.29 (s, 1H), 7.52 (d, J=9.7 Hz, 1H), 7.48-7.41 (m, 3H), 2.94 (s, 3H); LCMS (M+H)+: 240.1.

Step 3. 6-(3-Chlorobenzyl)-1-methyl-7-(1,3-oxazol-2-yl)-6H-pyrrolo[2,3-e][1,2,4]triazolo[4,3-a]pyridine trifluoroacetate salt A mixture of 2-(1-methyl-6H-pyrrolo[2,3-e][1,2,4]triazolo[4,3-a]pyridin-7yl)oxazole (10. mg, 0.042 mmol, from Step 2) in DMF (0.50 mL) was treated with K$_2$CO$_3$ (17 mg, 0.12 mmol) and 1-(bromomethyl)-3-chlorobenzene (17 mg, 0.084 mmol, Aldrich), and the reaction mixture was stirred at room temperature overnight. The reaction mixture was diluted with MeCN, filtered and purified via preparative HPLC-MS (Waters SunFire C18, eluting with a gradient of MeCN/H$_2$O containing 0.1% TFA). Yield: (5.7 mg, 28%).

$^1$H NMR (400 MHz, d$_6$-DMSO) δ 8.36 (d, J=0.6 Hz, 1H), 8.01 (d, J=9.6 Hz, 1H), 7.73 (s, 1H), 7.63 (d, J=9.6 Hz, 1H), 7.50 (d, J=0.6 Hz, 1H), 7.35-7.27 (m, 2H), 7.22-7.16 (m, 1H), 7.00-6.93 (m, 1H), 6.22 (s, 2H), 3.02 (s, 3H); LCMS (M+H)+: 364.2.

Example 195

6-[3-(Azetidin-1-ylmethyl)-5-chlorobenzyl]-1-methyl-7-(1,3-oxazol-2-yl)-6H-pyrrolo[2,3-e][1,2,4]triazolo[4,3-a]pyridine bis(trifluoroacetate) salt

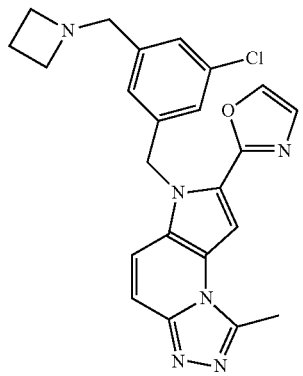 [SMILES: Cc1nnc2ccc3c(cc(-c4ncco4)n3Cc3cc(Cl)cc(CN4CCC4)c3)n12]

Step 1. 6-[3-({[tert-Butyl(diphenyl)silyl]oxy}methyl)-5-chlorobenzyl]-1-methyl-7-(1,3-oxazol-2-yl)-6H-pyrrolo[2,3-e][1,2,4]triazolo[4,3-a]pyridine

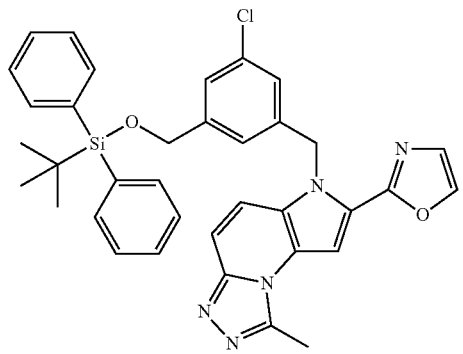 [SMILES: Cc1nnc2ccc3c(cc(-c4ncco4)n3Cc3cc(Cl)cc(CO[Si](c4ccccc4)(c4ccccc4)C(C)(C)C)c3)n12]

A solution of 2-(1-methyl-6H-pyrrolo[2,3-e][1,2,4]triazolo[4,3-a]pyridin-7yl)oxazole (20. mg, 0.084 mmol, Example 194, Step 2) in DMF (10.0 mL) was treated with K₂CO₃ (58 mg, 0.42 mmol) and 3-{[tert-butyl(diphenyl)silyl]oxy}-5-chlorobenzyl methanesulfonate (44 mg, 0.092 mmol, prepared as in Example 131, Step 1-3) and stirred for 3 days. The reaction mixture was diluted with EtOAc and washed with water, followed by brine. The organic layer was dried over sodium sulfate, filtered and concentrated to afford a light yellow solid, which was used without further purification in Step 2. Yield: (51 mg, 96%).

¹H NMR (400 MHz, d₆-DMSO) δ 8.30 (d, J=0.7 Hz, 1H), 7.74 (d, J=9.9 Hz, 1H), 7.59 (s, 1H), 7.51 (d, J=9.8 Hz, 1H), 7.44 (d, J=0.7 Hz, 1H), 7.43-7.36 (m, 6H), 7.36-7.33 (m, 1H), 7.32-7.26 (m, 4H), 7.14-7.12 (m, 1H), 6.80-6.75 (m, 1H), 6.22 (s, 2H), 4.58 (s, 2H), 2.90 (s, 3H), 0.68 (s, 9H); LCMS (M+H)+: 632.3.

Step 2. 6-[3-(Azetidin-1-ylmethyl)-5-chlorobenzyl]-1-methyl-7-(1,3-oxazol-2-yl)-6H-pyrrolo[2,3-e][1,2,4]triazolo[4,3-a]pyridine bis(trifluoroacetate) salt 6-[3-({[tert-Butyl(diphenyl)silyl]oxy}methyl)-5-chlorobenzyl]-1-methyl-7-(1,3-oxazol-2-yl)-6H-pyrrolo[2,3-e][1,2,4]triazolo[4,3-a]pyridine (48 mg, 0.076 mmol, from Step 1) in THF (4 mL) was treated with 1.0 M TBAF in THF (84 μL, 0.084 mmol, Aldrich). After 30 minutes, DCM (5.2 mL), triethylamine (53 μL, 0.38 mmol), and methanesulfonyl chloride (24 μL, 0.30 mmol, Aldrich) were added. After 30 minutes, the solvents were removed in vacuo. The residue was dissolved in THF (2.1 mL) and MeOH (2.1 mL), and azetidine (51 μL, 0.76 mmol, Aldrich) was added to the reaction mixture. After 40 minutes, the solvent was removed in vacuo and the crude reaction mixture was dissolved in MeOH and purified via preparative HPLC-MS (Waters SunFire C18, eluting with a gradient of MeCN/H₂O containing 0.1% TFA). Yield: (24.2 mg, 48%).

¹H NMR (400 MHz, d₆-DMSO) δ 9.98 (s, 1H), 8.35 (d, J=0.8 Hz, 1H), 7.88 (d, J=9.7 Hz, 1H), 7.73 (s, 1H), 7.61 (d, J=9.8 Hz, 1H), 7.47 (d, J=0.8 Hz, 1H), 7.45-7.42 (m, 1H), 7.26-7.21 (m, 1H), 7.10-7.05 (m, 1H), 6.21 (s, 2H), 4.25 (d, J=6.0 Hz, 2H), 4.05-3.76 (m, 4H), 3.02 (s, 3H), 2.41-2.09 (m, 2H); LCMS (M+H)+: 433.2.

Example 196

6-{3-Chloro-5-[(3,3-dimethylazetidin-1-yl)methyl]benzyl}-1-methyl-7-(1,3-oxazol-2-yl)-6H-pyrrolo[2,3-e][1,2,4]triazolo[4,3-a]pyridine bis(trifluoroacetate) salt

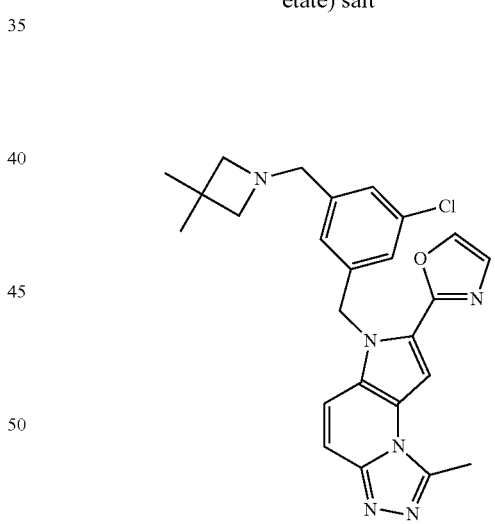

The title compound was prepared according to the methods of Example 195, Step 2, using 3,3-dimethylazetidine hydrochloride (Synthonix) and triethylamine in the displacement step. The reaction time was 3 hours. Yield: (5.4 mg, 29%).

¹H NMR (400 MHz, d₆-DMSO) δ 10.13 (s, 1H), 8.34 (d, J=0.8 Hz, 1H), 7.82 (d, J=9.8 Hz, 1H), 7.70 (s, 1H), 7.59 (d, J=9.8 Hz, 1H), 7.47 (d, J=0.8 Hz, 1H), 7.46-7.43 (m, 1H), 7.23-7.19 (m, 1H), 7.11-7.07 (m, 1H), 6.21 (s, 2H), 4.28 (d,

J=5.8 Hz, 2H), 3.82-3.74 (m, 2H), 3.65-3.58 (m, 2H), 3.00 (s, 3H), 1.23 (s, 3H), 1.16 (s, 3H); LCMS (M+H)+: 461.2.

Example 197

6-[3-Chloro-5-(pyrrolidin-1-ylmethyl)benzyl]-1-methyl-7-(1,3-oxazol-2-yl)-6H-pyrrolo[2,3-e][1,2,4]triazolo[4,3-a]pyridine bis(trifluoroacetate) salt

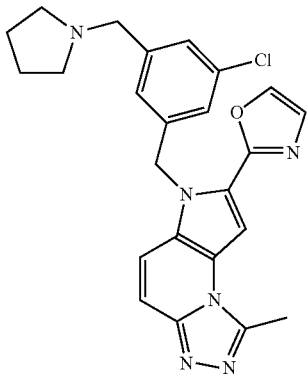 [SMILES: Cc1nnc2ccc3c(cc(-c4ncco4)n3Cc3cc(Cl)cc(CN4CCCC4)c3)n12]

The title compound was prepared according to the methods of Example 195, using pyrrolidine (Aldrich) in Step 2. Yield: (8.7 mg, 48%).
$^1$H NMR (400 MHz, d$_6$-DMSO) δ 9.72 (s, 1H), 8.33 (s, 1H), 7.82 (d, J=9.8 Hz, 1H), 7.70 (s, 1H), 7.58 (d, J=9.8 Hz, 1H), 7.54-7.50 (m, 1H), 7.46 (d, J=0.6 Hz, 1H), 7.24-7.20 (m, 1H), 7.15-7.10 (m, 1H), 6.21 (s, 2H), 4.27 (d, J=5.7 Hz, 2H), 3.31-3.21 (m, 2H), 3.00 (s, 3H), 2.99-2.89 (m, 2H), 2.01-1.88 (m, 2H), 1.87-1.73 (m, 2H); LCMS (M+H)+: 447.2.

Example 198

1-(3-Chloro-5-{[1-methyl-7-(1,3-oxazol-2-yl)-6H-pyrrolo[2,3-e][1,2,4]triazolo[4,3-a]pyridin-6-yl]methyl}benzyl)azetidin-3-ol bis(trifluoroacetate) salt

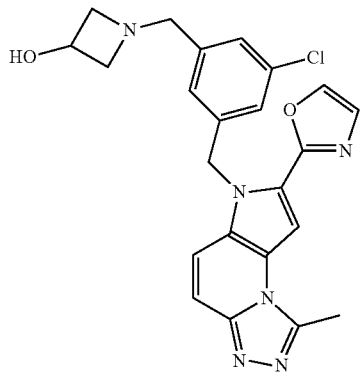 [SMILES: Cc1nnc2ccc3c(cc(-c4ncco4)n3Cc3cc(Cl)cc(CN4CC(O)C4)c3)n12]

The title compound was prepared according to the methods of Example 195, Step 2, using azetidin-3-ol hydrochloride (Aldrich) and triethylamine in the displacement reaction. Yield: (6.4 mg, 40%).
$^1$H NMR (400 MHz, d$_6$-DMSO) δ 10.27 (br s, 0.3H), 9.89 (br s, 0.7H), 8.35 (d, J=0.8 Hz, 1H), 7.91 (dd, J=9.8, 3.6 Hz, 1H), 7.74 (s, 1H), 7.62 (d, J=9.8 Hz, 1H), 7.47 (d, J=0.6 Hz, 1H), 7.47-7.43 (m, 1H), 7.25-7.22 (m, 1H), 7.14-7.08 (m, 1H), 6.21 (s, 2H), 4.57-4.48 (m, 0.3H), 4.39 (p, J=6.8 Hz, 0.7H), 4.30-4.22 (m, 2H), 4.18-4.03 (m, 2H), 3.84-3.69 (m, 2H), 3.02 (s, 3H); LCMS (M+H)+: 449.0.

Example 199

1-(3-Chloro-5-{[1-methyl-7-(1,3-oxazol-2-yl)-6H-pyrrolo[2,3-e][1,2,4]triazolo[4,3-a]pyridin-6-yl]methyl}benzyl)pyrrolidin-3-ol bis(trifluoroacetate) salt (racemic)

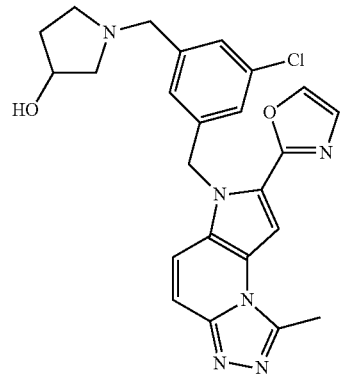 [SMILES: Cc1nnc2ccc3c(cc(-c4ncco4)n3Cc3cc(Cl)cc(CN4CCC(O)C4)c3)n12]

The title compound was prepared according to the methods of Example 195, using 3-pyrrolidinol (Aldrich) in Step 2. Yield: (8.3 mg, 51%).
$^1$H NMR (400 MHz, d$_6$-DMSO) δ 10.23 (br s, 0.6H), 9.97 (br s, 0.4H), 8.34 (d, J=0.6 Hz, 1H), 7.93-7.86 (m, 1H), 7.73 (s, 1H), 7.61 (d, J=9.8 Hz, 1H), 7.55-7.51 (m, 1H), 7.47 (d, J=0.5 Hz, 1H), 7.25-7.20 (m, 1H), 7.20-7.13 (m, 1H), 6.21 (s, 2H), 4.43-4.18 (m, 3H), 3.51-3.03 (m, 4H), 3.02 (s, 3H), 2.27-1.69 (m, 2H); LCMS (M+H)+: 463.0.

Example 200

6-Benzyl-1,7-dimethyl-N-1H-pyrazol-3-yl-6H-pyrrolo[2,3-e][1,2,4]triazolo[4,3-a]pyridin-4-amine tris(trifluoroacetate) salt

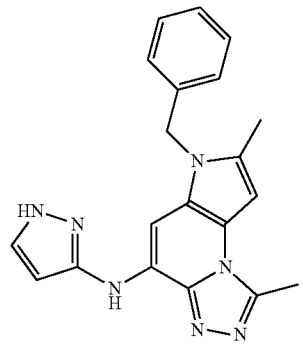 [SMILES: Cc1cc2c(cc(Nc3cc[nH]n3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (25 mg, 0.080 mmol, from Example 228, Step 7), 1H-pyrazol-3-amine (20. mg, 0.24 mmol, Aldrich), tBuBrettPhos Pd G3 (6.9 mg, 0.0080 mmol, Aldrich) and NaO$^t$Bu (15 mg, 0.16 mmol, Aldrich) in tert-butyl alcohol (1.0 mL) was heated at 50° C. for 1 hour and then at 80° C. for 7 minutes. The product was isolated via preparative HPLC-MS (Waters SunFire C18, eluting with a gradient of MeCN/H$_2$O containing 0.1% TFA). Yield: (11 mg, 20%).

$^1$H NMR (400 MHz, d$_6$-DMSO) δ 8.74 (s, 1H), 8.31 (s, 1H), 7.60 (d, J=2.2 Hz, 1H), 7.37-7.29 (m, 2H), 7.29-7.22 (m, 1H), 7.09-7.01 (m, 2H), 6.84 (s, 1H), 6.04 (d, J=2.2 Hz, 1H), 5.44 (s, 2H), 2.96 (s, 3H), 2.40 (s, 3H); LCMS (M+H)$^+$: 358.1.

Example 201

6-Benzyl-1,7-dimethyl-N-pyrimidin-2-yl-6H-pyrrolo [2,3-e][1,2,4]triazolo[4,3-a]pyridin-4-amine tris(trifluoroacetate) salt

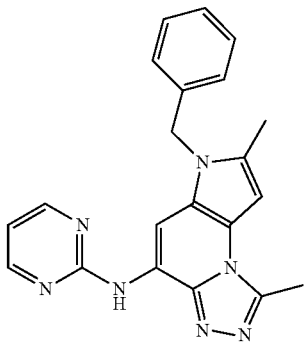 [SMILES: Cc1cc2c(cc(Nc3ncccn3)c3nnc(C)n32)n1Cc1ccccc1]

The title compound was prepared according to the methods of Example 200, using 2-amino-pyrimidine (Aldrich) at 80° C. for 10 minutes. Yield: (13 mg, 30%).

$^1$H NMR (400 MHz, d$_6$-DMSO) δ 9.44 (s, 1H), 8.47-8.41 (m, 3H), 7.37-7.30 (m, 2H), 7.30-7.23 (m, 1H), 7.10-7.03 (m, 3H), 6.90 (t, J=4.8 Hz, 1H), 5.62 (s, 2H), 3.01 (s, 3H), 2.49 (s, 3H); LCMS (M+H)$^+$: 370.1.

Example 202

6-Benzyl-1,7-dimethyl-N-(1-methyl-1H-pyrazol-3-yl)-6H-pyrrolo[2,3-e][1,2,4]triazolo[4,3-a]pyridin-4-amine tris(trifluoroacetate) salt

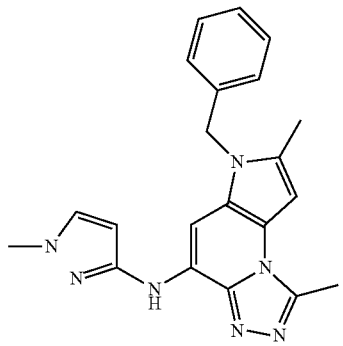

The title compound was prepared according to the methods of Example 200, using 1-methyl-1H-pyrazol-3-amine (Combi-Blocks) at 80° C. for 10 minutes. Yield: 9.6 mg, 21%).

$^1$H NMR (400 MHz, d$_6$-DMSO) δ 8.70 (s, 1H), 8.24 (s, 1H), 7.52 (d, J=2.1 Hz, 1H), 7.37-7.30 (m, 2H), 7.29-7.22 (m, 1H), 7.20-7.13 (m, 2H), 6.77 (s, 1H), 5.98 (d, J=2.1 Hz, 1H), 5.41 (s, 2H), 3.77 (s, 3H), 2.92 (s, 3H), 2.46 (s, 3H); LCMS (M+H)$^+$: 371.9.

Example 203

N-1,3-Benzoxazol-2-yl-6-benzyl-1,7-dimethyl-6H-pyrrolo[2,3-e][1,2,4]triazolo[4,3-a]pyridin-4-amine bis(trifluoroacetate) salt

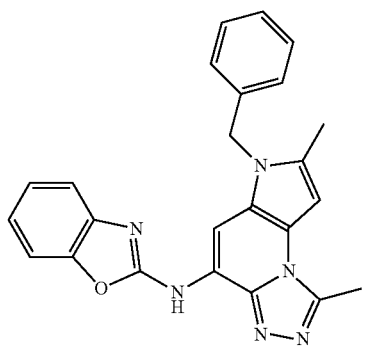 [SMILES: Cc1cc2c(cc(Nc3nc4ccccc4o3)c3nnc(C)n32)n1Cc1ccccc1]

The title compound was prepared according to the methods of Example 200, using 1,3-benzoxazol-2-amine (Matrix) at 80° C. for 10 minutes. Yield: (6.8 mg, 12%).

$^1$H NMR (400 MHz, d$_6$-DMSO) δ 8.47 (s, 1H), 7.48 (d, J=7.7 Hz, 1H), 7.41-7.30 (m, 3H), 7.30-7.25 (m, 1H), 7.22 (td, J=7.7, 1.1 Hz, 1H), 7.16-7.09 (m, 3H), 6.95 (s, 1H), 5.56 (s, 2H), 2.97 (s, 3H), 2.47 (s, 3H); LCMS (M+H)$^+$: 409.2.

Example 204

6-Benzyl-1,7-dimethyl-6H-pyrrolo[2,3-e][1,2,4]triazolo[4,3-a]pyridin-4-ol trifluoroacetate salt

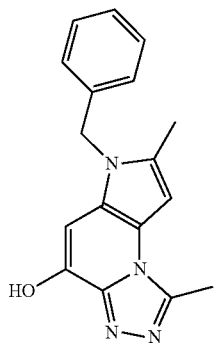 [SMILES: Cc1cc2c(cc(O)c3nnc(C)n32)n1Cc1ccccc1]

The title compound was obtained as a byproduct in Example 200. The title product was isolated via preparative HPLC-MS (Waters SunFire C18, eluting with a gradient of MeCN/H$_2$O containing 0.1% TFA). Yield: (5.0 mg, 26%).

$^1$H NMR (400 MHz, d$_6$-DMSO) δ 11.13 (br s, 1H), 7.36-7.29 (m, 3H), 7.29-7.23 (m, 1H), 7.03-6.97 (m, 2H), 6.92 (s, 1H), 5.53 (s, 2H), 2.95 (s, 3H), 2.43 (s, 3H); LCMS (M+H)$^+$: 293.0.

Example 205

N-1H-Benzimidazol-2-yl-6-benzyl-1,7-dimethyl-6H-pyrrolo[2,3-e][1,2,4]triazolo[4,3-a]pyridin-4-amine trifluoroacetate salt

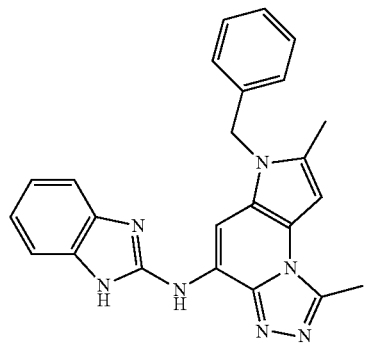 [SMILES: Cc1cc2c(cc(Nc3nc4ccccc4[nH]3)c3nnc(C)n32)n1Cc1ccccc1]

The title compound was prepared according to the methods of Example 200, using 2-aminobenzimidazole (Aldrich) at 80° C. for 30 minutes. Yield: (5.0 mg, 10%).

$^1$H NMR (400 MHz, d$_6$-DMSO) δ 8.15 (s, 1H), 7.42-7.25 (m, 7H), 7.07-7.03 (m, 2H), 7.00 (s, 1H), 5.58 (s, 2H), 2.97 (s, 3H), 2.45 (s, 3H); LCMS (M+H)$^+$: 408.2.

Example 206

6-Benzyl-1,7-dimethyl-N-piperidin-4-yl-6H-pyrrolo[2,3-e][1,2,4]triazolo[4,3-a]pyridin-4-amine

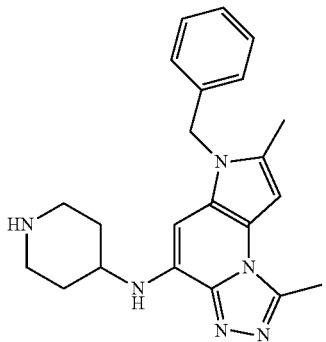 [SMILES: Cc1cc2c(cc(NC3CCNCC3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (80. mg, 0.26 mmol, from Example 228, Step 7), tert-butyl 4-aminopiperidine-1-carboxylate (210 mg, 1.0 mmol, Combi-Blocks), NaO$^t$Bu (49 mg, 0.51 mmol, Aldrich), (9,9-dimethyl-9H-xanthene-4,5-diyl)bis(diphenylphosphine) (30. mg, 0.051 mmol, Aldrich) and tris(dibenzylideneacetone)dipalladium (0) (24 mg, 0.026 mmol, Aldrich) in toluene (4.0 mL) was heated at 100° C. overnight. After cooling, the reaction mixture was diluted with EtOAc and washed sequentially with water and brine. The organic layer was dried over sodium sulfate, filtered and concentrated. The crude product was dissolved in DCM (5.0 mL) and was treated with 4.0 M HCl in dioxane (2.0 mL, 8.0 mmol) for 1 hour. The reaction mixture was concentrated in vacuo. The product was purified via preparative HPLC-MS (Waters XBridge C18, eluting with a gradient of MeCN/H$_2$O containing 0.15% NH$_4$OH). Yield: (40 mg, 38%).

$^1$H NMR (400 MHz, d$_6$-DMSO) δ 7.32-7.25 (m, 2H), 7.24-7.17 (m, 1H), 7.03-6.97 (m, 2H), 6.57 (s, 1H), 6.53 (s, 1H), 5.40 (s, 2H), 5.20 (d, J=8.6 Hz, 1H), 2.95-2.84 (m, 2H), 2.80 (s, 3H), 2.57-2.47 (m, 2H), 2.29 (s, 3H), 1.87-1.75 (m, 2H), 1.32-1.21 (m, 2H); LCMS (M+H)$^+$: 375.2.

Example 207

6-Benzyl-1,7-dimethyl-N-(1-methylpiperidin-4-yl)-6H-pyrrolo[2,3-e][1,2,4]triazolo[4,3-a]pyridin-4-amine

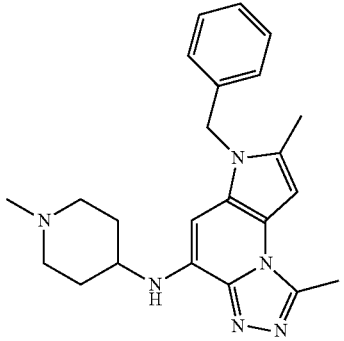

To a mixture of 6-benzyl-1,7-dimethyl-N-piperidin-4-yl-6H-pyrrolo[2,3-e][1,2,4]triazolo[4,3-a]pyridin-4-amine (50. mg, 0.13 mmol, from Example 206) and formaldehyde (37 wt % solution in water, 12 mg, 0.15 mmol, Aldrich) in DCM (2.6 mL) was added Na(OAc)$_3$BH (42 mg, 0.20 mmol, Aldrich). After 25 minutes, volatile solvent was removed in vacuo. The mixture was diluted with water and methanol, and the product was purified via preparative HPLC-MS (Waters XBridge C18, eluting with a gradient of MeCN/H$_2$O containing 0.15% NH$_4$OH). Yield: (24.8 mg, 49%).

$^1$H NMR (400 MHz, d$_6$-DMSO) δ 7.32-7.25 (m, 2H), 7.24-7.18 (m, 1H), 7.03-6.96 (m, 2H), 6.58 (s, 1H), 6.54 (s, 1H), 5.40 (s, 2H), 5.27 (d, J=8.7 Hz, 1H), 3.40-3.29 (m, 1H), 2.81 (s, 3H), 2.72-2.61 (m, 2H), 2.29 (s, 3H), 2.14 (s, 3H), 2.03-1.94 (m, 2H), 1.87-1.79 (m, 2H), 1.52-1.40 (m, 2H); LCMS (M+H)+: 389.3.

Example 208

6-Benzyl-1,7-dimethyl-N-(2-morpholin-4-ylethyl)-6H-pyrrolo[2,3-e][1,2,4]triazolo[4,3-a]pyridin-4-amine

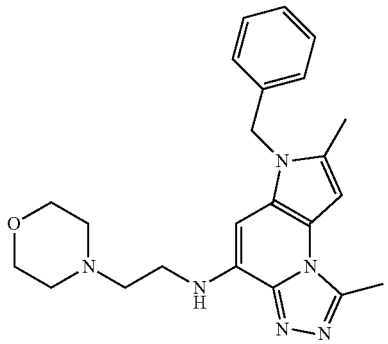 [SMILES: Cc1cc2c(cc(NCCN3CCOCC3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (25 mg, 0.080 mmol, from Example 228, Step 7), N-(2-aminoethyl)morpholine (42 µL, 0.32 mmol, Aldrich), NaO$^t$Bu (15 mg, 0.16 mmol, Aldrich), (9,9-dimethyl-9H-xanthene-4,5-diyl)bis(diphenylphosphine) (9.3 mg, 0.016 mmol, Aldrich) and tris(dibenzylideneacetone)dipalladium(0) (7.4 mg, 0.0080 mmol, Aldrich) in toluene (1.2 mL) was heated at 100° C. overnight. Upon cooling, the reaction mixture was diluted with MeCN, filtered and purified via preparative HPLC-MS (Waters XBridge C18, eluting with a gradient of MeCN/H$_2$O containing 0.15% NH$_4$OH). Yield: (4.8 mg, 15%).

$^1$H NMR (300 MHz, d$_6$-DMSO) δ 7.35-7.19 (m, 3H), 7.04-6.93 (m, 2H), 6.62 (s, 1H), 6.56 (s, 1H), 5.57 (t, J=6.6 Hz, 1H), 5.43 (s, 2H), 3.61-3.53 (m, 4H), 3.25 (app q, J=6.3 Hz, 2H), 2.83 (s, 3H), 2.57 (t, J=6.3 Hz, 2H), 2.43-2.34 (m, 4H), 2.30 (s, 3H); LCMS (M+H)+: 405.3.

Example 209

6-Benzyl-N-(2-methoxyethyl)-1,7-dimethyl-6H-pyrrolo[2,3-e][1,2,4]triazolo[4,3-a]pyridin-4-amine

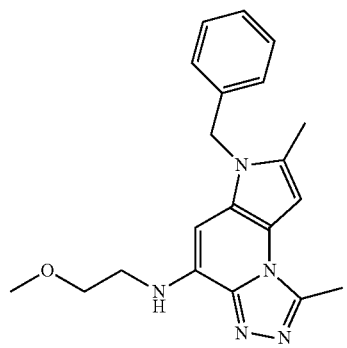

The title compound was prepared according to the methods of Example 208, using 2-methoxyethylamine (28 µL, 0.32 mmol, Aldrich). Yield: (3.3 mg, 12%).

$^1$H NMR (300 MHz, d$_6$-DMSO) δ 7.35-7.18 (m, 3H), 7.05-6.96 (m, 2H), 6.61 (s, 1H), 6.61 (s, 1H), 5.53 (t, J=5.8 Hz, 1H), 5.42 (s, 2H), 3.55 (t, J=5.6 Hz, 2H), 3.32 (t, J=5.8 Hz, 2H), 3.26 (s, 3H), 2.83 (s, 3H), 2.30 (s, 3H); LCMS (M+H)+: 350.1.

Example 210

2-[(6-Benzyl-1,7-dimethyl-6H-pyrrolo[2,3-e][1,2,4]triazolo[4,3-a]pyridin-4-yl)amino]ethanol

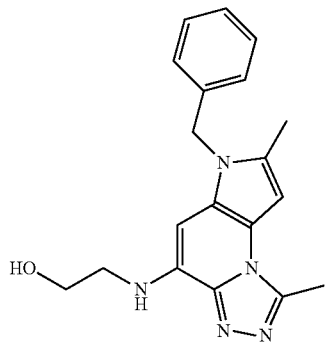 [SMILES: Cc1cc2c(cc(NCCO)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (25.0 mg, 0.0804 mmol, Example 228, Step 7), ethanolamine (44 mg, 0.72 mmol, Aldrich), Cs$_2$CO$_3$ (79 mg, 0.24 mmol, Aldrich) and tBuBrettPhos Pd G3 (8.2 mg, 0.0096 mmol, Aldrich) in NMP (1 mL) and Water (38 µL) was heated at 100° C. overnight. Upon cooling, the reaction mixture was diluted with MeCN, filtered and purified via preparative HPLC-MS (Waters XBridge C18, eluting with a gradient of MeCN/H$_2$O containing 0.15% NH$_4$OH). Yield: (5.9 mg, 22%).

$^1$H NMR (300 MHz, d$_6$-DMSO) δ 7.36-7.19 (m, 3H), 7.05-6.93 (m, 2H), 6.61 (s, 1H), 6.57 (s, 1H), 5.59 (t, J=5.6 Hz, 1H), 5.42 (s, 2H), 4.85 (t, J=5.5 Hz, 1H), 3.64 (app q, J=5.6 Hz, 2H), 3.22 (app q, J=5.7 Hz, 2H), 2.84 (s, 3H), 2.30 (s, 3H); LCMS (M+H)+: 336.2.

Example 211

6-Benzyl-1,7-dimethyl-N-[1-(methylsulfonyl)piperidin-4-yl]-6H-pyrrolo[2,3-e][1,2,4]triazolo[4,3-a]pyridin-4-amine

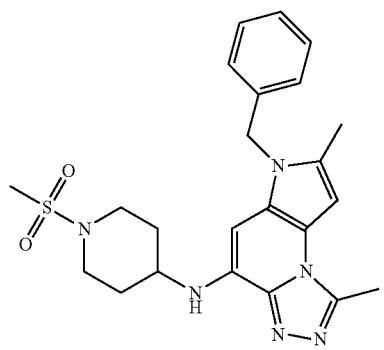

To 6-benzyl-1,7-dimethyl-N-piperidin-4-yl-6H-pyrrolo[2,3-e][1,2,4]triazolo[4,3-a]pyridin-4-amine (7.0 mg, 0.019 mmol, from Example 206) in DCM (2.4 mL) was added methanesulfonyl chloride (1.6 µL, 0.020 mmol, Aldrich) and triethylamine (5.2 µL, 0.037 mmol). After 25 minutes, the solvent was removed in vacuo, and the product was purified via preparative HPLC-MS (Waters XBridge C18, eluting with a gradient of MeCN/H$_2$O containing 0.15% NH$_4$OH). Yield: (4.2 mg, 50%).
$^1$H NMR (400 MHz, d$_6$-DMSO) δ 7.34-7.28 (m, 2H), 7.27-7.21 (m, 1H), 7.05-6.98 (m, 2H), 6.62 (s, 1H), 6.61 (s, 1H), 5.59 (d, J=8.9 Hz, 1H), 5.43 (s, 2H), 3.62-3.44 (m, 3H), 2.89 (s, 3H), 2.91-2.85 (m, 2H), 2.83 (s, 3H), 2.30 (s, 3H), 2.03-1.93 (m, 2H), 1.64-1.50 (m, 2H); LCMS (M+H)+: 453.2.

Example 212

6-Benzyl-N-(1-ethylpiperidin-4-yl)-1,7-dimethyl-6H-pyrrolo[2,3-e][1,2,4]triazolo[4,3-a]pyridin-4-amine

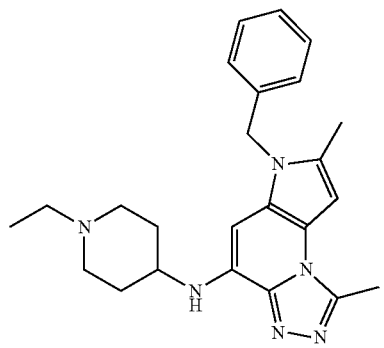 [SMILES: CCN1CCC(Nc2cc3c(cc(C)n3Cc3ccccc3)n3c(C)nnc23)CC1]

A mixture of 6-benzyl-1,7-dimethyl-N-piperidin-4-yl-6H-pyrrolo[2,3-e][1,2,4]triazolo[4,3-a]pyridin-4-amine (7.0 mg, 0.019 mmol, from Example 206) and acetaldehyde (5.2 µL, 0.093 mmol, Aldrich) in DCM (2.4 mL) was treated with Na(OAc)$_3$BH (5.2 mg, 0.024 mmol, Aldrich). After 8 minutes, the solvent was removed in vacuo, and the product was purified via preparative HPLC-MS (Waters XBridge C18, eluting with a gradient of MeCN/H$_2$O containing 0.15% NH$_4$OH). Yield: (2.0 mg, 26%).

$^1$H NMR (400 MHz, d$_6$-DMSO) δ 7.33-7.27 (m, 2H), 7.26-7.21 (m, 1H), 7.04-6.99 (m, 2H), 6.60 (s, 1H), 6.56 (s, 1H), 5.42 (s, 2H), 5.30 (d, J=8.7 Hz, 1H), 3.43-3.29 (m, 1H), 2.82 (s, 3H), 2.85-2.74 (m, 2H), 2.32 (q, J=7.2 Hz, 2H), 2.31 (s, 3H), 2.05-1.95 (m, 2H), 1.92-1.83 (m, 2H), 1.52-1.39 (m, 2H), 0.99 (t, J=7.2 Hz, 3H); LCMS (M+H)+: 403.3.

Example 213

6-Benzyl-N-(1-isopropylpiperidin-4-yl)-1,7-dimethyl-6H-pyrrolo[2,3-e][1,2,4]triazolo[4,3-a]pyridin-4-amine

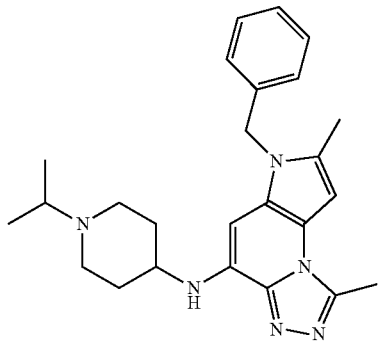 [SMILES: Cc1cc2c(cc(NC3CCN(C(C)C)CC3)c3nnc(C)n32)n1Cc1ccccc1]

The title compound was prepared according to the methods of Example 212, using acetone (12 µL, 0.228 mmol) and Na(OAc)$_3$BH (9.2 mg, 0.043 mmol, Aldrich) with stirring overnight. Yield: (2.9 mg, 37%).
$^1$H NMR (400 MHz, d$_6$-DMSO) δ 7.34-7.27 (m, 2H), 7.27-7.20 (m, 1H), 7.04-6.98 (m, 2H), 6.60 (s, 1H), 6.57 (s, 1H), 5.43 (s, 2H), 5.27 (d, J=8.7 Hz, 1H), 3.41-3.29 (m, 1H), 2.82 (s, 3H), 2.78-2.63 (m, 3H), 2.30 (s, 3H), 2.28-2.18 (m, 2H), 1.95-1.84 (m, 2H), 1.48-1.33 (m, 2H), 0.96 (d, J=6.6 Hz, 6H); LCMS (M+H)+: 417.3.

Example 214 tert-butyl 4-[(6-benzyl-1,7-dimethyl-6H-pyrrolo[2,3-e][1,2,4]triazolo[4,3-a]pyridin-4-yl)amino]piperidine-1-carboxylate

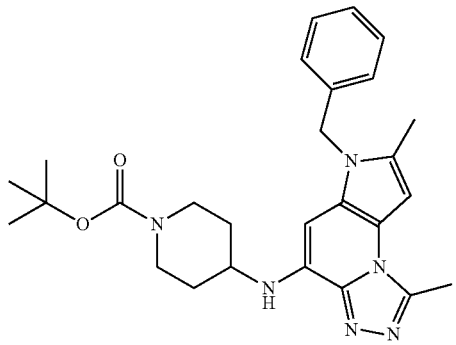 [SMILES: Cc1cc2c(cc(NC3CCN(C(=O)OC(C)(C)C)CC3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (200. mg, 0.644 mmol, Example 228, Step 7), tert-butyl 4-aminopiperidine-1-carboxylate (520 mg, 2.6 mmol, Combi-Blocks), NaO$^t$Bu (180 mg, 1.9 mmol, Aldrich), (9,9-dimethyl-9H-xanthene-4,5-diyl)bis(diphenylphosphine) (93 mg, 0.16 mmol, Aldrich) and tris(dibenzylideneacetone)dipalladium (0) (71 mg, 0.077 mmol, Aldrich) in toluene (10. mL) was heated at 120° C. for 4 hours. Upon cooling, the reaction mixture was diluted with EtOAc and washed sequentially with water and brine. The organic layer was dried over sodium sulfate, filtered and concentrated. Flash chromatography, eluting with a gradient from 0-5% MeOH in DCM afforded product as a light yellow solid (0.15 g, 49%). A portion (11 mg) of this solid was purified via preparative HPLC-MS (Waters XBridge C18, eluting with a gradient of MeCN/H$_2$O containing 0.15% NH$_4$OH). Yield: (7.1 mg, 65%).

$^1$H NMR (400 MHz, CDCl$_3$) δ 7.35-7.27 (m, 3H), 7.01-6.93 (m, 2H), 6.50 (s, 1H), 6.16 (s, 1H), 5.29 (s, 2H), 4.16-3.82 (m, 2H), 3.47-3.35 (m, 1H), 2.99-2.82 (m, 2H), 2.96 (s, 3H), 2.39 (s, 3H), 1.99-1.87 (m, 2H), 1.53-1.43 (m, 2H), 1.46 (s, 9H); LCMS (M+H)+: 475.3.

Example 215 a and 215 b

4-[(6-benzyl-1,7-dimethyl-6H-pyrrolo[2,3-e][1,2,4]triazolo[4,3-a]pyridin-4-yl)amino]cyclohexanecarbonitrile trifluoroacetate salt, trans-(215 a) and cis-(215 b) isomers isolated

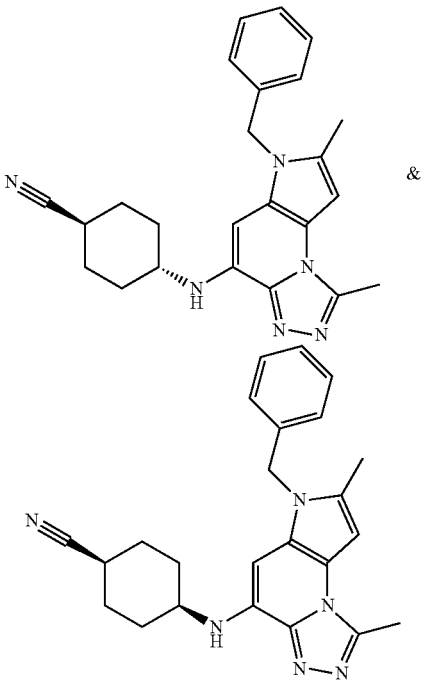

A degassed mixture of 6-benzyl-4-chloro-1,7-dimethyl-6H-pyrrolo[2,3-e][1,2,4]triazolo[4,3-a]pyridine (50. mg, 0.16 mmol, Example 228, Step 7), 4-aminocyclohexanecarbonitrile hydrochloride (78 mg, 0.48 mmol, J&W Pharmlab, mixture of cis- and trans-isomers), NaO$^t$Bu (93 mg, 0.96 mmol, Aldrich), (9,9-dimethyl-9H-xanthene-4,5-diyl)bis(diphenylphosphine) (23 mg, 0.040 mmol, Aldrich) and tris(dibenzylideneacetone)dipalladium(0) (18 mg, 0.019 mmol, Aldrich) in toluene (2.5 mL) was heated at 120° C. for 4 hours. Upon cooling, the mixture was diluted with acetonitrile, filtered and purified via preparative HPLC-MS (Waters SunFire C18, eluting with a gradient of 24-42% MeCN/H$_2$O, 0.1% TFA, flow rate 60 mL/min, separation time 12 min). Partial separation of the isomers was possible and purest fractions were collected for each peak. First eluting peak (peak 1) was the trans-isomer, 215 a. Yield: (4.4 mg, 5%). Second eluting peak (peak 2) was the cis-isomer, 215 b. Yield: (7.9 mg, 10%).

Peak 1 (trans-; 215 a): $^1$H NMR (400 MHz, d$_6$-DMSO) δ 7.34-7.28 (m, 2H), 7.28-7.22 (m, 1H), 7.17 (s, 1H), 7.07-7.01 (m, 2H), 6.83 (s, 1H), 5.53 (s, 2H), 3.60-3.50 (m, 1H), 3.17-3.10 (m, 1H), 2.94 (s, 3H), 2.37 (s, 3H), 1.98-1.87 (m, 4H), 1.80-1.65 (m, 2H), 1.57-1.44 (m, 2H).

LCMS (M+H)+: 399.2.

Peak 2 (cis-; 215 b): $^1$H NMR (400 MHz, d$_6$-DMSO) δ 7.36-7.29 (m, 2H), 7.29-7.21 (m, 1H), 7.11-7.01 (m, 3H), 6.79 (s, 1H), 5.52 (s, 2H), 3.56-3.42 (m, 1H), 2.92 (s, 3H), 2.74 (tt, J=11.5, 3.4 Hz, 1H), 2.37 (s, 3H), 2.12-2.02 (m, 2H), 2.02-1.92 (m, 2H), 1.65 (qd, J=12.7, 3.1 Hz, 2H), 1.37-1.19 (m, 2H); LCMS (M+H)+: 399.2.

Example 216

N-(1-Acetylpiperidin-4-yl)-6-benzyl-1,7-dimethyl-6H-pyrrolo[2,3-e][1,2,4]triazolo[4,3-a]pyridin-4-amine

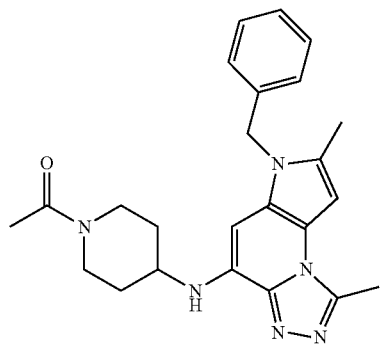 [SMILES: CC(=O)N1CCC(Nc2cc3c(cc(C)n3Cc3ccccc3)n3c(C)nnc23)CC1]

To 6-benzyl-1,7-dimethyl-N-piperidin-4-yl-6H-pyrrolo[2,3-e][1,2,4]triazolo[4,3-a]pyridin-4-amine (10. mg, 0.027 mmol, from Example 206) in DCM (1.0 mL) was added acetyl chloride (2.3 µL, 0.032 mmol, Aldrich), followed by the addition of triethylamine (7.4 µL, 0.053 mmol). After 15 minutes, volatiles were removed in vacuo. The mixture was diluted with water and MeOH, and the product was isolated via preparative HPLC-MS (Waters XBridge C18, eluting with a gradient of MeCN/H₂O containing 0.15% NH₄OH). Yield: (7.6 mg, 68%).

¹H NMR (400 MHz, CDCl₃) δ 7.35-7.28 (m, 3H), 7.00-6.95 (m, 2H), 6.50 (s, 1H), 6.13 (s, 1H), 5.35-5.21 (m, 2H), 4.38-4.28 (m, 1H), 3.87-3.76 (m, 1H), 3.57-3.45 (m, 1H), 3.25-3.17 (m, 1H), 2.95 (s, 3H), 2.97-2.87 (m, 1H), 2.39 (s, 3H), 2.11 (s, 3H), 2.07-1.89 (m, 2H), 1.80-1.32 (m, 2H); LCMS (M+H)+: 417.3.

Example 217 trans-N-(6-Benzyl-1,7-dimethyl-6H-pyrrolo[2,3-e][1,2,4]triazolo[4,3-a]pyridin-4-yl)cyclohexane-1,4-diamine

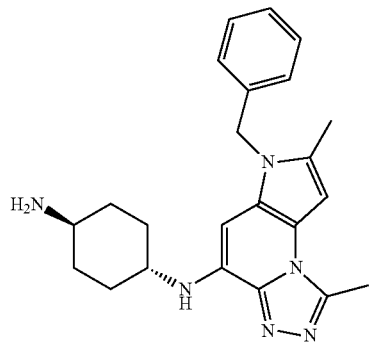 [SMILES: Cc1cc2c(cc(N[C@H]3CC[C@H](N)CC3)c3nnc(C)n32)n1Cc1ccccc1]

A degassed mixture of 6-benzyl-4-chloro-1,7-dimethyl-6H-pyrrolo[2,3-e][1,2,4]triazolo[4,3-a]pyridine (0.150 g, 0.483 mmol, Example 228, Step 7), tert-butyl (trans-4-aminocyclohexyl)carbamate (0.41 g, 1.9 mmol, Combi-Blocks), NaOtBu (0.14 g, 1.4 mmol, Aldrich), (9,9-dimethyl-9H-xanthene-4,5-diyl)bis(diphenylphosphine) (70. mg, 0.12 mmol, Aldrich) and tris(dibenzylideneacetone)dipalladium(0) (53 mg, 0.058 mmol, Aldrich) in toluene (7.5 mL) was heated at 120° C. for 2 hours. After cooling to room temperature, the reaction mixture was diluted with EtOAc and washed with water, followed by brine. The organic layer was dried over sodium sulfate, filtered and concentrated. The residue was dissolved in 1,4-dioxane (4.0 mL) and treated with 4.0 M HCl in dioxane (1.0 mL, 4.0 mmol). After stirring for one hour, solvent was removed in vacuo, and the product was purified via preparative HPLC-MS (Waters XBridge C18, eluting with a gradient of MeCN/H₂O containing 0.15% NH₄OH). Yield: (31 mg, 16%).

¹H NMR (300 MHz, CDCl₃) δ 7.35-7.24 (m, 3H), 7.03-6.93 (m, 2H), 6.46 (s, 1H), 6.07 (s, 1H), 5.27 (s, 2H), 4.81 (d, J=7.1 Hz, 1H), 3.34-3.13 (m, 1H), 2.93 (s, 3H), 2.35 (s, 3H), 2.19-1.98 (m, 4H), 1.48-1.14 (m, 4H), 3.03-2.83 (m, 1H); LCMS (M+H)+: 389.2.

Example 218 cis-N-(6-Benzyl-1,7-dimethyl-6H-pyrrolo[2,3-e][1,2,4]triazolo[4,3-a]pyridin-4-yl)cyclohexane-1,4-diamine

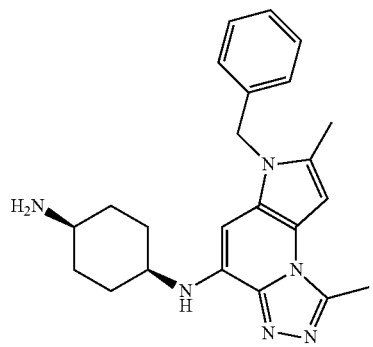 [SMILES: Cc1cc2c(cc(N[C@H]3CC[C@@H](N)CC3)c3nnc(C)n32)n1Cc1ccccc1]

The title compound was prepared according to the methods of Example 217, using tert-butyl (cis-4-aminocyclohexyl)carbamate (0.41 g, 1.9 mmol, Matrix). Yield: (58 mg, 31%).

¹H NMR (300 MHz, CDCl₃) δ 7.34-7.22 (m, 3H), 7.00-6.92 (m, 2H), 6.46 (s, 1H), 6.08 (s, 1H), 5.25 (s, 2H), 5.07 (d,

J=7.3 Hz, 1H), 3.59-3.44 (m, 1H), 3.01-2.85 (m, 1H), 2.93 (s, 3H), 2.35 (s, 3H), 2.11-1.50 (m, 8H); LCMS (M+H)+: 389.3.

Example 219 trans-N-(6-Benzyl-1,7-dimethyl-6H-pyrrolo[2,3-e][1,2,4]triazolo[4,3-a]pyridin-4-yl)-N'-methylcyclohexane-1,4-diamine

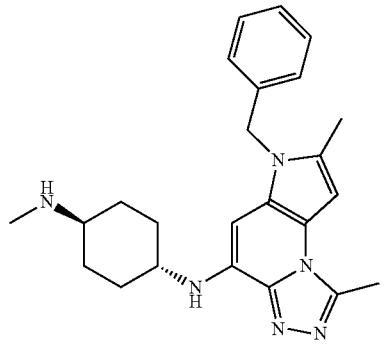

Sodium triacetoxyborohydride (11 mg, 0.053 mmol) was added to a mixture of trans-N-(6-benzyl-1,7-dimethyl-6H-pyrrolo[2,3-e][1,2,4]triazolo[4,3-a]pyridin-4-yl)cyclohexane-1,4-diamine (10. mg, 0.027 mmol, from Example 217) and formaldehyde solution (37 wt % in water, 3.2 mg, 0.040 mmol, Aldrich) in DCM (0.5 mL). After 30 minutes, both monomethylated and dimethylated products were observed by LCMS. Purification via preparative HPLC-MS (Waters XBridge C18, eluting with a gradient of MeCN/H2O containing 0.15% NH4OH) afforded monomethylated product. (Yield: 0.8 mg, 7%).
LCMS (M+H)+: 403.3.

Example 220 trans-N'-(6-Benzyl-1,7-dimethyl-6H-pyrrolo[2,3-e][1,2,4]triazolo[4,3-a]pyridin-4-yl)-N,N-dimethylcyclohexane-1,4-diamine

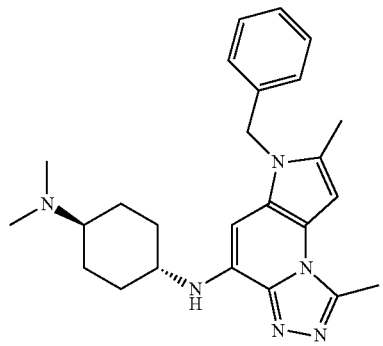

The title compound was isolated from the reaction mixture given in Example 219. The purification via preparative HPLC-MS (Waters XBridge C18, eluting with a gradient of MeCN/H2O containing 0.15% NH4OH) afforded dimethylated product. Yield: (5.9 mg, 53%).
1H NMR (400 MHz, CDCl3) δ 7.34-7.27 (m, 3H), 7.00-6.95 (m, 2H), 6.46 (s, 1H), 6.07 (s, 1H), 5.27 (s, 2H), 4.84 (d, J=8.0 Hz, 1H), 3.25-3.14 (m, 1H), 2.93 (s, 3H), 2.36 (s, 3H), 2.32 (s, 6H), 2.29-2.19 (m, 1H), 2.18-2.11 (m, 2H), 1.99-1.93 (m, 2H), 1.41-1.13 (m, 4H); LCMS (M+H)+: 417.2.

Example 221 cis-N-(6-Benzyl-1,7-dimethyl-6H-pyrrolo[2,3-e][1,2,4]triazolo[4,3-a]pyridin-4-yl)-N'-methylcyclohexane-1,4-diamine

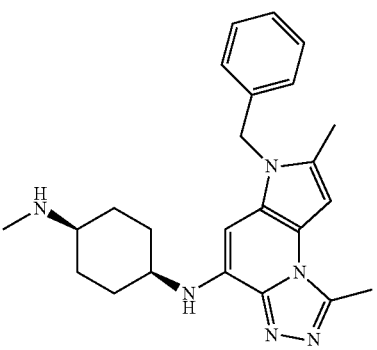

The title compound was prepared according to the methods of Example 219, using cis-N-(6-benzyl-1,7-dimethyl-6H-pyrrolo[2,3-e][1,2,4]triazolo[4,3-a]pyridin-4-yl)cyclohexane-1,4-diamine (10. mg, 0.027 mmol, from Example 218) as a starting material. Purification via preparative HPLC-MS (Waters XBridge C18, eluting with a gradient of MeCN/H2O containing 0.15% NH4OH) afforded monomethylated product. Yield: (1.2 mg, 11%).
LCMS (M+H)+: 403.3.

Example 222 cis-N'-(6-Benzyl-1,7-dimethyl-6H-pyrrolo[2,3-e][1,2,4]triazolo[4,3-a]pyridin-4-yl)-N,N-dimethylcyclohexane-1,4-diamine

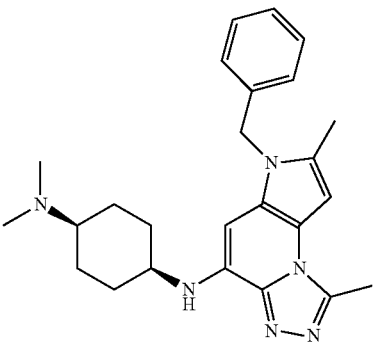

The title compound was isolated from the reaction mixture given in Example 221. The purification via preparative HPLC-MS (Waters XBridge C18, eluting with a gradient of MeCN/H2O containing 0.15% NH4OH) afforded dimethylated product. Yield: (4.2 mg, 38%).
1H NMR (400 MHz, CDCl3) δ 7.33-7.26 (m, 3H), 6.99-6.95 (m, 2H), 6.46 (s, 1H), 6.08 (s, 1H), 5.25 (s, 2H), 5.08 (d, J=7.2 Hz, 1H), 3.62-3.56 (m, 1H), 2.93 (s, 3H), 2.35 (s, 3H), 2.33 (s, 6H), 2.43-1.49 (m, 9H).
LCMS (M+H)+: 417.3.

Example 223

3-Benzyl-2,8-dimethyl-N-(1-methylpiperidin-4-yl)-3H-imidazo[4,5-e][1,2,4]triazolo[4,3-a]pyridin-5-amine

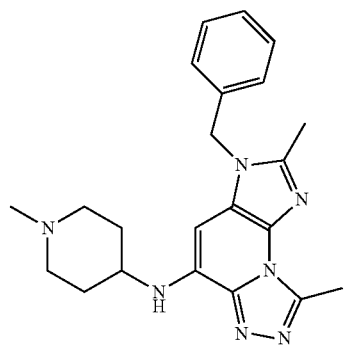

Step 1. 3-Benzyl-5-chloro-2,8-dimethyl-3H-imidazo[4,5-e][1,2,4]triazolo[4,3-c]pyridine

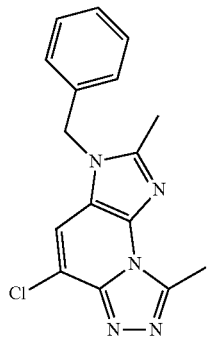 [SMILES: Cc1nc2c(cc(Cl)c3nnc(C)n32)n1Cc1ccccc1]

A suspension of 3-benzyl-2,8-dimethyl-3H-imidazo[4,5-e][1,2,4]triazolo[4,3-a]pyridine (0.50 g, 1.8 mmol, Example 55) and N-chlorosuccinimide (0.29 g, 2.2 mmol, Aldrich) in DCE (9 mL) was heated at 60° C. for 2 hours. Upon cooling to room temperature, the mixture was diluted with DCM. The solution was washed with saturated NaHCO$_3$, followed by water, and finally, brine. The organic layer was dried over sodium sulfate, filtered and concentrated. Flash chromatography, eluting with a gradient from 0-2.5% MeOH in DCM, afforded product as a light yellow solid. Yield: (0.21 g, 37%).

$^1$H NMR (400 MHz, CDCl$_3$) δ 7.40-7.33 (m, 3H), 7.29 (s, 1H), 7.06-7.01 (m, 2H), 5.35 (s, 2H), 3.17 (s, 3H), 2.61 (s, 3H); LCMS (M+H)$^+$: 312.1.

Step 2. 3-Benzyl-2,8-dimethyl-N-(1-methylpiperidin-4-yl)-3H-imidazo[4,5-e][1,2,4]triazolo[4,3-a]pyridin-5-amine A degassed mixture of 3-benzyl-5-chloro-2,8-dimethyl-3H-imidazo[4,5-e][1,2,4]triazolo[4,3-a]pyridine (37 mg, 0.12 mmol, from Step 1), 1-methylpiperidin-4-amine hydrochloride (54 mg, 0.36 mmol, Matrix), NaO$^t$Bu (57 mg, 0.59 mmol, Aldrich), (9,9-dimethyl-9H-xanthene-4,5-diyl)bis(diphenylphosphine) (17 mg, 0.030 mmol, Aldrich) and tris(dibenzylideneacetone)dipalladium(0) (13 mg, 0.014 mmol, Aldrich) in toluene (1.8 mL) was heated at 125° C. for 80 minutes. After cooling to room temperature, the mixture was diluted with acetonitrile, filtered and concentrated. The product was isolated via preparative HPLC-MS (Waters XBridge C18, eluting with a gradient of MeCN/H$_2$O containing 0.15% NH$_4$OH). Yield: (9.8 mg, 21%).

$^1$H NMR (400 MHz, CDCl$_3$) δ 7.39-7.31 (m, 3H), 7.09-7.04 (m, 2H), 5.95 (s, 1H), 5.29 (s, 2H), 5.11 (d, J=7.4 Hz, 1H), 3.42-3.30 (m, 1H), 3.12 (s, 3H), 2.91-2.77 (m, 2H), 2.53 (s, 3H), 2.35 (s, 3H), 2.41-1.41 (m, 6H); LCMS (M+H)$^+$: 390.2.

Example 224

6-Benzyl-N-[(2S,4S)-1,2-dimethylpiperidin-4-yl]-1,7-dimethyl-6H-pyrrolo[2,3-e][1,2,4]triazolo[4,3-a]pyridin-4-amine and 6-Benzyl-N-[(2R,4R)-1,2-dimethylpiperidin-4-yl]-1,7-dimethyl-6H-pyrrolo[2,3-e][1,2,4]triazolo[4,3-a]pyridin-4-amine (racemic mixture prepared)

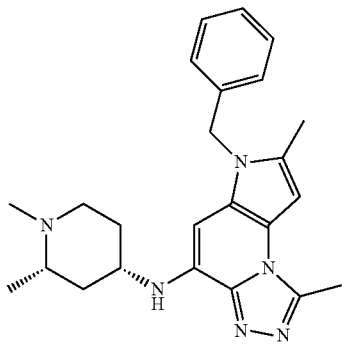

and

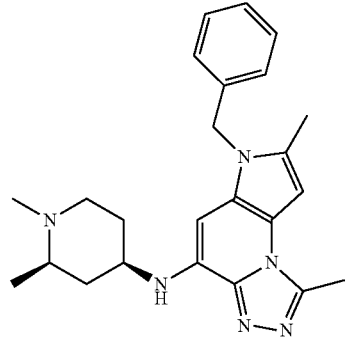

Step 1. 6-Benzyl-1,7-dimethyl-N-[(2S,4S)-2-methylpiperidin-4-yl]-6H-pyrrolo[2,3-e][1,2,4]triazolo[4,3-a]pyridin-4-amine and 6-Benzyl-1,7-dimethyl-N-[(2R,4R)-2-methylpiperidin-4-yl]-6H-pyrrolo[2,3-e][1,2,4]triazolo[4,3-a]pyridin-4-amine (racemic mixture prepared)

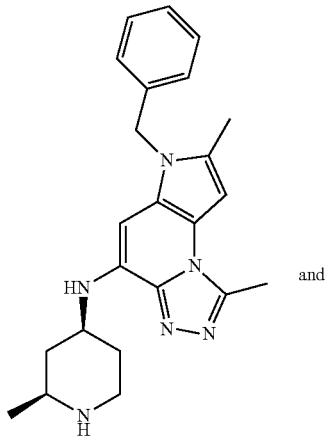 and

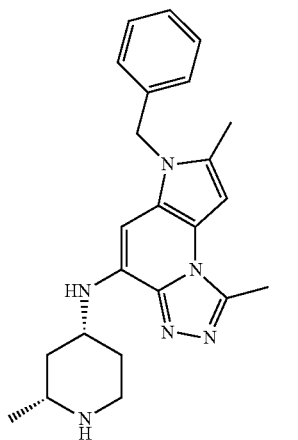

A degassed mixture of 6-benzyl-4-chloro-1,7-dimethyl-6H-pyrrolo[2,3-e][1,2,4]triazolo[4,3-a]pyridine (0.10 g, 0.32 mmol, Example 228, Step 7), tert-butyl cis-4-amino-2-methylpiperidine-1-carboxylate hydrochloride (0.24 g, 0.96 mmol, Chembridge), NaO$^t$Bu (0.15 g, 1.6 mmol, Aldrich), (9,9-dimethyl-9H-xanthene-4,5-diyl)bis(diphenylphosphine) (46 mg, 0.080 mmol, Aldrich) and tris(dibenzylideneacetone)dipalladium(0) (35 mg, 0.039 mmol, Aldrich) in toluene (5.0 mL) was heated at 125° C. for 2 hours. Upon cooling, the mixture was diluted with EtOAc and washed with water, followed by brine. The organic layer was dried over sodium sulfate, filtered and concentrated. The residue was dissolved in 1,4-dioxane (3.0 mL) and treated with 4.0 M HCl in dioxane (1.0 mL, 4.0 mmol). After 1 hour, the product was purified via preparative HPLC-MS (Waters XBridge C18, eluting with a gradient of MeCN/H$_2$O containing 0.15% NH$_4$OH). Yield: (38 mg, 31%).
LCMS (M+H)$^+$: 389.3.

Step 2. 6-Benzyl-N-[(2S,4S)-1,2-dimethylpiperidin-4-yl]-1,7-dimethyl-6H-pyrrolo[2,3-e][1,2,4]triazolo[4,3-a]pyridin-4-amine and 6-Benzyl-N-[(2R,4R)-1,2-dimethylpiperidin-4-yl]-1,7-dimethyl-6H-pyrrolo[2,3-e][1,2,4]triazolo[4,3-a]pyridin-4-amine (racemic mixture prepared)

To a mixture of 6-benzyl-1,7-dimethyl-N-[(2S,4S)-2-methylpiperidin-4-yl]-6H-pyrrolo[2,3-e][1,2,4]triazolo[4,3-a]pyridin-4-amine and 6-benzyl-1,7-dimethyl-N-[(2R,4R)-2-methylpiperidin-4-yl]-6H-pyrrolo[2,3-e][1,2,4]triazolo[4,3-a]pyridin-4-amine (15 mg, 0.031 mmol, from Step 1) in DCM (0.6 mL) was added formaldehyde (37 wt % in water, 2.5 mg, 0.031 mmol, Aldrich), followed by the addition of Na(OAc)$_3$BH (9.8 mg, 0.046 mmol, Aldrich). After 25 minutes, volatile solvent was removed in vacuo. The mixture was diluted with water and MeOH, and the product was purified via preparative HPLC-MS (Waters XBridge C18, eluting with a gradient of MeCN/H$_2$O containing 0.15% NH$_4$OH). Yield: (9.7 mg, 78%).
$^1$H NMR (400 MHz, CDCl$_3$) δ 7.35-7.27 (m, 3H), 7.02-6.94 (m, 2H), 6.47 (s, 1H), 6.07 (s, 1H), 5.27 (s, 2H), 4.85 (d, J=8.4 Hz, 1H), 3.41-3.29 (m, 1H), 3.02-2.94 (m, 1H), 2.93 (s, 3H), 2.37 (s, 3H), 2.34 (s, 3H), 2.26-1.21 (m, 6H), 1.13 (d, J=6.1 Hz, 3H); LCMS (M+H)$^+$: 403.2.

Example 225

6-Benzyl-N-[(2R,4S)-1,2-dimethylpiperidin-4-yl]-1,7-dimethyl-6H-pyrrolo[2,3-e][1,2,4]triazolo[4,3-a]pyridin-4-amine and 6-Benzyl-N-[(2S,4R)-1,2-dimethylpiperidin-4-yl]-1,7-dimethyl-6H-pyrrolo[2,3-e][1,2,4]triazolo[4,3-a]pyridin-4-amine (racemic mixture prepared)

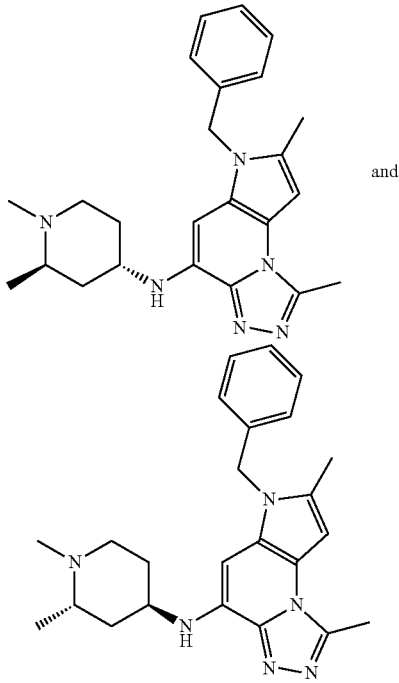

The title compounds were prepared according to the methods of Example 224, using tert-butyl trans-4-amino-2-methylpiperidine-1-carboxylate (0.21 g, 0.96 mmol, Chembridge). Yield: (8.9 mg, 72%).

$^1$H NMR (400 MHz, CDCl$_3$) δ 7.33-7.27 (m, 3H), 6.97 (d, J=6.7 Hz, 2H), 6.47 (s, 1H), 6.06 (s, 1H), 5.26 (s, 2H), 5.10 (d, J=6.8 Hz, 1H), 3.76-3.67 (m, 1H), 2.94 (s, 3H), 2.78-2.66 (m, 1H), 2.63-2.45 (m, 2H), 2.37 (s, 3H), 2.35 (s, 3H), 2.06-1.50 (m, 4H), 1.10 (d, J=6.2 Hz, 3H); LCMS (M+H)$^+$: 403.2.

Example 226

6-Benzyl-1,7-dimethyl-N-((1R,3r,5S)-8-methyl-8-azabicyclo[3.2.1]octan-3-yl)-6H-pyrrolo[2,3-e][1,2,4]triazolo[4,3-a]pyridin-4-amine

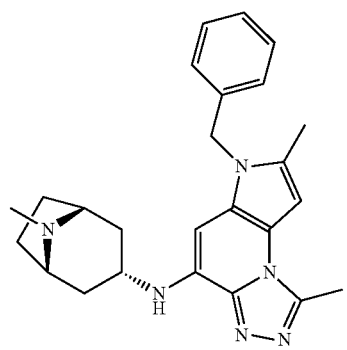

A degassed mixture of 6-benzyl-4-chloro-1,7-dimethyl-6H-pyrrolo[2,3-e][1,2,4]triazolo[4,3-a]pyridine (50. mg, 0.16 mmol), (1R,3r,5S)-8-methyl-8-azabicyclo[3.2.1]octan-3-amine (68 mg, 0.48 mmol, Synthonix), NaO$^t$Bu (46 mg, 0.48 mmol, Aldrich), (9,9-dimethyl-9H-xanthene-4,5-diyl)bis(diphenylphosphine) (23 mg, 0.040 mmol, Aldrich) and tris(dibenzylideneacetone)dipalladium(0) (18 mg, 0.019 mmol, Aldrich) in toluene (2.5 mL) was heated at 125° C. for 1.5 hours. Upon cooling to room temperature, the reaction was diluted with acetonitrile, filtered and concentrated. The product was purified via preparative HPLC-MS (Waters XBridge C18, eluting with a gradient of MeCN/H$_2$O containing 0.15% NH$_4$OH). Yield: (3.3 mg, 5%).

$^1$H NMR (400 MHz, CDCl$_3$) δ 7.34-7.26 (m, 3H), 6.97 (d, J=6.7 Hz, 2H), 6.46 (s, 1H), 5.96 (s, 1H), 5.25 (s, 2H), 5.28-5.21 (m, 1H), 3.62 (q, J=6.2 Hz, 1H), 3.20 (br s, 2H), 2.93 (s, 3H), 2.36 (s, 3H), 2.33 (s, 3H), 1.91 (br m, 8H); LCMS (M+H)$^+$: 415.3.

Example 227

6-Benzyl-1-methyl-6H-pyrrolo[2,3-e][1,2,4]triazolo[4,3-a]pyridine-7-carbonitrile trifluoroacetate salt

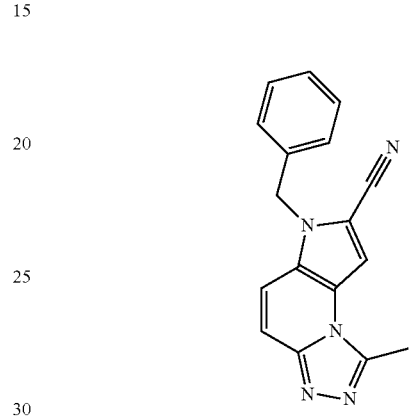

Step 1. 5-Chloro-1-(phenylsulfonyl)-1H-pyrrolo[3,2-b]pyridine-2-carbonitrile

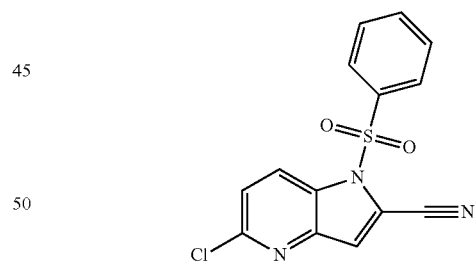

A degassed mixture of 2-bromo-5-chloro-1-(phenylsulfonyl)-1H-pyrrolo[3,2-b]pyridine (3.0 g, 8.1 mmol, prepared as in Example 62, Step 1, isolated as the free base), zinc cyanide (9.5 g, 81 mmol, Aldrich) and tetrakis(triphenylphosphine)palladium(0) (1.6 g, 1.4 mmol, Strem) in DMF (51 mL) was heated at 120° C. for 3 hours. Upon cooling to room temperature, the mixture was diluted with EtOAc and washed sequentially with diluted aqueous ammonia, water, and brine. The organic layer was dried over sodium sulfate, filtered and concentrated. Flash chromatography, eluting with a gradient from 0-20% EtOAc in hexanes, was used to purify the product. Yield: (1.2 g. 47%).

LCMS (M+H)$^+$: 318.0.

Step 2.
5-Chloro-1H-pyrrolo[3,2-b]pyridine-2-carbonitrile

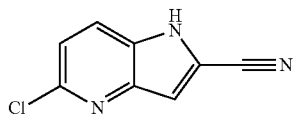 [SMILES: N#Cc1cc2nc(Cl)ccc2[nH]1]

5-Chloro-1-(phenylsulfonyl)-1H-pyrrolo[3,2-b]pyridine-2-carbonitrile (0.50 g, 1.6 mmol, from Step 1) in THF (10. mL) was treated with 1.0 M NaOH (10. mL, 10. mmol) until removal of phenylsulfonyl protecting group was complete as determined by LCMS. The reaction mixture was extracted with three portions of EtOAc. The combined organic extracts were dried over sodium sulfate, filtered and concentrated until solid product precipitated. The solid was collected via filtration and triturated with EtOAc. Yield: (0.21 g, 75%).

$^1$H NMR (300 MHz, $d_6$-DMSO) δ 7.98 (d, J=8.7 Hz, 1H), 7.44 (s, 1H), 7.35 (d, J=8.7 Hz, 1H); LCMS (M+H)$^+$: 178.1.

Step 3. 1-Benzyl-5-chloro-1H-pyrrolo[3,2-b]pyridine-2-carbonitrile

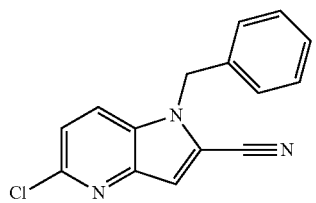 [SMILES: N#Cc1cc2nc(Cl)ccc2n1Cc1ccccc1]

5-Chloro-1H-pyrrolo[3,2-b]pyridine-2-carbonitrile (0.10 g, 0.56 mmol, from Step 2) in DMF (1.3 mL) was treated with $K_2CO_3$ (0.12 g, 0.84 mmol) and benzyl bromide (74 μL, 0.62 mmol, Aldrich) overnight. The reaction mixture was diluted with EtOAc and washed three times with water and once with brine. The organic layer was dried over sodium sulfate, filtered and concentrated. Flash chromatography, eluting with a gradient from 0-20% EtOAc in hexanes afforded purified product. Yield: (0.12 g, 80%).

$^1$H NMR (400 MHz, CDCl$_3$) δ 7.58 (dd, J=8.8, 0.8 Hz, 1H), 7.37-7.29 (m, 4H), 7.25 (d, J=8.8 Hz, 1H), 7.15-7.11 (m, 2H), 5.49 (s, 2H); LCMS (M+H)$^+$: 268.1.

Step 4. Di-tert-butyl 1-(1-benzyl-2-cyano-1H-pyrrolo[3,2-b]pyridin-5-yl)hydrazine-1,2-dicarboxylate

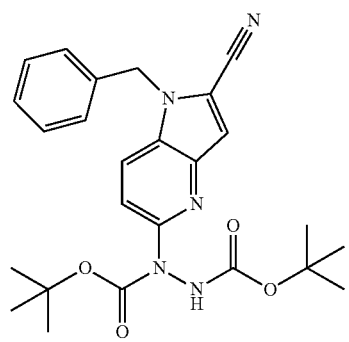 [SMILES: CC(C)(C)OC(=O)NN(C(=O)OC(C)(C)C)c1ccc2c(cc(C#N)n2Cc2ccccc2)n1]

A degassed mixture of 1-benzyl-5-chloro-1H-pyrrolo[3,2-b]pyridine-2-carbonitrile (0.12 g, 0.45 mmol, from Step 3), di-tert-butyl hydrazine-1,2-dicarboxylate (0.12 g, 0.54 mmol, Aldrich), dicyclohexyl(2',4',6'-triisopropylbiphenyl-2-yl)phosphine-(2'-aminobiphenyl-2-yl)(chloro)palladium (1:1) (35 mg, 0.045 mmol, Aldrich) and $Cs_2CO_3$ (0.18 g, 0.54 mmol, Aldrich) in toluene (2.5 mL) was heated at 100° C. for 3 hours. Upon cooling to room temperature, the reaction mixture was diluted with DCM, filtered to remove solids, and the solvent was removed in vacuo. Flash chromatography, eluting with a gradient from 0-20% EtOAc in hexanes afforded purified product. Yield: (0.14 g, 67%).

$^1$H NMR (400 MHz, CDCl$_3$) δ 7.69 (d, J=9.1 Hz, 1H), 7.61 (d, J=8.5 Hz, 1H), 7.36-7.28 (m, 4H), 7.18-7.06 (m, 3H), 5.47 (s, 2H), 1.50 (s, 9H), 1.47 (s, 9H); LCMS (M+H)$^+$: 463.3.

Step 5. 6-Benzyl-1-methyl-6H-pyrrolo[2,3-e][1,2,4]triazolo[4,3-a]pyridine-7-carbonitrile trifluoroacetate salt Di-tert-butyl 1-(1-benzyl-2-cyano-1H-pyrrolo[3,2-b]pyridin-5-yl)hydrazine-1,2-dicarboxylate (0.14 g, 0.30 mmol, from Step 4) was dissolved in acetic acid (6.0 mL) and heated at 130° C. for 1.5 hours. Acetic acid was removed in vacuo, and the residue was dissolved in EtOAc/DCM and washed with saturated NaHCO$_3$ solution. The aqueous layer was extracted with EtOAc/DCM, and the combined organic extracts were dried over sodium sulfate, filtered and concentrated to afford product as an off-white solid. Yield: (76 mg, 88%). A small portion of the product was further purified via preparative HPLC-MS (Waters SunFire C18, eluting with a gradient of MeCN/H$_2$O containing 0.1% TFA) to afford product as the trifluoroacetate salt.

¹H NMR (400 MHz, d₆-DMSO) δ 7.96 (s, 1H), 7.89 (d, J=9.9 Hz, 1H), 7.68 (d, J=9.9 Hz, 1H), 7.40-7.27 (m, 3H), 7.21-7.14 (m, 2H), 5.72 (s, 2H), 2.88 (s, 3H); LCMS (M+H)⁺: 288.2.

Example 228

6-Benzyl-N-(cyclopropylmethyl)-1,7-dimethyl-6H-pyrrolo[2,3-e][1,2,4]triazolo[4,3-a]pyridin-4-amine

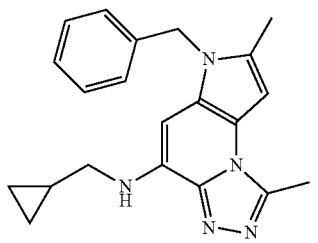 [SMILES: Cc1cc2c(cc(NCC3CC3)c3nnc(C)n32)n1Cc1ccccc1]

Step 1. 5-Chloro-1-(phenylsulfonyl)-1H-pyrrolo[3,2-b]pyridine

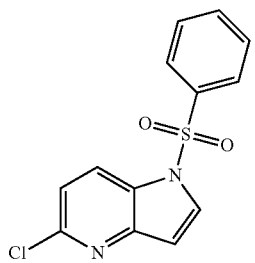 [SMILES: O=S(=O)(c1ccccc1)n1ccc2nc(Cl)ccc21]

To a suspension of 5-chloro-1H-pyrrolo[3,2-b]pyridine (20. g, 130 mmol, Adesis) in DCM (200 mL) was added benzenesulfonyl chloride (20. mL, 160 mmol, Aldrich), triethylamine (27 mL, 200 mmol) and 4-dimethylaminopyridine (0.80 g, 6.6 mmol, Aldrich). The reaction mixture was stirred overnight. Water was added and the mixture was stirred for 4 h. Layers were separated and the organic phase was washed sequentially with 1 N HCl, water, saturated solution of NaHCO₃, and brine. The organic layer was dried over sodium sulfate, filtered and concentrated to give an orange solid, which was triturated with MeOH (100 mL). The solid was filtered, washed with MeOH, and dried at 40° C. under high vacuum overnight. Additional product was obtained by flash chromatography of the filtrate (eluting with a gradient from 0-60% EtOAc in hexanes). Yield: (26.8 g, 95%).

¹H NMR (400 MHz, CDCl₃) δ 8.23 (d, J=8.7 Hz, 1H), 7.88-7.86 (m, 2H), 7.80 (d, J=3.8 Hz, 1H), 7.65-7.56 (m, 1H), 7.49 (t, J=7.8 Hz, 2H), 7.32-7.22 (m, 1H), 6.81 (d, J=3.7 Hz, 1H). LCMS (M+H)⁺: 293.

Step 2. 5-Chloro-2-methyl-1-(phenylsulfonyl)-1H-pyrrolo[3,2-b]pyridine

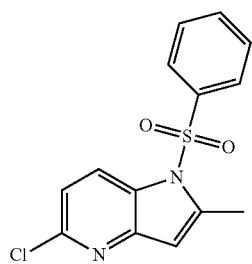 [SMILES: Cc1cc2nc(Cl)ccc2n1S(=O)(=O)c1ccccc1]

To N,N-diisopropylamine (13 mL, 93 mmol, Aldrich) in tetrahydrofuran (200 mL) at −78° C. was added 1.6 M n-butyllithium in hexanes (55 mL, 88 mmol, Aldrich). The reaction mixture was warmed to 0° C., and the mixture was stirred for 30 minutes. The reaction mixture was cooled to −78° C., and 5-chloro-1-(phenylsulfonyl)-1H-pyrrolo[3,2-b]pyridine (17.1 g, 58.4 mmol, from Step 1) in tetrahydrofuran (86 mL) was added dropwise over 30 minutes. The reaction mixture was then stirred for 1 hour at −78° C., and methyl iodide (7.3 mL, 120 mmol, Aldrich) was added dropwise over 5 minutes. The reaction was allowed to warm to 5° C. over 3 hours, then cooled to −20° C. and quenched by the addition of 1 N HCl. EtOAc was added, and the solution was stirred for 15 minutes and left at ambient temperature overnight. The layers were separated and the organic layer was washed sequentially with water and brine, dried over sodium sulfate, filtered and concentrated in vacuo to give a wet orange solid that was then triturated with MeOH (18 mL). The solid was isolated by filtration, washed and dried at 40° C. under high vacuum for 2.2 h to give 14.4 g of product. Additional amount of product was obtained by flash chromatography of the filtrate (eluting with a gradient from 0-40% EtOAc in hexanes) afforded 1.87 g. (Yield: 16.3 g, 91%).

¹H NMR (400 MHz, CDCl₃) δ 8.37 (s, 1H), 7.75 (d, J=7.8 Hz, 2H), 7.61 (t, J=7.3 Hz, 1H), 7.57-7.38 (m, 2H), 7.34-7.09 (m, 1H), 6.49 (s, 1H), 2.62 (s, 3H). LCMS (M+H)⁺: 307.

Step 3. Di-tert-butyl 1-[2-methyl-1-(phenylsulfonyl)-1H-pyrrolo[3,2-b]pyridin-5-yl]hydrazine-1,2-dicarboxylate

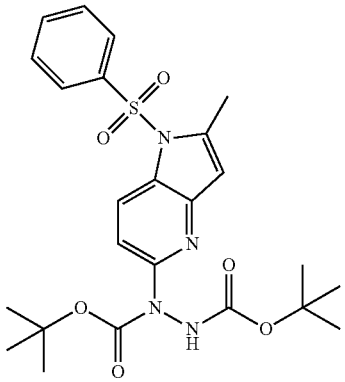 [SMILES: Cc1cc2nc(N(NC(=O)OC(C)(C)C)C(=O)OC(C)(C)C)ccc2n1S(=O)(=O)c1ccccc1]

A mixture of 5-chloro-2-methyl-1-(phenylsulfonyl)-1H-pyrrolo[3,2-b]pyridine (16.29 g, 53.10 mmol, from Step 2), di-tert-butyl hydrazine-1,2-dicarboxylate (12 g, 53 mmol, Aldrich), dicyclohexyl(2',4',6'-triisopropylbiphenyl-2-yl)phosphine-(2'-amino biphenyl-2-yl)(chloro)palladium (1:1) (4.2 g, 5.3 mmol, Aldrich), and Cs₂CO₃ (17.3 g, 53.1 mmol) in toluene (170 mL) was degassed and heated at 100° C. overnight. Upon cooling to room temperature, the solid product was isolated by filtration and washed with several portions of DCM. The solid was then triturated with DCM, and again isolated by filtration, and dried at 40° C. under vacuum (19.5 g). Flash chromatography of the filtrate (eluting with a gradient from 0-40% EtOAc in hexanes) afforded an additional 2.5 g of product. Yield: (22 g, 82%).
¹H NMR (400 MHz, CDCl₃) δ 8.42 (s, 1H), 7.76 (dd, J=8.5, 1.2 Hz, 2H), 7.64-7.55 (m, 2H), 7.50-7.43 (m, 2H), 7.18 (s, 1H), 6.50 (s, 1H), 2.62 (d, J=0.9 Hz, 3H), 1.50 (s, 9H), 1.46 (s, 9H). LCMS (M+H)⁺: 503.

Step 4. 1,7-Dimethyl-6-(phenylsulfonyl)-6H-pyrrolo[2,3-e][1,2,4]triazolo[4,3-a]pyridine

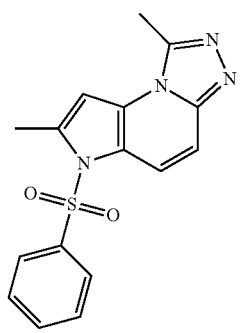 [SMILES: Cc1cc2c(ccc3nnc(C)n32)n1S(=O)(=O)c1ccccc1]

A mixture of di-tert-butyl 1-[2-methyl-1-(phenylsulfonyl)-1H-pyrrolo[3,2-b]pyridin-5-yl]hydrazine-1,2-dicarboxylate (19.53 g, 38.86 mmol, from Step 3) in acetic acid (200 mL) was heated at 120° C. overnight. Precipitate was filtered off, and the filtrate was concentrated in vacuo. Dichloroethane (15 mL) was added, and the suspension was heated at reflux for 15 minutes. Upon cooling to 0° C., the solid product was isolated by filtration and dried at 40° C. under vacuum to give an off-white solid (5.94 g). Solvent was removed from the filtrate in vacuo and the above procedure was repeated using DCE (6 mL) to afford additional solid (3.6 g). Additional product was obtained by flash chromatography of the filtrate, (eluting with a gradient of 0-1% MeOH/DCM containing 1% NH₄OH). The chromatography afforded product as a glass, which was recrystallized from MeOH (6 mL). Upon recrystallization, product was isolated as white crystals and air dried (2.19 g). Yield: (11.7 g, 92%).
¹H NMR (400 MHz, d₆-DMSO) δ 8.08 (d, 1H), 7.94 (d, J=7.7 Hz, 2H), 7.74 (t, J=7.4 Hz, 1H), 7.68-7.55 (m, 2H), 7.50 (d, J=10.0 Hz, 1H), 7.17 (s, 1H), 2.82 (s, 3H), 2.64 (s, 3H). LCMS (M+H)⁺: 327.

Step 5. 4-Chloro-1,7-dimethyl-6-(phenylsulfonyl)-6H-pyrrolo[2,3-e][1,2,4]triazolo[4,3-a]pyridine

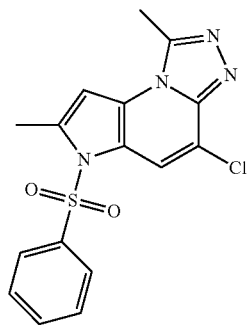 [SMILES: Cc1cc2c(cc(Cl)c3nnc(C)n32)n1S(=O)(=O)c1ccccc1]

A suspension of 1,7-dimethyl-6-(phenylsulfonyl)-6H-pyrrolo[2,3-e][1,2,4]triazolo[4,3-a]pyridine (2.0 g, 6.1 mmol, from Step 4) and N-chlorosuccinimide (0.91 g, 6.8 mmol, Aldrich) in 1,2-dichloroethane (40 mL) was heated at 60° C. overnight. Flash chromatography, eluting with a gradient from 0-5% MeOH/DCM (0.5% NH₄OH), afforded an orange solid which was refluxed in 10 mL MeOH for 15 minutes. The product was isolated by filtration. Yield: (2.2 g, 80%). ¹H NMR (500 MHz, d₆-DMSO) δ 8.23 (s, 1H), 8.01-7.96 (m, 2H), 7.80-7.74 (m, 1H), 7.68-7.61 (m, 2H), 7.22 (s, 1H), 2.86 (s, 3H), 2.62 (s, 3H); LCMS (M+H)⁺: 361.

Step 6. 4-Chloro-1,7-dimethyl-6H-pyrrolo[2,3-e][1,2,4]triazolo[4,3-c]pyridine

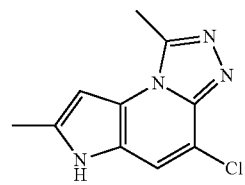

To a suspension of 4-chloro-1,7-dimethyl-6-(phenylsulfonyl)-6H-pyrrolo[2,3-e][1,2,4]triazolo[4,3-a]pyridine (2.34 g, 6.48 mmol, from Step 5) in tetrahydrofuran (15 mL) and ethanol (15 mL) was added 10% (w/w) KOH in water (16.0 mL, 28.5 mmol). After stirring for 1.5 hours, the reaction mixture was diluted with DCM and water and stirred for 3 hours. The solid product was isolated by filtration and dried at 40° C. under vacuum overnight. Yield: (1.33 g, 93%).

¹H NMR (400 MHz, d₆-DMSO): δ 11.83 (s, 1H), 7.62 (d, J=0.6 Hz, 1H), 6.65 (s, 1H), 2.84 (s, 3H), 2.40 (s, 3H). LCMS (M+H)⁺: 221.

Step 7. 6-Benzyl-4-chloro-1,7-dimethyl-6H-pyrrolo[2,3-e][1,2,4]triazolo[4,3-c]pyridine

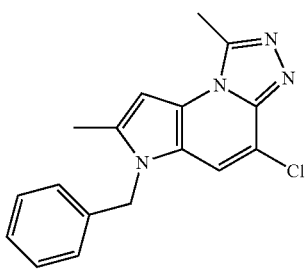 [SMILES: Cc1cc2c(cc(Cl)c3nnc(C)n32)n1Cc1ccccc1]

To a suspension of 4-chloro-1,7-dimethyl-6H-pyrrolo[2,3-e][1,2,4]triazolo[4,3-a]pyridine (1.0 g, 4.5 mmol, from Step 6) in N,N-dimethylformamide (20 mL) at 0° C. was added NaH (60% in mineral oil, 0.246 g, 6.14 mmol). After stirring for 1 h, benzyl bromide (0.65 mL, 5.4 mmol, Aldrich) was added. The reaction mixture was allowed to warm to room temperature and was stirred overnight. The mixture was cooled in an ice bath, and water (50 mL) and ethyl acetate (50 mL) were added. The mixture was stirred for 5.5 h. The product was isolated by filtration and was washed with ethyl acetate and water. The solid was dried at 40° C. vacuum overnight. Yield: (1.12 g, 80%).

¹H NMR (400 MHz, d₆-DMSO) δ 8.01 (s, 1H), 7.33-7.27 (m, 2H), 7.27-7.22 (m, 1H), 6.96 (d, J=7.2 Hz, 2H), 6.83 (s, 1H), 5.56 (s, 2H), 2.87 (s, 3H), 2.35 (s, 3H). LCMS (M+H)⁺: 311.

Step 8. 6-Benzyl-N-(cyclopropylmethyl)-1,7-dimethyl-6H-pyrrolo[2,3-e][1,2,4]triazolo[4,3-a]pyridin-4-amine A suspension of 6-benzyl-4-chloro-1,7-dimethyl-6H-pyrrolo[2,3-e][1,2,4]triazolo[4,3-a]pyridine (20.0 mg, 0.0644 mmol, from Step 7), cyclopropylmethylamine (51 µL, 0.60 mmol, Aldrich), tBuBrettPhos Pd G3 (6.5 mg, 0.0076 mmol, Aldrich) and Cs₂CO₃ (0.045 g, 0.14 mmol) in N-methylpyrrolidinone (0.3 mL) and water (0.030 g) was degassed and heated at 100° C. for 4.5 h, after which time the reaction mixture was filtered and the product was purified by preparative HPLC-MS (Waters XBridge C18, eluting with a gradient of MeCN/H₂O containing 0.15% NH₄OH). Yield: (10.5 mg, 47%).

¹H NMR (400 MHz, CDCl₃) δ 7.36-7.28 (m, 3H), 6.96-6.89 (m, 2H), 6.58 (s, 1H), 6.52 (s, 1H), 5.34 (s, 2H), 3.02 (s, 3H), 3.02 (d, J=6.6 Hz, 2H), 2.42 (s, 3H), 1.17-1.03 (m, 1H), 0.58-0.51 (m, 2H), 0.28-0.21 (m, 2H); LCMS (M+H)⁺: 346.

Examples 229-260

The Examples in Table 1 were Made by Procedures Analogous to Those Used to Prepare Example 228

TABLE 1

| Ex | Name | Structure | Salt | MS [M + H]⁺ |
|---|---|---|---|---|
| 229 | 1-(6-Benzyl-1,7-dimethyl-6H-pyrrolo[2,3-e][1,2,4]triazolo[4,3-a]pyridin-4-yl)-3-methylurea | 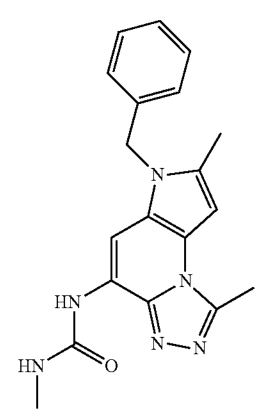 [SMILES: CNC(=O)Nc1cc2c(cc(C)n2Cc2ccccc2)n2c(C)nnc12] | n/a | 349 |

TABLE 1-continued

| # | Name | Structure | | MS |
|---|---|---|---|---|
| 230 | 1-(1,7-Dimethyl-6-(3-(trifluoromethyl)benzyl)-6H-pyrrolo[2,3-e][1,2,4]triazolo[4,3-a]pyridin-4-yl)urea | 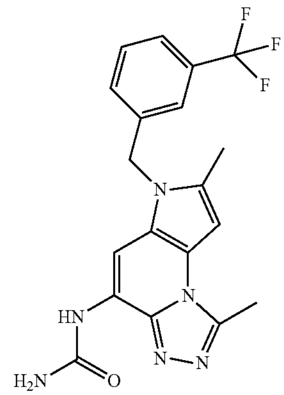 [SMILES: Cc1cc2c(cc(NC(N)=O)c3nnc(C)n32)n1Cc1cccc(C(F)(F)F)c1] | n/a | 403 |
| 231 | 1-(6-(3-Chlorobenzyl)-1,7-dimethyl-6H-pyrrolo[2,3-e][1,2,4]triazolo[4,3-a]pyridin-4-yl)urea | 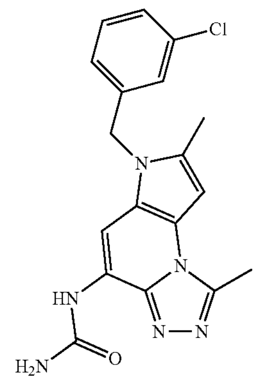 [SMILES: Cc1cc2c(cc(NC(N)=O)c3nnc(C)n32)n1Cc1cccc(Cl)c1] | n/a | 369 |
| 232 | 6-Benzyl-N-cyclohexyl-1,7-dimethyl-6H-pyrrolo[2,3-e][1,2,4]triazolo[4,3-a]pyridin-4-amine | 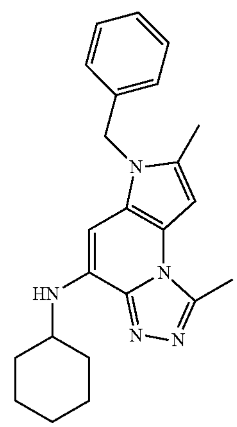 [SMILES: Cc1cc2c(cc(NC3CCCCC3)c3nnc(C)n32)n1Cc1ccccc1] | n/a | 374 |
| 233 | 1-(6-(3,5-Difluorobenzyl)-1,7-dimethyl-6H-pyrrolo[2,3-e][1,2,4]triazolo[4,3-a]pyridin-4-yl)urea | 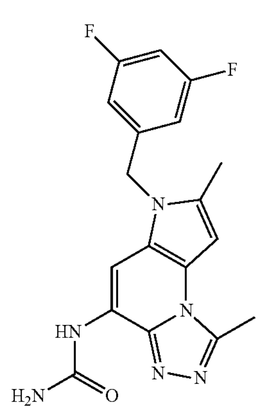 [SMILES: Cc1cc2c(cc(NC(N)=O)c3nnc(C)n32)n1Cc1cc(F)cc(F)c1] | n/a | 371 |

| | | | | |
|---|---|---|---|---|
| 234 | 1-(6-(3,4-Difluorobenzyl)-1,7-dimethyl-6H-pyrrolo[2,3-e][1,2,4]triazolo[4,3-a]pyridin-4-yl)urea | 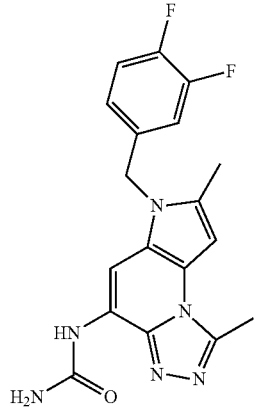 [SMILES: Cc1cc2c(cc(NC(N)=O)c3nnc(C)n32)n1Cc1ccc(F)c(F)c1] | n/a | 371 |
| 235 | 1-(6-(3-Fluorobenzyl)-1,7-dimethyl-6H-pyrrolo[2,3-e][1,2,4]triazolo[4,3-a]pyridin-4-yl)urea | 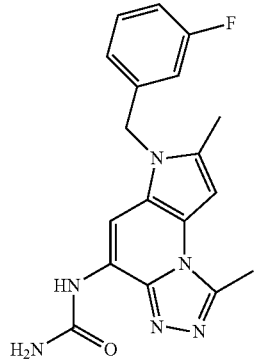 [SMILES: Cc1cc2c(cc(NC(N)=O)c3nnc(C)n32)n1Cc1cccc(F)c1] | n/a | 353 |
| 236 | 1-(6-(2,4-Difluorobenzyl)-1,7-dimethyl-6H-pyrrolo[2,3-e][1,2,4]triazolo[4,3-a]pyridin-4-yl)urea | 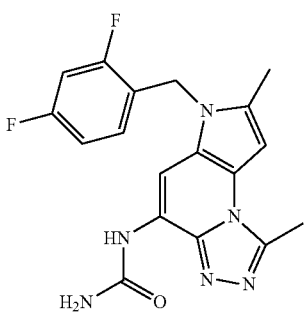 [SMILES: Cc1cc2c(cc(NC(N)=O)c3nnc(C)n32)n1Cc1ccc(F)cc1F] | n/a | 371 |
| 237 | 1-(6-(2,3-Difluorobenzyl)-1,7-dimethyl-6H-pyrrolo[2,3-e][1,2,4]triazolo[4,3-a]pyridin-4-yl)urea | 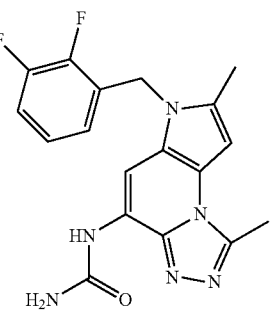 | n/a | 371 |

TABLE 1-continued
| 238 | 1-(6-(2-Fluorobenzyl)-1,7-dimethyl-6H-pyrrolo[2,3-e][1,2,4]triazolo[4,3-a]pyridin-4-yl)urea | 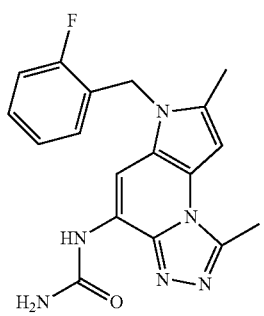 [SMILES: Cc1cc2c(cc(NC(N)=O)c3nnc(C)n32)n1Cc1ccccc1F] | n/a | 353 |
| 239 | 1-(6-(4-Fluorobenzyl)-1,7-dimethyl-6H-pyrrolo[2,3-e][1,2,4]triazolo[4,3-a]pyridin-4-yl)urea | 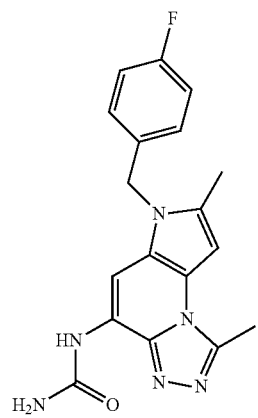 [SMILES: Cc1cc2c(cc(NC(N)=O)c3nnc(C)n32)n1Cc1ccc(F)cc1] | n/a | 353 |
| 240 | 6-benzyl-1,7-Dimethyl-N-(pyridin-2-yl)-6H-pyrrolo[2,3-e][1,2,4]triazolo[4,3-a]pyridin-4-amine | 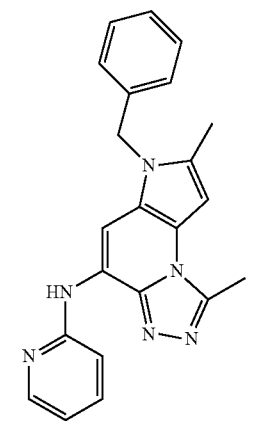 [SMILES: Cc1cc2c(cc(Nc3ccccn3)c3nnc(C)n32)n1Cc1ccccc1] | n/a | 369 |
| 241 | 6-Benzyl-N-(cyclobutylmethyl)-1,7-dimethyl-6H-pyrrolo[2,3-e][1,2,4]triazolo[4,3-a]pyridin-4-amine | 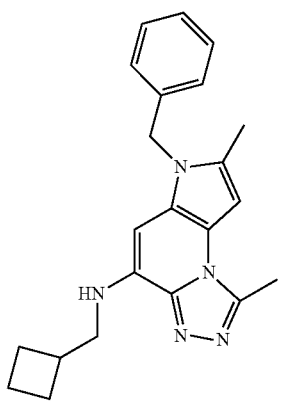 [SMILES: Cc1cc2c(cc(NCC3CCC3)c3nnc(C)n32)n1Cc1ccccc1] | n/a | 360 |

| | | | | |
|---|---|---|---|---|
| 242 | tert-Butyl 4-((6-benzyl-1,7-dimethyl-6H-pyrrolo[2,3-e][1,2,4]triazolo[4,3-a]pyridin-4-ylamino)methyl)piperidine-1-carboxylate | 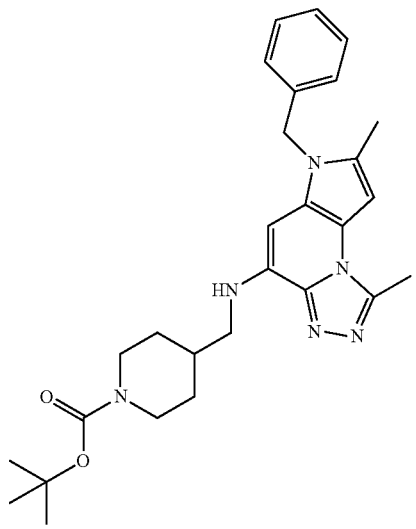 [SMILES: Cc1cc2c(cc(NCC3CCN(C(=O)OC(C)(C)C)CC3)c3nnc(C)n32)n1Cc1ccccc1] | n/a | 489 |
| 243 | tert-Butyl 3-((6-benzyl-1,7-dimethyl-6H-pyrrolo[2,3-e][1,2,4]triazolo[4,3-a]pyridin-4-ylamino)methyl)azetidine-1-carboxylate | 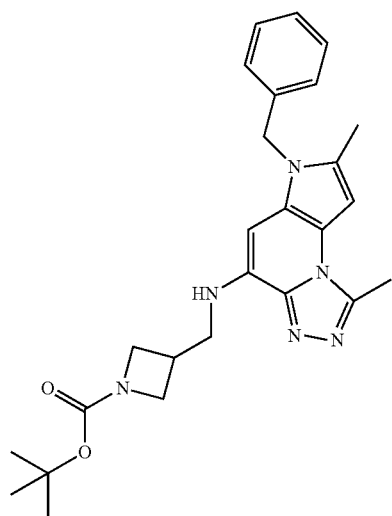 [SMILES: Cc1cc2c(cc(NCC3CN(C(=O)OC(C)(C)C)C3)c3nnc(C)n32)n1Cc1ccccc1] | n/a | 461 |
| 244 | tert-Butyl 3-(6-benzyl-1,7-dimethyl-6H-pyrrolo[2,3-e][1,2,4]triazolo[4,3-a]pyridin-4-ylamino)azetidine-1-carboxylate | 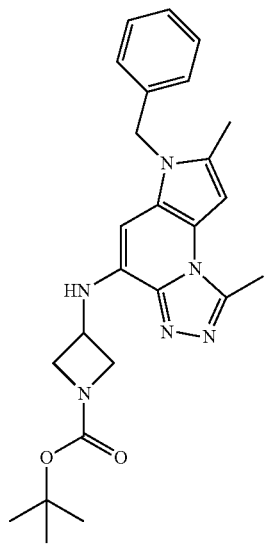 [SMILES: Cc1cc2c(cc(NC3CN(C(=O)OC(C)(C)C)C3)c3nnc(C)n32)n1Cc1ccccc1] | n/a | 447 |

TABLE 1-continued
| 245 | N1-(6-Benzyl-1,7-dimethyl-6H-pyrrolo[2,3-e][1,2,4]triazolo[4,3-a]pyridin-4-yl)-N3,N3-dimethylpropane-1,3-diamine | 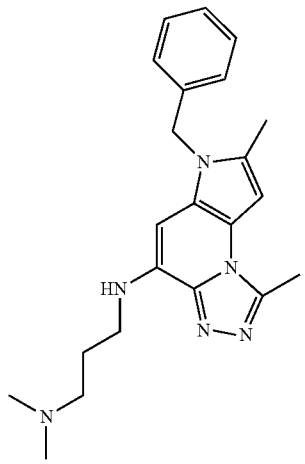 | n/a | 377 |
| 246 | N1-(6-Benzyl-1,7-dimethyl-6H-pyrrolo[2,3-e][1,2,4]triazolo[4,3-a]pyridin-4-yl)-N2,N2-dimethylethane-1,2-diamine | 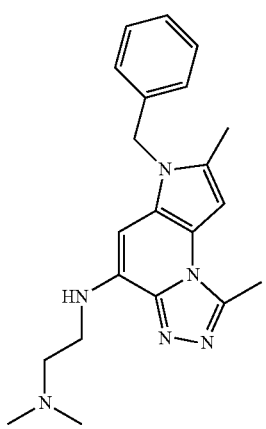 | n/a | 363 |
| 247 | trans-3-(6-Benzyl-1,7-dimethyl-6H-pyrrolo[2,3-e][1,2,4]triazolo[4,3-a]pyridin-4-ylamino)cyclobutanol | 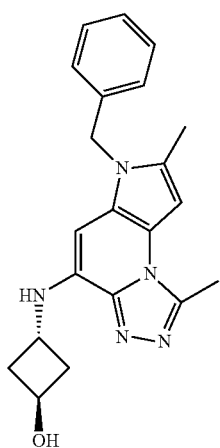 [SMILES: Cc1cc2c(cc(N[C@H]3C[C@H](O)C3)c3nnc(C)n32)n1Cc1ccccc1] | n/a | 362 |

TABLE 1-continued
| | | | | |
|---|---|---|---|---|
| 248 | tert-Butyl 6-benzyl-1,7-dimethyl-6H-pyrrolo[2,3-e][1,2,4]triazolo[4,3-a]pyridin-4-ylcarbamate | 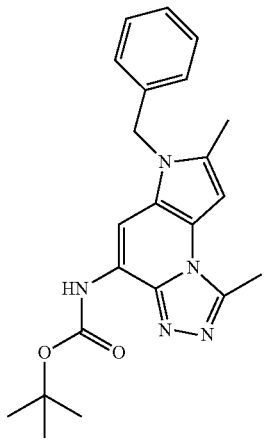 [SMILES: Cc1cc2c(cc(NC(=O)OC(C)(C)C)c3nnc(C)n32)n1Cc1ccccc1] | n/a | 392 |
| 249 | 1-(6-Benzyl-1,7-dimethyl-6H-pyrrolo[2,3-e][1,2,4]triazolo[4,3-a]pyridin-4-yl)-3-ethylurea | 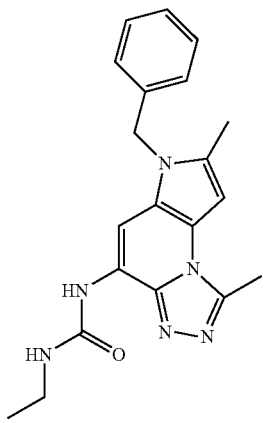 [SMILES: CCNC(=O)Nc1cc2c(cc(C)n2Cc2ccccc2)n2c(C)nnc12] | n/a | 363 |
| 250 | 1-(6-Benzyl-1,7-dimethyl-6H-pyrrolo[2,3-e][1,2,4]triazolo[4,3-a]pyridin-4-yl)-3-isopropylurea | 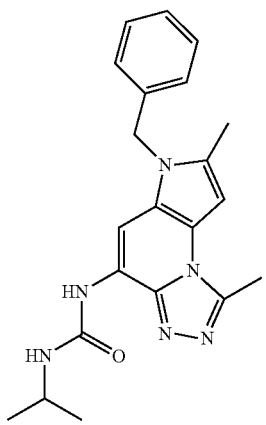 [SMILES: Cc1cc2c(cc(NC(=O)NC(C)C)c3nnc(C)n32)n1Cc1ccccc1] | n/a | 377 |

TABLE 1-continued
| | | | | |
|---|---|---|---|---|
| 251 | 3-(6-Benzyl-1,7-dimethyl-6H-pyrrolo[2,3-e][1,2,4]triazolo[4,3-a]pyridin-4-yl)-1,1-dimethylurea | 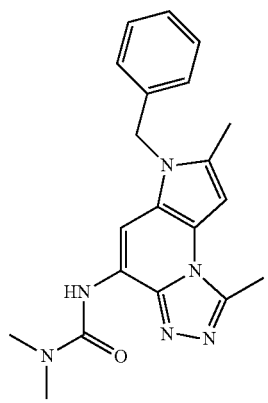 | n/a | 363 |
| 252 | 1-(6-Benzyl-1,7-dimethyl-6H-pyrrolo[2,3-e][1,2,4]triazolo[4,3-a]pyridin-4-yl)urea | 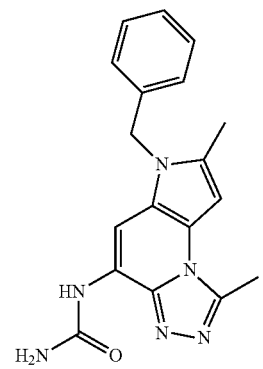 [SMILES: Cc1cc2c(cc(NC(N)=O)c3nnc(C)n32)n1Cc1ccccc1] | n/a | 335 |
| 253 | 6-Benzyl-N-(1H-imidazol-2-yl)-1,7-dimethyl-6H-pyrrolo[2,3-e][1,2,4]triazolo[4,3-a]pyridin-4-amine | 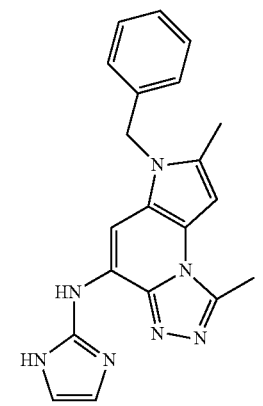 [SMILES: Cc1cc2c(cc(Nc3ncc[nH]3)c3nnc(C)n32)n1Cc1ccccc1] | TFA | 358 |
| 254 | 1-(6-(2,6-Difluorobenzyl)-1,7-dimethyl-6H-pyrrolo[2,3-e][1,2,4]triazolo[4,3-a]pyridin-4-yl)urea | 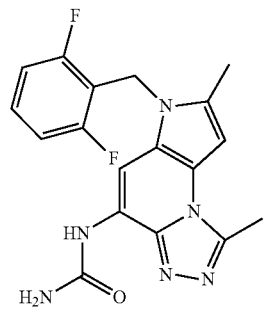 [SMILES: Cc1cc2c(cc(NC(N)=O)c3nnc(C)n32)n1Cc1c(F)cccc1F] | TFA | 371 |

TABLE 1-continued
| 255 | 6-Benzyl-1,7-dimethyl-N-(pyridin-4-yl)-6H-pyrrolo[2,3-e][1,2,4]triazolo[4,3-a]pyridin-4-amine | 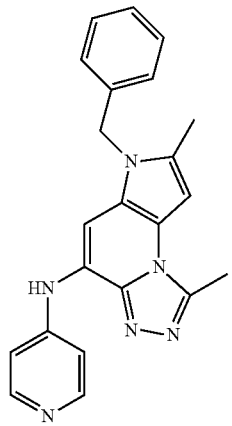 [SMILES: Cc1cc2c(cc(Nc3ccncc3)c3nnc(C)n32)n1Cc1ccccc1] | 3x TFA | 369 |
| --- | --- | --- | --- | --- |
| 256 | 6-Benzyl-1,7-dimethyl-N-(pyridin-3-yl)-6H-pyrrolo[2,3-e][1,2,4]triazolo[4,3-a]pyridin-4-amine | 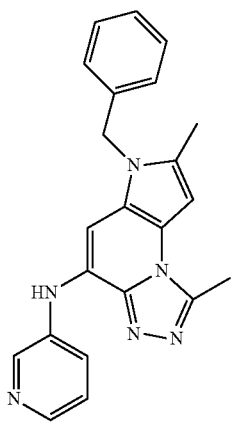 [SMILES: Cc1cc2c(cc(Nc3cccnc3)c3nnc(C)n32)n1Cc1ccccc1] | 3x TFA | 369 |
| 257 | N1-(6-Benzyl-1,7-dimethyl-6H-pyrrolo[2,3-e][1,2,4]triazolo[4,3-a]pyridin-4-yl)propane-1,3-diamine | 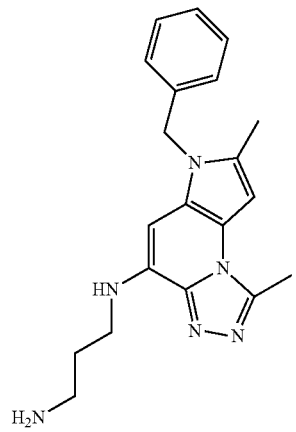 [SMILES: Cc1cc2c(cc(NCCCN)c3nnc(C)n32)n1Cc1ccccc1] | 3x TFA | 349 |

TABLE 1-continued

| # | Name | Salt | MS |
|---|---|---|---|
| 258 | N1-(6-benzyl-1,7-dimethyl-6H-pyrrolo[2,3-e][1,2,4]triazolo[4,3-a]pyridin-4-yl)ethane-1,2-diamine | 3x TFA | 335 |
| 259 | 6-Benzyl-N-ethyl-1,7-dimethyl-6H-pyrrolo[2,3-e][1,2,4]triazolo[4,3-a]pyiridin-4-amine | 2x TFA | 320 |
| 260 | 6-Benzyl-1,7-dimethyl-N-phenyl-6H-pyrrolo[2,3-e][1,2,4]triazolo[4,3-a]pyridin-4-amine | 2x TFA | 368 |

| $^1$H NMR data for examples 229-260 | |
|---|---|
| Example # | $^1$H NMR Spectrum |
| 229 | $^1$H NMR (500 MHz, d$_6$-DMSO) δ 8.74 (s, 1H), 8.21 (s, 1H), 7.31 (t, J = 7.4 Hz, 2H), 7.25 (t, J = 7.3 Hz, 1H), 6.99 (d, J = 7.3 Hz, 2H), 6.84 (s, 1H), 6.77 (s, 1H), 5.45 (s, 2H), 2.93 (s, 3H), 2.65 (s, 3H), 2.40 (s, 3H). |
| 230 | $^1$H NMR (400 MHz, d$_6$-DMSO) δ 8.80 (s, 1H), 8.10 (s, 1H), 7.66-7.60 (m, 1H), 7.56-7.49 (m, 1H), 7.46 (s, 1H), 7.08 (d, J = 7.8 Hz, 1H), 6.75 (s, 1H), 6.40 (s, 2H), 5.51 (s, 2H), 2.87 (s, 3H), 2.34 (s, 3H). |
| 231 | $^1$H NMR (300 MHz, CDCl$_3$) δ 8.16 (s, 1H), 7.22-7.18 (m, 2H), 6.88-6.85 (m, 1H), 6.84-6.78 (m, 1H), 6.54 (s, 1H), 5.30 (s, 2H), 2.94 (s, 3H), 2.34 (s, 3H). |
| 232 | $^1$H NMR (400 MHz, CDCl$_3$) δ 7.35-7.24 (m, 3H), 6.99 (d, J = 6.8 Hz, 2H), 6.46 (s, 1H), 6.08 (s, 1H), 5.26 (s, 2H), 4.90 (d, J = 7.8 Hz, 1H), 3.32-3.19 (m, 1H), 2.93 (s, 3H), 2.35 (s, 3H), 2.06-1.92 (m, 2H), 1.81-1.71 (m, 2H), 1.41-1.12 (m, 6H). |
| 233 | $^1$H NMR (400 MHz, d$_6$-DMSO) δ 8.81 (s, 1H), 8.07 (s, 1H), 7.16 (tt, J = 9.4, 2.3 Hz, 1H), 6.74 (s, 1H), 6.68-6.60 (m, 2H), 6.40 (s, 2H), 5.43 (s, 2H), 2.86 (s, 3H), 2.34 (s, 3H). |

TABLE 1-continued

| | |
|---|---|
| 234 | $^1$H NMR (400 MHz, d$_6$-DMSO) δ 8.80 (s, 1H), 8.09 (s, 1H), 7.38 (dt, J = 10.7, 8.5 Hz, 1H), 7.09 (ddd, J = 11.3, 7.7, 2.1 Hz, 1H), 6.79-6.66 (m, 2H), 6.40 (s, 2H), 5.38 (s, 2H), 2.86 (s, 3H), 2.34 (s, 3H). |
| 235 | $^1$H NMR (400 MHz, d$_6$-DMSO) δ 8.79 (s, 1H), 8.10 (s, 1H), 7.34 (td, J = 8.0, 6.1 Hz, 1H), 7.08 (td, J = 8.3, 2.2 Hz, 1H), 6.84-6.70 (m, 3H), 6.39 (s, 2H), 5.41 (s, 2H), 2.86 (s, 3H), 2.34 (s, 3H). |
| 236 | $^1$H NMR (400 MHz, d$_6$-DMSO) δ 8.80 (s, 1H), 8.12 (s, 1H), 7.33 (ddd, J = 10.8, 9.3, 2.6 Hz, 1H), 6.98 (td, J = 8.7, 2.4 Hz, 1H), 6.73 (s, 1H), 6.64 (td, J = 8.7, 6.7 Hz, 1H), 6.39 (br s, 2H), 5.39 (s, 2H), 2.85 (s, 3H), 2.35 (s, 3H). |
| 237 | $^1$H NMR (400 MHz, d$_6$-DMSO) δ 8.75 (s, 1H), 8.07 (s, 1H), 7.50-7.17 (m, 1H), 7.10-6.96 (m, 1H), 6.69 (s, 1H), 6.47-6.17 (m, 3H), 5.44 (s, 2H), 2.81 (s, 3H), 2.30 (s, 3H). |
| 238 | $^1$H NMR (400 MHz, CDCl$_3$) δ 8.27 (s, 1H), 7.24-7.16 (m, 1H), 7.10-7.00 (m, 1H), 6.95 (td, J = 7.6, 0.9 Hz, 1H), 6.56 (s, 1H), 6.54-6.47 (m, 1H), 5.37 (s, 2H), 2.93 (s, 3H), 2.37 (s, 3H). |
| 239 | $^1$H NMR (400 MHz, d$_6$-DMSO) δ 8.80 (s, 1H), 8.12 (s, 1H), 7.20-7.09 (m, 2H), 7.07-6.90 (m, 2H), 6.71 (s, 1H), 6.40 (s, 2H), 5.37 (s, 2H), 2.86 (s, 3H), 2.33 (s, 3H). |
| 240 | $^1$H NMR (400 MHz, CDCl$_3$) δ 8.72 (s, 1H), 8.24 (dd, J = 4.8, 1.4 Hz, 1H), 8.04 (br s, 1H), 7.52 (ddd, J = 8.6, 7.3, 1.9 Hz, 1H), 7.34-7.27 (m, 3H), 7.09-7.04 (m, 2H), 6.88 (d, J = 8.2 Hz, 1H), 6.77 (dd, J = 6.7, 5.4 Hz, 1H), 6.53 (s, 1H), 5.36 (s, 2H), 2.98 (s, 3H), 2.40 (s, 3H). |
| 241 | $^1$H NMR (300 MHz, CDCl$_3$) δ 7.27-7.18 (m, 3H), 7.15-6.60 (m, 2H), 6.40 (s, 1H), 6.07 (s, 1H), 5.20 (s, 2H), 5.15 (br s, 1H), 3.09 (d, J = 6.6 Hz, 2H), 2.87 (s, 3H), 2.67 (app hept, J = 7.3 Hz, 1H), 2.27 (s, 3H), 2.12-2.00 (m, 2H), 1.90-1.75 (m, 2H), 1.74-1.62 (m, 2H). |
| 242 | $^1$H NMR (400 MHz, CDCl$_3$) δ 7.33-7.26 (m, 3H), 6.98-6.93 (m, 2H), 6.46 (s, 1H), 6.06 (s, 1H), 5.27 (s, 2H), 5.04 (t, J = 4.9 Hz, 1H), 4.08 (br s, 2H), 3.10-2.98 (m, 2H), 2.93 (s, 3H), 2.72-2.50 (m, 2H), 2.35 (s, 3H), 2.02-1.64 (m, 3H), 1.44 (s, 9H), 1.23-1.07 (m, 2H). |
| 243 | $^1$H NMR (400 MHz, CDCl$_3$) δ 7.35-7.27 (m, 3H), 6.97-6.91 (m, 2H), 6.52 (s, 1H), 6.29 (s, 1H), 5.31 (s, 2H), 4.05 (t, J = 8.5 Hz, 2H), 3.64 (dd, J = 8.3, 4.7 Hz, 2H), 3.35 (d, J = 7.6 Hz, 2H), 2.95 (s, 3H), 2.91-2.78 (m, 1H), 2.38 (s, 3H), 1.41 (s, 9H). |
| 244 | $^1$H NMR (400 MHz, CDCl$_3$) δ 7.34-7.26 (m, 3H), 6.98-6.92 (m, 2H), 6.48 (s, 1H), 5.88 (s, 1H), 5.32 (d, J = 4.5 Hz, 1H), 5.25 (s, 2H), 4.24-4.17 (m, 3H), 3.83-3.74 (m, 2H), 2.94 (s, 3H), 2.38 (s, 3H), 1.43 (s, 9H). |
| 245 | $^1$H NMR (400 MHz, CDCl$_3$) δ 7.33-7.24 (m, 3H), 6.98-6.91 (m, 2H), 6.47 (s, 1H), 6.16 (s, 1H), 5.27 (s, 2H), 5.13 (br s, 1H), 3.23 (t, J = 6.9 Hz, 2H), 2.94 (s, 3H), 2.42 (t, J = 6.9 Hz, 2H), 2.33 (s, 3H), 2.23 (s, 6H), 1.86 (t, J = 6.9 Hz, 2H). |
| 246 | $^1$H NMR (400 MHz, CDCl$_3$) δ 7.33-7.24 (m, 3H), 6.98-6.93 (m, 2H), 6.47 (s, 1H), 6.13 (s, 1H), 5.35 (t, J = 5.2 Hz, 1H), 5.27 (s, 2H), 3.23 (app q, J = 6.0 Hz, 2H), 2.94 (s, 3H), 2.60 (t, J = 6.3 Hz, 2H), 2.34 (s, 3H), 2.25 (s, 6H). |
| 247 | $^1$H NMR (300 MHz, CDCl$_3$) δ 7.34-7.25 (m, 3H), 6.99-6.93 (m, 2H), 6.48 (s, 1H), 6.13 (s, 1H), 5.27 (s, 2H), 4.10 (p, J = 7.3 Hz, 1H), 3.48 (p, J = 7.5 Hz, 1H), 2.93 (s, 3H), 2.87 (ddd, J = 12.8, 6.9, 2.9 Hz, 2H), 2.38 (s, 3H), 2.11 (ddd, J = 12.5, 10.4, 7.9 Hz, 2H). |
| 248 | $^1$H NMR (300 MHz, CDCl$_3$) δ 8.02 (s, 1H), 7.85 (s, 1H), 7.35-7.19 (m, 3H), 6.99-6.86 (m, 2H), 6.54 (s, 1H), 5.33 (s, 2H), 2.97 (s, 3H), 2.34 (s, 3H), 1.51 (s, 9H). |
| 249 | $^1$H NMR (400 MHz, CDCl$_3$) δ 8.17 (s, 1H), 7.23-7.12 (m, 3H), 6.90-6.83 (m, 2H), 6.48 (s, 1H), 6.38 (t, J = 4.9 Hz, 1H), 5.28 (s, 2H), 3.21 (qd, J = 7.2, 5.5 Hz, 2H), 2.88 (s, 3H), 2.30 (s, 3H), 1.10 (t, J = 7.2 Hz, 3H). |
| 250 | $^1$H NMR (400 MHz, CDCl$_3$) δ 9.15 (s, 1H), 8.27 (s, 1H), 7.30-7.20 (m, 3H), 7.15 (d, J = 5.8 Hz, 1H), 6.96-6.90 (m, 2H), 6.52 (s, 1H), 5.34 (s, 2H), 4.09-4.00 (m, 1H), 2.96 (s, 3H), 2.34 (s, 3H), 1.23 (d, J = 6.5 Hz, 6H). |
| 251 | $^1$H NMR (400 MHz, CDCl$_3$) δ 8.23 (s, 1H), 7.75 (s, 1H), 7.32-7.17 (m, 3H), 6.96-6.87 (m, 2H), 6.53 (s, 1H), 5.33 (s, 2H), 3.10 (s, 6H), 2.97 (s, 3H), 2.35 (s, 3H). |
| 252 | $^1$H NMR (400 MHz, d$_6$-DMSO) δ 8.80 (s, 1H), 8.23 (s, 1H), 7.35-7.29 (m, 2H), 7.29-7.22 (m, 1H), 7.04-6.93 (m, 2H), 6.87 (s, 1H), 6.39 (s, 2H), 5.48 (s, 2H), 2.94 (s, 3H), 2.40 (s, 3H). |
| 253 | $^1$H NMR (400 MHz, CDCl$_3$) δ 7.49 (s, 1H), 7.33-7.23 (m, 3H), 7.04-6.98 (m, 2H), 6.74 (s, 2H), 6.62 (s, 1H), 5.40 (s, 2H), 3.01 (s, 3H), 2.47 (s, 3H). |
| 254 | $^1$H NMR (400 MHz, d$_6$-DMSO) δ 8.78 (s, 1H), 8.31 (s, 1H), 7.51-7.38 (m, 1H), 7.18-7.04 (m, 2H), 6.79 (s, 1H), 6.38 (s, 2H), 5.49 (s, 2H), 2.90 (s, 3H), 2.45 (s, 3H). |
| 255 | $^1$H NMR (400 MHz, d$_6$-DMSO) δ 10.70 (s, 1H), 8.28 (d, J = 6.9 Hz, 2H), 8.00 (s, 1H), 7.36-7.30 (m, 2H), 7.30-7.24 (m, 1H), 7.07-7.00 (m, 4H), 5.58 (s, 2H), 2.95 (s, 3H), 2.45 (s, 3H). |
| 256 | $^1$H NMR (400 MHz, CDCl$_3$) δ 10.67 (s, 1H), 9.16 (d, J = 2.4 Hz, 1H), 8.12 (dd, J = 8.5, 1.9 Hz, 1H), 8.09 (d, J = 5.2 Hz, 1H), 7.93 (s, 1H), 7.64 (dd, J = 8.6, 5.3 Hz, 1H), 7.34-7.22 (m, 3H), 6.92-6.88 (m, 2H), 6.80 (s, 1H), 5.67 (s, 2H), 3.10 (s, 3H), 2.55 (s, 3H). |
| 257 | $^1$H NMR (400 MHz, d$_6$-DMSO) δ 7.83 (s, 1H), 7.74 (s, 2H), 7.33-7.27 (m, 2H), 7.26-7.21 (m, 1H), 7.02-6.92 (m, 2H), 6.88 (s, 1H), 6.73 (s, 1H), 5.47 (s, 2H), 3.27 (t, J = 6.6 Hz, 2H), 2.93-2.83 (m, 2H), 2.90 (s, 3H), 2.29 (s, 3H), 1.87 (app p, J = 6.8 Hz, 2H). |

TABLE 1-continued

| | |
|---|---|
| 258 | $^1$H NMR (400 MHz, CDCl$_3$) δ 7.28-7.19 (m, 3H), 7.05 (s, 1H), 6.92-6.86 (m, 2H), 6.60 (s, 1H), 5.43 (s, 2H), 3.57 (t, J = 5.8 Hz, 2H), 3.23 (t, J = 5.8 Hz, 2H), 2.99 (s, 3H), 2.39 (s, 3H). |
| 259 | $^1$H NMR (400 MHz, CDCl$_3$) δ 7.36-7.27 (m, 3H), 6.98-6.92 (m, 2H), 6.59 (s, 1H), 6.53 (s, 1H), 5.34 (s, 2H), 3.19 (q, J = 7.2 Hz, 2H), 3.01 (s, 3H), 2.43 (s, 3H), 1.31 (t, J = 7.2 Hz, 3H). |
| 260 | $^1$H NMR (400 MHz, d$_6$-DMSO) δ 8.27 (br s, 1H), 7.79 (s, 1H), 7.37-7.31 (m, 2H), 7.31-7.24 (m, 1H), 7.22-7.14 (m, 2H), 7.06-7.00 (m, 2H), 6.96 (s, 1H), 6.92 (d, J = 7.9 Hz, 2H), 6.86-6.80 (m, 1H), 5.55 (s, 2H), 2.97 (s, 3H), 2.48 (s, 3H). |

Example 261

6-Benzyl-N,1,7-trimethyl-6H-pyrrolo[2,3-e][1,2,4]triazolo[4,3-a]pyridin-4-amine

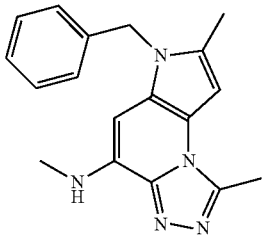 [SMILES: CNc1cc2c(cc(C)n2Cc2ccccc2)n2c(C)nnc12]

To a solution of tert-butyl (6-benzyl-1,7-dimethyl-6H-pyrrolo[2,3-e][1,2,4]triazolo[4,3-a]pyridin-4-yl)carbamate (9.0 mg, 0.023 mmol, Example 248) in tetrahydrofuran (1 mL) at 0° C. was added NaH (60% in mineral oil, 2.4 mg, 0.060 mmol). After 30 minutes, a solution of methyl iodide (2.9 µL, 0.046 mmol, Aldrich) in THF (95 µL) was added to the reaction mixture, and the reaction mixture was stirred overnight, after which time additional NaH (60% in mineral oil, 8.3 mg, 0.21 mmol) and a solution of methyl iodide (5.8 µL in 0.19 mL THF, 0.092 mmol) were added. After 4 hours, water and ethyl acetate were added. Layers were separated, and the organic phase was washed with brine, dried over sodium sulfate, filtered and concentrated. The crude tert-butyl (6-benzyl-1,7-dimethyl-6H-pyrrolo[2,3-e][1,2,4]triazolo[4,3-a]pyridin-4-yl)(methyl)carbamate was treated with Trifluoroacetic Acid (2.0 mL, 26 mmol) for 1 hour. The solvent was removed in vacuo, and the title product was isolated by preparative HPLC-MS (Waters XBridge C18, eluting with a gradient of MeCN/H$_2$O containing 0.15% NH$_4$OH). Yield: (2.5 mg, 36%).

$^1$H NMR (500 MHz, CDCl$_3$) δ 7.42-7.20 (m, 3H), 7.00-6.95 (m, 2H), 6.45 (s, 1H), 6.07 (s, 1H), 5.26 (s, 2H), 5.02 (s, 1H), 2.92 (s, 3H), 2.90 (s, 3H), 2.32 (s, 3H). LCMS (M+H)$^+$: 306.

Example 262

6-Benzyl-N-propyl-1,7-dimethyl-6H-pyrrolo[2,3-e][1,2,4]triazolo[4,3-a]pyridin-4-amine

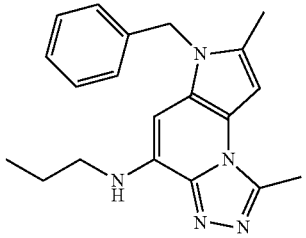 [SMILES: CCCNc1cc2c(cc(C)n2Cc2ccccc2)n2c(C)nnc12]

The title compound was prepared according to the methods of Example 261 using 1-iodopropane (Aldrich).

$^1$H NMR (400 MHz, CDCl$_3$) δ 7.36-7.24 (m, 3H), 7.00-6.92 (m, 2H), 6.47 (s, 1H), 6.10 (s, 1H), 5.27 (s, 2H), 4.99-4.89 (m, 1H), 3.12 (app q, J=6.8 Hz, 2H), 2.94 (s, 3H), 2.34 (s, 3H), 1.71 (app h, J=7.4 Hz, 2H), 1.01 (t, J=7.4 Hz, 3H); LCMS (M+H)$^+$: 334.

Example 263

6-Benzyl-N-isopropyl-1,7-dimethyl-6H-pyrrolo[2,3-e][1,2,4]triazolo[4,3-a]pyridin-4-amine

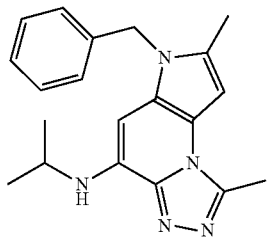 [SMILES: Cc1cc2c(cc(NC(C)C)c3nnc(C)n32)n1Cc1ccccc1]

To a suspension of 6-benzyl-4-chloro-1,7-dimethyl-6H-pyrrolo[2,3-e][1,2,4]triazolo[4,3-a]pyridine (20.0 mg, 0.0644 mmol, from Example 228, Step 7), 2-propanamine (51 µL, 0.60 mmol, Aldrich) and tBuXPhos Pd G1 (7.1 mg, 0.0096 mmol, Aldrich) in tetrahydrofuran (0.3 mL) was added 1.0 M LHMDS in THF (0.19 mL, 0.19 mmol, Aldrich). The reaction was stirred for 3 days, after which time additional amounts of tBuXPhos Pd G1 (6 mg, 0.008 mmol), 2-propanamine (51 uL, 0.60 mmol), THF (0.3 mL) and 1.0 M LHMDS in THF (0.2 mL, 0.2 mmol) were added and the mixture was heated at 100° C. for 2.5 hours. After cooling to room temperature, MeOH was added, and the mixture was filtered. The product was purified by preparative HPLC-MS (Waters XBridge C18, eluting with a gradient of MeCN/H$_2$O containing 0.15% NH$_4$OH). Yield: (0.2 mg, 1%).

$^1$H NMR (400 MHz, CDCl$_3$) δ 7.35-7.26 (m, 3H), 7.02-6.89 (m, 2H), 6.48 (s, 1H), 6.14 (s, 1H), 5.27 (s, 2H), 3.69-3.52 (m, 1H), 2.95 (s, 3H), 2.36 (s, 3H), 1.24 (d, J=6.4 Hz, 6H); LCMS (M+H)$^+$: 334.

Example 264

6-Benzyl-4-methoxy-1,7-dimethyl-6H-pyrrolo[2,3-e][1,2,4]triazolo[4,3-a]pyridine

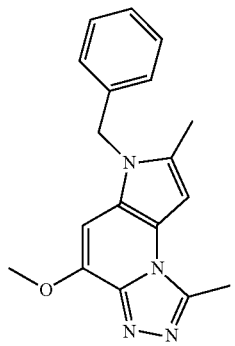

A suspension of 6-benzyl-4-chloro-1,7-dimethyl-6H-pyrrolo[2,3-e][1,2,4]triazolo[4,3-a]pyridine (10.0 mg, 0.0322 mmol, from Example 228, Step 7) in 25 wt % solution of NaOMe in MeOH (1.3 mL, 5.6 mmol, Aldrich) was heated at 150° C. in the microwave for 3 hours. The reaction was purified by preparative HPLC-MS (Waters XBridge C18, eluting with a gradient of MeCN/H$_2$O containing 0.15% NH$_4$OH). Yield: (0.7 mg, 7%).

$^1$H NMR (400 MHz, CDCl$_3$) δ 7.36-7.26 (m, 3H), 7.21 (s, 1H), 6.97-6.89 (m, 2H), 6.61 (s, 1H), 5.35 (s, 2H), 5.01 (s, 3H), 2.99 (s, 3H), 2.41 (s, 3H); LCMS (M+H)$^+$: 307.

Example 266

N-(6-Benzyl-1,7-dimethyl-6H-pyrrolo[2,3-e][1,2,4]triazolo[4,3-a]pyridin-4-yl)acetamide

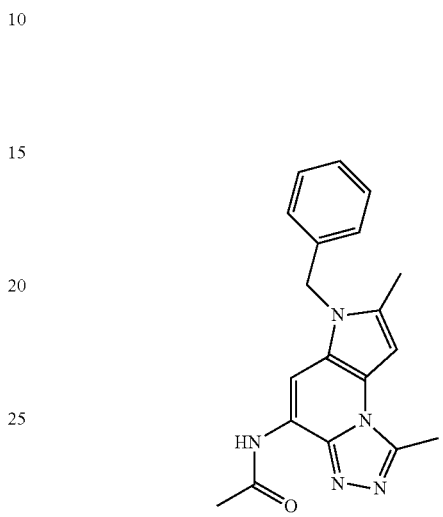

Step 1. 1,7-Dimethyl-4-nitro-6H-pyrrolo[2,3-e][1,2,4]triazolo[4,3-a]pyridine

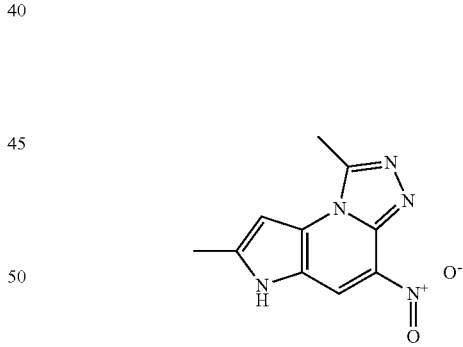

To a solution of 1,7-dimethyl-6-(phenylsulfonyl)-6H-pyrrolo[2,3-e][1,2,4]triazolo[4,3-a]pyridine (1.0 g, 3.1 mmol, from Example 228, Step 4) in 1,2-dichloroethane (20 mL) was added nitronium tetrafluoroborate (0.57 g, 4.3 mmol, Aldrich). The reaction mixture was stirred overnight, filtered and washed with DCE, and air-dried overnight. To a suspension of the nitrated product in Methanol (7 mL) was added 10% (w/w) KOH in water (7 mL, 10 mmol) and the reaction mixture was stirred for 3 hours, after which time the reaction mixture was diluted with DCM and water. 2.0 M solution of HCl in water (4.0 mL, 8.0 mmol) was added to adjust pH 10 and the mixture was stirred for 2 hours. The precipitated solid was isolated by filtration, washed with DCM and water, and then dried at 50° C. under high vacuum for 2 hours. Yield: (0.30 g, 40%).

LCMS (M+H)$^+$: 231.

Step 2. 6-Benzyl-1,7-dimethyl-4-nitro-6H-pyrrolo[2,3-e][1,2,4]triazolo[4,3-a]pyridine

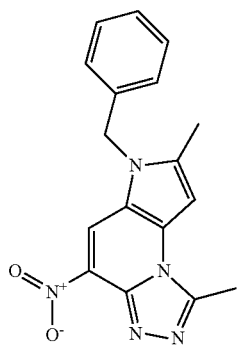 [SMILES: Cc1cc2c(cc([N+](=O)[O-])c3nnc(C)n32)n1Cc1ccccc1]

To a suspension of 1,7-dimethyl-4-nitro-6H-pyrrolo[2,3-e][1,2,4]triazolo[4,3-a]pyridine (0.30 g, 1.3 mmol, from Step 1) in N,N-dimethylformamide (5 mL) was added Cs$_2$CO$_3$ (0.51 g, 1.6 mmol). After stirring for 1 hour, benzyl bromide (0.18 mL, 1.6 mmol, Aldrich) was added, and the reaction mixture was stirred overnight, after which time water was added, and the reaction mixture was stirred for 5 minutes. Ethyl acetate was added, and the mixture was stirred overnight. The product, which had precipitated, was isolated by filtration. The product was washed sequentially with ethyl acetate, water, and again with ethyl acetate. Yield: (0.20 g, 48%). LCMS (M+H)$^+$: 322.

Step 3. 6-Benzyl-1,7-dimethyl-6H-pyrrolo[2,3-e][1,2,4]triazolo[4,3-a]pyridin-4-amine

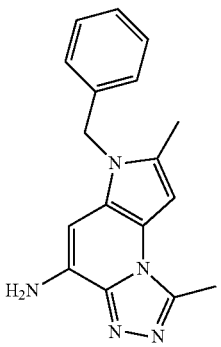 [SMILES: Cc1cc2c(cc(N)c3nnc(C)n32)n1Cc1ccccc1]

A degassed suspension of 6-benzyl-1,7-dimethyl-4-nitro-6H-pyrrolo[2,3-e][1,2,4]triazolo[4,3-a]pyridine (0.20 g, 0.62 mmol, from Step 2) in methanol (20 mL) and tetrahydrofuran (20 mL) was hydrogenated over Palladium (10% on carbon (Degussa type, Aldrich), 0.066 g, 0.062 mmol) under 1 atm H2 overnight. The reaction mixture was filtered, and the solvent was removed in vacuo. The product was purified by flash chromatography, eluting with 7% MeOH/DCM (0.7% NH$_4$OH). The product thus obtained (190 mg) was triturated in 2.5 mL MTBE and 0.25 mL DCM. The solid title product of step 3 was isolated by filtration and dried at 40° C. under vacuum overnight. Yield: (0.13 g, 69%).

LCMS (M+H)$^+$: 292.

Step 4. N-(6-Benzyl-1,7-dimethyl-6H-pyrrolo[2,3-e][1,2,4]triazolo[4,3-a]pyridin-4-yl)acetamide To a suspension of 6-benzyl-1,7-dimethyl-6H-pyrrolo[2,3-e][1,2,4]triazolo[4,3-a]pyridin-4-amine (32.0 mg, 0.110 mmol, from Step 3) in tetrahydrofuran (1 mL) was added acetyl chloride (15.1 µL, 0.213 mmol, Aldrich) and N,N-diisopropylethylamine (76 µL, 0.44 mmol). After 3.5 hours, the product was purified by preparative HPLC-MS (Waters XBridge C18, eluting with a gradient of MeCN/H$_2$O containing 0.15% NH$_4$OH). Yield: (19 mg, 52%).

$^1$H NMR (400 MHz, CDCl$_3$) δ 8.63 (s, 1H), 8.41 (s, 1H), 7.33-7.21 (m, 3H), 7.00-6.91 (m, 2H), 6.55 (s, 1H), 5.33 (s, 2H), 2.97 (s, 3H), 2.39 (s, 3H), 2.26 (s, 3H); LCMS (M+H)$^+$: 334.

Examples 267-272

The Examples in Table 2 were Made by Procedures Analogous to Those Used to Prepare Example 266

TABLE 2

| Ex | Name | Structure | Salt | MS [M + H]+ |
|---|---|---|---|---|
| 267 | N-(6-Benzyl-1,7-dimethyl-6H-pyrrolo[2,3-e][1,2,4]triazolo[4,3-a]pyridin-4-yl)butyramide | 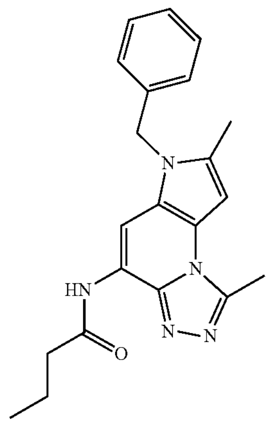 [SMILES: CCCC(=O)Nc1cc2c(cc(C)n2Cc2ccccc2)n2c(C)nnc12] | n/a | 362 |
| 268 | N-(6-Benzyl-1,7-dimethyl-6H-pyrrolo-[2,3-e][1,2,4]triazolo[4,3-a]pyridin-4-yl)propionamide | 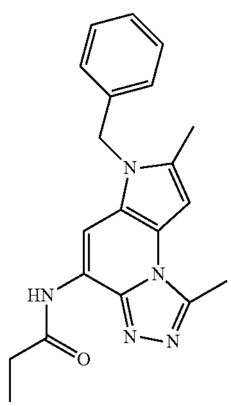 [SMILES: CCC(=O)Nc1cc2c(cc(C)n2Cc2ccccc2)n2c(C)nnc12] | 3x TFA | 348 |
| 269 | N-(6-Benzyl-1,7-dimethyl-6H-pyrrolo[2,3-e][1,2,4]triazolo[4,3-a]pyridin-4-yl)cyclopropanecarboxamide | 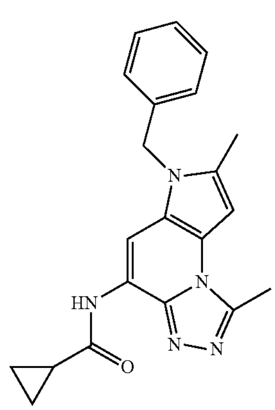 [SMILES: Cc1cc2c(cc(NC(=O)C3CC3)c3nnc(C)n32)n1Cc1ccccc1] | n/a | 360 |

TABLE 2-continued

| | | | | |
|---|---|---|---|---|
| 270 | N-(6-Benzyl-1,7-dimethyl-6H-pyrrolo[2,3-e][1,2,4]triazolo[4,3-a]pyridin-4-yl)isobutyramide | 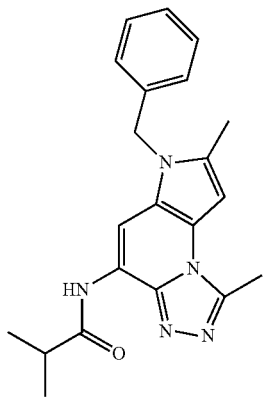 [SMILES: Cc1cc2c(cc(NC(=O)C(C)C)c3nnc(C)n32)n1Cc1ccccc1] | n/a | 362 |
| 271 | N-(6-Benzyl-1,7-dimethyl-6H-pyrrolo[2,3-e][1,2,4]triazolo[4,3-a]pyridin-4-yl)methanesulfonamide | 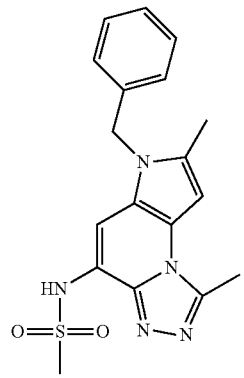 [SMILES: Cc1cc2c(cc(NS(C)(=O)=O)c3nnc(C)n32)n1Cc1ccccc1] | n/a | 370 |
| 272 | Methyl 6-benzyl-1,7-dimethyl-6H-pyrrolo[2,3-c][1,2,4]triazolo[4,3-a]pyridin-4-ylcarbamate | 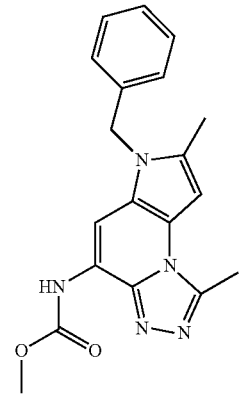 [SMILES: COC(=O)Nc1cc2c(cc(C)n2Cc2ccccc2)n2c(C)nnc12] | n/a | 350 |

$^1$H NMR data for Examples 267-272

| Example # | $^1$H NMR Spectrum |
|---|---|
| 267 | $^1$H NMR (400 MHz, CDCl$_3$) δ 8.55 (s, 1H), 8.47 (s, 1H), 7.33-7.20 (m, 3H), 6.94 (d, J = 6.8 Hz, 2H), 6.56 (s, 1H), 5.33 (s, 2H), 2.98 (s, 3H), 2.45 (t, J = 7.5 Hz, 2H), 2.38 (s, 3H), 1.77 (app h, J = 7.4 Hz, 2H), 1.00 (t, J = 7.4 Hz, 3H). |
| *268 | N/A |
| 269 | $^1$H NMR (300 MHz, d$_6$-DMSO) δ 10.36 (s, 1H), 8.23 (s, 1H), 7.35-7.20 (m, 3H), 7.00-6.93 (m, 2H), 6.79 (s, 1H), 5.41 (s, 2H), 2.86 (s, 3H), 2.37 (s, 3H), 2.32-2.22 (m, 1H), 0.82-0.73 (m, 4H). |
| 270 | N/A |
| 271 | $^1$H NMR (400 MHz, CDCl$_3$) δ 7.50 (s, 1H), 7.35-7.26 (m, 3H), 6.99-6.93 (m, 2H), 6.59 (s, 1H), 5.35 (s, 2H), 2.98 (s, 3H), 2.98 (s, 3H), 2.43 (s, 3H). |
| 272 | $^1$H NMR (400 MHz, CDCl$_3$) δ 8.05 (s, 1H), 7.95 (s, 1H), 7.33-7.26 (m, 3H), 6.98-6.92 (m, 2H), 6.55 (s, 1H), 5.34 (s, 2H), 3.79 (s, 3H), 2.97 (s, 3H), 2.38 (s, 3H). |

Example A1

BRD4 AlphaScreen™ Assay

BRD4-BD1 and BRD4-BD2 assays were conducted in white 384-well polystyrene plate in a final volume of 20 µL for BD1 and 40 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone H4 peptide (H4Ac4), 3.8 nM (BRD4-BD1, BPS Bioscience #31040) or 20 nM (BRD4-BD2, BPS Bioscience #31041). The reaction followed by the addition of 20 µL of assay buffer supplemented with Streptavidin donor beads (PerkinElmer 6760002) and GSH Acceptor beads (PerkinElmer-AL109C) at 4 µg/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software. $IC_{50}$ data for the Examples is presented in Table 3 as determined by Assay A1.

TABLE 3

| Example No.* | BRD4 BD-1 enzyme $IC_{50}$ (nM)** | BRD4 BD-2 enzyme $IC_{50}$ (nM)** |
| --- | --- | --- |
| 1 | ++ | + |
| 2 | + | + |
| 2a | + | ++ |
| 3 | ++ | ++ |
| 4 (rac) | ++ | + |
| 5 (enant) | ++ | + |
| 6 | ++ | ++ |
| 7 | ++ | ++ |
| 8 | ++ | + |
| 9 | + | + |
| 10 | + | + |
| 11 | ++ | ++ |
| 12 | ++ | ++ |
| 13 | ++ | + |
| 14 | + | + |
| 15 | + | + |
| 16 | + | + |
| 17 | + | + |
| 18 | + | + |
| 19 | + | + |
| 20 | ++ | + |
| 21 | ++ | + |
| 22 | ++ | + |
| 23 | + | + |
| 24 (rac) | ++ | ++ |
| 25 | ++ | + |
| 26 | + | + |
| 27 | + | + |
| 28 | + | + |
| 29 (rac) | ++ | ++ |
| 30 | ++ | + |
| 31 | ++ | + |
| 32 | ++ | + |
| 33 | ++ | + |
| 34 | + | + |
| 35 | + | + |
| 36 | + | + |
| 37 | ++ | + |
| 38 | ++ | + |
| 39 | ++ | + |
| 40 | + | + |
| 41 | + | + |
| 42 | + | + |
| 43 | ++ | + |
| 44 | ++ | + |
| 45 | + | + |
| 46 | + | + |
| 47 | ++ | + |
| 48 | ++ | + |
| 49 | ++ | + |
| 50 | + | + |
| 51 | ++ | ++ |
| 52 | ++ | ++ |
| 53 | ++ | ++ |
| 54 | ++ | + |
| 55 | ++ | + |
| 56 | ++ | + |
| 57 | +++ | ++ |
| 58 | + | + |
| 59 | + | + |
| 60 | ++ | + |
| 61 | +++ | ++ |
| 62 | + | + |
| 63 | + | + |
| 64 | + | + |
| 65 | + | + |
| 66 | + | + |
| 67 | + | + |
| 68 | ++ | + |
| 69 | ++ | + |
| 70 | + | + |
| 71 | ++ | +++ |
| 72 | + | + |
| 73 | ++ | + |
| 74 | + | + |
| 75 | + | + |
| 76 | + | + |
| 77 | + | + |
| 78 | + | + |
| 79 | + | + |
| 80 | + | + |
| 81 | + | + |
| 82 | + | + |
| 83 | + | + |
| 84 | ++ | ++ |
| 85 | + | + |
| 86 | ++ | ++ |
| 87 (rac) | + | + |
| 88 (rac) | + | + |
| 89 | ++ | + |
| 90 | + | + |
| 91 | + | + |
| 92 | + | + |
| 93 | + | + |
| 94 | ++ | ++ |
| 95 | + | + |
| 96 | + | + |
| 97 | + | + |
| 98 | + | + |
| 99 | + | + |
| 100 | + | + |
| 101 | ++ | ++ |
| 102 | + | + |
| 103 | + | + |
| 104 | + | + |
| 105 | + | + |
| 106 | + | + |
| 107 | + | + |
| 108 | + | + |
| 109 | + | + |
| 110 | + | + |
| 111 | + | + |
| 112 | ++ | ++ |
| 113 | + | + |
| 114 | + | + |
| 115 | ++ | ++ |
| 116 | +++ | +++ |

TABLE 3-continued

| Example No.* | BRD4 BD-1 enzyme IC$_{50}$ (nM)** | BRD4 BD-2 enzyme IC$_{50}$ (nM)** |
|---|---|---|
| 117 | + | + |
| 118 | ++ | ++ |
| 119 | + | + |
| 120 | ++ | ++ |
| 121 | + | + |
| 122 | + | + |
| 123 | ++ | + |
| 124 | +++ | +++ |
| 125 | ++ | ++ |
| 126 | ++ | ++ |
| 127 | + | + |
| 128 | ++ | ++ |
| 129 | + | + |
| 130 | + | + |
| 131 | + | + |
| 132 | + | + |
| 133 | + | + |
| 134 | + | + |
| 135 | + | + |
| 136 | + | + |
| 137 | + | + |
| 138 | ++ | ++ |
| 139 | + | + |
| 140 | + | + |
| 141 | + | + |
| 142 | + | + |
| 143 | + | + |
| 144 (rac) | + | + |
| 145 (rac) | + | + |
| 146 | + | + |
| 147 (enant) | + | + |
| 148 (enant) | + | + |
| 149 (enant) | ++ | + |
| 150 (enant) | + | + |
| 151 (enant) | + | + |
| 152 (enant) | + | + |
| 153 | + | + |
| 154 | + | + |
| 155 | + | + |
| 156 | + | + |
| 157 | + | + |
| 158 | + | + |
| 159 | + | + |
| 160 | + | + |
| 161 | + | + |
| 162 | + | + |
| 163 | + | + |
| 164 | + | + |
| 165 | + | + |
| 166 | + | + |
| 167 | + | + |
| 168 | + | + |
| 169 | + | + |
| 170 | + | + |
| 171 | + | + |
| 172 | + | + |
| 173 | + | + |
| 174 | + | + |
| 175 | + | + |
| 176 | + | + |
| 177 | + | + |
| 178 | + | + |
| 179 | + | + |
| 180 | + | + |
| 181 | + | + |
| 182 | + | + |
| 183 | + | + |
| 184 | + | + |
| 185 | + | + |
| 186 (rac) | +++ | ++ |
| 187 (rac) | +++ | +++ |
| 188 | + | + |
| 189 | + | + |
| 190 | + | + |
| 191 | + | + |
| 192 | + | + |
| 193 | + | + |
| 194 | + | + |
| 195 | + | + |
| 196 | + | + |
| 197 | + | + |
| 198 | + | + |
| 199 (rac) | + | + |
| 200 | + | + |
| 201 | + | + |
| 202 | + | + |
| 203 | + | + |
| 204 | + | + |
| 205 | + | + |
| 206 | + | + |
| 207 | + | + |
| 208 | + | + |
| 209 | + | + |
| 210 | + | + |
| 211 | + | + |
| 212 | + | + |
| 213 | + | + |
| 214 | ++ | + |
| 215 a (trans) | ++ | + |
| 215 b (cis) | + | + |
| 216 | + | + |
| 217 | + | + |
| 218 | + | + |
| 219 | + | + |
| 220 | + | + |
| 221 | + | + |
| 222 | + | + |
| 223 | + | + |
| 224 (rac) | + | + |
| 225 (rac) | + | + |
| 226 (enant) | ++ | + |
| 227 | + | + |
| 228 | + | + |
| 229 | + | + |
| 230 | + | + |
| 231 | + | + |
| 232 | ++ | ++ |
| 233 | + | + |
| 234 | + | + |
| 235 | + | + |
| 236 | + | + |
| 237 | + | + |
| 238 | + | + |
| 239 | + | + |
| 240 | + | + |
| 241 | ++ | + |
| 242 | ++ | + |
| 243 | ++ | + |
| 244 | + | + |
| 245 | + | + |
| 246 | + | + |
| 247 | + | + |
| 248 | ++ | + |
| 249 | + | + |
| 250 | + | + |
| 251 | ++ | + |
| 252 | + | + |
| 253 | + | + |
| 254 | + | + |
| 255 | ++ | + |
| 256 | + | + |
| 257 | + | + |
| 258 | + | + |
| 259 | + | + |
| 260 | + | + |
| 261 | + | + |
| 262 | + | + |
| 263 | + | + |
| 264 | ++ | ++ |
| 266 | + | + |
| 267 | ++ | + |
| 268 | + | + |

TABLE 3-continued

| Example No.* | BRD4 BD-1 enzyme IC$_{50}$ (nM)** | BRD4 BD-2 enzyme IC$_{50}$ (nM)** |
|---|---|---|
| 269 | + | + |
| 270 | + | + |
| 271 | ++ | + |
| 272 | + | + |

*"rac" refer to racemic;
"enant" refers to the more potent enantiomer
**column symbols: + refers to ≤100 nM; ++ refers to >100 nM and ≤1000 nM; +++ refers to >1000 nM and ≤10,000 nM.

Example B1

KMS.12.BM Cell Viability Assay

KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells well per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 minutes at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the 1050 is reported as the compound concentration required for 50% cell death. 1050 data for the Examples is presented in Table 4 as determined by Assay B1.

TABLE 4

| Example No.* | KMS cellular IC$_{50}$ (nM)* |
|---|---|
| 1 | ++ |
| 2 | + |
| 2a | ++ |
| 3 | ++ |
| 4 (rac) | ++ |
| 5 (enant) | ++ |
| 6 | ++ |
| 7 | ++ |
| 8 | + |
| 9 | + |
| 10 | + |
| 11 | ++ |
| 12 | NA |
| 13 | ++ |
| 14 | + |
| 15 | + |
| 16 | + |
| 17 | + |
| 18 | + |
| 19 | + |
| 20 | + |
| 21 | + |
| 22 | + |
| 23 | + |
| 24 (rac) | ++ |
| 25 | + |
| 26 | + |
| 27 | + |
| 28 | + |
| 29 (rac) | NA |

TABLE 4-continued

| Example No.* | KMS cellular IC$_{50}$ (nM)* |
|---|---|
| 30 | ++ |
| 31 | ++ |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | ++ |
| 44 | ++ |
| 45 | + |
| 46 | + |
| 47 | ++ |
| 48 | ++ |
| 49 | + |
| 50 | ++ |
| 51 | NA |
| 52 | ++ |
| 53 | ++ |
| 54 | + |
| 55 | + |
| 56 | ++ |
| 57 | ++ |
| 58 | + |
| 59 | + |
| 60 | + |
| 61 | ++ |
| 62 | + |
| 63 | + |
| 64 | + |
| 65 | + |
| 66 | + |
| 67 | + |
| 68 | + |
| 69 | + |
| 70 | + |
| 71 | NA |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | NA |
| 85 | + |
| 86 | NA |
| 87 (rac) | + |
| 88 (rac) | + |
| 89 | + |
| 90 | + |
| 91 | + |
| 92 | + |
| 93 | + |
| 94 | NA |
| 95 | + |
| 96 | + |
| 97 | + |
| 98 | + |
| 99 | + |
| 100 | ++ |
| 101 | ++ |
| 102 | + |
| 103 | + |
| 104 | + |
| 105 | + |
| 106 | + |
| 107 | + |

TABLE 4-continued

| Example No.* | KMS cellular IC$_{50}$ (nM)* |
|---|---|
| 108 | + |
| 109 | + |
| 110 | + |
| 111 | + |
| 112 | NA |
| 113 | + |
| 114 | + |
| 115 | NA |
| 116 | NA |
| 117 | + |
| 118 | NA |
| 119 | + |
| 120 | NA |
| 121 | + |
| 122 | ++ |
| 123 | + |
| 124 | NA |
| 125 | + |
| 126 | + |
| 127 | + |
| 128 | NA |
| 129 | + |
| 130 | + |
| 131 | + |
| 132 | + |
| 133 | + |
| 134 | + |
| 135 | + |
| 136 | + |
| 137 | + |
| 138 | NA |
| 139 | ++ |
| 140 | + |
| 141 | + |
| 142 | + |
| 143 | + |
| 144 (rac) | ++ |
| 145 (rac) | + |
| 146 | ++ |
| 147 (enant) | ++ |
| 148 (enant) | ++ |
| 149 (enant) | ++ |
| 150 (enant) | ++ |
| 151 (enant) | + |
| 152 (enant) | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | + |
| 182 | + |
| 183 | + |
| 184 | + |
| 185 | + |
| 186 (rac) | NA |
| 187 (rac) | NA |
| 188 | + |
| 189 | + |
| 190 | + |
| 191 | + |
| 192 | + |
| 193 | + |
| 194 | + |
| 195 | + |
| 196 | + |
| 197 | + |
| 198 | + |
| 199 (rac) | + |
| 200 | + |
| 201 | + |
| 202 | + |
| 203 | + |
| 204 | ++ |
| 205 | + |
| 206 | + |
| 207 | + |
| 208 | ++ |
| 209 | ++ |
| 210 | ++ |
| 211 | + |
| 212 | + |
| 213 | + |
| 214 | ++ |
| 215 a (trans) | NA |
| 215 b (cis) | ++ |
| 216 | ++ |
| 217 | + |
| 218 | ++ |
| 219 | + |
| 220 | ++ |
| 221 | ++ |
| 222 | ++ |
| 223 | + |
| 224 (rac) | + |
| 225 (rac) | + |
| 226 (enant) | NA |
| 227 | + |
| 228 | ++ |
| 229 | + |
| 230 | + |
| 231 | + |
| 232 | NA |
| 233 | + |
| 234 | + |
| 235 | + |
| 236 | + |
| 237 | + |
| 238 | ++ |
| 239 | + |
| 240 | ++ |
| 241 | ++ |
| 242 | NA |
| 243 | ++ |
| 244 | + |
| 245 | + |
| 246 | + |
| 247 | + |
| 248 | + |
| 249 | + |
| 250 | + |
| 251 | + |
| 252 | + |
| 253 | + |
| 254 | + |
| 255 | + |
| 256 | + |
| 257 | + |
| 258 | + |
| 259 | + |
| 260 | ++ |
| 261 | + |
| 262 | ++ |

TABLE 4-continued

| Example No.* | KMS cellular IC$_{50}$ (nM)* |
|---|---|
| 263 | ++ |
| 264 | NA |
| 266 | + |
| 267 | + |
| 268 | + |
| 269 | + |
| 270 | + |
| 271 | + |
| 272 | + |

*"rac" refer to racemic;
"enant" refers to the more potent enantiomer
**column symbols:
+ refers to ≤1000 nM;
++ refers to >1000 nM and ≤10,000 nM;
NA indicates that data was not available Example C1

KMS.12.BM C-myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells well per 200 µL into a 96-well flat bottom polystyrene tissue culture plate (Corning through VWR, NJ), in the presence or absence of a concentration range of test compounds. After 2 hours, cell are pelleted and lysed with Cell Extraction Buffer (BioSource, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the IC$_{50}$ is reported as the compound concentration required for 50% C-myc inhibition.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

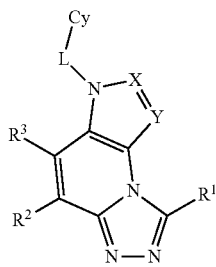

or a pharmaceutically acceptable salt thereof, wherein:
X is $CR^4$;
Y is $CR^5$;
L is $C_{1-6}$ alkylene or —$(C_{1-4}$ alkylene$)_n$-S(=O)$_2$—$(C_{1-4}$ alkylene$)_m$-, wherein each alkylene moiety of any of the aforementioned L groups is optionally substituted by 1, 2, or 3 substituents independently selected from F, Cl, OH, $C_{1-4}$ alkoxy, $CF_3$, and CN;

Cy is $C_{6-10}$ aryl, $C_{3-10}$ cycloalkyl, 5-10 membered heteroaryl, 4-10 membered heterocycloalkyl, each of which is optionally substituted by 1, 2, or 3 $R^{Cy}$;

$R^1$ is H, $C_{1-6}$ alkyl, cyclopropyl, cyclobutyl, $C_{2-6}$ alkenyl, $C_{2-6}$ alkynyl, $C_{1-6}$ haloalkyl, or $C_{1-6}$ hydroxyalkyl;

$R^2$ and $R^3$ are each independently selected from H, halo, $C_{1-6}$ alkyl, $C_{2-6}$ alkenyl, $C_{2-6}$ alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, and $C_{2-6}$ alkynyl are each optionally substituted with 1, 2, 3, 4, or 5 substituents independently selected from halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

$R^4$ is H, halo, $C_{1-6}$ alkyl, $C_{2-6}$ alkenyl, $C_{2-6}$ alkynyl, haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_3$-10 cycloalkyl-$C_{1-4}$ alkyl, (5-10 membered heteroaryl)-$C_1$-4 alkyl, (4-10 membered heterocycloalkyl)-$C_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_1$-4 alkyl, and (4-10 membered heterocycloalkyl)-$C_{1-4}$ alkyl are each optionally substituted with 1, 2, 3, 4, or 5 substituents independently selected from $R^A$;

$R^5$ is H, halo, $C_{1-4}$ alkyl, $C_{2-4}$ alkenyl, $C_{1-4}$ haloalkyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, or S(O)$_2$NR$^{c2}$R$^{d2}$;

each $R^{Cy}$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-10 membered heterocycloalkyl)-$C_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_1$-4 alkyl, and (4-10 membered heterocycloalkyl)-$C_{1-4}$ alkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c4}$S(O)$_2$R$^{b3}$, NR$^{c3}$S(O)$_2$ NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^A$ is independently selected from Cy$^1$, halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, and C$_{2-6}$ alkynyl are each optionally substituted with 1, 2, 3, 4, or 5 substituents independently selected from Cy$^1$, halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$) NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each Cy$^1$ is independently selected from C$_{6-10}$ aryl, C$_{3-10}$ cycloalkyl, 5-10 membered heteroaryl, and 4-10 membered heterocycloalkyl, each of which is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said C$_{1-6}$ alkyl, C$_{2-6}$ alkenyl, and C$_{2-6}$ alkynyl are each optionally substituted with 1, 2, 3, 4, or 5 substituents independently selected from halo, C$_{1-6}$ haloalkyl, CN, NO$_2$, OR$^{a5}$, SR$^{a5}$, C(O) R$^{b5}$, C(O)NR$^{c5}$R$^{d5}$, C(O)OR$^{a5}$, OC(O)R$^{b5}$, OC(O) NR$^{c5}$R$^{d5}$, C(=NR$^{e5}$)NR$^{c5}$R$^{d5}$, NR$^{c5}$C(=NR$^{e5}$) NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$ R$^{b5}$, and S(O)$_2$NR$^{c5}$R$^{d5}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, R$^{d4}$, R$^{a5}$, R$^{b5}$, R$^{c5}$, and R$^{d5}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalky-C$_{1-6}$ alkyl, (5-10 membered heteroaryl)-C$_{1-6}$ alkyl, and (4-10 membered heterocycloalkyl)-C$_{1-6}$ alkyl, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalky-C$_{1-6}$ alkyl, (5-10 membered heteroaryl)-C$_{1-6}$ alkyl, and (4-10 membered heterocycloalkyl)-C$_{1-6}$ alkyl is optionally substituted with 1, 2, 3, 4, or 5 substituents independently selected from C$_{1-4}$ alkyl, C$_{1-4}$ haloalkyl, halo, CN, OR$^{a6}$, SR$^{a6}$, C(O)R$^{b6}$, C(O)NR$^{c6}$R$^{d6}$, C(O) OR$^{a6}$, OC(O)R$^{b6}$, OC(O)NR$^{c6}$R$^{d6}$, NR$^{c6}$R$^{d6}$, NR$^{c6}$C (O)R$^{b6}$, NR$^{c6}$C(O)OR$^{a6}$, NR$^{c6}$C(O)NR$^{c6}$R$^{d6}$, C(=NR$^{e6}$)NR$^{c6}$R$^{d6}$, NR$^{c6}$C(=NR$^{e6}$)NR$^{c6}$R$^{d6}$, S(O) R$^{b6}$, S(O)NR$^{c6}$R$^{d6}$, S(O)$_2$R$^{b6}$, NR$^{c6}$S(O)$_2$R$^{b6}$, NR$^{c6}$S (O)$_2$NR$^{c6}$R$^{d6}$, and S(O)$_2$NR$^{c6}$R$^{d6}$;

or any R$^c$ and R$^d$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$) NR$^{c6}$R$^{d6}$, NR$^{c6}$C(=NR$^{e6}$)NR$^{c6}$R$^{d6}$, S(O)R$^{b6}$, S(O) NR$^{c6}$R$^{d6}$, S(O)$_2$R$^{b6}$, NR$^{c6}$S(O)$_2$R$^{b6}$, NR$^{c6}$S(O)$_2$ NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O) R$^{b6}$, S(O)NR$^{c6}$R$^{d6}$, S(O)$_2$R$^{b6}$, NR$^{c6}$S(O)$_2$R$^{b6}$, NR$^{c6}$S (O)$_2$NR$^{c6}$R$^{d6}$, and S(O)$_2$NR$^{c6}$R$^{d6}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$) NR$^{c6}$R$^{d6}$, NR$^{c6}$C(=NR$^{e6}$)NR$^{c6}$R$^{d6}$, S(O)R$^{b6}$, S(O) NR$^{c6}$R$^{d6}$, S(O)$_2$R$^{b6}$, NR$^{c6}$S(O)$_2$R$^{b6}$, NR$^{c6}$S(O)$_2$ NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O) R$^{b6}$, S(O)NR$^{c6}$R$^{d6}$, S(O)$_2$R$^{b6}$, NR$^{c6}$S(O)$_2$R$^{b6}$, NR$^{c6}$S (O)$_2$NR$^{c6}$R$^{d6}$, and S(O)$_2$NR$^{c6}$R$^{d6}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$) NR$^{c6}$R$^{d6}$, NR$^{c6}$C(=NR$^{e6}$)NR$^{c6}$R$^{d6}$, S(O)R$^{b6}$, S(O) NR$^{c6}$R$^{d6}$, S(O)$_2$R$^{b6}$, NR$^{c6}$S(O)$_2$R$^{b6}$, NR$^{c6}$S(O)$_2$ NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O) R$^{b6}$, S(O)NR$^{c6}$R$^{d6}$, S(O)$_2$R$^{b6}$, NR$^{c6}$S(O)$_2$R$^{b6}$, NR$^{c6}$S (O)$_2$NR$^{c6}$R$^{d6}$, and S(O)$_2$NR$^{c6}$R$^{d6}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from C$_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^e$, $R^{e1}$, $R^{e3}$, $R^{e4}$, and $R^{e5}$ is independently selected from H, $C_{1-4}$ alkyl, CN, $OR^{a6}$, $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e6}$ is independently selected from H, $C_{1-4}$ alkyl, and CN;

n is 0 or 1; and m is 0 or 1.

2. The compound of claim 1, or a pharmaceutically acceptable salt thereof, wherein L is $CH_2$, $S(=O)_2$, —CH($CH_2OH$)—, or —CH(($CH_2)_3CH_3$)—.

3. The compound of claim 1, or a pharmaceutically acceptable salt thereof, wherein L is $CH_2$ or $S(=O)_2$.

4. The compound of claim 1, or a pharmaceutically acceptable salt thereof, wherein L is $CH_2$.

5. The compound of claim 1, or a pharmaceutically acceptable salt thereof, wherein Cy is $C_{6-10}$ aryl, $C_{3-10}$ cycloalkyl, or 5-10 membered heteroaryl, each of which is optionally substituted by 1, 2, or 3 $R^{Cy}$.

6. The compound of claim 1, or a pharmaceutically acceptable salt thereof, wherein Cy is phenyl, cyclopentyl, quinolinyl, or pyridyl, each of which is optionally substituted by 1, 2, or 3 $R^{Cy}$.

7. The compound of claim 1, or a pharmaceutically acceptable salt thereof, wherein Cy is phenyl or pyridyl, each of which is optionally substituted by 1, 2, or 3 $R^{Cy}$.

8. The compound of claim 1, or a pharmaceutically acceptable salt thereof, wherein Cy is phenyl optionally substituted by 1, 2, or 3 $R^{Cy}$.

9. The compound of claim 1, or a pharmaceutically acceptable salt thereof, wherein each $R^{Cy}$ is independently selected from halo, $C_{1-6}$ alkyl, $C_{1-4}$ haloalkyl, (4-10 membered heterocycloalkyl)-$C_{1-4}$ alkyl, CN, $OR^{a3}$, $C(O)NR^{c3}R^{d3}$, $NR^{c3}C(O)R^{b3}$, and $NR^{c3}C(O)NR^{c3}R^{d3}$ wherein said $C_{1-6}$ alkyl and (4-10 membered heterocycloalkyl)-$C_{1-4}$ alkyl are each optionally substituted with 1, 2, or 3 substituents independently selected from halo, $C_{1-6}$ alkyl, $OR^{a3}$, and $NR^{c3}R^{d3}$.

10. The compound of claim 1, or a pharmaceutically acceptable salt thereof, wherein each $R^{Cy}$ is independently selected from halo, $C_{1-6}$ alkyl, (4-10 membered heterocycloalkyl)-$C_{1-4}$ alkyl, CN, $OR^{a3}$, $C(O)NR^{c3}R^{d3}$, $NR^{c3}C(O)R^{b3}$, and $NR^{c3}C(O)NR^{c3}R^{d3}$ wherein said $C_{1-6}$ alkyl and (4-10 membered heterocycloalkyl)-$C_{1-4}$ alkyl are each optionally substituted with 1, 2, or 3 substituents independently selected from $C_{1-6}$ alkyl, $OR^{a3}$, and $NR^{c3}R^{d3}$.

11. The compound of claim 1, or a pharmaceutically acceptable salt thereof, wherein each $R^{Cy}$ is independently selected from fluoro, chloro, methyl, cyano, hydroxy, methoxy, aminocarbonyl, methylcarbonylamino, methylaminocarbonyl, ethylaminocarbonyl, azetidinylmethyl, pyrrolidinylmethyl, piperidinylmethyl, piperazinylmethyl, morpholinomethyl, ureido, and ethylureido, wherein said methyl, azetidinylmethyl, pyrrolidinylmethyl, piperidinylmethyl, piperazinylmethyl, and morpholinomethyl are each optionally substituted with 1, 2, or 3 substituents independently selected from fluoro, methyl, hydroxy, methoxy, methylamino, ethylamino, dimethylamino, hydroxycyclobutylamino, hydroxyethyl(methyl)amino, and hydroxyethylamino.

12. The compound of claim 1, or a pharmaceutically acceptable salt thereof, wherein $R^1$ is H or $C_{1-6}$ alkyl.

13. The compound of claim 1, or a pharmaceutically acceptable salt thereof, wherein $R^1$ is $C_{1-6}$ alkyl.

14. The compound of claim 1, or a pharmaceutically acceptable salt thereof, wherein $R^1$ is methyl.

15. The compound of claim 1, or a pharmaceutically acceptable salt thereof, wherein $R^2$ and $R^3$ are both H.

16. The compound of claim 1, or a pharmaceutically acceptable salt thereof, wherein $R^3$ is H.

17. The compound of claim 1, or a pharmaceutically acceptable salt thereof, wherein $R^2$ is H, $OR^a$, $NR^cR^d$, $NR^cC(O)R^b$, $NR^cC(O)OR^a$, $NR^cC(O)NR^cR^d$, or $NR^cS(O)_2R^b$.

18. The compound of claim 1, or a pharmaceutically acceptable salt thereof, wherein $R^2$ is H, —OH, —NHC(=O)OCH$_3$, —NHC(=O)CH$_3$, —NHC(=O)CH$_2$CH$_3$, —NHC(=O)CH$_2$CH$_2$CH$_3$, —NHC(=O)CH(CH$_3$)$_2$, —NHS(=O)$_2$CH$_3$, —OCH$_3$, —NHCH$_3$, —NHCH$_2$CH$_3$, —NHCH(CH$_3$)$_2$, —NHCH$_2$CH$_2$CH$_3$, —NH-(phenyl), —NH-(imidazolyl), —NH-(pyridyl), —NHCH$_2$CH$_2$NH$_2$, —NHCH$_2$CH$_2$CH$_2$NH$_2$, —NHC(=O)NH$_2$, —NHC(=O)NH(CH$_3$), —NHC(=O)N(CH$_3$)$_2$, —NHC(=O)NHCH(CH$_3$)$_2$, —NHC(=O)NHCH$_2$CH$_3$, —NHC(=O)O-(t-butyl), —NH-(hydroxycyclobutyl), —NHCH$_2$CH$_2$N(CH$_3$)$_2$, —NHCH$_2$CH$_2$N(CH$_3$)$_2$, —NH-(t-butyloxycarbonylazetidinyl), —NH-(t-butyloxycarbonylazetidinylmethyl), —NH-(t-butyloxycarbonylpiperidinylmethyl), —NH-(cyclobutylmethyl), —NH-(cyclohexyl), —NH-(cyclopropylmethyl), —NH-(8-azabicyclo[3,2,1]octan-3-yl), —NH-(dimethylpiperidinyl), —NH-(methylpiperidinyl), —NH-(piperidinyl), —NH-(methylpiperidinyl), —NH-(dimethylaminocyclohexyl), —NH-(methylaminocyclohexyl), —NH-(aminocyclohexyl), —NH-(acetylpiperidinyl), —NH-(cyanocyclohexyl), —NH-(t-butyloxycarbonylpiperidinyl), —NH-(2-propylpiperidinyl), —NH-(ethylpiperidinyl), —NH-(methylsulfonylpiperidinyl), —NHCH$_2$CH$_2$OH, —NHCH$_2$CH$_2$OCH$_3$, —NH-(morpholinoethyl), —NH-(benzimidazolyl), —NH-(benzoxazolyl), —NH-(methylpyrazolyl), —NH-(pyrimidinyl), —NH-(pyrazolyl), —NH-(pyrrolidinyl), —NH-(methylpyrrolidinyl), —NH-(t-butyloxycarbonylpyrrolidinyl), —NH-(tetrahydrofuranyl), or —NH-(tetrahydropyranyl).

19. The compound of claim 1, or a pharmaceutically acceptable salt thereof, wherein $R^4$ is H, CN, $C_{1-6}$ alkyl, $C_{1-4}$ haloalkyl, 5-10 membered heteroaryl, (5-10 membered heteroaryl)-$C_{1-4}$ alkyl, 4-10 membered heterocycloalkyl, C(O)NR$^{c1}$R$^{d1}$, C(O)OR$^{a1}$, or NR$^{c1}$R$^{d1}$; wherein said $C_{1-6}$ alkyl, 5-10 membered heteroaryl, 4-10 membered heterocycloalkyl and (5-10 membered heteroaryl)-$C_{1-4}$ alkyl are each optionally substituted with 1, 2, 3, 4, or 5 substituents independently selected from $R^4$.

20. The compound of claim 1, or a pharmaceutically acceptable salt thereof, wherein $R^4$ is H, $C_{1-6}$ alkyl, 5-10 membered heteroaryl, (5-10 membered heteroaryl)-$C_{1-4}$ alkyl, C(O)NR$^{c1}$R$^{d1}$, C(O)OR$^{a1}$, or NR$^{c1}$R$^{d1}$; wherein said $C_{1-6}$ alkyl, 5-10 membered heteroaryl, and (5-10 membered heteroaryl)-$C_{1-4}$ alkyl are each optionally substituted with 1, 2, 3, 4, or 5 substituents independently selected from $R^4$.

21. The compound of claim 1, or a pharmaceutically acceptable salt thereof, wherein $R^4$ is H, $C_{1-4}$ alkyl, 5 to 6-membered heteroaryl, (5-membered heteroaryl)-$C_{1-4}$ alkyl, C(O)NR$^{c1}$R$^{d1}$; C(O)OR$^{a1}$, or NR$^{c1}$R$^{d1}$; wherein said $C_{1-4}$ alkyl, 5 to 6-membered heteroaryl, and (5-membered heteroaryl)-$C_{1-4}$ alkyl are each optionally substituted with 1, 2, 3, 4, or 5 substituents independently selected from $R^4$.

22. The compound of claim 1, or a pharmaceutically acceptable salt thereof, wherein $R^4$ is H, $C_{1-4}$ alkyl, pyrazolyl, imidazolyl, thienyl, thiazolyl, pyridyl, imidazolylmethyl, C(O)NR$^{c1}$R$^{d1}$, C(O)OR$^{a1}$, or NR$^{c1}$R$^{d1}$; wherein said $C_{1-4}$ alkyl, pyrazolyl, imidazolyl, thienyl, thiazolyl, pyridyl, and imidazolylmethyl, are each optionally substituted with 1, 2, or 3 substituents independently selected from $R^4$.

23. The compound of claim 1, or a pharmaceutically acceptable salt thereof, wherein $R^4$ is H, CN, methyl, ethyl, pyrazolyl, imidazolyl, thienyl, thiazolyl, pyridyl, imidazolylmethyl, oxadiazolyl, oxazolyl, dihydrooxazolyl, pyrrolidinyl, —C(=O)NH-(methyl), —C(=O)NH-(ethyl), —C(=O)—NH-(t-butyl), —C(=O)—NH-(s-butyl), —C(=O)NH-(pyridylmethyl), —C(=O)NH-(isopropyl), —C(=O)NH-(hydroxypropyl), —C(=O)NH-(azetidinylmethyl), —C(=O)NH-(morpholinoethyl), —C(=O)-(methylazetidinyl), —C(=O)NH-(hydroxyethyl), —C(=O)-(morpholino), —C(=O)NH-(dimethylaminoethyl), —C(=O)NH-(cyclopropylmethyl), —C(=O)NH-(cyclobutyl), —C(=O)NH-(cyanocyclobutyl), —C(=O)NH$_2$, —C(=O)N(CH$_3$)$_2$, —C(=O)NH-(2,2,2-trifluoro-1-methylethyl), or —C(=O)-(cyanoazetidinyl), wherein said methyl, ethyl, pyrazolyl, imidazolyl, thienyl, thiazolyl, pyridyl, imidazolylmethyl, oxadiazolyl, oxazolyl, dihydrooxazolyl, and pyrrolidinyl are each optionally substituted with 1, 2, or 3 substituents independently selected from $R^4$.

24. The compound of claim 1, or a pharmaceutically acceptable salt thereof, wherein each $R^A$ is independently selected from Cy$^1$, C(O)R$^{b4}$, and $C_{1-6}$ alkyl, wherein said $C_{1-6}$ alkyl is optionally substituted with 1, 2, or 3 substituents independently selected from Cy$^1$, CN, OR$^{a4}$, C(O)NR$^{c4}$R$^{d4}$, and NR$^{c4}$R$^{d4}$.

25. The compound of claim 1, or a pharmaceutically acceptable salt thereof, wherein each $R^A$ is independently selected from Cy$^1$ and $C_{1-6}$ alkyl, wherein said $C_{1-6}$ alkyl is optionally substituted with 1, 2, or 3 substituents independently selected from Cy$^1$, CN, C(O)NR$^{c4}$R$^{d4}$, and NR$^{c4}$R$^{d4}$.

26. The compound of claim 1, or a pharmaceutically acceptable salt thereof, wherein $R^5$ is H.

27. The compound of claim 1, or a pharmaceutically acceptable salt thereof, having Formula III:

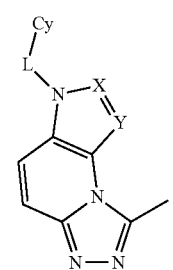

III

28. The compound of claim 1, or a pharmaceutically acceptable salt thereof, having Formula IVa:

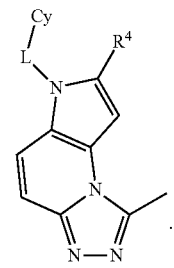

IVa

29. A compound of claim 1 selected from:
6-benzyl-1-methyl-6H-pyrrolo[2,3-e][1,2,4]triazolo[4,3-a]pyridine;
6-benzyl-1,7-dimethyl-6H-pyrrolo[2,3-e][1,2,4]triazolo[4,3-a]pyridine;

1-methyl-6-(phenylsulfonyl)-6H-pyrrolo[2,3-e][1,2,4]triazolo[4,3-a]pyridine;
1-methyl-6-(1-phenylethyl)-6H-pyrrolo[2,3-e][1,2,4]triazolo[4,3-a]pyridine;
(S)-1,7-dimethyl-6-(1-phenylethyl)-6H-pyrrolo[2,3-e][1,2,4]triazolo[4,3-a]pyridine;
(R)-1,7-dimethyl-6-(1-phenylethyl)-6H-pyrrolo[2,3-e][1,2,4]triazolo[4,3-a]pyridine;
1,7-dimethyl-6-(2-phenylethyl)-6H-pyrrolo[2,3-e][1,2,4]triazolo[4,3-a]pyridine;
1,7-dimethyl-6-(pyridin-2-ylmethyl)-6H-pyrrolo[2,3-e][1,2,4]triazolo[4,3-a]pyridine;
6-(2-chlorobenzyl)-1,7-dimethyl-6H-pyrrolo[2,3-e][1,2,4]triazolo[4,3-a]pyridine;
6-(3-chlorobenzyl)-1,7-dimethyl-6H-pyrrolo[2,3-e][1,2,4]triazolo[4,3-a]pyridine;
6-(4-chlorobenzyl)-1,7-dimethyl-6H-pyrrolo[2,3-e][1,2,4]triazolo[4,3-a]pyridine
1,7-dimethyl-6-(pyridin-3-ylmethyl)-6H-pyrrolo[2,3-e][1,2,4]triazolo[4,3-a]pyridine
1,7-dimethyl-6-(pyridin-4-ylmethyl)-6H-pyrrolo[2,3-e][1,2,4]triazolo[4,3-a]pyridine;
6-(cyclopentylmethyl)-1,7-dimethyl-6H-pyrrolo[2,3-e][1,2,4]triazolo[4,3-a]pyridine;
6-(2-fluorobenzyl)-1,7-dimethyl-6H-pyrrolo[2,3-e][1,2,4]triazolo[4,3-a]pyridine
6-(3-fluorobenzyl)-1,7-dimethyl-6H-pyrrolo[2,3-e][1,2,4]triazolo[4,3-a]pyridine;
6-(4-fluorobenzyl)-1,7-dimethyl-6H-pyrrolo[2,3-e][1,2,4]triazolo[4,3-a]pyridine;
1,7-dimethyl-6-(2-methylbenzyl)-6H-pyrrolo[2,3-e][1,2,4]triazolo[4,3-a]pyridine;
1,7-dimethyl-6-(3-methylbenzyl)-6H-pyrrolo[2,3-e][1,2,4]triazolo[4,3-a]pyridine;
1,7-dimethyl-6-(4-methylbenzyl)-6H-pyrrolo[2,3-e][1,2,4]triazolo[4,3-a]pyridine;
3-[(1,7-dimethyl-6H-pyrrolo[2,3-e][1,2,4]triazolo[4,3-a]pyridine-6-yl)methyl]benzonitrile;
1,7-dimethyl-6-(quinolin-2-ylmethyl)-6H-pyrrolo[2,3-e][1,2,4]triazolo[4,3-a]pyridine;
6-(3-methoxybenzyl)-1,7-dimethyl-6H-pyrrolo[2,3-e][1,2,4]triazolo[4,3-a]pyridine;
3-[(1,7-dimethyl-6H-pyrrolo[2,3-e][1,2,4]triazolo[4,3-a]pyridin-6-yl)methyl]phenol;
1,7-dimethyl-6-(1-phenylpentyl)-6H-pyrrolo[2,3-e][1,2,4]triazolo[4,3-a]pyridine;
N-{3-[(1,7-dimethyl-6H-pyrrolo[2,3-e][1,2,4]triazolo[4,3-a]pyridin-6-yl)methyl]phenyl}acetamide;
{3-[(1,7-dimethyl-6H-pyrrolo[2,3-e][1,2,4]triazolo[4,3-a]pyridin-6-yl)methyl]phenyl}methanol;
1-(3-((1,7-dimethyl-6H-pyrrolo[2,3-e][1,2,4]triazolo[4,3-a]pyridin-6-yl)methyl)benzyl)azetidin-3-ol;
6-[3-(azetidin-1-ylmethyl)benzyl]-1,7-dimethyl-6H-pyrrolo[2,3-e][1,2,4]triazolo[4,3-a]pyridine;
2-(1,7-dimethyl-6H-pyrrolo[2,3-e][1,2,4]triazolo[4,3-a]pyridin-6-yl)-2-phenylethanol;
3-((1,7-dimethyl-6H-pyrrolo[2,3-e][1,2,4]triazolo[4,3-a]pyridin-6-yl)methyl)benzamide;
3-[(1,7-dimethyl-6H-pyrrolo[2,3-e][1,2,4]triazolo[4,3-a]pyridin-6-yl)methyl]-N-methylbenzamide;
3-[(1,7-dimethyl-6H-pyrrolo[2,3-e][1,2,4]triazolo[4,3-a]pyridin-6-yl)methyl]-N-ethylbenzamide;
6-(4-methoxybenzyl)-1,7-dimethyl-6H-pyrrolo[2,3-e][1,2,4]triazolo[4,3-a]pyridine
4-[(1,7-dimethyl-6H-pyrrolo[2,3-e][1,2,4]triazolo[4,3-a]pyridin-6-yl)methyl]phenol;
2-({3-[(1,7-dimethyl-6H-pyrrolo[2,3-e][1,2,4]triazolo[4,3-a]pyridin-6-yl)methyl]benzyl}amino)ethanol;
2-[{3-[(1,7-dimethyl-6H-pyrrolo[2,3-e][1,2,4]triazolo[4,3-a]pyridin-6-yl)methyl]benzyl}(methyl)amino]ethanol;
1,7-dimethyl-6-[3-(morpholin-4-ylmethyl)benzyl]-6H-pyrrolo[2,3-e][1,2,4]triazolo[4,3-a]pyridine;
(1r,3r)-3-((3-((1,7-dimethyl-6H-pyrrolo[2,3-e][1,2,4]triazolo[4,3-a]pyridin-6-yl)methyl)benzyl)amino)cyclobutanol;
1-{3-[(1,7-dimethyl-6H-pyrrolo[2,3-e][1,2,4]triazolo[4,3-a]pyridin-6-yl)methyl]phenyl}-N,N-dimethylmethanamine;
1-{3-[(1,7-dimethyl-6H-pyrrolo[2,3-e][1,2,4]triazolo[4,3-a]pyridin-6-yl)methyl]phenyl}-N-methylmethanamine;
N-{3-[(1,7-dimethyl-6H-pyrrolo[2,3-e][1,2,4]triazolo[4,3-a]pyridin-6-yl)methyl]benzyl}ethanamine;
N-{3-[(1,7-dimethyl-6H-pyrrolo[2,3-e][1,2,4]triazolo[4,3-a]pyridin-6-yl)methyl]phenyl}-N'-ethylurea;
N-{3-[(1,7-dimethyl-6H-pyrrolo[2,3-e][1,2,4]triazolo[4,3-a]pyridin-6-yl)methyl]phenyl}urea;
1,7-dimethyl-6-[3-(pyrrolidin-1-ylmethyl)benzyl]-6H-pyrrolo[2,3-e][1,2,4]triazolo[4,3-a]pyridine;
1,7-dimethyl-6-[3-(piperidin-1-ylmethyl)benzyl]-6H-pyrrolo[2,3-e][1,2,4]triazolo[4,3-a]pyridine;
1,7-dimethyl-6-{3-[(4-methylpiperazin-1-yl)methyl]benzyl}-6H-pyrrolo[2,3-e][1,2,4]triazolo[4,3-a]pyridine;
1,7-dimethyl-6-[3-(piperazin-1-ylmethyl)benzyl]-6H-pyrrolo[2,3-e][1,2,4]triazolo[4,3-a]pyridine;
{4-[(1,7-dimethyl-6H-pyrrolo[2,3-e][1,2,4]triazolo[4,3-a]pyridin-6-yl)methyl]phenyl}methanol;
6-[4-(azetidin-1-ylmethyl)benzyl]-1,7-dimethyl-6H-pyrrolo[2,3-e][1,2,4]triazolo[4,3-a]pyridine;
1,7-dimethyl-6-[4-(pyrrolidin-1-ylmethyl)benzyl]-6H-pyrrolo[2,3-e][1,2,4]triazolo[4,3-a]pyridine;
1-{4-[(1,7-dimethyl-6H-pyrrolo[2,3-e][1,2,4]triazolo[4,3-a]pyridin-6-yl)methyl]benzyl}azetidin-3-ol;
1-{4-[(1,7-dimethyl-6H-pyrrolo[2,3-e][1,2,4]triazolo[4,3-a]pyridin-6-yl)methyl]phenyl}-N,N-dimethylmethanamine;
6-{3-[(3-methoxyazetidin-1-yl)methyl]benzyl}-1,7-dimethyl-6H-pyrrolo[2,3-e][1,2,4]triazolo[4,3-a]pyridine;
(6-benzyl-1-methyl-6H-pyrrolo[2,3-e][1,2,4]triazolo[4,3-a]pyridin-7-yl)methanol;
6-benzyl-7-(1H-imidazol-1-ylmethyl)-1-methyl-6H-pyrrolo[2,3-e][1,2,4]triazolo[4,3-a]pyridine;
6-benzyl-1-methyl-6H-pyrrolo[2,3-e][1,2,4]triazolo[4,3-a]pyridine-7-carboxamide
6-benzyl-N-ethyl-1-methyl-6H-pyrrolo[2,3-e][1,2,4]triazolo[4,3-a]pyridine-7-carboxamide;
1-[(6-benzyl-1-methyl-6H-pyrrolo[2,3-e][1,2,4]triazolo[4,3-a]pyridin-7-yl)carbonyl]azetidine-3-carbonitrile;
2-(6-benzyl-1-methyl-6H-pyrrolo[2,3-e][1,2,4]triazolo[4,3-a]pyridin-7-yl)ethano 1;
6-benzyl-1-methyl-7-(1H-pyrazol-5-yl)-6H-pyrrolo[2,3-e][1,2,4]triazolo[4,3-a]pyridine;
6-benzyl-1-methyl-7-(1H-pyrazol-4-yl)-6H-pyrrolo[2,3-e][1,2,4]triazolo[4,3-a]pyridine;
[4-(6-benzyl-1-methyl-6H-pyrrolo[2,3-e][1,2,4]triazolo[4,3-a]pyridin-7-yl)-1H-pyrazol-1-yl]acetonitrile;
[3-(6-benzyl-1-methyl-6H-pyrrolo[2,3-e][1,2,4]triazolo[4,3-a]pyridin-7-yl)-1H-pyrazol-1-yl]acetonitrile;
6-benzyl-1-methyl-7-(1,3-thiazol-4-yl)-6H-pyrrolo[2,3-e][1,2,4]triazolo[4,3-a]pyridine;
6-benzyl-1-methyl-7-(1,3-thiazol-2-yl)-6H-pyrrolo[2,3-e][1,2,4]triazolo[4,3-a]pyridine;

6-benzyl-1-methyl-7-pyridin-2-yl-6H-pyrrolo[2,3-e][1,2,4]triazolo[4,3-a]pyridine;
6-benzyl-1-methyl-7-(1,3-thiazol-5-yl)-6H-pyrrolo[2,3-e][1,2,4]triazolo[4,3-a]pyridine;
6-benzyl-1-methyl-7-(1-methyl-1H-imidazol-4-yl)-6H-pyrrolo[2,3-e][1,2,4]triazolo[4,3-a]pyridine;
6-benzyl-1-methyl-7-(1-methyl-1H-imidazol-5-yl)-6H-pyrrolo[2,3-e][1,2,4]triazolo[4,3-a]pyridine;
6-benzyl-1-methyl-7-(3-thienyl)-6H-pyrrolo[2,3-e][1,2,4]triazolo[4,3-a]pyridine;
6-benzyl-1-methyl-7-(2-thienyl)-6H-pyrrolo[2,3-e][1,2,4]triazolo[4,3-a]pyridine;
6-benzyl-7-(1H-imidazol-4-yl)-1-methyl-6H-pyrrolo[2,3-e][1,2,4]triazolo[4,3-a]pyridine;
6-benzyl-1-methyl-7-[1-(2-morpholin-4-ylethyl)-1H-imidazol-4-yl]-6H-pyrrolo[2,3-e][1,2,4]triazolo[4,3-a]pyridine;
6-benzyl-1-methyl-7-(1-methyl-1H-pyrazol-3-yl)-6H-pyrrolo[2,3-e][1,2,4]triazolo[4,3-a]pyridine;
6-benzyl-1-methyl-7-[1-(2-morpholin-4-ylethyl)-1H-pyrazol-3-yl]-6H-pyrrolo[2,3-e][1,2,4]triazolo[4,3-a]pyridine;
3-[3-(6-benzyl-1-methyl-6H-pyrrolo[2,3-e][1,2,4]triazolo[4,3-a]pyridin-7-yl)-1H-pyrazol-1-yl]propanenitrile;
6-benzyl-7-(1-ethyl-1H-pyrazol-3-yl)-1-methyl-6H-pyrrolo[2,3-e][1,2,4]triazolo[4,3-a]pyridine;
6-benzyl-7-(1-ethyl-1H-imidazol-4-yl)-1-methyl-6H-pyrrolo[2,3-e][1,2,4]triazolo[4,3-a]pyridine;
3-[4-(6-benzyl-1-methyl-6H-pyrrolo[2,3-e][1,2,4]triazolo[4,3-a]pyridin-7-yl)-1H-imidazol-1-yl]propanenitrile;
6-benzyl-N,1-dimethyl-6H-pyrrolo[2,3-e][1,2,4]triazolo[4,3-a]pyridine-7-carboxamide;
6-benzyl-1-methyl-N-propyl-6H-pyrrolo[2,3-e][1,2,4]triazolo[4,3-a]pyridine-7-carboxamide;
6-benzyl-N-isopropyl-1-methyl-6H-pyrrolo[2,3-e][1,2,4]triazolo[4,3-a]pyridine-7-carboxamide;
6-benzyl-N-cyclobutyl-1-methyl-6H-pyrrolo[2,3-e][1,2,4]triazolo[4,3-a]pyridine-7-carboxamide;
6-benzyl-1-methyl-N-[(1R)-2,2,2-trifluoro-1-methylethyl]-6H-pyrrolo[2,3-e][1,2,4]triazolo[4,3-a]pyridine-7-carboxamide;
3-[3-(6-benzyl-1-methyl-6H-pyrrolo[2,3-e][1,2,4]triazolo[4,3-a]pyridin-7-yl)-1H-pyrazol-1-yl]butanenitrile;
3-[3-(6-benzyl-1-methyl-6H-pyrrolo[2,3-e][1,2,4]triazolo[4,3-a]pyridin-7-yl)-1H-pyrazol-1-yl]-2-methylpropanenitrile;
2-[3-(6-benzyl-1-methyl-6H-pyrrolo[2,3-e][1,2,4]triazolo[4,3-a]pyridin-7-yl)-1H-pyrazol-1-yl]-N,N-dimethylethanamine;
{3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile;
{1-acetyl-3-[3-(6-benzyl-1-methyl-6H-pyrrolo[2,3-e][1,2,4]triazolo[4,3-a]pyridin-7-yl)-1H-pyrazol-1-yl]azetidin-3-yl}acetonitrile;
[3-[3-(6-benzyl-1-methyl-6H-pyrrolo[2,3-e][1,2,4]triazolo[4,3-a]pyridin-7-yl)-1H-pyrazol-1-yl]-1-(methylsulfonyl)azetidin-3-yl]acetonitrile;
{3-[3-(6-benzyl-1-methyl-6H-pyrrolo[2,3-e][1,2,4]triazolo[4,3-a]pyridin-7-yl)-1H-pyrazol-1-yl]-1-methylazetidin-3-yl}acetonitrile;
6-benzyl-N,N,1-trimethyl-6H-pyrrolo[2,3-e][1,2,4]triazolo[4,3-a]pyridine-7-carboxamide;
3-[3-(6-benzyl-1-methyl-6H-pyrrolo[2,3-e][1,2,4]triazolo[4,3-a]pyridin-7-yl)-1H-pyrazol-1-yl]-N,N-dimethylpropanamide;
3-[3-(6-benzyl-1-methyl-6H-pyrrolo[2,3-e][1,2,4]triazolo[4,3-a]pyridin-7-yl)-1H-pyrazol-1-yl]-N-ethylpropanamide;
3-[3-(6-benzyl-1-methyl-6H-pyrrolo[2,3-e][1,2,4]triazolo[4,3-a]pyridin-7-yl)-1H-pyrazol-1-yl]-N-methylpropanamide;
3-[3-(6-benzyl-1-methyl-6H-pyrrolo[2,3-e][1,2,4]triazolo[4,3-a]pyridin-7-yl)-1H-pyrazol-1-yl]propanamide;
6-(3-chlorobenzyl)-N,1-dimethyl-6H-pyrrolo[2,3-e][1,2,4]triazolo[4,3-a]pyridine-7-carboxamide;
6-benzyl-N-(trans-3-cyanocyclobutyl)-1-methyl-6H-pyrrolo[2,3-e][1,2,4]triazolo[4,3-a]pyridine-7-carboxamide;
6-benzyl-N-(cis-3-cyanocyclobutyl)-1-methyl-6H-pyrrolo[2,3-e][1,2,4]triazolo[4,3-a]pyridine-7-carboxamide;
6-(3-fluorobenzyl)-N,1-dimethyl-6H-pyrrolo[2,3-e][1,2,4]triazolo[4,3-a]pyridine-7-carboxamide;
3-{3-[6-(3-chlorobenzyl)-1-methyl-6H-pyrrolo[2,3-e][1,2,4]triazolo[4,3-a]pyridin-7-yl]-1H-pyrazol-1-yl}-N,N-dimethylpropanamide;
7-[1-(3-azetidin-1-yl-3-oxopropyl)-1H-pyrazol-3-yl]-6-(3-chlorobenzyl)-1-methyl-6H-pyrrolo[2,3-e][1,2,4]triazolo[4,3-a]pyridine;
6-(3-chlorobenzyl)-1-methyl-7-{1-[3-(4-methylpiperazin-1-yl)-3-oxopropyl]-1H-pyrazol-3-yl}-6H-pyrrolo[2,3-e][1,2,4]triazolo[4,3-a]pyridine;
(1-acetyl-3-{3-[6-(3-chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile;
[3-{3-[6-(3-chlorobenzyl)-1-methyl-6H-pyrrolo[2,3-e][1,2,4]triazolo[4,3-a]pyridin-7-yl]-1H-pyrazol-1-yl}-1-(methylsulfonyl)azetidin-3-yl]acetonitrile;
7-[1-(1-acetylazetidin-3-yl)-1H-pyrazol-3-yl]-6-(3-chlorobenzyl)-1-methyl-6H-pyrrolo[2,3-e][1,2,4]triazolo[4,3-a]pyridine;
6-(3-chlorobenzyl)-1-methyl-7-{1-[1-(methylsulfonyl)azetidin-3-yl]-1H-pyrazol-3-yl}-6H-pyrrolo[2,3-e][1,2,4]triazolo[4,3-a]pyridine;
{3-[3-(6-benzyl-1-methyl-6H-pyrrolo[2,3-e][1,2,4]triazolo[4,3-a]pyridin-7-yl)-1H-pyrazol-1-yl]-1-ethylazetidin-3-yl}acetonitrile; and
{3-[3-(6-benzyl-1-methyl-6H-pyrrolo[2,3-e][1,2,4]triazolo[4,3-a]pyridin-7-yl)-1H-pyrazol-1-yl]-1-isopropylazetidin-3-yl}acetonitrile;

or a pharmaceutically acceptable salt of any of the aforementioned.

30. A compound of claim 1 selected from:
(3-{3-[6-(3-Chlorobenzyl)-1-methyl-6H-pyrrolo[2,3-e][1,2,4]triazolo[4,3-a]pyridin-7-yl]-1H-pyrazol-1-yl}-1-ethylazetidin-3-yl)acetonitrile;
(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-3-yl)acetonitrile;
1-(1,7-Dimethyl-6-(3-(trifluoromethyl)benzyl)-6H-pyrrolo[2,3-e][1,2,4]triazolo[4,3-a]pyridin-4-yl)urea;
1-(3-Chloro-5-{[ 1-methyl-7-(1,3,4-oxadiazol-2-yl)-6H-pyrrolo[2,3-e][1,2,4]triazolo[4,3-a]pyridin-6-yl]methyl}benzyl)azetidin-3-ol;
1-(3-Chloro-5-{[1-methyl-7-(1,3-oxazol-2-yl)-6H-pyrrolo[2,3-e][1,2,4]triazolo[4,3-a]pyridin-6-yl]methyl}benzyl)azetidin-3-ol;
1-(3-Chloro-5-{[1-methyl-7-(1,3-oxazol-2-yl)-6H-pyrrolo[2,3-e][1,2,4]triazolo[4,3-a]pyridin-6-yl]methyl}benzyl)pyrrolidin-3-ol;

1-(3-Chloro-5-{[1-methyl-7-(1-methyl-1H-pyrazol-3-yl)-6H-pyrrolo[2,3-e][1,2,4]triazolo[4,3-a]pyridin-6-yl]methyl}phenyl)-N,N-dimethylmethanamine;

1-(6-(2,3-Difluorobenzyl)-1,7-dimethyl-6H-pyrrolo[2,3-e][1,2,4]triazolo[4,3-a]pyridin-4-yl)urea;

1-(6-(2,4-Difluorobenzyl)-1,7-dimethyl-6H-pyrrolo[2,3-e][1,2,4]triazolo[4,3-a]pyridin-4-yl)urea;

1-(6-(2,6-Difluorobenzyl)-1,7-dimethyl-6H-pyrrolo[2,3-e][1,2,4]triazolo[4,3-a]pyridin-4-yl)urea;

1-(6-(2-Fluorobenzyl)-1,7-dimethyl-6H-pyrrolo[2,3-e][1,2,4]triazolo[4,3-a]pyridin-4-yl)urea;

1-(6-(3,4-Difluorobenzyl)-1,7-dimethyl-6H-pyrrolo[2,3-e][1,2,4]triazolo[4,3-a]pyridin-4-yl)urea;

1-(6-(3,5-Difluorobenzyl)-1,7-dimethyl-6H-pyrrolo[2,3-e][1,2,4]triazolo[4,3-a]pyridin-4-yl)urea;

1-(6-(3-Chlorobenzyl)-1,7-dimethyl-6H-pyrrolo[2,3-e][1,2,4]triazolo[4,3-a]pyridin-4-yl)urea;

1-(6-(3-Fluorobenzyl)-1,7-dimethyl-6H-pyrrolo[2,3-e][1,2,4]triazolo[4,3-a]pyridin-4-yl)urea;

1-(6-(4-Fluorobenzyl)-1,7-dimethyl-6H-pyrrolo[2,3-e][1,2,4]triazolo[4,3-a]pyridin-4-yl)urea;

1-(6-Benzyl-1,7-dimethyl-6H-pyrrolo[2,3-e][1,2,4]triazolo[4,3-a]pyridin-4-yl)-3-ethylurea;

1-(6-Benzyl-1,7-dimethyl-6H-pyrrolo[2,3-e][1,2,4]triazolo[4,3-a]pyridin-4-yl)-3-isopropylurea;

1-(6-Benzyl-1,7-dimethyl-6H-pyrrolo[2,3-e][1,2,4]triazolo[4,3-a]pyridin-4-yl)-3-methylurea;

1-(6-Benzyl-1,7-dimethyl-6H-pyrrolo[2,3-e][1,2,4]triazolo[4,3-a]pyridin-4-yl)urea;

1,7-dimethyl-N-(1-methylpiperidin-4-yl)-6-(pyridin-2-ylmethyl)-6H-pyrrolo[2,3-e][1,2,4]triazolo[4,3-a]pyridin-4-amine;

1,7-dimethyl-N-(1-methylpiperidin-4-yl)-6-(pyridin-3-ylmethyl)-6H-pyrrolo[2,3-e][1,2,4]triazolo[4,3-a]pyridin-4-amine;

2-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)ethano 1;

2-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)-N,N-dimethyl-2-oxoethanamine;

2-[(6-Benzyl-1,7-dimethyl-6H-pyrrolo[2,3-e][1,2,4]triazolo[4,3-a]pyridin-4-yl)amino]ethanol;

2-{3-[6-(3-Chlorobenzyl)-1-methyl-6H-pyrrolo[2,3-e][1,2,4]triazolo[4,3-a]pyridin-7-yl]-1H-pyrazol-1-yl}ethano 1;

3-(3-{3-[6-(3-Chlorobenzyl)-1-methyl-6H-pyrrolo[2,3-e][1,2,4]triazolo[4,3-a]pyridin-7-yl]-1H-pyrazol-1-yl}azetidin-1-yl)propanenitrile;

3-(3-{6-[3-(Azetidin-1-ylmethyl)benzyl]-1-methyl-6H-pyrrolo[2,3-e][1,2,4]triazolo[4,3-a]pyridin-7-yl}-1H-pyrazol-1-yl)propanenitrile;

3-(6-Benzyl-1,7-dimethyl-6H-pyrrolo[2,3-e][1,2,4]triazolo[4,3-a]pyridin-4-yl)-1,1-dimethylurea;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-(1-methylazetidin-3-yl)propanamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-(tetrahydro-2H-pyran-4-yl)propanamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N,N-dimethylazetidine-1-sulfonamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-ethylpropanamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-methylpropanamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}-N-oxetan-3-ylpropanamide;

3-{3-[6-(3-Chlorobenzyl)-1-methyl-6H-pyrrolo[2,3-e][1,2,4]triazolo[4,3-a]pyridin-7-yl]-1H-pyrazol-1-yl}propan-1-ol;

3-{3-[6-(3-Chlorobenzyl)-1-methyl-6H-pyrrolo[2,3-e][1,2,4]triazolo[4,3-a]pyridin-7-yl]-1H-pyrazol-1-yl}propanamide;

6-(3-(Azetidin-1-ylmethyl)-5-chlorobenzyl)-7-(1-ethyl-1H-pyrazol-3-yl)-1-methyl-6H-pyrrolo[2,3-e][1,2,4]triazolo[4,3-a]pyridine;

6-(3-Chloro-5-(pyrrolidin-1-ylmethyl)benzyl)-7-(1-ethyl-1H-pyrazol-3-yl)-1-methyl-6H-pyrrolo[2,3-e][1,2,4]triazolo[4,3-a]pyridine;

6-(3-Chlorobenzyl)-1-methyl-7-(1,3,4-oxadiazol-2-yl)-6H-pyrrolo[2,3-e][1,2,4]triazolo[4,3-a]pyridine;

6-(3-Chlorobenzyl)-1-methyl-7-(1,3-oxazol-2-yl)-6H-pyrrolo[2,3-e][1,2,4]triazolo[4,3-a]pyridine;

6-(3-chlorobenzyl)-1-methyl-7-(1H-pyrazol-5-yl)-6H-pyrrolo[2,3-e][1,2,4]triazolo[4,3-a]pyridine;

6-(3-Chlorobenzyl)-1-methyl-7-(1-oxetan-3-yl-1H-pyrazol-3-yl)-6H-pyrrolo[2,3-e][1,2,4]triazolo[4,3-a]pyridine;

6-(3-Chlorobenzyl)-1-methyl-7-(morpholin-4-ylcarbonyl)-6H-pyrrolo[2,3-e][1,2,4]triazolo[4,3-a]pyridine;

6-(3-Chlorobenzyl)-1-methyl-7-[1-(1-methylazetidin-3-yl)-1H-pyrazol-3-yl]-6H-pyrrolo[2,3-e][1,2,4]triazolo[4,3-a]pyridine;

6-(3-Chlorobenzyl)-1-methyl-7-[1-(1-propionylazetidin-3-yl)-1H-pyrazol-3-yl]-6H-pyrrolo[2,3-e][1,2,4]triazolo[4,3-a]pyridine;

6-(3-Chlorobenzyl)-1-methyl-7-[1-(3-morpholin-4-yl-3-oxopropyl)-1H-pyrazol-3-yl]-6H-pyrrolo[2,3-e][1,2,4]triazolo[4,3-a]pyridine;

6-(3-Chlorobenzyl)-1-methyl-N-(1-methylazetidin-3-yl)-6H-pyrrolo[2,3-e][1,2,4]triazolo[4,3-a]pyridine-7-carboxamide;

6-(3-Chlorobenzyl)-1-methyl-N-(2-morpholin-4-ylethyl)-6H-pyrrolo[2,3-e][1,2,4]triazolo[4,3-a]pyridine-7-carboxamide;

6-(3-Chlorobenzyl)-1-methyl-N-(pyridin-4-ylmethyl)-6H-pyrrolo[2,3-e][1,2,4]triazolo[4,3-a]pyridine-7-carboxamide;

6-(3-Chlorobenzyl)-7-(1H-imidazol-4-yl)-1-methyl-6H-pyrrolo[2,3-e][1,2,4]triazolo[4,3-a]pyridine;

6-(3-Chlorobenzyl)-7-(4,5-dihydro-1,3-oxazol-2-yl)-1-methyl-6H-pyrrolo[2,3-e][1,2,4]triazolo[4,3-a]pyridine;

6-(3-Chlorobenzyl)-7-[1-(1-ethylazetidin-3-yl)-1H-pyrazol-3-yl]-1-methyl-6H-pyrrolo[2,3-e][1,2,4]triazolo[4,3-a]pyridine;

6-(3-Chlorobenzyl)-7-{1-[1-(cyclopropylcarbonyl)azetidin-3-yl]-1H-pyrazol-3-yl}-1-methyl-6H-pyrrolo[2,3-e][1,2,4]triazolo[4,3-a]pyridine;

6-(3-Chlorobenzyl)-7-{1-[1-(cyclopropylsulfonyl)azetidin-3-yl]-1H-pyrazol-3-yl}-1-methyl-6H-pyrrolo[2,3-e][1,2,4]triazolo[4,3-a]pyridine;

6-(3-Chlorobenzyl)-7-{1-[1-(ethylsulfonyl)azetidin-3-yl]-1H-pyrazol-3-yl}-1-methyl-6H-pyrrolo[2,3-e][1,2,4]triazolo[4,3-a]pyridine;

6-(3-Chlorobenzyl)-N-(2-hydroxyethyl)-1-methyl-6H-pyrrolo[2,3-e][1,2,4]triazolo[4,3-a]pyridine-7-carboxamide;

6-(3-Chlorobenzyl)-N-(3-hydroxypropyl)-1-methyl-6H-pyrrolo[2,3-e][1,2,4]triazolo[4,3-a]pyridine-7-carboxamide;

6-(3-Chlorobenzyl)-N-(cyclopropylmethyl)-1-methyl-6H-pyrrolo[2,3-e][1,2,4]triazolo[4,3-a]pyridine-7-carboxamide;

6-(3-Chlorobenzyl)-N-[2-(dimethylamino)ethyl]-1-methyl-6H-pyrrolo[2,3-e][1,2,4]triazolo[4,3-a]pyridine-7-carboxamide;

6-(3-Chlorobenzyl)-N-ethyl-1-methyl-6H-pyrrolo[2,3-e][1,2,4]triazolo[4,3-a]pyridine-7-carboxamide;

6-(3-Chlorobenzyl)-N-isobutyl-1-methyl-6H-pyrrolo[2,3-e][1,2,4]triazolo[4,3-a]pyridine-7-carboxamide;

6-[3-(Azetidin-1-ylmethyl)-5-chlorobenzyl]-1-methyl-7-(1,3,4-oxadiazol-2-yl)-6H-pyrrolo[2,3-e][1,2,4]triazolo[4,3-a]pyridine;

6-[3-(Azetidin-1-ylmethyl)-5-chlorobenzyl]-1-methyl-7-(1,3-oxazol-2-yl)-6H-pyrrolo[2,3-e][1,2,4]triazolo[4,3-a]pyridine;

6-[3-(Azetidin-1-ylmethyl)-5-chlorobenzyl]-1-methyl-7-(1-methyl-1H-pyrazol-3-yl)-6H-pyrrolo[2,3-e][1,2,4]triazolo[4,3-a]pyridine;

6-[3-(Azetidin-1-ylmethyl)-5-chlorobenzyl]-N, 1-dimethyl-6H-pyrrolo[2,3-e][1,2,4]triazolo[4,3-a]pyridine-7-carboxamide;

6-[3-(Azetidin-1-ylmethyl)benzyl]-1-methyl-7-(1H-pyrazol-3-yl)-6H-pyrrolo[2,3-e][1,2,4]triazolo[4,3-a]pyridine;

6-[3-(Azetidin-1-ylmethyl)benzyl]-1-methyl-7-(1-methyl-1H-pyrazol-3-yl)-6H-pyrrolo[2,3-e][1,2,4]triazolo[4,3-a]pyridine;

6-[3-(Azetidin-1-ylmethyl)benzyl]-N, 1-dimethyl-6H-pyrrolo[2,3-e][1,2,4]triazolo[4,3-a]pyridine-7-carboxamide;

6-[3-(Azetidin-1-ylmethyl)benzyl]-N-ethyl-1-methyl-6H-pyrrolo[2,3-e][1,2,4]triazolo[4,3-a]pyridine-7-carboxamide;

6-[3-Chloro-5-(morpholin-4-ylmethyl)benzyl]-1-methyl-7-(1-methyl-1H-pyrazol-3-yl)-6H-pyrrolo[2,3-e][1,2,4]triazolo[4,3-a]pyridine;

6-[3-Chloro-5-(pyrrolidin-1-ylmethyl)benzyl]-1-methyl-7-(1,3-oxazol-2-yl)-6H-pyrrolo[2,3-e][1,2,4]triazolo[4,3-a]pyridine;

6-[3-Chloro-5-(pyrrolidin-1-ylmethyl)benzyl]-1-methyl-7-(1-methyl-1H-pyrazol-3-yl)-6H-pyrrolo[2,3-e][1,2,4]triazolo[4,3-a]pyridine;

6-[3-Chloro-5-(pyrrolidin-1-ylmethyl)benzyl]-N, 1-dimethyl-6H-pyrrolo[2,3-e][1,2,4]triazolo[4,3-a]pyridine-7-carboxamide;

6-[3-Chloro-5-(pyrrolidin-1-ylmethyl)benzyl]-N-ethyl-1-methyl-6H-pyrrolo[2,3-e][1,2,4]triazolo[4,3-a]pyridine-7-carboxamide;

6-{3-Chloro-5-[(3,3-difluoropyrrolidin-1-yl)methyl]benzyl}-N, 1-dimethyl-6H-pyrrolo[2,3-e][1,2,4]triazolo[4,3-a]pyridine-7-carboxamide;

6-{3-Chloro-5-[(3,3-dimethylazetidin-1-yl)methyl]benzyl}-1-methyl-7-(1,3-oxazol-2-yl)-6H-pyrrolo[2,3-e][1,2,4]triazolo[4,3-a]pyridine;

6-{3-Chloro-5-[(3,3-dimethylazetidin-1-yl)methyl]benzyl}-N, 1-dimethyl-6H-pyrrolo[2,3-e][1,2,4]triazolo[4,3-a]pyridine-7-carboxamide;

6-Benzyl-1,7-dimethyl-6H-pyrrolo[2,3-e][1,2,4]triazolo[4,3-a]pyridin-4-ol;

6-Benzyl-1,7-dimethyl-N-((1R,3r,5S)-8-methyl-8-azabicyclo[3.2.1]octan-3-yl)-6H-pyrrolo[2,3-e][1,2,4]triazolo[4,3-a]pyridin-4-amine;

6-Benzyl-1,7-dimethyl-N-(1-methyl-1H-pyrazol-3-yl)-6H-pyrrolo[2,3-e][1,2,4]triazolo[4,3-a]pyridin-4-amine;

6-benzyl-1,7-dimethyl-N-(1-methylpiperidin-3-yl)-6H-pyrrolo[2,3-e][1,2,4]triazolo[4,3-a]pyridin-4-amine;

6-Benzyl-1,7-dimethyl-N-(1-methylpiperidin-4-yl)-6H-pyrrolo[2,3-e][1,2,4]triazolo[4,3-a]pyridin-4-amine;

6-benzyl-1,7-dimethyl-N-(1-methylpyrrolidin-3-yl)-6H-pyrrolo[2,3-e][1,2,4]triazolo[4,3-a]pyridin-4-amine;

6-Benzyl-1,7-dimethyl-N-(2-morpholin-4-ylethyl)-6H-pyrrolo[2,3-e][1,2,4]triazolo[4,3-a]pyridin-4-amine;

6-benzyl-1,7-Dimethyl-N-(pyridin-2-yl)-6H-pyrrolo[2,3-e][1,2,4]triazolo[4,3-a]pyridin-4-amine;

6-Benzyl-1,7-dimethyl-N-(pyridin-3-yl)-6H-pyrrolo[2,3-e][1,2,4]triazolo[4,3-a]pyridin-4-amine;

6-Benzyl-1,7-dimethyl-N-(pyridin-4-yl)-6H-pyrrolo[2,3-e][1,2,4]triazolo[4,3-a]pyridin-4-amine;

6-benzyl-1,7-dimethyl-N-(tetrahydro-2H-pyran-4-yl)-6H-pyrrolo[2,3-e][1,2,4]triazolo[4,3-a]pyridin-4-amine;

6-benzyl-1,7-dimethyl-N-[(3R)-pyrrolidin-3-yl]-6H-pyrrolo[2,3-e][1,2,4]triazolo[4,3-a]pyridin-4-amine;

6-benzyl-1,7-dimethyl-N-[(3R)-tetrahydrofuran-3-yl]-6H-pyrrolo[2,3-e][1,2,4]triazolo[4,3-a]pyridin-4-amine;

6-benzyl-1,7-dimethyl-N-[(3S)-pyrrolidin-3-yl]-6H-pyrrolo[2,3-e][1,2,4]triazolo[4,3-a]pyridin-4-amine;

6-benzyl-1,7-dimethyl-N-[(3S)-tetrahydrofuran-3-yl]-6H-pyrrolo[2,3-e][1,2,4]triazolo[4,3-a]pyridin-4-amine;

6-Benzyl-1,7-dimethyl-N-[1-(methylsulfonyl)piperidin-4-yl]-6H-pyrrolo[2,3-e][1,2,4]triazolo[4,3-a]pyridin-4-amine;

6-Benzyl-1,7-dimethyl-N-1H-pyrazol-3-yl-6H-pyrrolo[2,3-e][1,2,4]triazolo[4,3-a]pyridin-4-amine;

6-Benzyl-1,7-dimethyl-N-phenyl-6H-pyrrolo[2,3-e][1,2,4]triazolo[4,3-a]pyridin-4-amine;

6-Benzyl-1,7-dimethyl-N-piperidin-4-yl-6H-pyrrolo[2,3-e][1,2,4]triazolo[4,3-a]pyridin-4-amine;

6-Benzyl-1,7-dimethyl-N-pyrimidin-2-yl-6H-pyrrolo[2,3-e][1,2,4]triazolo[4,3-a]pyridin-4-amine;

6-Benzyl-1-methyl-6H-pyrrolo[2,3-e][1,2,4]triazolo[4,3-a]pyridine-7-carbonitrile;

6-benzyl-1-methyl-7-(1,3-oxazol-2-yl)-6H-pyrrolo[2,3-e][1,2,4]triazolo[4,3-a]pyridine;

6-Benzyl-1-methyl-7-(trifluoromethyl)-6H-pyrrolo[2,3-e][1,2,4]triazolo[4,3-a]pyridine;

6-Benzyl-1-methyl-7-pyrrolidin-3-yl-6H-pyrrolo[2,3-e][1,2,4]triazolo[4,3-a]pyridine;

6-Benzyl-1-methyl-N-(pyridin-4-ylmethyl)-6H-pyrrolo[2,3-e][1,2,4]triazolo[4,3-a]pyridine-7-carboxamide;

6-Benzyl-4-methoxy-1,7-dimethyl-6H-pyrrolo[2,3-e][1,2,4]triazolo[4,3-a]pyridine;

6-Benzyl-N-(1-ethylpiperidin-4-yl)-1,7-dimethyl-6H-pyrrolo[2,3-e][1,2,4]triazolo[4,3-a]pyridin-4-amine;

6-Benzyl-N-(1H-imidazol-2-yl)-1,7-dimethyl-6H-pyrrolo[2,3-e][1,2,4]triazolo[4,3-a]pyridin-4-amine;

6-Benzyl-N-(1-isopropylpiperidin-4-yl)-1,7-dimethyl-6H-pyrrolo[2,3-e][1,2,4]triazolo[4,3-a]pyridin-4-amine;

6-Benzyl-N-(2-methoxyethyl)-1,7-dimethyl-6H-pyrrolo[2,3-e][1,2,4]triazolo[4,3-a]pyridin-4-amine;

6-Benzyl-N-(3-hydroxypropyl)-1-methyl-6H-pyrrolo[2,3-e][1,2,4]triazolo[4,3-a]pyridine-7-carboxamide;

6-Benzyl-N-(cyclobutylmethyl)-1,7-dimethyl-6H-pyrrolo[2,3-e][1,2,4]triazolo[4,3-a]pyridin-4-amine;

6-Benzyl-N-(cyclopropylmethyl)-1,7-dimethyl-6H-pyrrolo[2,3-e][1,2,4]triazolo[4,3-a]pyridin-4-amine;
6-Benzyl-N, 1,7-trimethyl-6H-pyrrolo[2,3-e][1,2,4]triazolo[4,3-a]pyridin-4-amine;
6-Benzyl-N-[(2R,4R)-1,2-dimethylpiperidin-4-yl]-1,7-dimethyl-6H-pyrrolo[2,3-e][1,2,4]triazolo[4,3-a]pyridin-4-amine;
6-Benzyl-N-[(2R,4S)-1,2-dimethylpiperidin-4-yl]-1,7-dimethyl-6H-pyrrolo[2,3-e][1,2,4]triazolo[4,3-a]pyridin-4-amine;
6-Benzyl-N-[(2S,4R)-1,2-dimethylpiperidin-4-yl]-1,7-dimethyl-6H-pyrrolo[2,3-e][1,2,4]triazolo[4,3-a]pyridin-4-amine;
6-Benzyl-N-[(2S,4S)-1,2-dimethylpiperidin-4-yl]-1,7-dimethyl-6H-pyrrolo[2,3-e][1,2,4]triazolo[4,3-a]pyridin-4-amine;
6-Benzyl-N-cyclohexyl-1,7-dimethyl-6H-pyrrolo[2,3-e][1,2,4]triazolo[4,3-a]pyridin-4-amine;
6-Benzyl-N-ethyl-1,7-dimethyl-6H-pyrrolo[2,3-e][1,2,4]triazolo[4,3-a]pyridin-4-amine;
6-Benzyl-N-isobutyl-1-methyl-6H-pyrrolo[2,3-e][1,2,4]triazolo[4,3-a]pyridine-7-carboxamide;
6-Benzyl-N-isopropyl-1,7-dimethyl-6H-pyrrolo[2,3-e][1,2,4]triazolo[4,3-a]pyridin-4-amine;
6-Benzyl-N-propyl-1,7-dimethyl-6H-pyrrolo[2,3-e][1,2,4]triazolo[4,3-a]pyridin-4-amine;
7-(1-Acetylpyrrolidin-3-yl)-6-benzyl-1-methyl-6H-pyrrolo[2,3-e][1,2,4]triazolo[4,3-a]pyridine;
7-(1-azetidin-3-yl-1H-pyrazol-3-yl)-6-(3-chlorobenzyl)-1-methyl-6H-pyrrolo[2,3-e][1,2,4]triazolo[4,3-a]pyridine;
cis-4-[(6-benzyl-1,7-dimethyl-6H-pyrrolo[2,3-e][1,2,4]triazolo[4,3-a]pyridin-4-yl)amino]cyclohexanecarbonitrile;
cis-N-(6-Benzyl-1,7-dimethyl-6H-pyrrolo[2,3-e][1,2,4]triazolo[4,3-a]pyridin-4-yl)cyclohexane-1,4-diamine;
cis-N'-(6-Benzyl-1,7-dimethyl-6H-pyrrolo[2,3-e][1,2,4]triazolo[4,3-a]pyridin-4-yl)-N,N-dimethylcyclohexane-1,4-diamine;
cis-N-(6-Benzyl-1,7-dimethyl-6H-pyrrolo[2,3-e][1,2,4]triazolo[4,3-a]pyridin-4-yl)-N'-methylcyclohexane-1,4-diamine;
Ethyl 3-{3-[ 6-(3-chlorobenzyl)-1-methyl-6H-pyrrolo[2,3-e][1,2,4]triazolo[4,3-a]pyridin-7-yl]-1H-pyrazol-1-yl}azetidine-1-carboxylate;
Methyl 6-benzyl-1,7-dimethyl-6H-pyrrolo[2,3-e][1,2,4]triazolo[4,3-a]pyridin-4-ylcarbamate;
N-(1-Acetylpiperidin-4-yl)-6-benzyl-1,7-dimethyl-6H-pyrrolo[2,3-e][1,2,4]triazolo[4,3-a]pyridin-4-amine;
N-(6-Benzyl-1,7-dimethyl-6H-pyrrolo[2,3-e][1,2,4]triazolo[4,3-a]pyridin-4-yl)acetamide;
N-(6-Benzyl-1,7-dimethyl-6H-pyrrolo[2,3-e][1,2,4]triazolo[4,3-a]pyridin-4-yl)butyramide;
N-(6-Benzyl-1,7-dimethyl-6H-pyrrolo[2,3-e][1,2,4]triazolo[4,3-a]pyridin-4-yl)cyclopropanecarboxamide;
N-(6-Benzyl-1,7-dimethyl-6H-pyrrolo[2,3-e][1,2,4]triazolo[4,3-a]pyridin-4-yl)isobutyramide;
N-(6-Benzyl-1,7-dimethyl-6H-pyrrolo[2,3-e][1,2,4]triazolo[4,3-a]pyridin-4-yl)methanesulfonamide;
N-(6-Benzyl-1,7-dimethyl-6H-pyrrolo[2,3-e][1,2,4]triazolo[4,3-a]pyridin-4-yl)propionamide;
N-(Azetidin-3-ylmethyl)-6-(3-chlorobenzyl)-1-methyl-6H-pyrrolo[2,3-e][1,2,4]triazolo[4,3-a]pyridine-7-carboxamide;
N-(Azetidin-3-ylmethyl)-6-benzyl-1-methyl-6H-pyrrolo[2,3-e][1,2,4]triazolo[4,3-a]pyridine-7-carboxamide;
N-(tert-Butyl)-3-{3-[6-(3-chlorobenzyl)-1-methyl-6H-pyrrolo[2,3-e][1,2,4]triazolo[4,3-a]pyridin-7-yl]-1H-pyrazol-1-yl}propanamide;
N-(tert-Butyl)-6-(3-chlorobenzyl)-1-methyl-6H-pyrrolo[2,3-e][1,2,4]triazolo[4,3-a]pyridine-7-carboxamide;
N,1-dimethyl-6-[3-(trifluoro methyl)benzyl]-6H-pyrrolo[2,3-e][1,2,4]triazolo[4,3-a]pyridine-7-carboxamide;
N-{6-[3-Chloro-5-(pyrrolidin-1-ylmethyl)benzyl]-1,7-dimethyl-6H-pyrrolo[2,3-e][1,2,4]triazolo[4,3-a]pyridin-4-yl}-N'-methylurea;
N1-(6-benzyl-1,7-dimethyl-6H-pyrrolo[2,3-e][1,2,4]triazolo[4,3-a]pyridin-4-yl)ethane-1,2-diamine;
N1-(6-Benzyl-1,7-dimethyl-6H-pyrrolo[2,3-e][1,2,4]triazolo[4,3-a]pyridin-4-yl)-N2,N2-dimethylethane-1,2-diamine;
N1-(6-Benzyl-1,7-dimethyl-6H-pyrrolo[2,3-e][1,2,4]triazolo[4,3-a]pyridin-4-yl)-N3,N3-dimethylpropane-1,3-diamine;
N1-(6-Benzyl-1,7-dimethyl-6H-pyrrolo[2,3-e][1,2,4]triazolo[4,3-a]pyridin-4-yl)propane-1,3-diamine;
N-1,3-Benzoxazol-2-yl-6-benzyl-1,7-dimethyl-6H-pyrrolo[2,3-e][1,2,4]triazolo[4,3-a]pyridin-4-amine;
N-1H-Benzimidazol-2-yl-6-benzyl-1,7-dimethyl-6H-pyrrolo[2,3-e][1,2,4]triazolo[4,3-a]pyridin-4-amine;
N-Ethyl-1-methyl-6-[3-(trifluoromethyl)benzyl]-6H-pyrrolo[2,3-e][1,2,4]triazolo[4,3-a]pyridine-7-carboxamide;
tert-butyl (3R)-3-[(6-benzyl-1,7-dimethyl-6H-pyrrolo[2,3-e][1,2,4]triazolo[4,3-a]pyridin-4-yl)amino]pyrrolidine-1-carboxylate;
tert-butyl (3 S)-3-[(6-benzyl-1,7-dimethyl-6H-pyrrolo[2,3-e][1,2,4]triazolo[4,3-a]pyridin-4-yl)amino]pyrrolidine-1-carboxylate;
tert-Butyl 3-((6-benzyl-1,7-dimethyl-6H-pyrrolo[2,3-e][1,2,4]triazolo[4,3-a]pyridin-4-ylamino)methyl)azetidine-1-carboxylate;
tert-Butyl 3-(6-benzyl-1,7-dimethyl-6H-pyrrolo[2,3-e][1,2,4]triazolo[4,3-a]pyridin-4-ylamino)azetidine-1-carboxylate;
tert-Butyl 4-((6-benzyl-1,7-dimethyl-6H-pyrrolo[2,3-e][1,2,4]triazolo[4,3-a]pyridin-4-ylamino)methyl)piperidine-1-carboxylate;
tert-Butyl 4-[(6-benzyl-1,7-dimethyl-6H-pyrrolo[2,3-e][1,2,4]triazolo[4,3-a]pyridin-4-yl)amino]piperidine-1-carboxylate;
tert-Butyl 6-benzyl-1,7-dimethyl-6H-pyrrolo[2,3-e][1,2,4]triazolo[4,3-a]pyridin-4-ylcarbamate;
trans-3-(6-Benzyl-1,7-dimethyl-6H-pyrrolo[2,3-e][1,2,4]triazolo[4,3-a]pyridin-4-ylamino)cyclobutanol;
trans-4-[(6-benzyl-1,7-dimethyl-6H-pyrrolo[2,3-e][1,2,4]triazolo[4,3-a]pyridin-4-yl)amino]cyclohexanecarbonitrile;
trans-N-(6-Benzyl-1,7-dimethyl-6H-pyrrolo[2,3-e][1,2,4]triazolo[4,3-a]pyridin-4-yl)cyclohexane-1,4-diamine;
trans-N'-(6-Benzyl-1,7-dimethyl-6H-pyrrolo[2,3-e][1,2,4]triazolo[4,3-a]pyridin-4-yl)-N,N-dimethylcyclohexane-1,4-diamine; and
trans-N-(6-Benzyl-1,7-dimethyl-6H-pyrrolo[2,3-e][1,2,4]triazolo[4,3-a]pyridin-4-yl)-N'-methylcyclohexane-1,4-diamine;
or a pharmaceutically acceptable salt of any of the aforementioned.

31. A pharmaceutical composition comprising a compound of claim 1, or a pharmaceutically acceptable salt thereof, and at least one pharmaceutically acceptable carrier.

32. A method of inhibiting a BET protein comprising contacting a compound of claim 1, or a pharmaceutically acceptable salt thereof, with said BET protein.

\* \* \* \* \*

UNITED STATES PATENT AND TRADEMARK OFFICE
CERTIFICATE OF CORRECTION

PATENT NO. : 9,309,246 B2
APPLICATION NO. : 14/575284
DATED : April 12, 2016
INVENTOR(S) : James D. Rodgers et al.

It is certified that error appears in the above-identified patent and that said Letters Patent is hereby corrected as shown below:

In the Claims

Col. 327, Line 52, Claim 1, delete "cycloalky" and insert -- cycloalkyl --.

Col. 327, Line 58, Claim 1, delete "cycloalky" and insert -- cycloalkyl --.

Col. 331, Line 58, Claim 21, delete "$R^{d1}$;" and insert -- $R^{d1}$, --.

Col. 333, Line 18, Claim 29, after "pyridine" insert -- ; --.

Col. 333, Line 20, Claim 29, after "pyridine" insert -- ; --.

Col. 333, Line 26, Claim 29, after "pyridine" insert -- ; --.

Col. 333, Line 65, Claim 29, after "pyridine" insert -- ; --.

Col. 334, Line 49, Claim 29, after "carboxamide" insert -- ; --.

Col. 334, Line 55, Claim 29, delete "ethano 1;" and insert -- ethanol; --.

Col. 336, Line 59, Claim 30, delete "{[ 1" and insert -- {[1 --.

Col. 337, Line 39, Claim 30, delete "ethano 1;" and insert -- ethanol; --.

Col. 337, Line 47, Claim 30, delete "ethano 1;" and insert -- ethanol; --.

Signed and Sealed this
Fourteenth Day of June, 2016

Michelle K. Lee
*Director of the United States Patent and Trademark Office*